(12) United States Patent
Miller et al.

(10) Patent No.: US 8,536,179 B2
(45) Date of Patent: Sep. 17, 2013

(54) INDOLES

(75) Inventors: William H. Miller, Collegeville, PA (US); Xinrong Tian, Collegeville, PA (US); Sharad Kumar Verma, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/696,362

(22) PCT Filed: May 5, 2011

(86) PCT No.: PCT/US2011/035336
§ 371 (c)(1),
(2), (4) Date: Nov. 6, 2012

(87) PCT Pub. No.: WO2011/140324
PCT Pub. Date: Nov. 10, 2011

(65) Prior Publication Data
US 2013/0053397 A1    Feb. 28, 2013

Related U.S. Application Data

(60) Provisional application No. 61/332,309, filed on May 7, 2010.

(51) Int. Cl.
*A61K 31/497* (2006.01)
(52) U.S. Cl.
USPC .................................................. 514/252.13
(58) Field of Classification Search
USPC .................................................. 514/252.13
See application file for complete search history.

(56) References Cited

U.S. PATENT DOCUMENTS

| 7,087,637 B2 | 8/2006 | Grandel et al. |
| 2009/0012031 A1 | 1/2009 | Chinnaiyan et al. |

FOREIGN PATENT DOCUMENTS

| EP | 0 213 984 A1 | 3/1987 |
| WO | WO 2009/103552 A1 | 8/2009 |
| WO | WO 2010/036213 A1 | 4/2010 |
| WO | WO 2012/118812 A2 | 9/2012 |

OTHER PUBLICATIONS

McCabe, et al. Nature, 1, DOI:10.1038/nature11606 (2012).

*Primary Examiner* — San-Ming Hui
(74) *Attorney, Agent, or Firm* — Duke M. Fitch; Kathryn A. Lutomski; John Lemanowicz

(57) ABSTRACT

Herein are disclosed indoles of formula (I) where the various groups are defined herein, and which are useful in treating cancer.

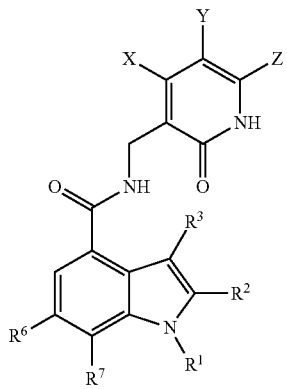

4 Claims, No Drawings

INDOLES

This application is a 371 of International Application No. PCT/US2011/035336, filed 5 May 2011, which claims the benefit of U.S. Provisional Application No. 61/332,309, filed 7 May 2010, which are incorporated herein in their entireties.

FIELD OF THE INVENTION

This invention relates to substituted indoles which inhibit EZH2 and thus are useful for inhibiting the proliferation of and/or inducing apoptosis in cancer cells.

BACKGROUND OF THE INVENTION

Epigenetic modifications play an important role in the regulation of many cellular processes including cell proliferation, differentiation, and cell survival. Global epigenetic modifications are common in cancer, and include global changes in DNA and/or histone methylation, dysregulation of non-coding RNAs and nucleosome remodeling leading to aberrant activation or inactivation of oncogenes, tumor suppressors and signaling pathways. However, unlike genetic mutations which arise in cancer, these epigenetic changes can be reversed through selective inhibition of the enzymes involved. Several methylases involved in histone or DNA methylation are known to be dysregulated in cancer. Thus, selective inhibitors of particular methylases will be useful in the treatment of proliferative diseases such as cancer.

EZH2 (enhancer of zeste homolog 2; human EZH2 gene: Cardoso, C, et al; *European J of Human Genetics*, Vol. 8, No. 3 Pages 174-180, 2000) is the catalytic subunit of the Polycomb Repressor Complex 2 (PRC2) which functions to silence target genes by tri-methylating lysine 27 of histone H3 (H3K27me3). Histone H3 is one of the five main histone proteins involved in the structure of chromatin in eukaryotic cells. Featuring a main globular domain and a long N-terminal tail, Histones are involved with the structure of the nucleosomes, a 'beads on a string' structure. Histone proteins are highly post-translationally modified however Histone H3 is the most extensively modified of the five histones. The term "Histone H3" alone is purposely ambiguous in that it does not distinguish between sequence variants or modification state. Histone H3 is an important protein in the emerging field of epigenetics, where its sequence variants and variable modification states are thought to play a role in the dynamic and long term regulation of genes.

Increased EZH2 expression has been observed in numerous solid tumors including those of the prostate, breast, skin, bladder, liver, pancreas, head and neck and correlates with cancer aggressiveness, metastasis and poor outcome (Varambally et al., 2002; Kleer et al., 2003; Breuer et al., 2004; Bachmann et al., 2005; Weikert et al., 2005; Sudo et al., 2005; Bachmann et al., 2006). For instance, there is a greater risk of recurrence after prostatectomy in tumors expressing high levels of EZH2, increased metastasis, shorter disease-free survival and increased death in breast cancer patients with high EZH2 levels (Varambally et al., 2002; Kleer et al., 2003). More recently, inactivating mutations in UTX (ubiquitously transcribed tetratricopeptixe repeats X), a H3K27 demethylase which functions in opposition to EZH2, have been identified in multiple solid and hematological tumor types (including renal, glioblastoma, esophageal, breast, colon, non-small cell lung, small cell lung, bladder, multiple myeloma, and chronic myeloid leukemia tumors), and low UTX levels correlate with poor survival in breast cancer suggesting that loss of UTX function leads to increased H3K27me3 and repression of target genes (Wang et al., 2010). Together, these data suggest that increased H3K27me3 levels contribute to cancer aggressiveness in many tumor types and that inhibition of EZH2 activity may provide therapeutic benefit.

Numerous studies have reported that direct knockdown of EZH2 via siRNA or shRNA or indirect loss of EZH2 via treatment with the SAH hydrolase inhibitor 3-deazaneplanocin A (DZNep) decreases cancer cell line proliferation and invasion in vitro and tumor growth in vivo (Gonzalez et al., 2008, GBM 2009). While the precise mechanism by which aberrant EZH2 activity leads to cancer progression is not known, many EZH2 target genes are tumor suppressors suggesting that loss of tumor suppressor function is a key mechanism. In addition, EZH2 overexpression in immortalized or primary epithelial cells promotes anchorage independent growth and invasion and requires EZH2 catalytic activity. (Kleer et al., 2003; Cao et al., 2008).

Thus, there is strong evidence to suggest that inhibition of EZH2 activity decreases cellular proliferation and invasion. Accordingly, compounds that inhibit EZH2 activity would be useful for the treatment of cancer. The indoles of this invention provide such treatment.

SUMMARY OF THE INVENTION

In a first instance, this invention relates to compounds of formula (I)

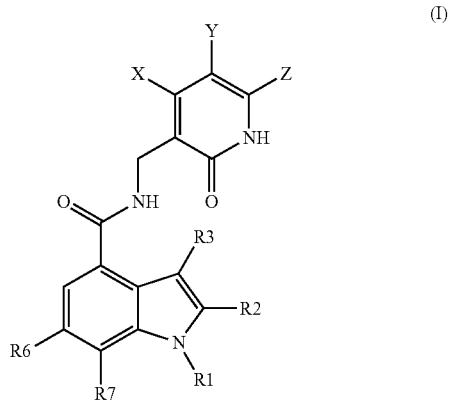

wherein

X and Z are selected independently from the group consisting of hydrogen, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, $(C_6-C_{10})$bicycloalkyl, unsubstituted or substituted heterocycloalkyl, unsubstituted or substituted heterocycloalkyl-$(C_1-C_8)$alkyl or —$(C_2-C_8)$alkenyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, halo, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$;

Y is H or halo;

$R^1$ is $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, unsubstituted or substituted $(C_6-C_{10})$bicycloalkyl, unsubstituted or substituted heterocycloalkyl or —$(C_2-C_8)$alkenyl, unsubstituted or substituted heterocycloalkyl-$(C_1-C_8)$alkyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, —$COR^a$, —$CO_2R^a$, —$CONR^aR^b$, —$CONR^aNR^aR^b$;

$R^2$ is hydrogen, $(C_1-C_8)$alkyl, trifluoromethyl, alkoxy, or halo, in which said $(C_1-C_8)$alkyl maybe substituted with one to two groups selected from: amino, and $(C_1-C_3)$alkylamino;

$R^7$ is hydrogen, $(C_1-C_3)$alkyl, or alkoxy; $R^3$ is hydrogen, $(C_1-C_8)$alkyl, cyano, trifluoromethyl, —$NR^aR^b$, or halo;

$R^6$ is selected from the group consisting of hydrogen, halo, $(C_1-C_8)$alkyl, $(C_2-C_8)$alkenyl, —$B(OH)_2$, substituted or unsubstituted $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl, unsubstituted or substituted $(C_5-C_8)$cycloalkenyl, unsubstituted or substituted $(C_5-C_8)$cycloalkenyl-$(C_1-C_8)$alkyl, $(C_6-C_{10})$bicycloalkyl, unsubstituted or substituted heterocycloalkyl, unsubstituted or substituted heterocycloalkyl-$(C_1-C_8)$alkyl, unsubstituted or substituted aryl, unsubstituted or substituted aryl-$(C_1-C_8)$alkyl, unsubstituted or substituted heteroaryl, unsubstituted or substituted heteroaryl-$(C_1-C_8)$alkyl, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR'SO_2R^a$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, —$OC(O)NR^aR^b$;

wherein any $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from the group consisting of —$O(C_1-C_6)$alkyl$(R^c)_{1-2}$, —$S(C_1-C_6)$alkyl$(R^c)_{1-2}$, —$(C_1-C_6)$alkyl$(R^c)_{1-2}$, $(C_1-C_8)$alkyl-heterocycloalkyl, $(C_3-C_8)$cycloalkyl-heterocycloalkyl, halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOW$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR'SO_2NR^aR^b$, —$OR^a$, —$OC(O)R^a$, —$OC(O)NR^aR^b$, heterocycloalkyl, aryl, heteroaryl, aryl$(C_1-C_4)$alkyl, and heteroaryl$(C_1-C_4)$alkyl;

wherein any aryl or heteroaryl moiety of said aryl, heteroaryl, aryl$(C_1-C_4)$alkyl, or heteroaryl$(C_1-C_4)$alkyl is optionally substituted by 1, 2 or 3 groups independently selected from the group consisting of halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, $((C_1-C_4)$alkyl)$((C_1-C_4)$alkyl)amino, —$CO_2H$, —$CO_2(C_1-C_4)$alkyl, —$CONH_2$, —$CONH(C_1-C_4)$alkyl, —$CON((C_1-C_4)$alkyl)$((C_1-C_4)$alkyl), —$SO_2(C_1-C_4)$alkyl, —$SO_2NH_2$, —$SO_2NH(C_1-C_4)$alkyl, or —$SO_2N((C_1-C_4)$alkyl)$((C_1-C_4)$alkyl);

each $R^c$ is independently $(C_1-C_4)$alkylamino, —$NR^aSO_2R^b$, —$SOW$, —$SO_2R^a$, —$NR^aC(O)OR^a$, —$NR^aR^b$, or —$CO_2R^a$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl)$((C_1-C_4)$alkyl)amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

or a salt thereof.

In a further iteration of this invention it relates to a method of inducing apoptosis in cancer cells of solid tumors; treating solid tumor cancers.

Another aspect of the invention are pharmaceutical preparations comprising compounds of formula (I) and pharmaceutically acceptable excipients.

In a fourth aspect, there is provided the use of a compound of formula (I) and/or a pharmaceutically acceptable salt or solvate thereof, in the preparation of a medicament for use in the treatment of a disorder mediated by inhibiting EZH2, such as inducing apoptosis in cancer cells.

In a fifth aspect there is provided methods of co-administering the presently invented compounds of formula (I) with another active ingredients.

DETAILED DESCRIPTION OF THE INVENTION

For the avoidance of doubt, unless otherwise indicated, the term "substituted" means substituted by one or more defined groups. In the case where groups may be selected from a number of alternative groups the selected groups may be the same or different.

The term "independently" means that where more than one substituent is selected from a number of possible substituents, those substituents may be the same or different.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having the specified number of carbon atoms, so for example, as used herein, the terms "$C_1$-$C_8$alkyl" refers to an alkyl group having at least 1 and up to 8 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, n-hexyl, n-heptyl, and n-octyl and branched analogs of the latter 5 normal alkanes.

The term "alkoxy" as used herein means —O($C_1$-$C_8$alkyl) including —OCH$_3$, —OCH$_2$CH$_3$ and —OC(CH$_3$)$_3$ and the like per the definition of alkyl above.

The term "alkylthio" as used herein is meant —S($C_1$-$C_8$alkyl) including —SCH$_3$, —SCH$_2$CH$_3$ and the like per the definition of alkyl above.

The term "acyloxy" means —OC(O)$C_1$-$C_8$alkyl and the like per the definition of alkyl above.

"Acylamino" means -N(H)C(O)$C_1$-$C_8$alkyl and the like per the definition of alkyl above.

"Aryloxy" means —O(aryl), —O (substituted aryl), —O (heteroaryl) or —O (substituted heteroaryl).

"Arylamino" means —NH(aryl), —NH (substituted aryl), —NH (heteroaryl) or —NH (substituted heteroaryl), and the like.

When the term "alkenyl" (or "alkenylene") is used it refers to straight or branched hydrocarbon chains containing the specified number of carbon atoms and at least 1 and up to 5 carbon-carbon double bonds. Examples include ethenyl (or ethenylene) and propenyl (or propenylene).

When the term "alkynyl" (or "alkynylene") is used it refers to straight or branched hydrocarbon chains containing the specified number of carbon atoms and at least 1 and up to 5 carbon-carbon triple bonds. Examples include ethynyl (or ethynylene) and propynyl (or propynylene).

"Haloalkyl" refers to an alkyl group group that is substituted with one or more halo substituents, suitably from 1 to 6 substituents. Haloalkyl includes trifluoromethyl.

When "cycloalkyl" is used it refers to a non-aromatic, saturated, cyclic hydrocarbon ring containing the specified number of carbon atoms. So, for example, the term "$C_3$-$C_8$cycloalkyl" refers to a non-aromatic cyclic hydrocarbon ring having from three to eight carbon atoms. Exemplary "$C_3$-$C_8$cycloalkyl" groups useful in the present invention include, but are not limited to, cyclopropyl, cyclobutyl, cyclopentyl, cyclohexyl, cycloheptyl and cyclooctyl.

The term "$C_5$-$C_8$cycloalkenyl" refers to a non-aromatic monocyclic carboxycyclic ring having the specified number of carbon atoms and up to 3 carbon-carbon double bonds. "Cycloalkenyl" includes by way of example cyclopentenyl and cyclohexenyl.

Where "$C_3$-$C_8$heterocycloalkyl" is used, it means a non-aromatic heterocyclic ring containing the specified number of ring atoms being, saturated or having one or more degrees of unsaturation and containing one or more heteroatom substitutions independently selected from O, S and N. Such a ring may be optionally fused to one or more other "heterocyclic" ring(s) or cycloalkyl ring(s). Examples are given herein below.

"Aryl" refers to optionally substituted monocyclic or polycarbocyclic unfused or fused groups having 6 to 14 carbon atoms and having at least one aromatic ring that complies with Hiickel's Rule. Examples of aryl groups are phenyl, biphenyl, naphthyl, anthracenyl, phenanthrenyl, and the like, as further illustrated below.

"Heteroaryl" means an optionally substituted aromatic monocyclic ring or polycarbocyclic fused ring system wherein at least one ring complies with Hiickel's Rule, has the specified number of ring atoms, and that ring contains at least one heteroatom independently selected from N, O and S. Examples of "heteroaryl" groups are given herein below.

The term "optionally" means that the subsequently described event(s) may or may not occur, and includes both event(s), which occur, and events that do not occur.

Herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

While the compounds encompassed by the general structure of formula (I) as defined herein are believed to be useful for inducing apoptosis in cancer cells, some of these compounds are more active that others. In that vein, the following subgroups delineate certain compounds believed to have greater potency or other properties which suggest they may be a better choice for use in therapy, versus other. Those subgroups are represented as follows:

Subgroup A

X and Z are selected from the group consisting of ($C_1$-$C_8$) alkyl, ($C_3$-$C_8$)cycloalkyl, heterocycloalkyl, aryl, heteroaryl, —NR$^a$R$^b$, and —OR$^a$;

Y is H or F;

$R^1$ is selected from the group consisting of ($C_1$-$C_8$)alkyl, ($C_3$-$C_8$)cycloalkyl, heterocycloalkyl, aryl, and heteroaryl;

$R^2$ is hydrogen, ($C_1$-$C_8$)alkyl, trifluoromethyl, alkoxy, or halo, in which said ($C_1$-$C_8$)alkyl maybe substituted with one to two groups selected from: amino, and ($C_1$-$C_3$)alkylamino;

$R^7$ is hydrogen, ($C_1$-$C_3$)alkyl, or alkoxy; $R^3$ is selected from the group consisting of hydrogen, ($C_1$-$C_8$)alkyl, cyano, trifluoromethyl, —NR$^a$R$^b$, and halo;

$R^6$ is selected from the group consisting of hydrogen, halo, cyano, trifluoromethyl, amino, ($C_1$-$C_8$)alkyl, ($C_3$-$C_8$)cycloalkyl, aryl, heteroaryl, acylamino, ($C_2$-$C_8$)alkynyl, arylalkynyl, heteroarylalkynyl, —SO$_2$R$^a$, —SO$_2$NR$^a$R$^b$, and —NR$^a$SO$_2$R$^b$;

wherein any ($C_1$-$C_8$)alkyl, ($C_3$-$C_8$)cycloalkyl, ($C_2$-$C_8$) alkynyl, arylalkynyl, heteroarylalkynyl group is optionally substituted by 1, 2 or 3 groups independently selected from —O($C_1$-$C_6$)alkyl(R$^c$)$_{1-2}$, —S($C_1$-$C_6$)alkyl(R$^c$)$_{1-2}$, —($C_1$-$C_6$) alkyl(R$^c$)$_{1-2}$, ($C_1$-$C_8$)alkyl-heterocycloalkyl, ($C_3$-$C_8$)cycloalkyl-heterocycloalkyl, halo, ($C_1$-$C_6$)alkyl, ($C_3$-$C_8$)cycloalkyl, ($C_5$-$C_8$)cycloalkenyl, ($C_1$-$C_6$)haloalkyl, cyano, —COR$^a$, —CO$_2$R$^a$, —CONR$^a$R$^b$, —SR$^a$, —SO$_2$R$^a$, —SO$_2$NR$^a$R$^b$, nitro, —NR$^a$R$^b$, —NR$^a$C(O)R$^b$, —NR$^a$C(O) NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$, heterocycloalkyl, aryl, heteroaryl, aryl($C_1$-$C_4$)alkyl, and heteroaryl($C_1$-$C_4$) alkyl;

each R$^c$ is independently ($C_1$-$C_4$)alkylamino, —NR$^a$SO$_2$R$^b$, —SO$_2$R$^a$, —NR$^a$C(O)OR$^a$, —NR$^a$R$^b$, or —CO$_2$R$^a$;

R$^a$ and R$^b$ are each independently hydrogen, ($C_1$-$C_8$)alkyl, ($C_2$-$C_8$)alkenyl, ($C_2$-$C_8$)alkynyl, ($C_3$-$C_8$)cycloalkyl, ($C_5$-$C_8$) cycloalkenyl, ($C_6$-$C_{10}$)bicycloalkyl, heterocycloalkyl, aryl, heteroaryl, wherein said ($C_1$-$C_8$)alkyl, ($C_2$-$C_8$)alkenyl, ($C_2$-$C_8$)alkynyl, cycloalkyl, cycloalkenyl, bicycloalkyl, heterocycloalkyl, aryl or heteroaryl group is optionally substituted by 1, 2 or 3 groups independently selected from halo, hydroxyl, ($C_1$-$C_4$)alkoxy, amino, ($C_1$-$C_4$)alkylamino, (($C_1$-$C_4$)alkyl) (($C_1$-$C_4$)alkyl)amino, —CO$_2$H, —CO$_2$($C_1$-$C_4$)alkyl, —CONH$_2$, —CONH($C_1$-$C_4$)alkyl, —CON(($C_1$-$C_4$)alkyl) (($C_1$-$C_4$)alkyl), —SO$_2$($C_1$-$C_4$)alkyl, —SO$_2$NH$_2$, —SO$_2$NH ($C_1$-$C_4$)alkyl, and —SO$_2$N(($C_1$-$C_4$)alkyl)(($C_1$-$C_4$)alkyl);

or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from ($C_1$-$C_4$)alkyl, ($C_1$-$C_4$)haloalkyl, amino, ($C_1$-$C_4$)alkylamino, (($C_1$-$C_4$)alkyl)(($C_1$-$C_4$)alkyl)amino, hydroxyl, oxo, ($C_1$-$C_4$)alkoxy, and ($C_1$-$C_4$)alkoxy($C_1$-$C_4$)alkyl, wherein said ring is optionally fused to a ($C_3$-$C_8$)cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a ($C_3$-$C_8$)cycloalkyl, heterocycloalkyl, aryl, or heteroaryl ring. An aryl or heteroaryl group in this particular subgroup A is selected independently from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or another aryl or heteroaryl group as follows:

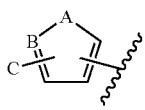

(1)

wherein in (1),

A is O, NH, or S; B is CH or N, and C is hydrogen or $C_1$-$C_8$ alkyl; or

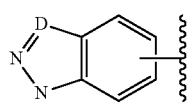

(2)

wherein in (2),

D is N or C optionally substituted by hydrogen or $C_1$-$C_8$ alkyl; or

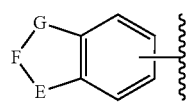

(3)

wherein in (3),

E is NH or $CH_2$; F is O or CO; and G is NH or $CH_2$; or

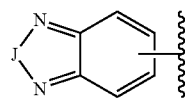

(4)

wherein in (4),

J is O, S or CO; or

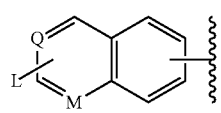

(5)

wherein in (5),

Q is CH or N;

M is CH or N; and

L/(5) is hydrogen, halo, amino, cyano, ($C_1$-$C_8$)alkyl, ($C_3$-$C_8$)cycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —NR'$NR^aC(O)R^b$, —$NR^aNR^aC(O)NR^aR^b$, —OR', wherein any ($C_1$-$C_8$)alkyl, ($C_3$-$C_8$)cycloalkyl, group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —SOW, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$; wherein $R^a$ and $R^b$ are defined as above; or

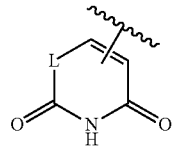

(6)

wherein in 6,

L/(6) is NH or $CH_2$; or

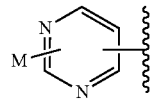

(7)

wherein in 7,

M/(7) is hydrogen, halo, amino, cyano, ($C_1$-$C_8$)alkyl, ($C_3$-$C_8$)cycloalkyl, heterocycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$OR^a$, wherein any ($C_1$-$C_8$)alkyl, ($C_3$-$C_8$)cycloalkyl, heterocycloalkyl group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —SOW, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$; wherein $R^a$ and $R^b$ are defined as above; or

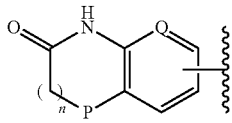

wherein in (8),

P is CH$_2$, NH, O, or S; Q/(8) is CH or N; and n is 0-2; or

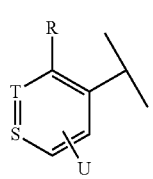

wherein in (9),

S/(9) and T(9) is C, or S/(9) is C and T(9) is N, or S/(9) is N and T/(9) is C;

R is hydrogen, amino, methyl, trifluoromethyl, halo;

U is hydrogen, halo, amino, cyano, nitro, trifluoromethyl, (C$_1$-C$_8$)alkyl, (C$_3$-C$_8$)cycloalkyl, —COR$^a$, —CO$_2$R$^a$, —CONR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —OR$^a$, 4-(1H-pyrazol-4-yl), wherein any (C$_1$-C$_8$)alkyl, (C$_3$-C$_8$)cycloalkyl, group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$; wherein R$^a$ and R$^b$ are defined as above.

Subgroup B

X and Z are selected independently from the group consisting of (C$_1$-C$_8$)alkyl, (C$_3$-C$_8$)cycloalkyl, heterocycloalkyl, aryl, heteroaryl, —NR$^a$R$^b$, and —OR$^a$;

Y is H;

R$^1$ is (C$_1$-C$_8$)alkyl, (C$_3$-C$_8$)cycloalkyl, or heterocycloalkyl;

R$_2$ is hydrogen, (C$_1$-C$_3$)alkyl, or halo, in which said (C$_1$-C$_3$)alkyl maybe substituted with one to two groups selected from amino, and (C$_1$-C$_3$)alkylamino;

R$^7$ is hydrogen, (C$_1$-C$_3$)alkyl, or alkoxy; R$^3$ is hydrogen, (C$_1$-C$_8$)alkyl or halo;

R$^6$ is hydrogen, halo, cyano, trifluoromethyl, amino, (C$_1$-C$_8$)alkyl, (C$_3$-C$_8$)cycloalkyl, aryl, heteroaryl, acylamino, (C$_2$-C$_8$)alkynyl, arylalkynyl, heteroarylalkynyl, —SO$_2$R$^a$, —SO$_2$NR$^a$R$^b$, or —NR$^a$SO$_2$R$^b$;

wherein any (C$_1$-C$_8$)alkyl, (C$_3$-C$_8$)cycloalkyl, (C$_2$-C$_8$)alkynyl, arylalkynyl, heteroarylalkynyl group is optionally substituted by 1, 2 or 3 groups independently selected from halo, (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$,—NR$^a$SO$_2$NR$^a$R$^b$, —OR$^a$, —OC(O)R$^a$, —OC(O)NR$^a$R$^b$, heterocycloalkyl, aryl, heteroaryl, aryl(C$_1$-C$_4$)alkyl, and heteroaryl(C$_1$-C$_4$)alkyl;

R$^a$ and R$^b$ are each independently hydrogen, (C$_1$-C$_8$)alkyl, (C$_2$-C$_8$)alkenyl, (C$_2$-C$_8$)alkynyl, (C$_3$-C$_8$)cycloalkyl, (C$_5$-C$_8$)cycloalkenyl, (C$_6$-C$_{10}$)bicycloalkyl, heterocycloalkyl, aryl, heteroaryl, wherein said (C$_1$-C$_8$)alkyl, (C$_2$-C$_8$)alkenyl, (C$_2$-C$_8$)alkynyl, cycloalkyl, cycloalkenyl, bicycloalkyl, heterocycloalkyl, aryl or heteroaryl group is optionally substituted by 1, 2 or 3 groups independently selected from halo, hydroxyl, (C$_1$-C$_4$)alkoxy, amino, (C$_1$-C$_4$)alkylamino, ((C$_1$-C$_4$)alkyl)((C$_1$-C$_4$)alkyl)amino, —CO$_2$H, —CO$_2$(C$_1$-C$_4$)alkyl, —CONH$_2$, —CONH(C$_1$-C$_4$)alkyl, —CON((C$_1$-C$_4$)alkyl)((C$_1$-C$_4$)alkyl), —SO$_2$(C$_1$-C$_4$)alkyl, —SO$_2$NH$_2$, —SO$_2$NH(C$_1$-C$_4$)alkyl, and —SO$_2$N((C$_1$-C$_4$)alkyl)((C$_1$-C$_4$)alkyl);

or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from (C$_1$-C$_4$)alkyl, (C$_1$-C$_4$)haloalkyl, amino, (C$_1$-C$_4$)alkylamino, ((C$_1$-C$_4$)alkyl)((C$_1$-C$_4$)alkyl)amino, hydroxyl, oxo, (C$_1$-C$_4$)alkoxy, and (C$_1$-C$_4$)alkoxy(C$_1$-C$_4$)alkyl, wherein said ring is optionally fused to a (C$_3$-C$_8$)cycloalkyl, heterocycloalkyl, aryl, or heteroaryl ring;

or R$^a$ and R$^b$ taken together with the nitrogen to which they are attached represent a 6- to 10-membered bridged bicyclic ring system optionally fused to a (C$_3$-C$_8$)cycloalkyl, heterocycloalkyl, aryl, or heteroaryl ring. Aryl and heteroaryl in this definition are selected from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine as or a compound of or another aryl or heteroaryl group as follows:

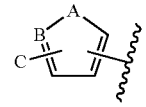

wherein in (1),

A is O, NH, or S; B is CH or N, and C is hydrogen or C$_1$-C$_8$ alkyl; or

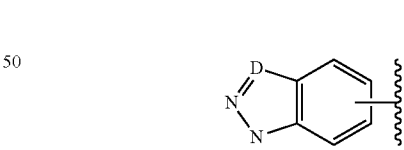

wherein in (2),

D is N or C optionally substituted by hydrogen or C$_1$-C$_8$ alkyl; or

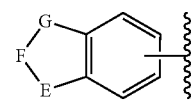

wherein in (3),

E is NH or CH$_2$; F is O or CO; and G is NH or CH$_2$; or

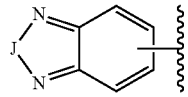
(4)

wherein in (4),
J is O, S or CO; or

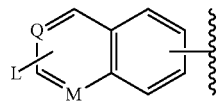
(5)

wherein in (5),
Q is CH or N;
M is CH or N; and
L/(5) is hydrogen, halo, amino, cyano, (C$_1$-C$_8$)alkyl, (C$_3$-C$_8$)cycloalkyl, —COR$^a$, —CO$_2$R$^a$, —CONR$^a$R$^b$, —CONR$^a$NR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, —OR$^a$,
wherein any (C$_1$-C$_8$)alkyl, (C$_3$-C$_8$)cycloalkyl, group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR'SO$_2$NR$^a$R$^b$, —OR$^a$, —OC(O)R$^a$, —OC(O)NR$^a$R$^b$,
wherein R$^a$ and R$^b$ are defined as above; or

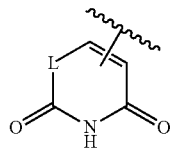
(6)

wherein in 6,
L/(6) is NH or CH$_2$; or

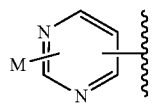
(7)

wherein in 7,
M/(7) is hydrogen, halo, amino, cyano, (C$_1$-C$_8$)alkyl, (C$_3$-C$_8$)cycloalkyl, heterocycloalkyl, —COR$^a$, —CO$_2$R$^a$, —CONR$^a$R$^b$, —CONR$^a$NR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, —OR$^a$,
wherein any (C$_1$-C$_8$)alkyl, (C$_3$-C$_8$)cycloalkyl, heterocycloalkyl group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOW, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$; wherein R$^a$ and R$^b$ are defined as above; or

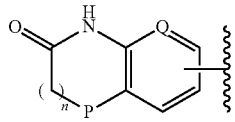
(8)

wherein in (8),
P is CH$_2$, NH, O, or S; Q/(8) is CH or N; and n is 0-2; or

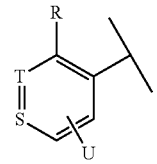
(9)

wherein in (9),
S/(9) and T(9) is C, or S/(9) is C and T(9) is N, or S/(9) is N and T/(9) is C;
R is hydrogen, amino, methyl, trifluoromethyl, halo;
U is hydrogen, halo, amino, cyano, nitro, trifluoromethyl, (C$_1$-C$_8$)alkyl, (C$_3$-C$_8$)cycloalkyl, —COR$^a$, —CO$_2$R$^a$, —CONR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —OR$^a$, 4-(1H-pyrazo-4-yl),
wherein any (C$_1$-C$_8$)alkyl, (C$_3$-C$_8$)cycloalkyl, group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$, wherein R$^a$ and R$^b$ are defined as above.

Subgroup C
X is methyl, ethyl, n-propyl, isopropyl, cyclopropyl, cyclobutyl, cyclopentyl, cyclohexyl, phenyl, trifluoromethyl, tetrahydropyran, hydroxymethyl, methoxymethyl, or benzyl;
Y is H;
Z is methyl, ethyl, n-propyl, isopropyl, trifluoromethyl, or benzyl;
R$^1$ is isopropyl, tert-butyl, cyclobutyl, cyclopentyl, cyclohexyl, (1-methylethyl)cyclopropyl, 1,1-dioxo-tetrahydrothiophene-3-yl, 1-Me-piperidin-4-yl, tetrahydrofuran-3-yl, tetrahydropyran-4-yl, N,N-dimethyl-1-propanaminyl, benzyl, or 4-pyridyl;
R$_2$ is hydrogen, (C$_1$-C$_3$)alkyl, or halo, in which said (C$_1$-C$_3$)alkyl maybe substituted with one to two groups selected from amino, and (C$_1$-C$_3$)alkylamino;
R$^7$ is hydrogen, (C$_1$-C$_3$)alkyl, or alkoxy; R$^3$ is H, methyl, or Br; and
R$^6$ is methyl, bis(1,1-dimethylethyl), bis(1-methylethyl), cyclopropyl, propyl, dimethylamino, ethylamino, (2-hydroxyethyl)amino, 2-propen-1-ylamino, 1-piperazinyl, 1-piperidinyl, 4-morpholinyl, 4-piperidinylamino, tetrahydro-2H-pyran-4-ylamino, phenylamino, (phenylmethyl)amino, (4-pyridinylmethyl)amino, [2-(2-pyridinylamino)ethyl]

amino, 2-(dimethylamino)ethyl]amino, 4-pyridinylamino, 4-(aminocarbonyl)phenyl]amino, 3-hydroxy-3-methyl-1-butyn-1-yl, 4-pyridinylethynyl, phenylethynyl, 2-furanyl, 3-thienyl; 1H-pyrazol-4-yl, 1H-indazol-5-yl, 1H-indazol-6-yl, 3-methyl-1H-indazol-5-yl, 1H-1,2,3-benzotriazol-5-yl, 2-oxo-2,3-dihydro-1H-benzimidazol-5-yl, 2-oxo-2,3-dihydro-1H-indol-5-yl, 2-oxo-2,3-dihydro-1H-indol-6-yl, 2,1,3-benzoxadiazol-5-yl, 2-amino-6-quinazolinyl, 2,4-dioxo-1,2,3,4-tetrahydro-5-pyrimidinyl, 2-amino-5-pyrimidinyl, 7-oxo-1,5,6,7-tetrahydro-1,8-naphthyridin-3-yl, phenyl, 2-methylphenyl, 2-nitrophenyl, 2-phenylethyl, 3-aminophenyl, 4-aminophenyl, 4-chlorophenyl, 4-fluorophenyl, 4-(methyloxy)phenyl, 3-(acetylamino)phenyl, 4-(acetylamino)phenyl, 4-(aminocarbonyl)phenyl, 4-(1H-pyrazol-4-yl)phenyl, 4-(aminosulfonyl)phenyl, 4-(methylsulfonyl)phenyl, 4-[(dimethylamino)sulfonyl]phenyl, 4-[(methylamino)carbonyl]phenyl, 4-[(methylamino)sulfonyl]phenyl, 4-[(methylsulfonyl)amino]phenyl, 3-pyridinyl, 4-pyridinyl, 2-(4-morpholinyl)-4-pyridinyl, 2-amino-4-pyridinyl, 5-(methyloxy)-3-pyridinyl, 5-(methylsulfonyl)-3-pyridinyl, 5-[(cyclopropylsulfonyl)amino]-6-(methyloxy)-3-pyridinyl, 5-[(phenylsulfonyl)amino]-3-pyridinyl, 6-(4-methyl-1-piperazinyl)-3-pyridinyl, 6-(4-morpholinyl)-3-pyridinyl, 6-(acetylamino)-3-pyridinyl, 6-(dimethylamino)-3-pyridinyl, 6-(methyloxy)-3-pyridinyl, 6-[(methylamino)carbonyl]-3-pyridinyl, 6-[(methylamino)sulfonyl]-3-pyridinyl, 6-methyl-3-pyridinyl, 4-pyridinyloxy.

Individual compounds can be found in the Examples set out below.

By the term "co-administering" and derivatives thereof as used herein is meant either simultaneous administration or any manner of separate sequential administration of one or more additional pharmaceutically active compounds, whether for treating cancer, the side effects of cancer or cancer therapy, or some other disease. Preferably, if the administration is not simultaneous, the compounds are administered in a close time proximity to each other. Furthermore, it does not matter if the compounds are administered in the same dosage form, e.g. one compound may be administered topically and another compound may be administered orally.

In certain embodiments, compounds according to Formula I may contain an acidic functional group, one acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate) and napthalene-2-sulfonate.

All tautomeric forms of the compounds described herein, including mixtures thereof, are intended to be encompassed within the scope of the invention. Generally, the compounds exemplified herein have been assigned names based on the structure of the tautomer of formaula (IA). It should be understood that any reference to named compounds of this invention is intended to encompass all tautomers of the named compounds and any mixtures of tautomers of the named compounds.

The compounds of formula (I) may be prepared in crystalline or non-crystalline form, and, if crystalline, may optionally be solvated, e.g. as the hydrate. This invention includes within its scope stoichiometric solvates (e.g. hydrates) as well as compounds containing variable amounts of solvent (e.g. water).

Certain of the compounds described herein may contain one or more chiral atoms, or may otherwise be capable of existing as two enantiomers. The compounds claimed below include mixtures of enantiomers as well as purified enantiomers or enantiomerically enriched mixtures. Also included within the scope of the invention are the individual isomers of the compounds represented by formula (I), or claimed below, as well as any wholly or partially equilibrated mixtures thereof. The present invention also covers the individual isomers of the claimed compounds as mixtures with isomers thereof in which one or more chiral centers are inverted.

Where there are different isomeric forms they may be separated or resolved one from the other by conventional methods, or any given isomer may be obtained by conventional synthetic methods or by stereospecific or asymmetric syntheses.

While it is possible that, for use in therapy, a compound of formula (I), as well as salts, solvates and the like, may be administered as a neat preparation, i.e. no additional carrier, the more usual practice is to present the active ingredient confected with a carrier or diluent. Accordingly, the invention further provides pharmaceutical compositions, which includes a compound of formula (I) and salts, solvates and the like, and one or more pharmaceutically acceptable carriers, diluents, or excipients. The compounds of formula (I) and salts, solvates, etc, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates etc, with one or more pharmaceutically acceptable carriers, diluents or excipients.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. It will further be appreciated by those skilled in the art, that certain moieties, known to those skilled in the art as "pro-moieties" may be placed on appropriate functionalities when such functionalities are present within compounds of the invention. Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Treatments

The compounds and compositions of the invention are used to treat cellular proliferation diseases. Disease states which can be treated by the methods and compositions provided herein include, but are not limited to, cancer (further discussed below), autoimmune disease, fungal disorders, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still requires treatment. For example, during wound healing, the cells may be proliferating "normally", but proliferation enhancement may be desired. Thus, in one embodiment, the invention herein includes application to cells or individuals afflicted or impending affliction with any one of these disorders or states.

The compositions and methods provided herein are particularly deemed useful for the treatment of cancer including tumors such as prostate, breast, brain, skin, cervical carcinomas, testicular carcinomas, etc. They are particularly useful in treating metastatic or malignant tumors. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one or related of the above identified conditions.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent. In yet another embodiment, the invention comprises a therapeutic regimen where the EZH2 inhibitors of this disclosure are not in and of themselves active or significantly active, but when combined with another therapy, which may or may not be active as a standalone therapy, the combination provides a useful therapeutic outcome.

By the term "co-administering" and derivatives thereof as used herein is meant either simultaneous administration or any manner of separate sequential administration of an EZH2 inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of specified cancers in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; DNA methyltransferase inhibitors such as azacitidine and decitabine; signal transduction pathway inhibitors; non-receptor tyrosine kinase angiogenesis inhibitors; immunotherapeutic agents; proapoptotic agents; and cell cycle signaling inhibitors.

Typically, any chemotherapeutic agent that has activity against a susceptible neoplasm being treated may be utilized in combination with the compounds the invention, provided that the particular agent is clinically compatible with therapy employing a compound of the invention. Typical anti-neoplastic agents useful in the present invention include, but are not limited to: alkylating agents, anti-metabolites, antitumor antibiotics, antimitotic agents, nucleoside analogues, topoisomerase I and II inhibitors, hormones and hormonal analogues; retinoids, histone deacetylase inhibitors; signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Nucleoside analogues are those compounds which are converted to deoxynucleotide triphosphates and incorporated into replicating DNA in place of cytosine. DNA methyltransferases become covalently bound to the modified bases resulting in an inactive enzyme and reduced DNA methylation. Examples of nucleoside analogues include azacitidine and decitabine which are used for the treatment of myelodysplastic disorder. Histone deacetylase (HDAC) inhibitors include vorinostat, for the treatment of cutaneous T-cell lymphoma. HDACs modify chromatin through the deactylation of histones. In addition, they have a variety of substrates including numerous transcription factors and signaling molecules. Other HDAC inhibitors are in development.

Signal transduction pathway inhibitors are those inhibitors which block or inhibit a chemical process which evokes an intracellular change. As used herein this change is cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha$_v$ beta$_3$) that inhibit angiogenesis; endostatin and angiostatin (non-RTK) may also prove useful in combination with the compounds of the invention. One example of a VEGFR antibody is bevacizumab (AVASTIN®).

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C225). Bevacizumab (Avastin®) is an example of a monoclonal antibody directed against VEGFR. Examples of small molecule inhibitors of epidermal growth factor receptors include but are not limited to lapatinib (Tykerb™) and erlotinib (TARCEVA®). Imatinib mesylate (GLEEVEC®) is one example of a PDGFR inhibitor. Examples of VEGFR inhibitors include pazopanib, ZD6474, AZD2171, PTK787, sunitinib and sorafenib.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G$_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxels capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavouring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of formula (I) for the treatment of anemia will generally be in the range of 0.001 to 100 mg/kg body weight of recipient per day, suitably in the range of 0.01 to 10 mg/kg body weight per day. For a 70 kg adult mammal, the actual amount per day would suitably be from 7 to 700 mg and this amount may be given in a single dose per day or in a number (such as two, three, four, five or six) of sub-doses per day such that the total daily dose is the same. An effective amount of a salt or solvate, etc., may be determined as a proportion of the effective amount of the compound of formula (I) per se. It is envisaged that similar dosages would be appropriate for treatment of the other conditions referred to above.

Chemical Background

The present compounds are automatically named by computer software, eg. ISISdraw, ChemDraw, or eLNB. A person skilled in the art understands that there might be slight differences in the chemical names generated by different software. The compounds of this invention may be made by a variety of methods, including standard chemistry. Any previously defined variable will continue to have the previously defined meaning unless otherwise indicated. Illustrative general synthetic methods are set out below and then specific compounds of the invention as prepared are given in the examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula (I). Those skilled in the art will recognize if a stereocenter exists in compounds of formula (I). Accordingly, the present invention includes both possible stereoisomers and includes not only racemic compounds but the individual enantiomers as well. Also included in the present invention are fully or partially deuterated forms of the present compounds. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

EXAMPLES

General Experimental Methods

The following abbreviations are used throughout the experimental and have the following meaning:
aq aqueous
BINAP 2,2'-bis(diphenylphosphino)-1,1'-binapthyl
ca. circa
$CDCl_3$-d chloroform-d
$CD_3OD$-$d_4$ methanol-$d_4$
$Cs_2CO_3$ cesium carbonate
$CHCl_3$ chloroform
ACN acetonitrile
$CH_3CN$ acetonitrile
Celite® registered trademark of Celite Corp. brand of diatomaceous earth
DBU 1,8-diazabicyclo[5.4.0]undeca-7-ene
DCE dichloroethane
DCM methylene chloride
DME 1,2 dimethoxyethane
DMF N,N-dimethylformamide
DIEA diisopropyl ethylamine
DMSO-$d_6$ dimethylsulfoxide-$d_6$
EtOAc ethyl acetate
EDC 1-(3-dimethylaminopropyl)-3-ethylcarbodimmide hydrochloride
h hour(s)
$^1$H NMR proton nuclear magnetic resonance
HCl hydrochloric acid
HOAT 1-hydroxy-7-azabenzotriazole
HPLC high performance liquid chromatography
IPA 2-propanol
$K_2CO_3$ potassium carbonate
KOH potassium hydroxide
LC/MS liquid chromatography/mass spectroscopy
$MgSO_4$ magnesium sulfate
MeOH methanol
min minute(s)
MTBE methyl tert-butyl ether
MS mass spectrometry
NaOH sodium hydroxide
$Na_2SO_4$ sodium sulfate
$NH_4OH$ ammonium hydroxide
NMM 4-methylmorpholine
NMP N-Methyl-2-pyrrolidone
Pd/C Palladium (10% by wt) on carbon
$PdCl_2$(dppf)-$CH_2Cl_2$ 1,1'-Bis(diphenylphosphino)ferrocene-palladium(II)dichloride dichloromethane complex
Pd($Ph_3P$)$_4$ tetrakis(triphenylphosphine)palladium(0)
$SOCl_2$ thionyl chloride SPhos 2-Dicyclohexylphosphino-2',6'-dimethoxybiphenyl
TFA trifluoroacetic acd
THF tetrahydrofuran
TLC thin layer chromatography The following guidelines apply to all experimental procedures described herein. All reactions were conducted under a positive pressure of nitrogen using oven-dried glassware, unless otherwise indicated. Temperatures designated are external (i.e. bath temperatures), and are approximate. Air and moisture-sensitive liquids were transferred via syringe. Reagents were used as received. Solvents utilized were those listed as "anhydrous" by vendors. Molarities listed for reagents in solutions are approximate, and were used without prior titration against a corresponding standard. All reactions were agitated by stir bar, unless otherwise indicated. Heating was conducted using heating baths containing silicon oil, unless otherwise indicated. Reactions conducted by microwave irradiation (0-400 W at 2.45 GHz) were done so using a Biotage Initiator™ 2.0 instrument with Biotage microwave EXP vials (0.2-20 mL) and septa and caps. Irradiation levels utilized (i.e. high, normal, low) based on solvent and ionic charge were based on vendor specifications. Cooling to temperatures below −70° C. was conducted using dry ice/acetone or dry ice/2-propanol. Magnesium sulfate and sodium sulfate used as drying agents were of anhydrous grade, and were used interchangeably. Solvents described as being removed "in vacuo" or "under reduced pressure" were done so by rotary evaporation.

Preparative normal phase silica gel chromatography was carried out using either a Teledyne ISCO CombiFlash Companion instrument with RediSep or ISCO Gold silica gel cartridges (4 g-330 g), or an Analogix IF280 instrument with SF25 silica gel cartridges (4 g-3-00 g), or a Biotage SP1 instrument with HP silica gel cartridges (10 g-100 g). Purification by reverse phase HPLC was conducted using a YMC-pack column (ODS-A 75×30 mm) as solid phase, unless otherwise noted. A mobile phase of 25 mL/min A (acetonitrile-0.1% TFA): B (water-0.1% TFA), 10-80% gradient A (10 min) was utilized with UV detection at 214 nM, unless otherwise noted.

A PE Sciex API 150 single quadrupole mass spectrometer (PE Sciex, Thornhill, Ontario, Canada) was operated using electrospray ionization in the positive ion detection mode. The nebulizing gas was generated from a zero air generator (Balston Inc., Haverhill, Mass., USA) and delivered at 65 psi and the curtain gas was high purity nitrogen delivered from a Dewar liquid nitrogen vessel at 50 psi. The voltage applied to the electrospray needle was 4.8 kV. The orifice was set at 25 V and mass spectrometer was scanned at a rate of 0.5 scan/sec using a step mass of 0.2 amu and collecting profile data.

Method A LCMS. Samples were introduced into the mass spectrometer using a CTC PAL autosampler (LEAP Technologies, Carrboro, N.C.) equipped with a hamilton 10 uL syringe which performed the injection into a Valco 10-port injection valve. The HPLC pump was a Shimadzu LC-10ADvp (Shimadzu Scientific Instruments, Columbia, Md.) operated at 0.3 mL/min and a linear gradient 4.5% A to 90% B in 3.2 min. with a 0.4 min. hold. The mobile phase was composed of 100% ($H_2O$ 0.02% TFA) in vessel A and 100% ($CH_3CN$ 0.018% TFA) in vessel B. The stationary phase is Aquasil (C18) and the column dimensions were 1 mm×40 mm. Detection was by UV at 214 nm, evaporative light-scattering (ELSD) and MS.

Method B, LCMS. Alternatively, an Agilent 1100 analytical HPLC system with an LC/MS was used and operated at 1 mL/min and a linear gradient 5% A to 100% B in 2.2 min with a 0.4 min hold. The mobile phase was composed of 100% ($H_2O$ 0.02% TFA) in vessel A and 100% ($CH_3CN$ 0.018% TFA) in vessel B. The stationary phase was Zobax (C8) with a 3.5 um partical size and the column dimensions were 2.1 mm×50 mm. Detection was by UV at 214 nm, evaporative light-scattering (ELSD) and MS.

Method C, LCMS. Alternatively, an MDSSCIEX API 2000 equipped with a capillary column of (50×4.6 mm, 5 µm) was used. HPLC was done on Agilent-1200 series UPLC system equipped with column Zorbax SB-C18 (50×4.6 mm, 1.8 µm) eluting with $CH_3CN$: ammonium acetate buffer. The reactions were performed in the microwave (CEM, Discover).

$^1$H-NMR spectra were recorded at 400 MHz using a Bruker AVANCE 400 MHz instrument, with ACD Spect manager v. 10 used for reprocessing. Multiplicities indicated are: s=singlet, d=doublet, t=triplet, q=quartet, quint=quintet, sxt=sextet, m=multiplet, dd=doublet of doublets, dt=doublet of triplets etc. and br indicates a broad signal. All NMRs in DMSO unless otherwise noted.

Analytical HPLC: Products were analyzed by Agilent 1100 Analytical Chromatography system, with 4.5×75 mm Zorbax XDB-C18 column (3.5 um) at 2 mL/min with a 4 min gradient from 5% $CH_3CN$ (0.1% formic acid) to 95% $CH_3CN$ (0.1% formic acid) in $H_2O$ (0.1% formic acid) and a 1 min hold.

The compounds of formula (I) can be made according to Scheme 1 or by analogous methods. Methyl 6-bromo-1H-indole-4-carboxylate (I) is alkylated with an alkyl halide in the presence of base (e.g. sodium hydride) or with an alcohol in the presence of (cyanomethyl)trimethylphosphonium chloride and base (e.g. sodium hydride) to give compounds of Formula II. Saponification of the ester with aqueous base provides compounds of Formula III, which are coupled to various aminomethylpyridones IV utilizing standard peptide coupling reagents (e.g. EDC, HOAT, NMM) to furnish compounds of Formula V. Palladium-mediated cross-coupling of various boronic acids (or boronates) with V provides compounds of Formula VI.

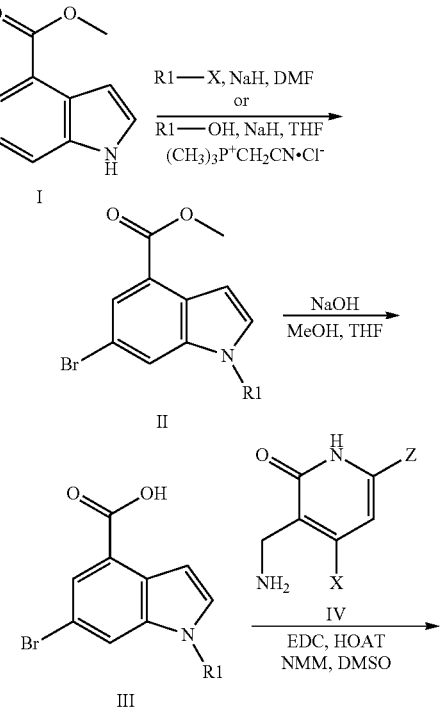

Scheme 1

-continued

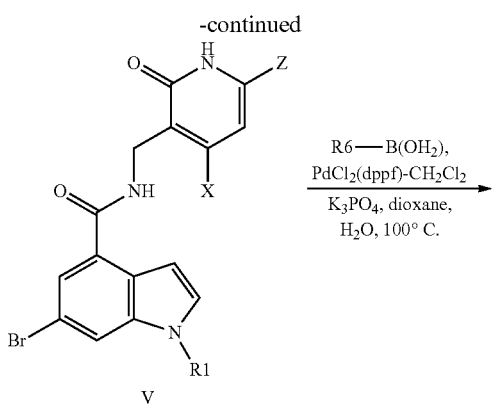

Example 1

6-Bromo-N-[(4,6-dimethyl-2-oxo-1,2-dihydro-3-pyridinyl)methyl]-1-(1-methylethyl)-1H-indole-4-carboxamide

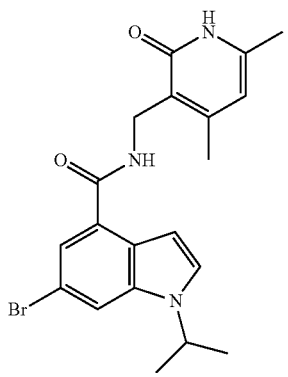 [SMILES: Cc1cc(C)c(CNC(=O)c2cc(Br)cc3c2ccn3C(C)C)c(=O)[nH]1]

The following examples are for illustrative purposes only and are not intended to limit the scope of the present invention. The compounds were named using ACD Name software [Advanced Chemistry Development, Inc., (ACD/Labs), Toronto, Canada. (http://www.acdlabs.com/products/name_lab/)].

1a) Methyl 6-bromo-1-(1-methylethyl)-1H-indole-4-carboxylate

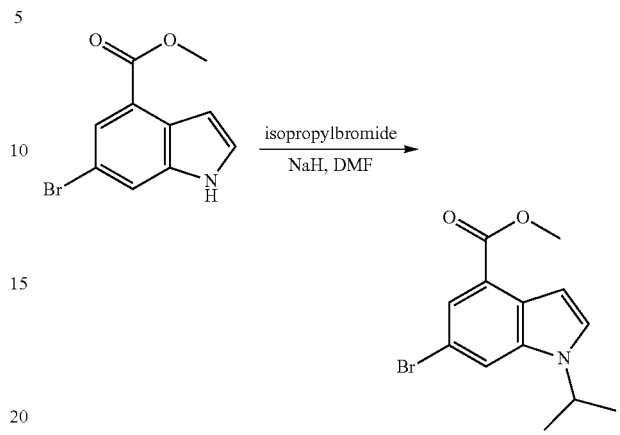

To a cooled (0° C.) solution of methyl 6-bromo-1H-indole-4-carboxylate (1.0 g, 3.94 mmol) solid in N,N-dimethylformamide (25 mL) was added sodium hydride (0.173 g, 4.33 mmol). The reaction was stirred for 15 min, at which time 2-bromopropane (0.554 mL, 5.90 mmol) was added. The reaction was then allowed to warm to RT and was maintained overnight. LCMS showed about 25% starting material remaining. The reaction was heated at 45° C. for 4 h, but no further conversion was noted. The reaction vessel was put back into an ice bath and stirred for 15 min. Then excess NaH (60%) was added, stirred for 10 min, and then 2-bromopropane (excess) was added. The ice bath was removed and the reaction stirred for 1 h. Approximately half of the reaction volume was removed in vacuo and poured into saturated $NH_4Cl$ (200 mL). This was extracted with ether (2×) and the combined organics were washed with brine, dried ($MgSO_4$), and concentrated. Purification by column chromatography (80 g Isco silica column; Gradient B: 5-25%, A: hexane, B: ethyl acetate) gave methyl 6-bromo-1-(1-methylethyl)-1H-indole-4-carboxylate (0.53 g, 1.718 mmol, 43.7% yield).

1b) 6-Bromo-1-(1-methylethyl)-1H-indole-4-carboxylic acid

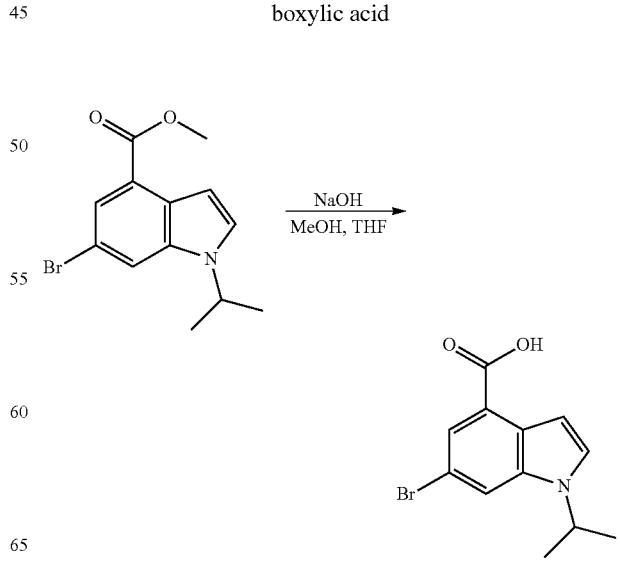

To a solution of methyl 6-bromo-1-(1-methylethyl)-1H-indole-4-carboxylate (0.52 g, 1.756 mmol) in methanol (15 mL) and tetrahydrofuran (3 mL) was added 3 M NaOH (1.756 mL, 5.27 mmol) via syringe drop wise (over 2 min). The solution was maintained at RT for 2 h, at which time LCMS showed only 12% conversion to product. Then 1.5 mL 3 M NaOH was added and the solution was maintained at RT overnight. LCMS showed complete conversion to product. Removed volatiles in vacuo and dissolved the residue in water and slowly acidified with 1 M HCl (solids precipitated). Extracted with EtOAc (2×), combined organics and dried over MgSO$_4$. Filtered and concentrated in vacuo to give 6-bromo-1-(1-methylethyl)-1H-indole-4-carboxylic acid (0.50 g, 1.737 mmol, 99% yield) as a white solid.

1c) 6-Bromo-N-[(4,6-dimethyl-2-oxo-1,2-dihydro-3-pyridinyl)methyl]-1-(1-methylethyl)-1H-indole-4-carboxamide

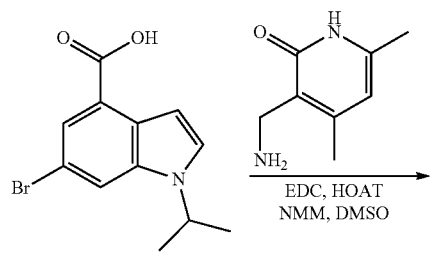

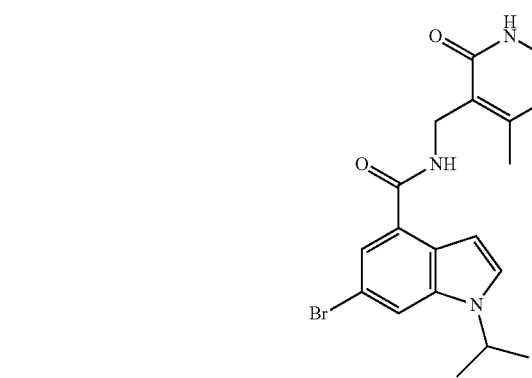

To a mixture of 6-bromo-1-(1-methylethyl)-1H-indole-4-carboxylic acid (0.71 g, 2.52 mmol), 3-(aminomethyl)-4,6-dimethyl-2(1H)-pyridinone (0.575 g, 3.77 mmol), 1-hydroxy-7-azabenzotriazole (0.514 g, 3.77 mmol), and EDC (0.724 g, 3.77 mmol) in dimethylsulfoxide (20 mL) was added quickly N-methylmorpholine (1.107 mL, 10.07 mmol) via syringe. The solids slowly dissolved and the reaction was maintained at RT overnight. The reaction was slowly poured into ice-water (300 mL), stirred for 10 min, then allowed to sit for 10 min. The solids were filtered and washed with water (100 mL), airdried for 15 min, then dried in vacuum oven at 45° C. for 4 h to give 6-bromo-N-[(4,6-dimethyl-2-oxo-1,2-dihydro-3-pyridinyl)methyl]-1-(1-methylethyl)-1H-indole-4-carboxamide (0.82 g, 1.871 mmol, 74.4% yield). $^1$H NMR (400 MHz, DMSO-d$_6$) δ ppm 1.39-1.46 (m, 6H) 2.09-2.15 (m, 3H) 2.21 (s, 3H) 4.32 (d, J=5.05 Hz, 2H) 4.82 (quin, J=6.63 Hz, 1H) 5.88 (s, 1H) 6.86 (d, J=3.28 Hz, 1H) 7.51 (d, J=1.77 Hz, 1H) 7.62 (d, J=3.28 Hz, 1H) 7.92 (s, 1H) 8.31 (t, J=4.93 Hz, 1H) 11.55 (br. s., 1H). MS (ES) [M+H]$^+$ 416.0.

Example 2

N-[(4,6-Dimethyl-2-oxo-1,2-dihydro-3-pyridinyl)methyl]-1-(1-methylethyl)-6-[6-(4-methyl-1-piperazinyl)-3-pyridinyl]-1H-indole-4-carboxamide

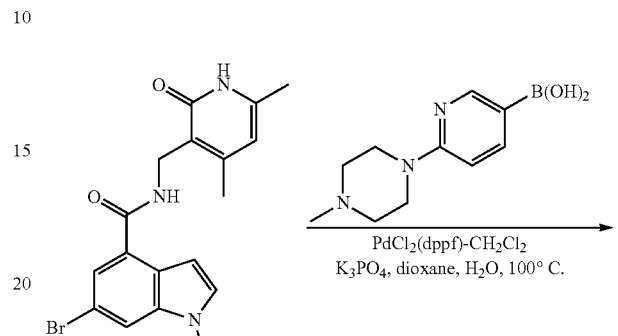

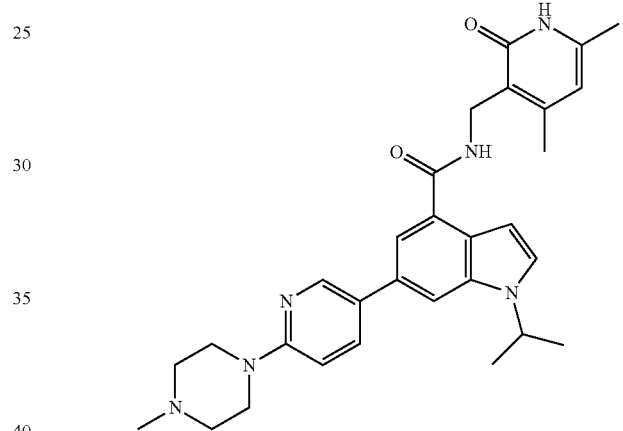

A mixture of 6-bromo-N-[(4,6-dimethyl-2-oxo-1,2-dihydro-3-pyridinyl)methyl]-1-(1-methylethyl)-1H-indole-4-carboxamide (0.10 g, 0.240 mmol), 1-methyl-4-[5-(4,4,5,5-tetramethyl-1,3,2-dioxaborolan-2-yl)-2-pyridinyl]piperazine (0.087 g, 0.288 mmol) and potassium phosphate (tribasic) (0.153 g, 0.721 mmol) in 1,4-dioxane (2 mL) and water (0.5 mL) was degassed with N$_2$ for 10 min, at which time PdCl$_2$(dppf)-CH$_2$Cl$_2$ (0.029 g, 0.036 mmol) was added. The reaction was sealed and heated at 100° C. for 2 h. The reaction was then allowed to cool to RT and sat overnight, at which time it was diluted with EtOAc, filtered through Celite, washed with EtOAc, and concentrated in vacuo. Purification of the residue by column chromatography (12 g Isco GOLD silica column; Gradient B: 5-90%; A: dichloromethane, B: 10% chloroform containing 2 M ammonia in methanol) gave N-[(4,6-dimethyl-2-oxo-1,2-dihydro-3-pyridinyl)methyl]-1-(1-methylethyl)-6-[6-(4-methyl-1-piperazinyl)-3-pyridinyl]-1H-indole-4-carboxamide (94 mg, 0.180 mmol, 74.8% yield). $^1$H NMR (400 MHz, DMSO-d$_6$) δ ppm 1.46 (d, J=6.57 Hz, 6H) 2.12 (s, 3H) 2.17-2.28 (m, 6H) 2.38-2.46 (m, 4H) 3.49-3.57 (m, 4H) 4.37 (d, J=5.05 Hz, 2H) 4.86-4.98 (m, 1H) 5.88 (s, 1H) 6.87 (d, J=3.03 Hz, 1H) 6.93 (d, J=8.84 Hz, 1H) 7.58 (d, J=3.28 Hz, 1H) 7.65 (d, J=1.26 Hz, 1H) 7.87 (s, 1H) 7.98 (dd, J=8.97, 2.65 Hz, 1H) 8.28 (t, J=5.05 Hz, 1H) 8.57 (d, J=2.27 Hz, 1H) 11.55 (s, 1H). MS (ES) [M+H]$^+$ 513.3.

Examples 3-xx were prepared by the methods described above for Examples 1 and 2 or routine variations thereof, starting from the requisite 4-aminomethylpyridones and 6-substituuted-4-indolecarboxylates. Routine variations include, but are not limited to, reversing the bromide and boronate coupling partners for the Suzuki type couplings or using a one pot procedure in which the boroate is formed in situ.

| Ex | Structure | Name | $^1$H NMR (400 MHz, DMSO-$d_6$) δ ppm | MS (ES) [M + H]$^+$ |
|---|---|---|---|---|
| 3 | 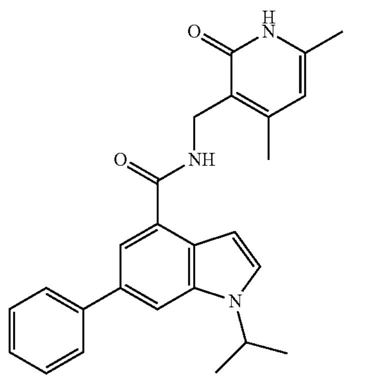 [SMILES: Cc1cc(C)c(CNC(=O)c2cc(-c3ccccc3)cc3c2ccn3C(C)C)c(=O)[nH]1] | N-[(4,6-Dimethyl-2-oxo-1,2-dihydro-3-pyridinyl)methyl]-1-(1-methylethyl)-6-phenyl-1H-indole-4-carboxamide | 1.45-1.51 (m, 6 H) 2.12 (s, 3 H) 2.23 (s, 3 H) 4.37 (d, J = 5.05 Hz, 2 H) 4.89-5.02 (m, 1 H) 5.88 (s, 1 H) 6.88 (d, J = 3.28 Hz, 1 H) 7.30-7.37 (m, 1 H) 7.47 (t, J = 7.71 Hz, 2 H) 7.62 (d, J = 3.28 Hz, 1 H) 7.71 (d, J = 1.52 Hz, 1 H) 7.76-7.84 (m, 2 H) 7.92 (s, 1 H) 8.32 (t, J = 5.05 Hz, 1 H) 11.55 (s, 1 H) | 414.1 |
| 4 | 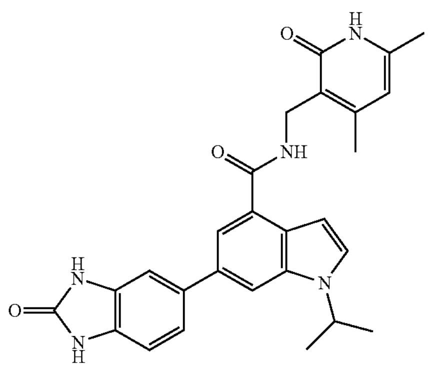 [SMILES: Cc1cc(C)c(CNC(=O)c2cc(-c3ccc4[nH]c(=O)[nH]c4c3)cc3c2ccn3C(C)C)c(=O)[nH]1] | N-[(4,6-Dimethyl-2-oxo-1,2-dihydro-3-pyridinyl)methyl]-1-(1-methylethyl)-6-(2-oxo-2,3-dihydro-1H-benzimidazol-5-yl)-1H-indole-4-carboxamide | 1.47 (d, J = 6.57 Hz, 6 H) 2.12 (s, 3 H) 2.23 (s, 3 H) 4.38 (d, J = 5.05 Hz, 2 H) 4.86-5.01 (m, 1 H) 5.89 (s, 1 H) 6.86 (d, J = 3.03 Hz, 1 H) 7.00 (d, J = 8.08 Hz, 1 H) 7.30 (s, 1 H) 7.36 (dd, J = 8.08, 1.77 Hz, 1 H) 7.59 (d, J = 3.28 Hz, 1 H) 7.65 (d, J = 1.26 Hz, 1 H) 7.83 (s, 1 H) 8.30 (t, J = 5.18 Hz, 1 H) 10.70 (s, 1 H) 10.66 (s, 1 H) 11.55 (s, 1 H) | 469.2 |
| 5 | 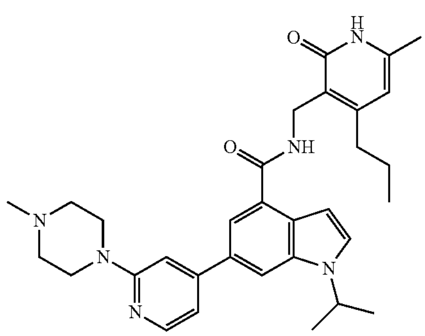 | 1-(1-methylethyl)-N-[(6-methyl-2-oxo-4-propyl-1,2-dihydro-3-pyridinyl)methyl]-6-[2-(4-methyl-1-piperazinyl)-4-pyridinyl]-1H-indole-4-carboxamide | 0.91 (t, J = 7.33 Hz, 3 H) 1.48 (d, J = 6.57 Hz, 6 H) 1.51-1.59 (m, 2 H) 2.13 (s, 3 H) 2.23 (s, 3 H) 2.43 (t, J = 4.93 Hz, 4 H) 2.52-2.59 (m, 2 H) 3.50-3.65 (m, 4 H) 4.41 (d, J = 5.05 Hz, 2 H) 4.91-5.09 (m, 1 H) 5.91 (s, 1 H) 6.89 (d, J = 3.03 Hz, 1 H) 7.05-7.21 (m, 2 H) 7.66-7.78 (m, 2 H) 8.05 (s, 1 H) 8.16 (d, J = 5.31 Hz, 1 H) 8.32 (t, J = 5.05 Hz, 1 H) 11.56 (s, 1 H) | 541.3 |
| 6 | 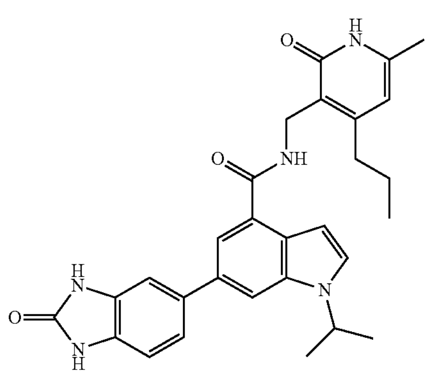 [SMILES: CCCc1cc(C)[nH]c(=O)c1CNC(=O)c1cc(-c2ccc3[nH]c(=O)[nH]c3c2)cc2c1ccn2C(C)C] | 1-(1-Methylethyl)-N-[(6-methyl-2-oxo-4-propyl-1,2-dihydro-3-pyridinyl)methyl]-6-(2-oxo-2,3-dihydro-1H-benzimidazol-5-yl)-1H-indole-4-carboxamide | 0.91 (t, J = 7.33 Hz, 3 H) 1.47 (d, J = 6.57 Hz, 6 H) 1.50-1.60 (m, 2 H) 2.13 (s, 3 H) 2.55 (d, J = 7.07 Hz, 2 H) 4.41 (d, J = 5.05 Hz, 2 H) 4.94 (quin, J = 6.63 Hz, 1 H) 5.91 (s, 1 H) 6.85 (d, J = 3.28 Hz, 1 H) 7.00 (d, J = 7.83 Hz, 1 H) 7.29 (s, 1 H) 7.35 (dd, J = 8.08, 1.77 Hz, 1 H) 7.57-7.69 (m, 2 H) 7.83 (s, 1 H) 8.30 (t, J = 5.05 Hz, 1 H) 10.70 (s, 1 H) 10.66 (s, 1 H) 11.56 (s, 1 H) | 498.3 |

-continued

| Ex | Structure | Name | ¹H NMR (400 MHz, DMSO-d₆) δ ppm | MS (ES) [M + H]⁺ |
|---|---|---|---|---|
| 7 | 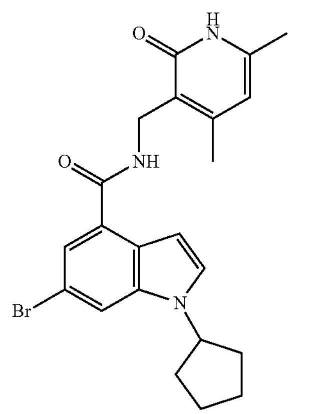 [SMILES: Cc1cc(C)c(CNC(=O)c2cc(Br)cc3c2ccn3C2CCCC2)c(=O)[nH]1] | 6-Bromo-1-cyclopentyl-N-[(4,6-dimethyl-2-oxo-1,2-dihydro-3-pyridinyl)methyl]-1H-indole-4-carboxamide | 1.64-1.87 (m, 6 H) 2.08-2.18 (m, 5 H) 2.21 (s, 3 H) 4.32 (d, J = 5.05 Hz, 2 H) 4.86-5.02 (m, 1 H) 5.88 (s, 1 H) 6.86 (d, J = 3.03 Hz, 1 H) 7.52 (d, J = 1.77 Hz, 1 H) 7.58 (d, J = 3.28 Hz, 1 H) 7.92 (s, 1 H) 8.24-8.38 (m, 1 H) 11.54 (s, 1 H) | 442.0, 444.2 |
| 8 | 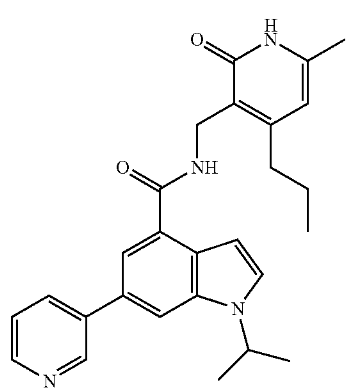 [SMILES: CCCc1cc(C)[nH]c(=O)c1CNC(=O)c1cc(-c2cccnc2)cc2c1ccn2C(C)C] | 1-(1-Methylethyl)-N-[(6-methyl-2-oxo-4-propyl-1,2-dihydro-3-pyridinyl)methyl]-6-(3-pyridinyl)-1H-indole-4-carboxamide | 0.90 (t, J = 7.33 Hz, 3 H) 1.44-1.59 (m, 8 H) 2.13 (s, 3 H) 2.54 (dd, J = 8.59, 6.82 Hz, 2 H) 4.41 (d, J = 5.05 Hz, 2 H) 4.98 (quin, J = 6.63 Hz, 1 H) 5.91 (s, 1 H) 6.92 (d, J = 3.28 Hz, 1 H) 7.49 (dd, J = 7.33, 4.80 Hz, 1 H) 7.66 (d, J = 3.03 Hz, 1 H) 7.75 (d, J = 1.26 Hz, 1 H) 8.04 (s, 1 H) 8.20 (dt, J = 8.27, 1.80 Hz, 1 H) 8.34 (t, J = 5.05 Hz, 1 H) 8.54 (dd, J = 4.67, 1.64 Hz, 1 H) 9.04 (d, J = 1.77 Hz, 1 H) 11.56 (s, 1 H) | 443.2 |
| 9 | 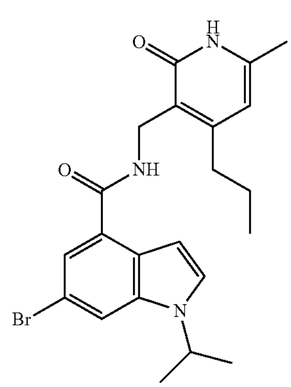 [SMILES: CCCc1cc(C)[nH]c(=O)c1CNC(=O)c1cc(Br)cc2c1ccn2C(C)C] | 6-Bromo-1-(1-methylethyl)-N-[(6-methyl-2-oxo-4-propyl-1,2-dihydro-3-pyridinyl)methyl]-1H-indole-4-carboxamide | 0.90 (t, J = 7.33 Hz, 3 H) 1.43 (d, J = 6.57 Hz, 6 H) 1.47-1.62 (m, 2 H) 2.13 (s, 3 H) 2.53 (d, J = 7.83 Hz, 2 H) 4.35 (d, J = 5.05 Hz, 2 H) 4.76-4.88 (m, 1 H) 5.91 (s, 1 H) 6.86 (d, J = 3.03 Hz, 1 H) 7.51 (d, J = 1.52 Hz, 1 H) 7.63 (d, J = 3.28 Hz, 1 H) 7.92 (s, 1 H) 8.29 (t, J = 5.05 Hz, 1 H) 11.56 (br. s., 1 H) | 444.2, 446.0 |

-continued

| Ex | Structure | Name | $^1$H NMR (400 MHz, DMSO-d$_6$) δ ppm | MS (ES) [M + H]$^+$ |
|---|---|---|---|---|
| 10 | 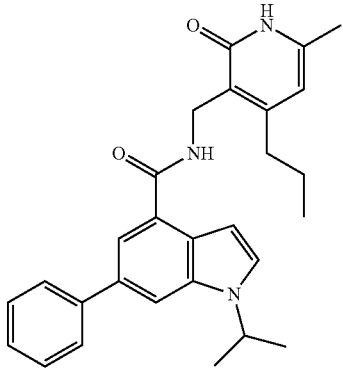 [SMILES: CCCc1cc(C)[nH]c(=O)c1CNC(=O)c1cc(-c2ccccc2)cc2c1ccn2C(C)C] | 1-(1-Methylethyl)-N-[(6-methyl-2-oxo-4-propyl-1,2-dihydro-3-pyridinyl)methyl]-6-phenyl-1H-indole-4-carboxamide | 0.91 (t, J = 7.33 Hz, 3 H) 1.48 (d, J = 6.57 Hz, 6 H) 1.50-1.60 (m, 2 H) 2.13 (s, 3 H) 2.54 (dd, J = 8.59, 6.82 Hz, 2 H) 4.41 (d, J = 5.05 Hz, 2 H) 4.88-5.02 (m, 1 H) 5.91 (s, 1 H) 6.88 (d, J = 3.03 Hz, 1 H) 7.28-7.38 (m, 1 H) 7.43-7.51 (m, 2 H) 7.63 (d, J = 3.28 Hz, 1 H) 7.71 (d, J = 1.26 Hz, 1 H) 7.75-7.83 (m, 2 H) 7.93 (s, 1 H) 8.32 (t, J = 5.05 Hz, 1 H) 11.57 (s, 1 H) | 442.1 |
| 11 | 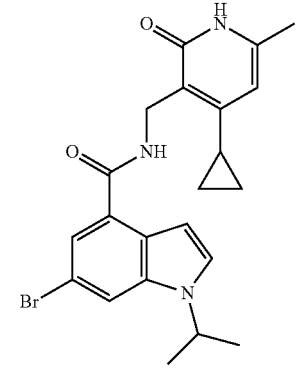 [SMILES: Cc1cc(C2CC2)c(CNC(=O)c2cc(Br)cc3c2ccn3C(C)C)c(=O)[nH]1] | 6-Bromo-N-[(4-cyclopropyl-6-methyl-2-oxo-1,2-dihydro-3-pyridinyl)methyl]-1-(1-methylethyl)-1H-indole-4-carboxamide | 11.48 (s, 1 H) 8.36 (t, J = 4.93 Hz, 1 H) 7.92 (s, 1 H) 7.63 (d, J = 3.28 Hz, 1 H) 7.52 (d, J = 1.52 Hz, 1 H) 6.84 (d, J = 3.28 Hz, 1 H) 5.52 (s, 1 H) 4.80-4.86 (m, 1 H) 4.52 (d, J = 5.05 Hz, 2 H) 2.14-2.19 (m, 1 H) 2.10 (s, 3 H) 1.43 (d, J = 6.57 Hz, 6 H) 0.91-0.98 (m, 2 H) 0.70-0.77 (m, 2 H) | 442.0, 444.1 |
| 12 | 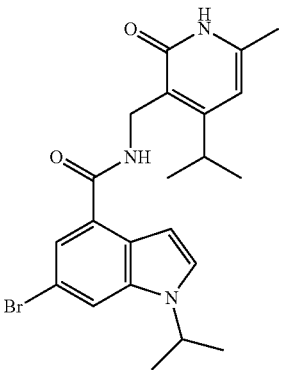 | 6-Bromo-1-(1-methylethyl)-N-{[6-methyl-4-(1-methylethyl)-2-oxo-1,2-dihydro-3-pyridinyl]methyl}-1H-indole-4-carboxamide | 11.54 (s, 1 H) 8.31 (t, J = 5.05 Hz, 1 H) 7.92 (s, 1 H) 7.63 (d, J = 3.28 Hz, 1 H) 7.51 (d, J = 1.52 Hz, 1 H) 6.86 (d, J = 3.28 Hz, 1 H) 6.02 (s, 1 H) 4.78-4.87 (m, 1 H) 4.40 (d, J = 4.80 Hz, 2 H) 3.36-3.40 (m, 1 H) 3.24-3.28 (m, 1 H) 2.16 (s, 3 H) 1.43 (d, J = 6.57 Hz, 6 H) 1.09-1.15 (m, 6 H) | 444.1, 446.0 |
| 13 | 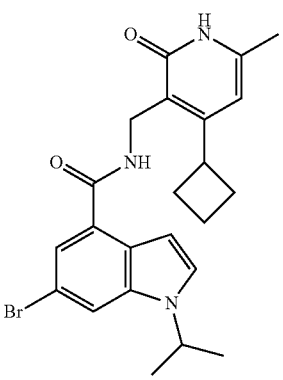 [SMILES: Cc1cc(C2CCC2)c(CNC(=O)c2cc(Br)cc3c2ccn3C(C)C)c(=O)[nH]1] | 6-Bromo-N-[(4-cyclobutyl-6-methyl-2-oxo-1,2-dihydro-3-pyridinyl)methyl]-1-(1-methylethyl)-1H-indole-4-carboxamide | 11.60 (s, 1 H) 8.26 (t, J = 4.80 Hz, 1 H) 7.92 (s, 1 H) 7.63 (d, J = 3.28 Hz, 1 H) 7.50 (d, J = 1.52 Hz, 1 H) 6.87 (d, J = 3.28 Hz, 1 H) 6.12 (s, 1 H) 4.78-4.86 (m, 1 H) 4.31 (d, J = 4.80 Hz, 2 H) 3.80 (m, 1 H) 2.21-2.26 (m, 2 H) 2.18 (s, 3 H) 2.05-2.13 (m, 2 H) 1.93-2.03 (m, 1 H) 1.78 (m, 1 H) 1.43 (d, J = 6.57 Hz, 6 H) | 455.9, 458.1 |

| Ex | Structure | Name | $^1$H NMR (400 MHz, DMSO-$d_6$) δ ppm | MS (ES) [M + H]$^+$ |
|---|---|---|---|---|
| 14 | 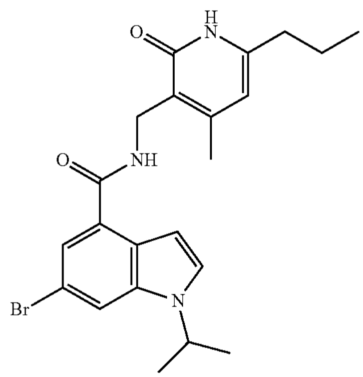 [SMILES: CCCc1cc(C)c(CNC(=O)c2cc(Br)cc3c2ccn3C(C)C)c(=O)[nH]1] | 6-Bromo-1-(1-methylethyl)-N-[(4-methyl-2-oxo-6-propyl-1,2-dihydro-3-pyridinyl)methyl]-1H-indole-4-carboxamide | 8.33 (br. s., 1H), 7.92 (s, 1H), 7.63 (d, J = 3.28 Hz, 1H), 7.52 (d, J = 1.52 Hz, 1H), 6.87 (d, J = 3.28 Hz, 1H), 5.90 (s, 1H), 4.78-4.87 (m, 1H), 4.33 (d, J = 5.05 Hz, 2H), 2.37 (t, J = 7.58 Hz, 2H), 2.23 (s, 3H), 1.58 (sxt, J = 7.43 Hz, 2H), 1.43 (d, J = 6.57 Hz, 6H), 0.88 (t, J = 7.33 Hz, 3H) | 444.2, 446.0 |
| 15 | 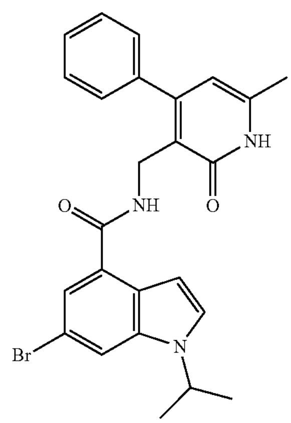 [SMILES: Cc1cc(-c2ccccc2)c(CNC(=O)c2cc(Br)cc3c2ccn3C(C)C)c(=O)[nH]1] | 6-Bromo-1-(1-methylethyl)-N-[(6-methyl-2-oxo-4-phenyl-1,2-dihydro-3-pyridinyl)methyl]-1H-indole-4-carboxamide | 11.88 (s, 1 H) 8.35 (t, J = 4.42 Hz, 1 H) 7.93 (s, 1 H) 7.63 (d, J = 3.28 Hz, 1 H) 7.40-7.50 (m, 6 H) 6.86 (d, J = 3.03 Hz, 1 H) 6.00 (s, 1 H) 4.78-4.87 (m, 1 H) 4.19 (d, J = 4.29 Hz, 2 H) 2.22 (s, 3 H) 1.44 (d, J = 6.57 Hz, 6 H) | 447.9, 479.7 |
| 16 | 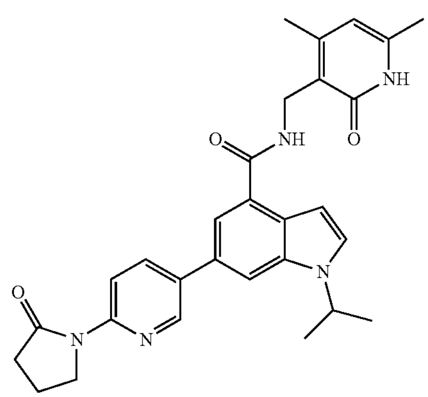 [SMILES: Cc1cc(C)c(CNC(=O)c2cc(-c3ccc(N4CCCC4=O)nc3)cc3c2ccn3C(C)C)c(=O)[nH]1] | N-((4,6-dimethyl-2-oxo-1,2-dihydropyridin-3-yl)methyl)-1-isopropyl-6-(6-(2-oxopyrrolidin-1-yl)pyridin-3-yl)-1H-indole-4-carboxamide | 1.49 (d, J = 4.00 Hz 6 H), 2.03-2.15 (m, 5 H), 2.24 (s, 3 H), 2.61 (t, J = 8.08 Hz, 2 H), 4.06 (t, J = 7.20 Hz, 2 H), 4.38 (d, J = 5.05 Hz, 2 H), 4.96 (quin, J = 6.69 Hz, 1 H), 5.89 (s, 1 H), 6.91 (d, J = 3.28 Hz, 1 H), 7.65 (d, J = 3.28 Hz, 1 H), 7.75 (d, J = 1.26 Hz, 1 H), 8.01 (s, 1 H), 8.25 (dd, J = 8.59, 2.53 Hz, 1 H), 8.32 (t, J = 5.05 Hz, 1 H), 8.39 (d, J = 8.84 Hz, 1 H), 8.85 (d, J = 2.02 Hz, 1 H), 11.55 (s, 1 H) | 498.3 |
| 17 | 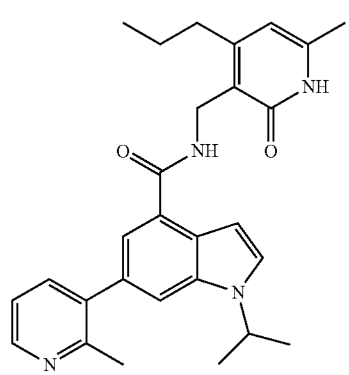 [SMILES: CCCc1cc(C)[nH]c(=O)c1CNC(=O)c1cc(-c2cccnc2C)cc2c1ccn2C(C)C] | 1-isopropyl-N-((6-methyl-2-oxo-4-propyl-1,2-dihdyropyridin-3-yl)methyl)-6-(2-methylpyridin-3-yl)-1H-indole-4-carboxamide | 0.86-0.94 (m, 3 H), 1.46 (d, J = 6.57 Hz, 6 H), 1.50-1.59 (m, 2 H) 2.12 (s, 3 H), 4.38 (d, J = 5.31 Hz, 2 H), 4.80-4.94 (m, 1 H), 5.90 (s, 1 H), 6.92 (d, J = 3.03 Hz, 1 H), 7.31 (dd, J = 7.71, 4.93 Hz, 1 H), 7.42 (d, J = 1.26 Hz, 1 H), 7.66 (d, J = 3.28 Hz, 1 H), 7.67-7.72 (m, 3 H), 8.17 (s, 1 H), 8.24 (t, J = 5.18 Hz, 1 H), 8.46 (dd, J = 4.80, 1.77 Hz, 1 H) | 457.1 |

-continued

| Ex | Structure | Name | ¹H NMR (400 MHz, DMSO-d₆) δ ppm | MS (ES) [M + H]⁺ |
|---|---|---|---|---|
| 18 | 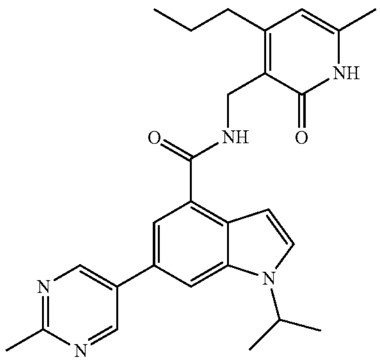 | 1-isopropyl-N-((6-methyl-2-oxo-4-propyl-1,2-dihydropyridin-3-yl)methyl)-6-(2-methylpyrimidin-5-yl)-1H-indole-4-carboxamide | 0.85-0.95 (m, 3 H), 1.44-1.60 (m, 8 H), 2.13 (s, 3 H), 3.33 (br. s., 2 H), 2.67 (s, 3H), 4.41 (d, J = 5.31 Hz, 2 H), 4.97 (quin, J = 6.63 Hz, 1 H), 5.92 (s, 1 H), 6.90 (d, J = 3.03 Hz, 1 H), 7.65 (d, J = 3.28 Hz, 1 H), 7.78 (d, J = 1.26 Hz, 2 H), 8.11 (s, 1 H), 8.32 (m, 1 H) | 458.2 |
| 19 | 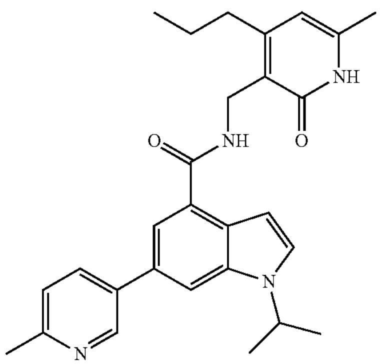 | 1-isopropyl-N-((6-methyl-2-oxo-4-propyl-1,2-dihydropyridin-3-yl)methyl)-6-(6-methylpyridin-3-yl)-1H-indole-4-carboxamide | 0.85-0.96 (m, 3 H), 1.48 (d, J = 8.00 Hz, 6 H), 1.55 (m, 2 H), 2.13 (s, 3 H), 3.33 (br. s., 1 H), 4.41 (d, J = 5.31 Hz, 2 H), 4.97 (quin, J = 6.63 Hz, 1 H), 5.92 (s, 1 H), 6.90 (d, J = 3.03 Hz, 1 H), 7.35 (d, J = 8.08 Hz, 1 H), 7.65 (d, J = 3.28 Hz, 1 H), 7.72 (d, J = 1.26 Hz, 1 H), 7.99 (s, 1 H), 8.09 (dd, J = 8.08, 2.53 Hz, 1 H), 8.15 (s, 1 H), 8.33 (t, J = 5.05 Hz, 1 H), 8.89 (d, J = 2.02 Hz, 1 H) | 457.1 |
| 20 | 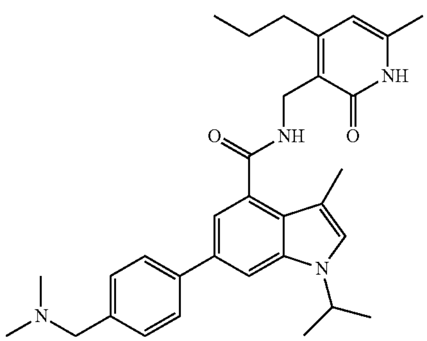 | N-((4,6-dimethyl-2-oxo-1,2-dihydropyridin-3-yl)methyl)-6-(4-((dimethylamino)methyl)phenyl)-1-isopropyl-3-methyl-1H-indole-4-carboxamide | 1.44 (m, 6 H), 1.73-1.80 (m, 2 H), 2.11 (s, 3 H), 2.17 (s, 3 H), 2.22-2.26 (m, 9 H), 3.58-3.65 (m, 2 H), 4.36 (d, J = 5.05 Hz, 2 H), 4.87 (quin, J = 6.69 Hz, 1 H), 5.87 (s, 1 H), 7.25 (d, J = 1.26 Hz, 1 H), 7.32 (d, J = 1.01 Hz, 1 H), 7.38 (d, J = 8.08 Hz, 2 H), 7.71 (d, J = 8.34 Hz, 2 H), 7.78 (d, J = 1.26 Hz, 1 H), 8.12-8.23 (m, 1 H) | 485.3 |
| 21 | 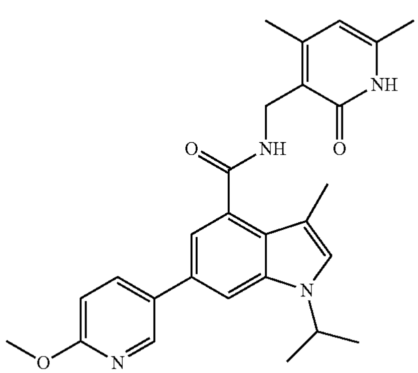 | N-((4,6-dimethyl-2-oxo-1,2-dihydropyridin-3-yl)methyl)-1-isopropyl-6-(6-methoxypyridin-3-yl)-3-methyl-1H-indole-4-carboxamide | 1.38-1.47 (m, 6 H), 2.11 (s, 3 H), 2.17 (s, 3 H), 2.24 (s, 3 H), 3.90 (s, 3 H), 4.35 (d, J = 5.05 Hz, 2 H), 4.86 (quin, J = 6.57 Hz, 1 H), 5.87 (s, 1 H), 6.88-6.96 (m, 1 H), 7.22 (d, J = 1.26 Hz, 1 H), 7.33 (d, J = 1.01 Hz, 1 H), 7.79 (d, J = 1.52 Hz, 1 H), 8.09 (dd, J = 8.59, 2.53 Hz, 1 H), 8.17 (t, J = 5.05 Hz, 1 H), 8.54 (d, J = 2.02 Hz, 1 H) | 459.3 |

-continued

| Ex | Structure | Name | ¹H NMR (400 MHz, DMSO-d₆) δ ppm | MS (ES) [M + H]⁺ |
|---|---|---|---|---|
| 22 | 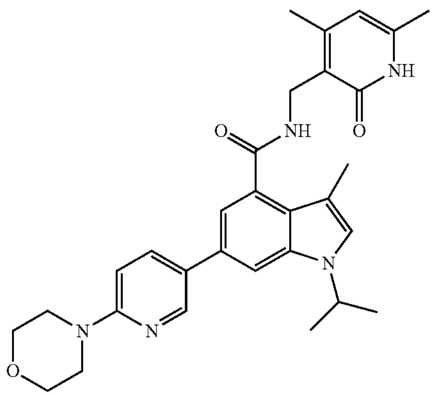 [SMILES: Cc1cc(C)c(CNC(=O)c2cc(-c3ccc(N4CCOCC4)nc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(6-morpholinopyridin-3-yl)-1H-indole-4-carboxamide | 1.43 (m, 6 H), 2.11 (s, 3 H), 2.16 (s, 3 H), 2.24 (s, 3 H), 3.45-3.54 (m, 4 H), 3.70-3.79 (m, 4 H), 4.35 (d, J = 5.05 Hz, 2 H), 4.85 (quin, J = 6.63 Hz, 1 H), 5.87 (s, 1 H), 6.93 (d, J = 8.84 Hz, 1 H), 7.20 (d, J = 1.26 Hz, 1 H), 7.29 (s, 1 H), 7.69-7.77 (m, 1 H), 7.96 (dd, J = 8.97, 2.65 Hz, 1 H), 8.15 (t, J = 5.05 Hz, 1 H), 8.54 (d, J = 2.27 Hz, 1 H), 11.48 (s, 1 H) | 514.3 |
| 23 | 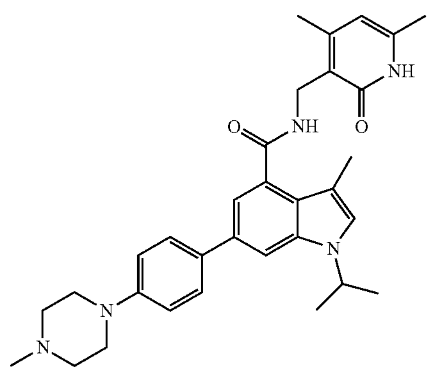 | N-((4,6-dimethyl-2-oxo-1,2-dihydropyridin-3-yl)methyl)-1-isopropyl-3-methyl-6-(4-(4-methylpiperazin-1-yl)phenyl)-1H-indole-4-carboxamide | 1.43 (m, 6 H), 2.11 (s, 3 H), 2.16 (s, 3 H), 2.24 (s, 3 H), 2.29 (s, 3 H), 2.53-2.58 (m, 4 H), 3.15-3.28 (m, 4 H), 4.35 (d, J = 5.05 Hz, 2 H), 4.84 (quin, J = 6.69 Hz, 1 H), 5.87 (s, 1 H), 7.02 (d, J = 8.84 Hz, 2 H), 7.19 (d, J = 1.26 Hz, 1 H), 7.27 (s, 1 H), 7.60 (d, J = 8.84 Hz, 2 H), 7.67 (d, J = 1.26 Hz, 1 H), 8.09-8.21 (m, 2 H) | 526.3 |
| 24 | 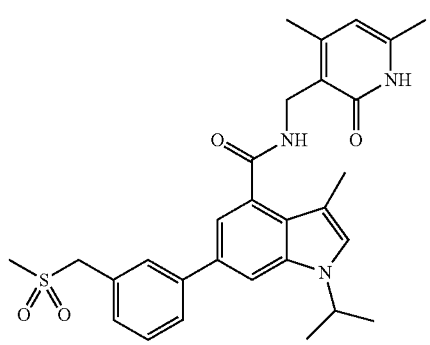 | N-((4,6-dimethyl-2-oxo-1,2-dihydropyridin-3-yl)methyl)-1-isopropyl-3-methyl-6-(3-((methylsulfonyl)methyl)phenyl)-1H-indole-4-carboxamide | 1.45 (m, 6 H), 2.11 (s, 3 H), 2.17 (s, 3 H), 2.24 (s, 3 H), 2.95 (s, 3 H), 4.36 (d, J = 5.05 Hz, 2 H), 4.57 (s, 2 H), 4.85 (quin, J = 6.63 Hz, 1 H), 5.87 (s, 1 H), 7.25 (d, J = 1.52 Hz, 1 H), 7.33-7.40 (m, 2 H), 7.49 (t, J = 7.71 Hz, 1 H), 7.72-7.82 (m, 3 H), 8.19 (t, J = 5.05 Hz, 1 H), 11.47 (s, 1 H) | 520.0 |
| 25 | 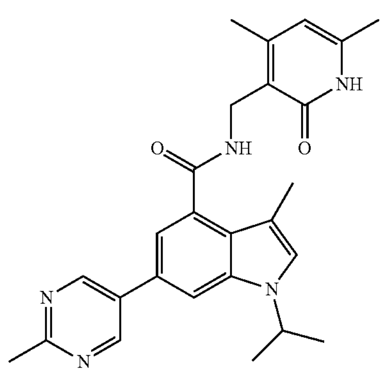 | N-((4,6-dimethyl-2-oxo-1,2-dihydropyridin-3-yl)methyl)-1-isopropyl-3-methyl-6-(2-methylpyrimidin-5-yl)-1H-indole-4-carboxamide | 1.44 (m, 6 H), 2.11 (s, 3 H), 2.17 (s, 3 H), 2.25 (s, 3 H), 2.67 (s, 3 H), 4.36 (d, J = 5.05 Hz, 2 H), 4.90 (quin, J = 6.63 Hz, 1 H), 5.87 (s, 1 H), 7.33 (d, J = 1.52 Hz, 1 H), 7.39 (d, J = 1.01 Hz, 1 H), 7.96 (d, J = 1.26 Hz, 1 H), 8.20 (t, J = 5.05 Hz, 1 H), 9.09 (s, 2 H), 11.49 (s, 1 H) | 444.2 |

| Ex | Structure | Name | ¹H NMR (400 MHz, DMSO-d₆) δ ppm | MS (ES) [M + H]⁺ |
|---|---|---|---|---|
| 26 | 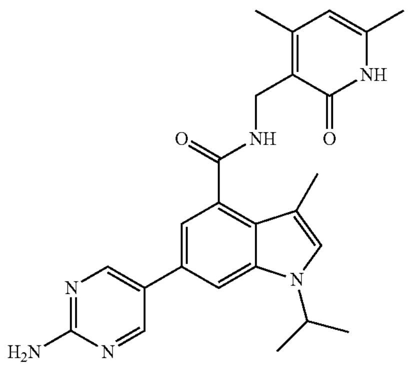 [SMILES: Cc1cc(C)c(CNC(=O)c2cc(-c3cnc(N)nc3)cc3c2c(C)cn3C(C)C)c(=O)[nH]1] | 6-(2-aminopyrimidin-5-yl)-N-((4,6-dimethyl-2-oxo-1,2-dihydropyridin-3-yl)methyl)-1-isopropyl-3-methyl-1H-indole-4-carboxamide | 1.43 (d, 6 H), 2.11 (s, 3 H), 2.15-2.20 (m, 3 H), 2.24 (s, 3 H), 4.35 (d, J = 5.05 Hz, 2 H), 4.85 (quin, J = 6.69 Hz, 1 H), 5.87 (s, 1 H), 6.70 (s, 2 H), 7.18 (d, J = 1.26 Hz, 1 H), 7.30 (s, 1 H), 7.75 (d, J = 1.26 Hz, 1 H), 8.10-8.19 (m, 1 H), 8.61-8.68 (m, 2H), 11.49 (br. s., 1 H) | 445.2 |
| 27 | 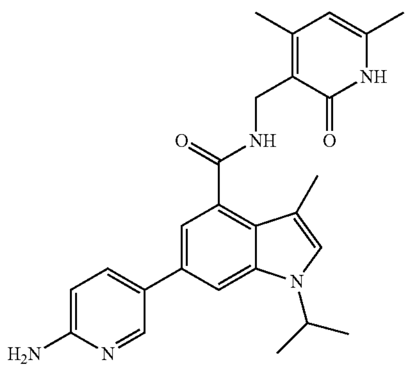 [SMILES: Cc1cc(C)c(CNC(=O)c2cc(-c3ccc(N)nc3)cc3c2c(C)cn3C(C)C)c(=O)[nH]1] | 6-(6-aminopyridin-3-yl)-N-((4,6-dimethyl-2-oxo-1,2-dihydropyridin-3-yl)methyl)-1-isopropyl-3-methyl-1H-indole-4-carboxamide | 1.42 (d, J = 8.00 Hz, 6 H), 2.11 (s, 3 H), 2.16 (s, 3 H), 2.24 (s, 3 H), 4.35 (d, J = 5.05 Hz, 2 H), 4.83 (quin, J = 6.63 Hz, 1 H), 5.87 (s, 1 H), 6.02 (s, 2 H), 6.54 (d, J = 8.59 Hz, 1 H), 7.14 (d, J = 1.52 Hz, 1 H), 7.27 (s, 1 H), 7.66 (d, J = 1.26 Hz, 1 H), 7.78 (dd, J = 8.59, 2.53 Hz, 1 H), 8.11-8.18 (m, 1 H), 8.30 (d, J = 2.02 Hz, 1 H) | 444.2 |
| 28 | 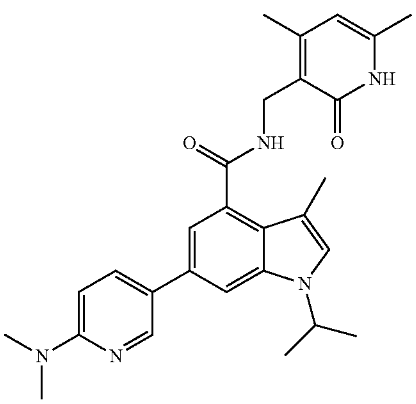 | N-((4,6-dimethyl-2-oxo-1,2-dihydropyridin-3-yl)methyl)-6-(6-(dimethylamino)pyridin-3-yl)-1-isopropyl-3-methyl-1H-indole-4-carboxamide | 1.43 (d, J = 8.00 Hz, 6 H), 2.11 (s, 3 H), 2.16 (s, 3 H), 2.24 (s, 3 H), 3.07 (s, 6 H), 4.35 (d, J = 5.05 Hz, 2 H), 4.84 (quin, J = 6.57 Hz, 1 H), 5.87 (s, 1 H), 6.73 (d, J = 8.59 Hz, 1 H), 7.17 (d, J = 1.52 Hz, 1 H), 7.28 (d, J = 1.01 Hz, 1 H), 7.68-7.74 (m, 1 H), 7.90 (dd, J = 8.84, 2.53 Hz, 1 H), 8.11-8.18 (m, 1 H), 8.48 (d, J = 2.02 Hz, 1 H) | 472.5 |
| 29 | 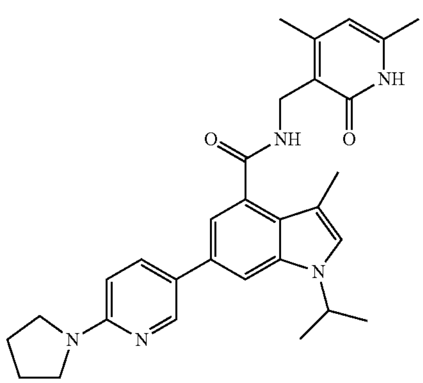 [SMILES: Cc1cc(C)c(CNC(=O)c2cc(-c3ccc(N4CCCC4)nc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(6-(pyrrolidin-1-yl)pyridin-3-yl)-1H-indole-4-carboxamide | 1.39-1.47 (d, J = 8.00 Hz, 6 H), 1.93-2.01 (m, 4 H), 2.11 (s, 3 H), 2.16 (s, 3 H), 2.24 (s, 3 H), 3.41-3.48 (m, 4 H), 4.35 (d, J = 5.05 Hz, 2 H), 4.84 (quin, J = 6.63 Hz, 1 H), 5.87 (s, 1 H), 6.56 (d, J = 8.59 Hz, 1 H), 7.17 (d, J = 1.52 Hz, 1 H), 7.27 (d, J = 1.01 Hz, 1 H), 7.69 (d, J = 1.26 Hz, 1 H), 7.91 (dd, J = 8.72, 2.15 Hz, 1 H), 8.10-8.17 (m, 1 H), 8.45 (d, J = 2.27 Hz, 1 H) | 498.4 |

-continued

| Ex | Structure | Name | ¹H NMR (400 MHz, DMSO-d₆) δ ppm | MS (ES) [M + H]⁺ |
|---|---|---|---|---|
| 30 | 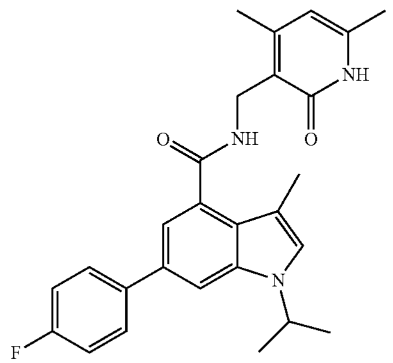 [SMILES: Cc1cc(C)c(CNC(=O)c2cc(-c3ccc(F)cc3)cc3c2c(C)cn3C(C)C)c(=O)[nH]1] | N-((4,6-dimethyl-2-oxo-1,2-dihydropyridin-3-yl)methyl)-6-(4-fluorophenyl)-1-isopropyl-3-methyl-1H-indole-4-carboxamide | 1.43 (m, 6 H), 2.11 (s, 3 H), 2.17 (s, 3 H), 2.24 (s, 3 H), 4.31-4.41 (m, 2 H), 4.80-4.93 (m, 1 H), 5.87 (s, 1 H), 7.17-7.36 (m, 4 H), 7.74-7.84 (m, 3 H), 8.16-8.24 (m, 1 H), 11.43-11.55 (m, 1 H) | 446.0 |
| 31 | 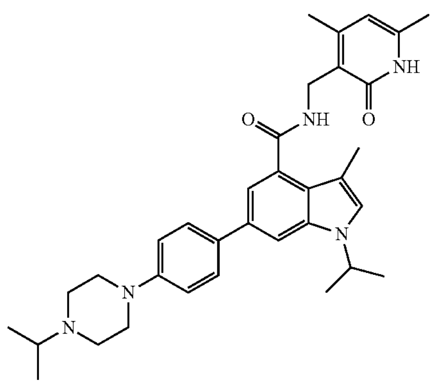 [SMILES: Cc1cc(C)c(CNC(=O)c2cc(-c3ccc(N4CCN(C(C)C)CC4)cc3)cc3c2c(C)cn3C(C)C)c(=O)[nH]1] | N-((4,6-dimethyl-2-oxo-1,2-dihydropyridin-3-yl)methyl)-1-isopropyl-6-(4-(4-isopropylpiperazin-1-yl)phenyl)-3-methyl-1H-indole-4-carboxamide | 1.01-1.11 (m, 6 H), 1.43 (d, J = 6.57 Hz, 6 H), 2.11 (s, 3 H), 2.16 (s, 3 H), 2.24 (s, 3 H), 2.68 (br. s., 4 H), 2.74-2.84 (m, 1 H), 3.15-3.26 (m, 4 H), 4.35 (d, J = 5.05 Hz, 2 H), 4.83 (quin, J = 6.57 Hz, 1 H), 5.87 (s, 1 H), 7.02 (d, J = 8.84 Hz, 2 H), 7.19 (d, J = 1.52 Hz, 1 H), 7.27 (s, 1 H), 7.60 (d, J = 8.84 Hz, 2 H), 7.67 (d, J = 1.26 Hz, 1 H), 8.11-8.21 (m, 2 H) | 554.2 |
| 32 | 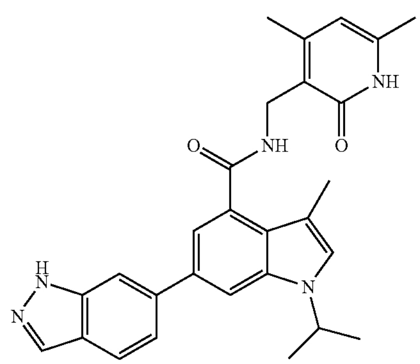 [SMILES: Cc1cc(C)c(CNC(=O)c2cc(-c3ccc4cn[nH]c4c3)cc3c2c(C)cn3C(C)C)c(=O)[nH]1] | N-((4,6-dimethyl-2-oxo-1,2-dihydropyridin-3-yl)methyl)-6-(1H-indazol-6-yl)-1-isopropyl-3-methyl-1H-indole-4-carboxamide | 1.40-1.51 (m, 6 H), 2.11 (s, 3 H), 2.19 (s, 3 H), 2.25 (s, 3 H), 4.33-4.46 (m, 2 H), 4.90 (quin, J = 6.63 Hz, 1 H), 5.87 (s, 1 H), 7.33 (dd, J = 12.76, 1.14 Hz, 2 H), 7.54 (dd, J = 8.46, 1.39 Hz, 1 H), 7.76-7.89 (m, 3 H), 8.09 (s, 1 H), 8.24 (t, J = 5.05 Hz, 1 H), 11.48 (br. s., 1 H), 13.07 (br. s., 1 H) | 468.3 |
| 33 | 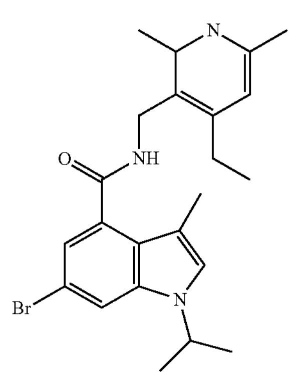 [SMILES: CCC1=C(CNC(=O)c2cc(Br)cc3c2c(C)cn3C(C)C)C(C)NC(C)=C1] | 6-bromo-N-[(4-ethyl-6-methyl-2-oxo-1,2-dihydro-3-pyridinyl)methyl]-3-methyl-1-(1-methylethyl)-1H-indole-4-carboxamide | 11.49 (s, 1 H), 8.23 (t, J = 5.05 Hz, 1 H) 7.77 (d, J = 1.77 Hz, 1 H), 7.33 (s, 1 H) 7.00 (d, J = 1.77 Hz, 1 H) 5.91 (s, 1 H) 4.74 (quin, J = 6.63 Hz, 1 H) 4.33 (s, 1 H) 4.32 (s, 1 H) 2.56 (q, J = 7.58 Hz, 2 H) 2.13 (s, 6 H) 1.40 (s, 3 H) 1.38 (s, 3 H) 1.13 (t, J = 7.58 Hz, 3 H) | 444.1/ 446.0 |

-continued

| Ex | Structure | Name | ¹H NMR (400 MHz, DMSO-d₆) δ ppm | MS (ES) [M + H]⁺ |
|---|---|---|---|---|
| 34 | 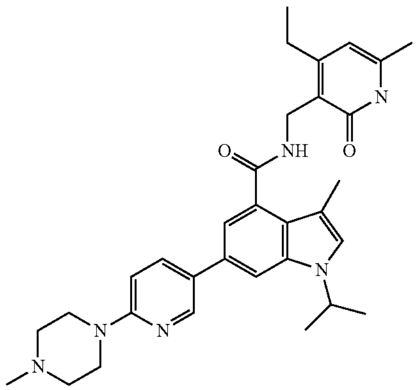 | N-[(4-ethyl-6-methyl-2-oxo-1,2-dihydro-3-pyridinyl)methyl]-3-methyl-1-(1-methylethyl)-6-[6-(4-methyl-1-piperazinyl)-3-pyridinyl]-1H-indole-4-carboxamide | 11.46 (br. s., 1 H) 8.50 (d, J = 2.27 Hz, 1 H) 8.10-8.18 (m, 1 H) 7.92 (dd, J = 8.84, 2.53 Hz, 1 H) 7.72 (d, J = 1.26 Hz, 1 H) 7.29 (s, 1 H) 7.18 (d, J = 1.52 Hz, 1 H) 6.92 (d, J = 8.84 Hz, 1 H) 5.92 (s, 1 H) 4.84 (quin, J = 6.57 Hz, 1 H) 4.37 (d, J = 4.80 Hz, 2 H) 3.49-3.55 (m, 4 H) 2.59 (q, J = 7.41 Hz, 2 H) 2.40-2.44 (m, 4 H) 2.23 (s, 3 H) 2.17 (s, 3 H) 2.13 (s, 3 H) 1.44 (s, 3 H) 1.42 (s, 3 H) 1.14 (t, J = 7.58 Hz, 3 H) | 541.5 |
| 35 | 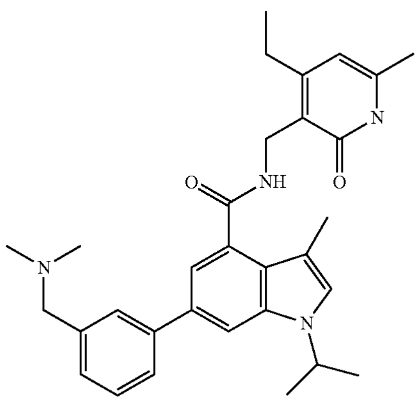 | 6-{3-[(dimethylamino)methyl]phenyl}-N-[(4-ethyl-6-methyl-2-oxo-1,2-dihydro-3-pyridinyl)methyl]-3-methyl-1-(1-methylethyl)-1H-indole-4-carboxamide | 11.48 (br. s., 1 H) 8.18 (t, J = 5.05 Hz, 1 H) 7.76 (d, J = 1.26 Hz, 1 H) 7.59-7.65 (m, 2 H) 7.40 (t, J = 7.58 Hz, 1 H) 7.33 (s, 1 H) 7.22-7.26 (m, 2 H) 5.92 (s, 1 H) 4.88 (dt, J = 13.33, 6.60 Hz, 1 H) 4.38 (s, 1 H) 4.37 (s, 1 H) 3.46 (s, 2 H) 2.59 (q, J = 7.58 Hz, 2 H) 2.18 (s, 9 H) 2.13 (s, 3 H) 1.45 (s, 3 H) 1.43 (s, 3 H) 1.15 (t, J = 7.58 Hz, 3 H) | 499.3 |
| 36 | 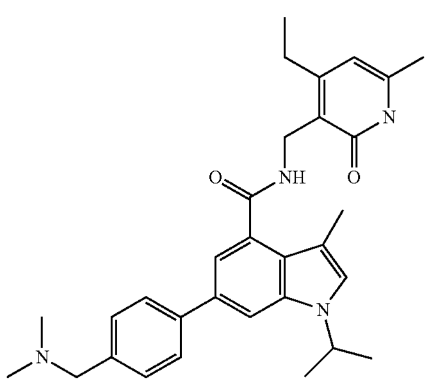 | 6-{4-[(dimethylamino)methyl]phenyl}-N-[(4-ethyl-6-methyl-2-oxo-1,2-dihydro-3-pyridinyl)methyl]-3-methyl-1-(1-methylethyl)-1H-indole-4-carboxamide | 11.48 (br. s., 1 H) 8.16 (t, J = 4.93 Hz, 1 H) 7.77 (s, 1 H) 7.70 (s, 1 H) 7.68 (s, 1 H) 7.37 (s, 1 H) 7.35 (s, 1 H) 7.32 (s, 1 H) 7.25 (s, 1 H) 5.92 (s, 1 H) 4.87 (dt, J = 13.14, 6.57 Hz, 1 H) 4.38 (br. s., 1 H) 4.37 (br. s., 1 H) 3.42 (s, 2 H) 2.59 (q, J = 7.58 Hz, 2 H) 2.17 (s, 9 H) 2.13 (s, 3 H) 1.44 (s, 3 H) 1.43 (s, 3 H) 1.15 (t, J = 7.45 Hz, 3 H) | 499.4 |

-continued

| Ex | Structure | Name | ¹H NMR (400 MHz, DMSO-d₆) δ ppm | MS (ES) [M + H]⁺ |
|---|---|---|---|---|
| 37 | 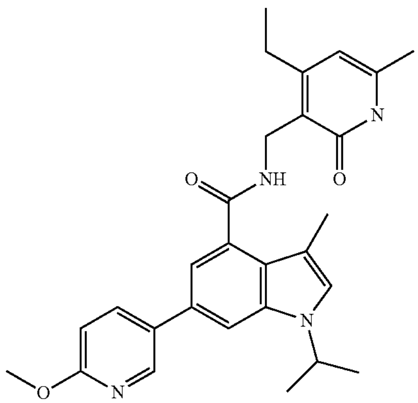 | N-[(4-ethyl-6-methyl-2-oxo-1,2-dihydro-3-pyridinyl)methyl]-3-methyl-1-(1-methylethyl)-6-[6-(methyloxy)-3-pyridinyl]-1H-indole-4-carboxamide | 11.49 (s, 1 H) 8.53 (d, J = 2.02 Hz, 1 H) 8.16 (t, J = 5.05 Hz, 1 H) 8.09 (dd, J = 8.59, 2.53 Hz, 1 H) 7.79 (d, J = 1.26 Hz, 1 H) 7.33 (s, 1 H) 7.22 (d, J = 1.26 Hz, 1 H) 6.91 (d, J = 8.59 Hz, 1 H) 5.92 (s, 1 H) 4.86 (quin, J = 6.63 Hz, 1 H) 4.38 (s, 1 H) 4.36 (s, 1 H) 3.90 (s, 3 H) 2.59 (q, J = 7.58 Hz, 2 H) 2.17 (s, 3 H) 2.13 (s, 3 H) 1.44 (s, 3 H) 1.43 (s, 3 H) 1.14 (t, J = 7.58 Hz, 3 H) | 473.1 |
| 38 | 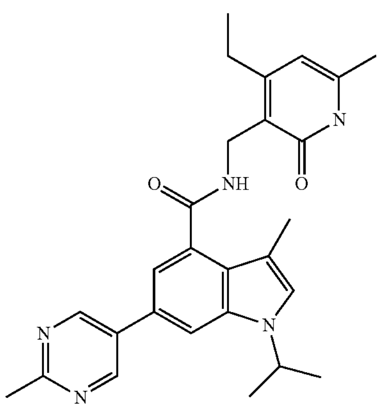 | N-[(4-ethyl-6-methyl-2-oxo-1,2-dihydro-3-pyridinyl)methyl]-3-methyl-1-(1-methylethyl)-6-(2-methyl-5-pyrimidinyl)-1H-indole-4-carboxamide | 11.50 (s, 1 H) 9.09 (s, 2 H) 8.18 (t, J = 5.05 Hz, 1 H) 7.96 (d, J = 1.26 Hz, 1 H) 7.39 (s, 1 H) 7.32 (d, J = 1.52 Hz, 1 H) 5.92 (s, 1 H) 4.90 (quin, J = 6.69 Hz, 1 H) 4.38 (s, 1 H) 4.37 (s, 1 H) 2.65-2.68 (m, 3 H) 2.60 (q, J = 7.58 Hz, 2 H) 2.18 (s, 3 H) 2.13 (s, 3 H) 1.45 (s, 3 H) 1.43 (s, 3 H) 1.14 (t, J = 7.58 Hz, 3 H) | 458.3 |
| 39 | 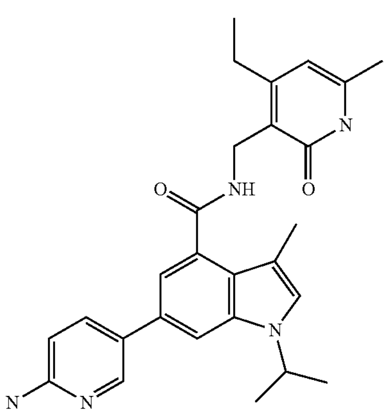 [SMILES: CCc1cc(C)[nH]c(=O)c1CNC(=O)c1cc(-c2ccc(N)nc2)cc2c1c(C)cn2C(C)C] | 6-(6-amino-3-pyridinyl)-N-[(4-ethyl-6-methyl-2-oxo-1,2-dihydro-3-pyridinyl)methyl]-3-methyl-1-(1-methylethyl)-1H-indole-4-carboxamide | 11.50 (s, 1 H) 8.30 (d, J = 2.02 Hz, 1 H) 8.12 (t, J = 5.05 Hz, 1 H) 7.76 (dd, J = 8.59, 2.53 Hz, 1 H) 7.66 (d, J = 1.26 Hz, 1 H) 7.27 (s, 1 H) 7.14 (d, J = 1.52 Hz, 1 H) 6.53 (d, J = 8.59 Hz, 1 H) 5.98 (s, 2 H) 5.92 (s, 1 H) 4.83 (quin, J = 6.63 Hz, 1 H) 4.37 (s, 1 H) 4.36 (s, 1 H) 2.59 (q, J = 7.58 Hz, 2 H) 2.16 (s, 3 H) 2.13 (s, 3 H) 1.43 (s, 3 H) 1.41 (s, 3 H) 1.14 (t, J = 7.45 Hz, 3 H) | 458.2 |

-continued

| Ex | Structure | Name | ¹H NMR (400 MHz, DMSO-d₆) δ ppm | MS (ES) [M + H]⁺ |
|---|---|---|---|---|
| 40 | 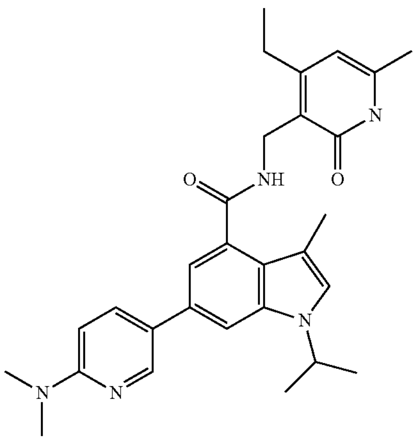 | 6-[6-(dimethylamino)-3-pyridinyl]-N-[(4-ethyl-6-methyl-2-oxo-1,2-dihydro-3-pyridinyl)methyl]-3-methyl-1-(1-methylethyl)-1H-indole-4-carboxamide | 11.47 (br. s., 1 H) 8.48 (d, J = 2.27 Hz, 1 H) 8.14 (t, J = 4.67 Hz, 1 H) 7.89 (dd, J = 8.72, 2.65 Hz, 1 H) 7.70 (d, J = 1.26 Hz, 1 H) 7.28 (s, 1 H) 7.17 (d, J = 1.52 Hz, 1 H) 6.73 (d, J = 8.84 Hz, 1 H) 5.92 (s, 1 H) 4.84 (quin, J = 6.57 Hz, 1 H) 4.37 (s, 1 H) 4.36 (s, 1 H) 3.07 (s, 6 H) 2.59 (q, J = 7.58 Hz, 2 H) 2.16 (s, 3 H) 2.13 (s, 3 H) 1.44 (s, 3 H) 1.42 (s, 3 H) 1.15 (t, J = 7.58 Hz, 3 H) | 486.3 |
| 41 | 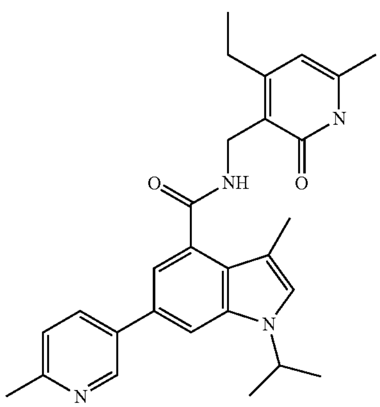 | N-[(4-ethyl-6-methyl-2-oxo-1,2-dihydro-3-pyridinyl)methyl]-3-methyl-1-(1-methylethyl)-6-(6-methyl-3-pyridinyl)-1H-indole-4-carboxamide | 11.44 (br. s., 1 H) 8.83 (d, J = 2.02 Hz, 1 H) 8.20 (t, J = 4.93 Hz, 1 H) 8.03 (dd, J = 8.08, 2.53 Hz, 1 H) 7.84 (d, J = 1.52 Hz, 1 H) 7.31-7.36 (m, 2 H) 7.26 (d, J = 1.52 Hz, 1 H) 5.92 (s, 1 H) 4.88 (quin, J = 6.63 Hz, 1 H) 4.38 (s, 1 H) 4.37 (s, 1 H) 2.59 (q, J = 7.58 Hz, 2 H) 2.18 (s, 3 H) 2.13 (s, 3 H) 1.44 (s, 3 H) 1.43 (s, 3 H) 1.14 (t, J = 7.58 Hz, 3 H) | 457.2 |
| 42 | 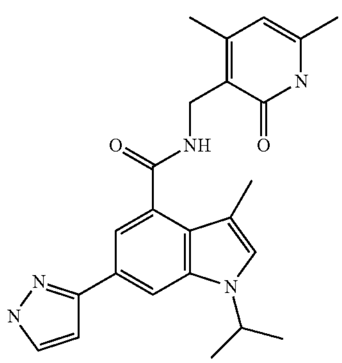 [SMILES: Cc1cc(C)c(CNC(=O)c2cc(-c3cc[nH]n3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(1H-pyrazol-3-yl)-1H-indole-4-carboxamide | 12.77 (br. s., 1 H) 11.48 (br. s., 1 H) 8.10 (br. s., 1 H) 7.89 (s, 1 H) 7.76 (br. s., 1 H) 7.46 (br. s., 1 H) 7.29 (br. s., 1 H) 6.75 (br. s., 1 H) 5.87 (s, 1 H) 4.79 (br. s., 1 H) 4.36 (s, 1 H) 4.35 (s, 1 H) 2.25 (s, 3 H) 2.15 (s, 3 H) 2.11 (s, 3 H) 1.45 (s, 3 H) 1.43 (s, 3 H) | 418.2 |

| Ex | Structure | Name | ¹H NMR (400 MHz, DMSO-d₆) δ ppm | MS (ES) [M + H]⁺ |
|---|---|---|---|---|
| 43 | 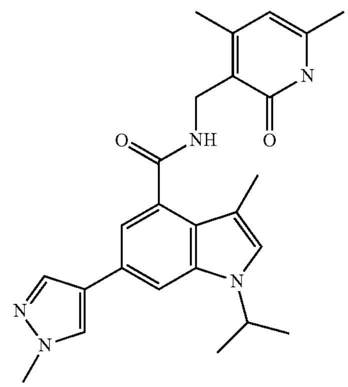 [SMILES: Cc1cc(C)c(CNC(=O)c2cc(-c3cnn(C)c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(1-methyl-1H-pyrazol-4-yl)-1H-indole-4-carboxamide | 11.47 (s, 1 H) 8.14 (s, 1 H) 8.05 (t, J = 5.18 Hz, 1 H) 7.89 (s, 1 H) 7.69 (d, J = 1.26 Hz, 1 H) 7.23 (s, 1 H) 7.15 (d, J = 1.52 Hz, 1 H) 5.87 (s, 1 H) 4.77 (quin, J = 6.69 Hz, 1 H) 4.35 (s, 1 H) 4.34 (s, 1 H) 3.86 (s, 3 H) 2.24 (s, 3 H) 2.13 (s, 3 H) 2.11 (s, 3 H) 1.43 (s, 3 H) 1.41 (s, 3 H) | 432.2 |
| 44 | 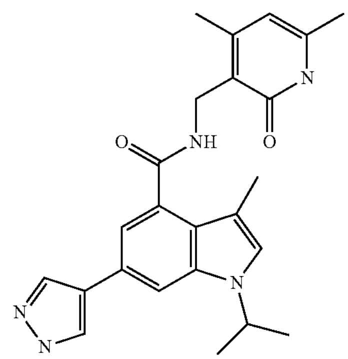 [SMILES: Cc1cc(C)c(CNC(=O)c2cc(-c3cn[nH]c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(1H-pyrazol-4-yl)-1H-indole-4-carboxamide | 11.50 (br. s., 1 H) 7.95-8.17 (m, 3 H) 7.72 (d, J = 1.01 Hz, 1 H) 7.23 (s, 1 H) 7.20 (d, J = 1.52 Hz, 1 H) 5.87 (s, 1 H) 4.79 (quin, J = 6.63 Hz, 1 H) 4.35 (s, 1 H) 4.34 (s, 1 H) 2.24 (s, 3 H) 2.13 (s, 3 H) 2.11 (s, 3 H) 1.43 (s, 3 H) 1.42 (s, 3 H) | 418.2 |
| 45 | 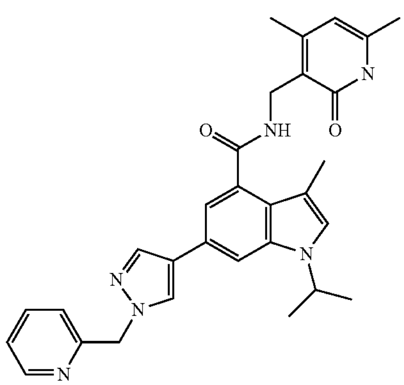 [SMILES: Cc1cc(C)c(CNC(=O)c2cc(-c3cnn(Cc4ccccn4)c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[1-(2-pyridinylmethyl)-1H-pyrazol-4-yl]-1H-indole-4-carboxamide | 11.47 (s, 1 H) 8.56 (d, J = 4.04 Hz, 1 H) 8.33 (s, 1 H) 8.07 (t, J = 5.05 Hz, 1 H) 7.99 (s, 1 H) 7.76-7.81 (m, 1 H) 7.73 (s, 1 H) 7.33 (dd, J = 6.69, 4.93 Hz, 1 H) 7.24 (s, 1 H) 7.18 (d, J = 1.26 Hz, 1 H) 7.10 (d, J = 7.83 Hz, 1 H) 5.87 (s, 1 H) 5.45 (s, 2 H) 4.79 (dt, J = 13.14, 6.57 Hz, 1 H) 4.35 (s, 1 H) 4.34 (s, 1 H) 2.24 (s, 3 H) 2.13 (s, 3 H) 2.11 (s, 3 H) 1.43 (s, 3 H) 1.41 (s, 3 H) | 509.0 |
| 46 | 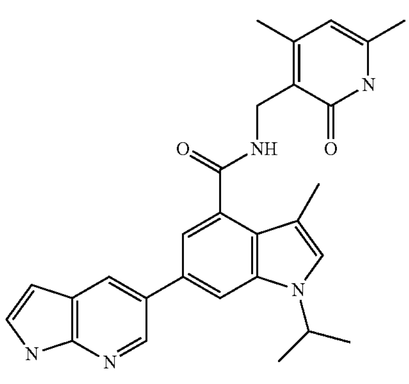 [SMILES: Cc1cc(C)c(CNC(=O)c2cc(-c3cnc4[nH]ccc4c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(1H-pyrrolo[2,3-b]pyridin-5-yl)-1H-indole-4-carboxamide | 11.67 (br. s., 1 H) 11.48 (s, 1 H) 8.60 (d, J = 2.27 Hz, 1 H) 8.27 (d, J = 2.02 Hz, 1 H) 8.20 (t, J = 5.05 Hz, 1 H) 7.82 (d, J = 1.26 Hz, 1 H) 7.49-7.52 (m, 1 H) 7.32 (s, 1 H) 7.29 (d, J = 1.52 Hz, 1 H) 6.51 (dd, J = 3.28, 1.77 Hz, 1 H) 5.87 (s, 1 H) 4.89 (dt, J = 13.33, 6.60 Hz, 1 H) 4.38 (s, 1 H) 4.36 (s, 1 H) 2.25 (s, 3 H) 2.19 (s, 3 H) 2.11 (s, 3 H) 1.45 (s, 3 H) 1.44 (s, 3 H) | 468.0 |

-continued

| Ex | Structure | Name | ¹H NMR (400 MHz, DMSO-d₆) δ ppm | MS (ES) [M + H]⁺ |
|---|---|---|---|---|
| 47 | 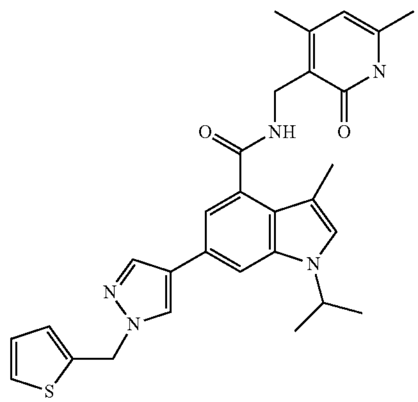 [SMILES: Cc1cc(C)c(CNC(=O)c2cc(-c3cnn(Cc4cccs4)c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[1-(2-thienylmethyl)-1H-pyrazol-4-yl]-1H-indole-4-carboxamide | 11.38 (br. s., 1 H) 8.26 (s, 1 H) 8.08 (t, J = 4.93 Hz, 1 H) 7.96 (s, 1 H) 7.70 (d, J = 1.26 Hz, 1 H) 7.48 (dd, J = 5.05, 1.26 Hz, 1 H) 7.23 (s, 1 H) 7.16 (s, 2 H) 7.01 (dd, J = 5.05, 3.28 Hz, 1 H) 5.87 (s, 1 H) 5.53 (s, 2 H) 4.78 (quin, J = 6.63 Hz, 1 H) 4.35 (s, 1 H) 4.33 (s, 1 H) 2.24 (s, 3 H) 2.13 (s, 3 H) 2.11 (s, 3 H) 1.42 (s, 3 H) 1.41 (s, 3 H) | 514.2 |
| 48 | 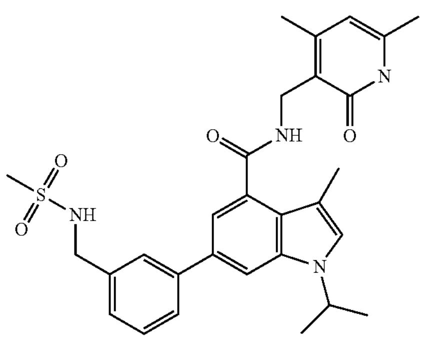 | N-((4,6-dimethyl-2-oxo-1,2-dihydropyridin-3-yl)methyl)-1-isopropyl-3-methyl-6-(3-(methylsulfonamidomethyl)phenyl)-1H-indole-4-carboxamide | 11.47 (s, 1 H) 8.18 (t, J = 4.93 Hz, 1 H) 7.70-7.78 (m, 2 H) 7.61-7.68 (m, 2 H) 7.44 (t, J = 7.71 Hz, 1 H) 7.30-7.35 (m, 2 H) 7.26 (d, J = 1.52 Hz, 1 H) 5.87 (s, 1 H) 4.86 (quin, J = 6.69 Hz, 1 H) 4.37 (br. s., 1 H) 4.35 (br. s., 1 H) 4.26 (s, 1 H) 4.24 (s, 1 H) 2.87-2.90 (m, 3 H) 2.22-2.26 (m, 3 H) 2.17 (s, 3 H) 2.11 (s, 3 H) 1.45 (s, 3 H) 1.41-1.45 (m, 3 H) | 534.9 |
| 49 | 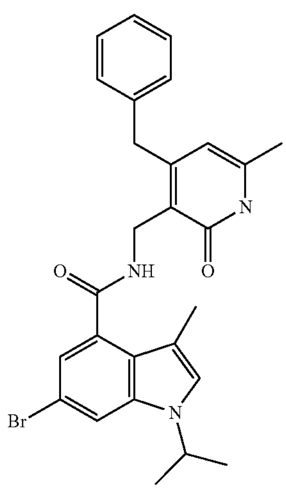 [SMILES: Cc1cc(Cc2ccccc2)c(CNC(=O)c2cc(Br)cc3c2c(C)cn3C(C)C)c(=O)[nH]1] | N-((4-benzyl-6-methyl-2-oxo-1,2-dihydropyridin-3-yl)methyl)-6-bromo-1-isopropyl-3-methyl-1H-indole-4-carboxamide | 11.56 (s, 1 H) 8.34 (t, J = 5.05 Hz, 1 H) 7.76 (d, J = 1.52 Hz, 1 H) 7.29-7.34 (m, 3 H) 7.20-7.26 (m, 3 H) 6.97 (d, J = 1.77 Hz, 1 H) 5.78 (s, 1 H) 4.74 (quin, J = 6.63 Hz, 1 H) 4.40 (s, 1 H) 4.39 (s, 1 H) 3.97 (s, 2 H) 2.13 (s, 3 H) 2.09 (s, 3 H) 1.40 (s, 3 H) 1.38 (s, 3 H) | 505.8/ 507.9 |
| 50 | 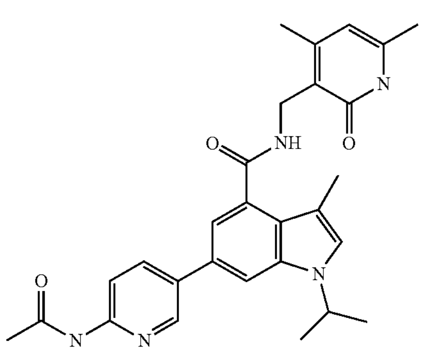 [SMILES: CC(=O)Nc1ccc(-c2cc(C(=O)NCc3c(C)cc(C)[nH]c3=O)c3c(C)cn(C(C)C)c3c2)cn1] | 6-(6-acetamidopyridin-3-yl)-N-((4,6-dimethyl-2-oxo-1,2-dihydropyridin-3-yl)methyl)-1-isopropyl-3-methyl-1H-indole-4-carboxamide | 11.48 (br. s., 1 H) 10.58 (s, 1 H) 8.71 (t, J = 1.64 Hz, 1 H) 8.12-8.21 (m, 3 H) 7.85 (d, J = 1.26 Hz, 1 H) 7.34 (s, 1 H) 7.27 (d, J = 1.52 Hz, 1 H) 5.87 (s, 1 H) 4.89 (quin, J = 6.57 Hz, 1 H) 4.36 (s, 1 H) 4.35 (s, 1 H) 2.25 (s, 3 H) 2.17 (s, 3 H) 2.12 (s, 3 H) 2.11 (s, 3 H) 1.45 (s, 3 H) 1.43 (s, 3 H) | 486.2 |

-continued

| Ex | Structure | Name | ¹H NMR (400 MHz, DMSO-d₆) δ ppm | MS (ES) [M + H]⁺ |
|---|---|---|---|---|
| 51 | 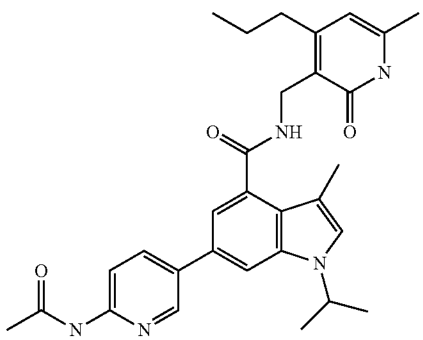 [SMILES: CCCc1cc(C)[nH]c(=O)c1CNC(=O)c1cc(-c2ccc(NC(C)=O)nc2)cc2c1c(C)cn2C(C)C] | 6-(6-acetamidopyridin-3-yl)-1-isopropyl-3-methyl-N-((6-methyl-2-oxo-4-propyl-1,2-dihydropyridin-3-yl)methyl)-1H-indole-4-carboxamide | 11.49 (s, 1 H) 10.58 (s, 1 H) 8.70 (s, 1 H) 8.13-8.18 (m, 3 H) 7.83-7.87 (m, 1 H) 7.35 (s, 1 H) 7.26 (d, J = 1.26 Hz, 1 H) 5.90 (s, 1 H) 4.89 (dt, J = 13.20, 6.66 Hz, 1 H) 4.38 (br. s., 1 H) 4.36 (br. s., 1 H) 2.53-2.58 (m, 2 H) 2.18 (s, 3 H) 2.12 (s, 5 H) 1.54-1.62 (m, 2 H) 1.45 (s, 3 H) 1.43 (s, 3 H) 0.94 (t, J = 7.33 Hz, 3 H) | 514.2 |
| 52 | 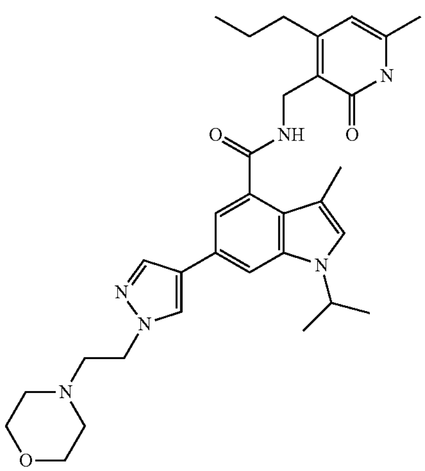 [SMILES: CCCc1cc(C)[nH]c(=O)c1CNC(=O)c1cc(-c2cnn(CCN3CCOCC3)c2)cc2c1c(C)cn2C(C)C] | 1-isopropyl-3-methyl-N-((6-methyl-2-oxo-4-propyl-1,2-dihydropyridin-4-yl)methyl)-6-(1-(2-morpholinoethyl)-1H-pyrazol-4-yl)-1H-indole-4-carboxamide | 11.47 (br. s., 1 H) 8.18 (s, 1 H) 8.03 (t, J = 5.05 Hz, 1 H) 7.89 (s, 1 H) 7.69 (d, J = 1.01 Hz, 1 H) 7.24 (d, J = 1.01 Hz, 1 H) 7.15 (d, J = 1.26 Hz, 1 H) 5.90 (s, 1 H) 4.78 (quin, J = 6.63 Hz, 1 H) 4.37 (s, 1 H) 4.35 (s, 1 H) 4.24 (t, J = 6.69 Hz, 2 H) 3.52-3.58 (m, 4 H) 2.75 (t, J = 6.69 Hz, 2 H) 2.52-2.58 (m, 2 H) 2.39-2.47 (m, 4 H) 2.13 (s, 3 H) 2.12 (s, 3 H) 1.53-1.62 (m, 2 H) 1.43 (s, 3 H) 1.42 (s, 3 H) 0.95 (t, J = 7.33 Hz, 3 H) | 559.0 |
| 53 | 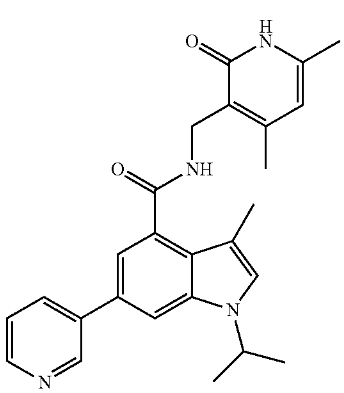 [SMILES: Cc1cc(C)c(CNC(=O)c2cc(-c3cccnc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(3-pyridinyl)-1H-indole-4-carboxamide | 1.44 (d, J = 6.57 Hz, 6 H), 2.10 (s, 3 H), 2.17 (s, 3 H), 2.24 (s, 3 H), 4.36 (d, J = 5.05 Hz, 2 H) 4.89 (dt, J = 13.14, 6.57 Hz, 1 H) 5.87 (s, 1 H), 7.35 (s, 1 H), 7.40 (s, 1 H), 7.73 (dd, J = 7.83, 5.31 Hz, 1 H), 7.98 (s, 1 H), 8.21 (t, J = 5.05 Hz, 1 H), 8.49 (d, J = 8.08 Hz, 1 H), 8.65 (d, J = 4.55 Hz, 1 H), 9.13 (s, 1 H), 11.48 (br. s., 1 H) | 429.0 |

| Ex | Structure | Name | ¹H NMR (400 MHz, DMSO-d₆) δ ppm | MS (ES) [M + H]⁺ |
|---|---|---|---|---|
| 54 | 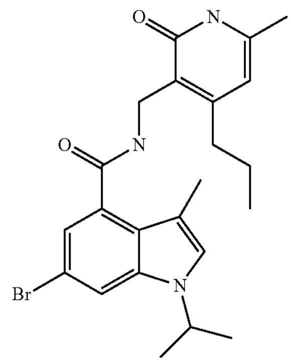 [SMILES: CCCc1cc(C)[nH]c(=O)c1CNC(=O)c1cc(Br)cc2c1c(C)cn2C(C)C] | 6-bromo-3-methyl-1-(1-methylethyl)-N-[(6-methyl-2-oxo-4-propyl-1,2-dihydro-3-pyridinyl)methyl]-1H-indole-4-carboxamide | 0.93 (t, 3 H), 1.38 (d, J = 6.57 Hz, 6 H), 1.44-1.67 (m, 2 H), 2.12 (d, J = 5.31 Hz, 6 H), 4.31 (d, J = 5.05 Hz, 2 H), 4.73 (dt, J = 13.14, 6.57 Hz, 1 H), 5.89 (s, 1 H), 6.99 (d, J = 1.52 Hz, 1 H), 7.33 (s, 1 H), 7.76 (d, J = 1.52 Hz, 1 H), 8.20 (t, J = 4.80 Hz, 1 H), 11.48 (s, 1 H) | 458.2/ 460.1 |
| 55 | 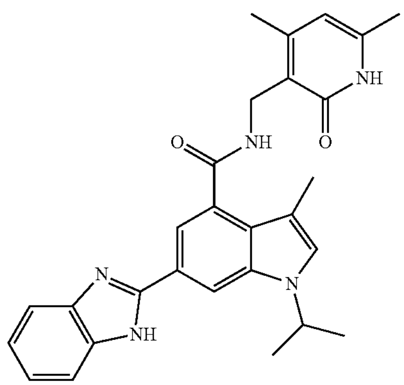 [SMILES: Cc1cc(C)c(CNC(=O)c2cc(-c3nc4ccccc4[nH]3)cc3c2c(C)cn3C(C)C)c(=O)[nH]1] | 6-(1H-benzo[d]imidazol-2-yl)-N-((4,6-dimethyl-2-oxo-1,2-dihydropyridin-3-yl)methyl)-1-isopropyl-3-methyl-1H-indole-4-carboxamide | 1.50 (d, J = 6.82 Hz, 6 H), 2.12 (s, 3 H), 2.19 (s, 3 H), 2.26 (s, 3 H), 4.39 (d, J = 5.05 Hz, 2 H), 4.82 (spt, J = 6.44 Hz, 1 H), 5.88 (s, 1 H), 7.12-7.24 (m, 2 H), 7.44 (s, 1 H), 7.51 (d, J = 6.82 Hz, 1 H), 7.64 (d, J = 7.07 Hz, 1 H), 7.82 (d, J = 1.52 Hz, 1 H), 8.22 (t, J = 5.05 Hz, 1 H), 8.33 (d, J = 1.26 Hz, 1 H), 11.49 (br. s., 1 H), 12.83 (s, 1 H) | 468.4 |
| 56 | 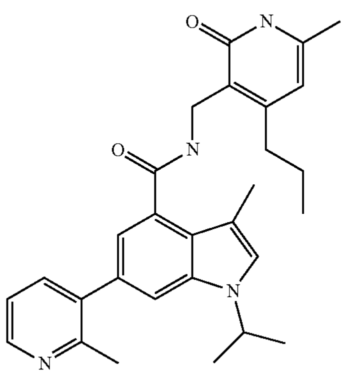 [SMILES: CCCc1cc(C)[nH]c(=O)c1CNC(=O)c1cc(-c2cccnc2C)cc2c1c(C)cn2C(C)C] | 3-methyl-1-(1-methylethyl)-N-[(6-methyl-2-oxo-4-propyl-1,2-dihydro-3-pyridinyl)methyl]-6-(2-methyl-3-pyridinyl)-1H-indole-4-carboxamide | 0.87-0.97 (m, 3 H), 1.41 (d, J = 6.57 Hz, 6 H), 1.55 (m, J = 15.16, 7.52, 7.36, 7.36 Hz, 2 H), 2.11 (s, 3 H), 2.19 (s, 3 H), 2.48 (s, 3 H), 3.17 (d, J = 5.31 Hz, 5 H), 4.34 (d, J = 5.05 Hz, 2 H), 4.78 (dt, J = 13.20, 6.66 Hz, 1 H), 5.88 (s, 1 H), 6.91 (d, J = 1.52 Hz, 1 H), 7.29 (dd, J = 7.58, 4.80 Hz, 2 H), 7.35 (s, 1 H), 7.54 (d, J = 1.26 Hz, 1 H), 7.65 (dd, J = 7.58, 1.52 Hz, 1 H), 8.11 (t, J = 5.05 Hz, 1 H), 8.44 (dd, J = 4.80, 1.52 Hz, 1 H), 11.47 (br. s., 1 H) | 471.4 |
| 57 | 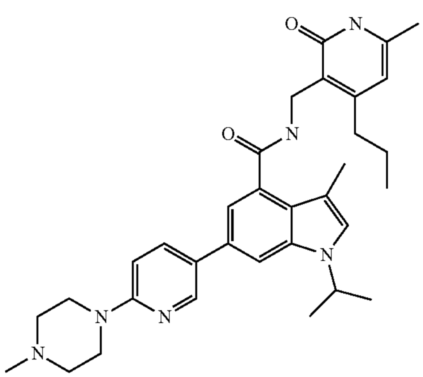 | 3-methyl-1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide | 0.93 (t, J = 7.33 Hz, 3 H), 1.42 (d, J = 6.57 Hz, 5 H), 1.56 (m, J = 7.60, 7.60, 7.60, 7.39, 7.20 Hz, 2 H), 2.12 (s, 3 H), 2.16 (s, 3 H), 2.23 (s, 3 H), 2.43 (t, J = 4.93 Hz, 4 H), 3.44-3.61 (m, 5 H), 4.36 (d, J = 5.05 Hz, 2 H), 4.84 (ddd, J = 13.26, 6.57, 6.44 Hz, 1 H), 5.89 (s, 1 H), 6.92 (d, J = 8.84 Hz, 1 H), 7.17 (d, J = 1.52 Hz, 1 H), 7.28 (s, 1 H), 7.72 (d, J = 1.26 Hz, 1 H), 7.91 (dd, J = 8.84, 2.53 Hz, 1 H), 8.11 (t, J = 4.93 Hz, 1 H), 8.17 (s, 1 H), 8.49 (d, J = 2.53 Hz, 1 H), 11.49 (br. s., 1 H) | 555.1 |

-continued

| Ex | Structure | Name | ¹H NMR (400 MHz, DMSO-d₆) δ ppm | MS (ES) [M + H]⁺ |
|---|---|---|---|---|
| 58 | 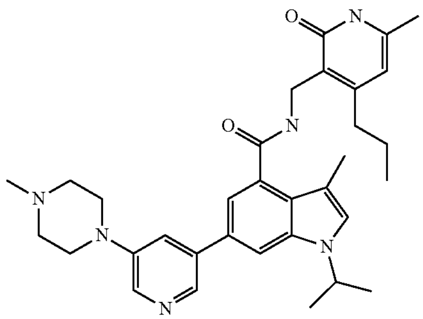 | 3-methyl-1-(1-methylethyl)-N-[(6-methyl-2-oxo-4-propyl-1,2-dihydro-3-pyridinyl)methyl]-6-[5-(4-methyl-1-piperazinyl)-3-pyridinyl]-1H-indole-4-carboxamide | 0.93 (t, J = 7.33 Hz, 3 H), 1.43 (d, J = 6.57 Hz, 6 H), 1.57 (m, J = 7.54, 7.54, 7.54, 7.33, 7.20 Hz, 2 H), 2.12 (s, 3 H), 2.17 (s, 3 H), 2.24 (s, 3 H), 2.44 (t, J = 4.80 Hz, 4 H), 2.52-2.58 (m, 2 H), 3.52-3.61 (m, 4 H), 4.36 (d, J = 4.80 Hz, 2 H), 4.92 (dt, J = 13.14, 6.57 Hz, 1 H), 5.90 (s, 1 H), 7.03 (d, J = 5.31 Hz, 1 H), 7.11 (s, 1 H), 7.30 (d, J = 1.26 Hz, 1 H), 7.38 (s, 1 H), 7.90 (d, J = 1.26 Hz, 1 H), 8.09-8.31 (m, 3 H) | 555.1 |
| 59 | 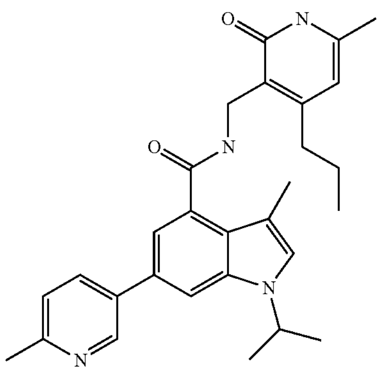 | 3-methyl-1-(1-methylethyl)-N-[(6-methyl-2-oxo-4-propyl-1,2-dihydro-3-pyridinyl)methyl]-6-(6-methyl-3-pyridinyl)-1H-indole-4-carboxamide | 0.93 (t, J = 7.33 Hz, 3 H), 1.45 (d, J = 6.57 Hz, 6 H), 1.57 (m, J = 15.16, 7.52, 7.36, 7.36, 7.36 Hz, 2 H), 2.12 (s, 3 H), 2.17 (s, 3 H), 2.53-2.59 (m, 2 H), 2.68 (s, 3 H), 4.37 (d, J = 5.05 Hz, 2 H), 4.90 (dt, J = 13.33, 6.60 Hz, 1 H), 5.91 (s, 1 H), 7.11 (s, 1 H), 7.37 (d, J = 1.26 Hz, 1 H), 7.43 (s, 6 H), 7.81 (d, J = 8.34 Hz, 6 H), 8.02 (d, J = 1.26 Hz, 6 H), 8.17 (t, J = 5.05 Hz, 6 H), 8.66 (br. s., 6 H), 9.09 (d, J = 1.77 Hz, 1 H), 11.50 (br. s., 1 H) | 471.4 |
| 60 | 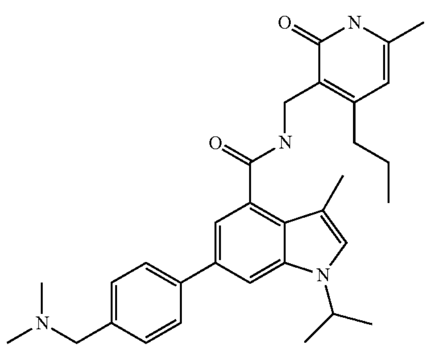 | 6-{4-[(dimethylamino)methyl]phenyl}-3-methyl-1-(1-methylethyl)-N-[(6-methyl-2-oxo-4-propyl-1,2-dihydro-3-pyridinyl)methyl]-1H-indole-4-carboxamide | 0.93 (t, J = 7.33 Hz, 3 H), 1.43 (d, J = 6.82 Hz, 6 H), 1.57 (dq, J = 15.06, 7.44 Hz, 2H), 2.12 (s, 3 H), 2.15-2.20 (m, 9 H), 2.53 (1H), 3.41 (s, 2 H), 4.36 (d, J = 5.05 Hz, 2 H), 4.86 (quin, J = 6.63 Hz, 1 H), 5.89 (s, 1 H), 7.24 (d, J = 1.26 Hz, 1 H), 7.32 (s, 1 H), 7.35 (d, J = 8.34 Hz, 2 H), 7.68 (d, J = 8.08 Hz, 2 H), 7.76 (d, J = 1.26 Hz, 1 H), 8.15 (t, J = 4.93 Hz, 1 H), 11.47 (br. s., 1 H) | 513.4 |
| 61 | 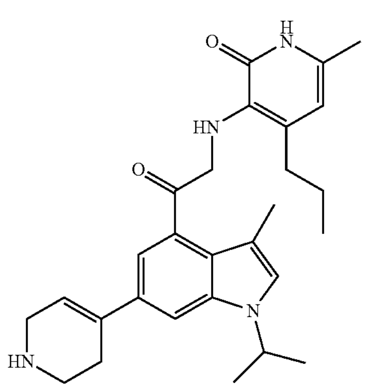 [SMILES: CCCc1cc(C)[nH]c(=O)c1NCC(=O)c1cc(C2=CCNCC2)cc2c1c(C)cn2C(C)C] | 6-methyl-3-({2-[3-methyl-1-(1-methylethyl)-6-(1,2,3,6-tetrahydro-4-pyridinyl)-1H-indol-4-yl]-2-oxoethyl}amino)-4-propyl-2(1H)-pyridinone | 0.93 (t, J = 7.33 Hz, 3 H), 1.40 (d, J = 6.57 Hz, 6 H), 1.50-1.65 (m, 2 H), 2.12 (d, J = 6.06 Hz, 6 H), 3.08 (br. s., 2 H), 3.52 (br. s., 2 H), 4.34 (d, J = 5.05 Hz, 2 H), 4.78 (dt, J = 13.20, 6.66 Hz, 1 H), 5.89 (s, 1 H), 6.18 (br. s., 1 H), 7.05 (d, J = 1.26 Hz, 1 H), 7.27 (s, 1 H), 7.50 (s, 3 H), 8.03 (t, J = 5.05 Hz, 1 H), 11.49 (br. s., 1 H) | 461.2 |

-continued

| Ex | Structure | Name | $^1$H NMR (400 MHz, DMSO-d$_6$) δ ppm | MS (ES) [M + H]$^+$ |
|---|---|---|---|---|
| 62 | 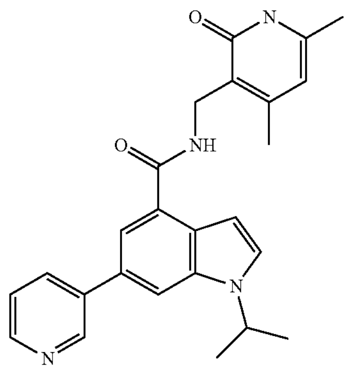 [SMILES: Cc1cc(C)c(CNC(=O)c2cc(-c3cccnc3)cc3c2ccn3C(C)C)c(=O)[nH]1] | N-[(4,6-dimethyl-2-oxo-1,2-dihydro-3-pyridinyl)methyl]-1-(1-methylethyl)-6-(3-pyridinyl)-1H-indole-4-carboxamide | 11.55 (br. s., 1 H), 9.11 (d, J = 1.8 Hz, 1 H), 8.60 (dd, J = 5.1, 1.5 Hz, 1 H), 8.36 (m, 2 H), 8.08 (s, 1 H), 7.78 (d, J = 1.5 Hz, 1 H), 7.68 (d, J = 3.3 Hz, 1 H), 7.61 (dd, J = 8.0, 4.9 Hz, 1 H), 6.93 (d, J = 3.3 Hz, 1 H), 5.89 (s, 1 H), 4.98 (quin, J = 6.6 Hz, 1 H), 4.38 (d, J = 5.1 Hz, 2 H), 2.23 (s, 3 H), 2.12 (s, 3 H), 1.49 (d, J = 6.8 Hz, 6 H) | 415.0 |
| 63 | 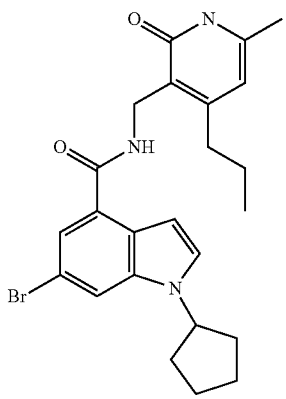 [SMILES: CCCc1cc(C)[nH]c(=O)c1CNC(=O)c1cc(Br)cc2c1ccn2C1CCCC1] | 6-bromo-1-cyclopentyl-N-[(6-methyl-2-oxo-4-propyl-1,2-dihydro-3-pyridinyl)methyl]-1H-indole-4-carboxamide | 11.56 (s, 1 H), 8.30 (t, J = 5.2 Hz, 1 H), 7.93 (s, 1 H), 7.59 (d, J = 3.3 Hz, 1 H), 7.52 (d, J = 1.5 Hz, 1 H), 6.85 (d, J = 3.3 Hz, 1 H), 5.91 (s, 1 H), 4.94 (m, 1 H), 4.35 (d, J = 5.1 Hz, 2 H), 2.53 (d, J = 7.8 Hz, 2 H), 2.12 (m, 5 H), 1.80 (m, 4 H), 1.71 (m, 2 H), 1.52 (m, 2 H), 0.90 (t, J = 7.3 Hz, 3 H) | 470.1 |
| 64 | 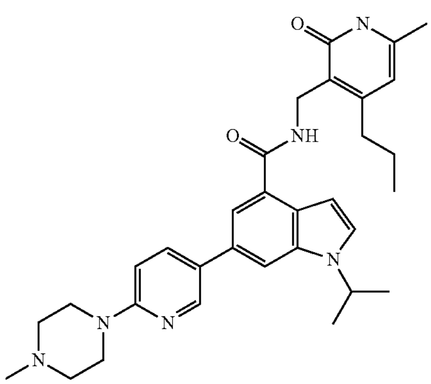 | 1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide | 11.56 (s, 1 H), 8.56 (d, J = 2.5 Hz, 1 H), 8.27 (t, J = 5.2 Hz, 1 H), 7.97 (dd, J = 9.0, 2.7 Hz, 1 H), 7.87 (s, 1 H), 7.65 (d, J = 1.3 Hz, 1 H), 7.58 (d, J = 3.3 Hz, 1 H), 6.93 (d, J = 9.1 Hz, 1 H), 6.86 (d, J = 3.0 Hz, 1 H), 5.91 (s, 1 H), 4.92 (m, 1 H), 4.39 (d, J = 5.1 Hz, 2 H), 3.52 (m, 4 H), 2.54 (m, 2 H), 2.41 (m, 4 H), 2.22 (m, 3 H), 2.13 (s, 3 H), 1.53 (m, 2 H), 1.47 (d, J = 6.6 Hz, 6 H), 0.90 (t, J = 7.3 Hz, 3 H) | 541.5 |
| 65 | 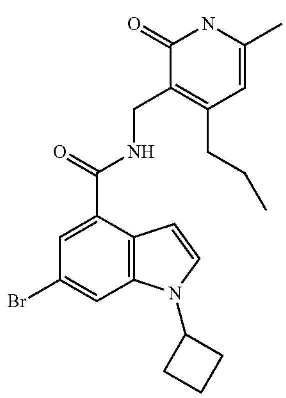 [SMILES: CCCc1cc(C)[nH]c(=O)c1CNC(=O)c1cc(Br)cc2c1ccn2C1CCC1] | 6-bromo-1-cyclobutyl-N-[(6-methyl-2-oxo-4-propyl-1,2-dihydro-3-pyridinyl)methyl]-1H-indole-4-carboxamide | 11.56 (s, 1 H), 8.31 (t, J = 5.1 Hz, 1 H), 7.87 (s, 1 H), 7.73 (d, J = 3.3 Hz, 1 H), 7.53 (d, J = 1.5 Hz, 1 H), 6.88 (d, J = 3.3 Hz, 1 H), 5.91 (s, 1 H), 5.04 (t, J = 8.3 Hz, 1 H), 4.35 (d, J = 5.1 Hz, 2 H), 2.54 (s, 1 H), 2.41 (m, 4 H), 2.13 (s, 3 H), 1.83 (m, 2 H), 1.52 (m, 2 H), 0.90 (t, J = 7.3 Hz, 3 H) | 445.9 |

-continued

| Ex | Structure | Name | ¹H NMR (400 MHz, DMSO-d₆) δ ppm | MS (ES) [M + H]⁺ |
|---|---|---|---|---|
| 66 | 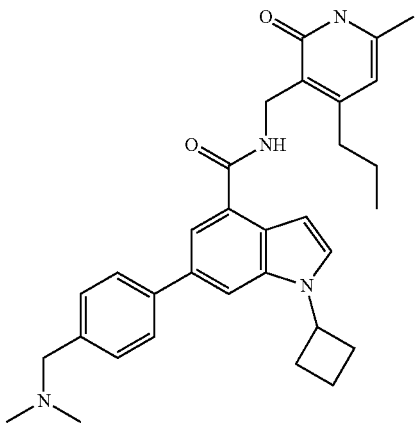 | 1-cyclobutyl-6-{4-[(dimethyl-amino)methyl]phenyl}-N-[(6-methyl-2-oxo-4-propyl-1,2-dihydro-3-pyridinyl)methyl]-1H-indole-4-carboxamide | 11.55 (s, 1 H), 8.32 (t, J = 5.1 Hz, 1 H), 7.89 (s, 1 H), 7.73 (m, 4 H), 7.37 (d, J = 8.1 Hz, 2 H), 6.90 (d, J = 3.0 Hz, 1 H), 5.91 (s, 1 H), 5.16 (t, J = 8.5 Hz, 1 H), 4.40 (d, J = 5.1 Hz, 2 H), 3.42 (s, 2 H), 2.55 (m, 3 H), 2.43 (m, 2 H), 2.15 (m, 9 H), 1.85 (dt, J = 9.8, 4.8 Hz, 2 H), 1.54 (m, 2 H), 0.90 (t, J = 7.3 Hz, 3 H) | 511.3 |
| 67 | 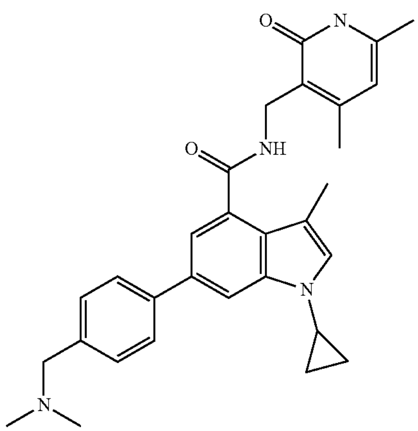 | 1-cyclopropyl-6-{4-[(dimethyl-amino)methyl]phenyl}-N-[(4,6-dimethyl-2-oxo-1,2-dihydro-3-pyridinyl)methyl]-3-methyl-1H-indole-4-carboxamide | 11.46 (s, 1 H), 8.19 (t, J = 5.1 Hz, 1 H), 7.76 (d, J = 1.5 Hz, 1 H), 7.67 (m, J = 8.1 Hz, 2 H), 7.37 (m, J = 8.1 Hz, 2 H), 7.28 (d, J = 1.5 Hz, 1 H), 7.14 (d, J = 1.0 Hz, 1 H), 5.86 (s, 1 H), 4.34 (d, J = 5.1 Hz, 2 H), 3.43 (m, 3 H), 2.23 (s, 3 H), 2.14 (m, 12 H), 1.06 (m, 2 H), 0.92 (m, 2 H) | 483.1 |
| 68 | 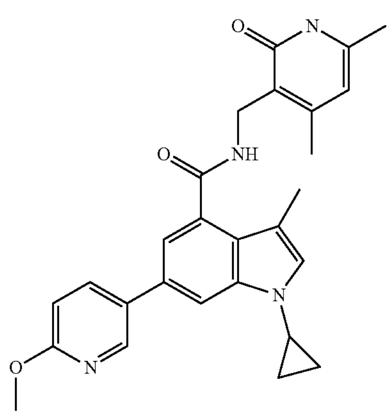 [SMILES: COc1ccc(-c2cc(C(=O)NCc3c(C)cc(C)[nH]c3=O)c3c(C)cn(C4CC4)c3c2)cn1] | 1-cyclopropyl-N-[(4,6-dimethyl-2-oxo-1,2-dihydro-3-pyridinyl)methyl]-3-methyl-6-[6-(methyloxy)-3-pyridinyl]-1H-indole-4-carboxamide | 11.46 (br. s., 1 H), 8.52 (d, J = 2.3 Hz, 1 H), 8.19 (t, J = 4.9 Hz, 1 H), 8.07 (dd, J = 8.6, 2.5 Hz, 1 H), 7.76 (d, J = 1.5 Hz, 1 H), 7.25 (d, J = 1.5 Hz, 1 H), 7.15 (d, J = 1.0 Hz, 1 H), 6.92 (d, J = 8.6 Hz, 1 H), 5.86 (s, 1 H), 4.34 (d, J = 5.1 Hz, 2 H), 3.90 (s, 3 H), 3.42 (m, 1 H), 2.22 (m, 3 H), 2.10 (s, 3 H), 2.13 (s, 3 H), 1.06 (m, 2 H), 0.92 (m, 2 H) | 457.1 |

| Ex | Structure | Name | ¹H NMR (400 MHz, DMSO-d₆) δ ppm | MS (ES) [M + H]⁺ |
|---|---|---|---|---|
| 69 | 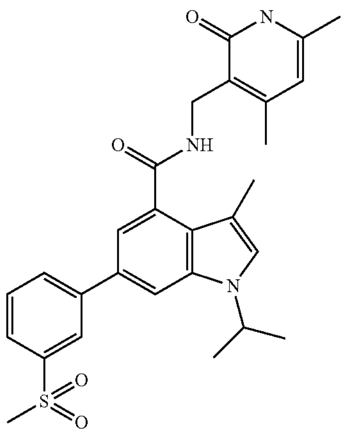 [SMILES: Cc1cc(C)c(CNC(=O)c2cc(-c3cccc(S(C)(=O)=O)c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[3-(methylsulfonyl)phenyl]-1H-indole-4-carboxamide | 11.47 (s, 1 H), 8.23 (m, 2 H), 8.12 (d, J = 7.8 Hz, 1 H), 7.89 (m, 2 H), 7.73 (m, 1 H), 7.39 (s, 1 H), 7.32 (d, J = 1.5 Hz, 1 H), 5.87 (s, 1 H), 4.92 (m, 1 H), 4.36 (d, J = 4.8 Hz, 2 H), 3.31 (s, 3 H), 2.23 (m, 3 H), 2.18 (m, 3 H), 2.11 (s, 3 H), 1.42 (m, 6 H) | 505.9 |
| 70 | 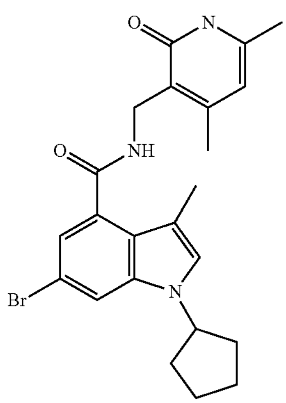 [SMILES: Cc1cc(C)c(CNC(=O)c2cc(Br)cc3c2c(C)cn3C2CCCC2)c(=O)[nH]1] | 6-bromo-1-cyclopentyl-N-[(4,6-dimethyl-2-oxo-1,2-dihydro-3-pyridinyl)methyl]-3-methyl-1H-indole-4-carboxamide | 11.48 (s, 1 H), 8.24 (t, J = 4.9 Hz, 1 H), 7.77 (d, J = 1.8 Hz, 1 H), 7.29 (s, 1 H), 7.00 (d, J = 1.8 Hz, 1 H), 5.86 (s, 1 H), 4.86 (t, J = 7.1 Hz, 1 H), 4.30 (d, J = 4.8 Hz, 2 H), 2.21 (s, 3 H), 2.08 (m, 8 H), 1.74 (m, 6 H) | 455.9 |
| 71 | 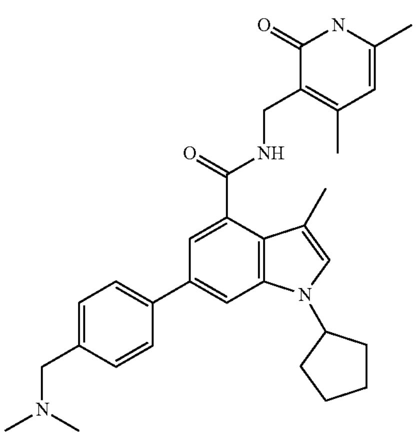 | 1-cyclopentyl-6-{4-[(dimethylamino)methyl]phenyl}-N-[(4,6-dimethyl-2-oxo-1,2-dihydro-3-pyridinyl)methyl]-3-methyl-1H-indole-4-carboxamide | 11.47 (s, 1 H), 8.18 (t, J = 5.1 Hz, 1 H), 7.78 (d, J = 1.5 Hz, 1 H), 7.69 (m, J = 8.1 Hz, 2 H), 7.36 (m, J = 8.3 Hz, 2 H), 7.26 (m, 2 H), 5.86 (s, 1 H), 5.00 (d, J = 7.1 Hz, 1 H), 4.35 (d, J = 5.1 Hz, 2 H), 3.41 (s, 2 H), 2.23 (s, 3 H), 2.14 (m, 14 H), 1.78 (m, 6 H) | 511.3 |

-continued

| Ex | Structure | Name | ¹H NMR (400 MHz, DMSO-d₆) δ ppm | MS (ES) [M + H]⁺ |
|---|---|---|---|---|
| 72 | 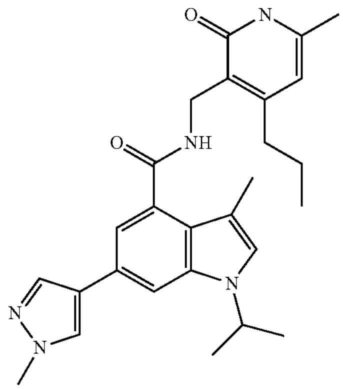 [SMILES: CCCc1cc(C)[nH]c(=O)c1CNC(=O)c1cc(-c2cnn(C)c2)cc2c1c(C)cn2C(C)C] | 3-methyl-1-(1-methylethyl)-N-[(6-methyl-2-oxo-4-propyl-1,2-dihydro-3-pyridinyl)methyl]-6-(1-methyl-1H-pyrazol-4-yl)-1H-indole-4-carboxamide | 11.49 (s, 1 H), 8.12 (s, 1 H), 8.01 (t, J = 5.1 Hz, 1 H), 7.87 (s, 1 H), 7.69 (d, J = 1.3 Hz, 1H), 7.23 (s, 1 H), 7.14 (d, J = 1.5 Hz, 1 H), 5.90 (s, 1 H), 4.77 (quin, J = 6.6 Hz, 1 H), 4.35 (d, J = 5.1 Hz, 2 H), 3.86 (s, 3 H), 2.54 (m, 2 H), 2.11 (m, 6 H), 1.57 (sxt, J = 7.5 Hz, 2 H), 1.42 (d, J = 6.6 Hz, 6 H), 0.94 (t, J = 7.3 Hz, 3 H) | 460.1 |
| 73 | 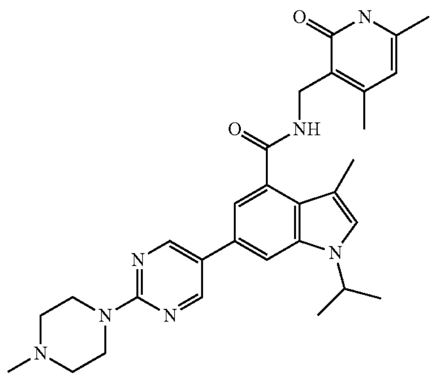 | N-((4,6-dimethyl-2-oxo-1,2-dihydropyridin-3-yl)methyl)-1-isopropyl-3-methyl-6-(2-(4-methylpiperazin-1-yl)pyrimidin-5-yl)-1H-indole-4-carboxamide | 11.48 (s, 1 H), 8.76 (s, 2 H), 8.13 (t, J = 5.2 Hz, 1 H), 7.77 (d, J = 1.5 Hz, 1 H), 7.30 (d, J = 1.3 Hz, 1 H), 7.19 (d, J = 1.3 Hz, 1 H), 5.87 (s, 1 H), 4.83 (quin, J = 6.6 Hz, 1 H), 4.35 (d, J = 5.1 Hz, 2 H), 3.77 (m, 4 H), 2.38 (t, J = 5.1 Hz, 4 H), 2.23 (d, J = 6.3 Hz, 6 H), 2.16 (s, 3 H), 2.11 (s, 3 H), 1.42 (d, J = 6.6 Hz, 6 H) | 528.0 |
| 74 | 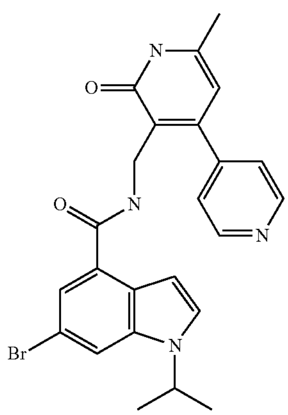 [SMILES: Cc1cc(-c2ccncc2)c(CNC(=O)c2cc(Br)cc3c2ccn3C(C)C)c(=O)[nH]1] | 6-bromo-1-(1-methylethyl)-N-[(6-methyl-2-oxo-1,2-dihydro-4,4'-bipyridin-3-yl)methyl]-1H-indole-4-carboxamide | 11.99 (br. s., 1 H) 8.66 (d, J = 6.06 Hz, 2 H) 8.33 (t, J = 4.42 Hz, 1 H) 7.93 (s, 1 H) 7.63 (d, J = 3.28 Hz, 1 H) 7.42-7.48 (m, 3 H) 6.84 (d, J = 3.03 Hz, 1 H) 6.00 (s, 1 H) 4.76-4.88 (m, 1 H) 4.16 (d, J = 4.29 Hz, 2 H), 2.23 (s, 3 H) 1.43 (d, J = 6.57 Hz, 6 H) | 480.7 |
| 75 | 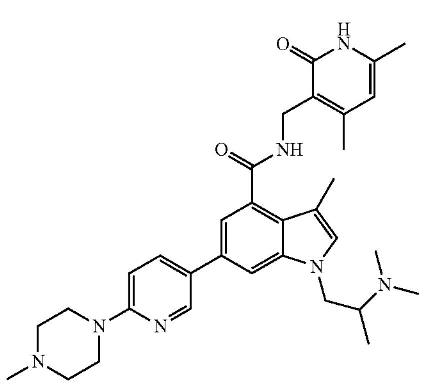 | N-((4,6-dimethyl-2-oxo-1,2-dihydropyridin-3-yl)methyl)-1-(2-(dimethylamino)propyl)-3-methyl-6-(6-(4-methylpiperazin-1-yl)pyridin-3-yl)-1H-indole-4-carboxamide | 0.82 (d, J = 6.57 Hz, 3 H), 2.10 (s, 3 H), 2.14 (s, 3 H), 2.20 (s, 6 H), 2.23 (d, J = 5.05 Hz, 6 H), 2.37-2.46 (m, 4 H), 2.98 (q, J = 6.82 Hz, 1 H), 3.48-3.58 (m, 4 H), 3.95-4.27 (m, 1 H), 4.34 (d, J = 5.05 Hz, 2 H), 5.86 (s, 1 H), 6.92 (d, J = 9.09 Hz, 1 H), 7.14 (s, 1 H), 7.17 (d, J = 1.26 Hz, 1 H), 7.68 (d, J = 1.26 Hz, 1 H), 7.90 (dd, J = 8.84, 2.78 Hz, 1 H), 8.17 (t, J = 5.05 Hz, 1 H), 8.50 (d, J = 2.27 Hz, 1 H), 11.47 (br. s., 1 H) | 570.6 |

| Ex | Structure | Name | $^1$H NMR (400 MHz, DMSO-d$_6$) δ ppm | MS (ES) [M + H]$^+$ |
|---|---|---|---|---|
| 76 | 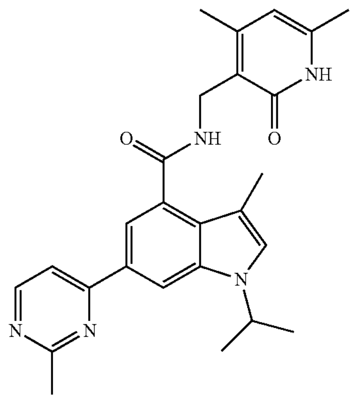 [SMILES: Cc1nccc(-c2cc(C(=O)NCc3c(C)cc(C)[nH]c3=O)c3c(C)cn(C(C)C)c3c2)n1] | N-((4,6-dimethyl-2-oxo-1,2-dihydropyridin-3-yl)methyl)-1-isopropyl-3-methyl-6-(2-methylpyrimidin-4-yl)-1H-indole-4-carboxamide | 1.46 (d, J = 6.57 Hz, 6 H), 2.12 (s, 3 H), 2.18 (s, 3 H), 2.25 (s, 3 H), 2.68 (s, 3 H), 4.37 (d, J = 4.80 Hz, 2 H), 4.92 (spt, J = 6.57 Hz, 1 H), 5.88 (s, 1 H), 7.48 (s, 1 H), 7.84 (d, J = 1.26 Hz, 1 H), 7.98 (d, J = 5.56 Hz, 1 H), 8.22 (t, J = 4.93 Hz, 1 H), 8.37 (d, J = 1.26 Hz, 1 H), 8.68 (d, J = 5.56 Hz, 1 H), 11.48 (s, 1 H) | 444.4 |
| 77 | 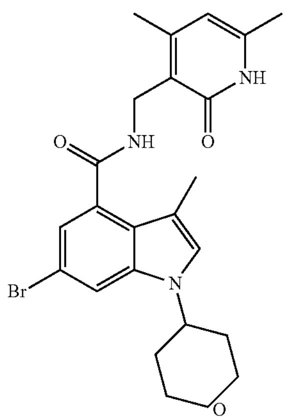 | 6-bromo-N-((4,6-dimethyl-2-oxo-1,2-dihydropyridin-3-yl)methyl)-3-methyl-1-(tetrahydro-2H-pyran-4-yl)-1H-indole-4-carboxamide | 1.76-1.86 (m, 2 H), 1.93 (dd, J = 12.00, 4.17 Hz, 2 H), 2.12 (d, J = 5.81 Hz, 6 H), 2.22 (s, 3 H), 3.49-3.62 (m, 2 H), 3.97 (dd, J = 11.12, 3.79 Hz, 2 H), 4.31 (d, J = 5.05 Hz, 2 H), 4.64 (br. s., 1 H), 5.86 (s, 1 H), 7.02 (d, J = 1.52 Hz, 1 H), 7.36 (s, 1 H), 7.88 (d, J = 1.52 Hz, 1 H), 8.24 (t, J = 4.93 Hz, 1 H), 11.47 (br. s., 1 H) | 472, 474 |
| 78 | 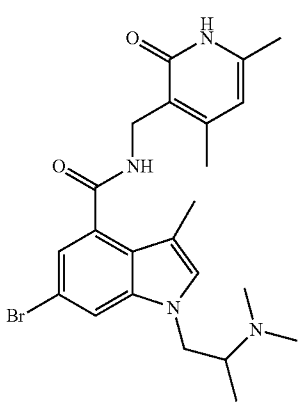 [SMILES: Cc1cc(C)c(CNC(=O)c2cc(Br)cc3c2c(C)cn3CC(C)N(C)C)c(=O)[nH]1] | 6-bromo-N-((4,6-dimethyl-2-oxo-1,2-dihydropyridin-3-yl)methyl)-1-(2-(dimethylamino)propyl)-3-methyl-1H-indole-4-carboxamide | (CHLOROFORM-d) 0.90 (d, J = 6.57 Hz, 3 H), 2.15 (s, 3 H), 2.22 (s, 3 H), 2.34 (s, 6 H), 2.39 (s, 3 H), 2.88-3.11 (m, 1 H), 3.81 (dd, J = 14.27, 8.46 Hz, 1 H), 4.19 (dd, J = 14.02, 4.42 Hz, 1 H), 4.57 (d, J = 5.56 Hz, 2 H), 5.93 (s, 1 H), 6.86 (s, 1 H), 7.20 (d, J = 1.52 Hz, 1 H), 7.45 (d, J = 1.52 Hz, 1 H), 12.52 (br. s., 1 H) | 473.2, 475.2 |

-continued

| Ex | Structure | Name | ¹H NMR (400 MHz, DMSO-d₆) δ ppm | MS (ES) [M + H]⁺ |
|---|---|---|---|---|
| 79 | 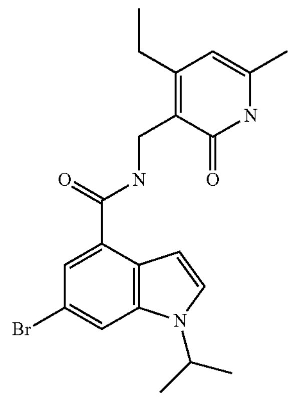 [SMILES: CCc1cc(C)[nH]c(=O)c1CNC(=O)c1cc(Br)cc2c1ccn2C(C)C] | 6-bromo-N-[(4-ethyl-6-methyl-2-oxo-1,2-dihydro-3-pyridinyl)methyl]-1-(1-methylethyl)-1H-indole-4-carboxamide | 11.56 (s, 1 H) 8.31 (t, J = 5.18 Hz, 1 H) 7.92 (s, 1 H) 7.63 (d, J = 3.03 Hz, 1 H) 7.52 (d, J = 1.52 Hz, 1 H) 6.86 (d, J = 3.28 Hz, 1 H) 5.93 (s, 1 H) 4.75-4.90 (m, 1 H) 4.35 (d, J = 5.05 Hz, 2 H) 2.54-2.60 (m, 2 H) 2.14 (s, 3 H) 1.43 (d, J = 6.57 Hz, 6 H), 1.11 (t, J = 7.33 Hz, 3 H) | |
| 80 | 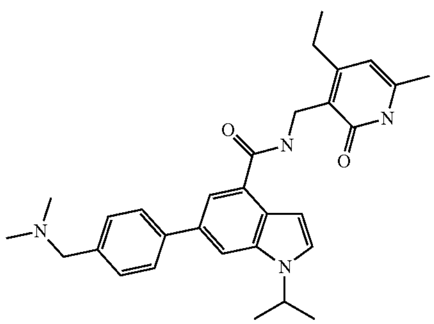 | 6-{4-[(dimethylamino)methyl]phenyl}-N-[(4-ethyl-6-methyl-2-oxo-1,2-dihydro-3-pyridinyl)methyl]-1-(1-methylethyl)-1H-indole-4-carboxamide | 11.56 (s, 1 H) 8.33 (t, J = 5.05 Hz, 1 H) 7.92 (s, 1 H) 7.70-7.78 (m, 3 H) 7.62 (d, J = 3.28 Hz, 1 H) 7.37 (d, J = 8.34 Hz, 2 H) 6.88 (d, J = 3.28 Hz, 1 H) 5.93 (s, 1 H) 4.87-5.04 (m, 1 H) 4.41 (d, J = 5.31 Hz, 2 H) 3.42 (s, 2 H) 2.59 (q, J = 7.58 Hz, 2 H) 2.17 (s, 6 H) 2.14 (s, 3 H) 1.48 (d, J = 6.82 Hz, 6 H) 1.12 (t, J = 7.33 Hz, 3 H) | 485.3 |
| 81 | 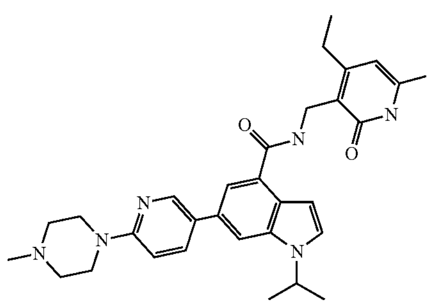 | N-[(4-ethyl-6-methyl-2-oxo-1,2-dihydro-3-pyridinyl)methyl]-1-(1-methylethyl)-6-[6-(4-methyl-1-piperazinyl)-3-pyridinyl]-1H-indole-4-carboxamide | 11.57 (br. s., 1 H) 8.57 (d, J = 2.27 Hz, 1 H) 8.30 (t, J = 5.05 Hz, 1 H) 7.98 (dd, J = 8.97, 2.65 Hz, 1 H) 7.88 (s, 1 H) 7.66 (d, J = 1.26 Hz, 1 H) 7.59 (d, J = 3.28 Hz, 1 H) 6.93 (d, J = 9.09 Hz, 1 H) 6.87 (d, J = 3.03 Hz, 1 H) 5.93 (s, 1 H) 4.88-4.98 (m, 1 H) 4.40 (d, J = 5.05 Hz, 2 H) 3.49-3.59 (m, 4 H) 2.58 (q, J = 7.58 Hz, 2 H) 2.37-2.45 (m, 4 H) 2.23 (s, 3 H) 2.14 (s, 3 H) 1.47 (d, J = 6.82 Hz, 6 H) 1.12 (t, J = 7.33 Hz, 3 H) | 527.2 |
| 82 | 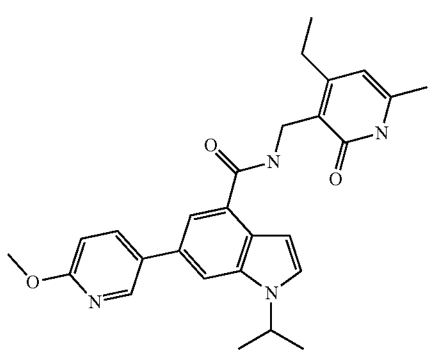 | N-[(4-ethyl-6-methyl-2-oxo-1,2-dihydro-3-pyridinyl)methyl]-1-(1-methylethyl)-6-[6-(methyloxy)-3-pyridinyl]-1H-indole-4-carboxamide | 11.57 (br. s., 1 H) 8.60 (br. s., 1 H) 8.31 (br. s., 1 H) 8.11-8.19 (m, 1 H) 7.94 (s, 1 H) 7.58-7.73 (m, 2 H) 6.85-6.99 (m, 2 H) 5.93 (s, 1 H) 4.87-5.02 (m, 1 H) 4.40 (d, J = 4.29 Hz, 2 H) 3.91 (s, 3 H) 2.55-2.64 (m, 2 H) 2.14 (s, 3 H) 1.48 (d, J = 6.57 Hz, 6 H) 1.12 (t, J = 7.33 Hz, 3 H) | 459.2 |

| Ex | Structure | Name | ¹H NMR (400 MHz, DMSO-d₆) δ ppm | MS (ES) [M + H]⁺ |
|---|---|---|---|---|
| 83 | 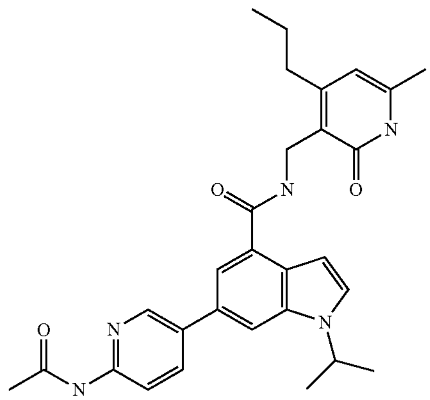 | 6-[6-(acetylamino)-3-pyridinyl]-1-(1-methylethyl)-N-[(6-methyl-2-oxo-4-propyl-1,2-dihydro-3-pyridinyl)methyl]-1H-indole-4-carboxamide | 11.56 (s, 1 H) 10.58 (s, 1 H) 8.76 (d, J = 2.02 Hz, 1 H) 8.32 (t, J = 4.93 Hz, 1 H) 8.14-8.23 (m, 2 H) 8.00 (s, 1 H) 7.73 (d, J = 1.26 Hz, 1 H) 7.65 (d, J = 3.03 Hz, 1 H) 6.90 (d, J = 3.28 Hz, 1 H) 5.92 (s, 1 H) 4.92-5.03 (m, 1 H) 4.41 (d, J = 5.05 Hz, 2 H) 2.53-2.58 (m, 2 H) 2.13 (d, J = 4.04 Hz, 6 H) 1.51-1.61 (m, 2 H) 1.48 (d, J = 6.57 Hz, 6 H) 0.91 (t, J = 7.33, 3 H) | 500.1 |
| 84 | 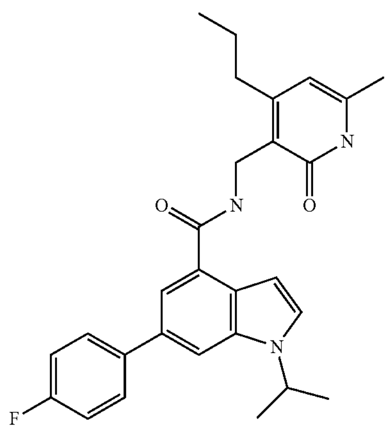 [SMILES: CCCc1cc(C)[nH]c(=O)c1CNC(=O)c1cc(-c2ccc(F)cc2)cc2c1ccn2C(C)C] | 6-(4-fluorophenyl)-1-(1-methylethyl)-N-[(6-methyl-2-oxo-4-propyl-1,2-dihydro-3-pyridinyl)methyl]-1H-indole-4-carboxamide | 11.56 (s, 1 H) 8.31 (t, J = 5.05 Hz, 1 H) 7.92 (s, 1 H) 7.80-7.86 (m, 2 H) 7.68 (d, J = 1.52 Hz, 1 H) 7.63 (d, J = 3.28 Hz, 1 H) 7.27-7.34 (m, 2 H) 6.88 (d, J = 3.03 Hz, 1 H) 5.92 (s, 1 H) 4.91-5.00 (m, 1 H) 4.41 (d, J = 5.05 Hz, 2 H) 2.53-2.58 (m, 2 H) 2.13 (s, 3 H) 1.51-1.59 (m, 2 H) 1.48 (d, J = 6.82 Hz, 6 H) 0.91 (t, J = 7.33 Hz, 3 H) | 460.1 |
| 85 | 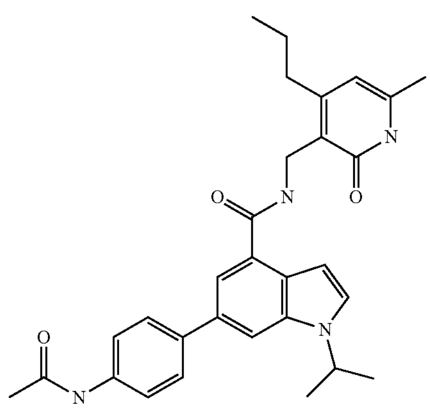 [SMILES: CCCc1cc(C)[nH]c(=O)c1CNC(=O)c1cc(-c2ccc(NC(C)=O)cc2)cc2c1ccn2C(C)C] | 6-[4-(acetylamino)phenyl]-1-(1-methylethyl)-N-[(6-methyl-2-oxo-4-propyl-1,2-dihydro-3-pyridinyl)methyl]-1H-indole-4-carboxamide | 11.56 (br. s., 1 H) 10.02 (s, 1 H) 8.29 (t, J = 5.05 Hz, 1 H) 7.89 (s, 1 H) 7.57-7.75 (m, 6 H) 6.86 (d, J = 3.28 Hz, 1 H) 5.92 (s, 1 H) 4.94 (quin, J = 6.57 Hz, 1 H) 4.41 (d, J = 5.05 Hz, 2 H) 2.57-2.53 (m, 2 H) 2.13 (s, 3 H) 2.07 (s, 3 H) 1.51-1.60 (m, 2 H) 1.48 (d, J = 6.57 Hz, 6 H) 0.91 (t, J = 7.33 Hz, 3 H) | 499.4 |

-continued

| Ex | Structure | Name | ¹H NMR (400 MHz, DMSO-d$_6$) δ ppm | MS (ES) [M + H]$^+$ |
|---|---|---|---|---|
| 86 | 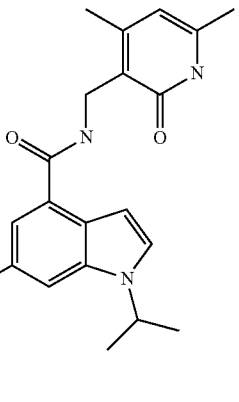 | methyl 4-[4-({[(4,6-dimethyl-2-oxo-1,2-dihydro-3-pyridinyl)methyl]amino}carbonyl)-3-methyl-1-(1-methylethyl)-1H-indol-6-yl]benzoate | 11.48 (s, 1 H) 8.23 (t, J = 5.05 Hz, 1 H) 8.01-8.07 (m, 2 H) 7.90-7.96 (m, 3 H) 7.39 (s, 1 H), 7.33 (d, J = 1.26 Hz, 1 H) 5.87 (s, 1 H), 4.91 (t, J = 6.69 Hz, 1 H) 4.36 (d, J = 4.80 Hz, 2 H) 3.88 (s, 3 H) 2.24 (s, 3 H) 2.18 (s, 3 H) 2.11 (s, 3 H) 1.44 (d, J = 6.57 Hz, 6 H) | 486.1 |
| 87 | 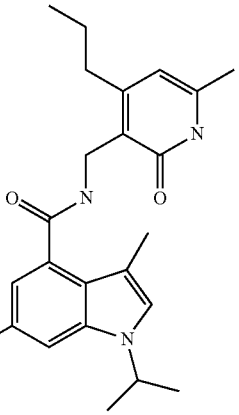 | methyl 5-[3-methyl-1-(1-methylethyl)-4-({[(6-methyl-2-oxo-4-propyl-1,2-dihydro-3-pyridinyl)methyl]amino}carbonyl)-1H-indol-6-yl]-2-pyridinecarboxylate | 11.50 (s, 1 H) 9.13 (d, J = 1.77 Hz, 1 H) 8.36 (dd, J = 8.34, 2.27 Hz, 1 H) 8.23 (t, J = 5.05 Hz, 1 H) 8.13 (d, J = 8.34 Hz, 1 H) 8.02 (d, J = 1.52 Hz, 1 H) 7.43 (s, 1 H) 7.37 (d, J = 1.52 Hz, 1 H) 5.91 (s, 1 H) 4.88-4.99 (m, 1 H) 4.38 (d, J = 5.05 Hz, 2 H) 3.91 (s, 3 H) 2.53-2.59 (m, 2 H) 2.19 (s, 3 H) 2.13 (s, 3 H) 1.52-1.64 (m, 2 H) 1.45 (d, J = 6.57 Hz, 6 H) 0.94 (t, J = 7.33 Hz, 3 H) | 515.1 |
| 88 | 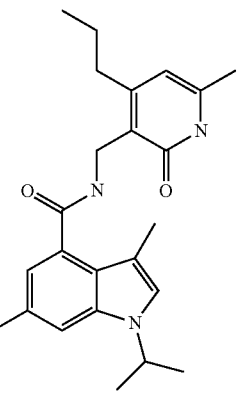 | methyl 3-[3-methyl-1-(1-methylethyl)-4-({[(6-methyl-2-oxo-4-propyl-1,2-dihydro-3-pyridinyl)methyl]amino}carbonyl)-1H-indol-6-yl]benzoate | 11.49 (br. s., 1 H) 8.19-8.31 (m, 2 H) 8.01-8.08 (m, 1 H), 7.95-7.90 (m, 1 H) 7.85 (s, 1 H) 7.59-7.65 (m, 1 H) 7.37 (s, 1 H) 7.26 (s, 1 H) 5.91 (br. s., 1 H) 4.87-4.97 (m, 1 H) 4.38 (d, J = 4.29 Hz, 2 H) 3.91 (s, 3 H) 2.55-2.62 (m, 2 H) 2.19 (s, 3 H) 2.12 (s, 3 H) 1.55-1.65 (m, 2 H) 1.44 (d, J = 6.57 Hz, 6 H) 0.94 (t, J = 7.2 Hz, 3 H) | 514.2 |

-continued

| Ex | Structure | Name | ¹H NMR (400 MHz, DMSO-d₆) δ ppm | MS (ES) [M + H]⁺ |
|---|---|---|---|---|
| 89 | 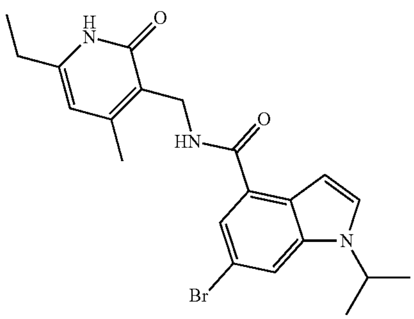 [SMILES: CCc1cc(C)c(CNC(=O)c2cc(Br)cc3c2ccn3C(C)C)c(=O)[nH]1] | 6-bromo-N-((6-ethyl-4-methyl-2-oxo-1,2-dihydropyridin-3-yl)methyl)-1-isopropyl-1H-indole-4-carboxamide | 8.36 (br. s., 1H), 7.92 (s, 1H), 7.63 (d, J = 3.28 Hz, 1 H), 7.53 (d, J = 1.77 Hz, 1H), 6.88 (d, J = 3.28 Hz, 1H), 5.91 (s, 1H), 4.82 (dt, J = 6.60, 13.33 Hz, 1H), 4.33 (d, J = 5.05 Hz, 2H), 2.42 (q, J = 7.58 Hz, 2H), 2.23 (s, 3H), 1.43 (d, J = 6.57 Hz, 6H), 1.14 (t, J = 7.58 Hz, 3H) | 432.2 |
| 90 | 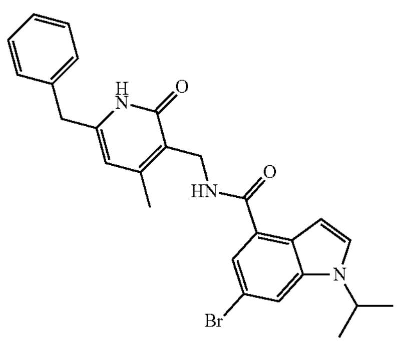 [SMILES: Cc1cc(Cc2ccccc2)[nH]c(=O)c1CNC(=O)c1cc(Br)cc2c1ccn2C(C)C] | N-((6-benzyl-4-methyl-2-oxo-1,2-dihydropyridin-3-yl)methyl)-6-bromo-1-isopropyl-1H-indole-4-carboxamide | 7.62 (d, J = 3.28 Hz, 1 H), 7.51 (d, J = 1.52 Hz, 1H), 7.32 (s, 4H), 7.23 (td, J = 2.78, 5.56 Hz, 1H), 6.87 (d, J = 3.28 Hz, 1H), 5.89 (s, 1H), 4.82 (ddd, J = 6.44, 6.57, 13.26 Hz, 1H), 4.31 (d, J = 5.05 Hz, 2H), 3.74 (s, 2 H), 2.19 (s, 3H), 1.43 (d, J = 6.82 Hz, 6H) | 494.2 |
| 91 | 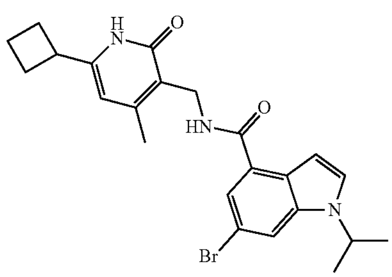 [SMILES: Cc1cc(C2CCC2)[nH]c(=O)c1CNC(=O)c1cc(Br)cc2c1ccn2C(C)C] | 6-bromo-N-((6-cyclobutyl-4-methyl-2-oxo-1,2-dihydropyridin-3-yl)methyl)-1-isopropyl-1H-indole-4-carboxamide | 8.40 (br. s., 1 H) 7.92 (s, 1 H), 7.63 (d, J = 3.28 Hz, 1H), 7.53 (d, J = 1.77 Hz, 1H), 6.88 (d, J = 3.28 Hz, 1H), 5.96 (s, 1H), 4.82 (quin, J = 6.63 Hz, 1H), 4.33 (d, J = 4.80 Hz, 2H), 3.25-3.38 (m, 2H), 2.25 (s, 3H), 2.06-2.22 (m, 4H), 1.84-1.99 (m, 1H), 1.70-1.82 (m, 1H), 1.43 (d, J = 6.57 Hz, 6H) | 455.9 |
| 92 | 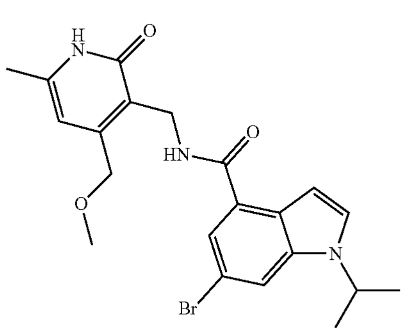 [SMILES: COCc1cc(C)[nH]c(=O)c1CNC(=O)c1cc(Br)cc2c1ccn2C(C)C] | 6-bromo-1-(1-methylethyl)-N-({6-methyl-4-[(methyloxy)methyl]-2-oxo-1,2-dihydro-3-pyridinyl}methyl)-1H-indole-4-carboxamide | 11.70 (s, 1H), 8.32 (t, J = 5.05 Hz, 1H), 7.93 (s, 1H), 7.63 (d, J = 3.28 Hz, 1H), 7.51 (d, J = 1.52 Hz, 1H), 6.87 (d, J = 3.03 Hz, 1H), 6.09 (s, 1H), 4.82 (quin, J = 6.63 Hz, 1H), 4.49 (s, 2H), 4.30 (d, J = 5.05 Hz, 2H), 3.32 (s, 3H), 2.17 (s, 3H), 1.43 (d, J = 6.57 Hz, 6H) | 447.8 |

| Ex | Structure | Name | $^1$H NMR (400 MHz, DMSO-d$_6$) δ ppm | MS (ES) [M + H]$^+$ |
|---|---|---|---|---|
| 93 | 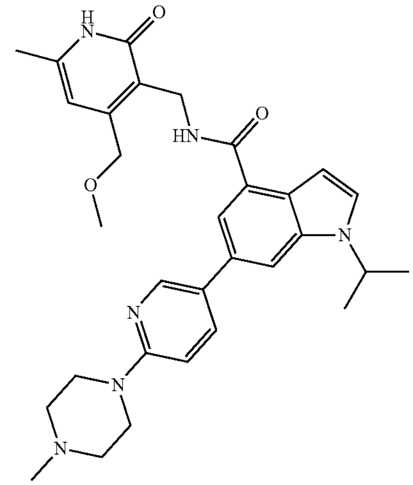 [SMILES: COCc1cc(C)[nH]c(=O)c1CNC(=O)c1cc(-c2ccc(N3CCN(C)CC3)nc2)cc2c1ccn2C(C)C] | 1-(1-methylethyl)-N-({6-methyl-4-[(methyloxy)methyl]-2-oxo-1,2-dihydro-3-pyridinyl}methyl)-6-[6-(4-methyl-1-piperazinyl)-3-pyridinyl]-1H-indole-4-carboxamide | 8.58 (d, J = 2.53 Hz, 1 H), 8.31 (t, J = 5.05 Hz, 1H), 8.17 (s, 1H), 7.99 (dd, J = 2.53, 8.84 Hz, 1H), 7.88 (s, 1H), 7.66 (d, J = 1.26 Hz, 1H), 7.59 (d, J = 3.28 Hz, 1H), 6.94 (d, J = 8.84 Hz, 1H), 6.87 (d, J = 3.28 Hz, 1H), 6.10 (s, 1H), 4.93 (dq, J = 6.65, 6.82 Hz, 1H), 4.52 (s, 2H), 4.35 (d, J = 5.05 Hz, 2H), 3.50-3.58 (m, 4H), 3.32 (s, 3H), 2.45 (t, J = 4.93 Hz, 4H), 2.25 (s, 3H), 2.17 (s, 3H), 1.47 (d, J = 6.57 Hz, 6H) | 543.1 |
| 94 | 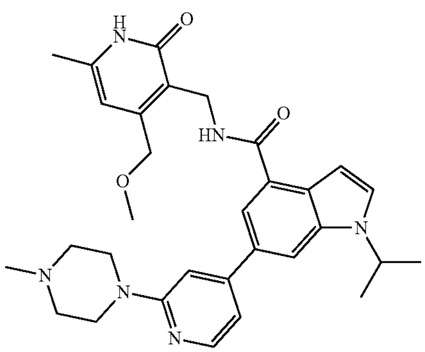 [SMILES: COCc1cc(C)[nH]c(=O)c1CNC(=O)c1cc(-c2ccnc(N3CCN(C)CC3)c2)cc2c1ccn2C(C)C] | 1-(1-methylethyl)-N-({6-methyl-4-[(methyloxy)methyl]-2-oxo-1,2-dihydro-3-pyridinyl}methyl)-6-[2-(4-methyl-1-piperazinyl)-4-pyridinyl]-1H-indole-4-carboxamide | 8.35 (t, J = 5.18 Hz, 1H), 8.18 (s, 1H), 8.16 (s, 2H), 8.05 (s, 1H), 7.74 (d, J = 1.26 Hz, 1H), 7.69 (d, J = 3.28 Hz, 1H), 7.17 (s, 1H), 7.11 (dd, J = 1.01, 5.31 Hz, 1H), 6.90 (d, J = 3.28 Hz, 1H), 6.10 (s, 1H), 5.01 (quin, J = 6.57 Hz, 1H), 4.53 (s, 2H), 4.35 (d, J = 5.31 Hz, 2H), 3.54-3.68 (m, 4H), 3.32 (s, 3H), 2.51-2.54 (m, 4H), 2.30 (s, 3H), 2.17 (s, 3H), 1.48 (d, J = 6.57 Hz, 6H) | 543.2 |
| 95 | 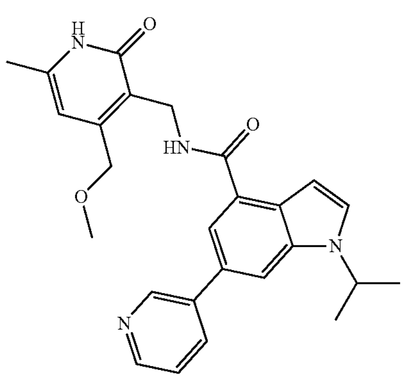 [SMILES: COCc1cc(C)[nH]c(=O)c1CNC(=O)c1cc(-c2cccnc2)cc2c1ccn2C(C)C] | 1-(1-methylethyl)-N-({6-methyl-4-[(methyloxy)methyl]-2-oxo-1,2-dihydro-3-pyridinyl}methyl)-6-(3-pyridinyl)-1H-indole-4-carboxamide | 11.75 (s, 1H), 9.05 (d, J = 2.02 Hz, 1H), 8.55 (dd, J = 1.52, 4.80 Hz, 1H), 8.39 (t, J = 5.18 Hz, 1H), 8.21 (dddd, J = 1.17, 1.52, 8.02 Hz, 1H), 8.15 (s, 1H), 8.05 (s, 1H), 7.76 (d, J = 1.52 Hz, 1H), 7.66 (d, J = 3.28 Hz, 1H), 7.49 (qd, J = , , Hz, 1H), 6.93 (d, J = 3.28 Hz, 1H), 6.10 (s, 1H), 4.98 (quin, J = 6.63 Hz, 1H), 4.52 (s, 2H), 4.36 (d, J = 5.05 Hz, 2H), 3.32 (s, 3H), 2.17 (s, 3H), 1.48 (d, J = 6.57 Hz, 6H) | 445.2 |

| Ex | Structure | Name | ¹H NMR (400 MHz, DMSO-d₆) δ ppm | MS (ES) [M + H]⁺ |
|---|---|---|---|---|
| 96 | 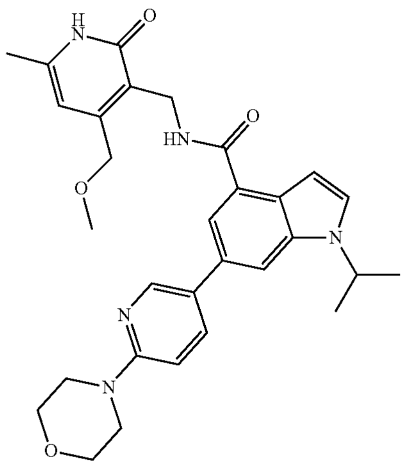 [SMILES: COCc1cc(C)[nH]c(=O)c1CNC(=O)c1cc(-c2ccc(N3CCOCC3)nc2)cc2c1ccn2C(C)C] | 1-(1-methylethyl)-N-({6-methyl-4-[(methyloxy)methyl]-2-oxo-1,2-dihydro-3-pyridinyl}methyl)-6-[6-(4-morpholinyl)-3-pyridinyl]-1H-indole-4-carboxamide | 11.71 (br. s., 1 H), 8.60 (d, J = 2.53 Hz, 1H), 8.31 (t, J = 5.05 Hz, 1H), 8.15 (s, 1H), 8.02 (dd, J = 2.53, 8.84 Hz, 1H), 7.89 (s, 1H), 7.67 (d, J = 1.26 Hz, 1H), 7.59 (d, J = 3.28 Hz, 1H), 6.95 (d, J = 8.59 Hz, 1H), 6.88 (d, J = 3.28 Hz, 1H), 6.10 (s, 1H), 4.93 (quin, J = 6.63 Hz, 1H), 4.52 (s, 2H), 4.35 (d, J = 5.05 Hz, 2H), 3.70-3.77 (m, 4H), 3.46-3.52 (m, 4H), 3.32 (s, 3H), 2.17 (s, 3H), 1.47 (d, J = 6.57 Hz, 6H) | 530.9 |
| 97 | 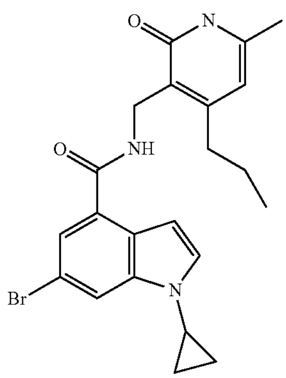 [SMILES: CCCc1cc(C)[nH]c(=O)c1CNC(=O)c1cc(Br)cc2c1ccn2C1CC1] | 6-bromo-1-cyclopropyl-N-[(6-methyl-2-oxo-4-propyl-1,2-dihydro-3-pyridinyl)methyl]-1H-indole-4-carboxamide | 11.56 (s, 1 H), 8.32 (t, J = 4.9 Hz, 1 H), 7.85 (s, 1 H), 7.56 (d, J = 1.8 Hz, 1 H), 7.45 (d, J = 3.3 Hz, 1 H), 6.78 (d, J = 3.0 Hz, 1 H), 5.90 (s, 1 H), 4.34 (d, J = 5.1 Hz, 2 H), 3.47 (dt, J = 7.0, 3.4 Hz, 1 H), 2.53 (br. s.,1 H), 2.13 (s, 3 H), 1.52 (m, 2 H), 1.07 (m, 2 H), 0.92 (m, 5 H) | 442.0 |
| 98 | 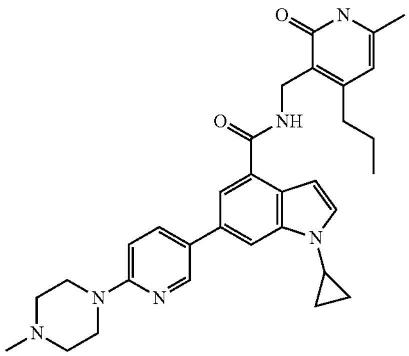 | 1-cyclopropyl-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide | 11.56 (s, 1 H), 8.54 (d, J = 2.5 Hz, 1 H), 8.30 (t, J = 5.1 Hz, 1 H), 7.95 (dd, J = 9.0, 2.7 Hz, 1 H), 7.85 (s, 1 H), 7.68 (d, J = 1.5 Hz, 1 H), 7.41 (d, J = 3.0 Hz, 1 H), 6.94 (d, J = 8.8 Hz, 1 H), 6.80 (d, J = 3.3 Hz, 1 H), 5.91 (s, 1 H), 4.39 (d, J = 5.1 Hz, 2 H), 3.51 (m, 5 H), 2.54 (m, 2 H), 2.41 (m, 4 H), 2.21 (m, 3 H), 2.13 (s, 3 H), 1.53 (m, 2 H), 1.09 (m, 2 H), 0.98 (m, 2 H), 0.89 (t, J = 7.3 Hz, 3 H) | 539.4 |

-continued

| Ex | Structure | Name | ¹H NMR (400 MHz, DMSO-d₆) δ ppm | MS (ES) [M + H]⁺ |
|---|---|---|---|---|
| 99 | 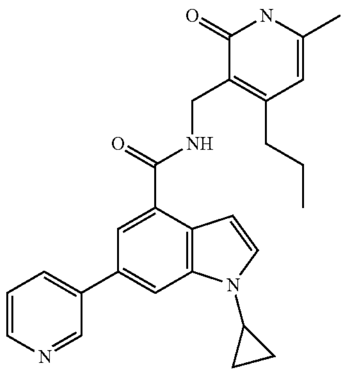 [SMILES: CCCc1cc(C)[nH]c(=O)c1CNC(=O)c1cc(-c2cccnc2)cc2c1ccn2C1CC1] | 1-cyclopropyl-N-[(6-methyl-2-oxo-4-propyl-1,2-dihydro-3-pyridinyl)methyl]-6-(3-pyridinyl)-1H-indole-4-carboxamide | 11.56 (s, 1 H), 9.02 (d, J = 1.8 Hz, 1 H), 8.56 (dd, J = 4.8, 1.5 Hz, 1 H), 8.37 (t, J = 5.1 Hz, 1 H), 8.18 (dt, J = 8.3, 1.9 Hz, 1 H), 7.99 (s, 1 H), 7.78 (d, J = 1.5 Hz, 1 H), 7.50 (m, 2 H), 6.85 (d, J = 3.3 Hz, 1 H), 5.91 (s, 1 H), 4.40 (d, J = 5.1 Hz, 2 H), 3.55 (tt, J = 7.0, 3.6 Hz, 1 H), 2.54 (m, 2 H), 2.13 (s, 3 H), 1.53 (m, 2 H), 1.11 (m, 2 H), 1.00 (m, 2 H), 0.89 (t, J = 7.3 Hz, 3 H) | 441.0 |
| 100 | 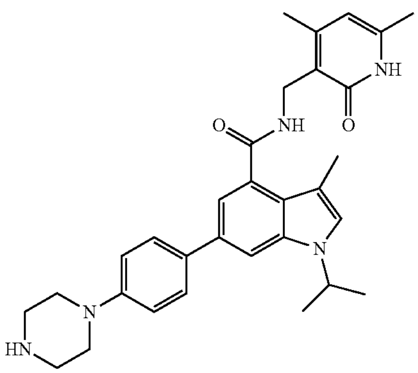 [SMILES: Cc1cc(C)c(CNC(=O)c2cc(-c3ccc(N4CCNCC4)cc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(4-(piperazin-1-yl)phenyl)-1H-indole-4-carboxamide | 1.43 (d, J = 6.57 Hz, 6 H), 2.11 (s, 3 H), 2.16 (s, 3 H), 2.24 (s, 3 H), 2.82-2.90 (m, 4 H), 3.04-3.12 (m, 4 H), 4.35 (d, J = 5.05 Hz, 2 H), 4.84 (quin, J = 6.63 Hz, 1 H), 5.87 (s, 1 H), 7.00 (d, J = 8.84 Hz, 2 H), 7.19 (d, J = 1.52 Hz, 1 H), 7.25-7.31 (m, 1 H), 7.59 (d, J = 8.84 Hz, 2 H), 7.67 (d, J = 1.26 Hz, 1 H), 8.14 (t, J = 5.05 Hz, 1 H) | 512.4 |
| 101 | 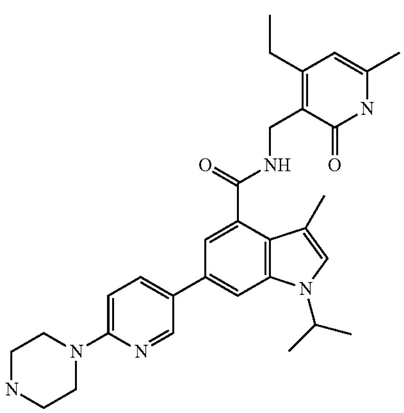 [SMILES: CCc1cc(C)[nH]c(=O)c1CNC(=O)c1cc(-c2ccc(N3CCNCC3)nc2)cc2c1c(C)cn2C(C)C] | N-[(4-ethyl-6-methyl-2-oxo-1,2-dihydro-3-pyridinyl)methyl]-3-methyl-1-(1-methylethyl)-6-[6-(1-piperazinyl)-3-pyridinyl]-1H-indole-4-carboxamide | 11.50 (br. s., 1 H) 8.50 (d, J = 2.53 Hz, 1 H) 8.13 (t, J = 4.80 Hz, 1 H) 7.91 (dd, J = 8.84, 2.53 Hz, 1 H) 7.69-7.76 (m, 1 H) 7.29 (s, 1 H) 7.18 (d, J = 1.26 Hz, 1 H) 6.88 (d, J = 8.84 Hz, 1 H) 5.92 (s, 1 H) 4.80-4.89 (m, 1 H) 4.38 (br. s., 1 H) 4.36 (br. s., 1 H) 3.39-3.51 (m, 4 H) 2.71-2.85 (m, 4 H) 2.53-2.63 (m, 3 H) 2.16 (s, 3 H) 2.13 (s, 3 H) 1.44 (s, 3 H) 1.42 (s, 3 H) 1.14 (t, J = 7.58 Hz, 3 H) | 527.2 |
| 102 | 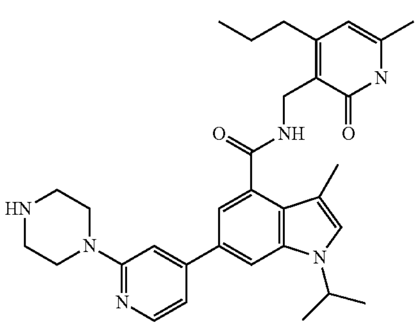 [SMILES: CCCc1cc(C)[nH]c(=O)c1CNC(=O)c1cc(-c2ccnc(N3CCNCC3)c2)cc2c1c(C)cn2C(C)C] | 1-isopropyl-3-methyl-N-((6-methyl-2-oxo-4-propyl-1,2-dihydropyridin-3-yl)methyl)-6-(2-(piperazin-1-yl)pyridin-4-yl)-1H-indole-4-carboxamide | 11.51 (br. s., 1 H) 8.18 (t, J = 5.05 Hz, 1 H) 8.11-8.16 (m, 1 H) 7.90 (d, J = 1.52 Hz, 1 H) 7.39 (s, 1 H) 7.30 (d, J = 1.52 Hz, 1 H) 6.99-7.12 (m, 2 H) 5.90 (s, 1 H) 4.93 (quin, J = 6.63 Hz, 1 H) 4.38 (br. s., 1 H) 4.36 (br. s., 1 H) 3.42-3.61 (m, 4 H) 2.79-2.83 (m, 3 H) 2.53-2.58 (m, 2 H) 2.17 (s, 3 H) 2.12 (s, 3 H) 1.53-1.62 (m, 2 H) 1.45 (s, 3 H) 1.43 (s, 3 H) 0.94 (t, J = 7.33 Hz, 3 H) | 541.4 |

-continued

| Ex | Structure | Name | ¹H NMR (400 MHz, DMSO-d₆) δ ppm | MS (ES) [M + H]⁺ |
|---|---|---|---|---|
| 103 | 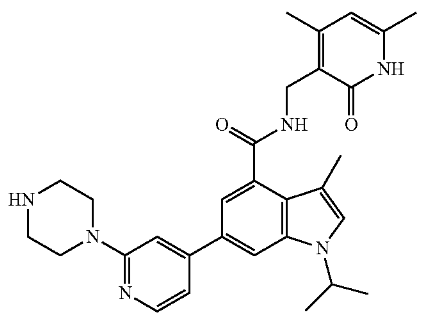 [SMILES: Cc1cc(C)c(CNC(=O)c2cc(-c3ccnc(N4CCNCC4)c3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(2-(piperazin-1-yl)pyridin-4-yl)-1H-indole-4-carboxamide | 11.51 (br. s., 1 H) 8.21 (t, J = 4.93 Hz, 1 H) 8.14 (d, J = 5.05 Hz, 1 H) 7.90 (d, J = 1.52 Hz, 1 H) 7.38 (s, 1 H) 7.31 (d, J = 1.52 Hz, 1 H) 7.08 (s, 1 H) 7.02 (d, J = 4.80 Hz, 1 H) 5.87 (s, 1 H) 4.93 (quin, J = 6.57 Hz, 1 H) 4.36 (s, 1 H) 4.35 (s, 1 H) 3.43-3.52 (m, 4 H) 3.35 (br. s., 2 H) 2.79-2.84 (m, 3 H) 2.25 (s, 3 H) 2.16 (s, 3 H) 2.11 (s, 3 H) 1.44 (s, 3 H) 1.43 (s, 3 H) | 513.3 |
| 104 | 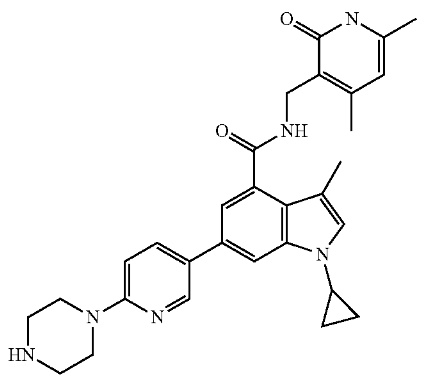 [SMILES: Cc1cc(C)c(CNC(=O)c2cc(-c3ccc(N4CCNCC4)nc3)cc3c2c(C)cn3C2CC2)c(=O)[nH]1] | 1-cyclopropyl-N-[(4,6-dimethyl-2-oxo-1,2-dihydro-3-pyridinyl)methyl]-3-methyl-6-[6-(1-piperazinyl)-3-pyridinyl]-1H-indole-4-carboxamide | 11.46 (br. s., 1 H), 8.48 (d, J = 2.3 Hz, 1 H), 8.16 (t, J = 5.1 Hz, 1 H), 7.89 (dd, J = 9.0, 2.7 Hz, 1 H), 7.70 (d, J = 1.5 Hz, 1 H), 7.22 (d, J = 1.5 Hz, 1 H), 7.11 (d, J = 1.0 Hz, 1 H), 6.89 (d, J = 8.8 Hz, 1 H), 5.86 (s, 1 H), 4.34 (d, J = 5.1 Hz, 2 H), 3.42 (m, 5 H), 2.80 (m, 4 H), 2.23 (s, 3 H), 2.12 (d, J = 7.1 Hz, 6 H), 1.05 (m, 2 H), 0.91 (m, 2 H) | 511.3 |
| 105 | 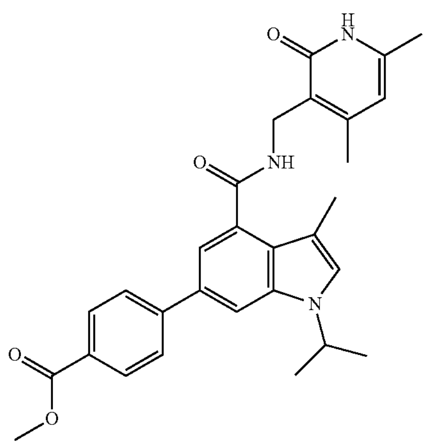 [SMILES: COC(=O)c1ccc(-c2cc(C(=O)NCc3c(C)cc(C)[nH]c3=O)c3c(C)cn(C(C)C)c3c2)cc1] | methyl 4-[4-({[(4,6-dimethyl-2-oxo-1,2-dihydro-3-pyridinyl)methyl]amino}carbonyl)-3-methyl-1-(1-methylethyl)-1H-indol-6-yl]benzoate | 11.48 (s, 1 H) 8.23 (t, J = 5.05 Hz, 1 H) 8.01-8.07 (m, 2 H) 7.90-7.96 (m, 3 H) 7.39 (s, 1 H) 7.33 (d, J = 1.26 Hz, 1 H) 5.87 (s, 1 H) 4.91 (t, J = 6.69 Hz, 1 H) 4.36 (d, J = 4.80 Hz, 2 H) 3.88 (s, 3 H) 2.24 (s, 3 H) 2.18 (s, 3 H) 2.11 (s, 3 H) 1.44 (d, J = 6.57 Hz, 6 H) | 486.1 |
| 106 | 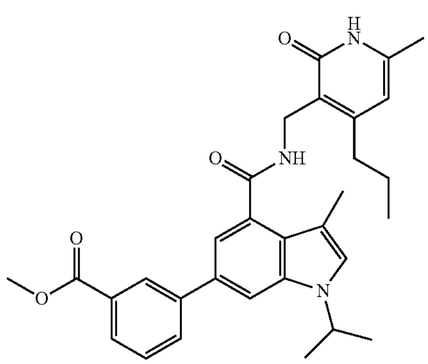 | methyl 3-[3-methyl-1-(1-methylethyl)-4-({[(6-methyl-2-oxo-4-propyl-1,2-dihydro-3-pyridinyl)methyl]amino}carbonyl)-1H-indol-6-yl]benzoate | 11.49 (br. s., 1 H) 8.19-8.31 (m, 2 H) 8.01-8.08 (m, 1 H) 7.95-7.90 (m, 1 H) 7.85 (s, 1 H) 7.59-7.65 (m, 1 H) 7.37 (s, 1 H) 7.26 (s, 1 H) 5.91 (br. s., 1 H) 4.87-4.97 (m, 1 H) 4.38 (d, J = 4.29 Hz, 2 H) 3.91 (s, 3 H) 2.55-2.62 (m, 2 H) 2.19 (s, 3 H) 2.12 (s, 3 H) 1.55-1.65 (m, 2 H) 1.44 (d, J = 6.57 Hz, 6 H) 0.94 (t, J = 7.2 Hz, 3 H) | 514.2 |

-continued

| Ex | Structure | Name | ¹H NMR (400 MHz, DMSO-d₆) δ ppm | MS (ES) [M + H]⁺ |
|---|---|---|---|---|
| 107 | 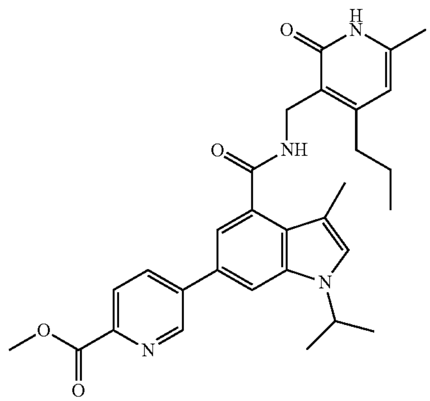 | methyl 5-[3-methyl-1-(1-methylethyl)-4-({[(6-methyl-2-oxo-4-propyl-1,2-dihydro-3-pyridinyl)methyl]amino}carbonyl)-1H-indol-6-yl]-2-pyridinecarboxylate | 11.50 (s, 1 H) 9.13 (d, J = 1.77 Hz, 1 H) 8.36 (dd, J = 8.34, 2.27 Hz, 1 H) 8.23 (t, J = 5.05 Hz, 1 H) 8.13 (d, J = 8.34 Hz, 1 H) 8.02 (d, J = 1.52 Hz, 1 H) 7.43 (s, 1 H) 7.37 (d, J = 1.52 Hz, 1 H) 5.91 (s, 1 H) 4.88-4.99 (m, 1 H) 4.38 (d, J = 5.05 Hz, 2 H) 3.91 (s, 3 H) 2.53-2.59 (m, 2 H) 2.19 (s, 3 H) 2.13 (s, 3 H) 1.52-1.64 (m, 2 H) 1.45 (d, J = 6.57 Hz, 6 H) 0.94 (t, J = 7.33 Hz, 3 H) | 515.1 |
| 108 | 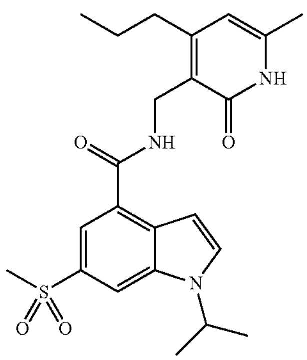 | 1-isopropyl-N-(6-methyl-2-oxo-4-propyl-1,2-dihydropyridin-3-yl)methyl)-6-(methylsulfonyl)-1H-indole-4-carboxamide | 0.91 (t, J = 8.00 Hz, 3 H), 1.45-1.60 (m, 8 H), 2.14 (s, 3 H), 3.23 (s, 3 H), 4.40 (d, J = 4.80 Hz, 2 H), 4.92-5.04 (m, 1 H) 5.92 (s, 1 H), 6.99 (d, J = 3.03 Hz, 1 H), 7.86 (d, J = 1.26 Hz, 1 H), 7.94 (d, J = 3.28 Hz, 1 H), 8.20 (s, 1 H), 8.44 (t, J = 4.80 Hz, 1 H), 11.58 (s, 1 H) | 444.2 |
| 109 | 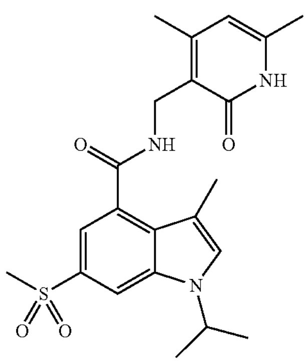 | N-((4,6-dimethyl-2-oxo-1,2-dihydropyridin-3-yl)methyl)-1-isopropyl-3-methyl-6-(methylsulfonyl)-1H-indole-4-carboxamide | 1.42-1.51 (d, J = 8.00 Hz, 6 H), 2.12 (s, 3 H), 2.19 (s, 3 H), 2.24 (s, 3 H), 3.20 (s, 3 H), 4.35 (d, J = 5.05 Hz, 2 H), 4.89 (quin, J = 6.69 Hz, 1 H), 5.88 (s, 1 H), 7.41 (s, 1 H) 7.66 (s, 1 H), 8.07 (d, J = 1.52 Hz, 1 H), 8.37 (t, J = 4.93 Hz, 1 H), 11.50 (s, 1 H) | 430.0 |
| 110 | 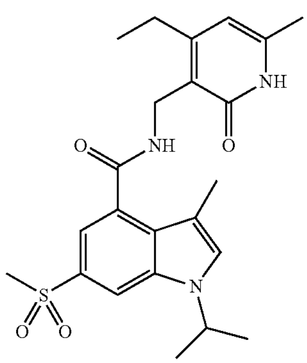 | N-((4-ethyl-6-methyl-2-oxo-1,2-dihydropyridin-3-yl)methyl)-1-isopropyl-3-methyl-6-(methylsulfonyl)-1H-indole-4-carboxamide | 1.14 (m, 3 H), 1.45 (d, J = 6.57 Hz, 6 H), 2.13 (s, 3 H), 2.19 (s, 3 H), 2.54-2.65 (m, 3 H), 3.20 (s, 3 H), 4.37 (d, J = 5.05 Hz, 2 H), 4.89 (quin, J = 6.69 Hz, 1 H), 5.93 (s, 1 H), 7.40 (d, J = 1.52 Hz, 1 H), 7.66 (s, 1 H), 8.07 (d, J = 1.52 Hz, 1 H), 8.36 (t, J = 5.05 Hz, 1 H), 11.51 (s, 1 H) | 444.2 |

-continued

| Ex | Structure | Name | ¹H NMR (400 MHz, DMSO-d$_6$) δ ppm | MS (ES) [M + H]⁺ |
|---|---|---|---|---|
| 111 | 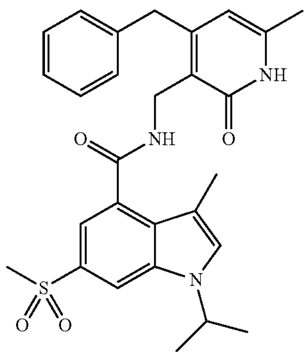 | N-((4-benzyl-6-methyl-2-oxo-1,2-dihydropyridin-3-yl)methyl)-1-isopropyl-3-methyl-6-(methylsulfonyl)-1H-indole-4-carboxamide | 1.45 (m, 6 H), 2.09 (s, 3 H), 2.18 (s, 3 H), 3.20 (s, 3 H), 3.99 (s, 2 H), 4.44 (d, J = 5.05 Hz, 2 H), 4.89 (quin, J = 6.69 Hz, 1 H), 5.79 (s, 1 H), 7.16-7.28 (m, 3 H), 7.30-7.36 (m, 2 H), 7.42 (d, J = 1.52 Hz, 1 H), 7.66 (s, 1 H), 8.08 (d, J = 1.52 Hz, 1 H), 8.05 (t, J = 5.05 Hz, 1 H), 11.58 (s, 1 H) | 505.9 |
| 112 | 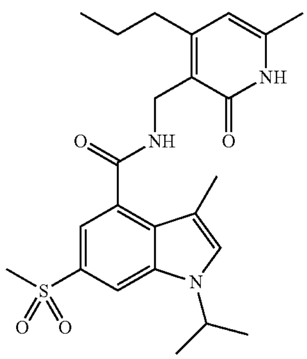 | 1-isopropyl-3-methyl-N-((6-methyl-2-oxo-4-propyl-1,2-dihydropyridin-3-yl)methyl)-6-(methylsulfonyl)-1H-indole-4-carboxamide | 0.94 (m, 3 H), 1.45 (d, J = 6.57 Hz, 6 H), 1.56 (sxt, J = 7.53 Hz, 2 H), 2.13 (s, 3 H), 2.19 (s, 3 H), 3.19 (s, 3 H), 4.37 (d, J = 4.80 Hz, 2 H), 4.89 (dt, J = 13.33, 6.60 Hz, 1 H), 5.91 (s, 1 H), 7.40 (d, J = 1.52 Hz, 1 H), 7.66 (s, 1 H), 8.08 (d, J = 1.26 Hz, 1 H), 8.35 (t, J = 4.67 Hz, 1 H), 11.51 (s, 1 H) | 458.2 |
| 113 | 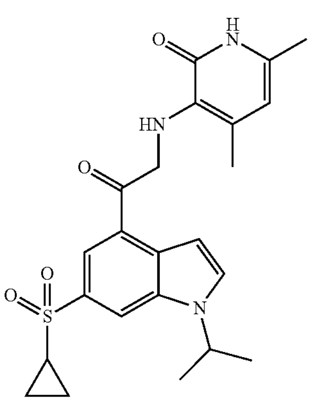 [SMILES: Cc1cc(C)c(NCC(=O)c2cc(S(=O)(=O)C3CC3)cc3c2ccn3C(C)C)c(=O)[nH]1] | 3-({2-[5-(cyclopropylsulfonyl)-3-methyl-1-(1-methylethyl)-1H-indol-4-yl]-2-oxoethyl}amino)-4,6-dimethyl-2(1H)-pyridinone | 0.93-1.06 (m, 2 H), 1.11-1.25 (m, 2 H), 1.49 (d, J = 6.57 Hz, 6 H), 2.13 (s, 3 H), 2.24 (s, 3 H), 2.81-2.98 (m, 1 H), 4.37 (d, J = 5.05 Hz, 2 H), 4.99 (dt, J = 13.33, 6.60 Hz, 1 H), 5.90 (s, 1 H), 6.99 (d, J = 3.28 Hz, 1 H), 7.85 (d, J = 1.52 Hz, 1 H), 7.93 (d, J = 3.28 Hz, 1 H), 8.16 (s, 1 H), 8.49 (t, J = 4.93 Hz, 1 H), 11.57 (br. s., 1 H) | 442.0 |
| 114 | 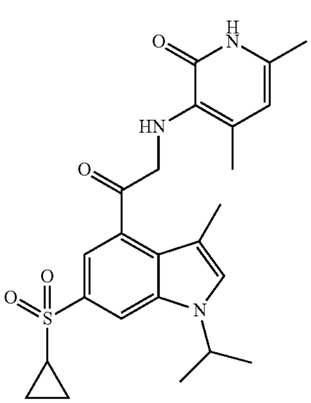 [SMILES: Cc1cc(C)c(NCC(=O)c2cc(S(=O)(=O)C3CC3)cc3c2c(C)cn3C(C)C)c(=O)[nH]1] | 3-({2-[6-(cyclopropylsulfonyl)-3-methyl-1-(1-methylethyl)-1H-indol-4-yl]-2-oxoethyl}amino)-4,6-dimethyl-2(1H)-pyridinone | 1.00 (dd, J = 7.71, 2.65 Hz, 2 H), 1.13 (dd, J = 4.67, 2.40 Hz, 2 H), 1.45 (d, J = 6.57 Hz, 6 H), 2.12 (s, 3 H), 2.19 (s, 3 H), 2.23 (s, 3 H), 2.76-2.95 (m, 1 H), 4.35 (d, J = 5.05 Hz, 2 H), 4.91 (quin, J = 6.63 Hz, 1 H), 5.88 (s, 1 H), 7.36 (d, J = 1.52 Hz, 1 H), 7.66 (s, 1 H), 8.03 (d, J = 1.52 Hz, 1 H), 8.40 (t, J = 4.93 Hz, 1 H), 11.51 (s, 1 H) | 455.9 |

| Ex | Structure | Name | $^1$H NMR (400 MHz, DMSO-d$_6$) δ ppm | MS (ES) [M + H]$^+$ |
|---|---|---|---|---|
| 115 | 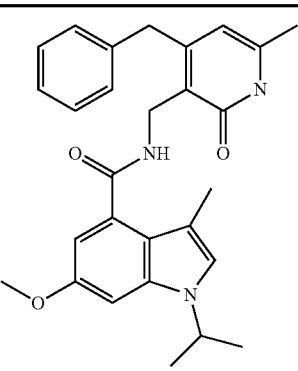 | 3-methyl-1-(1-methylethyl)-N-{[6-methyl-2-oxo-4-(phenylmethyl)-1,2-dihydro-3-pyridinyl]methyl}-6-(methyloxy)-1H-indole-4-carboxamide | 11.54 (br. s., 1 H) 8.13 (t, J = 5.18 Hz, 1 H) 7.29-7.33 (m, 2 H) 7.19-7.26 (m, 3 H) 7.12 (d, J = 1.01 Hz, 1 H) 7.03 (d, J = 2.27 Hz, 1 H) 6.58 (d, J = 2.27 Hz, 1 H) 5.78 (s, 1 H) 4.67 (quin, J = 6.63 Hz, 1 H) 4.40 (s, 1 H) 4.39 (s, 1 H) 3.98 (s, 2 H) 3.78-3.81 (m, 3 H) 2.10 (s, 3 H) 2.08 (s, 3 H) 1.40 (s, 3 H) 1.38 (s, 3 H) | 458.2 |
| 116 | 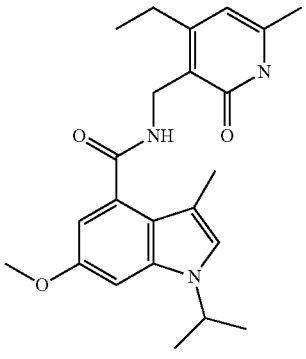 | N-[(4-ethyl-6-methyl-2-oxo-1,2-dihydro-3-pyridinyl)methyl]-3-methyl-1-(1-methylethyl)-6-(methyloxy)-1H-indole-4-carboxamide | 11.47 (br. s., 1 H) 8.00 (t, J = 4.93 Hz, 1 H) 7.12 (s, 1 H) 7.02 (d, J = 2.02 Hz, 1 H) 6.57 (d, J = 2.27 Hz, 1 H) 5.91 (s, 1 H) 4.67 (quin, J = 6.63 Hz, 1 H) 4.33 (s, 1 H) 4.32 (s, 1 H) 3.79 (s, 3 H) 2.53-2.60 (m, 2 H) 2.13 (s, 3 H) 2.10 (s, 3 H) 1.39 (s, 3 H) 1.38 (s, 3 H) 1.13 (t, J = 7.45 Hz, 3 H) | 395.8 |
| 117 | 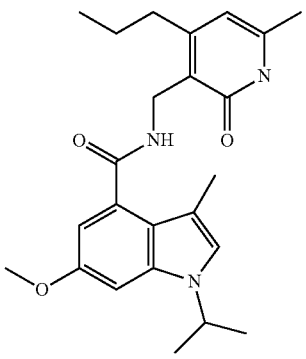 | 3-methyl-1-(1-methylethyl)-N-[(6-methyl-2-oxo-4-propyl-1,2-dihydro-3-pyridinyl)methyl]-6-(methyloxy)-1H-indole-4-carboxamide | 11.48 (br. s., 1 H) 7.98 (t, J = 5.05 Hz, 1 H) 7.10-7.13 (m, 1 H) 7.02 (d, J = 2.02 Hz, 1 H) 6.57 (d, J = 2.02 Hz, 1 H) 5.90 (s, 1 H) 4.66 (quin, J = 6.63 Hz, 1 H) 4.33 (s, 1 H) 4.32 (s, 1 H) 3.79 (s, 3 H) 2.55 (m, 2 H) 2.12 (s, 3 H) 2.10 (s, 3 H) 1.51-1.59 (m, 2 H) 1.39 (s, 3 H) 1.38 (s, 3 H) 0.93 (t, J = 7.33 Hz, 3 H) | 410.3 |
| 118 | 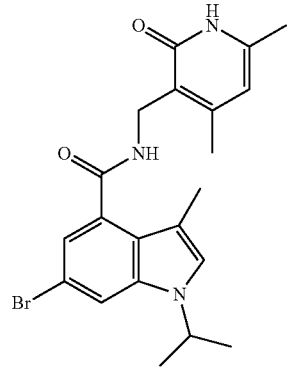 | 6-bromo-N-[(4,6-dimethyl-2-oxo-1,2-dihydro-3-pyridinyl)methyl]-3-methyl-1-(1-methylethyl)-1H-indole-4-carboxamide | 11.48 (br. s., 1 H), 8.24 (t, J = 4.93 Hz, 1H), 7.76 (d, J = 1.52 Hz, 1H), 7.33 (d, J = 0.76 Hz, 1H), 7.00 (d, J = 1.77 Hz, 1H), 5.86 (s, 1H), 4.74 (quin, J = 6.63 Hz, 1H), 4.31 (d, J = 4.80 Hz, 2H), 2.22 (s, 3H), 2.12 (d, J = 7.07 Hz, 6H), 1.39 (d, J = 6.57 Hz, 6H) | 429.9 |

| Ex | Structure | Name | ¹H NMR (400 MHz, DMSO-d₆) δ ppm | MS (ES) [M + H]⁺ |
|---|---|---|---|---|
| 119 | 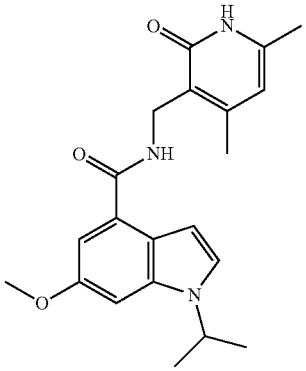 | N-[(4,6-dimethyl-2-oxo-1,2-dihydro-3-pyridinyl)methyl]-1-(1-methylethyl)-6-(methyloxy)-1H-indole-4-carboxamide | 11.55 (s, 1H), 8.12 (t, J = 5.18 Hz, 1H), 7.43 (d, J = 3.28 Hz, 1H), 7.19 (d, J = 2.02 Hz, 1H), 7.06 (d, J = 2.27 Hz, 1H), 6.74 (d, J = 3.28 Hz, 1H), 5.89 (s, 1H), 4.75 (quin, J = 6.63 Hz, 1H), 4.34 (d, J = 5.31 Hz, 2H), 3.82 (s, 3H), 2.23 (s, 3H), 2.12 (s, 3H), 1.43 (d, J = 6.57 Hz, 6H) | 368.1 |
| 120 | 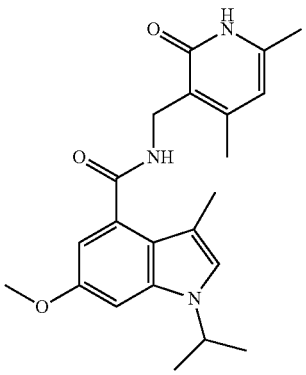 | N-[(4,6-dimethyl-2-oxo-1,2-dihydro-3-pyridinyl)methyl]-3-methyl-1-(1-methylethyl)-6-(methyloxy)-1H-indole-4-carboxamide | 11.47 (s, 1H), 8.02 (t, J = 5.05 Hz, 1H), 7.11 (s, 1H), 7.02 (d, J = 2.02 Hz, 1H), 6.57 (d, J = 2.02 Hz, 1H), 5.86 (s, 1H), 4.66 (quin, J = 6.63 Hz, 1H), 4.31 (d, J = 5.05 Hz, 2H), 3.79 (s, 3H), 2.22 (s, 3H), 2.10 (d, J = 4.80 Hz, 6H), 1.38 (d, J = 6.57 Hz, 6H) | 382.2 |
| 121 | 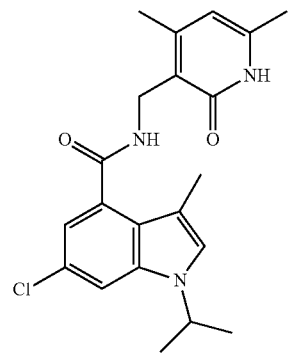 [SMILES: Cc1cc(C)c(CNC(=O)c2cc(Cl)cc3c2c(C)cn3C(C)C)c(=O)[nH]1] | 6-chloro-N-[(4,6-dimethyl-2-oxo-1,2-dihydro-3-pyridinyl)methyl]-3-methyl-1-(1-methylethyl)-1H-indole-4-carboxamide | 11.48 (br. s., 1H), 8.23 (t, J = 4.93 Hz, 1H), 7.63 (d, J = 1.77 Hz, 1H), 7.34 (d, J = 0.76 Hz, 1H), 6.90 (d, J = 2.02 Hz, 1H), 5.87 (s, 1H), 4.73 (quin, J = 6.63 Hz, 1H), 4.31 (d, J = 5.05 Hz, 2H), 2.22 (s, 3H), 2.12 (d, J = 7.07 Hz, 6H), 1.39 (d, J = 6.82 Hz, 6H) | 386.0 |
| 122 | 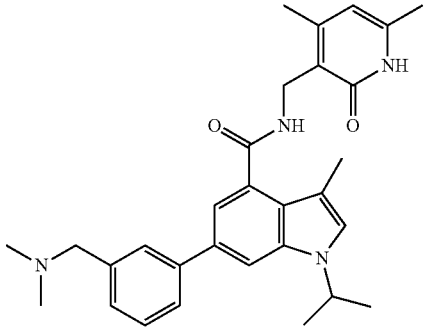 | 6-{3-[(dimethyl-amino)methyl]phenyl}-N-[(4,6-dimethyl-2-oxo-1,2-dihydro-3-pyridinyl)methyl]-3-methyl-1-(1-methylethyl)-1H-indole-4-carboxamide | 11.48 (s, 1H), 8.19 (t, J = 4.93 Hz, 1H), 7.77 (d, J = 1.26 Hz, 1H), 7.62-7.72 (m, 2H), 7.43 (t, J = 7.58 Hz, 1H), 7.33 (d, J = 0.76 Hz, 1H), 7.28 (d, J = 7.58 Hz, 1H), 7.24 (d, J = 1.52 Hz, 1H), 5.87 (s, 1H), 4.88 (quin, J = 6.63 Hz, 1H), 4.36 (d, J = 5.05 Hz, 2H), 3.62 (br. s., 2H), 2.28 (br. s., 6H), 2.24 (s, 3H), 2.17 (d, J = 1.01 Hz, 3H), 2.11 (s, 3H), 1.44 (d, J = 6.82 Hz, 6H) | 485.3 |

-continued

| Ex | Structure | Name | ¹H NMR (400 MHz, DMSO-d₆) δ ppm | MS (ES) [M + H]⁺ |
|---|---|---|---|---|
| 123 | 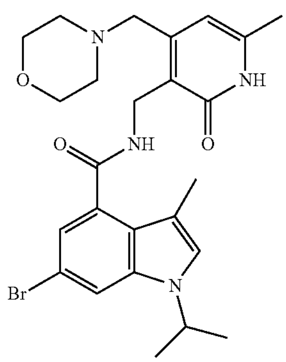 [SMILES: Cc1cc(CN2CCOCC2)c(CNC(=O)c2cc(Br)cc3c2c(C)cn3C(C)C)c(=O)[nH]1] | 6-bromo-3-methyl-1-(1-methylethyl)-N-{[6-methyl-4-(4-morpholinylmethyl)-2-oxo-1,2-dihydro-3-pyridinyl]methyl}-1H-indole-4-carboxamide | 11.64 (br. s., 1 H), 8.43 (br. s., 1 H), 7.78 (d, J = 1.3 Hz, 1 H), 7.33 (s, 1 H), 7.02 (d, J = 1.5 Hz, 1 H), 6.04 (s, 1 H), 4.75 (dt, J = 6.6, 13.0 Hz, 1 H), 4.41 (d, J = 4.8 Hz, 2 H), 3.40 (s, 2 H), 2.33 (br. s., 4 H), 2.25 (br. s., 4 H), 2.15 (s, 3 H), 2.11 (s, 3 H), 1.39 (d, J = 6.6 Hz, 6 H) | 515.2 |
| 124 | 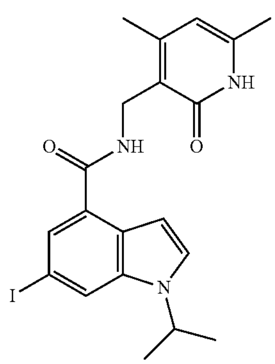 [SMILES: Cc1cc(C)c(CNC(=O)c2cc(I)cc3c2ccn3C(C)C)c(=O)[nH]1] | N-[(4,6-dimethyl-2-oxo-1,2-dihydro-3-pyridinyl)methyl]-6-iodo-1-(1-methylethyl)-1H-indole-4-carboxamide | 11.54 (s, 1 H), 8.27 (t, J = 5.1 Hz, 1 H) 8.05 (s, 1 H), 7.65 (d, J = 1.3 Hz, 1 H), 7.57 (d, J = 3.3 Hz, 1 H), 6.85 (d, J = 3.3 Hz, 1 H), 5.89 (s, 1 H), 4.81 (quin, J = 6.6 Hz, 1 H), 4.32 (d, J = 5.1 Hz, 2 H), 2.22 (s, 3 H), 2.12 (s, 3 H), 1.43 (d, J = 6.6 Hz, 6 H) | 464.0 |
| 125 | 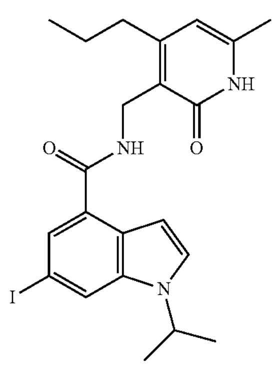 [SMILES: CCCc1cc(C)[nH]c(=O)c1CNC(=O)c1cc(I)cc2c1ccn2C(C)C] | 6-iodo-1-(1-methylethyl)-N-[(6-methyl-2-oxo-4-propyl-1,2-dihydro-3-pyridinyl)methyl]-1H-indole-4-carboxamide | 11.56 (s, 1 H), 8.27 (t, J = 5.1 Hz, 1 H), 8.05 (s, 1 H), 7.65 (d, J = 1.3 Hz, 1 H), 7.58 (d, J = 3.3 Hz, 1 H), 6.84 (d, J = 3.3 Hz, 1 H), 5.91 (s, 1 H), 4.82 (dt, J = 6.6, 13.3 Hz, 1 H), 4.35 (d, J = 5.3 Hz, 2 H), 2.52 (2 H under DMSO), 2.13 (s, 3 H), 1.53 (dq, J = 7.4, 15.1 Hz, 2 H), 0.91 (t, J = 7.3 Hz, 3 H) | 491.9 |
| 126 | 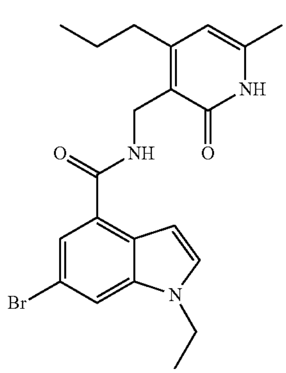 [SMILES: CCCc1cc(C)[nH]c(=O)c1CNC(=O)c1cc(Br)cc2c1ccn2CC] | 6-bromo-1-ethyl-N-[(6-methyl-2-oxo-4-propyl-1,2-dihydro-3-pyridinyl)methyl]-1H-indole-4-carboxamide | 0.92-0.88 (t, 3H), 1.34-1.31 (t, 3H), 1.53-1.49 (m, 2H), 2.13 (s, 3H), 2.54-2.49 (m, 2H), 4.25-4.20 (m, 2H), 4.35 (d, J = 4.8 Hz, 2H), 5.90 (s, 1H), 6.83 (d, J = 3.2 Hz, 1H), 7.51 (d, J = 3.2 Hz, 2H), 7.89 (s, 1H), 8.29-8.27 (t, 1H), 11.54 (s, 1H) | 432.15 |

-continued

| Ex | Structure | Name | $^1$H NMR (400 MHz, DMSO-d$_6$) δ ppm | MS (ES) [M + H]$^+$ |
|---|---|---|---|---|
| 127 | 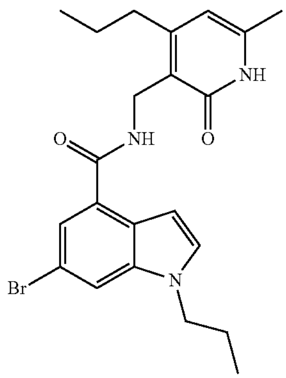 [SMILES: CCCc1cc(C)[nH]c(=O)c1CNC(=O)c1cc(Br)cc2c1ccn2CCC] | 6-bromo-N-[(6-methyl-2-oxo-4-propyl-1,2-dihydro-3-pyridinyl)methyl]-1-propyl-1H-indole-4-carboxamide | 0.83-0.79 δ (t, 3H), 0.92-0.88 (t, 3H), 1.55-1.51 (m, 2H), 1.74.1.71 (m, 2H), 1.76 (s, 3H), 2.54-2.45 (m, 2H), 4.17-4.14 (t, 2H), 4.35-4.34 (d, J = 5.2 Hz, 2H), 5.75 (s, 1H), 5.90 (s, 1H), 6.82 (d, J = 2.8 Hz), 7.51-7.49 (m, 2H), 7.90 (s, 1H), 8.28 (s, 1H), 11.54 (s, 1H) | 446.04 |
| 128 | 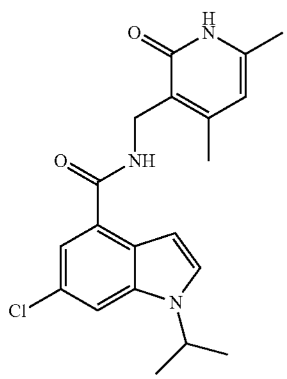 [SMILES: Cc1cc(C)c(CNC(=O)c2cc(Cl)cc3c2ccn3C(C)C)c(=O)[nH]1] | 3-({2-[6-chloro-1-(1-methylethyl)-1H-indol-4-yl]-2-oxoethyl}amino)-4,6-dimethyl-2(1H)-pyridinone | 1.43 (d, 6 H), 2.12 (s, 3 H), 2.21 (s, 3 H), 4.32 (d, J = 4.80 Hz, 2 H), 4.81 (dt, J = 13.33, 6.60 Hz, 1 H), 5.88 (s, 1 H), 6.86 (d, J = 3.03 Hz, 1 H), 7.40 (d, J = 1.52 Hz, 1 H), 7.63 (d, J = 3.28 Hz, 1 H), 7.79 (s, 1 H), 8.29 (t, J = 4.80 Hz, 1 H), 11.53 (br. s., 1 H) | 371.9 |
| 129 | 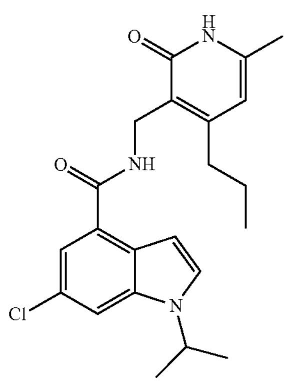 [SMILES: CCCc1cc(C)[nH]c(=O)c1CNC(=O)c1cc(Cl)cc2c1ccn2C(C)C] | 3-({2-[6-chloro-1-(1-methylethyl)-1H-indol-4-yl]-2-oxoethyl}amino)-6-methyl-4-propyl-2(1H)-pyridinone | 0.90 (t, J = 7.20 Hz, 3 H), 1.43 (d, J = 6.57 Hz, 6 H), 1.48-1.57 (m, 3 H), 2.13 (s, 3 H), 4.35 (d, J = 4.80 Hz, 2 H), 4.69-4.93 (m, 1 H), 5.90 (s, 1 H), 6.86 (d, J = 2.78 Hz, 1 H), 7.40 (s, 1 H), 7.64 (d, J = 3.28 Hz, 1 H), 7.79 (s, 1 H), 8.28 (br. s., 1 H), 11.55 (br. s., 1 H) | 399.8 |
| 130 | 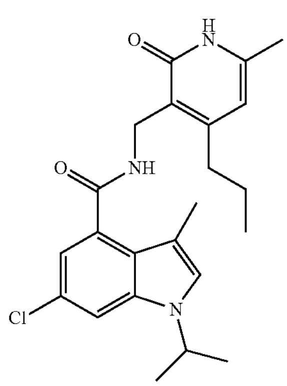 [SMILES: CCCc1cc(C)[nH]c(=O)c1CNC(=O)c1cc(Cl)cc2c1c(C)cn2C(C)C] | 3-({2-[6-chloro-3-methyl-1-(1-methylethyl)-1H-indol-4-yl]-2-oxoethyl}amino)-6-methyl-4-propyl-2(1H)-pyridinone | 0.93 (t, J = 7.33 Hz, 3 H), 1.39 (d, J = 6.57 Hz, 6 H), 1.47-1.67 (m, 2 H), 2.12 (d, J = 4.80 Hz, 6 H), 4.32 (d, J = 4.55 Hz, 2 H), 4.54-4.90 (m, 1 H), 5.89 (s, 1 H), 6.88 (s, 1 H), 7.34 (s, 1 H), 7.63 (s, 1 H), 8.20 (br. s., 1 H), 11.48 (br. s., 1 H) | 414.0 |

-continued

| Ex | Structure | Name | ¹H NMR (400 MHz, DMSO-d₆) δ ppm | MS (ES) [M + H]⁺ |
|---|---|---|---|---|
| 131 | 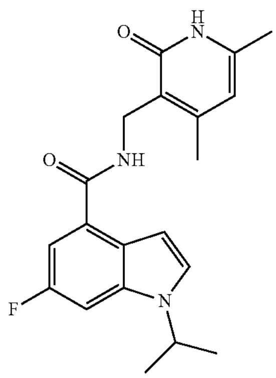 [SMILES: Cc1cc(C)c(CNC(=O)c2cc(F)cc3c2ccn3C(C)C)c(=O)[nH]1] | N-[(4,6-dimethyl-2-oxo-1,2-dihydro-3-pyridinyl)methyl]-6-fluoro-1-(1-methylethyl)-1H-indole-4-carboxamide | 1.42 (d, 6 H), 2.12 (s, 3 H), 2.22 (s, 3 H), 4.33 (d, J = 5.05 Hz, 2 H), 4.74 (dt, J = 13.14, 6.57 Hz, 1 H), 5.88 (s, 1 H), 6.85 (d, J = 3.03 Hz, 2 H), 7.25 (dd, J = 10.36, 1.77 Hz, 2 H), 7.51-7.67 (m, 4 H), 8.24 (t, J = 4.55 Hz, 2 H), 11.55 (br. s., 1 H) | 356.2 |
| 132 | 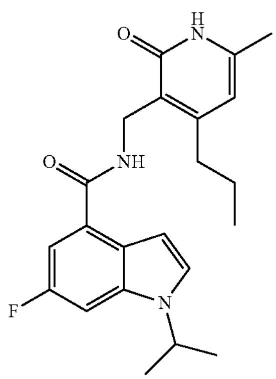 [SMILES: CCCc1cc(C)[nH]c(=O)c1CNC(=O)c1cc(F)cc2c1ccn2C(C)C] | 3-({2-[6-fluoro-1-(1-methylethyl)-1H-indol-4-yl]-2-oxoethyl}amino)-6-methyl-4-propyl-2(1H)-pyridinone | 0.90 (t, J = 7.20 Hz, 3 H), 1.43 (d, 6 H), 1.47-1.61 (m, 2 H), 2.13 (s, 3 H), 4.36 (d, J = 5.05 Hz, 2 H), 2.53 (2H), 4.75 (ddd, J = 13.20, 6.51, 6.32 Hz, 1 H), 5.91 (s, 1 H), 6.84 (d, J = 3.03 Hz, 1 H), 7.25 (dd, J = 10.36, 2.02 Hz, 1 H), 7.49-7.69 (m, 2 H), 8.23 (t, J = 4.93 Hz, 1 H), 11.57 (br. s., 1 H) | 384.0 |
| 133 | 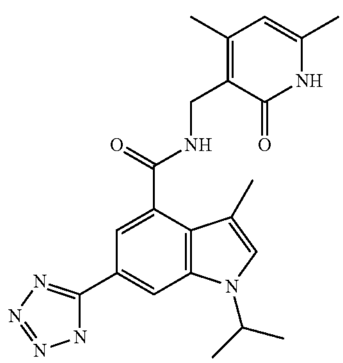 [SMILES: Cc1cc(C)c(CNC(=O)c2cc(-c3nnn[nH]3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(1H-tetrazol-5-yl)-1H-indole-4-carboxamide | 11.50 (br. s., 1 H), 8.29 (t, J = 4.9 Hz, 1 H), 8.21 (s, 1 H), 7.62 (d, J = 1.3 Hz, 1 H), 7.51 (s, 1 H), 5.88 (s, 1 H), 4.80 (dt, J = 6.6, 13.1 Hz, 1 H), 4.37 (d, J = 5.1 Hz, 2 H), 2.25 (s, 3 H), 2.19 (s, 3 H), 2.12 (s, 3 H), 1.48 (d, J = 6.6 Hz, 6 H) | 419.9 |
| 134 | 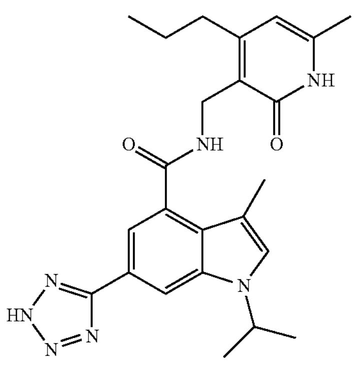 [SMILES: CCCc1cc(C)[nH]c(=O)c1CNC(=O)c1cc(-c2nn[nH]n2)cc2c1c(C)cn2C(C)C] | 1-isopropyl-3-methyl-N-((6-methyl-2-oxo-4-propyl-1,2-dihydropyridin-3-yl)methyl)-6-(2H-tetrazol-5-yl)-1H-indole-4-carboxamide | 11.50 (br. s., 1H), 8.25 (t, J = 4.93 Hz, 1H), 8.21 (d, J = 1.26 Hz, 1H), 7.63 (d, J = 0.76 Hz, 1H), 7.52 (s, 1H), 5.91 (s, 1H), 4.80 (qd, J = 6.19, 6.44 Hz, 1H), 4.38 (d, J = 5.05 Hz, 2H), 2.19 (s, 3H), 2.13 (s, 3H), 1.51-1.63 (m, 2H), 1.48 (d, J = 6.57 Hz, 6H), 1.10 (t, J = 6.95 Hz, 2H), 0.95 (t, J = 7.33 Hz, 3H) | 447.8 |

-continued

| Ex | Structure | Name | ¹H NMR (400 MHz, DMSO-d₆) δ ppm | MS (ES) [M + H]⁺ |
|---|---|---|---|---|
| 135 | 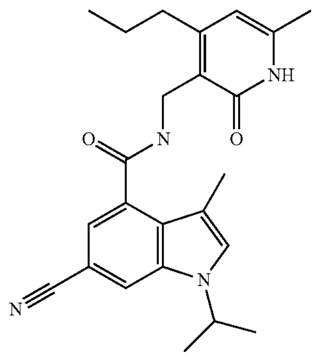 [SMILES: CCCc1cc(C)[nH]c(=O)c1CNC(=O)c1cc(C#N)cc2c1c(C)cn2C(C)C] | 6-cyano-3-methyl-1-(1-methylethyl)-N-[(6-methyl-2-oxo-4-propyl-1,2-dihydro-3-pyridinyl)methyl]-1H-indole-4-carboxamide | 11.50 (br. s., 1 H) 8.31 (t, J = 4.80 Hz, 1 H) 8.16 (d, J = 1.26 Hz, 1 H) 7.65 (s, 1 H) 7.19 (d, J = 1.26 Hz, 1 H) 5.90 (s, 1 H) 4.79-4.93 (m, 1 H) 4.33 (d, J = 5.05 Hz, 2 H) 2.55 (d, J = 1.52 Hz, 1 H) 2.17 (s, 3 H) 2.13 (s, 3 H) 1.51-1.61 (m, 2 H) 1.43 (d, J = 6.57 Hz, 6 H) 0.94 (t, J = 7.33 Hz, 3 H) | 405.1 |
| 136 | 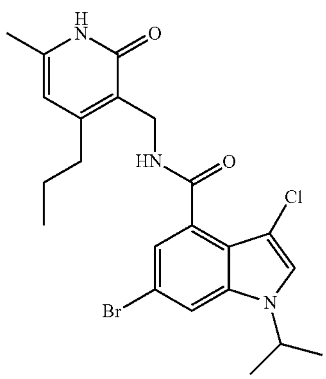 [SMILES: CCCc1cc(C)[nH]c(=O)c1CNC(=O)c1cc(Br)cc2c1c(Cl)cn2C(C)C] | 6-bromo-3-chloro-1-isopropyl-N-((6-methyl-2-oxo-4-propyl-1,2-dihydropyridin-3-yl)methyl)-1H-indole-4-carboxamide | 11.48 (s, 1H), 8.23 (t, J = 5.05 Hz, 1H), 7.93 (d, J = 1.52 Hz, 1H), 7.78 (s, 1H), 7.06 (d, J = 1.52 Hz, 1H), 5.89 (s, 1H), 4.84 (quin, J = 6.63 Hz, 1H), 4.33 (d, J = 5.05 Hz, 2H), 2.52-2.57 (m, 2H), 2.12 (s, 3H), 1.49-1.61 (m, J = 7.33, 7.52, 7.52, 7.52, 7.52 Hz, 2H), 1.41 (d, J = 6.82 Hz, 6H), 0.94 (t, J = 7.33 Hz, 3 H) | 479.7 |
| 137 | 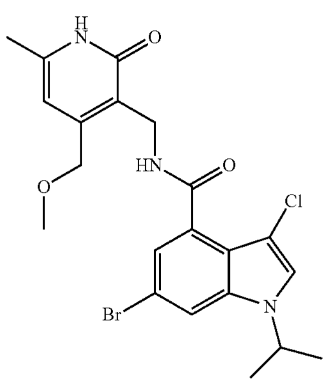 [SMILES: COCc1cc(C)[nH]c(=O)c1CNC(=O)c1cc(Br)cc2c1c(Cl)cn2C(C)C] | 6-bromo-3-chloro-1-(1-methylethyl)-N-({6-methyl-4-[(methyloxy)methyl]-2-oxo-1,2-dihydro-3-pyridinyl}methyl)-1H-indole-4-carboxamide | 8.32 (t, J = 4.80 Hz, 1H), 7.93 (s, 1H), 7.78 (s, 1H), 7.08 (s, 1H), 6.07 (s, 1H), 4.84 (q, J = 6.19, 6.38, 12.95 Hz, 1H), 4.48 (s, 2H), 4.29 (d, J = 5.05 Hz, 2H), 3.33 (br. s., 3H), 2.16 (s, 3H), 1.41 (d, J = 6.57 Hz, 6H) | 481.8 |
| 138 | 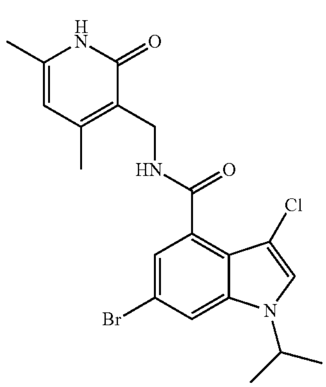 [SMILES: Cc1cc(C)c(CNC(=O)c2cc(Br)cc3c2c(Cl)cn3C(C)C)c(=O)[nH]1] | 6-bromo-3-chloro-N-[(4,6-dimethyl-2-oxo-1,2-dihydro-3-pyridinyl)methyl]-1-(1-methylethyl)-1H-indole-4-carboxamide | 8.27 (t, J = 4.93 Hz, 1H), 7.93 (d, J = 1.52 Hz, 1H), 7.78 (s, 1H), 7.07 (d, J = 1.77 Hz, 1H), 5.86 (s, 1H), 4.84 (quin, J = 6.63 Hz, 1H), 4.32 (d, J = 5.05 Hz, 2H), 2.21 (s, 3H), 2.11 (s, 3H), 1.41 (d, J = 6.57 Hz, 6H) | 451.8 |

| Ex | Structure | Name | ¹H NMR (400 MHz, DMSO-d₆) δ ppm | MS (ES) [M + H]⁺ |
|---|---|---|---|---|
| 139 | 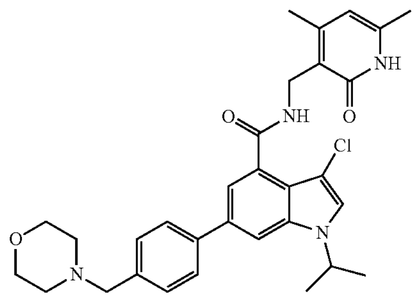 [SMILES: Cc1cc(C)c(CNC(=O)c2cc(-c3ccc(CN4CCOCC4)cc3)cc3c2c(Cl)cn3C(C)C)c(=O)[nH]1] | 3-chloro-N-((4,6-dimethyl-2-oxo-1,2-dihydropyridin-3-yl)methyl)-1-isopropyl-6-(4-(morpholinomethyl)phenyl)-1H-indole-4-carboxamide | 8.17 (t, J = 5.05 Hz, 1H), 8.15 (s, 1H), 7.90 (d, J = 1.26 Hz, 1H), 7.75 (s, 1H), 7.71 (d, J = 8.08 Hz, 2H), 7.40 (d, J = 8.34 Hz, 2H), 7.30 (d, J = 1.26 Hz, 1H), 5.87 (s, 1H), 4.96 (quin, J = 6.63 Hz, 1H), 4.37 (d, J = 5.05 Hz, 2H), 3.59 (t, J = 4.55 Hz, 4H), 3.51 (s, 2H), 2.39 (br. s., 4H), 2.24 (s, 3H), 2.11 (s, 3H), 1.46 (d, J = 6.82 Hz, 6H) | 547.0 |
| 140 | 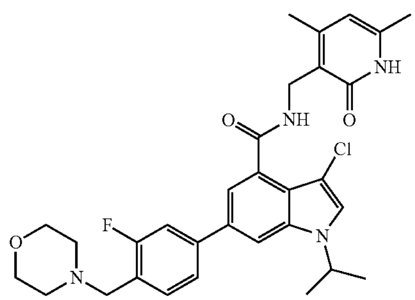 [SMILES: Cc1cc(C)c(CNC(=O)c2cc(-c3ccc(CN4CCOCC4)c(F)c3)cc3c2c(Cl)cn3C(C)C)c(=O)[nH]1] | 3-chloro-N-((4,6-dimethyl-2-oxo-1,2-dihydropyridin-3-yl)methyl)-6-(3-fluoro-4-(morpholinomethyl)phenyl)-1-isopropyl-1H-indole-4-carboxamide | 8.18 (t, J = 5.05 Hz, 1H), 8.14 (s, 1H), 7.98 (d, J = 1.26 Hz, 1H), 7.78 (s, 1H), 7.57-7.66 (m, 2H), 7.45-7.51 (m, 1H), 7.33 (d, J = 1.26 Hz, 1H), 5.87 (s, 1H), 4.99 (quin, J = 6.63 Hz, 1H), 4.37 (d, J = 5.05 Hz, 2H), 3.58 (dd, J = 4.04, 8.84 Hz, 6H), 2.42 (br. s., 4H), 2.24 (s, 3H), 2.11 (s, 3H), 1.46 (d, J = 6.57 Hz, 6H) | 565.3 |
| 141 | 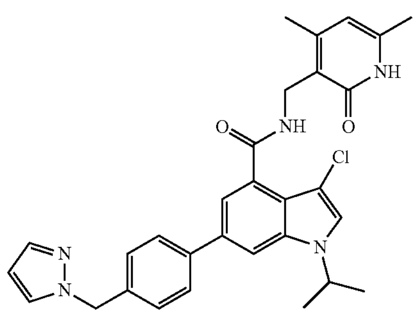 [SMILES: Cc1cc(C)c(CNC(=O)c2cc(-c3ccc(Cn4cccn4)cc3)cc3c2c(Cl)cn3C(C)C)c(=O)[nH]1] | 6-(4-((1H-pyrazol-1-yl)methyl)phenyl)-3-chloro-N-((4,6-dimethyl-2-oxo-1,2-dihydropyridin-3-yl)methyl)-1-isopropyl-1H-indole-4-carboxamide | 8.15 (s, 1H), 7.97 (s, 1H), 7.77 (s, 1H), 7.44 (s, 1H), 7.24-7.40 (m, 6H), 6.17 (br. s., 1H), 5.39 (s, 2H), 4.78-4.89 (m, 1H), 4.57 (br. s., 2H), 2.45 (s, 3H), 2.26 (br. s., 3H), 1.51 (d, J = 6.57 Hz, 6H) | 528.0 |
| 142 | 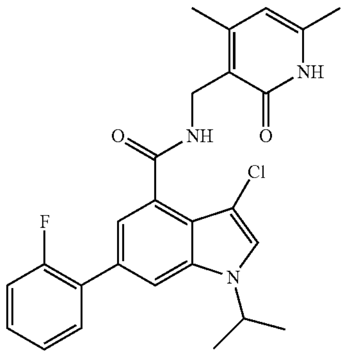 [SMILES: Cc1cc(C)c(CNC(=O)c2cc(-c3ccccc3F)cc3c2c(Cl)cn3C(C)C)c(=O)[nH]1] | 3-chloro-N-((4,6-dimethyl-2-oxo-1,2-dihydropyridin-3-yl)methyl)-6-(2-fluorophenyl)-1-isopropyl-1H-indole-4-carboxamide | 11.49 (br. s., 1H), 8.19 (t, J = 5.05 Hz, 1H), 7.76-7.83 (m, 2H), 7.56-7.68 (m, 1H), 7.38-7.46 (m, 1H), 7.29-7.36 (m, 2H), 7.17 (t, J = 1.39 Hz, 1H), 5.87 (s, 1H), 4.90 (quin, J = 6.63 Hz, 1H), 4.36 (d, J = 5.05 Hz, 2H), 2.23 (s, 3H), 2.11 (s, 3H), 1.45 (d, J = 6.82 Hz, 6H) | 465.9 |

| Ex | Structure | Name | ¹H NMR (400 MHz, DMSO-d₆) δ ppm | MS (ES) [M + H]⁺ |
|---|---|---|---|---|
| 143 | 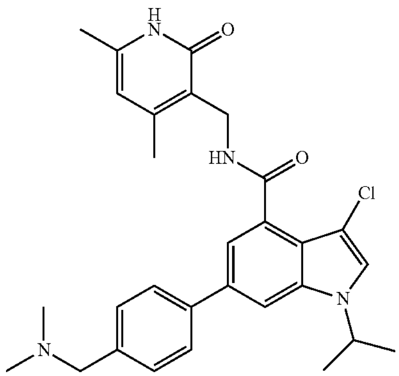 [SMILES: Cc1cc(C)c(CNC(=O)c2cc(-c3ccc(CN(C)C)cc3)cc3c2c(Cl)cn3C(C)C)c(=O)[nH]1] | 3-chloro-6-{4-[(dimethyl-amino)methyl]phenyl}-N-[(4,6-dimethyl-2-oxo-1,2-dihydro-3-pyridinyl)methyl]-1-(1-methylethyl)-1H-indole-4-carboxamide | 8.19 (s, 1H), 8.14-8.18 (m, 1H), 7.91 (d, J = 1.26 Hz, 1H), 7.75 (s, 1H), 7.73 (s, 1H), 7.71 (s, 1H), 7.39 (d, J = 8.08 Hz, 2H), 7.30 (d, J = 1.52 Hz, 1H), 5.87 (s, 1H), 4.97 (quin, J = 6.57 Hz, 1H), 4.37 (d, J = 5.05 Hz, 2H), 3.49 (s, 2H), 2.24 (s, 3H), 2.21 (s, 6H), 2.11 (s, 3H), 1.46 (d, J = 6.57 Hz, 6H) | 506.0 |
| 144 | 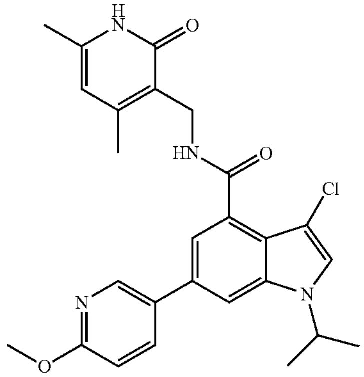 [SMILES: COc1ccc(-c2cc(C(=O)NCc3c(C)cc(C)[nH]c3=O)c3c(Cl)cn(C(C)C)c3c2)cn1] | 3-chloro-N-[(4,6-dimethyl-2-oxo-1,2-dihydro-3-pyridinyl)methyl]-1-(1-methylethyl)-6-[6-(methyloxy)-3-pyridinyl]-1H-indole-4-carboxamide | 11.46 (s, 1H), 8.56 (d, J = 2.02 Hz, 1H), 8.16 (t, J = 5.05 Hz, 1H), 8.11 (dd, J = 2.78, 8.59 Hz, 1H), 7.92 (d, J = 1.26 Hz, 1H), 7.75 (s, 1H), 7.28 (d, J = 1.26 Hz, 1H), 6.92 (d, J = 8.59 Hz, 1H), 5.87 (s, 1H), 4.96 (quin, J = 6.63 Hz, 1H), 4.36 (d, J = 5.05 Hz, 2H), 3.91 (s, 3H), 2.24 (s, 3H), 2.11 (s, 3H), 1.46 (d, J = 6.57 Hz, 6H) | 478.9 |
| 145 | 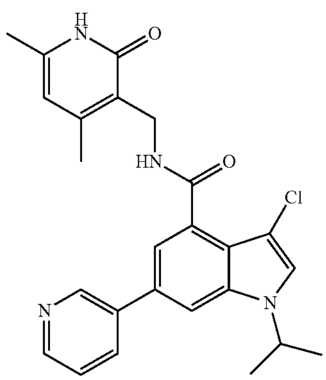 [SMILES: Cc1cc(C)c(CNC(=O)c2cc(-c3cccnc3)cc3c2c(Cl)cn3C(C)C)c(=O)[nH]1] | 3-chloro-N-[(4,6-dimethyl-2-oxo-1,2-dihydro-3-pyridinyl)methyl]-1-(1-methylethyl)-6-(3-pyridinyl)-1H-indole-4-carboxamide | 11.47 (br. s., 1H), 8.99 (d, J = 2.27 Hz, 1H), 8.56 (dd, J = 1.64, 4.67 Hz, 1H), 8.14-8.22 (m, 2H), 8.03 (d, J = 1.52 Hz, 1H), 7.80 (s, 1H), 7.49 (dd, J = 4.67, 7.96 Hz, 1H), 7.35 (d, J = 1.52 Hz, 1H), 5.87 (s, 1H), 4.94-5.05 (m, 1H), 4.37 (d, J = 5.05 Hz, 2H), 2.25 (s, 3H), 2.11 (s, 3H), 1.46 (d, J = 6.82 Hz, 6H) | 450.9 |
| 146 | 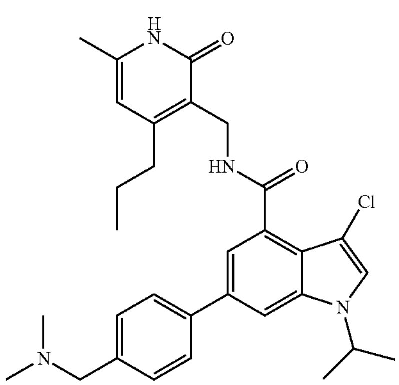 [SMILES: CCCc1cc(C)[nH]c(=O)c1CNC(=O)c1cc(-c2ccc(CN(C)C)cc2)cc2c1c(Cl)cn2C(C)C] | 3-chloro-6-{4-[(dimethyl-amino)methyl]phenyl}-1-(1-methylethyl)-N-[(6-methyl-2-oxo-4-propyl-1,2-dihydro-3-pyridinyl)methyl]-1H-indole-4-carboxamide | 11.48 (br. s., 1H), 8.14 (t, J = 4.80 Hz, 1H), 7.91 (d, J = 1.01 Hz, 1H), 7.75 (s, 1H), 7.71 (s, 1H), 7.69 (s, 1H), 7.39 (s, 1H), 7.37 (s, 1H), 7.29 (d, J = 1.01 Hz, 1H), 5.90 (s, 1H), 4.97 (qd, J = 6.44, 6.61 Hz, 1H), 4.38 (d, J = 5.05 Hz, 2H), 3.44 (s, 2H), 2.55 (dd, J = 6.95, 8.72 Hz, 2H), 2.18 (s, 6H), 2.12 (s, 3H), 1.57 (dq, J = 7.48, 15.19 Hz, 2H), 1.46 (d, J = 6.57 Hz, 6H), 0.95 (t, J = 7.33 Hz, 3H) | 534.4 |

| Ex | Structure | Name | ¹H NMR (400 MHz, DMSO-d₆) δ ppm | MS (ES) [M + H]⁺ |
|---|---|---|---|---|
| 147 | 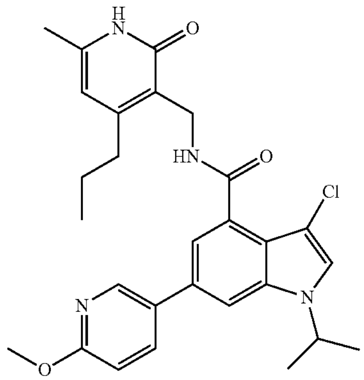 [SMILES: CCCc1cc(C)[nH]c(=O)c1CNC(=O)c1cc(-c2ccc(OC)nc2)cc2c1c(Cl)cn2C(C)C] | 3-chloro-1-(1-methylethyl)-N-[(6-methyl-2-oxo-4-propyl-1,2-dihydro-3-pyridinyl)methyl]-6-[6-(methyloxy)-3-pyridinyl]-1H-indole-4-carboxamide | 11.48 (s, 1H), 8.55 (d, J = 2.02 Hz, 1H), 8.13 (t, J = 5.05 Hz, 1H), 8.10 (dd, J = 2.53, 8.59 Hz, 1H), 7.93 (d, J = 1.52 Hz, 1H), 7.76 (s, 1H), 7.27 (d, J = 1.52 Hz, 1H), 6.93 (d, J = 8.59 Hz, 1H), 5.90 (s, 1H), 4.96 (quin, J = 6.63 Hz, 1H), 4.38 (d, J = 5.05 Hz, 2H), 3.91 (s, 3H), 2.55 (dd, J = 6.82, 8.84 Hz, 2H), 2.12 (s, 3H), 1.51-1.63 (m, 2H), 1.46 (d, J = 6.82 Hz, 6H), 0.94 (t, J = 7.33 Hz, 3H) | 509.0 |
| 148 | 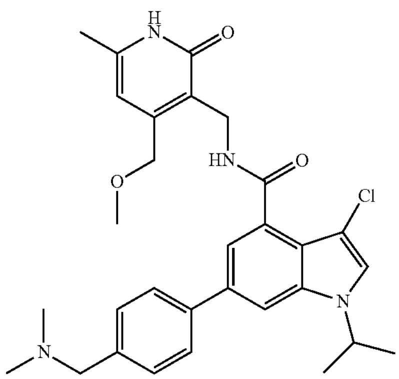 [SMILES: COCc1cc(C)[nH]c(=O)c1CNC(=O)c1cc(-c2ccc(CN(C)C)cc2)cc2c1c(Cl)cn2C(C)C] | 3-chloro-6-{4-[(dimethylamino)methyl]phenyl}-1-(1-methylethyl)-N-({6-methyl-4-[(methyloxy)methyl]-2-oxo-1,2-dihydro-3-pyridinyl}methyl)-1H-indole-4-carboxamide | 11.62 (br. s., 1H), 8.22 (t, J = 5.05 Hz, 1H), 8.16 (s, 1H), 7.90 (s, 1H), 7.74 (s, 1H), 7.72 (s, 1H), 7.70 (s, 1H), 7.39 (d, J = 8.34 Hz, 2H), 7.30 (s, 1H), 6.07 (s, 1H), 4.97 (dt, J = 6.69, 13.39 Hz, 1H), 4.51 (s, 2H), 4.33 (d, J = 5.05 Hz, 2H), 3.48 (s, 2H), 3.33 (s, 3H), 2.21 (s, 6H), 2.15 (s, 3H), 1.45 (d, J = 6.57 Hz, 6H) | 534.9 |
| 149 | 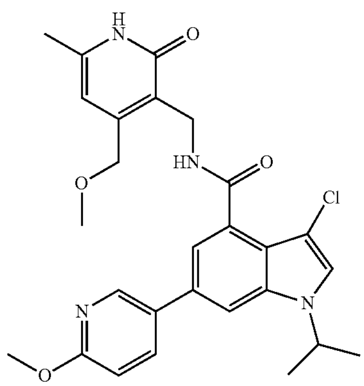 [SMILES: COCc1cc(C)[nH]c(=O)c1CNC(=O)c1cc(-c2ccc(OC)nc2)cc2c1c(Cl)cn2C(C)C] | 3-chloro-1-(1-methylethyl)-N-({6-methyl-4-[(methyloxy)methyl]-2-oxo-1,2-dihydro-3-pyridinyl}methyl)-6-[6-(methyloxy)-3-pyridinyl]-1H-indole-4-carboxamide | 11.63 (br. s., 1H), 8.56 (d, J = 2.02 Hz, 1H), 8.22 (t, J = 5.05 Hz, 1H), 8.11 (dd, J = 2.65, 8.72 Hz, 1H), 7.93 (d, J = 1.26 Hz, 1H), 7.75 (s, 1H), 7.29 (d, J = 1.52 Hz, 1H), 6.93 (d, J = 8.08 Hz, 1H), 6.08 (s, 1H), 4.96 (quin, J = 6.57 Hz, 1H), 4.52 (s, 2H), 4.34 (d, J = 5.31 Hz, 2H), 3.91 (s, 3H), 3.33 (br. s., 3H), 2.16 (s, 3H), 1.46 (d, J = 6.57 Hz, 6H) | 510.0 |
| 150 | 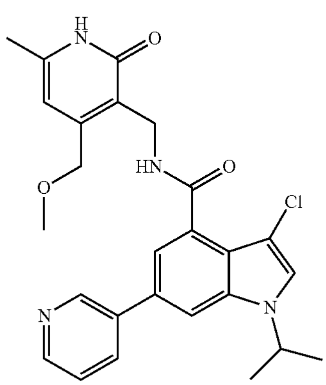 [SMILES: COCc1cc(C)[nH]c(=O)c1CNC(=O)c1cc(-c2cccnc2)cc2c1c(Cl)cn2C(C)C] | 3-chloro-1-isopropyl-N-((4-(methoxymethyl)-6-methyl-2-oxo-1,2-dihydropyridin-3-yl)methyl)-6-(pyridin-3-yl)-1H-indole-4-carboxamide | 11.63 (br. s., 1H), 9.00 (d, J = 1.77 Hz, 1H), 8.56 (dd, J = 1.52, 4.80 Hz, 1H), 8.26 (t, J = 5.18 Hz, 1H), 8.17 (ddd, J = 1.77, 2.02, 8.34 Hz, 1H), 8.04 (d, J = 1.52 Hz, 1H), 7.80 (s, 1H), 7.49 (ddd, J = 0.76, 4.74, 7.89 Hz, 1H), 7.36 (d, J = 1.26 Hz, 1H), 6.08 (s, 1H), 5.00 (quin, J = 6.63 Hz, 1H), 4.53 (s, 2H), 4.34 (d, J = 5.05 Hz, 2H), 3.33 (s, 3H), 2.16 (s, 3H), 1.46 (d, J = 6.57 Hz, 6H) | 479.0 |

-continued

| Ex | Name | ¹H NMR (400 MHz, DMSO-d₆) δ ppm | MS (ES) [M + H]⁺ |
|---|---|---|---|
| 151 | 3-chloro-1-isopropyl-N-((6-methyl-2-oxo-4-propyl-1,2-dihydropyridin-3-yl)methyl)-6-(6-(4-methylpiperazin-1-yl)pyridin-3-yl)-1H-indole-4-carboxamide | 8.51 (d, J = 2.53 Hz, 1H), 8.13 (t, J = 4.55 Hz, 1H), 7.93 (dd, J = 2.53, 8.84 Hz, 1H), 7.86 (d, J = 1.26 Hz, 1H), 7.71 (s, 1H), 7.24 (d, J = 1.26 Hz, 1H), 6.93 (d, J = 9.09 Hz, 1H), 5.89 (s, 1H), 4.95 (quin, J = 6.63 Hz, 1H), 4.37 (d, J = 4.80 Hz, 2H), 3.51-3.57 (m, 4H), 2.52-2.58 (m, 2H), 2.37-2.45 (m, 4H), 2.23 (s, 3H), 2.12 (s, 3H), 1.57 (dddd, J = 7.20, 7.33, 7.48, 15.13 Hz, 2H), 1.45 (d, J = 6.57 Hz, 6H), 0.94 (t, J = 7.33 Hz, 3H) | 575.3 |
| 152 | 3-chloro-N-((4-ethyl-6-methyl-2-oxo-1,2-dihydropyridin-3-yl)methyl)-1-isopropyl-6-(6-(4-methylpiperazin-1-yl)pyridin-3-yl)-1H-indole-4-carboxamide | 8.52 (d, J = 2.53 Hz, 1H), 8.13 (t, J = 5.05 Hz, 1H), 7.94 (dd, J = 2.65, 8.97 Hz, 1H), 7.86 (d, J = 1.52 Hz, 1H), 7.71 (s, 1H), 7.24 (d, J = 1.52 Hz, 1H), 6.93 (d, J = 8.84 Hz, 1H), 5.91 (s, 1H), 4.94 (quin, J = 6.57 Hz, 1H), 4.38 (d, J = 5.05 Hz, 2H), 3.50-3.57 (m, 4H), 2.59 (q, J = 7.58 Hz, 2H), 2.39-2.45 (m, 4H), 2.23 (s, 3H), 2.13 (s, 3H), 1.45 (d, J = 6.82 Hz, 6H), 1.14 (t, J = 7.58 Hz, 3H) | 561.1 |
| 153 | 3-chloro-N-((4,6-dimethyl-2-oxo-1,2-dihydropyridin-3-yl)methyl)-1-isopropyl-6-(6-(4-methylpiperazin-1-yl)pyridin-3-yl)-1H-indole-4-carboxamide | 8.52 (d, J = 2.27 Hz, 1H), 8.15 (t, J = 4.55 Hz, 1H), 7.94 (dd, J = 2.53, 8.84 Hz, 1H), 7.85 (d, J = 1.26 Hz, 1H), 7.71 (s, 1H), 7.25 (d, J = 1.26 Hz, 1H), 6.93 (d, J = 8.84 Hz, 1H), 5.86 (s, 1H), 4.94 (quin, J = 6.63 Hz, 1H), 4.36 (d, J = 5.05 Hz, 2H), 3.50-3.57 (m, 4H), 2.38-2.45 (m, 4H), 2.23 (d, J = 3.03 Hz, 6H), 2.11 (s, 3H), 1.45 (d, J = 6.57 Hz, 6H) | 547.0 |
| 154 | 3-chloro-N-((4,6-dimethyl-2-oxo-1,2-dihydropyridin-3-yl)methyl)-1-isopropyl-6-(4-(trifluoromethyl)phenyl)-1H-indole-4-carboxamide | 11.47 (s, 1H), 8.23 (t, J = 4.93 Hz, 1H), 7.98-8.05 (m, 3H), 7.79-7.86 (m, 3H), 7.37 (d, J = 1.26 Hz, 1H), 5.87 (s, 1H), 5.00 (qd, J = 6.44, 6.61 Hz, 1H), 4.37 (d, J = 4.80 Hz, 2H), 2.24 (s, 3H), 2.11 (s, 3H), 1.47 (d, J = 6.57 Hz, 6H) | 516.0 |

-continued

| Ex | Structure | Name | $^1$H NMR (400 MHz, DMSO-d$_6$) δ ppm | MS (ES) [M + H]$^+$ |
|---|---|---|---|---|
| 155 | 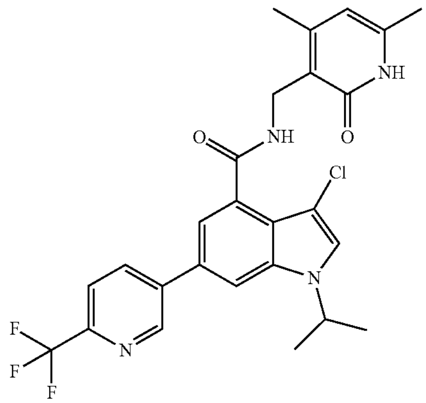 [SMILES: Cc1cc(C)c(CNC(=O)c2cc(-c3ccc(C(F)(F)F)nc3)cc3c2c(Cl)cn3C(C)C)c(=O)[nH]1] | 3-chloro-N-((4,6-dimethyl-2-oxo-1,2-dihydropyridin-3-yl)methyl)-1-isopropyl-6-(6-(trifluoromethyl)pyridin-3-yl)-1H-indole-4-carboxamide | 11.49 (br. s., 1H), 9.20 (d, J = 2.02 Hz, 1H), 8.47 (dd, J = 2.02, 8.08 Hz, 1H), 8.24 (t, J = 5.05 Hz, 1H), 8.16 (d, J = 1.26 Hz, 1H), 7.99 (d, J = 8.34 Hz, 1H), 7.86 (s, 1H), 7.45 (d, J = 1.52 Hz, 1H), 5.88 (s, 1H), 5.01 (quin, J = 6.63 Hz, 1H), 4.38 (d, J = 4.80 Hz, 2H), 2.25 (s, 3H), 2.11 (s, 3H), 1.47 (d, J = 6.57 Hz, 6H) | 517.0 |
| 156 | 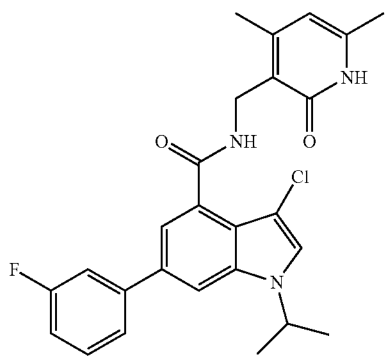 [SMILES: Cc1cc(C)c(CNC(=O)c2cc(-c3cccc(F)c3)cc3c2c(Cl)cn3C(C)C)c(=O)[nH]1] | 3-chloro-N-((4,6-dimethyl-2-oxo-1,2-dihydropyridin-3-yl)methyl)-6-(3-fluorophenyl)-1-isopropyl-1H-indole-4-carboxamide | 11.47 (br. s., 1H), 8.19 (t, J = 4.93 Hz, 1H), 7.99 (s, 1H), 7.79 (s, 1H), 7.44-7.69 (m, 4H), 7.34 (s, 1H), 7.18 (t, J = 7.33 Hz, 1H), 5.87 (s, 1H), 5.00 (dt, J = 6.66, 13.20 Hz, 1H), 4.37 (d, J = 4.80 Hz, 2H), 2.25 (s, 3H), 2.11 (s, 3H), 1.46 (d, J = 6.57 Hz, 6H) | 466.0 |
| 157 | 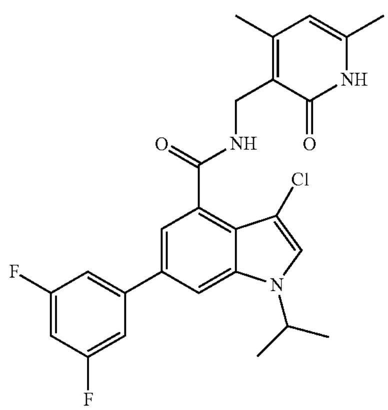 [SMILES: Cc1cc(C)c(CNC(=O)c2cc(-c3cc(F)cc(F)c3)cc3c2c(Cl)cn3C(C)C)c(=O)[nH]1] | 3-chloro-6-(3,5-difluorophenyl)-N-((4,6-dimethyl-2-oxo-1,2-dihydropyridin-3-yl)methyl)-1-isopropyl-1H-indole-4-carboxamide | 11.47 (s, 1H), 8.19 (t, J = 5.05 Hz, 1H), 8.06 (d, J = 1.52 Hz, 1H), 7.81 (s, 1H), 7.52-7.63 (m, 2H), 7.38 (d, J = 1.26 Hz, 1H), 7.20 (tt, J = 2.27, 9.35 Hz, 1H), 5.87 (s, 1H), 5.02 (quin, J = 6.63 Hz, 1H), 4.37 (d, J = 5.05 Hz, 2H), 2.25 (s, 3H), 2.11 (s, 3H), 1.46 (d, J = 6.57 Hz, 6H) | 484.0 |
| 158 | 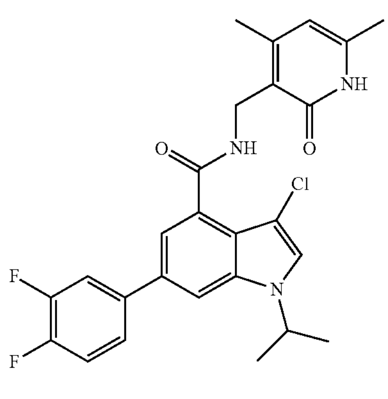 [SMILES: Cc1cc(C)c(CNC(=O)c2cc(-c3ccc(F)c(F)c3)cc3c2c(Cl)cn3C(C)C)c(=O)[nH]1] | 3-chloro-6-(3,4-difluorophenyl)-N-((4,6-dimethyl-2-oxo-1,2-dihydropyridin-3-yl)methyl)-1-isopropyl-1H-indole-4-carboxamide | 11.46 (s, 1H), 8.17 (t, J = 5.05 Hz, 1H), 7.98 (d, J = 1.52 Hz, 1H), 7.90 (ddd, J = 2.27, 7.83, 12.63 Hz, 1H), 7.78 (s, 1H), 7.59-7.69 (m, 1H), 7.52 (dt, J = 8.59, 10.61 Hz, 1H), 7.32 (d, J = 1.52 Hz, 1H), 5.87 (s, 1H), 4.99 (qd, J = 6.44, 6.61 Hz, 1H), 4.37 (d, J = 5.05 Hz, 2H), 2.24 (s, 3H), 2.11 (s, 3H), 1.46 (d, J = 6.57 Hz, 6H) | 484.0 |

-continued

| Ex | Structure | Name | ¹H NMR (400 MHz, DMSO-d₆) δ ppm | MS (ES) [M + H]⁺ |
|---|---|---|---|---|
| 159 | 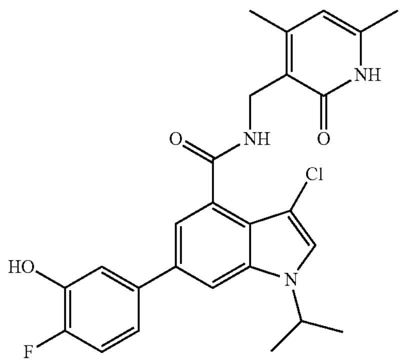 [SMILES: Cc1cc(C)c(CNC(=O)c2cc(-c3ccc(F)c(O)c3)cc3c2c(Cl)cn3C(C)C)c(=O)[nH]1] | 3-chloro-N-((4,6-dimethyl-2-oxo-1,2-dihydropyridin-3-yl)methyl)-6-(4-fluoro-3-hydroxyphenyl)-1-isopropyl-1H-indole-4-carboxamide | 11.46 (br. s., 1H), 9.94 (br. s., 1H), 8.18 (t, J = 5.05 Hz, 1H), 7.82 (d, J = 1.26 Hz, 1H), 7.74 (s, 1H), 7.29 (dd, J = 2.27, 8.59 Hz, 1H), 7.13-7.25 (m, 3H), 5.87 (s, 1H), 4.95 (quin, J = 6.63 Hz, 1H), 4.36 (d, J = 5.05 Hz, 2H), 2.24 (s, 3H), 2.11 (s, 3H), 1.45 (d, J = 6.82 Hz, 6H) | 481.8 |
| 160 | 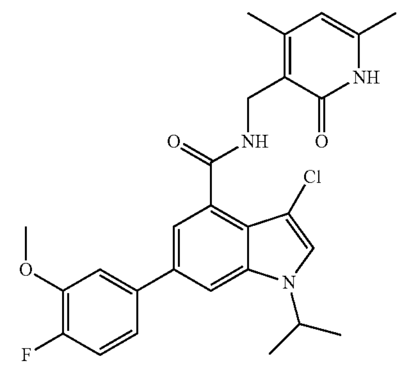 [SMILES: COc1cc(-c2cc(C(=O)NCc3c(C)cc(C)[nH]c3=O)c3c(Cl)cn(C(C)C)c3c2)ccc1F] | 3-chloro-N-((4,6-dimethyl-2-oxo-1,2-dihydropyridin-3-yl)methyl)-6-(4-fluoro-3-methoxyphenyl)-1-isopropyl-1H-indole-4-carboxamide | 11.46 (br. s., 1H), 8.16 (t, J = 5.05 Hz, 1H), 7.90 (s, 1H), 7.76 (s, 1H), 7.46 (d, J = 8.59 Hz, 1H), 7.24-7.34 (m, 3H), 5.87 (s, 1H), 4.98 (ddd, J = 6.44, 6.57, 13.26 Hz, 1H), 4.37 (d, J = 5.05 Hz, 2H), 3.97 (s, 3H), 2.25 (s, 3H), 2.11 (s, 3H), 1.46 (d, J = 6.57 Hz, 6H) | 496.1 |
| 161 | 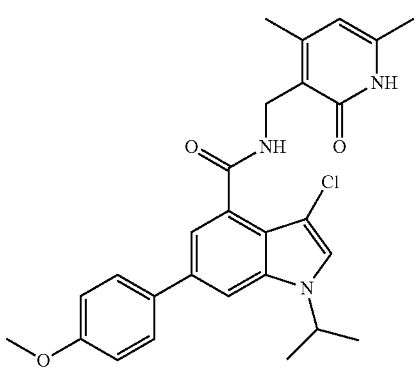 | 3-chloro-N-((4,6-dimethyl-2-oxo-1,2-dihydropyridin-3-yl)methyl)-1-isopropyl-6-(4-methoxyphenyl)-1H-indole-4-carboxamide | 11.48 (br. s., 1H), 8.16 (t, J = 5.05 Hz, 1H), 7.84 (d, J = 1.01 Hz, 1H), 7.64-7.75 (m, 3H), 7.26 (d, J = 1.01 Hz, 1H), 7.03 (d, J = 8.59 Hz, 2H), 5.87 (s, 1H), 4.95 (quin, J = 6.63 Hz, 1H), 4.36 (d, J = 5.05 Hz, 2H), 3.81 (s, 3H), 2.24 (s, 3H), 2.11 (s, 3H), 1.45 (d, J = 6.57 Hz, 6H) | 477.9 |
| 162 | 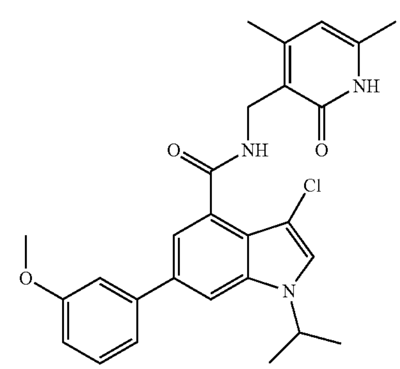 [SMILES: COc1cccc(-c2cc(C(=O)NCc3c(C)cc(C)[nH]c3=O)c3c(Cl)cn(C(C)C)c3c2)c1] | 3-chloro-N-((4,6-dimethyl-2-oxo-1,2-dihydropyridin-3-yl)methyl)-1-isopropyl-6-(3-methoxyphenyl)-1H-indole-4-carboxamide | 11.47 (br. s., 1H), 8.18 (t, J = 5.06 Hz, 1H), 7.91 (d, J = 1.01 Hz, 1H), 7.76 (s, 1H), 7.35-7.42 (m, 1H), 7.25-7.34 (m, 3H), 6.93 (dd, J = 1.77, 8.08 Hz, 1H), 5.87 (s, 1H), 4.99 (dt, J = 6.60, 13.33 Hz, 1H), 4.37 (d, J = 5.05 Hz, 2H), 3.85 (s, 3H), 2.24 (s, 3H), 2.11 (s, 3H), 1.46 (d, J = 6.57 Hz, 6H) | 477.9 |

-continued

| Ex | Structure | Name | ¹H NMR (400 MHz, DMSO-d₆) δ ppm | MS (ES) [M + H]⁺ |
|---|---|---|---|---|
| 163 | 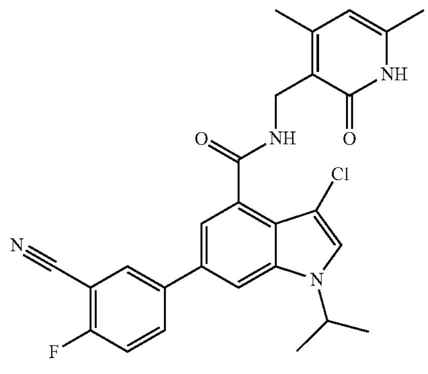 [SMILES: Cc1cc(C)c(CNC(=O)c2cc(-c3ccc(F)c(C#N)c3)cc3c2c(Cl)cn3C(C)C)c(=O)[nH]1] | 3-chloro-6-(3-cyano-4-fluorophenyl)-N-((4,6-dimethyl-2-oxo-1,2-dihydropyridin-3-yl)methyl)-1-isopropyl-1H-indole-4-carboxamide | 11.47 (s, 1H), 8.40 (dd, J = 2.40, 6.19 Hz, 1H), 8.15-8.24 (m, 2H), 8.06 (d, J = 1.52 Hz, 1H), 7.81 (s, 1H), 7.63 (t, J = 9.09 Hz, 1H), 7.38 (d, J = 1.52 Hz, 1H), 5.87 (s, 1H), 4.99 (quin, J = 6.63 Hz, 1H), 4.37 (d, J = 5.05 Hz, 2H), 2.25 (s, 3H), 2.11 (s, 3H), 1.47 (d, J = 6.57 Hz, 6H) | 491.0 |
| 164 | 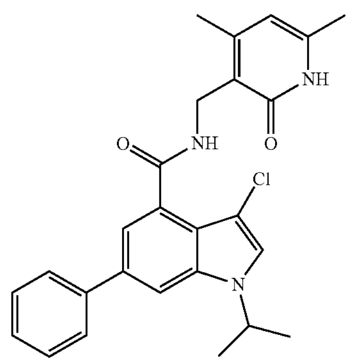 [SMILES: Cc1cc(C)c(CNC(=O)c2cc(-c3ccccc3)cc3c2c(Cl)cn3C(C)C)c(=O)[nH]1] | 3-chloro-N-((4,6-dimethyl-2-oxo-1,2-dihydropyridin-3-yl)methyl)-1-isopropyl-6-phenyl-1H-indole-4-carboxamide | 11.48 (br. s., 1H), 8.19 (t, J = 5.05 Hz, 1H), 7.91 (s, 1H), 7.72-7.80 (m, 3H), 7.47 (t, J = 7.58 Hz, 2H), 7.33-7.39 (m, 1H), 7.30 (d, J = 1.26 Hz, 1H), 5.87 (s, 1H), 4.97 (dt, J = 6.60, 13.33 Hz, 1H), 4.37 (d, J = 4.80 Hz, 2H), 2.24 (s, 3H), 2.11 (s, 3H), 1.46 (d, J = 6.82 Hz, 6H) | 447.8 |
| 165 | 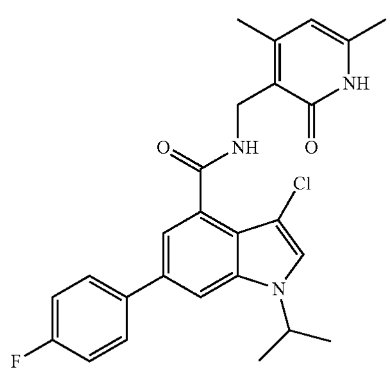 [SMILES: Cc1cc(C)c(CNC(=O)c2cc(-c3ccc(F)cc3)cc3c2c(Cl)cn3C(C)C)c(=O)[nH]1] | 3-chloro-N-((4,6-dimethyl-2-oxo-1,2-dihydropyridin-3-yl)methyl)-6-(4-fluorophenyl)-isopropyl-1H-indole-4-carboxamide | 11.47 (s, 1H), 8.18 (t, J = 5.05 Hz, 1H), 7.90 (d, J = 1.26 Hz, 1H), 7.80 (dd, J = 5.31, 8.84 Hz, 2H), 7.76 (s, 1H), 7.26-7.34 (m, 3H), 5.87 (s, 1H), 4.97 (quin, J = 6.57 Hz, 1H), 4.36 (d, J = 5.05 Hz, 2H), 2.24 (s, 3H), 2.11 (s, 3H), 1.45 (d, J = 6.57 Hz, 6H) | 466.0 |
| 166 | 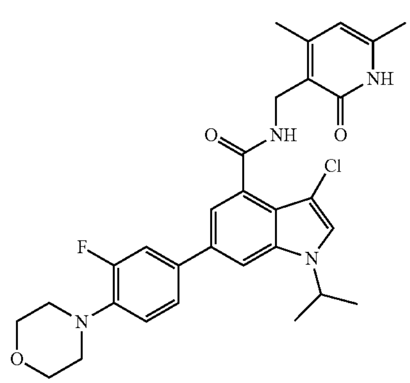 [SMILES: Cc1cc(C)c(CNC(=O)c2cc(-c3ccc(N4CCOCC4)c(F)c3)cc3c2c(Cl)cn3C(C)C)c(=O)[nH]1] | 3-chloro-N-((4,6-dimethyl-2-oxo-1,2-dihydropyridin-3-yl)methyl)-6-(3-fluoro-4-morpholinophenyl)-1-isopropyl-1H-indole-4-carboxamide | 11.48 (br. s., 1H), 8.16 (t, J = 4.93 Hz, 1H), 7.91 (d, J = 1.26 Hz, 1H), 7.74 (s, 1H), 7.63 (dd, J = 2.02, 14.65 Hz, 1H), 7.54 (dd, J = 1.77, 8.34 Hz, 1H), 7.30 (d, J = 1.01 Hz, 1H), 7.11 (t, J = 8.84 Hz, 1H), 5.87 (s, 1H), 4.98 (quin, J = 6.63 Hz, 1H), 4.36 (d, J = 5.05 Hz, 2H), 3.70-3.82 (m, 4H), 2.99-3.12 (m, 4H), 2.24 (s, 3H), 2.11 (s, 3H), 1.45 (d, J = 6.57 Hz, 6H) | 551.2 |

-continued

| Ex | Structure | Name | ¹H NMR (400 MHz, DMSO-d₆) δ ppm | MS (ES) [M + H]⁺ |
|---|---|---|---|---|
| 167 | 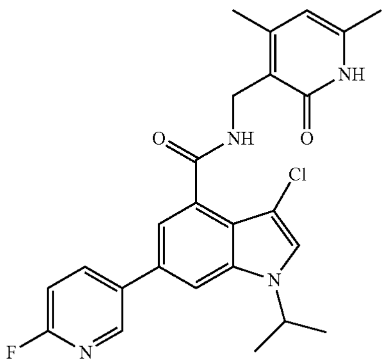 [SMILES: Cc1cc(C)c(CNC(=O)c2cc(-c3ccc(F)nc3)cc3c2c(Cl)cn3C(C)C)c(=O)[nH]1] | 3-chloro-N-((4,6-dimethyl-2-oxo-1,2-dihydropyridin-3-yl)methyl)-6-(6-fluoropyridin-3-yl)-1-isopropyl-1H-indole-4-carboxamide | 11.47 (s, 1H), 8.64 (d, J = 2.53 Hz, 1H), 8.39 (td, J = 2.53, 8.21 Hz, 1H), 8.19 (t, J = 4.93 Hz, 1H), 8.03 (d, J = 1.52 Hz, 1H), 7.80 (s, 1H), 7.34 (d, J = 1.52 Hz, 1H), 7.30 (dd, J = 2.78, 8.59 Hz, 1H), 5.87 (s, 1H), 4.98 (ddd, J = 6.69, 6.82, 13.26 Hz, 1H), 4.37 (d, J = 5.05 Hz, 2H), 2.25 (s, 3H), 2.11 (s, 3H), 1.46 (d, J = 6.82 Hz, 6H) | 467.3 |
| 168 | 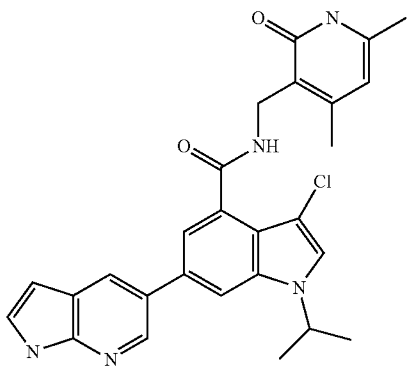 [SMILES: Cc1cc(C)c(CNC(=O)c2cc(-c3cnc4[nH]ccc4c3)cc3c2c(Cl)cn3C(C)C)c(=O)[nH]1] | 3-chloro-N-[(4,6-dimethyl-2-oxo-1,2-dihydro-3-pyridinyl)methyl]-1-(1-methylethyl)-6-(1H-pyrrolo[2,3-b]pyridin-5-yl)-1H-indole-4-carboxamide | 11.70 (br. s., 1 H) 11.42 (br. s., 1 H) 8.61 (d, J = 2.02 Hz, 1 H) 8.30 (d, J = 2.27 Hz, 1 H) 8.20 (t, J = 5.05 Hz, 1 H) 7.96 (d, J = 1.26 Hz, 1 H) 7.74 (s, 1 H) 7.52 (d, J = 3.54 Hz, 1 H) 7.35 (d, J = 1.26 Hz, 1 H) 6.51 (d, J = 3.54 Hz, 1 H) 5.87 (s, 1 H) 5.00 (quin, J = 6.63 Hz, 1 H) 4.38 (s, 1 H) 4.37 (s, 1 H) 2.25 (s, 3 H) 2.11 (s, 3 H) 1.48 (s, 3 H) 1.46 (s, 3 H) | 488.0 |
| 169 | 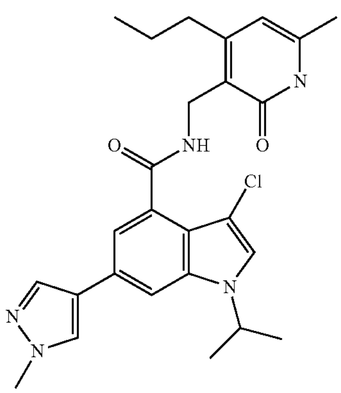 [SMILES: CCCc1cc(C)[nH]c(=O)c1CNC(=O)c1cc(-c2cnn(C)c2)cc2c1c(Cl)cn2C(C)C] | 3-chloro-1-(1-methylethyl)-N-[(6-methyl-2-oxo-4-propyl-1,2-dihydro-3-pyridinyl)methyl]-6-(1-methyl-1H-pyrazol-4-yl)-1H-indole-4-carboxamide | 11.47 (s, 1 H) 8.19 (s, 1 H) 8.02 (t, J = 5.05 Hz, 1 H) 7.92 (s, 1 H) 7.81-7.84 (m, 1 H) 7.66 (s, 1 H) 7.21 (d, J = 1.26 Hz, 1 H) 5.90 (s, 1 H) 4.87 (quin, J = 6.63 Hz, 1 H) 4.37 (s, 1 H) 4.36 (s, 1 H) 3.87 (s, 3 H) 2.53-2.58 (m, 2 H) 2.12 (s, 3 H) 1.53-1.61 (m, 2 H) 1.45 (s, 3 H) 1.44 (s, 3 H) 0.95 (t, J = 7.33 Hz, 3 H) | 479.8/ 481.9 |
| 170 | 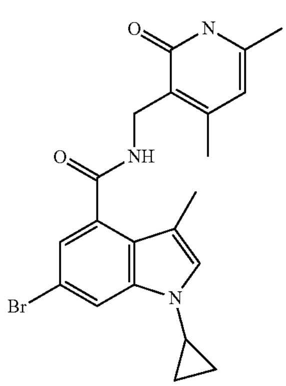 [SMILES: Cc1cc(C)c(CNC(=O)c2cc(Br)cc3c2c(C)cn3C2CC2)c(=O)[nH]1] | 6-bromo-1-cyclopropyl-N-[(4,6-dimethyl-2-oxo-1,2-dihydro-3-pyridinyl)methyl]-3-methyl-1H-indole-4-carboxamide | 11.48 (s, 1 H) 8.27 (t, J = 4.93 Hz, 1 H) 7.71 (d, J = 1.77 Hz, 1 H) 7.15 (s, 1 H) 7.06 (d, J = 1.52 Hz, 1 H) 5.86 (s, 1 H) 4.31 (s, 1 H) 4.29 (s, 1 H) 3.36-3.41 (m, 1 H) 2.21 (s, 3 H) 2.11 (s, 3 H) 2.10 (s, 3 H) 1.01-1.07 (m, 2 H) 0.86-0.91 (m, 2 H) | 427.7/ 429.9 |

-continued

| Ex | Structure | Name | $^1$H NMR (400 MHz, DMSO-d$_6$) δ ppm | MS (ES) [M + H]$^+$ |
|---|---|---|---|---|
| 171 | 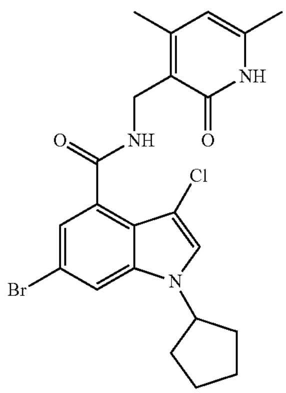 [SMILES: Cc1cc(C)c(CNC(=O)c2cc(Br)cc3c2c(Cl)cn3C2CCCC2)c(=O)[nH]1] | 6-bromo-3-chloro-1-cyclopentyl-N-((4,6-dimethyl-2-oxo-1,2-dihydropyridin-3-yl)methyl)-1H-indole-4-carboxamide | 1.62-1.90 (m, 6 H), 2.08-2.15 (m, 5 H), 2.22 (s, 3 H), 2.22 (s, 3 H), 4.32 (d, J = 4.80 Hz, 2 H), 4.87-5.04 (m, 1 H), 5.86 (s, 1 H), 7.08 (m, 1 H), 7.72 (m, 1 H), 7.93 (d, J = 1.52 Hz, 1 H), 8.25 (t, J = 4.93 Hz, 1 H), 11.47 (br. s., 1 H) | 475.7 |
| 172 | 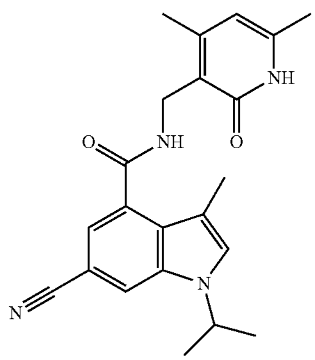 [SMILES: Cc1cc(C)c(CNC(=O)c2cc(C#N)cc3c2c(C)cn3C(C)C)c(=O)[nH]1] | 6-cyano-N-((4,6-dimethyl-2-oxo-1,2-dihydropyridin-3-yl)methyl)-1-isopropyl-3-methyl-1H-indole-4-carboxamide | 1.39-1.47 (m, 6 H), 2.12 (s, 3 H), 2.16 (s, 3 H), 2.22-2.26 (m, 3 H), 4.32 (d, J = 5.05 Hz, 2 H), 4.85 (quin, J = 6.63 Hz, 1 H), 5.87 (s, 1 H), 7.21 (d, J = 1.26 Hz, 1 H), 7.64 (s, 1 H), 8.16 (d, J = 1.26 Hz, 1 H), 8.33 (t, J = 5.05 Hz, 1 H), 11.48 (br. s., 1 H) | 377.2 |
| 173 | 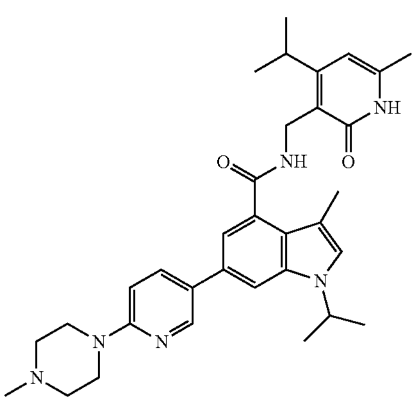 | 3-methyl-1-(1-methylethyl)-N-{[6-methyl-4-(1-methylethyl)-2-oxo-1,2-dihydro-3-pyridinyl]methyl}-6-[6-(4-methyl-1-piperazinyl)-3-pyridinyl]-1H-indole-4-carboxamide | 11.44 (br. s., 1 H) 8.50 (d, J = 2.27 Hz, 1 H) 8.18 (t, J = 4.80 Hz, 1 H) 7.92 (dd, J = 8.84, 2.53 Hz, 1 H) 7.72 (d, J = 1.26 Hz, 1 H) 7.29 (s, 1 H) 7.18 (d, J = 1.26 Hz, 1 H) 6.92 (d, J = 9.09 Hz, 1 H) 6.01 (s, 1 H) 4.84 (quin, J = 6.63 Hz, 1 H) 4.41 (br. s., 1 H) 4.40 (br. s., 1 H) 3.48-3.56 (m, 4 H) 3.24-3.31 (m, 1 H) 2.39-2.44 (m, 4 H) 2.23 (s, 3 H) 2.17 (s, 3 H) 2.14 (s, 3 H) 1.44 (s, 3 H) 1.42 (s, 3 H) 1.15 (s, 3 H) 1.13 (s, 3 H) | 555.4 |
| 174 | 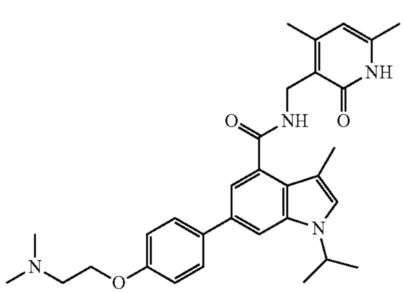 | 6-(4-{[2-(dimethylamino)ethyl]oxy}phenyl)-N-[(4,6-dimethyl-2-oxo-1,2-dihydro-3-pyridinyl)methyl]-3-methyl-1-(1-methylethyl)-1H-indole-4-carboxamide | 11.43 (br. s., 1 H) 8.09-8.27 (m, 1 H) 7.70 (d, J = 1.52 Hz, 1 H) 7.66-7.68 (m, 1 H) 7.63-7.66 (m, 1 H) 7.29 (d, J = 1.01 Hz, 1 H) 7.19 (d, J = 1.52 Hz, 1 H) 7.02-7.04 (m, 1 H) 7.00-7.02 (m, 1 H) 5.87 (s, 1 H) 4.85 (dt, J = 13.39, 6.69 Hz, 1 H) 4.36 (s, 1 H) 4.34 (s, 1 H) 4.09 (t, J = 5.81 Hz, 2 H) 2.61-2.67 (m, 2 H) 2.23 (s, 9 H) 2.17 (s, 3 H) 2.11 (s, 3 H) 1.44 (s, 3 H) 1.42 (s, 3 H) | 515.1 |

| Ex | Structure | Name | ¹H NMR (400 MHz, DMSO-d₆) δ ppm | MS (ES) [M + H]⁺ |
|---|---|---|---|---|
| 175 | 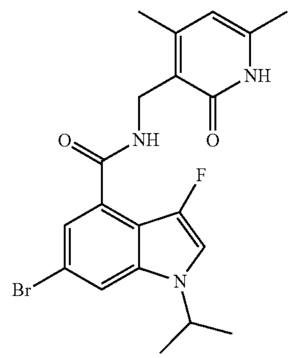 [SMILES: Cc1cc(C)c(CNC(=O)c2cc(Br)cc3c2c(F)cn3C(C)C)c(=O)[nH]1] | 6-bromo-N-[(4,6-dimethyl-2-oxo-1,2-dihydro-3-pyridinyl)methyl]-3-fluoro-1-(1-methylethyl)-1H-indole-4-carboxamide | 1H NMR (400 MHz, METHANOL-d4) δ 7.81 (t, J = 1.77 Hz, 1H), 7.40 (d, J = 1.52 Hz, 1H), 7.38 (d, J = 2.27 Hz, 1H), 6.13 (s, 1H), 4.71-4.81 (m, J = 1.52, 6.63, 6.63, 13.26 Hz, 1H), 4.54 (s, 2H), 2.40 (s, 3H), 2.26 (s, 3H), 1.47 (d, J = 6.82 Hz, 6H) | 434.1 |
| 176 | 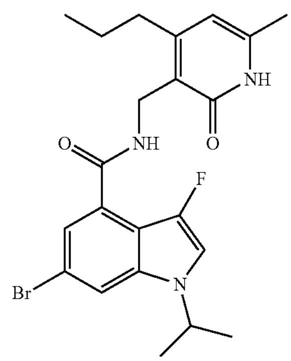 [SMILES: CCCc1cc(C)[nH]c(=O)c1CNC(=O)c1cc(Br)cc2c1c(F)cn2C(C)C] | 6-bromo-3-fluoro-1-(1-methylethyl)-N-[(6-methyl-2-oxo-4-propyl-1,2-dihydro-3-pyridinyl)methyl]-1H-indole-4-carboxamide | 11.49 (s, 1H), 8.20-8.28 (m, 1H), 7.94 (t, J = 1.77 Hz, 1H), 7.66 (d, J = 2.27 Hz, 1H), 7.24 (d, J = 1.52 Hz, 1H), 5.90 (s, 1H), 4.82 (dd, J = 1.52, 6.82 Hz, 1H), 4.33 (d, J = 5.05 Hz, 2H), 2.13 (s, 3H), 1.48-1.59 (m, 3H), 1.39 (d, J = 6.57 Hz, 6H), 0.92 (t, 3H) | 462.2 |
| 177 | 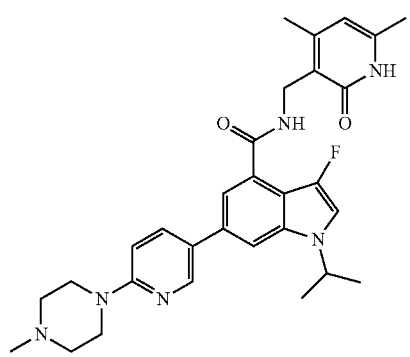 | N-[(4,6-dimethyl-2-oxo-1,2-dihydro-3-pyridinyl)methyl]-3-fluoro-1-(1-methylethyl)-6-[6-(4-methyl-1-piperazinyl)-3-pyridinyl]-1H-indole-4-carboxamide | 11.48 (d, J = 11.87 Hz, 1H), 8.54 (d, J = 2.53 Hz, 1H), 8.19 (t, J = 5.05 Hz, 1H), 8.16 (s, 1H), 7.96 (dd, J = 2.53, 8.84 Hz, 1H), 7.86 (s, 1H), 7.58 (d, J = 2.27 Hz, 1H), 7.43 (d, J = 1.01 Hz, 1H), 6.94 (d, J = 8.84 Hz, 1H), 5.88 (s, 1H), 4.86-5.03 (m, J = 7.07 Hz, 1H), 4.36 (d, J = 4.80 Hz, 2H), 3.48-3.59 (m, 4H), 2.44 (t, J = 4.93 Hz, 4H), 2.23 (d, J = 10.36 Hz, 6H), 2.12 (s, 3H), 1.42 (d, 6H) | 531.4 |
| 178 | 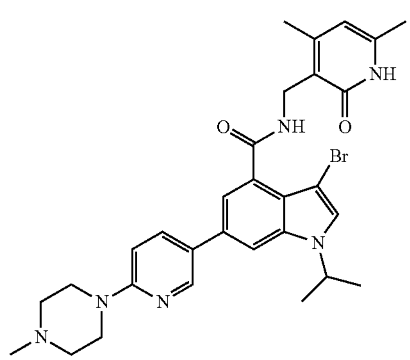 | 3-bromo-N-[(4,6-dimethyl-2-oxo-1,2-dihydro-3-pyridinyl)methyl]-1-(1-methylethyl)-6-[6-(4-methyl-1-piperazinyl)-3-pyridinyl]-1H-indole-4-carboxamide | 1H NMR (400 MHz, METHANOL-d4) δ 8.49 (d, J = 2.27 Hz, 1H), 7.97 (dd, J = 2.53, 8.84 Hz, 1H), 7.77 (d, J = 1.26 Hz, 1H), 7.55 (s, 1H), 7.37 (d, J = 1.26 Hz, 1H), 6.99 (d, J = 8.84 Hz, 1H), 6.14 (s, 1H), 4.60 (s, 2H), 3.74 (br. s., 4H), 2.96 (t, J = 4.55 Hz, 4H), 2.65 (s, 3H), 2.47 (s, 3H), 2.26 (s, 3H), 1.54 (d, J = 6.57 Hz, 6H) | 592.2 |

-continued

| Ex | Structure | Name | ¹H NMR (400 MHz, DMSO-d₆) δ ppm | MS (ES) [M + H]⁺ |
|---|---|---|---|---|
| 179 | 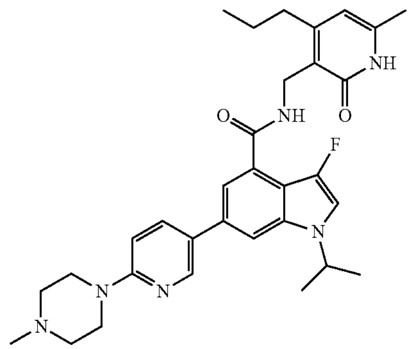 | 3-fluoro-1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide | 11.50 (br. s., 1H), 8.53 (d, J = 2.53 Hz, 1H), 8.12-8.21 (m, 1H), 7.95 (dd, J = 2.53, 8.84 Hz, 1H), 7.86 (s, 1H), 7.59 (d, J = 2.27 Hz, 1H), 7.43 (d, J = 1.26 Hz, 1H), 6.94 (d, J = 8.84 Hz, 1H), 5.90 (s, 1H), 4.86-5.03 (m, 1H), 4.37 (d, J = 5.05 Hz, 2H), 3.49-3.58 (m, 4H), 2.37-2.47 (m, 4H), 2.24 (s, 3H), 2.13 (s, 3H), 1.55 (sxt, J = 7.53 Hz, 2H), 1.42 (d, J = 6.57 Hz, 6H), 0.92 (t, J = 7.33 Hz, 3H) | 559.7 |
| 180 | 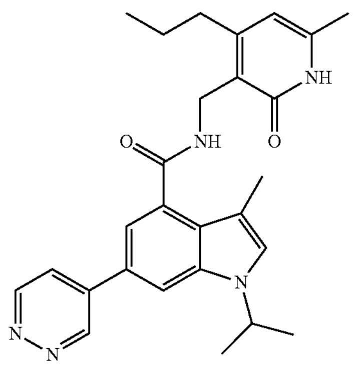 [SMILES: CCCc1cc(C)[nH]c(=O)c1CNC(=O)c1cc(-c2ccnnc2)cc2c1c(C)cn2C(C)C] | 3-methyl-1-(1-methylethyl)-N-[(6-methyl-2-oxo-4-propyl-1,2-dihydro-3-pyridinyl)methyl]-6-(4-pyridazinyl)-1H-indole-4-carboxamide | 11.00-11.70 (bs, 1H), 9.70-9.79 (m, 1H), 9.16-9.27 (m, 1H), 8.25 (t, J = 4.80 Hz, 1H), 8.19 (d, J = 1.52 Hz, 1H), 8.08 (dd, J = 2.53, 5.56 Hz, 1H), 7.48 (s, 2H), 5.91 (s, 1H), 4.96 (quin, J = 6.63 Hz, 1H), 4.38 (d, J = 4.80 Hz, 2H), 2.53-2.59 (m, 2H), 2.19 (s, 3H), 2.12 (s, 3H), 1.58 (sxt, J = 7.43 Hz, 2H), 1.46 (d, J = 6.82 Hz, 6H), 0.94 (t, J = 7.45 Hz, 3H) | 458.3 |
| 181 | 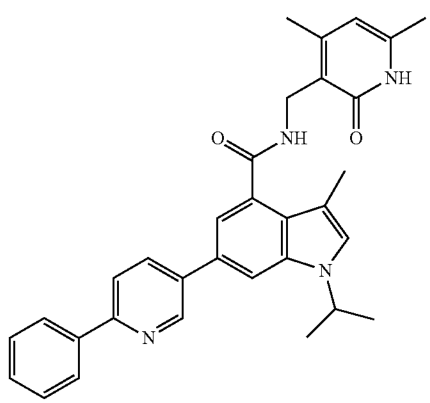 [SMILES: Cc1cc(C)c(CNC(=O)c2cc(-c3ccc(-c4ccccc4)nc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(6-phenyl-3-pyridinyl)-1H-indole-4-carboxamide | 11.52 (br. s., 1 H) 9.10 (d, J = 2.27 Hz, 1 H) 8.31 (dd, J = 8.21, 2.15 Hz, 1 H) 8.25 (t, J = 5.05 Hz, 1 H) 8.16 (d, J = 7.33 Hz, 2 H) 8.09 (d, J = 8.34 Hz, 1 H) 7.98 (d, J = 1.26 Hz, 1 H) 7.51-7.56 (m, 2 H) 7.45-7.49 (m, 1 H) 7.37-7.40 (m, 2 H) 5.89 (s, 1 H) 4.89-4.96 (m, 1 H) 4.37 (d, J = 5.05 Hz, 2 H) 2.26 (s, 3 H) 2.19 (s, 3 H) 2.12 (s, 3 H) 1.46 (d, J = 6.57 Hz, 6 H) | |
| 182 | 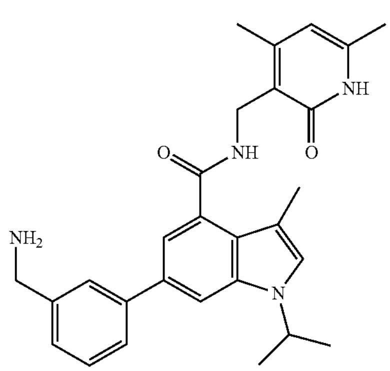 [SMILES: Cc1cc(C)c(CNC(=O)c2cc(-c3cccc(CN)c3)cc3c2c(C)cn3C(C)C)c(=O)[nH]1] | 6-[3-(aminomethyl)phenyl]-N-[(4,6-dimethyl-2-oxo-1,2-dihydro-3-pyridinyl)methyl]-3-methyl-1-(1-methylethyl)-1H-indole-4-carboxamide | 8.17 (br. s., 1 H) 7.78 (br. s., 2 H) 7.65 (br. s., 1 H) 7.43 (t, J = 7.83 Hz, 1 H) 7.33 (br. s., 2 H) 7.20-7.31 (m, 1 H) 5.87 (s, 1 H) 4.85 (d, J = 6.57 Hz, 1 H) 4.36 (br. s., 1 H) 4.35 (br. s., 1 H) 3.92 (s, 1 H) 2.24 (s, 3 H) 2.17 (s, 3 H) 2.11 (s, 3 H) 1.45 (br. s., 3 H) 1.44 (br. s., 3 H) | 457.3 |

| Ex | Structure | Name | ¹H NMR (400 MHz, DMSO-d₆) δ ppm | MS (ES) [M + H]⁺ |
|---|---|---|---|---|
| 183 | 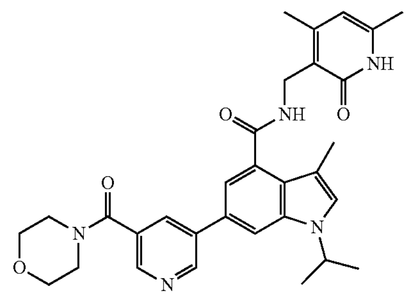 [SMILES: Cc1cc(C)c(CNC(=O)c2cc(-c3cncc(C(=O)N4CCOCC4)c3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[5-(4-morpholinylcarbonyl)-3-pyridinyl]-1H-indole-4-carboxamide | 11.48 (s, 1 H) 9.07 (d, J = 2.27 Hz, 1 H) 8.56 (d, J = 1.77 Hz, 1 H) 8.18-8.25 (m, 2 H) 7.96 (d, J = 1.26 Hz, 1 H) 7.39 (s, 1 H) 7.34 (d, J = 1.52 Hz, 1 H) 5.87 (s, 1 H) 4.92 (quin, J = 6.63 Hz, 1 H) 4.36 (d, J = 5.05 Hz, 2 H) 3.69 (br. s., 4 H) 3.54-3.62 (m, 2 H) 3.43 (br. s., 2 H) 2.25 (s, 3 H) 2.18 (s, 3 H) 2.11 (s, 3 H) 1.44 (d, J = 6.57 Hz, 6 H) | 542.4 |
| 184 | 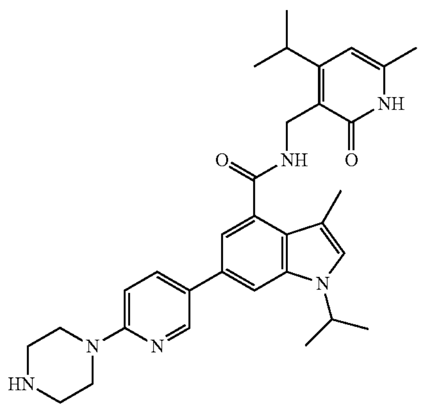 [SMILES: Cc1cc(C(C)C)c(CNC(=O)c2cc(-c3ccc(N4CCNCC4)nc3)cc3c2c(C)cn3C(C)C)c(=O)[nH]1] | 3-methyl-1-(1-methylethyl)-N-{[6-methyl-4-(1-methylethyl)-2-oxo-1,2-dihydro-3-pyridinyl]methyl}-6-[6-(1-piperazinyl)-3-pyridinyl]-1H-indole-4-carboxamide | 11.49 (br. s., 1 H) 8.49 (d, J = 2.27 Hz, 1 H) 8.18 (t, J = 4.67 Hz, 1 H) 7.90 (dd, J = 8.84, 2.27 Hz, 1 H) 7.72 (s, 1 H) 7.29 (s, 1 H) 7.18 (s, 1 H) 6.88 (d, J = 8.84 Hz, 1 H) 6.01 (s, 1 H) 4.79-4.90 (m, 1 H) 4.41 (br. s., 1 H) 4.40 (br. s., 1 H) 3.41-3.57 (m, 4 H) 3.22-3.30 (m, 1 H) 2.62-2.90 (m, 4 H) 2.55 (s, 1 H) 2.17 (s, 3 H) 2.14 (s, 3 H) 1.43 (s, 3 H) 1.42 (s, 3 H) 1.15 (s, 3 H) 1.13 (s, 3 H) | 541.3 |
| 185 | 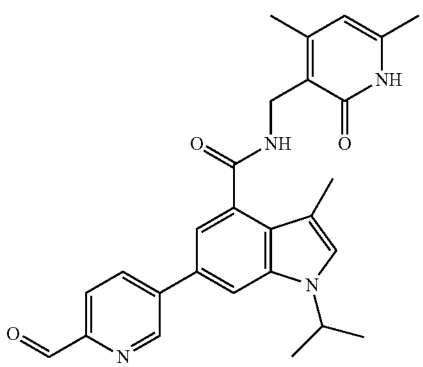 [SMILES: Cc1cc(C)c(CNC(=O)c2cc(-c3ccc(C=O)nc3)cc3c2c(C)cn3C(C)C)c(=O)[nH]1] | N-[(4,6-dimethyl-2-oxo-1,2-dihydro-3-pyridinyl)methyl]-6-(6-formyl-3-pyridinyl)-3-methyl-1-(1-methylethyl)-1H-indole-4-carboxamide | 11.50 (br. s., 1 H) 10.04 (s, 1 H) 9.27 (d, J = 1.52 Hz, 1 H) 8.44 (dd, J = 8.08, 1.77 Hz, 1 H) 8.27 (t, J = 5.05 Hz, 1 H) 8.07 (d, J = 1.26 Hz, 1 H) 8.01 (d, J = 8.08 Hz, 1 H) 7.42-7.45 (m, 2 H) 5.88 (s, 1 H) 4.89-4.99 (m, 1 H) 4.37 (d, J = 5.05 Hz, 2 H) 2.25 (s, 3 H) 2.18 (s, 3 H) 2.11 (s, 3 H) 1.45 (d, J = 6.57 Hz, 6 H) | 457.2 |
| 186 | 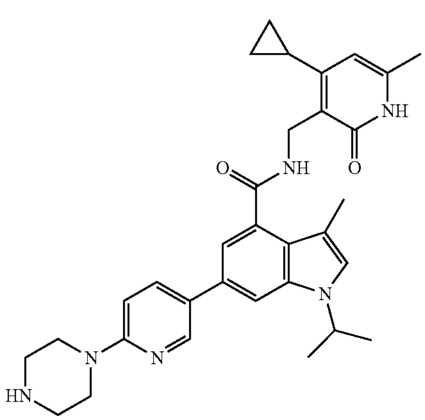 [SMILES: Cc1cc(C2CC2)c(CNC(=O)c2cc(-c3ccc(N4CCNCC4)nc3)cc3c2c(C)cn3C(C)C)c(=O)[nH]1] | N-[(4-cyclopropyl-6-methyl-2-oxo-1,2-dihydro-3-pyridinyl)methyl]-3-methyl-1-(1-methylethyl)-6-[6-(1-piperazinyl)-3-pyridinyl]-1H-indole-4-carboxamide | 11.42 (br. s., 1 H) 8.50 (d, J = 2.02 Hz, 1 H) 8.23 (t, J = 4.93 Hz, 1 H) 7.91 (dd, J = 8.84, 2.53 Hz, 1 H) 7.72 (s, 1 H) 7.29 (s, 1 H) 7.20 (s, 1 H) 6.88 (d, J = 9.09 Hz, 1 H) 5.49 (s, 1 H) 4.79-4.89 (m, 1 H) 4.54 (br. s., 1 H) 4.53 (br. s., 1 H) 3.42-3.50 (m, 4 H) 2.74-2.88 (m, 4 H) 2.15-2.23 (m, 4 H) 2.09 (s, 3 H) 1.44 (s, 3 H) 1.42 (s, 3 H) 0.94-1.01 (m, 2 H) 0.76 (d, J = 3.54 Hz, 2 H) | 539.3 |

| Ex | Structure | Name | $^1$H NMR (400 MHz, DMSO-d$_6$) δ ppm | MS (ES) [M + H]$^+$ |
|---|---|---|---|---|
| 187 | 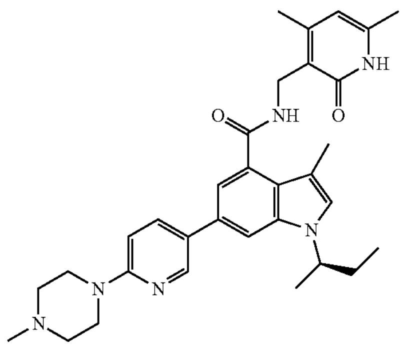 | N-[(4,6-dimethyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide | 11.47 (s, 1 H) 8.50 (d, J = 2.53 Hz, 1 H) 8.16 (t, J = 5.05 Hz, 1 H) 7.92 (dd, J = 8.84, 2.53 Hz, 1 H) 7.73 (d, J = 1.26 Hz, 1 H) 7.26 (s, 1 H) 7.17 (d, J = 1.52 Hz, 1 H) 6.92 (d, J = 9.09 Hz, 1 H) 5.87 (s, 1 H) 4.56-4.65 (m, 1 H) 4.36 (s, 1 H) 4.34 (s, 1 H) 3.49-3.55 (m, 4 H) 2.40-2.44 (m, 4 H) 2.24 (s, 3 H) 2.23 (s, 3 H) 2.16 (s, 3 H) 2.11 (s, 3 H) 1.76-1.87 (m, 2 H) 1.41 (d, J = 6.57 Hz, 3 H) 0.73 (t, J = 7.33 Hz, 3 H) | 541.6 |
| 188 | 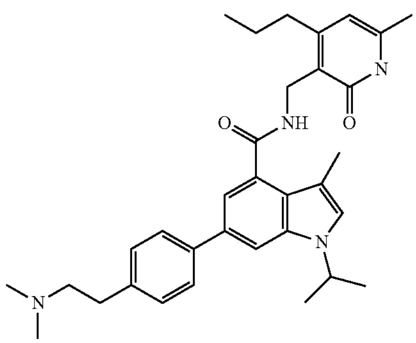 | 6-(4-(2-(dimethylamino)ethyl)phenyl)-1-isopropyl-3-methyl-N-((6-methyl-2-oxo-4-propyl-1,2-dihydropyridin-3-yl)methyl)-1H-indole-4-carboxamide | 11.50 (br. s., 1 H) 8.15 (t, J = 4.93 Hz, 1 H) 7.73-7.76 (m, 1 H) 7.61-7.66 (m, 2 H) 7.31 (d, J = 2.78 Hz, 2 H) 7.29 (s, 1 H) 7.22 (d, J = 1.26 Hz, 1 H) 5.90 (s, 1 H) 4.86 (quin, J = 6.63 Hz, 1 H) 4.37 (s, 1 H) 4.36 (br. s., 1 H) 2.72-2.78 (m, 2 H) 2.55 (d, J = 7.33 Hz, 2 H) 2.47 (d, J = 7.07 Hz, 2 H) 2.14-2.23 (m, 9 H) 2.12 (s, 3 H) 1.53-1.62 (m, 2 H) 1.44 (s, 3 H) 1.43 (s, 3 H) 0.94 (t, J = 7.45 Hz, 3 H) | 527.1 |
| 189 | 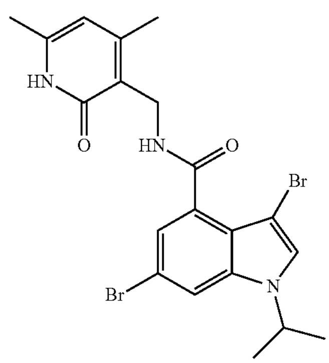 [SMILES: Cc1cc(C)c(CNC(=O)c2cc(Br)cc3c2c(Br)cn3C(C)C)c(=O)[nH]1] | 3,6-dibromo-N-[(4,6-dimethyl-2-oxo-1,2-dihydro-3-pyridinyl)methyl]-1-(1-methylethyl)-1H-indole-4-carboxamide | 1H NMR (400 MHz, METHANOL-d4) δ 7.81 (d, J = 1.52 Hz, 1H), 7.54 (s, 1H), 7.23 (d, J = 1.52 Hz, 1H), 6.12 (s, 1H), 4.77 (quin, J = 6.69 Hz, 1H), 4.55 (s, 2H), 2.44 (s, 3H), 2.25 (s, 3H), 1.50 (d, J = 6.57 Hz, 6H) | 495.8 |
| 190 | 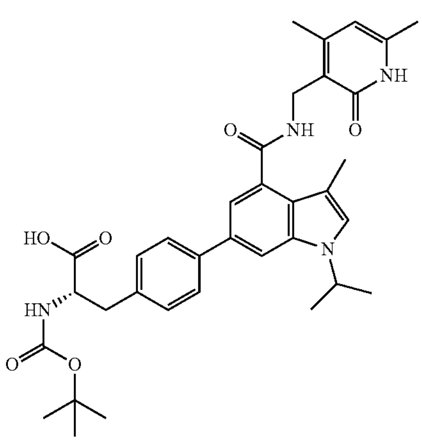 [SMILES: Cc1cc(C)c(CNC(=O)c2cc(-c3ccc(C[C@H](NC(=O)OC(C)(C)C)C(=O)O)cc3)cc3c2c(C)cn3C(C)C)c(=O)[nH]1] | N-{[(1,1-dimethyl-ethyl)oxy]carbonyl}-4-[4-({[(4,6-dimethyl-2-oxo-1,2-dihydro-3-pyridinyl)methyl]amino}carbonyl)-3-methyl-1-(1-methylethyl)-1H-indol-6-yl]-L-phenylalanine | 12.61 (br. s., 1 H) 11.49 (br. s., 1 H) 8.18 (t, J = 5.05 Hz, 1 H) 7.75 (s, 1 H) 7.65 (d, J = 8.34 Hz, 2 H) 7.34 (s, 1 H) 7.32 (s, 2 H) 7.23 (s, 1 H) 7.15 (s, 1 H) 5.87 (s, 1 H) 4.82-4.90 (m, 1 H) 4.35 (d, J = 5.31 Hz, 2 H) 4.12-4.08 (m, 1 H) 3.08-2.88 (m, 2 H) 2.24 (s, 3 H) 2.17 (s, 3 H) 2.11 (s, 3 H) 1.43 (d, J = 6.57 Hz, 6 H) | 615.4 |

| Ex | Structure | Name | $^1$H NMR (400 MHz, DMSO-$d_6$) δ ppm | MS (ES) [M + H]$^+$ |
|---|---|---|---|---|
| 191 | 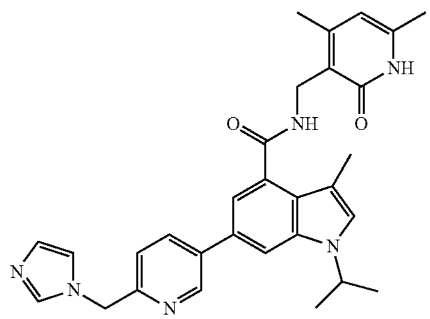 [SMILES: Cc1cc(C)c(CNC(=O)c2cc(-c3ccc(Cn4ccnc4)nc3)cc3c2c(C)cn3C(C)C)c(=O)[nH]1] | N-[(4,6-dimethyl-2-oxo-1,2-dihydro-3-pyridinyl)methyl]-6-[6-(1H-imidazol-1-ylmethyl)-3-pyridinyl]-3-methyl-1-(1-methylethyl)-1H-indole-4-carboxamide | 9.31 (br. s., 1 H) 9.04 (br. s., 1 H) 8.39 (d, J = 2.53 Hz, 1 H) 7.97 (br. s., 1 H) 7.70-7.86 (m, 3 H) 7.39 (br. s., 2 H) 6.25 (br. s., 1 H) 5.68 (br. s., 2 H) 4.80-4.95 (m, 1 H) 4.42 (br. s., 2 H) 2.34 (br. s., 3 H) 2.22 (br. s., 3 H) 2.15 (br. s., 3 H) 1.44 (br. s., 6 H); spiked with d-TFA | 509.6 |
| 192 | 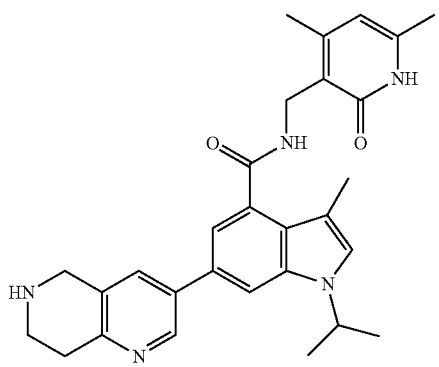 [SMILES: Cc1cc(C)c(CNC(=O)c2cc(-c3cnc4c(c3)CNCC4)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(5,6,7,8-tetrahydro-1,6-napthyridin-3-yl)-1H-indole-4-carboxamide | 11.49 (br. s., 1 H) 8.71 (d, J = 2.02 Hz, 1 H) 8.19 (t, J = 5.05 Hz, 1 H) 7.82 (dd, J = 11.49, 1.64 Hz, 2 H) 7.34 (s, 1 H) 7.26 (d, J = 1.52 Hz, 1 H) 5.87 (s, 1 H) 4.88 (quin, J = 6.63 Hz, 1 H) 4.36 (d, J = 5.05 Hz, 2 H) 3.94 (s, 2 H) 3.05 (t, J = 5.81 Hz, 2 H) 2.75-2.86 (m, 2 H) 2.24 (s, 3 H) 2.17 (s, 3 H) 2.11 (s, 3 H) 1.43 (d, J = 6.57 Hz, 6 H) | 484.3 |
| 193 | 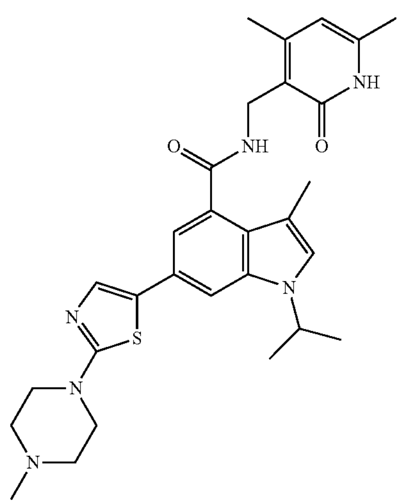 [SMILES: Cc1cc(C)c(CNC(=O)c2cc(-c3cnc(N4CCN(C)CC4)s3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[2-(4-methyl-1-piperazinyl)-1,3-thiazol-5-yl]-1H-indole-4-carboxamide | 11.47 (s, 1 H) 8.15 (t, J = 5.05 Hz, 1 H) 7.57 (s, 1 H) 7.56 (d, J = 1.26 Hz, 1 H) 7.28 (d, J = 1.01 Hz, 1 H) 7.05 (d, J = 1.26 Hz, 1 H) 5.87 (s, 1 H) 4.77 (quin, J = 6.63 Hz, 1 H) 4.34 (s, 1 H) 4.33 (s, 1 H) 3.41-3.47 (m, 4 H) 2.41-2.47 (m, 4 H) 2.23 (s, 6 H) 2.13 (s, 3 H) 2.11 (s, 3 H) 1.42 (s, 3 H) 1.40 (s, 3 H) | 533.6 |
| 194 | 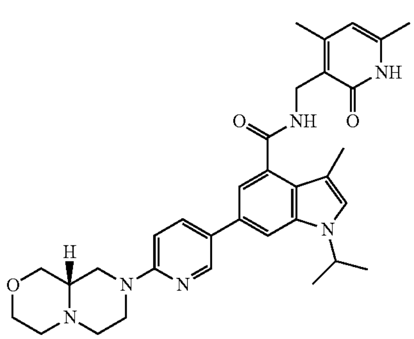 [SMILES: Cc1cc(C)c(CNC(=O)c2cc(-c3ccc(N4CCN5CCOC[C@@H]5C4)nc3)cc3c2c(C)cn3C(C)C)c(=O)[nH]1] | N-[(4,6-dimethyl-2-oxo-1,2-dihydro-3-pyridinyl)methyl]-6-{6-[(9aS)-hexahydropyrazino[2,1-c][1,4]oxazin-8(1H)-yl]-3-pyridinyl}-3-methyl-1-(1-methylethyl)-1H-indole-4-carboxamide | 11.44 (br. s., 1 H) 8.50 (d, J = 2.53 Hz, 1 H) 8.16 (t, J = 5.05 Hz, 1 H) 7.94 (dd, J = 8.84, 2.53 Hz, 1 H) 7.72 (d, J = 1.26 Hz, 1 H) 7.29 (s, 1 H) 7.18 (d, J = 1.52 Hz, 1 H) 6.93 (d, J = 8.84 Hz, 1 H) 5.87 (s, 1 H) 4.84 (quin, J = 6.63 Hz, 1 H) 4.35 (s, 1 H) 4.34 (s, 1 H) 4.24 (d, J = 12.63 Hz, 1 H) 4.14 (d, J = 11.62 Hz, 1 H) 3.78-3.82 (m, 1 H) 3.77 (br. s., 1 H) 3.56 (td, J = 11.37, 2.27 Hz, 1 H) 3.19 (t, J = 10.48 Hz, 1 H) 2.80-2.95 (m, 2 H) 2.69 (d, J = 11.87 Hz, 1 H) 2.39-2.46 (m, 1 H) 2.14-2.27 (m, 9 H) 2.11 (s, 3 H) 1.43 (s, 3 H) 1.42 (s, 3 H) | 569.5 |

| Ex | Name | ¹H NMR (400 MHz, DMSO-d₆) δ ppm | MS (ES) [M + H]⁺ |
|---|---|---|---|
| 195 | 3-methyl-1-(1-methylethyl)-N-[(6-methyl-2-oxo-4-propyl-1,2-dihydro-3-pyridinyl)methyl]-6-(5,6,7,8-tetrahydro-1,8-naphthyridin-3-y)-1H-indole-4-carboxamide | 11.49 (s, 1 H) 8.14 (d, J = 2.27 Hz, 1 H) 8.09 (t, J = 5.05 Hz, 1 H) 7.64 (d, J = 1.26 Hz, 1 H) 7.56 (d, J = 1.77 Hz, 1 H) 7.26 (s, 1 H) 7.14 (d, J = 1.26 Hz, 1 H) 6.51 (s, 1 H) 5.90 (s, 1 H) 4.83 (quin, J = 6.57 Hz, 1 H) 4.37 (br. s., 1 H) 4.35 (br. s., 1 H) 3.30 (br. s., 2 H) 2.76 (t, J = 6.06 Hz, 2 H) 2.56 (d, J = 7.33 Hz, 2 H) 2.16 (s, 3 H) 2.12 (s, 3 H) 1.78-1.85 (m, 2 H) 1.53-1.62 (m, 2 H) 1.43 (s, 3 H) 1.41 (s, 3 H) 0.94 (t, J = 7.33 Hz, 3 H) | 512.4 |
| 196 | 6-[6-(4-ethyl-1-piperazinyl)-3-pyridinyl]-3-methyl-1-(1-methylethyl)-N-[(6-methyl-2-oxo-4-propyl-1,2-dihydro-3-pyridinyl)methyl]-1H-indole-4-carboxamide | 11.49 (s, 1 H) 8.50 (d, J = 2.53 Hz, 1 H) 8.12 (t, J = 5.05 Hz, 1 H) 7.91 (dd, J = 8.84, 2.53 Hz, 1 H) 7.72 (d, J = 1.26 Hz, 1 H) 7.29 (s, 1 H) 7.18 (d, J = 1.52 Hz, 1 H) 6.92 (d, J = 8.84 Hz, 1 H) 5.90 (s, 1 H) 4.84 (quin, J = 6.63 Hz, 1 H) 4.37 (s, 1 H) 4.36 (s, 1 H) 3.48-3.56 (m, 4 H) 2.55 (dd, J = 8.72, 6.95 Hz, 2 H) 2.44-2.49 (m, 4 H) 2.38 (q, J = 7.24 Hz, 2 H) 2.17 (s, 3 H), 2.12 (s, 3 H) 1.53-1.62 (m, 2 H) 1.44 (s, 3 H) 1.42 (s, 3 H) 1.05 (t, J = 7.07 Hz, 3 H) 0.94 (t, J = 7.33 Hz, 3 H) | 569.8 |
| 197 | N-[(4,6-dimethyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide | 11.47 (s, 1 H) 8.50 (d, J = 2.53 Hz, 1 H) 8.16 (t, J = 5.05 Hz, 1 H) 7.92 (dd, J = 8.84, 2.53 Hz, 1 H) 7.72-7.75 (m, 1 H) 7.26 (s, 1 H) 7.17 (d, J = 1.26 Hz, 1 H) 6.92 (d, J = 8.84 Hz, 1 H) 5.87 (s, 1 H) 4.56-4.65 (m, 1 H) 4.36 (s, 1 H) 4.34 (s, 1 H) 3.50-3.55 (m, 4 H) 2.40-2.44 (m, 4 H) 2.24 (s, 3 H) 2.23 (s, 3 H) 2.16 (s, 3 H) 2.11 (s, 3 H) 1.81 (dq, J = 9.85, 7.16 Hz, 2 H) 1.41 (d, J = 6.57 Hz, 3 H) 0.73 (t, J = 7.33 Hz, 3 H) | 541.8 |
| 198 | 3-methyl-1-(1-methylethyl)-6-{6-[4-(1-methylethyl)-1-piperazinyl]-3-pyridinyl}-N-[(6-methyl-2-oxo-4-propyl-1,2-dihydro-3-pyridinyl)methyl]-1H-indole-4-carboxamide | 11.49 (br. s., 1 H) 8.50 (d, J = 2.53 Hz, 1 H) 8.12 (t, J = 5.05 Hz, 1 H) 7.91 (dd, J = 8.84, 2.53 Hz, 1 H) 7.72 (d, J = 1.26 Hz, 1 H) 7.29 (s, 1 H) 7.18 (d, J = 1.26 Hz, 1 H) 5.90 (s, 1 H) 4.84 (quin, J = 6.69 Hz, 1 H) 4.37 (br. s., 1 H) 4.36 (br. s., 1 H) 3.46-3.55 (m, 4 H) 2.66-2.73 (m, 1 H) 2.52-2.57 (m, 6 H) 2.17 (s, 3 H) 2.12 (s, 3 H) 1.53-1.62 (m, 2 H) 1.44 (s, 3 H) 1.42 (s, 3 H) 1.02 (s, 3 H) 1.01 (s, 3 H) 0.99 (d, J = 6.57 Hz, 1 H) 0.94 (t, J = 7.33 Hz, 3 H) | 583.6 |

| Ex | Name | ¹H NMR (400 MHz, DMSO-d₆) δ ppm | MS (ES) [M + H]⁺ |
|---|---|---|---|
| 199 | N-[(4,6-dimethyl-2-oxo-1,2-dihydro-3-pyridinyl)methyl]-3-methyl-1-(1-methylethyl)-6-[6-(4-morpholinylmethyl)-2-pyridinyl]-1H-indole-4-carboxamide | 1.45 (d, J = 6.82 Hz, 6 H), 2.11 (s, 3 H), 2.18 (s, 3 H), 2.25 (s, 3 H), 3.57-3.66 (m, 4 H), 3.69 (s, 2 H), 4.37 (d, J = 5.05 Hz, 2 H), 4.87 (spt, J = 6.40 Hz, 1 H), 5.87 (s, 1 H), 7.33-7.41 (m, 2 H), 7.74 (d, J = 1.52 Hz, 1 H), 7.83 (t, J = 7.71 Hz, 1 H), 7.93 (d, J = 7.83 Hz, 1 H), 8.15 (t, J = 5.05 Hz, 1 H), 8.19 (d, J = 1.26 Hz, 1 H), 11.47 (s, 1 H) | 528.4 |
| 200 | N-[(4,6-dimethyl-2-oxo-1,2-dihydro-3-pyridinyl)methyl]-3-methyl-1-(1-methylethyl)-6-[6-(4-morpholinyl)-2-pyridinyl]-1H-indole-4-carboxamide | 1.45 (d, J = 6.57 Hz, 6 H), 2.12 (s, 3 H), 2.17 (s, 3 H), 2.25 (s, 3 H), 3.48-3.61 (m, 4 H), 3.70-3.83 (m, 4 H), 4.36 (d, J = 5.05 Hz, 2 H), 4.86 (spt, J = 6.57 Hz, 1 H), 5.88 (s, 1 H), 6.75 (d, J = 8.59 Hz, 1 H), 7.30-7.43 (m, 2 H), 7.63 (t, J = 7.95 Hz, 1 H), 7.71 (d, J = 1.52 Hz, 1 H), 8.09-8.21 (m, 2 H), 11.46 (s, 1 H) | 514 |
| 201 | N-[(4,6-dimethyl-2-oxo-1,2-dihydro-3-pyridinyl)methyl]-3-methyl-1-(1-methylethyl)-6-(6-methyl-2-pyridinyl)-1H-indole-4-carboxamide | 1.45 (d, J = 6.82 Hz, 6 H), 2.11 (s, 3 H), 2.18 (s, 3 H), 2.25 (s, 3 H), 2.55 (s, 3 H), 4.37 (d, J = 5.05 Hz, 2 H), 4.87 (spt, J = 6.57 Hz, 1 H), 5.87 (s, 1 H), 7.16 (d, J = 7.33 Hz, 1 H), 7.37 (d, J = 1.01 Hz, 1 H), 7.70-7.78 (m, 2 H), 7.85 (d, J = 8.08 Hz, 1 H), 8.15 (t, J = 4.93 Hz, 1 H), 8.19 (d, J = 1.52 Hz, 1 H), 11.48 (s, 1 H) | 443 |
| 202 | N-[(4,6-dimethyl-2-oxo-1,2-dihydro-3-pyridinyl)methyl]-3-methyl-1-(1-methylethyl)-6-[2-(4-morpholinyl)-4-pyrimidinyl]-1H-indole-4-carboxamide | 1.45 (d, J = 6.57 Hz, 6 H), 2.12 (s, 3 H), 2.17 (s, 3 H), 2.25 (s, 3 H), 3.68-3.76 (m, 4 H), 3.76-3.86 (m, 4 H), 4.36 (d, J = 5.05 Hz, 2 H), 4.92 (spt, J = 6.48 Hz, 1 H), 5.88 (s, 1 H), 7.38 (d, J = 5.31 Hz, 1 H), 7.45 (s, 1 H), 7.79 (d, J = 1.26 Hz, 1 H), 8.20 (t, J = 5.05 Hz, 1 H), 8.29 (d, J = 1.26 Hz, 1 H), 8.41 (d, J = 5.31 Hz, 1 H), 11.46 (s, 1 H) | 515 |

| Ex | Structure | Name | ¹H NMR (400 MHz, DMSO-d₆) δ ppm | MS (ES) [M + H]⁺ |
|---|---|---|---|---|
| 203 | 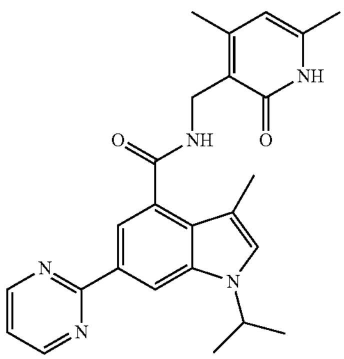 [SMILES: Cc1cc(C)c(CNC(=O)c2cc(-c3ncccn3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(2-pyrimidinyl)-1H-indole-4-carboxamide | 1.47 (d, J = 6.57 Hz, 6 H), 2.12 (s, 3 H), 2.19 (s, 3 H), 2.25 (s, 3 H), 4.37 (d, J = 5.05 Hz, 2 H), 4.84 (spt, J = 6.61 Hz, 1 H), 5.88 (s, 1 H), 7.38 (t, J = 4.80 Hz, 1 H), 7.46 (s, 1 H), 8.06 (d, J = 1.26 Hz, 1 H), 8.18 (t, J = 5.05 Hz, 1 H), 8.52 (d, J = 1.26 Hz, 1 H), 8.87 (d, J = 4.80 Hz, 2 H), 11.48 (s, 1 H) | |
| 204 | 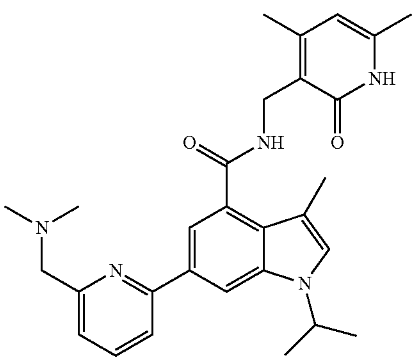 | 6-{6-[(dimethylamino)methyl]-2-pyridinyl}-N-[(4,6-dimethyl-2-oxo-1,2-dihydro-3-pyridinyl)methyl]-3-methyl-1-(1-methylethyl)-1H-indole-4-carboxamide | 1.45 (d, J = 6.82 Hz, 6 H), 2.11 (s, 3 H), 2.17 (s, 3 H), 2.25 (s, 9 H), 3.62 (s, 2 H), 4.37 (d, J = 4.80 Hz, 2 H), 4.87 (spt, J = 6.36 Hz, 1 H), 5.87 (s, 1 H), 7.33 (d, J = 7.58 Hz, 1 H), 7.37 (s, 1 H), 7.75 (d, J = 1.26 Hz, 1 H), 7.83 (t, J = 7.71 Hz, 1 H), 7.92 (d, J = 7.83 Hz, 1 H), 8.15 (t, J = 4.93 Hz, 1 H), 8.19 (d, J = 1.26 Hz, 1 H), 11.47 (s, 1 H) | |
| 205 | 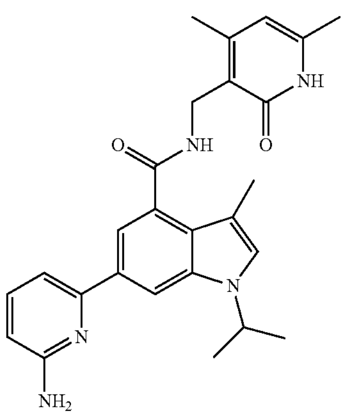 [SMILES: Cc1cc(C)c(CNC(=O)c2cc(-c3cccc(N)n3)cc3c2c(C)cn3C(C)C)c(=O)[nH]1] | 6-(6-amino-2-pyridinyl)-N-[(4,6-dimethyl-2-oxo-1,2-dihydro-3-pyridinyl)methyl]-3-methyl-1-(1-methylethyl)-1H-indole-4-carboxamide | 1.44 (d, J = 6.57 Hz, 6 H), 2.11 (s, 3 H), 2.16 (s, 3 H), 2.24 (s, 3 H), 4.35 (d, J = 5.05 Hz, 2 H), 4.74-4.87 (m, 1 H), 5.87 (s, 1 H), 5.96 (s, 2 H), 6.37 (d, J = 7.83 Hz, 1 H), 7.14 (d, J = 7.33 Hz, 1 H), 7.34 (s, 1 H), 7.44 (t, J = 7.83 Hz, 1 H), 7.65 (d, J = 1.26 Hz, 1 H), 8.04-8.13 (m, 2 H), 11.47 (s, 1 H). | 444 |
| 206 | 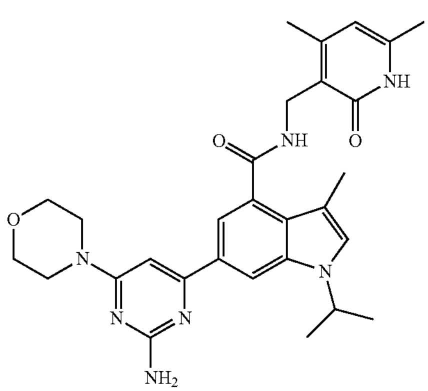 [SMILES: Cc1cc(C)c(CNC(=O)c2cc(-c3cc(N4CCOCC4)nc(N)n3)cc3c2c(C)cn3C(C)C)c(=O)[nH]1] | 6-[2-amino-6-(4-morpholinyl)-4-pyrimidinyl]-N-[(4,6-dimethyl-2-oxo-1,2-dihydro-3-pyridinyl)methyl]-3-methyl-1-(1-methylethyl)-1H-indole-4-carboxamide | 1.44 (d, 6 H), 2.11 (s, 3 H), 2.15 (s, 3 H), 2.24 (s, 3 H), 3.53-3.79 (m, 8 H), 4.35 (d, J = 4.29 Hz, 2 H), 4.80-4.95 (m, 1 H), 5.87 (s, 1 H), 6.10 (br. s., 2 H), 6.68 (s, 1 H), 7.38 (s, 1 H), 7.76 (s, 1 H), 8.06 (br. s., 1 H), 8.18 (s, 1 H), 11.46 (br. s., 1 H). | 530 |

-continued

| Ex | Structure | Name | ¹H NMR (400 MHz, DMSO-d₆) δ ppm | MS (ES) [M + H]⁺ |
|---|---|---|---|---|
| 207 | 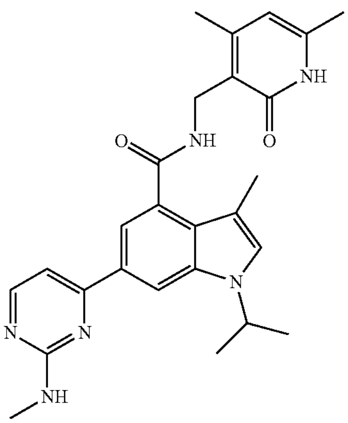 [SMILES: CNc1nccc(-c2cc(C(=O)NCc3c(C)cc(C)[nH]c3=O)c3c(C)cn(C(C)C)c3c2)n1] | N-[(4,6-dimethyl-2-oxo-1,2-dihydro-3-pyridinyl)methyl]-3-methyl-6-[2-(methylamino)-4-pyrimidinyl]-1-(1-methylethyl)-1H-indole-4-carboxamide | 1.45 (d, J = 6.82 Hz, 6 H), 2.11 (s, 3 H), 2.17 (s, 3 H), 2.25 (s, 3 H), 2.88 (br. s., 3 H), 4.36 (d, J = 5.05 Hz, 2 H), 4.81-4.94 (spt, J = 6.57 Hz, 1 H), 5.87 (s, 1 H), 7.07 (br. s., 1 H), 7.25 (d, J = 5.31 Hz, 1 H), 7.44 (s, 1 H), 7.78 (s, 1 H), 8.16 (t, J = 4.93 Hz, 1 H), 8.26 (s, 1 H), 8.31 (d, J = 4.80 Hz, 1 H), 11.47 (s, 1 H) | 459.1 |
| 208 | 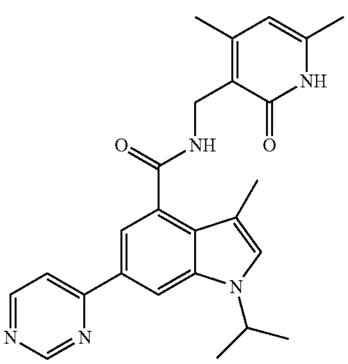 [SMILES: Cc1cc(C)c(CNC(=O)c2cc(-c3ccncn3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(4-pyrimidinyl)-1H-indole-4-carboxamide | 1.46 (d, J = 6.57 Hz, 6 H), 2.12 (s, 3 H), 2.19 (s, 3 H), 2.25 (s, 3 H), 4.37 (d, J = 5.05 Hz, 2 H), 4.92 (spt, J = 6.65 Hz, 1 H), 5.88 (s, 1 H), 7.49 (s, 1 H), 7.85 (d, J = 1.26 Hz, 1 H), 8.17-8.27 (m, 2 H), 8.42 (d, J = 1.52 Hz, 1 H), 8.80 (d, J = 5.31 Hz, 1 H), 9.19 (d, J = 1.01 Hz, 1 H), 11.48 (s, 1 H) | 430.0 |
| 209 | 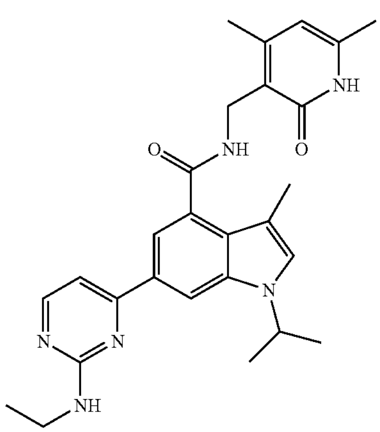 [SMILES: CCNc1nccc(-c2cc(C(=O)NCc3c(C)cc(C)[nH]c3=O)c3c(C)cn(C(C)C)c3c2)n1] | N-[(4,6-dimethyl-2-oxo-1,2-dihydro-3-pyridinyl)methyl]-6-[2-(ethylamino)-4-pyrimidinyl]-3-methyl-1-(1-methylethyl)-1H-indole-4-carboxamide | 1.17 (t, J = 7.07 Hz, 3 H), 1.45 (d, J = 6.57 Hz, 6 H), 2.11 (s, 3 H), 2.17 (s, 3 H), 2.24 (s, 3 H), 3.34-3.45 (m, 2 H), 4.36 (d, J = 5.05 Hz, 2 H), 4.86 (spt, J = 6.61 Hz, 1 H), 5.87 (s, 1 H), 7.12 (br. s., 1 H), 7.23 (d, J = 5.31 Hz, 1 H), 7.43 (s 1 H), 7.76 (d, J = 1.26 Hz, 1 H), 8.16 (t, J = 4.93 Hz, 1 H), 8.25 (s, 1 H), 8.30 (d, J = 5.05 Hz, 1 H), 11.47 (s, 1 H) | 473.0 |

-continued

| Ex | Structure | Name | ¹H NMR (400 MHz, DMSO-d₆) δ ppm | MS (ES) [M + H]⁺ |
|---|---|---|---|---|
| 210 | 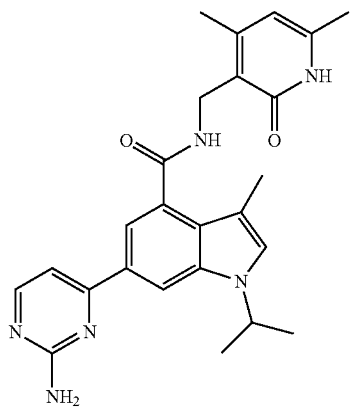 [SMILES: Cc1cc(C)c(CNC(=O)c2cc(-c3ccnc(N)n3)cc3c2c(C)cn3C(C)C)c(=O)[nH]1] | 6-(2-amino-4-pyrimidinyl)-N-[(4,6-dimethyl-2-oxo-1,2-dihydro-3-pyridinyl)methyl]-3-methyl-1-(1-methylethyl)-1H-indole-4-carboxamide | 1.45 (d, J = 6.57 Hz, 6 H), 2.11 (s, 3 H), 2.17 (s, 3 H), 2.24 (s, 3 H), 4.35 (d, J = 5.05 Hz, 2 H), 4.80-4.92 (m, 1 H), 5.87 (s, 1 H), 6.61 (s, 2 H), 7.25 (d, J = 5.31 Hz, 1 H), 7.44 (s, 1 H), 7.75 (d, J = 1.26 Hz, 1 H), 8.15 (t, J = 5.05 Hz, 1 H), 8.23 (d, J = 1.01 Hz, 1 H), 8.27 (d, J = 5.31 Hz, 1 H), 11.47 (s, 1 H) | 445 |
| 211 | 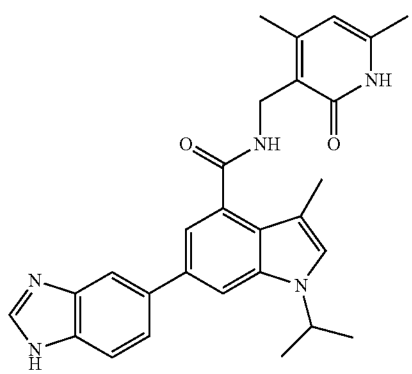 [SMILES: Cc1cc(C)c(CNC(=O)c2cc(-c3ccc4[nH]cnc4c3)cc3c2c(C)cn3C(C)C)c(=O)[nH]1] | 6-(1H-benzimidazol-5-yl)-N-[(4,6-dimethyl-2-oxo-1,2-dihydro-3-pyridinyl)methyl]-3-methyl-1-(1-methylethyl)-1H-indole-4-carboxamide | 1.45 (d, J = 6.57 Hz, 6 H), 2.11 (s, 3 H), 2.19 (s, 3 H), 2.25 (s, 3 H), 4.37 (d, J = 5.05 Hz, 2 H), 4.82-4.95 (m, 1 H), 5.87 (s, 1 H), 7.24-7.30 (m, 1 H), 7.30 (s, 1 H), 7.53-7.64 and 7.66-7.75 (m, 2 H), 7.79 (s, 1 H), 7.80-7.84 and 7.98-8.06 (m, 1 H), 8.20 (t, J = 5.05 Hz, 1 H), 8.23 (m, 1 H), 11.47 (br. s., 1 H), 12.45 (br. s., 1 H) | |
| 212 | 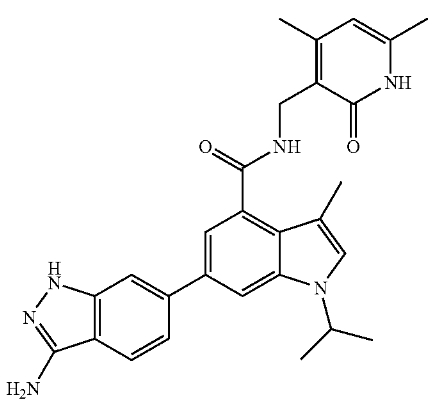 [SMILES: Cc1cc(C)c(CNC(=O)c2cc(-c3ccc4c(N)n[nH]c4c3)cc3c2c(C)cn3C(C)C)c(=O)[nH]1] | 6-(3-amino-1H-indazol-6-yl)-N-[(4,6-dimethyl-2-oxo-1,2-dihydro-3-pyridinyl)methyl]-3-methyl-1-(1-methylethyl)-1H-indole-4-carboxamide | 1.44 (d, J = 6.82 Hz, 6 H), 2.11 (s, 3 H), 2.18 (s, 3 H), 2.24 (s, 3 H), 4.37 (d, J = 4.80 Hz, 2 H), 4.89 (spt, J = 6.48 Hz, 1 H), 5.35 (s, 2 H), 5.87 (s, 1 H), 7.25-7.35 (m, 3 H), 7.50 (s, 1 H), 7.74 (d, J = 8.34 Hz, 1 H), 7.80 (d, J = 1.26 Hz, 1 H), 8.21 (t, J = 5.05 Hz, 1 H), 11.37 (br. s., 1 H), 11.47 (br. s., 1 H) | 483 |
| 213 | 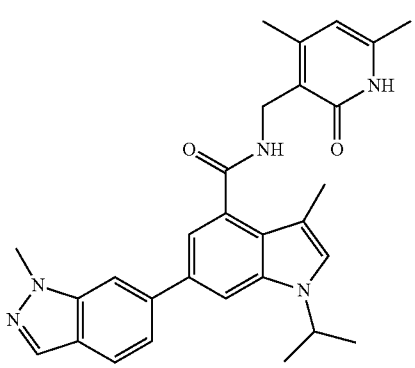 | N-[(4,6-dimethyl-2-oxo-1,2-dihydro-3-pyridinyl)methyl]-3-methyl-1-(1-methylethyl)-6-(1-methyl-1H-indazol-6-yl)-1H-indole-4-carboxamide | 1.46 (d, J = 6.57 Hz, 6 H), 2.11 (s, 3 H), 2.18 (s, 3 H), 2.26 (s, 3 H), 4.13 (s, 3 H), 4.37 (d, J = 5.05 Hz, 2 H), 4.91 (spt, J = 6.57 Hz, 1 H), 5.87 (s, 1 H), 7.35 (s, 1 H), 7.39 (d, J = 1.26 Hz, 1 H), 7.57 (dd, J = 8.46, 1.39 Hz, 1 H), 7.81 (d, J = 8.59 Hz, 1 H), 7.90 (d, J = 1.52 Hz, 1 H), 7.96 (s, 1 H), 8.04 (s, 1 H), 8.18 (t, J = 5.05 Hz, 1 H), 11.47 (s, 1 H) | |

| Ex | Structure | Name | ¹H NMR (400 MHz, DMSO-d₆) δ ppm | MS (ES) [M + H]⁺ |
|---|---|---|---|---|
| 214 | 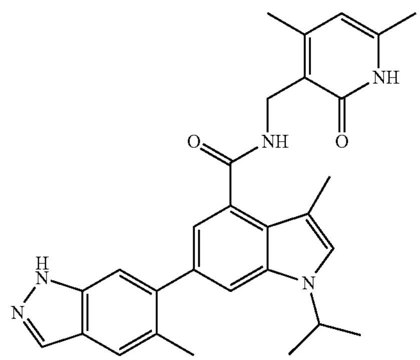 | N-[(4,6-dimethyl-2-oxo-1,2-dihydro-3-pyridinyl)methyl]-3-methyl-1-(1-methylethyl)-6-(5-methyl-1H-indazol-6-yl)-1H-indole-4-carboxamide | 1.42 (d, J = 6.57 Hz, 6 H), 2.09 (s, 3 H), 2.20 (s, 3 H), 2.22 (s, 3 H), 2.31 (s, 3 H), 4.34 (d, J = 5.05 Hz, 2 H), 4.78 (spt, J = 6.53 Hz, 1 H), 5.85 (s, 1 H), 6.93 (d, J = 1.52 Hz, 1 H), 7.33 (s, 1 H), 7.37 (s, 1 H), 7.50 (d, J = 1.26 Hz, 1 H), 7.65 (s, 1 H), 8.01 (s, 1 H), 8.13 (t, J = 5.05 Hz, 1 H), 11.45 (br. s., 1 H), 12.92 (br. s., 1 H) | |
| 215 | 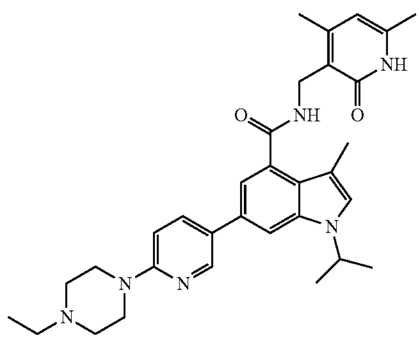 [SMILES: CCN1CCN(c2ccc(-c3cc(C(=O)NCc4c(C)cc(C)[nH]c4=O)c4c(C)cn(C(C)C)c4c3)cn2)CC1] | N-[(4,6-dimethyl-2-oxo-1,2-dihydro-3-pyridinyl)methyl]-6-[6-(4-ethyl-1-piperazinyl)-3-pyridinyl]-3-methyl-1-(1-methylethyl)-1H-indole-4-carboxamide | 1.05 (t, J = 7.20 Hz, 3 H) 1.43 (d, J = 6.57 Hz, 6 H) 2.11 (s, 3 H) 2.16 (s, 3 H) 2.24 (s, 3 H) 2.37 (q, J = 7.07 Hz, 2 H) 2.45-2.49 (m, 4 H) 3.49-3.55 (m, 4 H) 4.35 (d, J = 5.05 Hz, 2 H) 4.78-4.90 (m, 1 H) 5.87 (s, 1 H) 6.92 (d, J = 8.84 Hz, 1 H) 7.18 (d, J = 1.52 Hz, 1 H) 7.29 (s, 1 H) 7.72 (d, J = 1.26 Hz, 1 H) 7.92 (dd, J = 8.84, 2.78 Hz, 1 H) 8.15 (t, J = 5.05 Hz, 1 H) 8.51 (d, J = 2.53 Hz, 1 H) 11.48 (br. s., 1 H) | 541.6 |
| 216 | 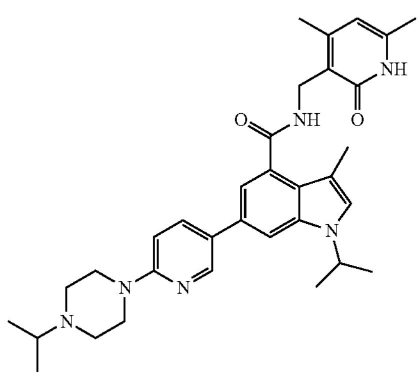 [SMILES: Cc1cc(C)c(CNC(=O)c2cc(-c3ccc(N4CCN(C(C)C)CC4)nc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-{6-[4-(1-methylethyl)-1-piperazinyl]-3-pyridinyl}-1H-indole-4-carboxamide | 1.01 (d, J = 6.57 Hz, 6 H) 1.43 (d, J = 6.57 Hz, 6 H) 2.11 (s, 3 H) 2.16 (s, 3 H) 2.24 (s, 3 H) 2.53-2.57 (m, 4 H) 2.67-2.73 (m, 1 H) 3.47-3.54 (m, 4 H) 4.35 (d, J = 5.31 Hz, 2 H) 4.84 (s, 1 H) 5.87 (s, 1 H) 6.91 (d, J = 8.84 Hz, 1H) 7.18 (d, J = 1.26 Hz, 1 H) 7.29 (s, 1 H) 7.72 (d, J = 1.52 Hz, 1 H) 7.92 (dd, J = 8.84, 2.53 Hz, 1 H) 8.14 (s, 1 H) 8.50 (d, J = 2.27 Hz, 1 H) 11.48 (s, 1 H) | 555.8 |
| 217 | 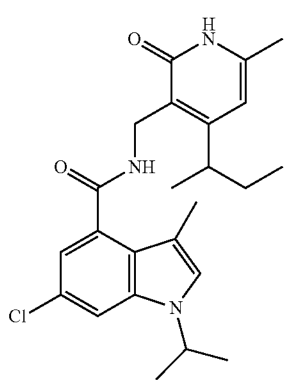 | 6-chloro-3-methyl-1-(1-methylethyl)-N-{[6-methyl-4-(1-methylpropyl)-2-oxo-1,2-dihydro-3-pyridinyl]methyl}-1H-indole-4-carboxamide | 0.79 (t, J = 7.33 Hz, 3 H) 1.11 (d, J = 6.82 Hz, 3 H) 1.39 (d, J = 6.57 Hz, 6 H) 1.50 (quin, J = 7.33 Hz, 2 H) 2.14 (s, 6 H) 2.98 (q, J = 6.91 Hz, 1 H) 4.36 (d, J = 5.05 Hz, 2 H) 4.73 (quin, J = 6.63 Hz, 1 H) 5.95 (s, 1 H) 6.88 (d, J = 1.77 Hz, 1 H) 7.34 (s, 1 H) 7.64 (d, J = 1.77 Hz, 1 H) 8.23 (t, J = 4.93 Hz, 1 H) 11.48 (s, 1 H) | 428.2 |

| Ex | Structure | Name | ¹H NMR (400 MHz, DMSO-d₆) δ ppm | MS (ES) [M + H]⁺ |
|---|---|---|---|---|
| 218 | 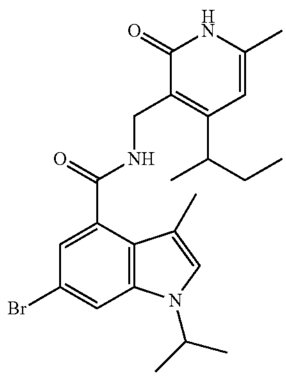 [SMILES: CCC(C)c1cc(C)[nH]c(=O)c1CNC(=O)c1cc(Cl)cc2c1c(C)cn2C(C)C] | 6-bromo-3-methyl-1-(1-methylethyl)-N-{[6-methyl-4-(1-methylpropyl)-2-oxo-1,2-dihydro-3-pyridinyl]methyl}-1H-indole-4-carboxamide | 0.79 (t, J = 7.33 Hz, 3 H) 1.11 (d, J = 6.82 Hz, 3 H) 1.33-1.44 (m, 6 H) 1.50 (quin, J = 7.33 Hz, 2 H) 2.07-2.20 (m, 6 H) 2.91-3.05 (m, 1 H) 4.36 (d, J = 5.05 Hz, 2 H) 4.74 (dt, J = 13.33, 6.60 Hz, 1 H) 5.95 (s, 1 H) 6.99 (d, J = 1.52 Hz, 1 H) 7.34 (s, 1 H) 7.76 (d, J = 1.52 Hz, 1 H) 8.24 (t, J = 4.80 Hz, 1 H) 11.48 (br. s., 1 H) | 474.2 |
| 219 | 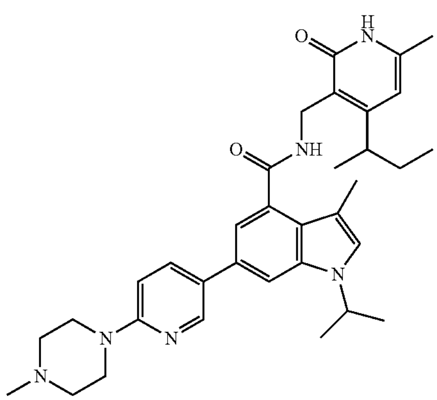 | 3-methyl-1-(1-methylethyl)-N-{[6-methyl-4-(1-methylpropyl)-2-oxo-1,2-dihydro-3-pyridinyl]methyl}-6-[6-(4-methyl-1-piperazinyl)-3-pyridinyl]-1H-indole-4-carboxamide | 0.80 (t, J = 7.33 Hz, 3 H) 1.10-1.15 (m, 3 H) 1.34-1.47 (m, 6 H) 1.51 (quin, J = 7.33 Hz, 2 H) 2.10-2.28 (m, 9 H) 2.35-2.44 (m, 4 H) 3.01 (sxt, J = 6.92 Hz, 1 H) 3.45-3.58 (m, 4 H) 4.33-4.50 (m, 2 H) 4.84 (quin, J = 6.63 Hz, 1 H) 5.96 (s, 1 H) 6.92 (d, J = 8.84 Hz, 1 H) 7.18 (d, J = 1.26 Hz, 1 H) 7.29 (s, 1 H) 7.72 (d, J = 1.26 Hz, 1 H) 7.90 (dd, J = 8.84, 2.53 Hz, 1 H) 8.16 (t, J = 4.93 Hz, 1 H) 8.49 (d, J = 2.53 Hz, 1 H) 11.48 (br. s., 1 H) | 569.4 |
| 220 | 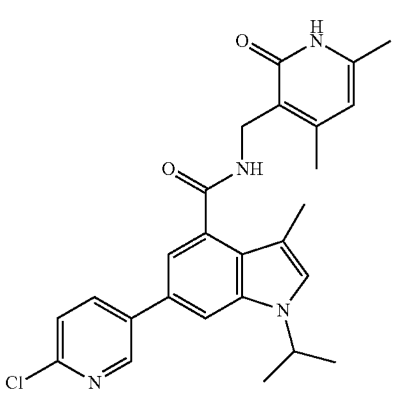 [SMILES: Cc1cc(C)c(CNC(=O)c2cc(-c3ccc(Cl)nc3)cc3c2c(C)cn3C(C)C)c(=O)[nH]1] | 6-(6-chloro-3-pyridinyl)-N-[(4,6-dimethyl-2-oxo-1,2-dihydro-3-pyridinyl)methyl]-3-methyl-1-(1-methylethyl)-1H-indole-4-carboxamide | 1.36-1.52 (m, 6 H) 2.11 (s, 3 H) 2.16-2.20 (m, 3 H) 2.21-2.28 (m, 3 H) 4.35 (d, J = 5.05 Hz, 2 H) 4.89 (quin, J = 6.63 Hz, 1 H) 5.87 (s, 1 H) 7.30 (d, J = 1.26 Hz, 1 H) 7.39 (s, 1 H) 7.59 (d, J = 8.34 Hz, 1 H) 7.92 (d, J = 1.52 Hz, 1 H) 8.18-8.29 (m, 2 H) 8.83 (d, J = 2.27 Hz, 1 H) 11.49 (s, 1 H) | 463.2 |

-continued

| Ex | Structure | Name | ¹H NMR (400 MHz, DMSO-d₆) δ ppm | MS (ES) [M + H]⁺ |
|---|---|---|---|---|
| 221 | 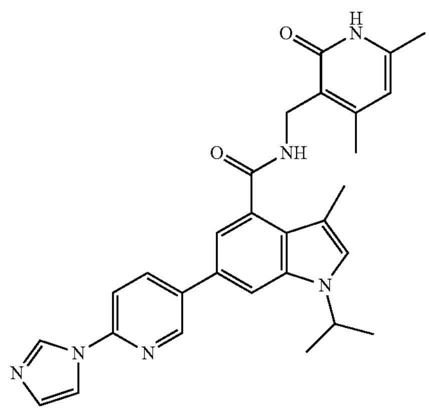 [SMILES: Cc1cc(C)c(CNC(=O)c2cc(-c3ccc(-n4ccnc4)nc3)cc3c2c(C)cn3C(C)C)c(=O)[nH]1] | N-[(4,6-dimethyl-2-oxo-1,2-dihydro-3-pyridinyl)methyl]-6-[6-(1H-imidazol-1-yl)-3-pyridinyl]-3-methyl-1-(1-methylethyl)-1H-indole-4-carboxamide | 1.42-1.48 (m, 6 H) 2.11 (s, 3 H) 2.18 (s, 3 H) 2.22-2.30 (m, 3 H) 4.36 (d, J = 5.05 Hz, 2 H) 4.84-4.97 (m, 1 H) 5.87 (s, 1 H) 7.16 (s, 1 H) 7.33-7.41 (m, 2 H) 7.91 (d, J = 8.34 Hz, 1 H) 7.95 (d, J = 1.26 Hz, 1 H) 8.02 (s, 1 H) 8.22 (t, J = 5.05 Hz, 1 H) 8.39 (dd, J = 8.59, 2.53 Hz, 1 H) 8.60 (s, 1 H) 8.90 (d, J = 2.27 Hz, 1 H) 11.49 (s, 1 H) | 495.2 |
| 222 | 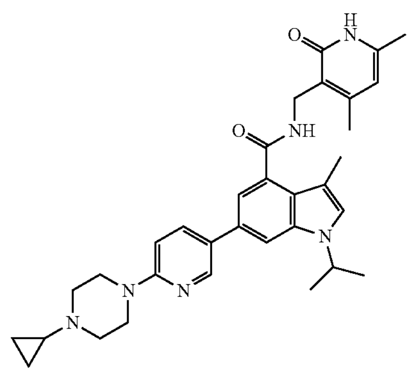 [SMILES: Cc1cc(C)c(CNC(=O)c2cc(-c3ccc(N4CCN(C5CC5)CC4)nc3)cc3c2c(C)cn3C(C)C)c(=O)[nH]1] | 6-[6-(4-cyclopropyl-1-piperazinyl)-3-pyridinyl]-N-[(4,6-dimethyl-2-oxo-1,2-dihydro-3-pyridinyl)methyl]-3-methyl-1-(1-methylethyl)-1H-indole-4-carboxamide | 0.34-0.49 (m, 4 H) 1.42 (d, J = 6.57 Hz, 6 H) 1.65 (tt, J = 6.57, 3.41 Hz, 1 H) 2.11 (s, 3 H) 2.16 (s, 3 H) 2.24 (s, 3 H) 2.59-2.69 (m, 4 H) 3.42-3.56 (m, 4 H) 4.34 (d, J = 5.05 Hz, 2 H) 4.84 (quin, J = 6.63 Hz, 1 H) 5.87 (s, 1 H) 6.91 (d, J = 8.84 Hz, 1 H) 7.18 (d, J = 1.26 Hz, 1 H) 7.28 (s, 1 H) 7.71 (d, J = 1.26 Hz, 1 H) 7.92 (dd, J = 8.84, 2.53 Hz, 1 H) 8.15 (t, J = 5.05 Hz, 1 H) 8.50 (d, J = 2.27 Hz, 1 H) 11.48 (s, 1 H) | 553.8 |
| 223 | 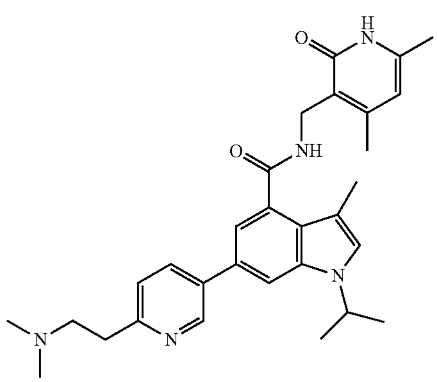 | 6-{6-[2-(dimethylamino)ethyl]-3-pyridinyl}-N-[(4,6-dimethyl-2-oxo-1,2-dihydro-3-pyridinyl)methyl]-3-methyl-1-(1-methylethyl)-1H-indole-4-carboxamide | 1.43 (d, J = 6.57 Hz, 6 H) 2.11 (s, 3 H) 2.14-2.22 (m, 9 H) 2.24 (s, 3 H) 2.61 (t, J = 7.58 Hz, 2 H) 2.89 (t, J = 7.45 Hz, 2 H) 4.35 (d, J = 5.05 Hz, 2 H) 4.81-4.94 (m, 1 H) 5.87 (s, 1 H) 7.25 (d, J = 1.26 Hz, 1 H) 7.32-7.40 (m, 2 H) 7.84 (d, J = 1.26 Hz, 1 H) 8.03 (dd, J = 8.08, 2.53 Hz, 1 H) 8.19 (t, J = 5.05 Hz, 1 H) 8.84 (d, J = 2.02 Hz, 1 H) 11.48 (s, 1 H) | 500.3 |
| 224 | 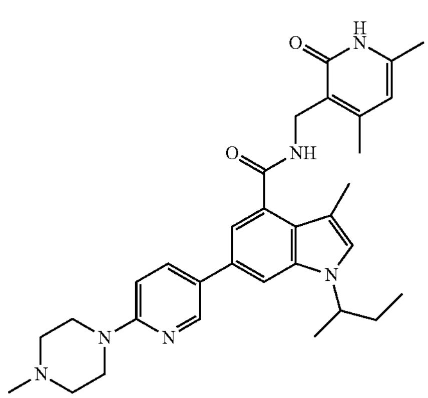 | N-[(4,6-dimethyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide | 0.72 (t, J = 7.33 Hz, 3 H) 1.40 (d, J = 6.82 Hz, 3 H) 1.80 (td, J = 7.26, 2.91 Hz, 2 H) 2.11 (s, 3 H) 2.16 (s, 3 H) 2.23 (d, J = 5.31 Hz, 6 H) 2.37-2.46 (m, 4 H) 3.46-3.56 (m, 4 H) 4.35 (d, J = 5.05 Hz, 2 H) 4.60 (d, J = 7.07 Hz, 1 H) 5.86 (s, 1 H) 6.91 (d, J = 8.84 Hz, 1 H) 7.17 (d, J = 1.26 Hz, 1 H) 7.26 (s, 1 H) 7.73 (d, J = 1.26 Hz, 1 H) 7.91 (dd, J = 8.84, 2.53 Hz, 1 H) 8.16 (t, J = 4.93 Hz, 1 H) 8.50 (d, J = 2.53 Hz, 1 H) 11.48 (s, 1 H) | 541.7 |

| Ex | Structure | Name | ¹H NMR (400 MHz, DMSO-d₆) δ ppm | MS (ES) [M + H]⁺ |
|---|---|---|---|---|
| 225 | 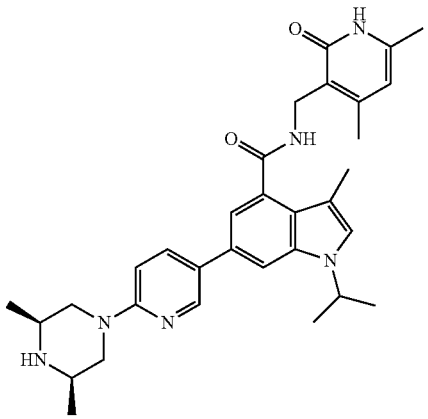 | N-[(4,6-dimethyl-2-oxo-1,2-dihydro-3-pyridinyl)methyl]-6-{6-[(3R,5S)-3,5-dimethyl-1-piperazinyl]-3-pyridinyl}-3-methyl-1-(1-methylethyl)-1H-indole-4-carboxamide | 1.00-1.07 (m, 6 H) 1.39-1.46 (m, 6 H) 2.11 (s, 3 H) 2.16 (s, 3 H) 2.21-2.34 (m, 6 H) 2.70-2.82 (m, 2 H) 4.17 (dd, J = 12.25, 2.15 Hz, 2 H) 4.35 (d, J = 5.05 Hz, 2 H) 4.83 (quin, J = 6.57 Hz, 1 H) 5.87 (s, 1 H) 6.89 (d, J = 9.09 Hz, 1 H) 7.17 (d, J = 1.26 Hz, 1 H) 7.89 (s, 1 H) 7.70 (d, J = 1.52 Hz, 1 H) 7.89 (dd, J = 8.84, 2.53 Hz, 1 H) 8.15 (t, J = 5.18 Hz, 1 H) 8.47 (d, J = 2.27 Hz, 1 H) 11.48 (br. s., 1 H) | 541.4 |
| 226 | 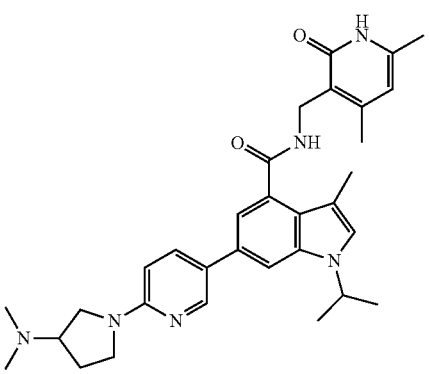 | 6-{6-[3-(dimethylamino)-1-pyrrolidinyl]-3-pyridinyl}-N-[(4,6-dimethyl-2-oxo-1,2-dihydro-3-pyridinyl)methyl]-3-methyl-1-(1-methylethyl)-1H-indole-4-carboxamide | 1.35-1.49 (m, 6 H) 1.75-1.88 (m, 1 H) 2.11 (s, 3 H) 2.13-2.19 (m, 4 H) 2.20-2.27 (m, 9 H) 2.72-2.84 (m, 1 H) 3.14 (dd, J = 9.85, 8.34 Hz, 1 H) 3.34-3.41 (m, 1 H) 3.61 (t, J = 8.59 Hz, 1 H) 3.71 (dd, J = 10.11, 7.07 Hz, 1 H) 4.35 (d, J = 5.05 Hz, 2 H) 4.83 (quin, J = 6.63 Hz, 1 H) 5.87 (s, 1 H) 6.54 (d, J = 8.84 Hz, 1 H) 7.16 (d, J = 1.52 Hz, 1 H) 7.27 (s, 1 H) 7.68 (d, J = 1.26 Hz, 1 H) 7.88 (dd, J = 8.59, 2.53 Hz, 1 H) 8.14 (t, J = 5.05 Hz, 1 H) 8.45 (d, J = 2.27 Hz, 1 H) 11.48 (s, 1 H) | 541.7 |
| 227 | 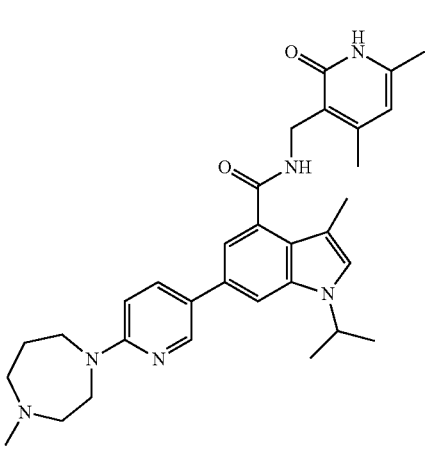 | N-[(4,6-dimethyl-2-oxo-1,2-dihydro-3-pyridinyl)methyl]-3-methyl-1-(1-methylethyl)-6-[6-(4-methylhexahydro-1H-1,4-diazepin-1-yl)-3-pyridinyl]-1H-indole-4-carboxamide | 1.42 (d, J = 6.57 Hz, 6 H) 1.87-1.97 (m, 2 H) 2.16 (s, 3 H) 2.11 (s, 3 H) 2.20-2.32 (m, 6 H) 2.59-2.72 (m, 2 H) 3.63 (t, J = 6.19 Hz, 2 H) 3.78 (br. s., 2 H) 4.34 (d, J = 5.05 Hz, 2 H) 4.76-4.89 (m, 1 H) 5.87 (s, 1 H) 6.70 (d, J = 8.84 Hz, 1 H) 7.16 (d, J = 1.52 Hz, 1 H) 7.27 (s, 1 H) 7.69 (d, J = 1.26 Hz, 1 H) 7.87 (dd, J = 8.84, 2.53 Hz, 1 H) 8.14 (t, J = 5.05 Hz, 1 H) 8.45 (d, J = 2.27 Hz, 1 H) 11.48 (s, 1 H) | 541.3 |

-continued

| Ex | Structure | Name | ¹H NMR (400 MHz, DMSO-d₆) δ ppm | MS (ES) [M + H]⁺ |
|---|---|---|---|---|
| 228 | 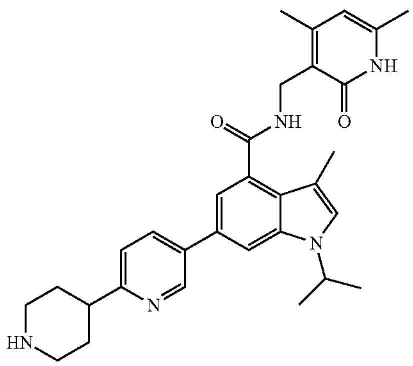 | N-[(4,6-dimethyl-2-oxo-1,2-dihydro-3-pyridinyl)methyl]-3-methyl-1-(1-methylethyl)-6-[6-(4-piperidinyl)-3-pyridinyl]-1H-indole-4-carboxamide | 1H NMR (400 MHz, MeOH-d4) 1.55 (d, J = 6.82 Hz, 6 H) 2.14-2.29 (m, 5 H) 2.35 (br. s., 2 H) 2.47 (s, 3 H) 2.60 (s, 3 H) 3.23-3.31 (m, 1 H) 3.47-3.59 (m, 1 H) 3.64 (br. s., 2 H) 4.68 (s, 2 H) 6.77 (br. s., 1 H) 7.45 (s, 1 H) 7.65 (s, 1 H) 8.08-8.17 (m, 2 H) 9.03 (d, J = 8.34 Hz, 1 H) 9.22 (d, J = 1.77 Hz, 1 H) | 585 |
| 229 | 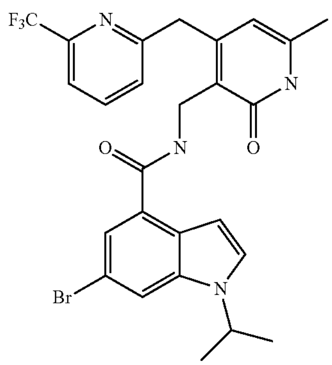 [SMILES: Cc1cc(Cc2cccc(C(F)(F)F)n2)c(CNC(=O)c2cc(Br)cc3c2ccn3C(C)C)c(=O)[nH]1] | 6-bromo-1-isopropyl-N-((6-methyl-2-oxo-4-((6-(trifluoromethyl)pyridin-2-yl)methyl)-1,2-dihydropyridin-3-yl)methyl)-1H-indole-4-carboxamide | 1.42 (s, 3 H), 1.44 (s, 3 H), 2.11 (s, 3 H), 4.27 (s, 2 H), 4.44 (d, J = 5.05 Hz, 2 H), 4.74-4.88 (m, 1 H), 5.88 (s, 1 H), 6.84 (d, J = 3.03 Hz, 1 H), 7.45 (d, J = 1.77 Hz, 1 H), 7.54-7.64 (m, 2 H), 7.71 (d, J = 7.58 Hz, 1 H), 7.91 (s, 1 H), 7.93-8.00 (m, 1 H), 8.35 (t, J = 5.05 Hz, 1 H), 11.68 (s, 1 H) | 461, 463 |
| 230 | 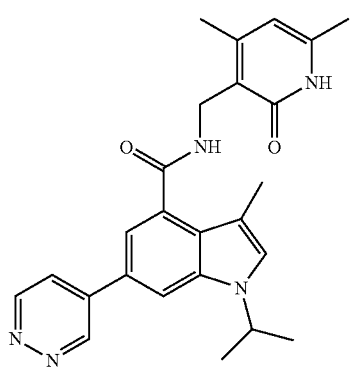 [SMILES: Cc1cc(C)c(CNC(=O)c2cc(-c3ccnnc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(pyridazin-4-yl)-1H-indole-4-carboxamide | 11.10-11.70 (br. s., 1H), 9.77 (dd, J = 1.26, 2.53 Hz, 1H), 9.22 (dd, J = 1.14, 5.43 Hz, 1H), 8.30 (br. s., 1H), 8.19 (d, J = 1.52 Hz, 1H), 8.09 (dd, J = 2.53, 5.56 Hz, 1H), 7.42-7.54 (m, 2H), 5.87 (s, 1H), 4.96 (quin, J = 6.63 Hz, 1H), 4.36 (d, J = 5.05 Hz, 2H), 2.25 (s, 3H), 2.18 (s, 3H), 2.11 (s, 3H), 1.45 (d, 6H) | 430.3 |
| 231 | 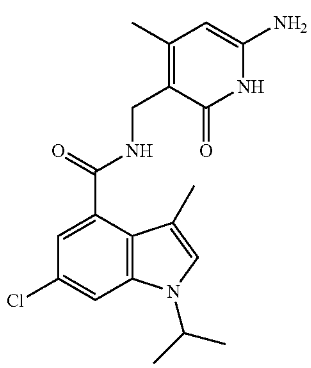 | N-[(6-amino-4-methyl-2-oxo-1,2-dihydro-3-pyridinyl)methyl]-6-chloro-3-methyl-1-(1-methylethyl)-1H-indole-4-carboxamide | 10.62 (br. s., 1 H), 8.14 (t, J = 4.4 Hz, 1 H), 7.63 (d, J = 1.8 Hz, 1 H), 7.34 (s, 1 H), 6.89 (d, J = 1.8 Hz, 1 H), 5.85 (br. s., 2 H), 5.20 (s, 1 H), 4.73 (dt, J = 6.7, 13.2 Hz, 1 H), 4.22 (d, J = 4.8 Hz, 2 H), 2.14 (s, 3 H), 2.12 (s, 3 H), 1.39 (d, J = 6.6 Hz, 6 H) | 387.2 |

-continued

| Ex | Structure | Name | ¹H NMR (400 MHz, DMSO-d₆) δ ppm | MS (ES) [M + H]⁺ |
|---|---|---|---|---|
| 232 | 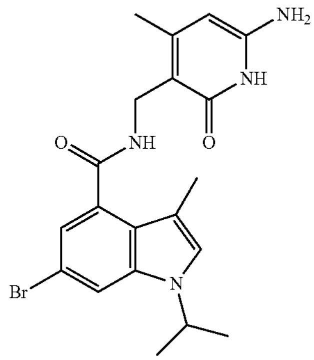 [SMILES: Cc1cc(N)[nH]c(=O)c1CNC(=O)c1cc(Cl)cc2c1c(C)cn2C(C)C] | N-[(6-amino-4-methyl-2-oxo-1,2-dihydro-3-pyridinyl)methyl]-6-bromo-3-methyl-1-(1-methylethyl)-1H-indole-4-carboxamide | 10.59 (br. s., 1 H), 8.13 (t, J = 4.4 Hz, 1 H), 7.76 (d, J = 1.5 Hz, 1 H), 7.33 (s, 1 H), 6.99 (d, J = 1.5 Hz, 1 H), 5.83 (br. s., 2 H), 5.19 (s, 1 H), 4.74 (dt, J = 6.6, 13.3 Hz, 1 H), 4.22 (d, J = 4.8 Hz, 2 H), 2.14 (s, 3 H), 2.11 (s, 3 H), 1.39 (d, J = 6.6 Hz, 6 H) | 431.1 |
| 233 | 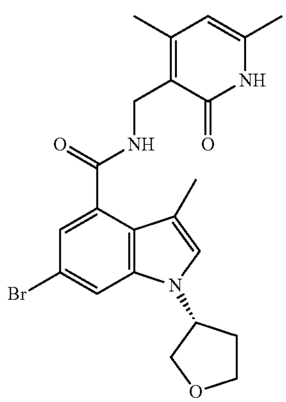 [SMILES: Cc1cc(C)c(CNC(=O)c2cc(Br)cc3c2c(C)cn3[C@@H]2CCOC2)c(=O)[nH]1] | 6-bromo-N-[(4,6-dimethyl-2-oxo-1,2-dihydro-3-pyridinyl)methyl]-3-methyl-1-[(3R)-tetrahydro-3-furanyl]-1H-indole-4-carboxamide | 1.94-2.07 (m, 1 H), 2.11, (s, 3 H), 2.12 (s, 3 H), 2.22 (s, 3 H), 2.40-2.48 (m, 1 H), 3.75-3.87 (m, 2 H), 3.88-3.96 (m, 1 H), 3.98-4.11 (m, 1 H), 4.31 (d, J = 5.05 Hz, 2 H), 5.17-5.32 (m, 1 H), 5.86 (s, 1 H), 7.04 (d, J = 1.52 Hz, 1 H), 7.23 (s, 1 H), 7.84 (d, J = 1.77 Hz, 1 H), 8.25 (t, J = 4.93 Hz, 1 H), 11.47 (s, 1 H) | 458, 460 |
| 234 | 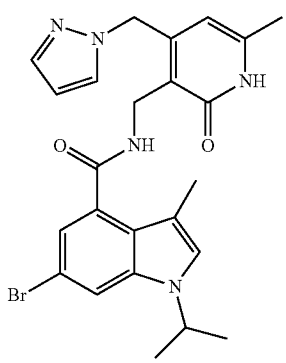 [SMILES: Cc1cc(Cn2cccn2)c(CNC(=O)c2cc(Br)cc3c2c(C)cn3C(C)C)c(=O)[nH]1] | 6-bromo-3-methyl-1-(1-methylethyl)-N-{[6-methyl-2-oxo-4-(1H-pyrazol-1-ylmethyl)-1,2-dihydro-3-pyridinyl]methyl}-1H-indole-4-carboxamide | 1.39 (d, J = 6.8 Hz, 6 H), 2.06 (s, 3 H), 2.11 (s, 3 H), 4.44 (d, J = 5.3 Hz, 2 H), 4.75 (dt, J = 13.3, 6.6 Hz, 1 H), 5.41 (s, 1 H), 5.44 (s, 2 H), 7.07 (d, J = 1.8 Hz, 1 H), 7.33 (s, 1 H), 7.47 (d, J = 1.3 Hz, 1 H), 7.78 (d, J = 1.5 Hz, 1 H), 7.84 (d, J = 1.8 Hz, 1 H), 8.52 (t, J = 5.2 Hz, 1 H), 11.67 (br. s., 1 H) | 496.3 |
| 235 | 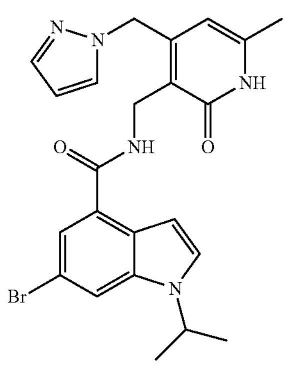 [SMILES: Cc1cc(Cn2cccn2)c(CNC(=O)c2cc(Br)cc3c2ccn3C(C)C)c(=O)[nH]1] | 6-bromo-1-(1-methylethyl)-N-{[6-methyl-2-oxo-4-(1H-pyrazol-1-ylmethyl)-1,2-dihydro-3-pyridinyl]methyl}-1H-indole-4-carboxamide | 1.44 (d, J = 6.6 Hz, 6 H), 2.06 (s, 3 H), 4.46 (d, J = 5.3 Hz, 2 H), 4.83 (dt, J = 13.2, 6.7 Hz, 1 H), 5.45 (s, 3 H), 6.31 (t, J = 2.0 Hz, 1 H), 6.90 (d, J = 3.0 Hz, 1 H), 7.51 (d, J = 1.8 Hz, 1 H), 7.57 (d, J = 1.5 Hz, 1 H), 7.64 (d, J = 3.3 Hz, 1 H), 7.87 (d, J = 2.3 Hz, 1 H), 7.94 (s, 1 H), 8.56 (t, J = 5.1 Hz, 1 H), 11.73 (br. s., 1 H) | 484.2 |

| Ex | Structure | Name | ¹H NMR (400 MHz, DMSO-d₆) δ ppm | MS (ES) [M + H]⁺ |
|---|---|---|---|---|
| 236 | 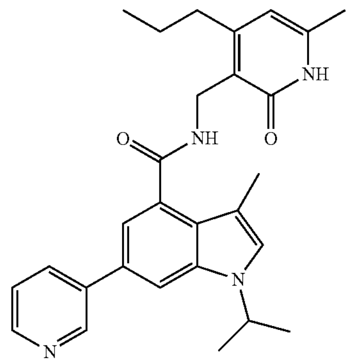 [SMILES: CCCc1cc(C)[nH]c(=O)c1CNC(=O)c1cc(-c2cccnc2)cc2c1c(C)cn2C(C)C] | 3-methyl-1-(1-methylethyl)-N-[(6-methyl-2-oxo-4-propyl-1,2-dihydro-3-pyridinyl)methyl]-6-(3-pyridinyl)-1H-indole-4-carboxamide | 0.94 (t, J = 7.3 Hz, 3 H), 1.44 (d, J = 6.6 Hz, 6 H), 1.51-1.67 (m, 2 H), 2.12 (s, 3 H), 2.19 (s, 3 H), 2.52-2.59 (m, 2 H), 4.38 (d, J = 4.0 Hz, 2 H), 4.81-4.98 (m, 1 H), 5.90 (s, 1 H), 7.28 (s, 1 H), 7.37 (s, 1 H), 7.47 (dd, J = 7.8, 4.5 Hz, 1 H), 7.89 (s, 1 H), 8.14 (d, J = 8.1 Hz, 1 H), 8.18 (br. s., 1 H), 8.53 (dd, J = 4.8, 1.3 Hz, 1 H), 8.97 (d, J = 1.8 Hz, 1 H), 11.49 (s, 1 H) | 457.3 |
| 237 | 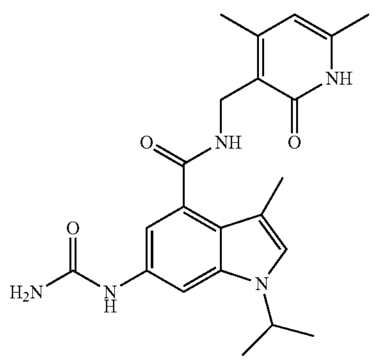 [SMILES: Cc1cc(C)c(CNC(=O)c2cc(NC(N)=O)cc3c2c(C)cn3C(C)C)c(=O)[nH]1] | 6-[(aminocarbonyl)amino]-N-[(4,6-dimethyl-2-oxo-1,2-dihydro-3-pyridinyl)methyl]-3-methyl-1-(1-methylethyl)-1H-indole-4-carboxamide | 1.39 (m, 6 H), 2.08-2.12 (m, 6 H), 2.22 (s, 3 H), 4.32 (d, J = 5.05 Hz, 2 H), 4.44-4.59 (m, 1 H), 5.76 (s, 2 H), 5.87 (s, 1 H), 6.79 (d, J = 1.77 Hz, 1 H), 7.11 (s, 1 H), 7.71 (d, J = 1.52 Hz, 1 H), 7.98 (t, J = 5.05 Hz, 1 H), 8.47 (s, 1 H), 11.46 (s, 1 H) | 410.3 |
| 238 | 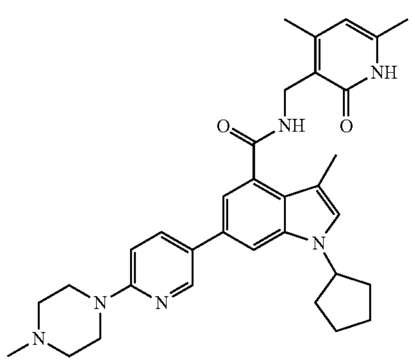 | 1-cyclopentyl-N-[(4,6-dimethyl-2-oxo-1,2-dihydro-3-pyridinyl)methyl]-3-methyl-6-[6-(4-methyl-1-piperazinyl)-3-pyridinyl]-1H-indole-4-carboxamide | 1.66-1.89 (m, 6 H), 2.05-2.20 (m, 8 H), 2.25 (d, J = 7.07 Hz, 6 H), 3.49-3.58 (m, 4 H), 2.47 (m, 4 H), 4.35 (d, J = 5.05 Hz, 2 H), 4.97 (quin, J = 6.88 Hz, 1 H), 5.87 (s, 1 H), 6.93 (d, J = 8.84 Hz, 1 H), 7.19 (d, J = 1.26 Hz, 1 H), 7.25 (s, 1 H), 7.74 (d, J = 1.26 Hz, 1 H), 7.93 (dd, J = 8.84, 2.53 Hz, 1 H), 8.14-8.21 (m, 1 H), 8.51 (d, J = 2.53 Hz, 1 H) | 553.8 |
| 239 | 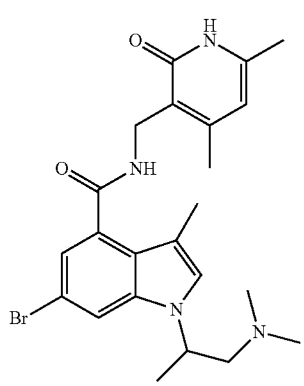 [SMILES: Cc1cc(C)c(CNC(=O)c2cc(Br)cc3c2c(C)cn3C(C)CN(C)C)c(=O)[nH]1] | 6-bromo-N-((4,6-dimethyl-2-oxo-1,2-dihydropyridin-3-yl)methyl)-1-(1-(dimethylamino)propan-2-yl)-3-methyl-1H-indole-4-carboxamide | (600 MHz, CHLOROFORM-d) 1.44 (d, J = 6.42 Hz, 3 H) 2.14 (s, 3 H) 2.22 (br. s., 9 H) 2.38 (s, 3 H) 2.55-2.60 (m, 1 H) 2.65-2.74 (m, 1 H) 4.45-4.54 (m, 1 H) 4.57 (d, J = 5.29 Hz, 2 H) 5.92 (s, 1 H) 6.93 (s, 1 H) 7.19 (s, 1 H) 7.23 (br. s., 1 H) 7.48 (s, 1 H) 12.53 (br. s., 1 H) | 473.2, 475.2 |

| Ex | Structure | Name | ¹H NMR (400 MHz, DMSO-d₆) δ ppm | MS (ES) [M + H]⁺ |
|---|---|---|---|---|
| 240 | 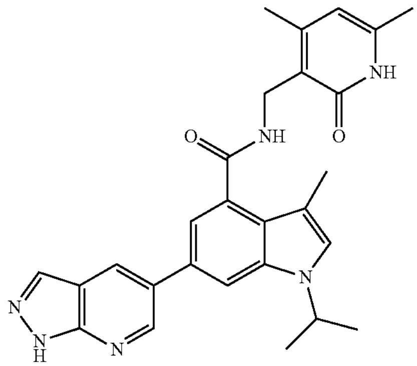 [SMILES: Cc1cc(C)c(CNC(=O)c2cc(-c3cnc4[nH]ncc4c3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(1H-pyrazolo[3,4-b]pyridin-5-yl)-1H-indole-4-carboxamide | 1.45 (d, J = 6.82 Hz, 6 H), 2.11 (s, 3 H), 2.19 (s, 3 H), 2.25 (s, 3 H), 4.37 (d, J = 5.05 Hz, 2 H), 4.84-4.96 (m, J = 13.29, 6.59, 6.59, 6.59, 6.59 Hz, 1 H), 5.87 (s, 1 H), 7.32 (d, J = 1.52 Hz, 1 H), 7.35 (s, 1 H), 7.90 (d, J = 1.26 Hz, 1 H), 8.16-8.25 (m, 2 H), 8.53 (d, J = 2.02 Hz, 1 H), 8.94 (d, J = 2.02 Hz, 1 H), 11.47 (s, 1 H), 13.67 (s, 1 H) | 469 |
| 241 | 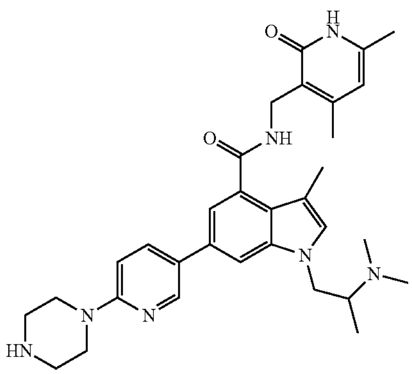 [SMILES: Cc1cc(C)c(CNC(=O)c2cc(-c3ccc(N4CCNCC4)nc3)cc3c2c(C)cn3CC(C)N(C)C)c(=O)[nH]1] | N-((4,6-dimethyl-2-oxo-1,2-dihydropyridin-3-yl)methyl)-1-(2-(dimethylamino)propyl)-3-methyl-6-(6-(piperazin-1-yl)pyridin-3-yl)-1H-indole-4-carboxamide | 0.82 (d, 3 H), 2.10 (s, 3 H), 2.14 (s, 3 H), 2.20 (s, 6 H), 2.23 (s, 3 H), 2.75-2.84 (m, 4 H), 2.91-3.04 (m, 1 H), 3.39-3.50 (m, 4 H), 4.03 (dd, J = 14.40, 7.07 Hz, 1 H), 4.20 (dd, J = 14.15, 7.07 Hz, 1 H), 4.34 (d, J = 5.05 Hz, 2 H), 5.86 (s, 1 H), 6.88 (d, J = 8.84 Hz, 1 H), 7.14 (s, 1 H), 7.17 (d, J = 1.26 Hz, 1 H), 7.67 (d, J = 1.26 Hz, 1 H), 7.89 (dd, J = 8.84, 2.53 Hz, 1 H), 8.17 (t, J = 4.93 Hz, 1 H), 8.49 (d, J = 2.27 Hz, 1 H), 11.48 (br. s., 1 H) | 556.7 |
| 242 | 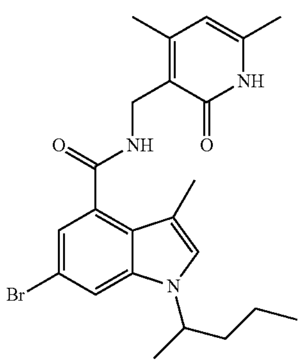 [SMILES: CCCC(C)n1cc(C)c2c(C(=O)NCc3c(C)cc(C)[nH]c3=O)cc(Br)cc21] | 6-bromo-N-((4,6-dimethyl-2-oxo-1,2-dihydropyridin-3-yl)methyl)-3-methyl-1-(pentan-2-yl)-1H-indole-4-carboxamide | 0.76-0.86 (m, 3 H), 0.92-1.20 (m, 2 H), 1.36 (d, J = 6.82 Hz, 3 H), 1.63-1.86 (m, 2 H), 2.08-2.15 (m, 6 H), 2.19-2.26 (m, 3 H), 4.30 (d, J = 5.05 Hz, 2 H), 4.51-4.68 (m, 1 H), 5.86 (s, 1 H), 6.99 (d, J = 1.52 Hz, 1 H), 7.31 (s, 1 H), 7.78 (d, J = 1.77 Hz, 1 H), 8.25 (t, J = 4.93 Hz, 1 H), 11.48 (s, 1 H) | |
| 243 | 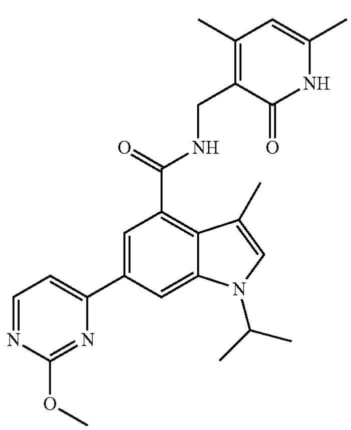 [SMILES: COc1nccc(-c2cc(C(=O)NCc3c(C)cc(C)[nH]c3=O)c3c(C)cn(C(C)C)c3c2)n1] | N-((4,6-dimethyl-2-oxo-1,2-dihydropyridin-3-yl)methyl)-1-isopropyl-6-(2-methoxypyrimidin-4-yl)-3-methyl-1H-indole-4-carboxamide | 1.46 (d, J = 6.57 Hz, 6 H), 2.12 (s, 3 H), 2.18 (s, 3 H), 2.25 (s, 3 H), 4.00 (s, 3 H), 4.37 (d, J = 4.80 Hz, 2 H), 4.92 (spt, J = 6.61 Hz, 1 H), 5.87 (s, 1 H), 7.49 (s, 1 H), 7.79-7.86 (m, 2 H), 8.22 (t, J = 5.05 Hz, 1 H), 8.38 (d, J = 1.26 Hz, 1 H), 8.60 (d, J = 5.30 Hz, 1 H), 11.48 (s, 1 H) | 460.4 |

| Ex | Structure | Name | ¹H NMR (400 MHz, DMSO-d₆) δ ppm | MS (ES) [M + H]⁺ |
|---|---|---|---|---|
| 244 | 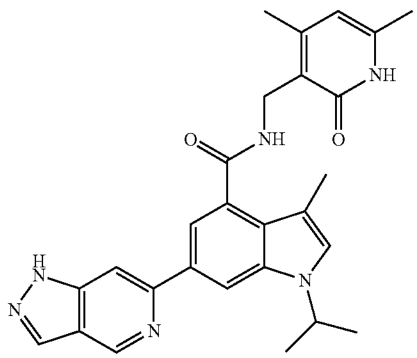 | N-(4,6-dimethyl-2-oxo-1,2-dihydropyridin-3-yl)methyl)-1-isopropyl-3-methyl-6-(1H-pyrazolo[4,3-c]pyridin-6-yl)-1H-indole-4-carboxamide | 1.46 (d, J = 6.57 Hz, 6 H), 2.12 (s, 3 H), 2.19 (s, 3 H), 2.26 (s, 3 H), 4.38 (d, J = 5.05 Hz, 2 H), 4.90 (spt, J = 6.61 Hz, 1 H), 5.88 (s, 1 H), 7.37 (s, 1 H), 7.79 (d, J = 1.26 Hz, 1 H), 8.08 (s, 1 H), 8.19 (t, J = 4.93 Hz, 1 H), 8.27-8.35 (m, 2 H), 9.18 (d, J = 1.01 Hz, 1 H), 11.48 (br. s., 1 H), 13.45 (br. s., 1 H) | 469.4 |
| 245 | 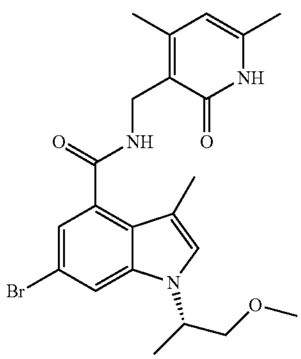 [SMILES: COC[C@H](C)n1cc(C)c2c(C(=O)NCc3c(C)cc(C)[nH]c3=O)cc(Br)cc21] | 6-bromo-N-[(4,6-dimethyl-2-oxo-1,2-dihydro-3-pyridinyl)methyl]-3-methyl-1-[(1R)-1-methyl-2-(methyloxy)ethyl]-1H-indole-4-carboxamide | 1.33-1.40 (m, 3 H), 2.12 (d, J = 4.80 Hz, 6 H), 2.22 (s, 3 H), 3.15-3.21 (m, 3 H), 3.49-3.65 (m, 2 H), 4.31 (d, J = 5.05 Hz, 2 H), 4.73-4.90 (m, 1 H), 5.87 (s, 1 H), 6.97-7.06 (m, 1 H), 7.31 (s, 1 H), 7.78 (d, J = 1.52 Hz, 1 H), 8.26 (t, J = 4.93 Hz, 1 H), 11.48 (s, 1 H) | 460.2 |
| 246 | 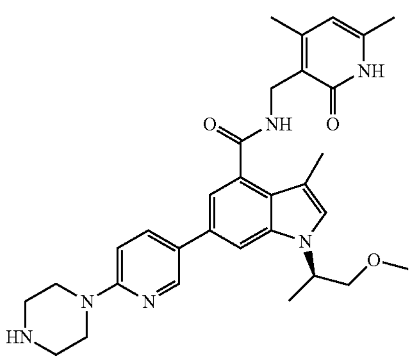 [SMILES: COC[C@@H](C)n1cc(C)c2c(C(=O)NCc3c(C)cc(C)[nH]c3=O)cc(-c3ccc(N4CCNCC4)nc3)cc21] | N-[(4,6-dimethyl-2-oxo-1,2-dihydro-3-pyridinyl)methyl]-3-methyl-1-[(1S)-1-methyl-2-(methyloxy)ethyl]-6-[6-(1-piperazinyl)-3-pyridinyl]-1H-indole-4-carboxamide | 1.41 (m, 3 H), 2.11 (s, 3 H), 2.15 (s, 3 H), 2.24 (s, 3 H), 2.77-2.83 (m, 3 H), 3.13-3.26 (m, 3 H), 3.41-3.48 (m, 3 H), 3.53-3.69 (m, 2 H), 4.35 (d, J = 5.05 Hz, 2 H), 4.85-4.99 (m, 1 H), 5.87 (s, 1 H), 6.85-6.93 (m, 1 H), 7.18 (d, J = 1.26 Hz, 1 H), 7.27 (s, 1 H), 7.74 (d, J = 1.26 Hz, 1 H), 7.88-7.96 (m, 1 H), 8.17 (t, J = 4.93 Hz, 1 H), 8.45-8.54 (m, 1 H) | 543.7 |
| 247 | 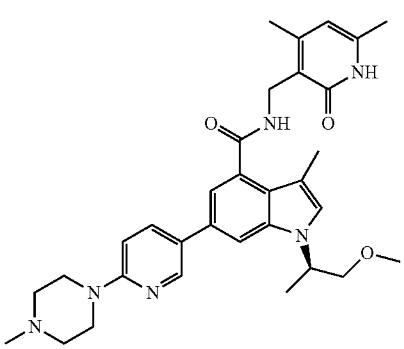 | N-[(4,6-dimethyl-2-oxo-1,2-dihydro-3-pyridinyl)methyl]-3-methyl-1-[(1S)-1-methyl-2-(methyloxy)ethyl]-6-[6-(4-methyl-1-piperazinyl)-3-pyridinyl]-1H-indole-4-carboxamide | 1.41 (d, J = 6.82 Hz, 3 H), 2.11 (s, 3 H), 2.16 (s, 3 H), 2.23 (d, J = 4.04 Hz, 5 H), 2.39-2.45 (m, 4 H), 3.31-3.38 (m, 1 H), 3.47-3.70 (m, 6 H), 4.35 (d, J = 5.05 Hz, 2 H), 4.84-4.99 (m, 1 H), 5.87 (s, 1 H), 6.92 (d, J = 8.84 Hz, 1 H), 7.19 (d, J = 1.52 Hz, 1 H), 7.27 (s, 1 H), 7.75 (d, J = 1.26 Hz, 1 H), 7.92 (dd, J = 8.84, 2.78 Hz, 1 H), 8.19 (t, J = 4.93 Hz, 1 H), 8.51 (d, J = 2.53 Hz, 1 H) | 557.8 |

-continued

| Ex | Structure | Name | ¹H NMR (400 MHz, DMSO-d₆) δ ppm | MS (ES) [M + H]⁺ |
|---|---|---|---|---|
| 248 | 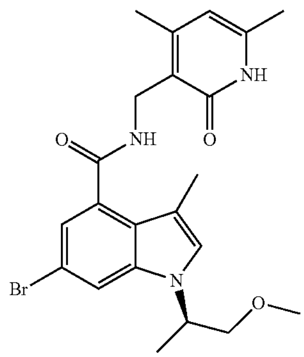 [SMILES: COC[C@@H](C)n1cc(C)c2c(C(=O)NCc3c(C)cc(C)[nH]c3=O)cc(Br)cc21] | 6-bromo-N-[(4,6-dimethyl-2-oxo-1,2-dihydro-3-pyridinyl)methyl]-3-methyl-1-[(1S)-1-methyl-2-(methyloxy)ethyl]-1H-indole-4-carboxamide | 1.37 (m, 3 H), 2.12 (d, J = 4.55 Hz, 6 H), 2.22 (s, 3 H), 3.18 (s, 3 H), 3.50-3.66 (m, 2 H), 4.30 (d, J = 5.05 Hz, 2 H), 4.72-4.87 (m, 1 H), 5.80-5.92 (m, 1 H), 7.00 (d, J = 1.52 Hz, 1 H), 7.31 (s, 1 H), 7.78 (d, J = 1.52 Hz, 1 H), 8.26 (t, J = 4.80 Hz, 1 H), 11.48 (s, 1 H) | 460.2 |
| 249 | 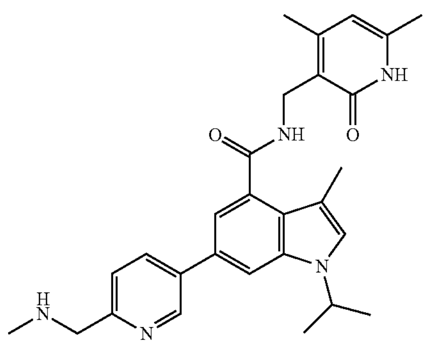 | N-[(4,6-dimethyl-2-oxo-1,2-dihydro-3-pyridinyl)methyl]-3-methyl-6-{6-[(methylamino)methyl]-3-pyridinyl}-1-(1-methylethyl)-1H-indole-4-carboxamide | 11.52 (s, 1 H) 8.87 (d, J = 2.27 Hz, 1 H) 8.21 (t, J = 5.05 Hz, 1 H) 8.08-8.14 (m, 1 H) 7.86 (d, J = 1.26 Hz, 1 H) 7.49 (d, J = 8.08 Hz, 1 H) 7.36 (s, 1 H) 7.28 (d, J = 1.26 Hz, 1 H) 5.87 (s, 1 H) 4.89 (dt, J = 13.33, 6.60 Hz, 1 H) 4.36 (s, 1 H) 4.35 (s, 1 H) 3.78 (s, 2 H) 2.29-2.38 (m, 3 H), 2.24 (s, 3 H) 2.18 (s, 3 H) 2.11 (s, 3 H) 1.45 (s, 3 H) 1.43 (s, 3 H) | 472.3 |
| 250 | 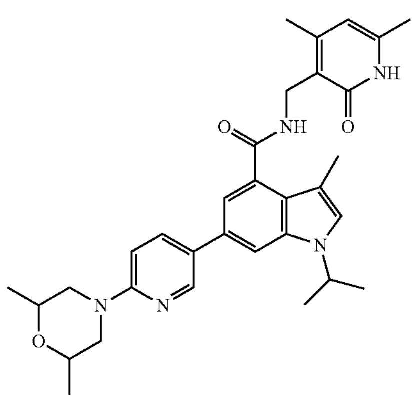 | 6-[6-(2,6-dimethyl-4-morpholinyl)-3-pyridinyl]-N-[(4,6-dimethyl-2-oxo-1,2-dihydro-3-pyridinyl)methyl]-3-methyl-1-(1-methylethyl)-1H-indole-4-carboxamide | 11.47 (s, 1 H) 8.51 (d, J = 2.27 Hz, 1 H) 8.15 (t, J = 4.93 Hz, 1 H) 7.94 (dd, J = 8.84, 2.53 Hz, 1 H) 7.72 (d, J = 1.26 Hz, 1 H) 7.27-7.31 (m, 1 H) 7.19 (d, J = 1.26 Hz, 1 H) 6.94 (d, J = 8.84 Hz, 1 H) 5.87 (s, 1 H), 4.85 (quin, J = 6.63 Hz, 1 H) 4.36 (s, 1 H) 4.34 (s, 1 H) 4.19-4.22 (m, 1 H) 4.17 (s, 1 H) 3.60-3.68 (m, 2 H) 2.42 (dd, J = 12.63, 10.61 Hz, 2 H) 2.24 (s, 3 H) 2.16 (s, 3 H) 2.11 (s, 3 H) 1.44 (s, 3 H) 1.42 (s, 3 H) 1.19 (s, 3 H) 1.18 (s, 3 H) | 542.5 |
| 251 | 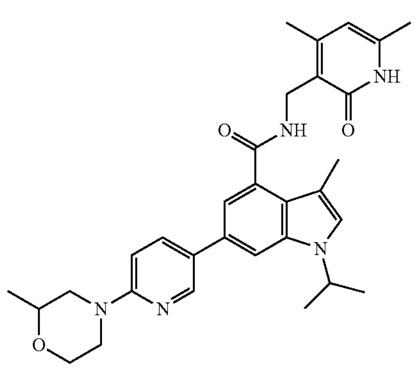 | N-[(4,6-dimethyl-2-oxo-1,2-dihydro-3-pyridinyl)methyl]-3-methyl-1-(1-methylethyl)-6-[6-(2-methyl-4-morpholinyl)-3-pyridinyl]-1H-indole-4-carboxamide | 11.48 (s, 1 H) 8.52 (d, J = 2.53 Hz, 1 H) 8.16 (t, J = 5.05 Hz, 1 H) 7.95 (dd, J = 8.84, 2.53 Hz, 1 H) 7.73 (d, J = 1.26 Hz, 1 H) 7.29 (s, 1 H) 7.19 (d, J = 1.26 Hz, 1 H) 6.93 (d, J = 8.84 Hz, 1 H) 5.87 (s, 1 H) 4.85 (dt, J = 13.20, 6.66 Hz, 1 H) 4.35 (s, 1 H) 4.34 (s, 1 H) 4.18 (d, J = 12.38 Hz, 1 H) 4.07 (s, 1 H) 3.93 (dd, J = 11.37, 2.27 Hz, 1 H) 3.54-3.64 (m, 2 H) 2.82 (td, J = 12.25, 3.54 Hz, 1 H) 2.52-2.56 (m, 1 H) 2.22-2.26 (m, 3 H) 2.16 (s, 3 H) 2.11 (s, 3 H) 1.44 (s, 3 H) 1.42 (s, 3 H) 1.18 (d, J = 6.32 Hz, 3 H) | 528.3 |

| Ex | Structure | Name | ¹H NMR (400 MHz, DMSO-d₆) δ ppm | MS (ES) [M + H]⁺ |
|---|---|---|---|---|
| 252 | 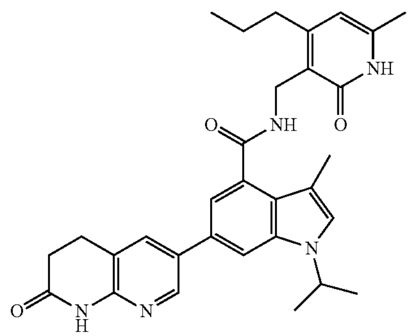 [SMILES: CCCc1cc(C)[nH]c(=O)c1CNC(=O)c1cc(-c2cnc3c(c2)CCC(=O)N3)cc2c1c(C)cn2C(C)C] | 3-methyl-1-(1-methylethyl)-N-[(6-methyl-2-oxo-4-propyl-1,2-dihydro-3-pyridinyl)methyl]-6-(7-oxo-5,6,7,8-tetrahydro-1,8-naphthyridin-3-yl)-1H-indole-4-carboxamide | 11.44 (br. s., 1 H) 10.53 (br. s., 1 H) 8.48 (d, J = 2.27 Hz, 1 H) 8.11-8.22 (m, 1 H) 8.01 (d, J = 2.27 Hz, 1 H) 7.82 (d, J = 1.26 Hz, 1 H) 7.34 (s, 1 H) 7.25 (d, J = 1.26 Hz, 1 H) 5.90 (s, 1 H) 4.88 (quin, J = 6.69 Hz, 1 H) 4.37 (br. s., 1 H) 4.36 (br. s., 1 H) 2.98 (t, J = 7.58 Hz, 2 H) 2.53-2.57 (m, 4 H) 2.17 (s, 3 H) 2.12 (s, 3 H) 1.53-1.62 (m, 2 H) 1.45 (s, 3 H) 1.43 (s, 3 H) 0.94 (t, J = 7.45 Hz, 3 H) | 526.2 |
| 253 | 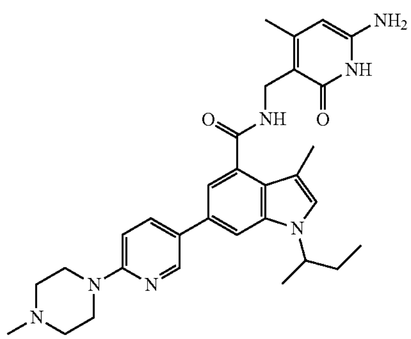 [SMILES: CCC(C)n1cc(C)c2c(C(=O)NCc3c(C)cc(N)[nH]c3=O)cc(-c3ccc(N4CCN(C)CC4)nc3)cc21] | N-[(6-amino-4-methyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide | 10.47 (br. s., 1 H) 8.50 (d, J = 2.53 Hz, 1 H) 7.98 (br. s., 1 H) 7.92 (dd, J = 8.84, 2.53 Hz, 1 H) 7.71-7.74 (m, 1 H) 7.26 (s, 1 H) 7.16 (d, J = 1.26 Hz, 1 H) 6.92 (d, J = 9.09 Hz, 1 H) 5.76 (s, 2 H) 5.16 (br. s., 1 H) 4.57-4.65 (m, 1 H) 4.26 (br. s., 1 H) 4.25 (br. s., 1 H) 3.52 (br. s., 4 H) 2.42 (br. s., 4 H) 2.23 (s, 3 H) 2.18 (s, 3 H) 2.13 (s, 3 H) 1.81 (td, J = 2.70, 3.03 Hz, 2 H) 1.41 (d, J = 6.82 Hz, 3 H) 0.73 (t, J = 7.20 Hz, 3 H) | 542.6 |
| 254 | 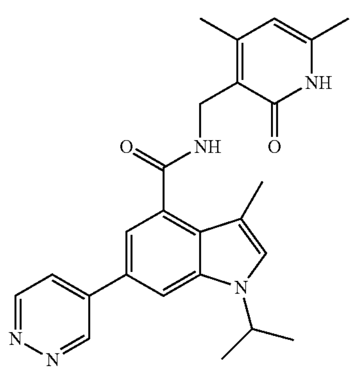 [SMILES: Cc1cc(C)c(CNC(=O)c2cc(-c3ccnnc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(pyridazin-4-yl)-1H-indole-4-carboxamide | 11.10-11.70 (br. s., 1H), 9.77 (dd, J = 1.26, 2.53 Hz, 1H), 9.22 (dd, J = 1.14, 5.43 Hz, 1H), 8.30 (br. s., 1H), 8.19 (d, J = 1.52 Hz, 1H), 8.09 (dd, J = 2.53, 5.56 Hz, 1H), 7.42-7.54 (m, 2H), 5.87 (s, 1H), 4.96 (quin, J = 6.63 Hz, 1H), 4.36 (d, J = 5.05 Hz, 2H), 2.25 (s, 3H), 2.18 (s, 3H), 2.11 (s, 3H), 1.45 (d, 6H) | 430.3 |
| 255 | 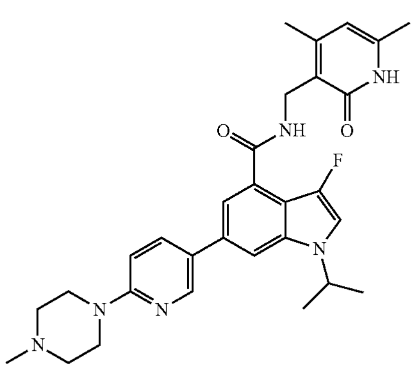 | N-((4,6-dimethyl-2-oxo-1,2-dihydropyridin-3-yl)methyl)-3-fluoro-1-isopropyl-6-(6-(4-methylpiperazin-1-yl)pyridin-3-yl)-1H-indole-4-carboxamide | 11.48 (d, J = 11.87 Hz, 1H), 8.54 (d, J = 2.53 Hz, 1H), 8.19 (t, J = 5.05 Hz, 1H), 8.16 (s, 1H), 7.96 (dd, J = 2.53, 8.84 Hz, 1H), 7.86 (s, 1H), 7.58 (d, J = 2.27 Hz, 1H), 7.43 (d, J = 1.01 Hz, 1H), 6.94 (d, J = 8.84 Hz, 1H), 5.88 (s, 1H), 4.86-5.03 (m, J = 7.07 Hz, 1H), 4.36 (d, J = 4.80 Hz, 2H), 3.48-3.59 (m, 4H), 2.44 (t, J = 4.93 Hz, 4H), 2.23 (d, J = 10.36 Hz, 6H), 2.12 (s, 3H), 1.42 (d, 6H) | 531.4 |

| Ex | Structure | Name | ¹H NMR (400 MHz, DMSO-d₆) δ ppm | MS (ES) [M + H]⁺ |
|---|---|---|---|---|
| 256 | 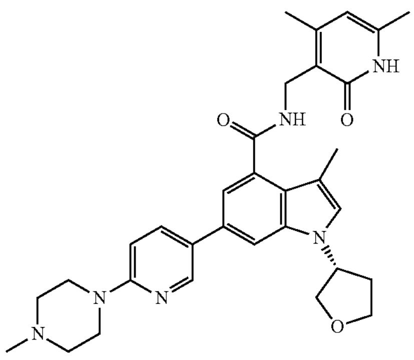 | (R)-N-((4,6-dimethyl-2-oxo-1,2-dihydropyridin-3-yl)methyl)-3-methyl-6-(6-(4-methylpiperazin-1-yl)pyridin-3-yl)-1-(tetrahydrofuran-3-yl)-1H-indole-4-carboxamide | 2.02-2.13 (m, 4 H), 2.15 (s, 3 H), 2.19-2.28 (m, 6 H), 2.37-2.49 (m, 5 H), 3.45-3.59 (m, 4 H), 3.77-3.89 (m, 2 H), 3.94-4.01 (m, 1 H), 4.01-4.11 (m, 1 H), 4.35 (d, J = 5.05 Hz, 2 H), 5.33 (dd, J = 7.96, 5.68 Hz, 1 H), 5.87 (s, 1 H), 6.93 (d, J = 8.84 Hz, 1 H), 7.15-7.26 (m, 2 H), 7.81 (d, J = 1.26 Hz, 1 H), 7.93 (dd, J = 8.84, 2.53 Hz, 1 H), 8.16 (t, J = 5.05 Hz, 1 H), 8.52 (d, J = 2.53 Hz, 1 H), 11.47 (s, 1 H) | 555.6 |
| 257 | 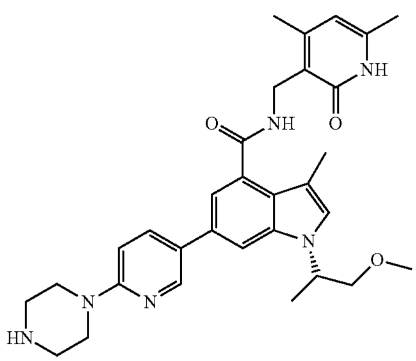 | (S)-N-((4,6-dimethyl-2-oxo-1,2-dihydropyridin-3-yl)methyl)-1-(1-methoxypropan-2-yl)-3-methyl-6-(6-(piperazin-1-yl)pyridin-3-yl)-1H-indole-4-carboxamide | 1.34-1.48 (m, 3 H), 2.11 (s, 3 H), 2.16 (s, 3 H), 2.24 (s, 3 H), 2.76-2.86 (m, 4 H), 3.34 (s, 3 H), 3.40-3.48 (m, 4 H), 3.53-3.69 (m, 2 H), 4.35 (d, J = 5.05 Hz, 2 H), 4.84-4.98 (m, 1 H), 5.87 (s, 1 H), 6.88 (d, J = 8.84 Hz, 1 H), 7.18 (d, J = 1.26 Hz, 1 H), 7.27 (d, J = 1.01 Hz, 1 H), 7.74 (d, J = 1.26 Hz, 1 H), 7.87-7.96 (m, 1 H), 8.17 (t, J = 5.05 Hz, 1 H), 8.44-8.54 (m, 1 H) | 543.5 |
| 258 | 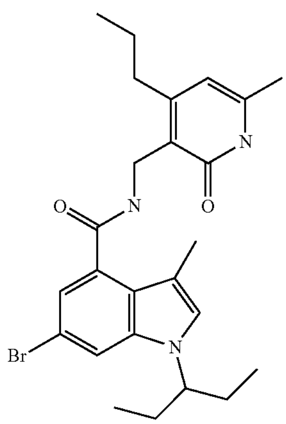 [SMILES: CCCc1cc(C)[nH]c(=O)c1CNC(=O)c1cc(Br)cc2c1c(C)cn2C(CC)CC] | 6-bromo-1-(1-ethylpropyl)-3-methyl-N-[(6-methyl-2-oxo-4-propyl-1,2-dihydro-3-pyridinyl)methyl]-1H-indole-4-carboxamide | 11.48 (br. s., 1 H) 8.24 (br. s., 1 H) 7.79 (s, 1 H) 7.28 (s, 1 H) 6.98 (s, 1 H) 5.89 (s, 1 H) 4.33 (d, J = 4.29 Hz, 2 H) 4.21-4.29 (m, 1 H) 2.58-2.55 (m, 2 H) 2.14 (d, J = 9.85 Hz, 6 H) 1.74-1.82 (m, 4 H) 1.55 (br. s., 2 H) 0.94 (t, J = 7.07 Hz, 3 H) 0.64 (t, J = 7.07 Hz, 6 H) | 486.3 |
| 259 | 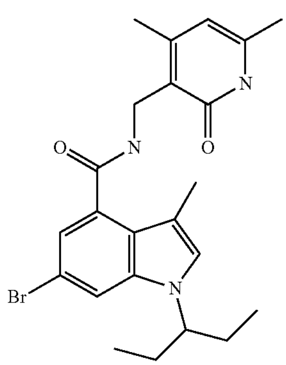 [SMILES: CCC(CC)n1cc(C)c2c(C(=O)NCc3c(C)cc(C)[nH]c3=O)cc(Br)cc21] | 6-bromo-N-[(4,6-dimethyl-2-oxo-1,2-dihydro-3-pyridinyl)methyl]-1-(1-ethylpropyl)-3-methyl-1H-indole-4-carboxamide | 11.47 (br. s., 1 H) 8.26 (t, J = 4.80 Hz, 1 H) 7.79 (d, J = 1.26 Hz, 1 H) 7.27 (s, 1 H) 6.99 (d, J = 1.52 Hz, 1 H) 5.86 (s, 1 H) 4.31 (d, J = 4.80 Hz, 2 H) 4.23-4.29 (m, 1 H) 2.22 (s, 3 H) 2.13 (d, J = 11.62 Hz, 6 H) 1.73-1.83 (m, 4 H) 0.64 (t, J = 7.33 Hz, 6 H) | 458.2 |

| Ex | Structure | Name | ¹H NMR (400 MHz, DMSO-d₆) δ ppm | MS (ES) [M + H]⁺ |
|---|---|---|---|---|
| 260 | 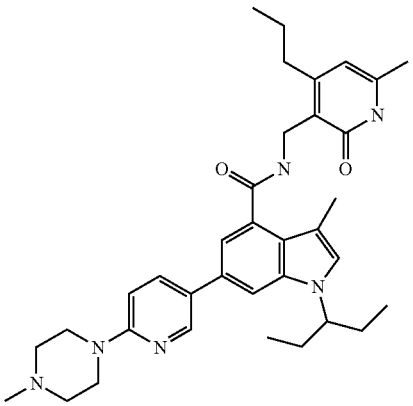 | 1-(1-ethylpropyl)-3-methyl-N-[(6-methyl-2-oxo-4-propyl-1,2-dihydro-3-pyridinyl)methyl]-6-[6-(4-methyl-1-piperazinyl)-3-pyridinyl]-1H-indole-4-carboxamide | 11.49 (br. s., 1 H) 8.49 (br. s., 1 H) 8.15 (br. s., 1 H) 7.90 (br. s., 1 H) 7.75 (br. s., 1 H) 7.11-7.26 (m, 2 H) 6.93 (br. s., 1 H) 5.90 (br. s., 1 H) 4.37 (br. s., 3 H) 3.47-3.57 (m, 4 H) 2.36-2.45 (m, 6 H) 2.10-2.25 (m, 9 H) 1.81 (br. s., 4 H) 1.58 (br. s., 2 H) 0.94 (br. s., 3 H) 0.67 (br. s., 6 H) | 583.8 |
| 261 | 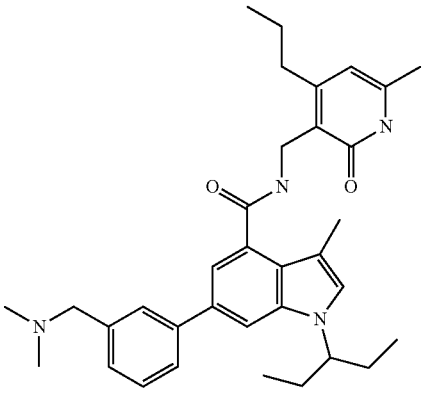 | 6-{3-[(dimethylamino)methyl]phenyl}-1-(1-ethylpropyl)-3-methyl-N-[(6-methyl-2-oxo-4-propyl-1,2-dihydro-3-pyridinyl)methyl]-1H-indole-4-carboxamide | 11.37 (br. s., 1 H) 7.39-7.58 (m, 7 H) 6.95 (br. s., 1 H) 5.89 (br. s., 1 H) 4.66 (d, J = 5.31 Hz, 2 H) 4.16 (br. s., 1 H) 3.53 (br. s., 2 H) 2.68-2.18 (m, 2 H) 2.31 (br. s., 9 H) 2.09 (br. s., 3 H) 1.80-1.96 (m, 4 H) 1.60-1.72 (m, 2 H) 0.98-1.09 (m, 3 H) 0.79 (d, J = 6.06 Hz, 6 H) | 541.2 |
| 262 | 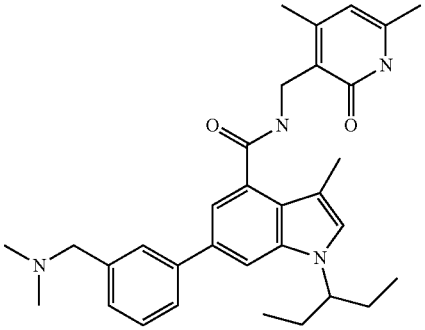 | 6-{3-[(dimethylamino)methyl]phenyl}-N-[(4,6-dimethyl-2-oxo-1,2-dihydro-3-pyridinyl)methyl]-1-(1-ethylpropyl)-3-methyl-1H-indole-4-carboxamide | 11.47 (br. s., 1 H) 8.23 (br. s., 1 H) 7.78 (br. s., 1 H) 7.61 (br. s., 2 H) 7.40 (br. s., 1 H) 7.19-7.29 (m, 3 H) 5.87 (br. s., 1 H) 4.33-4.45 (m, 3 H) 3.47 (br. s., 2 H) 2.24 (br. s., 9 H) 2.18 (br. s., 9 H) 2.11 (br. s., 3 H) 1.75-1.90 (m, 4 H) 0.68 (br. s., 6 H) | 513.4 |

| Ex | Structure | Name | $^1$H NMR (400 MHz, DMSO-$d_6$) δ ppm | MS (ES) [M + H]$^+$ |
|---|---|---|---|---|
| 263 | 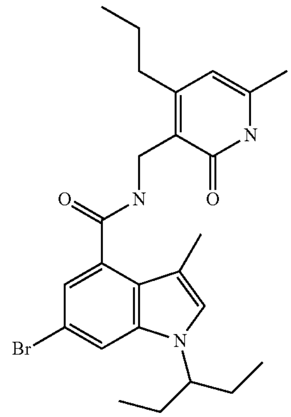 [SMILES: CCCc1cc(C)[nH]c(=O)c1CNC(=O)c1cc(Br)cc2c1c(C)cn2C(CC)CC] | 6-bromo-1-(1-ethylpropyl)-3-methyl-N-[(6-methyl-2-oxo-4-propyl-1,2-dihydro-3-pyridinyl)methyl]-1H-indole-4-carboxamide | 11.48 (br. s., 1 H) 8.24 (br. s., 1 H) 7.79 (s, 1 H) 7.28 (s, 1 H) 6.98 (s, 1 H) 5.89 (s, 1 H) 4.33 (d, J = 4.29 Hz, 2 H) 4.21-4.29 (m, 1 H) 2.58-2.55 (m, 2 H) 2.14 (d, J = 9.85 Hz, 6 H) 1.74-1.82 (m, 4 H) 1.55 (br. s., 2 H) 0.94 (t, J = 7.07 Hz, 3 H) 0.64 (t, J = 7.07 Hz, 6 H) | 486.3 |

Example 264

N-((4,6-dimethyl-2-oxo-1,2-dihydropyridin-3-yl)methyl)-1-isopropyl-3-methyl-6-(6-(4-methylpiperazin-1-yl)pyridin-3-yl)-1H-indole-4-carboxamide

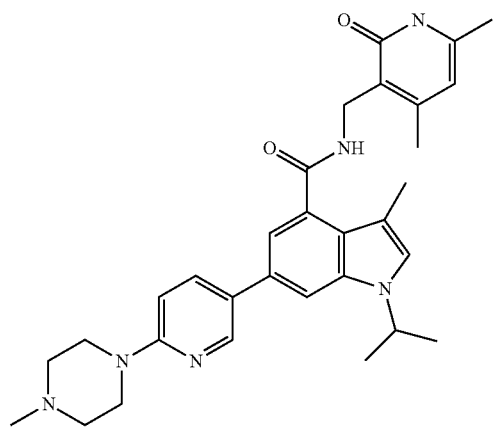

To a stirred solution of 6-bromo-N-((1,2-dihydro-4,6-dimethyl-2-oxopyridin-3-yl)methyl)-1-isopropyl-3-methyl-1H-indole-4-carboxamide (2 g, 4.65 mmol) in DMF (100 mL) was added 1-methyl-4-(5-(4,4,5,5-tetramethyl-1,3,2-dioxaborolan-2-yl)pyridin-2-yl)piperazine (1.55 g, 5.12 mmol) followed by a solution of sodium carbonate (1.23 g, 11.62 mmol) in water (10 mL) and the contents were degassed with argon for 30 min. After that PdCl$_2$(PPh$_3$)$_2$ (326 mg, 0.464 mmol) was added and the contents again degassed with argon for 10 min. The reaction mixture was stirred at reflux for 3 h. The reaction mixture was diluted with water (100 mL) and extracted with ethyl acetate (3×150 mL). The combined organic layers were dried over anhydrous Na$_2$SO$_4$, filtered, and concentrated to afford the crude product (2.8 g). The crude compound was purified by column chromatography over silica gel (100-200 mesh, eluent: 0-10% MeOH: DCM), and the obtained product was further triturated with diethyl ether (100 mL) to afford the title compound as an off white solid (1.2 g, 50%). $^1$H NMR (DMSO-$d_6$, 400 MHz): δ 1.493 (d, J=6.4 Hz, 6H), 2.092 (s, 3H), 2.286 (s, 3H), 2.409 (s, 3H), 2.424 (s, 3H), 2.632 (s, 4H), 3.621 (s, 4H), 4.603-4.685 (m, 3H), 5.880 (s, 1H), 6.606 (d, J=8.8 Hz, 1H), 7.016 (s, 1H), 7.261 (s, 1H), 7.433 (s, 1H), 7.675-7.704 (dd, J=9 Hz, 2.4 Hz, 1H), 8.425 (d, J=2.0 Hz, 1H), 11.699 (brs, 1H); LCMS (ES+): 525.23 [M–H].

Example 265

N-[(4,6-dimethyl-2-oxo-1,2-dihydro-3-pyridinyl)methyl]-3-methyl-1-(1-methylethyl)-6-[6-(1-piperazinyl)-3-pyridinyl]-1H-indole-4-carboxamide

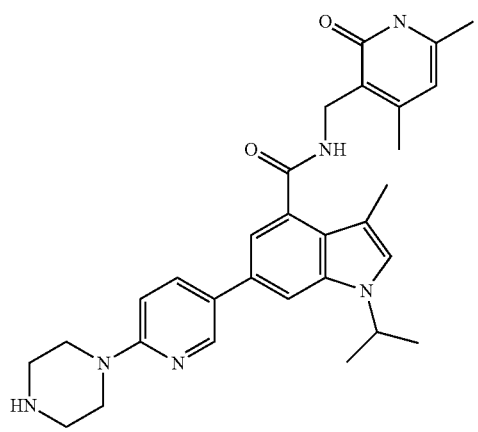

6-Bromo-N-[(4,6-dimethyl-2-oxo-1,2-dihydro-3-pyridinyl)methyl]-3-methyl-1-(1-methylethyl)-1H-indole-4-carboxamide (1.9 g, 4.42 mmol), 1-[5-(4,4,5,5-tetramethyl-1,3,2-dioxaborolan-2-yl)-2-pyridinyl]piperazine (1.277 g, 4.42 mmol) and potassium phosphate (tribasic) (2.81 g, 13.25 mmol) were placed in a 150 mL pressure vessel followed by addition of 1,4-dioxane (40 mL) and water (10.00 mL). The suspension was stirred and degassed under N$_2$ for 15 min. (emulsion). Next added in PdCl$_2$(dppf)-CH$_2$Cl$_2$ adduct (0.361 g, 0.442 mmol) and degassed for 2 min. The reaction flask was sealed and the contents heated at reflux for 2 h. The suspension was filtered, and dioxane was removed in vacuo. The resultant oil was partitioned between 300 mL of ethyl acetate and 100 mL of water, and the layers were separated. Decolorizing carbon was added, and after 10 min, the organic layer was filtered through short pad of silica. 300 mL of 1 M HCl was added and neutralized with NaOH (to pH ~9). The contents were extracted with ethyl acetate. The organic layer was separated, washed with brine, dried over MgSO$_4$, filtered and concentrated in vacuo. The product was suspended in diethyl ether and filtered. The title compound was isolated as a yellow solid (950 mg, 41% yield). $^1$H NMR (400 MHz, DMSO-d$_6$) δ 11.49 (br. s., 1H), 8.52 (d, J=2.27 Hz, 1H), 8.15 (t, J=5.05 Hz, 1H), 7.95 (dd, J=2.53, 8.84 Hz, 1H), 7.73 (d, J=1.26 Hz, 1H), 7.29 (s, 1H), 7.19 (d, J=1.52 Hz, 1H), 6.93 (d, J=9.09 Hz, 1H), 5.87 (s, 1H), 4.85 (quin, J=6.63 Hz, 1H), 4.35 (d, J=5.05 Hz, 2H), 3.49-3.63 (m, 4H), 2.81-3.02 (m, 4H), 2.24 (s, 3H), 2.16 (s, 3H), 2.11 (s, 3H), 1.43 (d, J=6.57 Hz, 6H); LCMS=513.3 (MH+).

Example 266

6-bromo-1-(sec-butyl)-N-((4,6-dimethyl-2-oxo-1,2-dihydropyridin-3-yl)methyl)-3-methyl-1H-indole-4-carboxamide

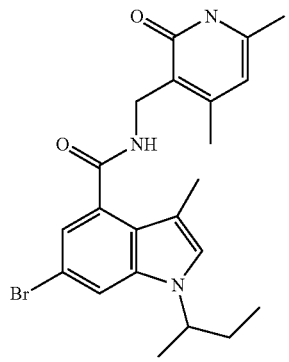 [SMILES: CCC(C)n1cc(C)c2c(C(=O)NCc3c(C)cc(C)[nH]c3=O)cc(Br)cc21]

Added sequentially to a reaction flask were 6-bromo-1-(sec-butyl)-3-methyl-1H-indole-4-carboxylic acid (1.33 g, 4.29 mmol), 3-(aminomethyl)-4,6-dimethyl-2(1H)-pyridinone (1.213 g, 6.43 mmol), 1-hydroxy-7-azabenzotriazole (0.875 g, 6.43 mmol), EDC (1.233 g, 6.43 mmol), followed by DMSO (30 mL, via syringe) and then N-methylmorpholine (1.886 mL, 17.15 mmol, via syringe). The contents were sealed and stirred at room temperature and the solids gradually dissolved. The contents were stirred at room temperature for 32 h, and then slowly diluted into 220 mL of ice-water with stirring. The contents were stirred for 10 min, and then allowed to stand for an additional 10 min. The contents were filtered and the filtered solid was washed with additional water (50 mL). The solid was then air dried for 10 min, and then in a vacuum oven at 50° C. for 23 h total. The product was collected as 1.75 g (87%). $^1$H NMR (400 MHz, DMSO-d$_6$) δ ppm 0.69 (t, J=7.33 Hz, 3H), 1.36 (d, J=6.57 Hz, 3H), 1.77 (dq, J=10.29, 7.09 Hz, 2H), 2.12 (d, J=9.09 Hz, 6H), 2.21 (s, 3H), 4.30 (d, J=5.05 Hz, 2H), 4.43-4.56 (m, 1H), 5.86 (s, 1H), 6.99 (d, J=1.52 Hz, 1H), 7.30 (s, 1H), 7.77 (d, J=1.77 Hz, 1H), 8.25 (t, J=4.93 Hz, 1H), 11.49 (br. s., 1H); LCMS=444.1 (MH+).

Examples 267 and 268

(S)-6-bromo-1-(sec-butyl)-N-((4,6-dimethyl-2-oxo-1,2-dihydropyridin-3-yl)methyl)-3-methyl-1H-indole-4-carboxamide (Ex 267) and (R)-6-Bromo-1-(sec-butyl)-N-((4,6-dimethyl-2-oxo-1,2-dihydropyridin-3-yl)methyl)-3-methyl-1H-indole-4-carboxamide (Ex 268)

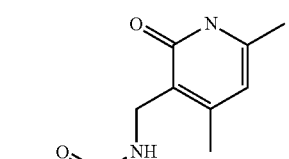

and

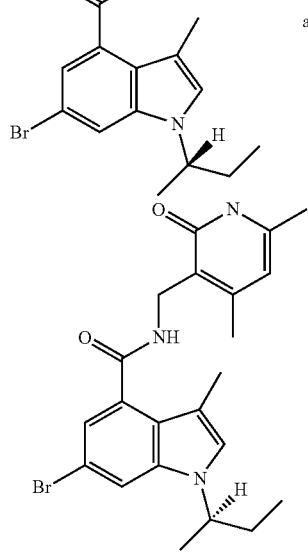

6-Bromo-1-(sec-butyl)-N-((4,6-dimethyl-2-oxo-1,2-dihydropyridin-3-yl)methyl)-3-methyl-1H-indole-4-carboxamide (racemic mixture, 1.9 g) was resolved by chiral HPLC (column: Chiralpak AD-H, 5 microns, 50 mm×250 mm, UV detection: 240 nM, flow rate: 100 mL/min, T=20 deg C., eluent: 60:40:0.1 n-heptane:ethanol:isopropylamine (isocratic)). For each run, 100 mg of the racemic compound was dissolved in 30 volumes (3.0 mL) of warm ethanol with a few drops of isopropylamine added. A total of 19 runs were performed. Baseline resolution was observed for each run. The isomer that eluted at 8.3-10.1 min was collected (following concentration) as a white solid, which was dried at 50° C. (<5 mm Hg) to afford 901 mg, and was determined to be the S isomer* (Ex. 267; chiral HPLC: >99.5% ee (no R isomer detected). The isomer that eluted at 10.8-13.0 min was collected as a white solid, which was dried at 50° C. (<5 mm Hg) to afford 865 mg, and was determined to be the R isomer* (Ex. 268; chiral HPLC: 99.2% ee; 0.4% S isomer detected). $^1$H NMR and LCMS were consistent with the parent racemate.

* The absolute configuration was determined by an independent synthesis of each enantiomer from the corresponding commercially available homochiral alcohols via Mitsunobu reaction. The sterochemical assignments were also consistent by vibrational circular dichroism (VCD) analysis.

Example 269

1-(sec-butyl)-N-((4,6-dimethyl-2-oxo-1,2-dihydro-pyridin-3-yl)methyl)-3-methyl-6-(6-(piperazin-1-yl)pyridin-3-yl)-1H-indole-4-carboxamide

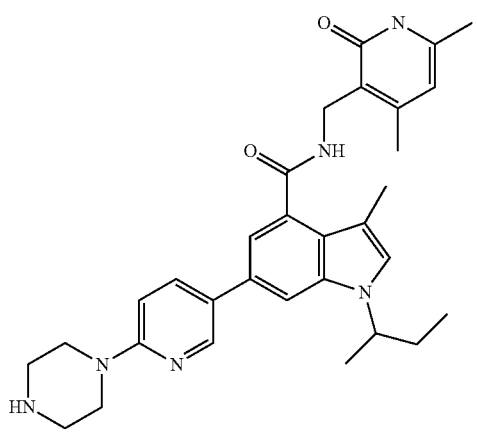 [SMILES: CCC(C)n1cc(C)c2c(C(=O)NCc3c(C)cc(C)[nH]c3=O)cc(-c3ccc(N4CCNCC4)nc3)cc21]

Added sequentially to a reaction vial were 6-bromo-1-(sec-butyl)-N-((4,6-dimethyl-2-oxo-1,2-dihydropyridin-3-yl)methyl)-3-methyl-1H-indole-4-carboxamide (0.15 g, 0.338 mmol), 1-(5-(4,4,5,5-tetramethyl-1,3,2-dioxaborolan-2-yl)pyridin-2-yl)piperazine (0.127 g, 0.439 mmol), and potassium phosphate (tribasic) (0.287 g, 1.350 mmol), followed by 1,4-Dioxane (3 mL) and water (0.75 mL). The suspension was stirred under $N_2$ degassing for 10 min., and then added $PdCl_2(dppf)$-$CH_2Cl_2$ adduct (0.028 g, 0.034 mmol). The reaction vial was sealed, placed into a heat block at 95° C., and stirred for 1.5 h. The contents were removed from heating and allowed to cool to room temperature. The aq layer was removed from bottom of the reaction vial via pipette. The reaction mixture was diluted into EtOAc (20 mL) followed by addition of 0.2 g each of Thiol-3 silicycle resin and silica gel. The volatiles were removed in vacuo and the residue dried on hi-vac for 1 h. The contents were purified by silica gel chromatography (dry loaded, eluent:A:Dichloromethane, B: 10% (2M Ammonia in Methanol) in Chloroform, Gradient B: 8-95%). The obtained solid was concentrated from TBME and dried in vacuum oven at 45° C. for 18 h. The product was collected as 129 mg (70%). $^1$H NMR (400 MHz, DMSO-$d_6$) δ ppm 0.73 (t, J=7.33 Hz, 3H), 1.40 (d, J=6.57 Hz, 3H), 1.80 (dq, J=10.07, 7.08 Hz, 2H), 2.11 (s, 3H), 2.14-2.19 (m, 3H), 2.24 (s, 3H), 2.76-2.85 (m, 4H), 3.41-3.49 (m, 4H), 4.35 (d, J=5.05 Hz, 2H), 4.54-4.67 (m, 1H), 5.87 (s, 1H), 6.88 (d, J=8.84 Hz, 1H), 7.17 (d, J=1.26 Hz, 1H), 7.26 (s, 1H), 7.73 (d, J=1.26 Hz, 1H), 7.91 (dd, J=8.84, 2.53 Hz, 1H), 8.16 (t, J=5.05 Hz, 1H), 8.50 (d, J=2.53 Hz, 1H), 11.48 (br. s., 1H); LCMS MH$^+$=527.3.

Example 270

N-[(4,6-dimethyl-2-oxo-1,2-dihydro-3-pyridinyl)methyl]-3-methyl-1-[(1S)-1-methylpropyl]-6-[6-(1-piperazinyl)-3-pyridinyl]-1H-indole-4-carboxamide

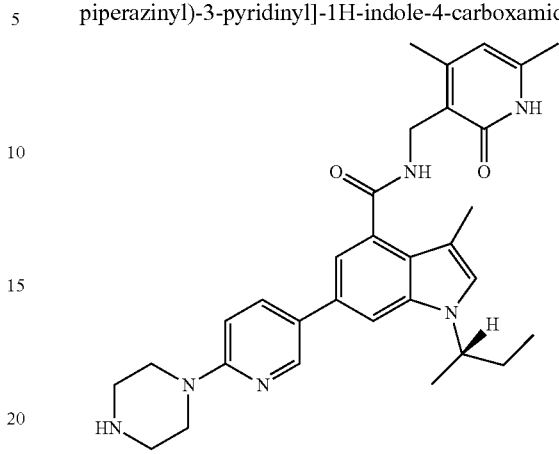

To a 30 mL microwave vial were added (S)-6-bromo-1-(sec-butyl)-N-((4,6-dimethyl-2-oxo-1,2-dihydropyridin-3-yl)methyl)-3-methyl-1H-indole-4-carboxamide (100 mg, 0.225 mmol), 1-(5-(4,4,5,5-tetramethyl-1,3,2-dioxaborolan-2-yl)pyridin-2-yl)piperazine (85 mg, 0.293 mmol), 1,2-Dimethoxyethane (DME) (3 mL), water (1.000 mL) and sodium carbonate (0.338 mL, 0.675 mmol), and the mixture was degassed for 5 min by bubbling nitrogen. $PdCl_2(dppf)$-$CH_2Cl_2$ adduct (14.70 mg, 0.018 mmol) was added and the tube was sealed. The mixture was irradiated (microwave) at 140° C. for 10 min. The mixture was concentrated and the residue was taken up into MeOH and filtered. The filtrate was purified using reverse-phase HPLC (eluent: 25% ACN/$H_2O$, 0.1% $NH_4OH$ to 60% ACN/$H_2O$, 0.1% $NH_4OH$) to give 91 mg of product as off-white solid. $^1$H NMR (400 MHz, DMSO-$d_6$) δ ppm 0.70-0.78 (m, 3H), 1.37-1.44 (m, 3H), 1.75-1.87 (m, 2H), 2.11 (s, 3H), 2.16 (s, 3H), 2.22-2.27 (m, 3H), 2.77-2.85 (m, 4H), 3.41-3.49 (m, 4H), 4.35 (d, J=5.31 Hz, 2H), 4.56-4.68 (m, 1H), 5.87 (s, 1H), 6.88 (d, J=8.84 Hz, 1H), 7.17 (d, J=1.52 Hz, 1H), 7.26 (s, 1H), 7.73 (d, J=1.26 Hz, 1H), 7.91 (dd, J=8.84, 2.53 Hz, 1H), 8.16 (t, J=5.05 Hz, 1H), 8.50 (d, J=2.53 Hz, 1H); LCMS: 527.8 (MH$^+$).

Example 271

N-[(4,6-dimethyl-2-oxo-1,2-dihydro-3-pyridinyl)methyl]-3-methyl-1-[(1R)-1-methylpropyl]-6-[6-(1-piperazinyl)-3-pyridinyl]-1H-indole-4-carboxamide

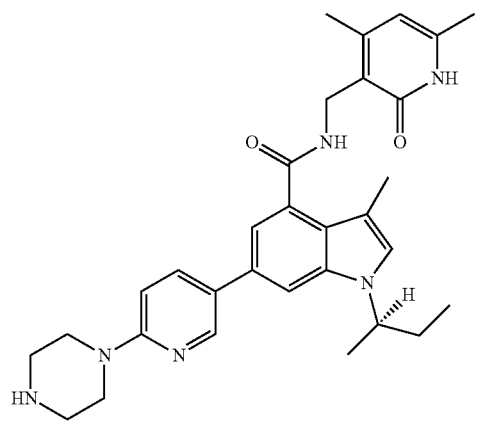 [SMILES: CC[C@@H](C)n1cc(C)c2c(C(=O)NCc3c(C)cc(C)[nH]c3=O)cc(-c3ccc(N4CCNCC4)nc3)cc21]

To a 30 mL microwave vial were added (R)-6-bromo-1-(sec-butyl)-N-((4,6-dimethyl-2-oxo-1,2-dihydropyridin-3-yl)methyl)-3-methyl-1H-indole-4-carboxamide (100 mg, 0.225 mmol), 1-(5-(4,4,5,5-tetramethyl-1,3,2-dioxaborolan-2-yl)pyridin-2-yl)piperazine (85 mg, 0.293 mmol), 1,2-Dimethoxyethane (DME) (3 mL), water (1.000 mL) and sodium carbonate (0.338 mL, 0.675 mmol), and the mixture was degassed for 5 min by bubbling nitrogen. PdCl$_2$(dppf)-CH$_2$Cl$_2$ adduct (14.70 mg, 0.018 mmol) was added and the tube was sealed. The mixture was irradiated (microwave) at 140° C. for 10 min. The mixture was concentrated and the residue was taken up into MeOH and filtered. The filtrate was purified using reverse-phase HPLC (eluent: 25% ACN/H$_2$O, 0.1% NH$_4$OH to 60% ACN/H$_2$O, 0.1% NH$_4$OH) to give 90 mg of product as off-white solid. $^1$H NMR (400 MHz, DMSO-d$_6$) δ ppm 0.73 (m, 3H), 1.41 (d, J=6.57 Hz, 3H), 1.81 (td, J=7.14, 2.91 Hz, 2H), 2.11 (s, 3H), 2.15-2.20 (m, 3H), 2.24 (s, 3H), 2.77-2.83 (m, 4H), 3.41-3.49 (m, 4H), 4.35 (d, J=5.05 Hz, 2H), 4.54-4.68 (m, 1H), 5.87 (s, 1H), 6.88 (d, J=8.84 Hz, 1H), 7.17 (d, J=1.52 Hz, 1H), 7.26 (s, 1H), 7.73 (d, J=1.26 Hz, 1H), 7.91 (dd, J=8.84, 2.53 Hz, 1H), 8.16 (t, J=5.05 Hz, 1H), 8.50 (d, J=2.27 Hz, 1H); LCMS: 527.7 (MH+).

Example 272

1-(sec-Butyl)-N-((4,6-dimethyl-2-oxo-1,2-dihydropyridin-3-yl)methyl)-6-(3-((dimethylamino)methyl)phenyl)-3-methyl-1H-indole-4-carboxamide

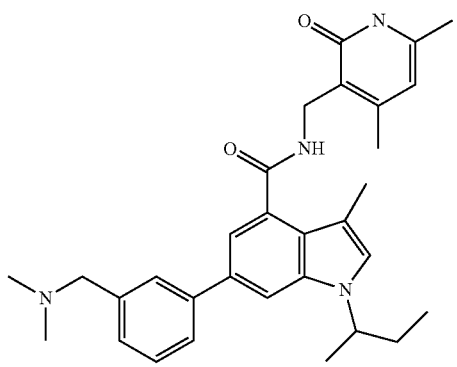

Added sequentially to a reaction vial were 6-bromo-1-(sec-butyl)-N-((4,6-dimethyl-2-oxo-1,2-dihydropyridin-3-yl)methyl)-3-methyl-1H-indole-4-carboxamide (0.15 g, 0.338 mmol), N,N-dimethyl-1-(3-(4,4,5,5-tetramethyl-1,3,2-dioxaborolan-2-yl)phenyl)methanamine-hydrochloride (0.131 g, 0.439 mmol) and potassium phosphate (tribasic) (0.287 g, 1.350 mmol), followed by 1,4-Dioxane (4 mL) and water (0.75 mL). The suspension was stirred under N$_2$ degassing for 10 min., and then added PdCl$_2$(dppf)-CH$_2$Cl$_2$ adduct (0.028 g, 0.034 mmol). The reaction vial was sealed, placed into a heat block at 95° C., and stirred for 1.5 h. The contents were removed from heating and allowed to cool to room temperature. The aq layer was removed from bottom of the reaction vial via pipette. The reaction mixture was diluted into EtOAc (20 mL) followed by addition of 0.2 g each of Thiol-3 silicycle resin and silica gel. The volatiles were removed in vacuo and the residue dried on hi-vac for 1 h. The contents were purified by silica gel chromatography (dry loaded, eluent:A:Dichloromethane, B: 10% (2M Ammonia in Methanol) in Chloroform; Gradient B: 8-95%). The obtained solid was concentrated from TBME to afford a foam, and was dried in vacuum oven at 45° C. for 18 h. The product was collected as 116 mg (65%). $^1$H NMR (400 MHz, DMSO-d$_6$) δ ppm 0.73 (t, J=7.33 Hz, 3H), 1.41 (d, J=6.57 Hz, 3H), 1.82 (dq, J=9.85, 7.16 Hz, 2H), 2.08-2.12 (m, 3H), 2.15-2.21 (m, 9H), 2.24 (s, 3H), 3.44-3.49 (m, 2H), 4.35 (d, J=5.05 Hz, 2H), 4.57-4.70 (m, 1H), 5.86 (s, 1H), 7.19-7.26 (m, 2H), 7.30 (s, 1H), 7.36-7.44 (m, 1H), 7.58-7.65 (m, 2H), 7.76 (d, J=1.26 Hz, H), 8.21 (t, J=5.05 Hz, 1H), 11.47 (s, 1H); LCMS M+H=499.3.

Example 273

6-{3-[(Dimethylamino)methyl]phenyl}-N-[(4,6-dimethyl-2-oxo-1,2-dihydro-3-pyridinyl)methyl]-3-methyl-1-[(1S)-1-methylpropyl]-1H-indole-4-carboxamide

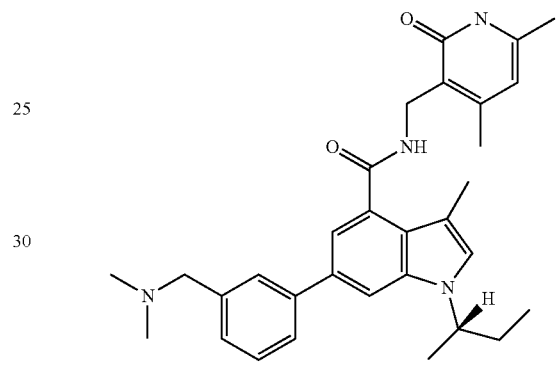

(S)-6-bromo-1-(sec-butyl)-N-((4,6-dimethyl-2-oxo-1,2-dihydropyridin-3-yl)methyl)-3-methyl-1H-indole-4-carboxamide (100 mg, 0.23 mmol), N,N-dimethyl-1-(3-(4,4,5,5-tetramethyl-1,3,2-dioxaborolan-2-yl)phenyl)methanamine, HCl (100 mg, 0.34 mmol) and Palladium Tetrakis (26 mg, 0.023 mmol) in DMF/water (3 ml:1 ml) were stirred for 10 min under nitrogen. Cesium carbonate (220 mg, 0.68 mmol) was added and the insoluble mixture was irradiated (microwave) at 150° C. for 15 min. The contents were evaporated, dissolved in DCM/MeOH (1:1), and pre-absorbed on silica gel and purified using silica gel chromatography (eluent: DCM/MeOH/NH$_4$OH, gradient 0 to 80:20:2 in DCM). The isolated product was first treated with EtOAc along with some hexanes. The product was then dissolved in MeOH and purified by reverse-phase HPLC (30×100 Varian Polaris C18 column, eluent: 10-80% gradient of MeCN in water with 0.1% TFA). The product fractions were combined, most of the solvent was evaporated, and a sat. solution of NaHCO$_3$ was added. Solids that crashed out were filtered, air-dried for 15 min, and dried in vacuum-oven overnight. The solid product was collected as 87 mg (75%). $^1$H NMR (400 MHz, DMSO-d6) δ ppm 11.38 (br. s., 1H), 8.23 (t, J=4.67 Hz, 1H), 7.77 (d, J=1.01 Hz, 1H), 7.60-7.64 (m, 2H), 7.40 (t, J=7.58 Hz, 1H), 7.30 (s, 1H), 7.20-7.26 (m, 2H), 5.87 (s, 1H), 4.59-4.68 (m, 1H), 4.36 (s, 1H), 4.35 (s, 1H), 3.46 (s, 2H), 2.24 (s, 3H), 2.18 (s, 9H), 2.11 (s, 3H), 1.76-1.88 (m, 2H), 1.41 (d, J=6.57 Hz, 3H), 0.74 (t, J=7.33 Hz, 3H); LCMS: 499.4 (MH+).

Example 274

6-{3-[(dimethylamino)methyl]phenyl}-N-[(4,6-dimethyl-2-oxo-1,2-dihydro-3-pyridinyl)methyl]-3-methyl-1-[(1R)-1-methylpropyl]-1H-indole-4-carboxamide

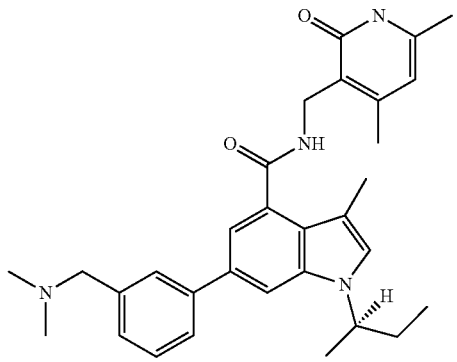

(R)-6-bromo-1-(sec-butyl)-N-((4,6-dimethyl-2-oxo-1,2-dihydropyridin-3-yl)methyl)-3-methyl-1H-indole-4-carboxamide (100 mg, 0.23 mmol), N,N-dimethyl-1-(3-(4,4,5,5-tetramethyl-1,3,2-dioxaborolan-2-yl)phenyl) methanamine, HCl (100 mg, 0.34 mmol) and Palladium Tetrakis (26 mg, 0.023 mmol) in DMF/water (3 mL:1 mL) were stirred for 10 min under nitrogen. Cesium carbonate (220 mg, 0.68 mmol) was added and the insoluble mixture was irradiated (microwave) at 150° C. for 15 min. The contents were evaporated, dissolved in DCM/MeOH (1:1), and pre-absorbed on silica gel and purified using silica gel chromatography (eluent: DCM/MeOH/NH$_4$OH, gradient 0 to 80:20:2 in DCM). The isolated product was first treated with EtOAc along with some hexanes. The product was then dissolved in MeOH and purified by reversed-phase HPLC (30× 100 Varian Polaris C18 column, eluent: 10-80% gradient of MeCN in water with 0.1% TFA). The product fractions were combined, most of the solvent was evaporated, and a sat. solution of NaHCO$_3$ was added. Solids that crashed out were filtered, air-dried for 15 min, and dried in vacuum-oven overnight. The solid product was collected as 85 mg (75%). $^1$H NMR (400 MHz, DMSO-d6) δ ppm 11.48 (s, 1H) 8.21 (t, J=5.05 Hz, 1H) 7.77 (d, J=1.26 Hz, 1H) 7.60-7.66 (m, 2H) 7.41 (t, J=7.58 Hz, 1H) 7.30 (s, 1H) 7.25 (d, J=7.58 Hz, 1H) 7.22 (d, J=1.52 Hz, 1H) 5.87 (s, 1H) 4.60-4.68 (m, 1H) 4.36 (s, 1H) 4.35 (s, 1H) 3.49 (br. s., 2H) 2.24 (s, 3H) 2.19 (d, J=8.84 Hz, 9H) 2.11 (s, 3H) 1.77-1.88 (m, 2H) 1.41 (d, J=6.57 Hz, 3H) 0.74 (t, J=7.33 Hz, 3H); LCMS: 499.4 (MH+).

Example 275

1-cyclopentyl-N-((4,6-dimethyl-2-oxo-1,2-dihydropyridin-3-yl)methyl)-3-methyl-6-(6-(piperazin-1-yl)pyridin-3-yl)-1H-indole-4-carboxamide

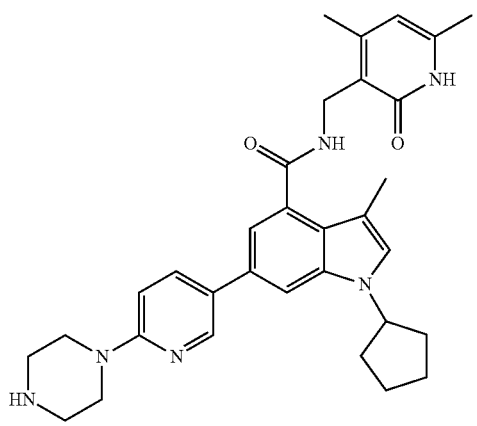 [SMILES: Cc1cc(C)c(CNC(=O)c2cc(-c3ccc(N4CCNCC4)nc3)cc3c2c(C)cn3C2CCCC2)c(=O)[nH]1]

To a 30 mL microwave vial were added 6-bromo-1-cyclopentyl-N-((4,6-dimethyl-2-oxo-1,2-dihydropyridin-3-yl)methyl)-3-methyl-1H-indole-4-carboxamide (80 mg, 0.175 mmol), 1-(5-(4,4,5,5-tetramethyl-1,3,2-dioxaborolan-2-yl)pyridin-2-yl)piperazine (65.9 mg, 0.228 mmol), 1,2-Dimethoxyethane (DME) (3 mL), Water (1.000 mL) and sodium carbonate (0.263 mL, 0.526 mmol), and the mixture was degassed for 5 min by bubbling nitrogen. PdCl$_2$(dppf)-CH$_2$Cl$_2$ adduct (11.45 mg, 0.014 mmol) was added and the tube was sealed. The mixture was irradiated (microwave) at 140° C. for 10 min. The mixture was concentrated and the residue was taken up into MeOH and filtered. The filtrate was purified using reverse-phase HPLC (eluent: 25% ACN/H$_2$O, 0.1% NH$_4$OH to 60% ACN/H$_2$O, 0.1% NH$_4$OH) to give 72 mg of product as off-white solid. $^1$H NMR (400 MHz, DMSO-d6) δ ppm 1.65-1.89 (m, 6H), 2.08-2.19 (m, 8H), 2.24 (s, 3H), 2.76-2.84 (m, 4H), 3.40-3.48 (m, 4H), 4.35 (d, J=5.05 Hz, 2H), 4.92-5.04 (m, 1H), 5.87 (s, 1H), 6.88 (d, J=8.84 Hz, 1H), 7.19 (d, J=1.26 Hz, 1H), 7.25 (s, 1H), 7.74 (d, J=1.26 Hz, 1H), 7.91 (dd, J=8.84, 2.53 Hz, 1H), 8.15 (t, J=5.05 Hz, 1H), 8.51 (d, J=2.53 Hz, 1H); LCMS: 539.8 (MH+).

Some examples were prepared as above from a boronic acid (or boronate) containing a Boc-protected amine. These examples required removal of the Boc-protecting group to provide the title compounds.

Example 276

1-isopropyl-N-((6-methyl-2-oxo-4-propyl-1,2-dihydropyridin-3-yl)methyl)-6-(6-(piperazin-1-yl)pyridin-3-yl)-1H-indole-4-carboxamide

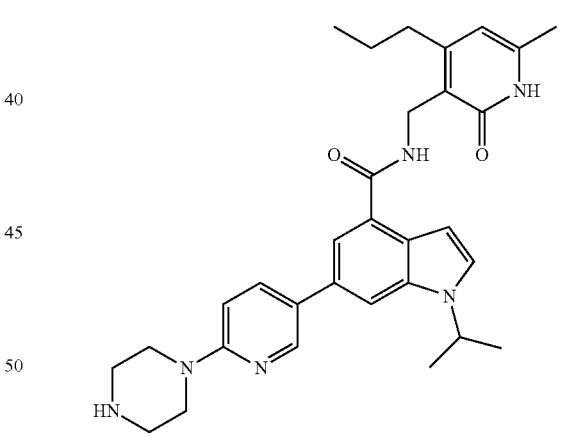

To a suspension of 1,1-dimethylethyl 4-{5-[1-(1-methylethyl)-4-({[(6-methyl-2-oxo-4-propyl-1,2-dihydro-3-pyridinyl)methyl]amino}carbonyl)-1H-indol-6-yl]-2-pyridinyl}-1-piperazinecarboxylate (70 mg, 0.112 mmol) in dichloromethane (2 mL) was added TFA (0.5 ml, 6.49 mmol), and the mixture was stirred for 1 h. The mixture was concentrated and the residue was treated with saturated aqueous NaHCO3 solution and filtered. The solid was purified using column chromatography (silica gel, 0 to 15% (9:1 MeOH/NH4OH)/CH2Cl2) to give 1-isopropyl-N-((6-methyl-2-oxo-4-propyl-1,2-dihydropyridin-3-yl)methyl)-6-(6-(piperazin-1-yl)pyridin-3-yl)-1H-indole-4-carboxamide (51 mg, 84%) as off-white solid. $^1$H NMR (400 MHz, DMSO-d$_6$) δ ppm 0.91 (m, 3H), 1.47 (d, J=4.00 Hz, 6H), 1.53-1.60 (m, 2H), 2.14 (s, 3H), 2.89-2.98 (m, 4H), 3.51-3.59 (m, 4H), 4.40 (d, J=5.05 Hz, 2H), 4.93 (quin, J=6.63 Hz, 1H), 5.92 (s, 1H), 6.87 (d, J=3.03 Hz, 1H), 6.94 (d, J=8.84 Hz, 1H), 7.60 (d, J=3.03 Hz, 1H), 7.66 (d, J=1.26 Hz, 1H), 7.88 (s, 1H), 8.00 (dd, J=8.84, 2.53 Hz, 1H), 8.28 (t, J=5.05 Hz, 1H), 8.58 (d, J=2.27 Hz, 1H). MS: (M+H)$^+$=527.2.

Examples 277-285 were prepared by the methods described above for Examples 276 or routine variations thereof, starting from the requisite N-Boc protected material:

| Ex | Structure | Name | $^1$H NMR (400 MHz, DMSO-d$_6$) δ ppm | MS(ES) [M + H]$^+$ |
|---|---|---|---|---|
| 277 | 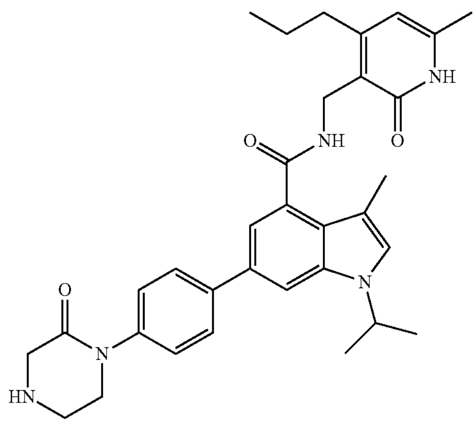 [SMILES: CCCc1cc(C)[nH]c(=O)c1CNC(=O)c1cc(-c2ccc(N3CCNCC3=O)cc2)cc2c1c(C)cn2C(C)C] | 1-isopropyl-3-methyl-N-((6-methyl-2-oxo-4-propyl-1,2-dihydropyridin-3-yl)methyl)-6-(4-(2-oxopiperazin-1-yl)phenyl)-1H-indole-4-carboxamide | 0.94 (m, 3 H), 1.44 (d, J = 6.57 Hz, 6 H), 1.54-1.63 (m, 2 H), 2.12 (s, 3 H), 2.18 (s, 3 H), 3.04 (t, J = 5.31 Hz, 2 H), 3.41 (s, 2 H), 3.64 (t, J = 5.31 Hz, 2 H), 4.37 (d, J = 5.05 Hz, 2 H), 4.87 (quin, J = 6.63 Hz, 1 H), 5.90 (s, 1 H), 7.25 (d, J = 1.26 Hz, 1 H), 7.34 (s, 1 H), 7.40 (d, J = 8.59 Hz, 2 H), 7.70-7.83(m, 3 H), 8.18 (t, J = 5.05 Hz, 1 H) | 554.4 |
| 278 | 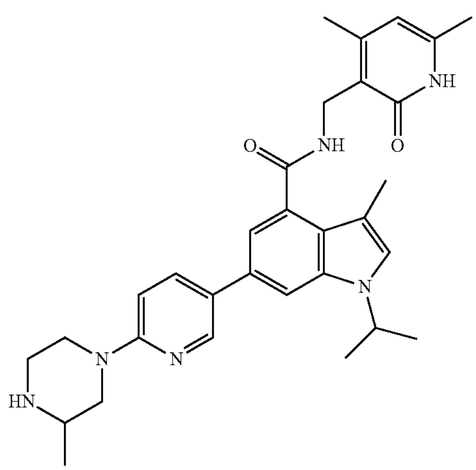 [SMILES: Cc1cc(C)c(CNC(=O)c2cc(-c3ccc(N4CCNC(C)C4)nc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[6-(3-methyl-1-piperazinyl)-3-pyridinyl]-1H-indole-4-carboxamide | 11.47 (s, 1 H) 8.50 (d, J = 2.53 Hz, 1 H) 8.16 (t, J = 5.05 Hz, 1 H) 7.92 (dd, J = 8.84, 2.53 Hz, 1 H) 7.73 (d, J = 1.26 Hz, 1 H) 7.26 (s, 1 H) 7.17 (d, J = 1.52 Hz, 1 H) 6.92 (d, J = 9.09 Hz, 1 H) 5.87 (s, 1 H) 4.56-4.65 (m, 1 H) 4.36 (s, 1 H) 4.34 (s, 1 H) 3.49-3.55 (m, 4 H) 2.40-2.44 (m, 4 H) 2.24 (s, 3 H) 2.23 (s, 3 H) 2.16 (s, 3 H) 2.11 (s, 3 H) 1.76-1.87 (m, 2 H) 1.41 (d, J = 6.57 Hz, 3 H) 0.73 (t, J = 7.33 Hz, 3 H) | 527.3 |
| 279 | 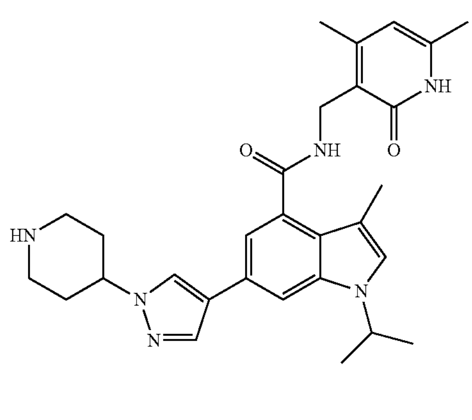 [SMILES: Cc1cc(C)c(CNC(=O)c2cc(-c3cnn(C4CCNCC4)c3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(1-(piperidin-4-yl)-1H-pyrazol-4-yl)-1H-indole-4-carboxamide | 1.42 (m, 6 H), 1.81 (qd, J = 11.96, 4.04 Hz, 2 H), 1.98 (m, 2 H), 2.12 (d, J = 6.57 Hz, 6 H), 2.24 (s, 3 H), 2.55-2.66 (m, 2 H), 3.05 (d, J = 12.63 Hz, 2 H), 4.18 (tt, J = 11.49, 4.04 Hz, 1 H), 4.34 (d, J = 5.05 Hz, 2 H), 4.78 (quin, J = 6.69 Hz, 1 H), 5.87 (s, 1 H), 7.18 (d, J = 1.26 Hz, 1 H), 7.22 (d, J = 1.01 Hz, 1 H), 7.71 (d, J = 1.01 Hz, 1 H), 7.89 (s, 1 H), 8.03 (t, J = 5.18 Hz, 1 H), 8.24 (s, 1 H) | 501.1 |

| Ex | Structure | Name | ¹H NMR (400 MHz, DMSO-d₆) δ ppm | MS(ES) [M + H]⁺ |
|---|---|---|---|---|
| 280 | 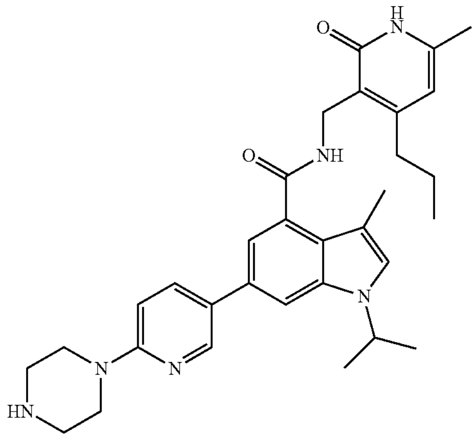 [SMILES: CCCc1cc(C)[nH]c(=O)c1CNC(=O)c1cc(-c2ccc(N3CCNCC3)nc2)cc2c1c(C)cn2C(C)C] | 6-methyl-3-[(2-{3-methyl-1-(1-methylethyl)-6-[6-(1-piperazinyl)-3-pyridinyl]-1H-indol-4-yl}-2-oxoethyl)amino]-4-propyl-2(1H)-pyridinone | 0.93 (t, J = 7.33 Hz, 3 H), 1.42 (d, J = 6.57 Hz, 6 H), 1.56 (qt, J = 7.56, 7.36 Hz, 2 H), 2.12 (s, 3 H), 2.16 (s, 3 H), 2.52-2.58 (m, 2 H), 2.77-2.90 (m, 4 H), 3.42-3.51 (m, 4 H), 4.36 (d, J = 5.05 Hz, 2 H), 4.84 (dt, J = 13.20, 6.66 Hz, 1 H), 5.90 (s, 1 H), 6.89 (d, J = 8.84 Hz, 1 H), 7.17 (d, J = 1.26 Hz, 1 H), 7.29 (s, 1 H), 7.72 (s, 1 H), 7.91 (dd, J = 8.84, 2.53 Hz, 1 H), 8.12 (t, J = 4.93 Hz, 1 H), 8.49 (d, J = 2.27 Hz, 1 H), 11.49 (br. s., 1 H) | 541.5 |
| 281 | 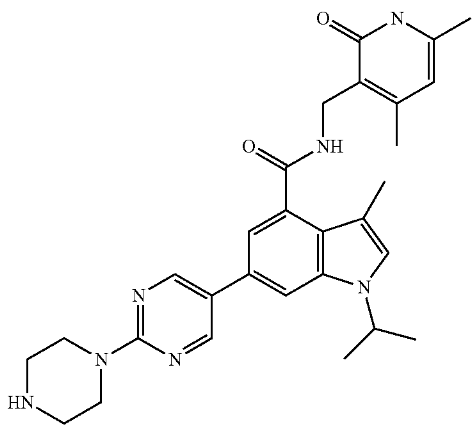 [SMILES: Cc1cc(C)c(CNC(=O)c2cc(-c3cnc(N4CCNCC4)nc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(2-(piperazin-1-yl)pyrimidin-5-yl)-1H-indole-4-carboxamide | 11.47 (br. s., 1 H), 8.75 (s, 2 H), 8.13 (t, J = 5.1 Hz, 1 H), 7.76 (d, J = 1.5 Hz, 1 H), 7.30 (s, 1 H), 7.19 (d, J = 1.3 Hz, 1 H), 5.87 (s, 1 H), 4.83 (m, 1 H), 4.34 (d, J = 5.1 Hz, 2 H), 3.71 (m, 4 H), 2.77 (m, 4 H), 2.24 (s, 3 H), 2.15 (s, 3 H), 2.11 (s, 3 H), 1.42 (d, J = 6.6 Hz, 6 H) | 514.2 |
| 282 | 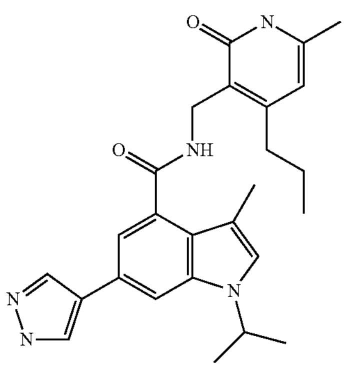 [SMILES: CCCc1cc(C)[nH]c(=O)c1CNC(=O)c1cc(-c2cn[nH]c2)cc2c1c(C)cn2C(C)C] | 3-methyl-1-(1-methylethyl)-N-[(6-methyl-2-oxo-4-propyl-1,2-dihydro-3-pyridinyl)methyl]-6-(1H-pyrazol-4-yl)-1H-indole-4-carboxamide | 12.85 (br. s., 1 H), 11.49 (br. s., 1 H), 8.01 (t, J = 5.2 Hz, 3 H), 7.72 (d, J = 1.3 Hz, 1 H), 7.20 (m, 2 H), 5.90 (s, 1 H), 4.78 (quin, J = 6.6 Hz, 1 H), 4.35 (d, J = 5.1 Hz, 2 H), 2.55 (m, 2 H), 2.11 (m, 6 H), 1.57 (sxt, J = 7.5 Hz, 2 H), 1.42 (d, J = 6.6 Hz, 6 H), 0.94 (m, 3 H) | 446.0 |
| 283 | 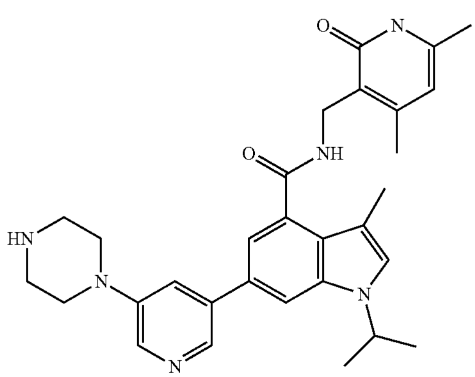 [SMILES: Cc1cc(C)c(CNC(=O)c2cc(-c3cncc(N4CCNCC4)c3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(5-(piperazin-1-yl)pyridin-3-yl)-1H-indole-4-carboxamide | 11.48 (br. s., 1 H), 8.36 (d, J = 1.8 Hz, 1 H), 8.20 (m, 2 H), 7.84 (d, J = 1.3 Hz, 1 H), 7.55 (t, J = 2.3 Hz, 1 H), 7.35 (d, J = 1.0 Hz, 1 H), 7.26 (d, J = 1.5 Hz, 1 H), 5.87 (s, 1 H), 4.91 (quin, J = 6.6 Hz, 1 H), 4.35 (d, J = 5.1 Hz, 2 H), 3.19 (m, 4 H), 2.88 (m, 4 H), 2.24 (s, 3 H), 2.16 (s, 3 H), 2.11 (s, 3 H), 1.43 (d, J = 6.6 Hz, 6 H) | 513.3 |

| Ex | Structure | Name | ¹H NMR (400 MHz, DMSO-d₆) δ ppm | MS(ES) [M + H]⁺ |
|---|---|---|---|---|
| 284 | 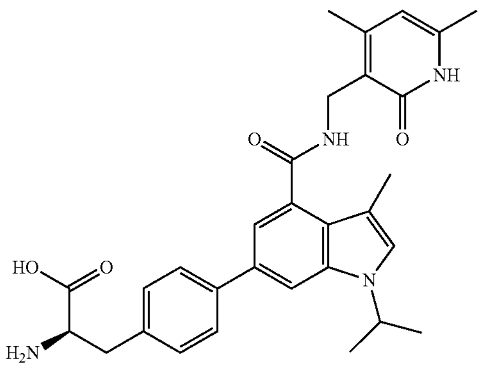 [SMILES: Cc1cc(C)c(CNC(=O)c2cc(-c3ccc(C[C@@H](N)C(=O)O)cc3)cc3c2c(C)cn3C(C)C)c(=O)[nH]1] | 4-[4-({[(4,6-dimethyl-2-oxo-1,2-dihydro-3-pyridinyl)methyl]amino}carbonyl)-3-methyl-1-(1-methylethyl)-1H-indol-6-yl]-L-phenylalanine | 11.48 (br. s., 1 H) 8.18 (t, J = 4.93 Hz, 1 H) 7.75 (s, 1 H) 7.70 (d, J = 8.08 Hz, 2 H) 7.31-7.37 (m, 3 H) 7.24 (s, 1 H) 5.87 (s, 1 H) 4.89-4.82 (m, 1 H) 4.35 (d, J = 4.80 Hz, 2 H) 3.85 (br. s., 1 H) 2.97-3.22 (m, 2 H) 2.24 (s, 3 H) 2.17 (s, 3 H) 2.11 (s, 3 H) 1.43 (d, J = 6.57 Hz, 6 H) | 515.3 |
| 285 | 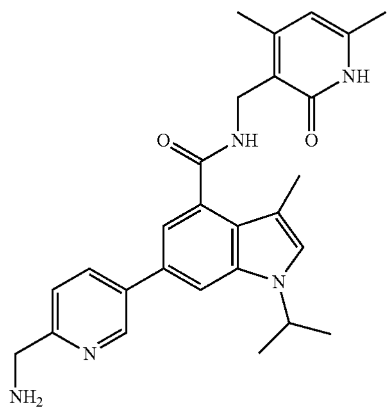 [SMILES: Cc1cc(C)c(CNC(=O)c2cc(-c3ccc(CN)nc3)cc3c2c(C)cn3C(C)C)c(=O)[nH]1] | 6-[6-(aminomethyl)-3-pyridinyl]-N-[(4,6-dimethyl-2-oxo-1,2-dihydro-3-pyridinyl)methyl]-3-methyl-1-(1-methylethyl)-1H-indole-4-carboxamide | 11.47 (br. s., 1 H) 8.37 ( s, 1 H) 8.13 (br. s., 1 H) 7.79-7.76 (m, 1 H) 7.66 (s, 1 H) 7.26 (s, 1 H) 7.14 (s, 1 H) 6.53 (d, J = 8.34 Hz, 2 H) 5.87 (br. s., 1 H) 4.88-4.75 (m, 1 H) 4.35 (d, J = 4.04 Hz, 2 H) 2.81 (d, J = 4.29 Hz, 3 H) 2.24 (s, 3 H) 2.16 (s, 3 H) 2.11 (s, 3 H) 1.43 (d, J = 6.32 Hz, 6 H) | 458.3 |

Some examples were prepared as above from a boronic acid (or boronate) containing an alkyl ester. These examples required saponification of the ester to provide the corresponding carboxylic acids.

Example 286

4-[4-({[(4,6-Dimethyl-2-oxo-1,2-dihydro-3-pyridinyl)methyl]amino}carbonyl)-3-methyl-1-(1-methylethyl)-1H-indol-6-yl]benzoic acid

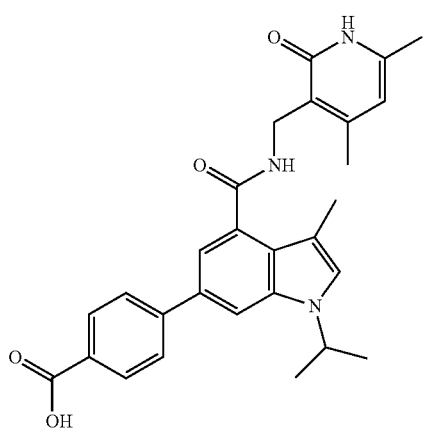 [SMILES: Cc1cc(C)c(CNC(=O)c2cc(-c3ccc(C(=O)O)cc3)cc3c2c(C)cn3C(C)C)c(=O)[nH]1]

To a solution of methyl 4-[4-({[(4,6-dimethyl-2-oxo-1,2-dihydro-3-pyridinyl)methyl]amino}carbonyl)-3-methyl-1-(1-methylethyl)-1H-indol-6-yl]benzoate (30 mg, 0.062 mmol) in MeOH (2 mL) and THF (1 mL) was 3 N NaOH (0.031 mL, 0.185 mmol). The reaction was heated at 50° C. for 12 h, at which time it was allowed to cool to ambient temperature and treated with acidic ice water to bring pH to 6. The solid was filtered and washed several times with water and an 8:2 mixture of acidic (pH2) ice water:MeOH. Purification by reverse phase Gilson HPLC (10-80%, acetonitrile/water+0.1% TFA, YMC ODS-A C18 Column 75×30 mm ID S-5 um, 12 nM Column 7 minutes) provided the title compound (12 mg, 0.024 mmol, 39.5% yield) as an off-white solid. ¹H NMR (400 MHz, DMSO-d₆) δ ppm 12.91 (br. s., 1H) 11.48 (br. s., 1H) 8.23 (t, J=5.05 Hz, 1H) 8.02 (d, J=8.34 Hz, 3H) 7.87-7.94 (m, 4H) 7.38 (s, 1H) 7.32 (d, J=1.52 Hz, 1H) 5.87 (s, 1H) 4.91 (quin, J=6.63 Hz, 1H) 4.36 (d, J=4.80 Hz, 2H) 2.24 (s, 3H) 2.18 (s, 3H) 2.11 (s, 3H) 1.44 (d, J=6.57 Hz, 6H). MS (ES) [M+H]⁺ 486.1.

Examples 287-288 were prepared by the methods described above for Example 286, or routine variations thereof, starting from the requisite alkylester:

| Ex | Structure | Name | ¹H NMR (400 MHz, DMSO-d₆) δ ppm | MS(ES) [M + H]⁺ |
|---|---|---|---|---|
| 287 | 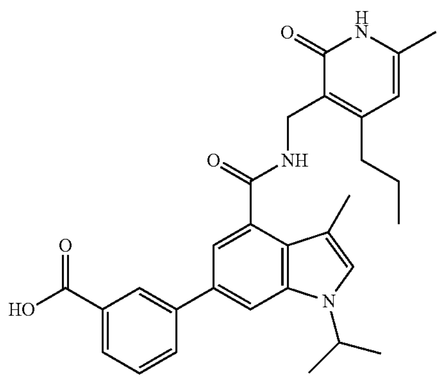 [SMILES: CCCc1cc(C)[nH]c(=O)c1CNC(=O)c1cc(-c2cccc(C(=O)O)c2)cc2c1c(C)cn2C(C)C] | 3-[3-methyl-1-(1-methylethyl)-4-({[(6-methyl-2-oxo-4-propyl-1,2-dihydro-3-pyridinyl)methyl]amino)carbonyl)-1H-indol-6-yl]benzoic acid | 13.07 (br. s., 1 H) 11.49 (br. s., 1 H) 8.27 (s, 1 H) 8.23 (t, J = 4.67 Hz, 1 H) 8.00 (d, J = 8.08 Hz, 1 H) 7.90 (d, J = 7.58 Hz, 1 H) 7.84 (s, 1 H) 7.59 (t, J = 7.71 Hz, 1 H) 7.36 (s, 1 H) 7.26 (s, 1 H) 5.90 (s, 1 H) 4.98-4.95 (m, 1 H) 4.38 (d, J = 5.05 Hz, 2 H) 2.56 (d, J = 7.58 Hz, 2 H) 2.19 (s, 3 H) 2.12 (s, 3H) 1.54-1.62 (m, 2 H) 1.44 (d, J = 6.57 Hz, 6 H) 0.94 (t, J = 7.33 Hz, 3 H) | 500.1 |
| 288 | 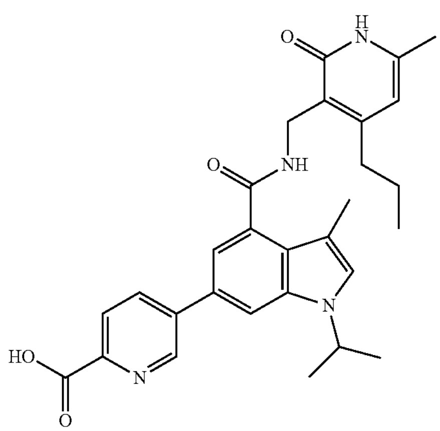 [SMILES: CCCc1cc(C)[nH]c(=O)c1CNC(=O)c1cc(-c2ccc(C(=O)O)nc2)cc2c1c(C)cn2C(C)C] | 5-[3-methyl-1-(1-methylethyl)-4-({[(6-methyl-2-oxo-4-propyl-1,2-dihydro-3-pyridinyl)methyl]amino)carbonyl)-1H-indol-6-yl]-2-pyridinecarboxylic acid | 13.22 (br. s., 1 H) 11.51 (br. s., 1 H) 9.11 (br. s., 1 H) 8.31-8.38 (m, 1 H) 8.23 (br. s., 1 H) 8.12 (br. s., 1 H) 8.02 (br. s., 1 H) 7.42 (br. s., 1 H) 7.37 (br.s., 1 H) 5.91 (br. s., 1 H) 4.88-4.98 (m, 1 H) 4.38 (br. s., 2 H) 2.55-2.61 (m, 2 H) 2.19 (br. s., 3 H) 2.12 (br. s., 3 H) 1.54-1.62 (m, 2 H) 1.46 (br. s., 6 H) 0.90-0.99 (m, 3 H) | 501.1 |

Example 289

N-[(4,6-Dimethyl-2-oxo-1,2-dihydro-3-pyridinyl)methyl]-1-(1-methylethyl)-1H-indole-4-carboxamide

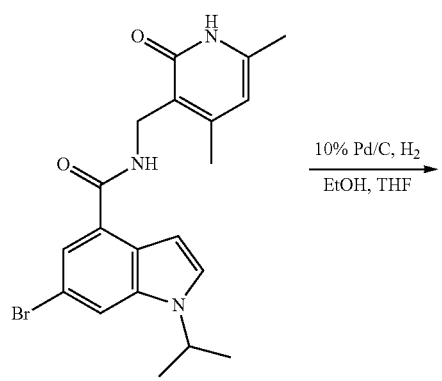

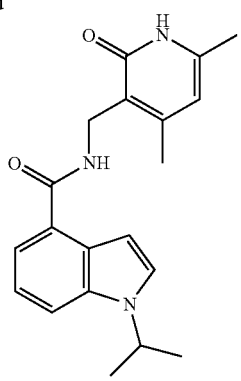

To a flask under N₂ atmosphere was added 10% palladium on carbon (0.028 g, 0.026 mmol) and ethanol (1 mL) (to wet catalyst). The flask was then charged with 6-bromo-N-[(4,6-dimethyl-2-oxo-1,2-dihydro-3-pyridinyl)methyl]-1-(1-methylethyl)-1H-indole-4-carboxamide (0.11 g, 0.264 mmol), ethanol (4 mL) and tetrahydrofuran (1 mL). The suspension was stirred under N₂, then evacuated and refilled with H₂ (balloon) and stirred overnight. The reaction was then placed back under N₂ and diluted with 10% methanol/dichloromethane. Celite was added and the mixture was stirred for 15 min, filtered through a pad of Celite, washed with 10% methanol/dichloromethane, and concentrated. The residue was dissolved in dimethylsulfoxide and acetonitrile (with 0.1% trifluoroacetic acid and purified by Gilson prep HPLC (Sunfire 30×75 mm; Gradient B: 15-75%; A: water+0.1% TFA; B: acetonitrile+0.1% TFA). The resulting residue was dissolved in 10% methanol/dichloromethane and treated with Silicycle carbonate resin (1.5 g). The mixture was stirred for 30 min, filtered through Celite, washed with 10% methanol/dichloromethane, and concentrated. The residue was dissolved in dichloromethane and treated with methyl-t-butylether. The solvents were removed by via $N_2$ stream and the solids dried in a vacuum oven at 45° C. for 18 h to give N-[(4,6-dimethyl-2-oxo-1,2-dihydro-3-pyridinyl)methyl]-1-(1-methylethyl)-1H-indole-4-carboxamide (56 mg, 0.159 mmol, 60% yield). $^1$H NMR (400 MHz, DMSO-$d_6$) δ ppm 1.41-1.48 (m, 6H) 2.09-2.15 (m, 3H) 2.24 (s, 3H) 4.35 (d, J=5.31 Hz, 2H) 4.79 (quin, J=6.63 Hz, 1H) 5.88 (s, 1H) 6.84 (d, J=3.03 Hz, 1H) 7.11-7.18 (m, 1H) 7.39 (d, J=6.57 Hz, 1H) 7.58 (d, J=3.28 Hz, 1H) 7.65 (d, J=8.34 Hz, 1H) 8.08 (t, J=5.31 Hz, 1H) 11.54 (br. s., 1H). MS (ES) [M+H]$^+$ 338.6.

Examples 290-295 were prepared by the methods described above for Example 289, or routine variations thereof, starting from the requisite 6-haloindole, alkene, or CBz-protected amine:

| Ex | Structure | Name | $^1$H NMR (400 MHz, DMSO-$d_6$) δ ppm | MS(ES) [M + H]$^+$ |
|---|---|---|---|---|
| 290 | 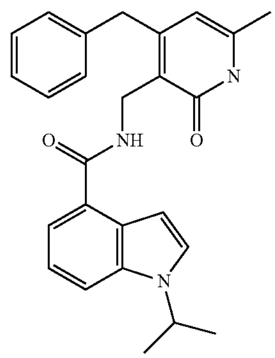 [SMILES: Cc1cc(Cc2ccccc2)c(CNC(=O)c2cccc3c2ccn3C(C)C)c(=O)[nH]1] | N-((4-benzyl-6-methyl-2-oxo-1,2-dihydropyridin-3-yl)methyl)-1-isopropyl-1H-indole-4-carboxamide | 11.60 (br. s., 1 H) 8.10-8.20 (m, 1 H) 7.66 (d, J = 8.34 Hz, 1 H) 7.59 (d, J = 3.28 Hz, 1 H) 7.40 (d, J = 7.07 Hz, 1 H) 7.14-7.31 (m, 6 H) 6.85 (d, J = 3.03 Hz, 1 H) 5.82 (s, 1 H) 4.80 (quin, J = 6.69 Hz, 1 H) 4.44 (s, 1 H) 4.42 (s, 1 H) 4.01 (s, 2 H) 2.10 (s, 3 H) 1.47 (s, 3 H) 1.45 (s, 3 H) | 413.9 |
| 291 | 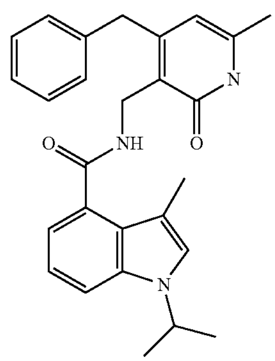 [SMILES: Cc1cc(Cc2ccccc2)c(CNC(=O)c2cccc3c2c(C)cn3C(C)C)c(=O)[nH]1] | N-((4-benzyl-6-methyl-2-oxo-1,2-dihydropyridin-3-yl)methyl)-1-isopropyl-3-methyl-1H-indole-4-carboxamide | 11.55 (s, 1 H) 8.08 (t, J = 5.18 Hz, 1 H) 7.50 (d, J = 7.83 Hz, 1 H) 7.20-7.33 (m, 6 H) 7.04-7.08 (m, 1 H) 6.90 (d, J = 7.07 Hz, 1 H) 5.79 (s, 1 H) 4.72 (quin, J = 6.63 Hz, 1 H) 4.41 (d, J = 5.31 Hz, 2 H) 3.99 (s, 2 H) 2.15 (s, 3 H) 2.09 (s, 3 H) 1.42 (s, 3 H) 1.40 (s, 3 H) | 427.8 |
| 292 | 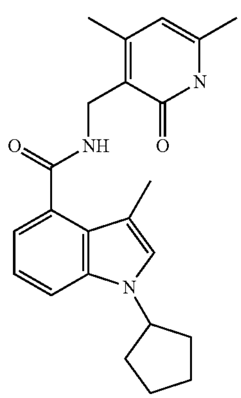 [SMILES: Cc1cc(C)c(CNC(=O)c2cccc3c2c(C)cn3C2CCCC2)c(=O)[nH]1] | 1-cyclopentyl-N-((4,6-dimethyl-2-oxo-1,2-dihydropyridin-3-yl)methyl)-3-methyl-1H-indole-4-carboxamide | 11.47 (br. s., 1 H) 7.99 (t, J = 4.93 Hz, 1 H) 7.51 (d, J = 7.83 Hz, 1 H) 7.24 (s, 1 H) 7.06 (t, J = 7.71 Hz, 1 H) 6.93 (d, J = 6.82 Hz, 1 H) 5.87 (s, 1 H) 4.86 (d, J = 7.33 Hz, 1 H) 4.33 (s, 1 H) 4.32 (s, 1 H) 2.23 (s, 3 H) 2.07-2.16 (m, 8 H) 1.76-1.86 (m, 4 H) 1.69 (d, J = 3.54 Hz, 2 H) | 378.3 |

| Ex | Structure | Name | ¹H NMR (400 MHz, DMSO-d₆) δ ppm | MS(ES) [M + H]⁺ |
|---|---|---|---|---|
| 293 | 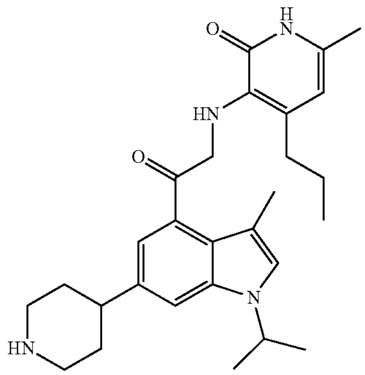 [SMILES: CCCc1cc(C)[nH]c(=O)c1NCC(=O)c1cc(C2CCNCC2)cc2c1c(C)cn2C(C)C] | 6-methyl-3-({2-[3-methyl-1-(1-methylethyl)-6-(4-piperidinyl)-1H-indol-4-yl]-2-oxoethyl}amino)-4-propyl-2(1H)-pyridinone | 0.93 (t, J = 7.33 Hz, 3 H), 1.39 (d, J = 6.57 Hz, 6 H), 1.48-1.64 (m, 4 H), 1.68 (br. s., 2 H), 2.12 (s, 6 H), 2.54 (m, 4 H), 3.01 (d, J = 11.87 Hz, 2 H), 3.16 (d, J = 4.55 Hz, 1 H), 4.33 (d, J = 5.05 Hz, 2 H), 4.70 (dt, J = 13.20, 6.66 Hz, 1 H), 5.89 (s, 1 H), 6.82 (s, 1 H), 7.19 (s, 1 H), 7.30 (s, 1 H), 7.93 (t, J = 4.80 Hz, 1 H), 8.55 (s, 1 H) | 463.1 |
| 294 | 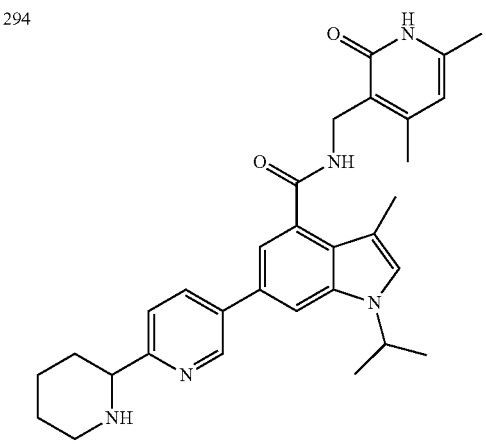 | N-[(4,6-dimethyl-2-oxo-1,2-dihydro-3-pyridinyl)methyl]-3-methyl-1-(1-methylethyl)-6-[6-(2-piperidinyl)-3-pyridinyl]-1H-indole-4-carboxamide | 1H NMR (400 MHz, METHANOL-d4) δ ppm 1.51-1.53 (d, 6 H) 1.82-1.84 (m, 3 H) 1.99-2.05 (m, 2 H) 2.24-2.26 (d, J = 7.83 Hz, 6 H) 2.26-2.31 (m, 1 H) 2.46 (s, 3 H) 3.13-3.25 (m, 1 H) 3.52-3.55 (m, 1 H) 4.36-4.49 (m, 1 H) 4.58 (s, 2 H) 4.83-4.89 (m, 1 H) 6.15 (s, 1 H) 7.30 (s, 1 H) 7.39 (s, 1 H) 7.52-7.54 (d, J = 8.08 Hz, 1 H) 7.80 (s, 1 H) 8.19-8.22 (dd, J = 8.08, 2.02 Hz, 1 H) 8.99-9.00 (d, J = 1.77 Hz, 1 H) | 512.3 |
| 295 | 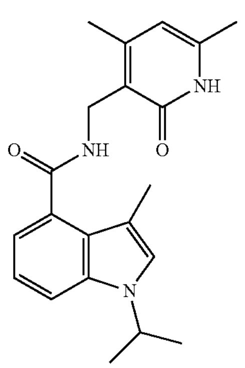 [SMILES: Cc1cc(C)c(CNC(=O)c2cccc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-1H-indole-4-carboxamide | 11.47 (s, 1 H) 7.99 (t, J = 5.05 Hz, 1 H) 7.49 (d, J = 8.08 Hz, 1 H) 7.28 (s, 1 H) 7.04-7.09 (m, 1 H) 6.92 (d, J = 6.32 Hz, 1 H) 5.87 (s, 1 H) 4.71 (quin, J = 6.63 Hz, 1 H) 4.33 (s, 1 H) 4.32 (s, 1 H) 2.23 (s, 3 H) 2.14 (s, 3 H) 2.11 (s, 3 H) 1.42 (s, 3 H) 1.40 (s, 3 H) | 352.2 |

Example 296

1-Cyclopropyl-N-[(4,6-dimethyl-2-oxo-1,2-dihydro-3-pyridinyl)methyl]-3-methyl-6-(methylsulfonyl)-1H-indole-4-carboxamide

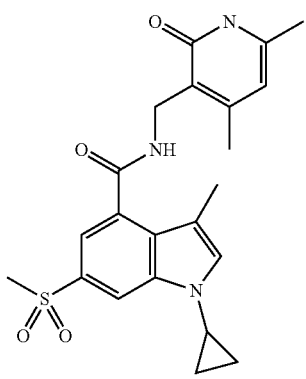

To a vial under a stream of N2 was added copper(II) trifluoromethanesulfonate (0.084 g, 0.233 mmol), sodium methanesulfinate (0.056 g, 0.467 mmol), DMSO (1.3 mL), and N,N-dimethyletylene diamine (0.053 mL, 0.490 mmol). The deep blue reaction was stirred for 5 min, then was added 6-bromo-1-cyclopropyl-N-[(4,6-dimethyl-2-oxo-1,2-dihydro-3-pyridinyl)methyl]-3-methyl-1H-indole-4-carboxamide (0.10 g, 0.233 mmol). The vial was sealed and heated at 120° C. for 3 h, at which time it was diluted with water (50 ml). The mixture was extracted with 30% THF/EtOAc (2×) (needed to warm to break up emulsion). Combined organics, dried over magnesium sulfate, filtered through Celite, and concentrated. Purification of the residue by column chromatography (12 gram Isco GOLD silica column; gradient B: 5-85%; A: dichloromethane, B: 10% (2 M ammonia in MeOH) in chloroform) provided 1-cyclopropyl-N-[(4,6-dimethyl-2-oxo-1,2-dihydro-3-pyridinyl)methyl]-3-methyl-6-(methylsulfonyl)-1H-indole-4-carboxamide (83 mg, 0.184 mmol, 79% yield) as a white solid. $^1$H NMR (400 MHz, DMSO-$d_6$) δ ppm 11.50 (s, 1H), 8.38 (t, J=5.1 Hz, 1H), 8.06 (d, J=1.8 Hz, 1H), 7.46 (dd, J=7.8, 1.3 Hz, 2H), 5.87 (s, 1H), 4.34 (d, J=5.1 Hz, 2H), 3.52 (tt, J=7.0, 3.6 Hz, 1H), 3.20 (s, 3H), 2.23 (s, 3H), 2.11 (s, 3H), 2.14 (s, 3H), 1.09 (m, 2H), 0.96 (m, 2H). MS (ES) [M+H]$^+$ 427.8.

Examples 297-302 were prepared by the methods described above for Example 296, or routine variations thereof, starting from the requisite 6-bromoindole:

| Ex | Structure | Name | $^1$H NMR (400 MHz, DMSO-$d_6$) δ ppm | MS(ES) [M + H]$^+$ |
| --- | --- | --- | --- | --- |
| 297 | 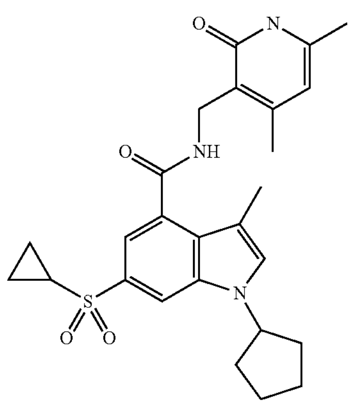 [SMILES: Cc1cc(C)c(CNC(=O)c2cc(S(=O)(=O)C3CC3)cc3c2c(C)cn3C2CCCC2)c(=O)[nH]1] | 1-cyclopentyl-6-(cyclopropylsulfonyl)-N-[(4,6-dimethyl-2-oxo-1,2-dihydro-3-pyridinyl)methyl]-3-methyl-1H-indole-4-carboxamide | 11.49 (s, 1 H), 8.39 (t, J = 4.9 Hz, 1 H), 8.04 (d, J = 1.5 Hz, 1 H), 7.61 (s, 1 H), 7.35 (d, J = 1.5 Hz, 1 H), 5.87 (s, 1 H), 5.03 (t, J = 6.9 Hz, 1 H), 4.34 (d, J = 4.8 Hz, 2 H), 2.85 (m, 1 H), 2.23 (s, 3 H), 2.14 (m, 8 H), 1.81 (m, 4 H), 1.74 (m, 2 H), 1.13 (m, 2 H), 1.00 (m, 2 H) | 481.9 |
| 298 | 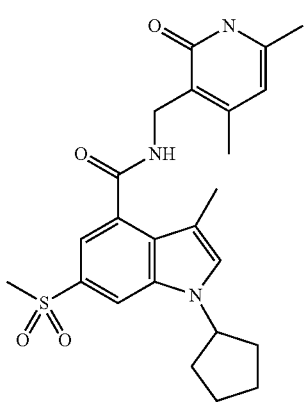 | 1-cyclopentyl-N-[(4,6-dimethyl-2-oxo-1,2-dihydro-3-pyridinyl)methyl]-3-methyl-6-(methylsulfonyl)-1H-indole-4-carboxamide | 11.50 (s, 1 H), 8.36 (t, J = 4.9 Hz, 1 H), 8.09 (d, J = 1.5 Hz, 1 H), 7.61 (s, 1 H), 7.40 (d, J = 1.5 Hz, 1 H), 5.87 (s, 1 H), 5.01 (t, J = 7.1 Hz, 1 H), 4.35 (d, J = 5.1 Hz, 2 H), 3.19 (s, 3 H), 2.23 (s, 3 H), 2.15 (m, 8 H), 1.78 (m, 6 H) | 455.9 |

-continued

| Ex | Structure | Name | ¹H NMR (400 MHz, DMSO-d₆) δ ppm | MS(ES) [M + H]⁺ |
|---|---|---|---|---|
| 299 | 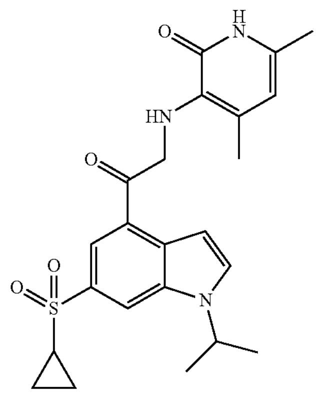 [SMILES: Cc1cc(C)c(NCC(=O)c2cc(S(=O)(=O)C3CC3)cc3c2ccn3C(C)C)c(=O)[nH]1] | 3-({2-[6-(cyclopropylsulfonyl)-3-methyl-1-(1-methylethyl)-1H-indol-4-yl]-2-oxoethyl}amino)-4,6-dimethyl-2(1H)-pyridinone | 0.93-1.06 (m, 2 H), 1.11-1.25 (m, 2 H), 1.49 (d, J = 6.57 Hz, 6 H), 2.13 (s, 3 H), 2.24 (s, 3 H), 2.81-2.98 (m, 1 H), 4.37 (d, J = 5.05 Hz, 2 H), 4.99 (dt, J = 13.33, 6.60 Hz, 1 H), 5.90 (s, 1 H), 6.99 (d, J = 3.28 Hz, 1 H), 7.85 (d, J = 1.52 Hz, 1 H), 7.93 (d, J = 3.28 Hz, 1 H), 8.16 (s, 1 H), 8.49 (t, J = 4.93 Hz, 1 H), 11.57 (br. s., 1 H) | 442.0 |
| 300 | 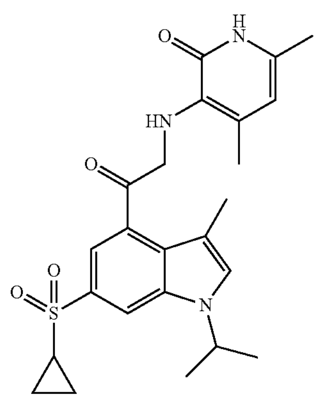 [SMILES: Cc1cc(C)c(NCC(=O)c2cc(S(=O)(=O)C3CC3)cc3c2c(C)cn3C(C)C)c(=O)[nH]1] | 3-({2-[6-(cyclopropylsulfonyl)-3-methyl-1-(1-methylethyl)-1H-indol-4-yl]-2-oxoethyl}amino)-4,6-dimethyl-2(1H)-pyridinone | 1.00 (dd, J = 7.71, 2.65 Hz, 2 H), 1.13 (dd, J = 4.67, 2.40 Hz, 2 H), 1.45 (d, J = 6.57 Hz, 6 H), 2.12 (s, 3 H), 2.19 (s, 3 H), 2.23 (s, 3 H), 2.76-2.95 (m, 1 H), 4.35 (d, J = 5.05 Hz, 2 H), 4.91 (quin, J = 6.63 Hz, 1 H), 5.88 (s, 1 H), 7.36 (d, J = 1.52 Hz, 1 H), 7.66 (s, 1 H), 8.03 (d, J = 1.52 Hz, 1 H), 8.40 (t, J = 4.93 Hz, 1 H), 11.51 (s, 1 H) | 455.9 |
| 301 | 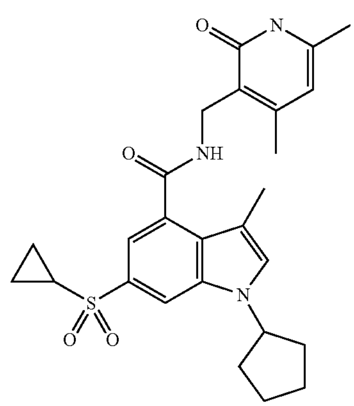 [SMILES: Cc1cc(C)c(CNC(=O)c2cc(S(=O)(=O)C3CC3)cc3c2c(C)cn3C2CCCC2)c(=O)[nH]1] | 1-cyclopentyl-6-(cyclopropylsulfonyl)-N-[(4,6-dimethyl-2-oxo-1,2-dihydro-3-pyridinyl)methyl]-3-methyl-1H-indole-4-carboxamide | 11.49 (s, 1 H), 8.39 (t, J = 4.9 Hz, 1 H), 8.04 (d, J = 1.5 Hz, 1 H), 7.61 (s, 1 H), 7.35 (d, J = 1.5 Hz, 1 H), 5.87 (s, 1 H), 5.03 (t, J = 6.9 Hz, 1 H), 4.34 (d, J = 4.8 Hz, 2 H), 2.85 (m, 1 H), 2.23 (s, 3 H), 2.14 (m, 8 H), 1.81 (m, 4 H), 1.74 (m, 2 H), 1.13 (m, 2 H), 1.00 (m, 2 H) | 481.9 |
| 302 | 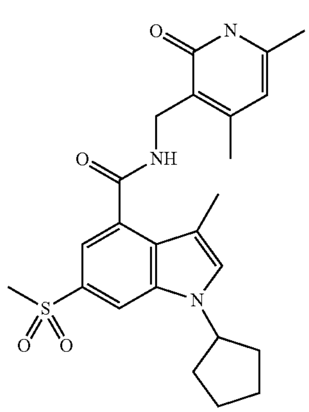 | 1-cyclopentyl-N-[(4,6-dimethyl-2-oxo-1,2-dihydro-3-pyridinyl)methyl]-3-methyl-6-(methylsulfonyl)-1H-indole-4-carboxamide | 11.50 (s, 1 H), 8.36 (t, J = 4.9 Hz, 1 H), 8.09 (d, J = 1.5 Hz, 1 H), 7.61 (s, 1 H), 7.40 (d, J = 1.5 Hz, 1 H), 5.87 (s, 1 H), 5.01 (t, J = 7.1 Hz, 1 H), 4.35 (d, J = 5.1 Hz, 2 H), 3.19 (s, 3 H), 2.23 (s, 3 H), 2.15 (m, 8 H), 1.78 (m, 6 H) | 455.9 |

Scheme 2

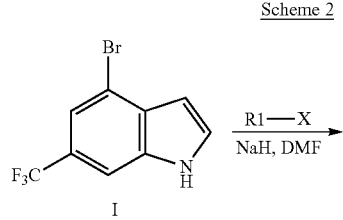
I

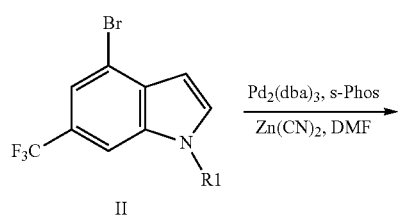
II

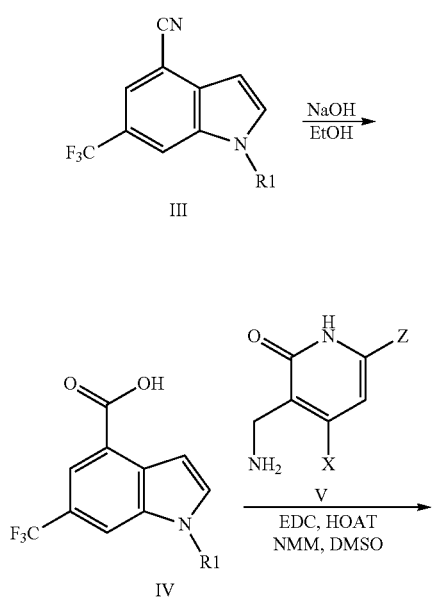
III

IV

V

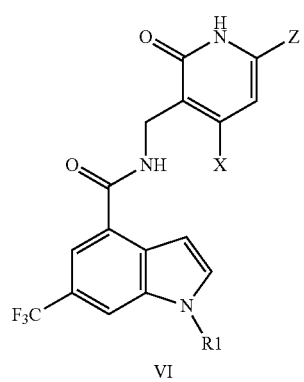
VI

Example 303

N-[(4,6-Dimethyl-2-oxo-1,2-dihydro-3-pyridinyl)methyl]-1-(1-methylethyl)-6-(trifluoromethyl)-1H-indole-4-carboxamide

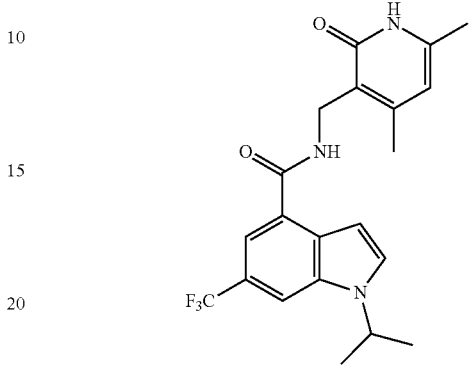

a) 4-Bromo-1-(1-methylethyl)-6-(trifluoromethyl)-1H-indole

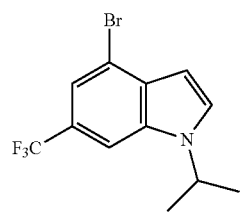 [SMILES: CC(C)n1ccc2c(Br)cc(C(F)(F)F)cc21]

To a solution of 4-bromo-6-(trifluoromethyl)-1H-indole (1 g, 3.79 mmol) in DMF (6 mL) was added 60% sodium hydride (0.182 g, 4.54 mmol), and the mixture was stirred for 30 min. 2-bromopropane (0.533 mL, 5.68 mmol) was added and the mixture was stirred overnight. The reaction was then quenched with 10% NaHCO3 and extracted with EtOAc (3×). The extract was dried over Na2SO4 and concentrated. The residue was purified using column chromatography (Silica gel, 0 to 100% EtOAc/hexanes) to give the title compound (460 mg, 40%) as white solid. $^1$H NMR (400 MHz, CHLOROFORM-d) δ ppm 1.56-1.61 (m, 6H), 4.66-4.79 (m, 1H), 6.65 (d, J=3.03 Hz, 1H), 7.27-7.31 (m, 1H), 7.45 (d, J=3.03 Hz, 1H), 7.54 (s, 1H), 7.63 (s, 1H). MS: (M+H)$^+$=306.2.

b) 1-Isopropyl-6-(trifluoromethyl)-1H-indole-4-carbonitrile

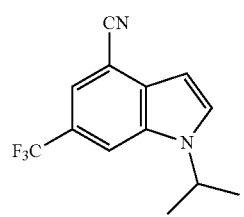 [SMILES: CC(C)n1ccc2c(C#N)cc(C(F)(F)F)cc21]

To a 10-mL microwave tube were added 4-bromo-1-(1-methylethyl)-6-(trifluoromethyl)-1H-indole (330 mg, 1.078 mmol), dicyanozinc (146 mg, 1.240 mmol), DMF (4 mL) and water (0.040 mL), and the mixture was degassed for 5 min by bubbling N₂. s-Phos (48.7 mg, 0.119 mmol) and tris(dibenzylideneacetone)dipalladium(0) (49.4 mg, 0.054 mmol) were added. The tube was sealed and the mixture was heated at 120° C. for 2.5 h. 1 N NaOH (3 mL) was added and the mixture was extracted with EtOAc (3×). The extract was dried over Na₂SO₄ and concentrated. The residue was purified using column chromatography (Silica gel, 0 to 70% EtOAc/hexanes) to give the title compound (210 mg, 77%) as white solid. ¹H NMR (400 MHz, CHLOROFORM-d) δ ppm 1.61 (m, 6H), 4.79 (spt, J=6.69 Hz, 1H), 6.84 (d, J=3.28 Hz, 1H), 7.59 (d, J=3.28 Hz, 1H), 7.73 (s, 1H), 7.88 (s, 1H). MS: (M+H)⁺=253.2.

c) 1-Isopropyl-6-(trifluoromethyl)-1H-indole-4-carboxylic acid

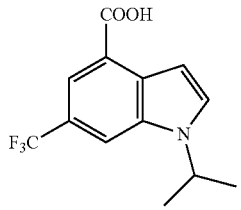 [SMILES: CC(C)n1ccc2c(C(=O)O)cc(C(F)(F)F)cc21]

To a solution of 1-(1-methylethyl)-6-(trifluoromethyl)-1H-indole-4-carbonitrile (180 mg, 0.714 mmol) in ethanol (5 mL) was added 10% sodium hydroxide (5 mL, 0.714 mmol), and the mixture was heated at reflux overnight. The mixture was concentrated to remove EtOH and the aqueous phase was acidified using 1N HCl to ~pH 4. The precipitate was collected by filtration and dried under high vacuum to give the title compound (167 mg, 86%) as brown solid. ¹H NMR (400 MHz, DMSO-d₆) δ ppm 1.43-1.60 (m, 6H), 4.96-5.13 (m, 1H), 7.11 (d, J=3.28 Hz, 1H), 7.89-8.05 (m, 2H), 8.25 (s, 1H), 13.15 (br. s., 1H). MS: (M+H)⁺=272.0.

d) N-((4,6-Dimethyl-2-oxo-1,2-dihydropyridin-3-yl)methyl)-1-isopropyl-6-(trifluoromethyl)-1H-indole-4-carboxamide

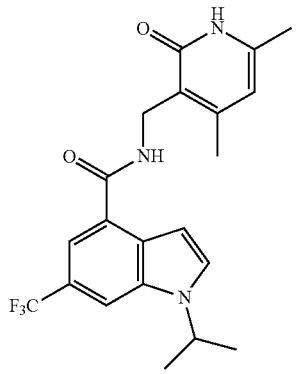 [SMILES: Cc1cc(C)c(CNC(=O)c2cc(C(F)(F)F)cc3c2ccn3C(C)C)c(=O)[nH]1]

To a solution of 1-(1-methylethyl)-6-(trifluoromethyl)-1H-indole-4-carboxylic acid (40 mg, 0.147 mmol) in dimethyl sulfoxide (1 mL) were added 3-(aminomethyl)-4,6-dimethyl-2(1H)-pyridinone (41.7 mg, 0.221 mmol), N-methylmorpholine (0.065 mL, 0.590 mmol), 1-hydroxy-7-azabenzotriazole (40.1 mg, 0.295 mmol) and EDC (56.5 mg, 0.295 mmol), and the mixture was stirred overnight. The mixture was quenched with water (5 mL) and stirred for 10 min. The precipitate was collected by filtration and dried under high vacuum to give the title compound (39 mg, 63%) as an off-white solid. ¹H NMR (400 MHz, DMSO-d₆) δ ppm 1.47 (m, 6H), 2.13 (s, 3H), 2.23 (s, 3H), 4.36 (d, J=5.05 Hz, 2H), 4.99 (dt, J=13.20, 6.66 Hz, 1H), 5.89 (s, 1H), 6.98 (d, J=3.03 Hz, 1H), 7.68 (s, 1H), 7.86 (d, J=3.28 Hz, 1H), 8.08 (s, 1H), 8.45 (t, J=4.93 Hz, 1H), 11.56 (s, 1H). MS: (M+H)⁺=406.1.

Example 304

1-Isopropyl-N-((6-methyl-2-oxo-4-propyl-1,2-dihydropyridin-3-yl)methyl)-6-(trifluoromethyl)-1H-indole-4-carboxamide

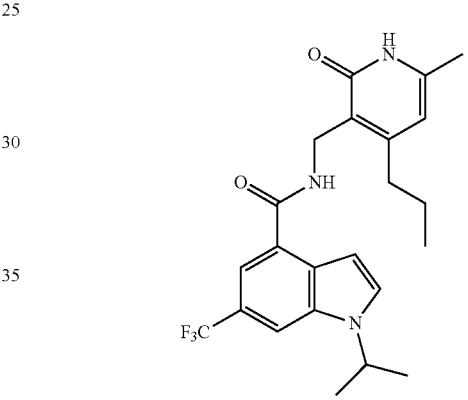

The title compound was prepared using procedures as described for N-((4,6-dimethyl-2-oxo-1,2-dihydropyridin-3-yl)methyl)-1-isopropyl-6-(trifluoromethyl)-1H-indole-4-carboxamide. ¹H NMR (400 MHz, DMSO-d₆) δ ppm 0.91 (t, J=8.00 Hz 3H), 1.39-1.63 (m, 8H), 2.14 (s, 3H), 4.39 (d, J=5.05 Hz, 2H), 4.99 (dt, J=13.26, 6.76 Hz, 1H), 5.92 (s, 1H), 6.98 (d, J=3.28 Hz, 1H), 7.68 (s, 1H), 7.87 (d, J=3.03 Hz, 1H), 8.08 (s, 1H), 8.44 (t, J=5.05 Hz, 1H), 11.57 (s, 1H). MS: (M+H)⁺=434.1.

Scheme 3

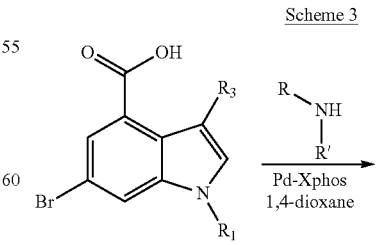

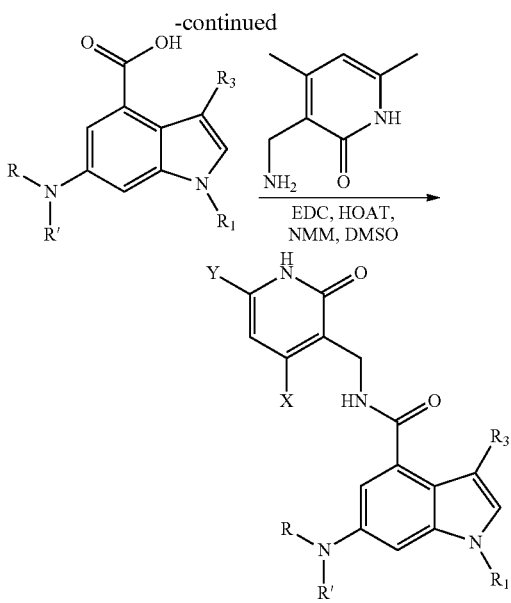

Example 305

N-((4,6-dimethyl-2-oxo-1,2-dihydropyridin-3-yl)methyl)-6-(4-((dimethylamino)methyl)piperidin-1-yl)-1-isopropyl-3-methyl-1H-indole-4-carboxamide

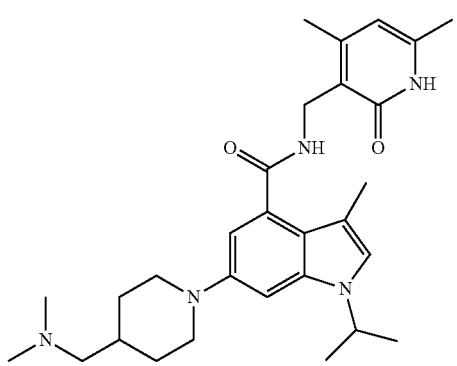

a) 6-(4-((Dimethylamino)methyl)piperidin-1-yl)-1-isopropyl-3-methyl-1H-indole-4

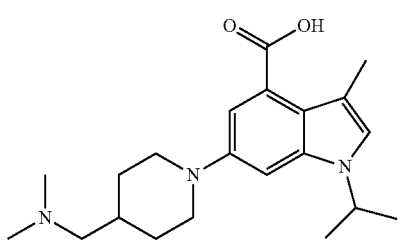 [SMILES: Cc1cn(C(C)C)c2cc(N3CCC(CN(C)C)CC3)cc(C(=O)O)c12]

To a 10-mL microwave tube were added 6-bromo-3-methyl-1-(1-methylethyl)-1H-indole-4-carboxylic acid (100 mg, 0.338 mmol), 1,4-dioxane (2 mL), N,N-dimethyl-1-(4-piperidinyl)methanamine (52.8 mg, 0.371 mmol) and sodium tert-butoxide (71.4 mg, 0.743 mmol), and the mixture was degassed for 5 min. Choro(2-dicyclohexylphosphino-2',4',6'-tri-1-propyl-1,1'-biphenyl)[2-(2-aminoethyl)phenyl]Pd(11) Me-t-butylether adduct (13.96 mg, 0.017 mmol) was added and the tube was sealed. The mixture was stirred at 98° C. with stirring for 20 h. The mixture was then concentrated and the residue was purified using reverse-phase HPLC (Gemini 5u C18(2) 100A, AXIA; 30×100 mm 5 micron; (30 mL/min, 7% ACN/H$_2$O, 0.1% formic acid to 37% ACN/H$_2$O, 0.1% formic acid) to give the title compound (65 mg, 54%) as pale yellow solid. $^1$H NMR (400 MHz, DMSO-d$_6$) δ ppm 1.19-1.34 (m, 2H), 1.39 (d, J=6.57 Hz, 6H), 1.58-1.71 (m, 1H), 1.82 (d, J=11.87 Hz, 2H), 2.23-2.31 (m, 10H), 2.66 (td, J=11.94, 1.89 Hz, 2H), 3.57-3.71 (m, 2H), 4.70 (quin, J=6.63 Hz, 1H), 7.09 (d, J=2.02 Hz, 1H), 7.15 (dd, J=9.60, 1.52 Hz, 2H). MS: (M+H)$^+$=358.2.

b) N-((4,6-Dimethyl-2-oxo-1,2-dihydropyridin-3-yl)methyl)-6-(4-((dimethylamino)methyl)piperidin-1-yl)-1-isopropyl-3-methyl-1H-indole-4-carboxamide

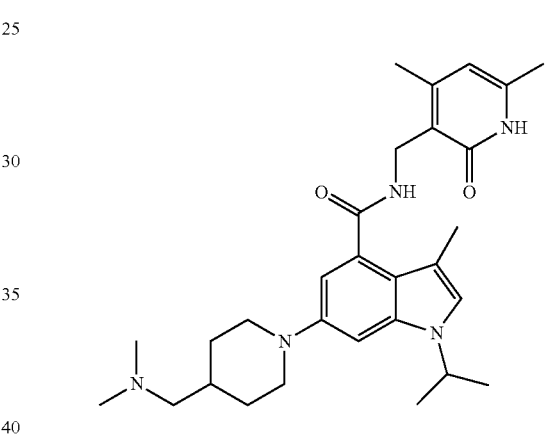

To a solution of 6-{4-[(dimethylamino)methyl]-1-piperidinyl}-3-methyl-1-(1-methylethyl)-1H-indole-4-carboxylic acid (62 mg, 0.173 mmol) in dimethyl sulfoxide (1 mL) were added 3-(aminomethyl)-4,6-dimethyl-2(1H)-pyridinone (42.5 mg, 0.225 mmol), N-methylmorpholine (0.095 mL, 0.867 mmol), 1-hydroxy-7-azabenzotriazole (47.2 mg, 0.347 mmol) and EDC (66.5 mg, 0.347 mmol), and the mixture was stirred overnight. The mixture was purified using reverse-phase HPLC (Gemini 5u C18(2) 100A, AXIA; 30×100 mm 5 micron; 30 mL/min, 8% ACN/H$_2$O, 0.1% formic acid to 38% ACN/H$_2$O, 0.1% formic acid) to give the title compound (52 mg, 55%) as an off-white solid. $^1$H NMR (400 MHz, DMSO-d$_6$) ppm 1.26 (m, 2H), 1.35-1.41 (m, 6H), 1.57-1.71 (m, 1H), 1.80 (d, J=11.12 Hz, 2H), 2.10 (d, J=10.36 Hz, 6H), 2.22 (s, 3H), 2.26-2.33 (m, 8H), 2.57-2.72 (m, 2H), 3.61 (d, J=12.13 Hz, 2H), 4.31 (d, J=5.05 Hz, 2H), 4.58-4.72 (m, 1H), 5.86 (s, 1H), 6.69 (d, J=2.02 Hz, 1H), 6.92 (d, J=1.77 Hz, 1H), 7.05 (d, J=1.01 Hz, 1H), 7.92-7.99 (m, 1H). MS: (M+H)$^+$=492.1.

Examples 306-317 were prepared by the methods described above for Example 305, or routine variations thereof, using the requisite amine:

| Ex | Structure | Name | ¹H NMR (400 MHz, DMSO-d₆) δ ppm | MS(ES) [M + H]⁺ |
|---|---|---|---|---|
| 306 | 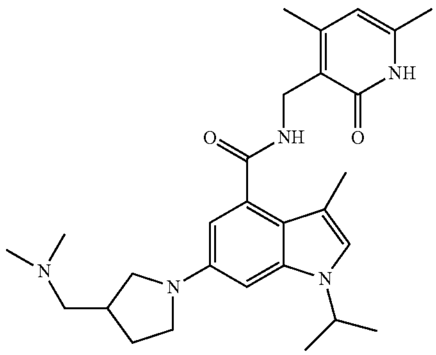 | N-((4,6-dimethyl-2-oxo-1,2-dihydropyridin-3-yl)methyl)-6-(3-((dimethylamino)methyl)pyrrolidin-1-yl)-1-isopropyl-3-methyl-1H-indole-4-carboxamide | 1.36 (m, 6 H), 1.68 (dd, J = 12.13, 7.58 Hz, 1 H), 2.01-2.38 (m, 20 H), 2.99 (dd, J = 9.09, 6.57 Hz, 1 H), 3.20-3.30 (m, 1 H), 3.35-3.44 (m, 1 H), 4.31 (d, J = 5.05 Hz, 2 H), 4.53-4.67 (m, 1 H), 5.87 (s, 1 H), 6.35 (d, J = 2.02 Hz, 1 H), 6.45 (d, J = 1.77 Hz, 1 H), 6.93 (d, J = 1.01 Hz, 1 H), 7.88 (t, J = 5.18 Hz, 1 H), 11.47 (s, 1 H) | 478.0 |
| 307 | 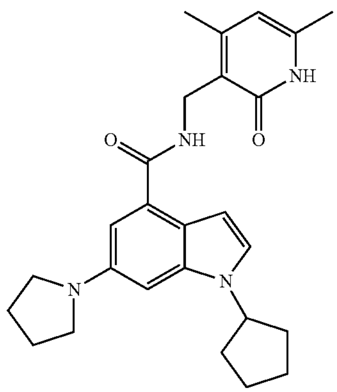 [SMILES: Cc1cc(C)c(CNC(=O)c2cc(N3CCCC3)cc3c2ccn3C2CCCC2)c(=O)[nH]1] | 1-cyclopentyl-N-((4,6-dimethyl-2-oxo-1,2-dihydropyridin-3-yl)methyl)-6-(pyrrolidin-1-yl)-1H-indole-4-carboxamide | 1.65-1.88 (m, 7 H), 1.95-2.02 (m, 5 H), 2.08-2.18 (m, 6 H), 2.24 (s, 3 H), 3.29 (t, J = 6.32 Hz, 4 H), 4.34 (d, J = 5.31 Hz, 2 H), 4.74-4.90 (m, 1 H), 5.89 (s, 1 H), 6.59-6.70 (m, 2 H), 6.83 (d, J = 1.77 Hz, 1 H), 7.22 (d, J = 3.28 Hz, 1 H), 8.03 (t, J = 5.31 Hz, 1 H) | 433.2 |
| 308 | 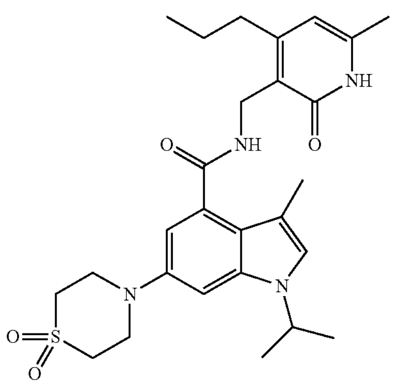 [SMILES: CCCc1cc(C)[nH]c(=O)c1CNC(=O)c1cc(N2CCS(=O)(=O)CC2)cc2c1c(C)cn2C(C)C] | 6-(1,1-dioxidothiomorpholino)-1-isopropyl-3-methyl-N-((6-methyl-2-oxo-4-propyl-1,2-dihydropyridin-3-yl)methyl)-1H-indole-4-carboxamide | 1.06 (m, 3 H), 1.43-1.54 (m, 6 H), 1.68 (sxt, J = 7.58 Hz, 2 H), 2.19 (s, 3 H), 2.27 (s, 3 H), 2.69-2.82 (m, 2 H), 3.17-3.26 (m, 4 H), 3.76-3.86 (m, 4 H), 4.52-4.58 (m, 2 H), 4.69 (dt, J = 13.39, 6.69 Hz, 1 H), 6.11-6.21 (m, 1 H), 6.88 (d, J = 2.02 Hz, 1 H), 7.09 (dd, J = 11.75, 1.64 Hz, 2H) | 513.2 |
| 309 | 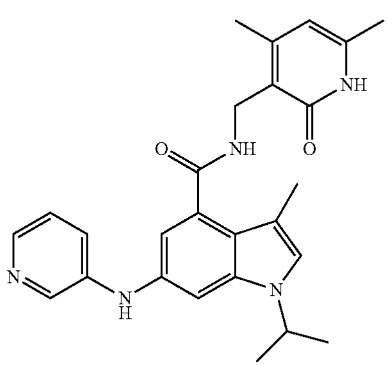 [SMILES: Cc1cc(C)c(CNC(=O)c2cc(Nc3cccnc3)cc3c2c(C)cn3C(C)C)c(=O)[nH]1] | N-((4,6-dimethyl-2-oxo-1,2-dihydropyridin-3-yl)methyl)-1-isopropyl-3-methyl-6-(pyridin-3-ylamino)-1H-indole-4-carboxamide | 1.39 (m, 6 H), 2.11 (d, J = 3.28 Hz, 6 H), 2.22 (s, 3 H), 4.32 (d, J = 4.80 Hz, 2 H), 4.59 (dt, J = 13.14, 6.57 Hz, 1 H), 5.86 (s, 1 H), 6.76 (d, J = 1.26 Hz, 1 H), 7.12-7.25 (m, 3 H), 7.41 (d, J = 8.34 Hz, 1 H), 7.95 (d, J = 3.54 Hz, 1 H), 8.10 (t, J = 4.80 Hz, 1 H), 8.25 (s, 1 H), 8.30-8.39 (m, 1 H), 11.47 (br. s., 1 H) | 444.1 |

| Ex | Name | ¹H NMR (400 MHz, DMSO-d₆) δ ppm | MS(ES) [M + H]⁺ |
|---|---|---|---|
| 310 | N-((4,6-dimethyl-2-oxo-1,2-dihydropyridin-3-yl)methyl)-6-(4-(4-fluorophenyl)piperidin-1-yl)-1-isopropyl-3-methyl-1H-indole-4-carboxamide | 11.48 (s, 1H), 8.01 (br. s., 1H), 6.48-7.39 (m, 6H), 5.87 (s, 1H), 4.68 (dt, J = 6.09, 12.32 Hz, 1H), 4.33 (d, J = 5.05 Hz, 2H), 3.74 (d, J = 12.13 Hz, 2H), 2.23 (s, 3H), 2.11 (s, 6H), 1.89 (br. s., 3H), 1.39 (d, J = 6.32 Hz, 6H) | 528.9 |
| 311 | N-((4,6-dimethyl-2-oxo-1,2-dihydropyridin-3-yl)methyl)-1-isopropyl-3-methyl-6-(4-(4-methylpiperazin-1-yl)piperidin-1-yl)-1H-indole-4-carboxamide | 7.97 (br. s., 1H), 7.05 (s, 1H), 6.92 (d, J = 1.77 Hz, 1H), 6.68 (d, J = 2.02 Hz, 1H), 5.86 (s, 1H), 4.60-4.69 (m, J = 6.44, 6.44 Hz, 1H), 4.31 (d, J = 4.80 Hz, 2H), 3.65 (d, J = 11.37 Hz, 2H), 3.25-3.32 (m, 4H), 2.68 (ddd, J = 1.89, 2.02, 3.66 Hz, 2H), 2.62 (dd, J = 1.14, 11.24 Hz, 2H), 2.33 (dt, J = 1.77, 3.54 Hz, 1H), 2.22 (s, 3H), 2.14 (s, 3H), 2.11 (s, 5H), 2.08 (s, 4H), 1.80-1.91 (m, J = 10.36 Hz, 2H), 1.55 (br. s., 1H), 1.37 (d, J = 6.57 Hz, 6H) | 533.0 |
| 312 | N-((4,6-dimethyl-2-oxo-1,2-dihydropyridin-3-yl)methyl)-1-isopropyl-3-methyl-6-(4-(1-methylpiperidin-4-yl)piperazin-1-yl)-1H-indole-4-carboxamide | 7.04 (s, 1H), 7.00 (d, J = 1.77 Hz, 1H), 6.87 (d, J = 2.02 Hz, 1H), 6.13 (s, 1H), 4.66 (quin, J = 6.69 Hz, 1H), 4.54 (s, 2H), 3.18-3.29 (m, 4H), 3.11-3.18 (m, 1H), 2.98 (d, J = 11.87 Hz, 2H), 2.76-2.85 (m, 4H), 2.43 (s, 3H), 2.27-2.35 (m, 5H), 2.26 (s, 3H), 2.17 (s, 3H), 2.04-2.14 (m, 2H), 1.93-2.02 (m, 2H), 1.54-1.72 (m, 2H), 1.45 (d, J = 6.57 Hz, 6H) | 533.0 |

| Ex | Structure | Name | ¹H NMR (400 MHz, DMSO-d₆) δ ppm | MS(ES) [M + H]⁺ |
|---|---|---|---|---|
| 313 | 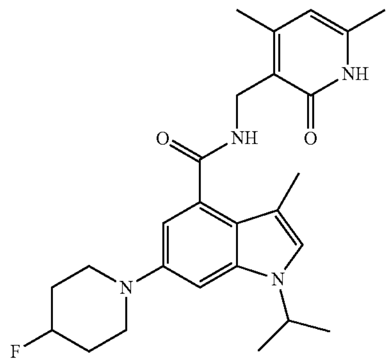 [SMILES: Cc1cc(C)c(CNC(=O)c2cc(N3CCC(F)CC3)cc3c2c(C)cn3C(C)C)c(=O)[nH]1] | N-((4,6-dimethyl-2-oxo-1,2-dihydropyridin-3-yl)methyl)-6-(4-fluoropiperidin-1-yl)-1-isopropyl-3-methyl-1H-indole-4-carboxamide | 7.01-7.06 (m, 2H), 6.88 (d, J = 2.02 Hz, 1H), 6.14 (s, 1H), 4.81-4.88 (m, 1H), 4.59-4.71 (m, 1H), 4.54 (s, 2H), 3.09-3.19 (m, 2H), 2.44 (s, 3H), 2.26 (s, 3H), 2.17 (s, 3H), 1.88-2.15 (m, 4H), 1.46 (d, J = 6.82 Hz, 6H) | 452.8 |
| 314 | 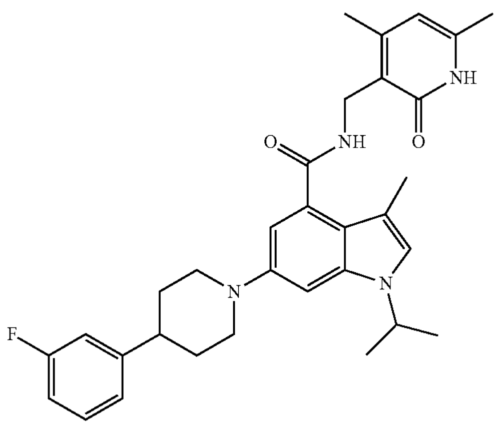 [SMILES: Cc1cc(C)c(CNC(=O)c2cc(N3CCC(c4cccc(F)c4)CC3)cc3c2c(C)cn3C(C)C)c(=O)[nH]1] | N-((4,6-dimethyl-2-oxo-1,2-dihydropyridin-3-yl)methyl)-6-(4-(3-fluorophenyl)piperidin-1-yl)-1-isopropyl-3-methyl-1H-indole-4-carboxamide | 8.01 (t, 1H), 7.36 (td, J = 6.32, 7.96 Hz, 1H), 7.12-7.19 (m, 2H), 7.07 (d, J = 1.01 Hz, 1H), 7.00-7.06 (m, 1H), 6.98 (d, J = 1.77 Hz, 1H), 6.74 (d, J = 2.02 Hz, 1H), 5.87 (s, 1H), 4.68 (quin, J = 6.57 Hz, 1H), 4.32 (d, J = 5.05 Hz, 2H), 3.75 (d, J = 11.87 Hz, 2H), 2.65-2.82 (m, 3H), 2.23 (s, 3H), 2.10 (d, J = 4.04 Hz, 6H), 1.75-1.96 (m, 4H), 1.38 (d, J = 6.57 Hz, 6H) | 529.0 |
| 315 | 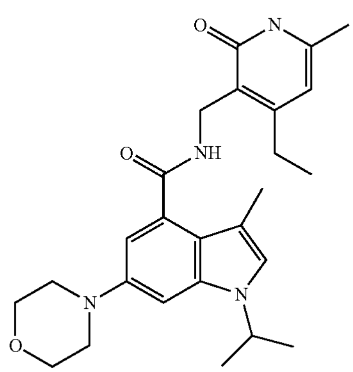 [SMILES: CCc1cc(C)[nH]c(=O)c1CNC(=O)c1cc(N2CCOCC2)cc2c1c(C)cn2C(C)C] | N-[(4-ethyl-6-methyl-2-oxo-1,2-dihydro-3-pyridinyl)methyl]-3-methyl-1-(1-methylethyl)-6-(4-morpholinyl)-1H-indole-4-carboxamide | 11.43 (br. s., 1 H) 7.96 (t, J = 5.05 Hz, 1 H) 7.08 (d, J = 1.01 Hz, 1 H) 6.95 (d, J = 2.02 Hz, 1 H) 6.70 (d, J = 2.02 Hz, 1 H) 5.91 (s, 1 H) 4.67 (quin, J = 6.63 Hz, 1 H) 4.34 (s, 1 H) 4.32 (s, 1 H) 3.74-3.77 (m, 4 H) 3.07-3.11 (m, 4 H) 2.54-2.60 (m, 2 H) 2.13 (s, 3 H) 2.09 (s, 3 H) 1.38 (s, 3 H) 1.37 (s, 3 H) 1.13 (t, J = 7.58 Hz, 3 H) | 451.0 |
| 316 | 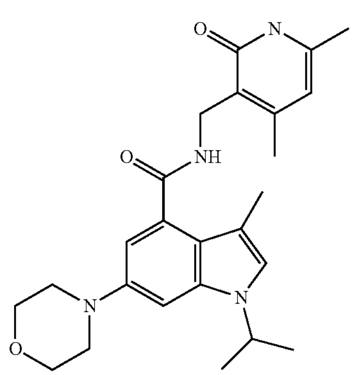 [SMILES: Cc1cc(C)c(CNC(=O)c2cc(N3CCOCC3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(4-morpholinyl)-1H-indole-4-carboxamide | 11.34 (br. s., 1 H) 7.99 (t, J = 4.93 Hz, 1 H) 7.08 (s, 1 H) 6.94 (d, J = 2.02 Hz, 1 H) 6.70 (d, J = 1.77 Hz, 1 H) 5.86 (s, 1 H) 4.67 (quin, J = 6.57 Hz, 1 H) 4.32 (s, 1 H) 4.30 (s, 1 H) 3.72-3.80 (m, 4 H) 3.06-3.13 (m, 4 H) 2.22 (s, 3 H) 2.11 (s, 3 H) 2.09 (s, 3 H) 1.38 (s, 3 H) 1.37 (s, 3 H) | 437.1 |

| Ex | Structure | Name | $^1$H NMR (400 MHz, DMSO-$d_6$) δ ppm | MS(ES) [M + H]$^+$ |
|---|---|---|---|---|
| 317 | 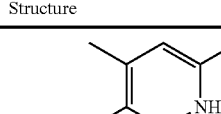 | N-[(4,6-dimethyl-2-oxo-1,2-dihydro-3-pyridinyl)methyl]-3-methyl-1-(1-methylethyl)-6-{[3-methyl-1-(1-methylethyl)-1H-pyrazol-5-yl]amino}-1H-indole-4-carboxamide | 1.30 (m, 6 H), 1.35 (d, J = 6.82 Hz, 6 H), 2.08 (s, 3 H), 2.11 (s, 3 H), 2.13 (s, 3 H), 2.21 (s, 3 H), 4.31 (d, J = 5.05 Hz, 2 H), 4.37-4.49 (m, 2 H), 5.70-5.77 (m, 1 H), 5.86 (s, 1 H), 6.60 (d, J = 1.77 Hz, 1 H), 6.71 (d, J = 1.77 Hz, 1 H), 6.99-7.07 (m, 1 H), 7.67 (s, 1 H), 7.93-8.03 (m, 1 H), 11.46 (br. s., 1 H) | 489.0 |

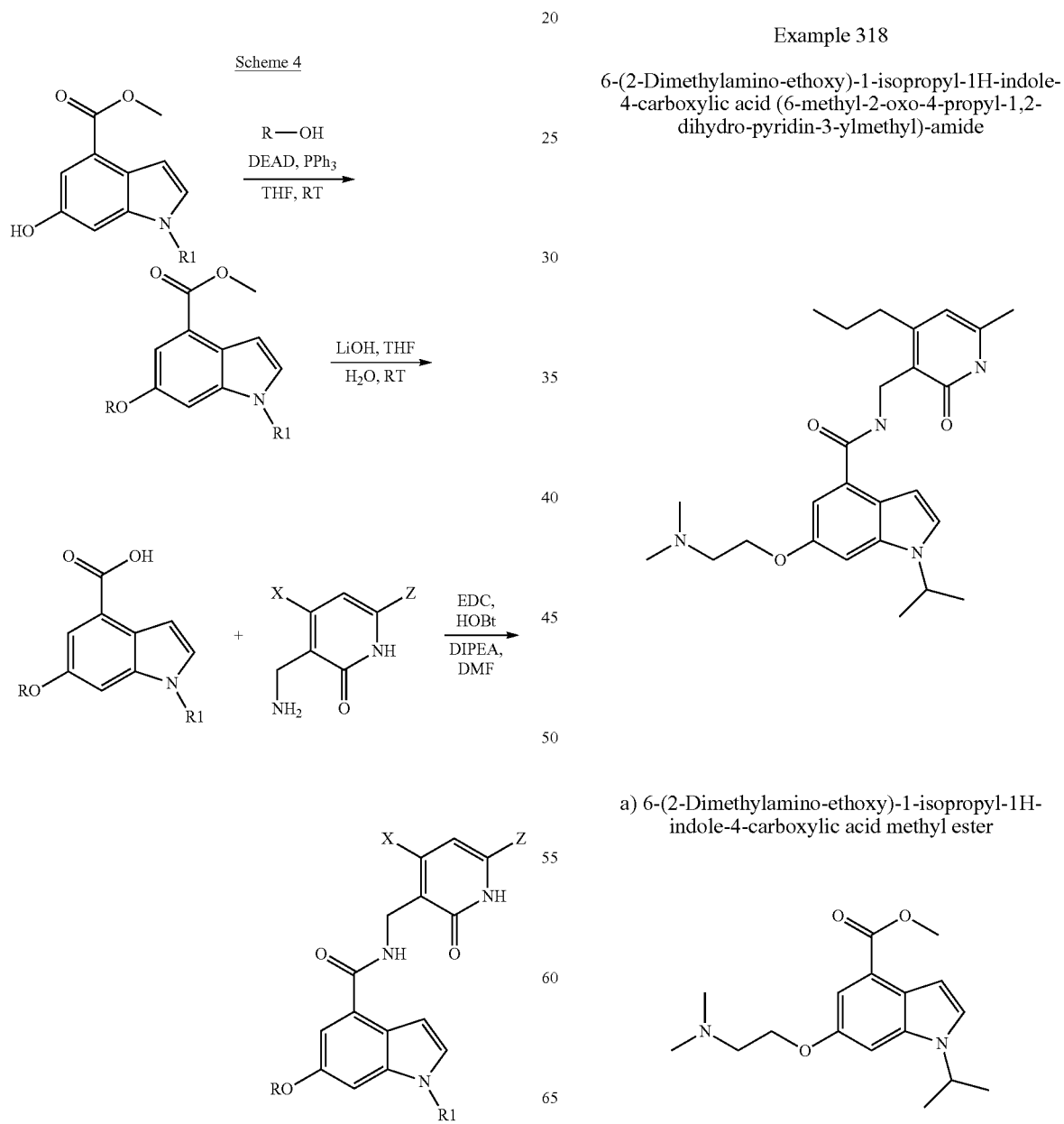

Example 318

6-(2-Dimethylamino-ethoxy)-1-isopropyl-1H-indole-4-carboxylic acid (6-methyl-2-oxo-4-propyl-1,2-dihydro-pyridin-3-ylmethyl)-amide a) 6-(2-Dimethylamino-ethoxy)-1-isopropyl-1H-indole-4-carboxylic acid methyl ester To a cooled (0° C.) mixture of 6-hydroxy-1-isopropyl-1H-indole-4-carboxylic acid methyl ester (700 mg, 3 mmol), 2-dimethylamino-ethanol (320 mg, 3.60 mmol) and PPh₃ (948 mg, 3.60 mmol) in THF (10 mL) was added DEAD (620 mg, 3.60 mmol) and stirred for 16 h at RT. Reaction mixture was concentrated under reduced pressure and the residue was purified by column chromatography by eluting with 2% MeOH in chloroform to afford the title compound (550 mg, 60%) as colorless gum. LCMS (ES+): m/z=305.36 [M+H].

b) 6-(2-Dimethylamino-ethoxy)-1-isopropyl-1H-indole-4-carboxylic acid

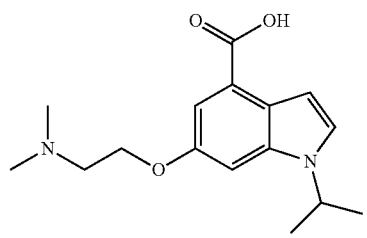

To a solution of 6-(2-dimethylamino-ethoxy)-1-isopropyl-1H-indole-4-carboxylic acid methyl ester (500 mg, 1.64 mmol) in THF (5 mL) was added LiOH.H₂O (200 mg, 4.93 mmol) in water (5 mL). The reaction was heated at reflux for 5 h, at which time the THF was removed under reduced pressure. The remaining mixture was acidified with 1 N HCl (pH ~6) and extracted with 10% MeOH in chloroform (4×30 mL). The combined organic layer was dried over anhydrous Na₂SO₄ and concentrated to yield 6-(2-dimethylamino-ethoxy)-1-isopropyl-1H-indole-4-carboxylic acid (400 mg), which was used in the next stage without further purification. LCMS (ES+): m/z=291.30 [M+H].

c) 6-(2-Dimethylamino-ethoxy)-1-isopropyl-1H-indole-4-carboxylic acid (6-methyl-2-oxo-4-propyl-1,2-dihydro-pyridin-3-ylmethyl)-amide

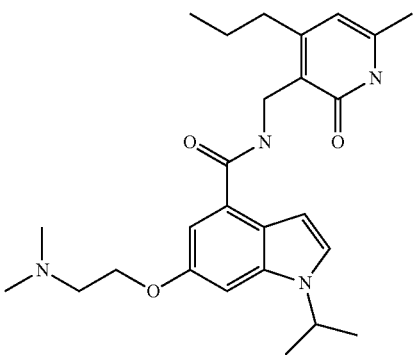

To a cooled (0° C.) mixture of 6-(2-dimethylamino-ethoxy)-1-isopropyl-1H-indole-4-carboxylic acid (400 mg, 1.37 mmol) in DMF (10 mL) was added EDC.HCl (310 mg, 1.65 mmol) and HOBt.H₂O (250 mg, 1.65 mmol). The reaction was stirred for 15 min, then DIPEA (1.2 mL, 6.89 mmol) and 3-aminomethyl-6-methyl-4-propyl-1H-pyridin-2-one (240 mg, 1.37 mmol) were added. The reaction was allowed to warm to RT and stirred for 16 h, at which time it was diluted with water (20 mL) and extracted with DCM (2×15 mL). The combined DCM layer was dried over Na₂SO₄ and concentrated. The residue was purified by flash column chromatography eluting with 3% MeOH in chloroform and then further purified by preparative HPLC to furnish 6-(2-dimethylamino-ethoxy)-1-isopropyl-1H-indole-4-carboxylic acid (6-methyl-2-oxo-4-propyl-1,2-dihydro-pyridin-3-ylmethyl)-amide (120 mg, 19%) as an off white solid. $^1$H NMR (400 MHz, DMSO-d₆): δ 0.92-0.88 (t, 3H), 1.43-1.41 (d, J=6.8 Hz, 6H), 1.56 (m, 2H), 2.12 (s, 3H), 2.22 (s, 6H), 2.55-2.53 (m, 2H), 2.06 (m, 2H), 4.11-4.09 (t, 2H), 4.36-4.34 (d, J=4.8 Hz, 2H), 4.76-4.73 (m, 1H), 5.90 (s, 1H), 6.74-6.73 (d, J=2.8 Hz, 1H), 7.04 (s, 1H), 7.20 (s, 1H), 7.43-7.42 (d, J=3.2 Hz, 1H), 8.10-8.07 (bs, 1H), 11.55 (bs, 1H). LCMS (ES+): m/z=453.23 [M+H].

Examples 319-320 were prepared by the methods described above for Example 318, or routine variations thereof, using the requisite alcohol (Mitsunobu reaction) and aminomethylpyridone:

| Ex | Structure | Name | $^1$H NMR (400 MHz, DMSO-d₆) δ ppm | MS(ES) [M + H]⁺ |
|---|---|---|---|---|
| 319 | 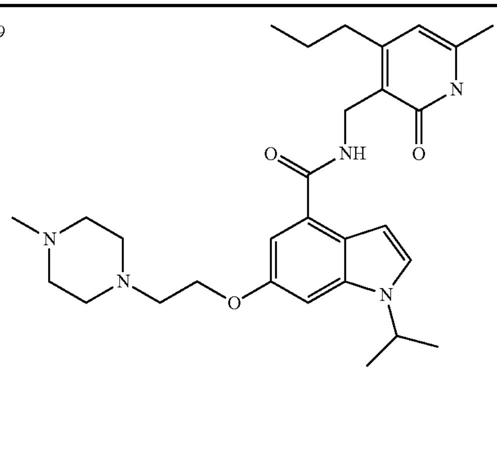 | 1-isopropyl-6-[2-(4-methyl-piperazin-1-yl)-ethoxy]-1H-indole-4-carboxylic acid (6-methyl-2-oxo-4-propyl-1,2-dihydro-pyridin-3-ylmethyl)-amide | 0.92 (t, 3H), 1.42 (d, J = 6.8 Hz, 6H), 1.57 (m, 2H), 2.14 (d, 6H), 2.32 (m, 8H), 2.54 (m, 2H), 2.71 (t, 2H), 4.13-4.11 (m, 2H), 4.35 (d, J = 5.2 Hz, 2H), 4.78-4.72 (m, 1H), 5.90 (s, 1H), 6.74 (d, J = 3.2 Hz, 1H), 7.05 (s, 1 H), 7.22 (s, 1H), 7.42 (d, J = 3.2 Hz, 1H), 8.12 (t, 1H), 11.55 (bs, 1H) | 506.26 |

| Ex | Structure | Name | $^1$H NMR (400 MHz, DMSO-$d_6$) δ ppm | MS(ES) [M + H]$^+$ |
|---|---|---|---|---|
| 320 | 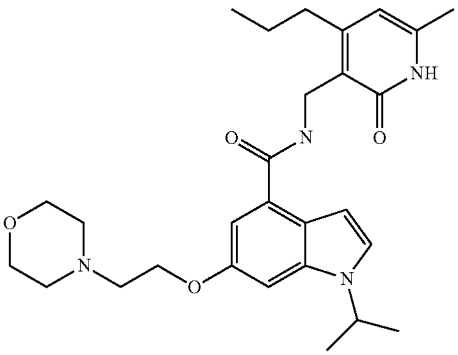 [SMILES: CCCc1cc(C)[nH]c(=O)c1CNC(=O)c1cc(OCCN2CCOCC2)cc2c1ccn2C(C)C] | 1-isopropyl-6-(2-morpholin-4-yl-ethoxy)-1H-indole-4-carboxylic acid (6-methyl-2-oxo-4-propyl-1,2-dihydro-pyridin-3-ylmethyl)-amide | 0.94 (t, 3H), 1.42 (d, J = 6.8 Hz, 6H), 1.57 (m, 2H), 2.14 (s, 3H), 2.46-2.50 (m, 4H), 2.75 (t, 2H), 2.68-2.75 (t, 4H), 4.15-4.19 (m, 2H), 4.35 (d, 2H), 4.78-4.72 (m, 1H), 5.91 (s, 1H), 6.73 (d, 1H), 7.10 (s, 1H), 7.25 (s, 1H), 7.62 (d, 1H), 8.12 (t, 1H), 11.55 (bs, 1H) | 495.22 |

Example 321

1-Isopropyl-6-(2-piperazin-1-yl-ethoxy)-1H-indole-4-carboxylic acid (6-methyl-2-oxo-4-propyl-1,2-dihydro-pyridin-3-ylmethyl)-amide

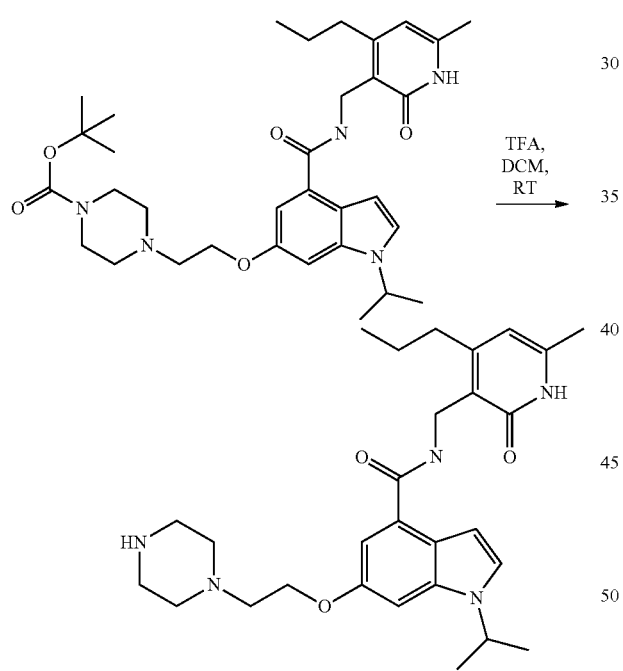

To a stirred solution of 4-(2-{1-isopropyl-4-[(6-methyl-2-oxo-4-propyl-1,2-dihydro-pyridin-3-ylmethyl)-carbamoyl]-1H-indol-6-yloxy}-ethyl)-piperazine-1-carboxylic acid tert-butyl ester (280 mg, 0.472 mmol; prepared following the procedure of Example xx) in dichloromethane (15 mL) was added TFA (1.5 mL) at room temperature and then stirred for 3 h at room temperature. Reaction mixture was concentrated under reduced pressure, diluted with water (20 mL) and washed the resulting aqueous layer with diethyl ether (2×15 mL). The aqueous layer was basified with (pH ~8) with saturated aqueous NaHCO$_3$ solution and extracted with dichloromethane (3×20 mL). The combined organic layer was washed with brine solution (2×25 mL) and concentrated.

Purification by preparative HPLC afforded 1-isopropyl-6-(2-piperazin-1-yl-ethoxy)-1H-indole-4-carboxylic acid (6-methyl-2-oxo-4-propyl-1,2-dihydro-pyridin-3-ylmethyl)-amide (48 mg, 20%) as an off white solid. $^1$H NMR (400 MHz, DMSO-$d_6$): δ 0.93 (t, 3H), 1.42 (d, 6H, J=6.8 Hz), 1.57 (m, 2H), 2.14 (s, 3H), 2.45-2.2 (m, 4H), 2.68 (t, 2H), 2.75 (t, 4H), 4.15-4.19 (m, 2H), 4.35 (d, 2H), 4.78-4.72 (m, 1H), 5.91 (s, 1H), 6.73 (d, 1H), 7.03 (s, 1H), 7.24 (s, 1H), 7.42 (d, 1H), 8.12 (t, 1H), 11.58 (bs, 1H). LCMS (ES+): m/z=494.57 [M+H].

Scheme 5

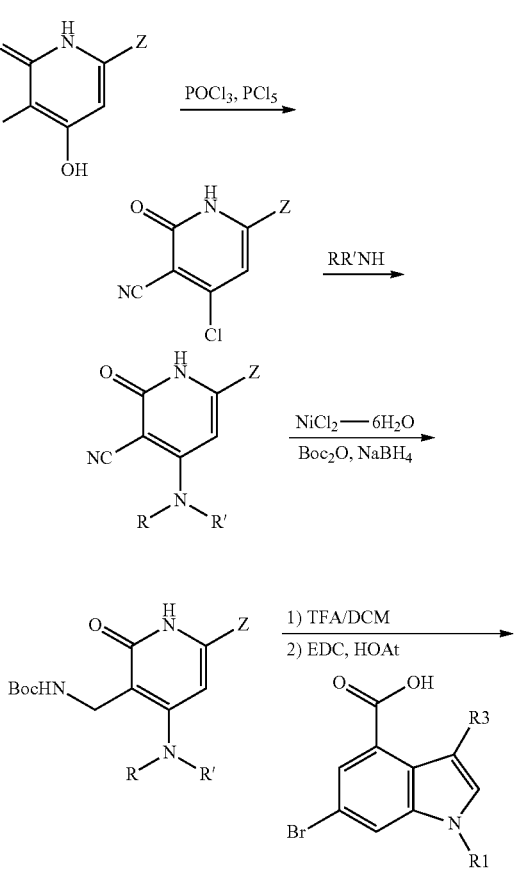

-continued

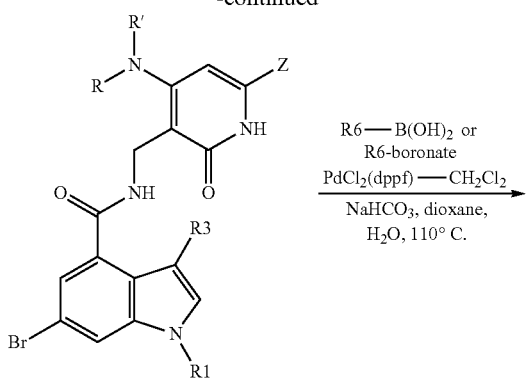

see: *Heterocycles*, vol. 60, No. 6, 2003, 1461-1468

Example 322

N-{[4-(ethylamino)-6-methyl-2-oxo-1,2-dihydro-3-pyridinyl]methyl}-1-(1-methylethyl)-6-[6-(4-methyl-1-piperazinyl)-3-pyridinyl]-1H-indole-4-carboxamide

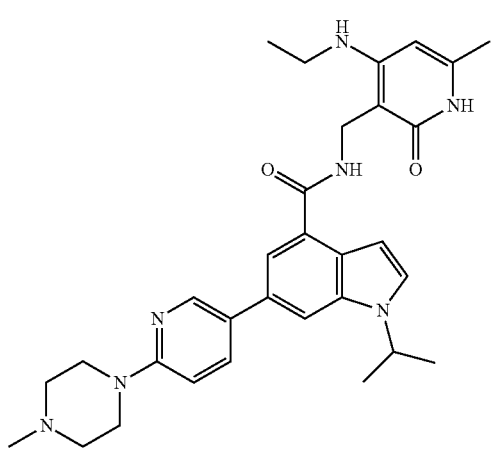

a) 4-Chloro-6-methyl-2-oxo-1,2-dihydro-3-pyridinecarbonitrile

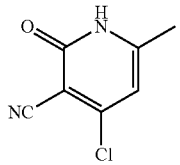

Using a 100 ml round bottom with reflux condenser, $PCl_5$ (6.7 g, 32 mmol), $POCl_3$ (3.0 mL, 32 mmol) and 30 ml $CHCl_3$ (dry) were stirred for 5 min (see: Heterocycles, vol. 60, No. 6, 2003, 1461-1468). Added 4-hydroxy-6-methyl-2-oxo-1,2-dihydro-3-pyridinecarbonitrile (4 g, 26.6 mmol) and stirred for 2 h at 80° C. Quenched reaction while hot and poured into 1 L beaker with 100 "g" ice, 24 mL $NH_4OH$, pH by paper was 8-9. Stirred 5 min and filtered. Washed solid with water. Suspended solid in ethanol and filtered and washed with ethanol. Gave: 4-chloro-6-methyl-2-oxo-1,2-dihydro-3-pyridinecarbonitrile (1.7 g, 9.58 mmol, 40% yield) $^1$H NMR (400 MHz, DMSO-$d_6$) δ ppm 12.85 (br. s., 1H) 6.53 (s, 1H) 2.28 (s, 3H) MS (ES) [M+H]$^+$ 168.9.

b) 4-(Ethylamino)-6-methyl-2-oxo-1,2-dihydro-3-pyridinecarbonitrile

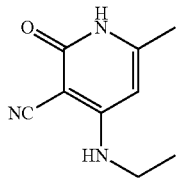

To a 10 ml microwave vial added 4-chloro-6-methyl-2-oxo-1,2-dihydro-3-pyridinecarbonitrile (750 mg, 4.45 mmol) and methanol (1 mL) then added ethylamine (5.56 mL, 11.12 mmol). One drop on conc. HCl was added and the vial was capped and the reaction was microwaved to 120° C. for 1 hr. The reaction was cooled and the solid was filtered and washed with cold MeOH. Gave 4-(ethylamino)-6-methyl-2-oxo-1,2-dihydro-3-pyridinecarbonitrile (500 mg, 2.77 mmol, 62.2% yield) $^1$H NMR (400 MHz, DMSO-$d_6$) δ ppm 11.05 (br. s., 1H) 7.11 (br. s., 1H) 5.78 (br. s., 1H) 3.22-3.32 (m, 2H) 2.11 (s, 3H) 1.10 (t, J=7.07 Hz, 3H)_MS (ES) [M+H]$^+$ 177.8.

c) 1,1-Dimethylethyl {[4-(ethylamino)-6-methyl-2-oxo-1,2-dihydro-3-pyridinyl]methyl}carbamate

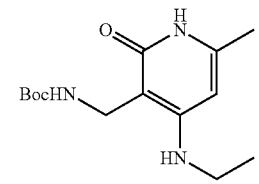 [SMILES: CCNc1cc(C)[nH]c(=O)c1CNC(=O)OC(C)(C)C]

In a 250 ml, round bottom flask under $N_2$ added 4-(ethylamino)-6-methyl-2-oxo-1,2-dihydro-3-pyridinecarbonitrile (500 mg, 2.82 mmol) as a solid then added Methanol (50 mL) and cooled to 0° C. in an ice bath. Next di-tert-butyl dicarbonate (1.310 mL, 5.64 mmol) was added and the suspension stirred for 5 min. Nickel Chloride-hexahydrate (335 mg, 1.411 mmol) solid was added followed by NaBH$_4$ (747 mg, 19.75 mmol) as a solid (in 3 portions-allowed 1 min in between portions b/c it turns black and there is gas evolution). After addiditon and stirring at 0° C. for ~10 min the ice bath was removed and the mix stirred at rt ON. The next morning the reaction was quenched with—Diethylene triamine (0.613 mL, 5.64 mmol) via syringe and the mix continued to stir 20 min. The reaction was diluted with EtOAc and was treated with sat NaHCO$_3$ and stirred 10 min. The mixture was transferred to a sep. funnel and the organic layer was separated out and washed (2×s) with sat NaHCO$_3$. The organic layer was concentrated in vacuo to a solid. The solid was stirred with 5% MeOH/Water (50 mL) then filtered. The solid was washed with 5% MeOH/Water and water (2×s) and dried to give 1,1-dimethylethyl {[4-(ethylamino)-6-methyl-2-oxo-1,2-dihydro-3-pyridinyl]methyl}carbamate (500 mg, 1.599 mmol, 56.7% yield). $^1$H NMR (400 MHz, DMSO-d$_6$) δ ppm 10.64 (br. s., 1H) 7.08 (br. s., 1H) 6.25 (br. s., 1H) 5.64 (s, 1H) 3.96 (d, J=6.06 Hz, 2H) 3.09-3.18 (m, 2H) 2.06 (s, 3H) 1.38 (s, 9H) 1.14 (t, 3H) [M+H]$^+$ 282.5.

d) 6-Bromo-N-{[4-(ethylamino)-6-methyl-2-oxo-1,2-dihydro-3-pyridinyl]methyl}-1-(1-methylethyl)-1H-indole-4-carboxamide

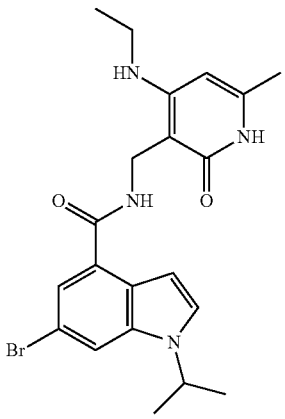 [SMILES: CCNc1cc(C)[nH]c(=O)c1CNC(=O)c1cc(Br)cc2c1ccn2C(C)C]

In a 50 mL round bottom was added 1,1-dimethylethyl {[4-(ethylamino)-6-methyl-2-oxo-1,2-dihydro-3-pyridinyl]methyl}carbamate (500 mg, 1.777 mmol) and Dichloromethane (DCM) (20.00 mL). TFA (1.095 mL, 14.22 mmol) was added and the reaction stirred at rt for 3.5 h. The LCMS indicated deprotection. The reaction was evaporated and evaporated from DCM. Dimethyl Sulfoxide (DMSO) (20 mL) was added to the round bottom followed by 6-bromo-1-(1-methylethyl)-1H-indole-4-carboxylic acid (501 mg, 1.777 mmol), to the solution was added N-methylmorpholine (1.172 mL, 10.66 mmol) 1-hydroxy-7-azabenzotriazole (363 mg, 2.67 mmol) and EDC (511 mg, 2.67 mmol). The reaction stirred at rt for 12 hr. The reaction was poured onto Ice water (10 mL) and was stirred for 20 min let it rest for 10 min and filter. Rinse solid with water (10 mL). Purification of solid by reverse phase Gilson HPLC (10-90% acetonitrile/water+0.1% TFA, YMC ODS-A C18 Column 75×30 mm ID S-5 um, 12 nM Column 7 minutes) provided the desired product as a white solid after neutralization with 0.1N NaOH and evaporation and precipitation from water. 6-bromo-N-{[4-(ethylamino)-6-methyl-2-oxo-1,2-dihydro-3-pyridinyl]methyl}-1-(1-methylethyl)-1H-indole-4-carboxamide (240 mg, 0.523 mmol, 29.4% yield). $^1$H NMR (400 MHz, DMSO-d$_6$) δ ppm 10.70 (s, 1H) 8.87 (m, 1H) 7.93 (s, 1H) 7.57-7.71 (m, 2H) 6.89 (d, J=3.28 Hz, 1H) 6.71 (m, 1H) 5.66 (s, 1H) 4.82 (m, 1H) 4.34 (d, J=5.81 Hz, 2H) 3.12-3.23 (m, 2H) 2.08 (s, 3H) 1.43 (d, J=6.57 Hz, 6H) 1.18 (t, 3H) MS (ES) [M+H]$^+$ 445.1.

e) N-{[4-(ethylamino)-6-methyl-2-oxo-1,2-dihydro-3-pyridinyl]methyl}-1-(1-methylethyl)-6-[6-(4-methyl-1-piperazinyl)-3-pyridinyl]-1H-indole-4-carboxamide

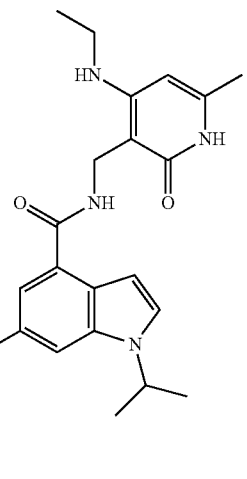

To a 20 mL microwave vial was added 6-bromo-N-{[4-(ethylamino)-6-methyl-2-oxo-1,2-dihydro-3-pyridinyl]methyl}-1-(1-methylethyl)-1H-indole-4-carboxamide (70 mg, 0.170 mmol), and 1-methyl-4-[5-(4,4,5,5-tetramethyl-1,3,2-dioxaborolan-2-yl)-2-pyridinyl]piperazine (59.9 mg, 0.198 mmol). PdC12(dppf)-CH$_2$Cl$_2$ adduct (14.67 mg, 0.018 mmol) and sodium bicarbonate (45.3 mg, 0.539 mmol) were added followed by 1,2-Dimethoxyethane (DME) (5 mL) and Water (2 mL). The vial was sealed and the reaction was heated to 85° C. for 1 hr. The reaction was cooled and evaporated. The material was taken into Methanol/DMSO and was filtered through an acrodisk and purified by reverse phase Gilson HPLC (5-80% acetonitrile/water+0.1% TFA, YMC ODS-A C18 Column 75×30 mm ID S-5 um, 12 nM Column, 6 minutes) the desired fractions were collected and evaporated from 0.1N NaOH which provided the desired product N-{[4-(ethylamino)-6-methyl-2-oxo-1,2-dihydro-3-pyridinyl]methyl}-1-(1-methylethyl)-6-[6-(4-methyl-1-piperazinyl)-3-pyridinyl]-1H-indole-4-carboxamide (57 mg, 0.101 mmol, 56.2% yield). $^1$H NMR (400 MHz, DMSO-d$_6$) δ ppm 10.68 (s, 1H) 8.89 (t, J=5.94 Hz, 1H) 8.66 (d, J=2.02 Hz, 1H) 8.09 (dd, J=8.59, 2.02 Hz, 1H) 7.91 (s, 1H) 7.80 (s, 1H) 7.60 (d, J=3.03 Hz, 1H) 6.99 (d, J=8.84 Hz, 1H) 6.89-6.96 (m, 2H) 5.66 (s, 1H) 4.85-4.98 (m, 1H) 4.39 (d, J=5.81 Hz, 2H) 3.63 (br. s., 4H) 3.11-3.24 (m, 2H) 2.7 (bs, 4H) 2.08 (s, 3H) 1.47 (d, J=6.57 Hz, 6H) 1.20 (t, 3H). MS (ES) [M+H]$^+$ 542.4.

Examples 323-324 were prepared by the methods described above for Example 322, or routine variations thereof, using the requisite amine:

| Ex | Structure | Name | ¹H NMR (400 MHz, DMSO-d₆) δ ppm | MS(ES) [M + H]⁺ |
|---|---|---|---|---|
| 323 | 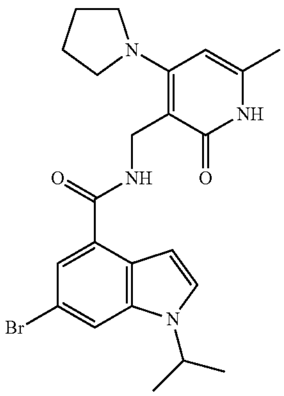 [SMILES: Cc1cc(N2CCCC2)c(CNC(=O)c2cc(Br)cc3c2ccn3C(C)C)c(=O)[nH]1] | 6-bromo-1-(1-methylethyl)-N-{[6-methyl-2-oxo-4-(1-pyrrolidinyl)-1,2-dihydro-3-pyridinyl]methyl}-1H-indole-4-carboxamide | 10.86 (s, 1 H) 8.22 (t, J = 4.29 Hz, 1 H) 7.93 (s, 1 H) 7.64 (d, J = 3.28 Hz, 1 H) 7.53 (d, J = 1.77 Hz, 1 H) 6.85 (d, J = 3.28 Hz, 1 H) 5.74 (s, 1 H) 4.78-4.89 (m, 1 H) 4.42 (d, J = 4.29 Hz, 2 H) 3.43-3.54 (m, 4 H) 2.09 (s, 3 H) 1.80-1.89 (m, 4 H) 1.44 (d, J = 6.57 Hz, 6 H) | 473.0 |
| 324 | 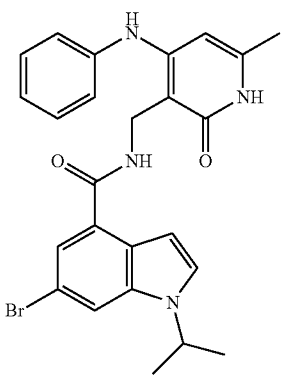 [SMILES: Cc1cc(Nc2ccccc2)c(CNC(=O)c2cc(Br)cc3c2ccn3C(C)C)c(=O)[nH]1] | 6-bromo-1-(1-methylethyl)-N-{[6-methyl-2-oxo-4-(phenylamino)-1,2-dihydro-3-pyridinyl]methyl)-1H-indole-4-carboxamide | 11.02 (s, 1 H) 9.45 (s, 1 H) 9.15-9.21 (m, 1 H) 7.96 (s, 1 H) 7.67 (dd, J = 10.11, 2.53 Hz, 2 H) 7.34-7.40 (m, 2 H) 7.15 (d, J = 7.33 Hz, 2 H) 7.04-7.09 (m, 1 H) 6.91 (d, J = 3.03 Hz, 1 H) 5.91 (s, 1 H) 4.80-4.87 (m, 1 H) 4.39 (d, J = 5.81 Hz, 2 H) 2.06 (s, 3 H) 1.44 (d, J = 6.57 Hz, 6 H) | 493.0 |

Example 325

N-((6-Amino-4-methyl-2-oxo-1,2-dihydropyridin-3-yl)methyl)-6-bromo-1-isopropyl-3-methyl-1H-indole-4-carboxamide

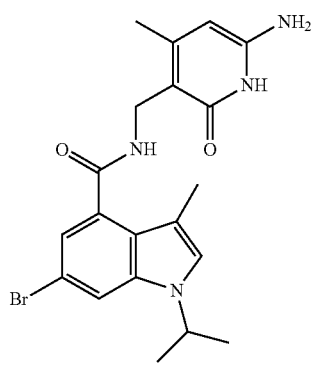

a) tert-Butyl (5-((6-bromo-1-isopropyl-3-methyl-1H-indole-4-carboxamido)methyl)-6-methoxy-4-methylpyridin-2-yl)carbamate

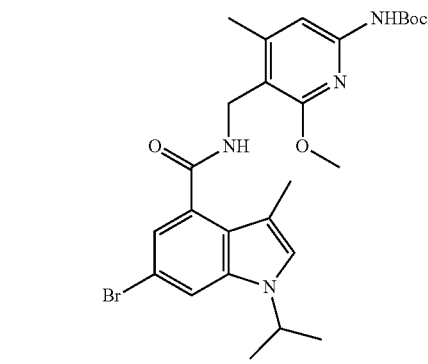 [SMILES: COc1nc(NC(=O)OC(C)(C)C)cc(C)c1CNC(=O)c1cc(Br)cc2c1c(C)cn2C(C)C]

To a stirred solution of tert-butyl (5-(aminomethyl)-6-methoxy-4-methylpyridin-2-yl)carbamate (0.40 g, 1.496 mmol), 6-bromo-1-isopropyl-3-methyl-1H-indole-4-carboxylic acid (0.44 g, 1.486 mmol), and HOAt (0.21 g, 1.543 mmol) in DMF (25 mL) was added EDC free base (0.25 g, 1.610 mmol). The reaction was stirred at RT overnight then evaporated to dryness under vacuum. The remaining was purified by silica gel chromatography (Analogix, SF25-60 g, 0 to 30% EtOAc in hexanes) to give the product tert-butyl (5-(((6-bromo-1-isopropyl-3-methyl-1H-indole-4-carboxa-mido)methyl)-6-methoxy-4-methylpyridin-2-yl)carbamate (0.81 g, 1.485 mmol, 99% yield) as a white solid. $^1$H NMR (400 MHz, DMSO-d$_6$) δ=9.42 (s, 1H), 8.41 (t, J=4.8 Hz, 1H), 7.77 (d, J=1.5 Hz, 1H), 7.33 (s, 1H), 7.21 (s, 1H), 6.99 (d, J=1.8 Hz, 1H), 4.40 (d, J=5.1 Hz, 2H), 3.81 (s, 3H), 2.35 (s, 3H), 2.10 (d, J=1.0 Hz, 3H), 1.47 (s, 9H), 1.38 (d, J=6.6 Hz, 6H). MS (ES)+m/e 545.2 [M+H]$^+$.

b) N-((6-Amino-4-methyl-2-oxo-1,2-dihydropyridin-3-yl)methyl)-6-bromo-1-isopropyl-3-methyl-1H-indole-4-carboxamide

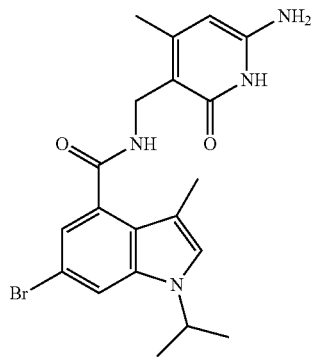

To a stirred solution of tert-butyl (5-(((6-bromo-1-isopropyl-3-methyl-1H-indole-4-carboxamido)methyl)-6-methoxy-4-methylpyridin-2-yl)carbamate (0.80 g, 1.467 mmol) in acetonitrile (20 mL) was added dropwise at RT TMSI (0.50 ml, 3.67 mmol). A reflux condenser was attached and the reaction was purged with N$_2$ and heated to 70° C. After stirring for 30 minutes LCMS indicated that the reaction was complete (89% pure with 11% possible iodinated side product as the only other impurity). Afterl hr the reaction was quenched with MeOH (5 mL) and stirred for 30 minutes. The clear brown solution was evaporated to dryness under vacuum, taken up in CH$_2$Cl$_2$, washed with aq. Na$_2$S$_2$O$_3$, (a ppt. formed that was filtered off), dried (Na$_2$SO$_4$), filtered, and concentrated under vacuum. Purification by silica gel chromatography (Analogix, SF25-10 g, 0 to 7% (5% NH$_4$OH/MeOH) in CH$_2$Cl$_2$) gave the product N-(((6-amino-4-methyl-2-oxo-1,2-dihydropyridin-3-yl)methyl)-6-bromo-1-isopropyl-3-methyl-1H-indole-4-carboxamide (59.6 mg, 0.138 mmol, 9.4% yield) as a white solid. Note: The ppt. that was filtered off during the aq. Na$_2$S$_2$O$_3$ wash was later shown to contain product. This solid was washed with water and dried under vacuum to give additional product as an off-white solid (602 mg, 1.4 mmol, 95%, 100% pure by LCMS). $^1$H NMR (400 MHz, DMSO-d$_6$) δ=10.59 (br. s., 1H), 8.13 (t, J=4.4 Hz, 1H), 7.76 (d, J=1.5 Hz, 1H), 7.33 (s, 1H), 6.99 (d, J=1.5 Hz, 1H), 5.83 (br. s., 2H), 5.19 (s, 1H), 4.74 (dt, J=6.6, 13.3 Hz, 1H), 4.22 (d, J=4.8 Hz, 2H), 2.14 (s, 3H), 2.11 (s, 3H), 1.39 (d, J=6.6 Hz, 6H). MS (ES)+m/e 431.1 [M+H]$^+$.

Examples 326-334 were prepared by the methods described above for Example 325, or routine variations thereof, using the requisite amine:

| Ex | Structure | Name | $^1$H NMR (400 MHz, DMSO-d$_6$) δ ppm | MS(ES) [M + H]$^+$ |
|---|---|---|---|---|
| 326 | 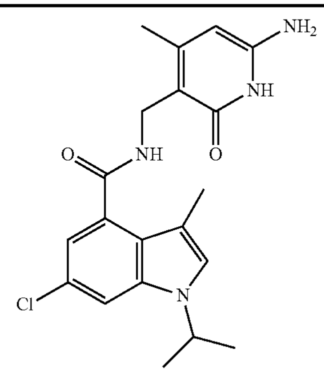 | N-((6-amino-4-methyl-2-oxo-1,2-dihydropyridin-3-yl)methyl)-6-chloro-1-isopropyl-3-methyl-1H-indole-4-carboxamide | 10.62 (br. s., 1 H), 8.14 (t, J = 4.4 Hz, 1 H), 7.63 (d, J = 1.8 Hz, 1 H), 7.34 (s, 1 H), 6.89 (d, J = 1.8 Hz, 1 H), 5.85 (br. s., 2 H), 5.20 (s, 1 H), 4.73 (dt, J = 6.7, 13.2 Hz, 1 H), 4.22 (d, J = 4.8 Hz, 2 H), 2.14 (s, 3 H), 2.12 (s, 3 H), 1.39 (d, J = 6.6 Hz, 6 H) | 387.2 |
| 327 | 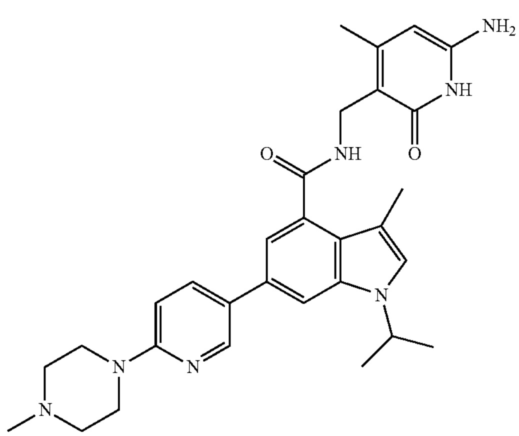 [SMILES: Cc1cc(N)[nH]c(=O)c1CNC(=O)c1cc(-c2ccc(N3CCN(C)CC3)nc2)cc2c1c(C)cn2C(C)C] | N-[(6-amino-4-methyl-2-oxo-1,2-dihydro-3-pyridinyl)methyl]-3-methyl-1-(1-methylethyl)-6-[6-(4-methyl-1-piperazinyl)-3-pyridinyl]-1H-indole-4-carboxamide | 10.49 (br. s., 1 H), 8.51 (d, J = 2.5 Hz, 1 H), 7.98 (t, J = 4.8 Hz, 1 H), 7.93 (dd, J = 2.5, 8.8 Hz, 1 H), 7.71 (d, J = 1.3 Hz, 1 H), 7.29 (s, 1 H), 7.17 (d, J = 1.5 Hz, 1 H), 6.92 (d, J = 8.8 Hz, 1 H), 5.77 (s, 2 H), 5.16 (s, 1 H), 4.84 (quin, J = 6.6 Hz, 1 H), 4.26 (d, J = 5.1 Hz, 2 H), 3.61-3.46 (m, 4 H), 2.43 (t, J = 4.7 Hz, 4 H), 2.24 (s, 3 H), 2.18 (s, 3 H), 2.13 (s, 3 H), 1.43 (d, J = 6.6 Hz, 6 H) | 528.6 |

| Ex | Structure | Name | ¹H NMR (400 MHz, DMSO-d₆) δ ppm | MS(ES) [M + H]⁺ |
|---|---|---|---|---|
| 328 | 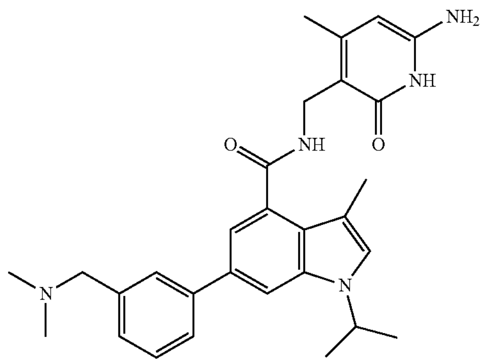 [SMILES: Cc1cc(N)[nH]c(=O)c1CNC(=O)c1cc(-c2cccc(CN(C)C)c2)cc2c1c(C)cn2C(C)C] | N-[(6-amino-4-methyl-2-oxo-1,2-dihydro-3-pyridinyl)methyl]-6-{3-[(dimethylamino)methyl]phenyl}-3-methyl-1-(1-methylethyl)-1H-indole-4-carboxamide | 10.48 (br. s., 1 H), 8.03 (t, J = 4.9 Hz, 1 H), 7.75 (d, J = 1.3 Hz, 1 H), 7.64 (s, 1 H), 7.63 (d, 1 H), 7.40 (t, J = 7.6 Hz, 1 H), 7.33 (s, 1 H), 7.24 (d, J = 7.6 Hz, 1 H), 7.22 (d, J = 1.5 Hz, 1 H), 5.77 (s, 2 H), 5.16 (s, 1 H), 4.88 (quin, J = 6.6 Hz, 1 H), 4.26 (d, J = 5.1 Hz, 2 H), 3.48 (s, 2 H), 2.19 (s, 9 H), 2.13 (s, 3 H), 1.44 (d, J = 6.6 Hz, 6 H) | 486.3 |
| 329 | 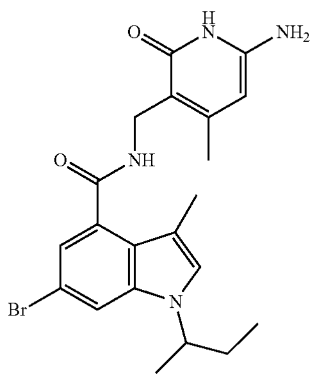 | N-[(6-amino-4-methyl-2-oxo-1,2-dihydro-3-pyridinyl)methyl]-6-bromo-3-methyl-1-(1-methylpropyl)-1H-indole-4-carboxamide | 0.70 (t, J = 7.33 Hz, 3 H) 1.36 (d, J = 6.82 Hz, 3 H) 1.69-1.84 (m, 2 H) 2.15 (s, 2 H) 2.10 (s, 4 H) 4.21 (d, J = 4.80 Hz, 2 H) 4.41-4.58 (m, 1 H) 5.15 (s, 1 H) 5.77 (s, 2 H) 6.97 (d, J = 1.52 Hz, 1 H) 7.29 (s, 1 H) 7.76 (d, J = 1.77 Hz, 1 H) 8.06 (t, J = 4.80 Hz, 1 H) 10.47 (br. s., 1 H) | 447.2 |
| 330 | 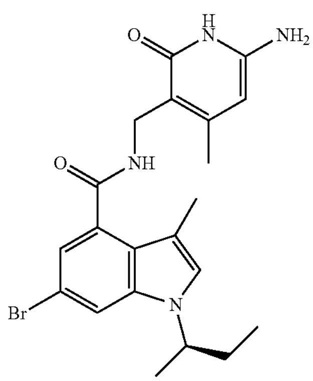 [SMILES: CC[C@@H](C)n1cc(C)c2c(C(=O)NCc3c(C)cc(N)[nH]c3=O)cc(Br)cc21] | N-[(6-amino-4-methyl-2-oxo-1,2-dihydro-3-pyridinyl)methyl]-6-bromo-3-methyl-1-(1-methylpropyl)-1H-indole-4-carboxamide | 0.668 (t, J = 7.4 Hz, 3H), 1.36 (d, J = 6.8 Hz, 3H), 1.76-1.78 (m, 2H), 2.11 (s, 3H), 2.15 (s, 3H), 4.21 (d, J = 4.8 Hz, 2H), 4.35-4.38 (m, 1H), 5.15 (s, 1H), 5.78 (s, 2H), 6.97 (s, 1H), 7.30 (s, 1H), 7.76 (s, 1H), 8.07-8,.09 (m, 1H), 10.4-10.5 (br s, 1H) | 445.2 |
| 331 | 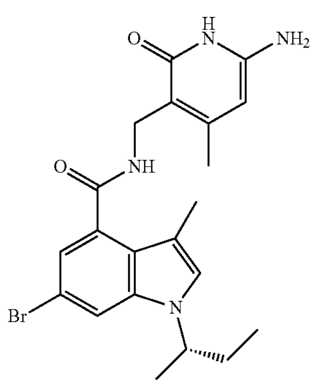 [SMILES: CC[C@H](C)n1cc(C)c2c(C(=O)NCc3c(C)cc(N)[nH]c3=O)cc(Br)cc21] | N-[(6-amino-4-methyl-2-oxo-1,2-dihydro-3-pyridinyl)methyl]-6-bromo-3-methyl-1-(1-methylpropyl)-1H-indole-4-carboxamide | 0.668 (t, J = 7.4 Hz, 3H), 1.36 (d, J = 6.8 Hz, 3H), 1.76-1.78 (m, 2H), 2.11 (s, 3H), 2.15 (s, 3H), 4.21 (d, J = 4.8 Hz, 2H), 4.35-4.38 (m, 1H), 5.15 (s, 1H), 5.78 (s, 2H), 6.97 (s, 1H), 7.30 (s, 1H), 7.76 (s, 1H), 8.07-8,.09 (m, 1H), 10.4-10.5 (br s, 1H) | 445.2 |

| Ex | Structure | Name | ¹H NMR (400 MHz, DMSO-d$_6$) δ ppm | MS(ES) [M + H]⁺ |
|---|---|---|---|---|
| 332 | 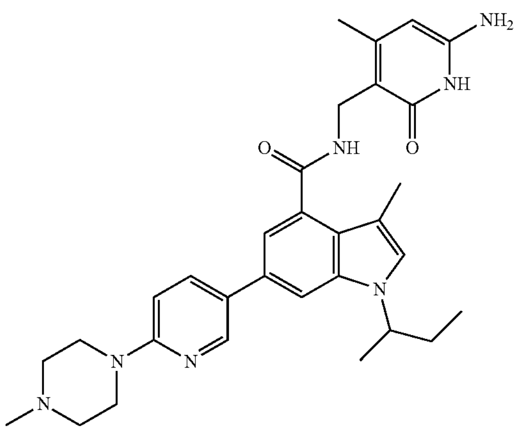 [SMILES: CCC(C)n1cc(C)c2c(C(=O)NCc3c(C)cc(N)[nH]c3=O)cc(-c3ccc(N4CCN(C)CC4)nc3)cc21] | N-[(6-amino-4-methyl-2-oxo-1,2-dihydro-3-pyridinyl)methyl]-3-methyl-6-[6-(4-methyl-1-piperazinyl)-3-pyridinyl]-1-(1-methylpropyl)-1H-indole-4-carboxamide | 10.47 (br. s., 1 H) 8.50 (d, J = 2.53 Hz, 1 H) 7.98 (br. s., 1 H) 7.92 (dd, J = 8.84, 2.53 Hz, 1 H) 7.71-7.74 (m, 1 H) 7.26 (s, 1 H) 7.16 (d, J = 1.26 Hz, 1 H) 6.92 (d, J = 9.09 Hz, 1 H) 5.76 (s, 2 H) 5.16 (br. s., 1 H) 4.57-4.65 (m, 1 H) 4.26 (br. s., 1 H) 4.25 (br. s., 1 H) 3.52 (br. s., 4 H) 2.42 (br. s., 4 H) 2.23 (s, 3 H) 2.18 (s, 3 H) 2.13 (s, 3 H) 1.81 (td, J = 7.20, 3.03 Hz, 2 H) 1.41 (d, J = 6.82 Hz, 3 H) 0.73 (t, J = 7.20 Hz, 3 H) | 542.6 |
| 333 | 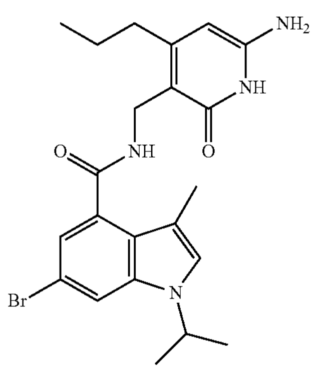 [SMILES: CCCc1cc(N)[nH]c(=O)c1CNC(=O)c1cc(Br)cc2c1c(C)cn2C(C)C] | N-((6-amino-2-oxo-4-propyl-1,2-dihydropyridin-3-yl)methyl)-6-bromo-1-isopropyl-3-methyl-1H-indole-4-carboxamide | 10.52 (br. s., 1 H), 8.04 (t, J = 4.7 Hz, 1 H), 7.76 (d, J = 1.8 Hz, 1 H), 7.33 (s, 1 H), 6.98 (d, J = 1.8 Hz, 1 H), 5.77 (s, 2 H), 5.17 (s, 1 H), 4.74 (quin, J = 6.6 Hz, 1 H), 4.23 (d, J = 4.8 Hz, 2 H), 2.45-2.34 (m, 2 H), 2.15 (s, 3 H), 1.52 (dq, J = 7.4, 15.1 Hz, 2 H), 1.39 (d, J = 6.6 Hz, 6 H), 0.93 (t, J = 7.3 Hz, 3 H) | 459.2 |
| 334 | 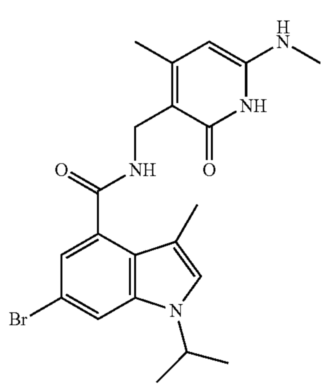 [SMILES: CNc1cc(C)c(CNC(=O)c2cc(Br)cc3c2c(C)cn3C(C)C)c(=O)[nH]1] | 6-bromo-1-isopropyl-3-methyl-N-((4-methyl-6-(methylamino)-2-oxo-1,2-dihydropyridin-3-yl)methyl)-1H-indole-4-carboxamide | 10.48 (br. s., 1 H), 8.11 (t, J = 4.5 Hz, 1 H), 7.75 (d, J = 1.5 Hz, 1 H), 7.33 (s, 1 H), 6.99 (d, J = 1.5 Hz, 1 H), 5.76 (q, J = 4.4 Hz, 1 H), 5.13 (br. s., 1 H), 4.74 (quin, J = 6.6 Hz, 1 H), 4.24 (d, J = 4.8 Hz, 2 H), 2.67 (d, J = 5.1 Hz, 3 H), 2.17 (s, 3 H), 2.15 (s, 3 H), 1.39 (d, J = 6.6 Hz, 6 H) | 445.2 |

Example 335

N-[(4,6-Dimethyl-2-oxo-1,2-dihydro-3-pyridinyl)methyl]-3-methyl-1-(1-methylethyl)-6-{6-[(2R)-2-methyl-1-piperazinyl]-3-pyridinyl}-1H-indole-4-carboxamide

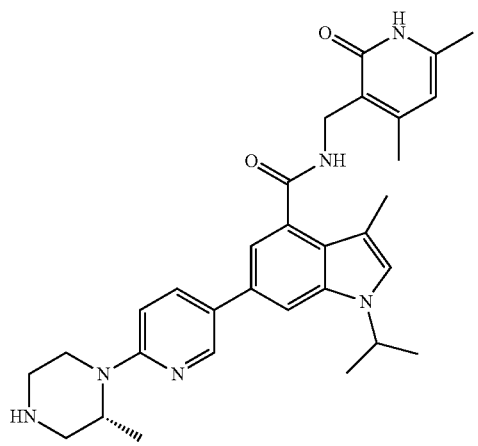 [SMILES: Cc1cc(C)c(CNC(=O)c2cc(-c3ccc(N4CCNC[C@H]4C)nc3)cc3c2c(C)cn3C(C)C)c(=O)[nH]1]

a) (R)-tert-Butyl 4-(5-(4-(((4,6-dimethyl-2-oxo-1,2-dihydropyridin-3-yl)methyl)carbamoyl)-1-isopropyl-3-methyl-1H-indol-6-yl)pyridin-2-yl)-3-methylpiperazine-1-carboxylate

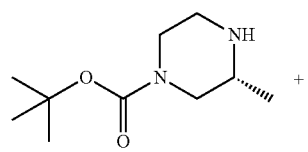  +

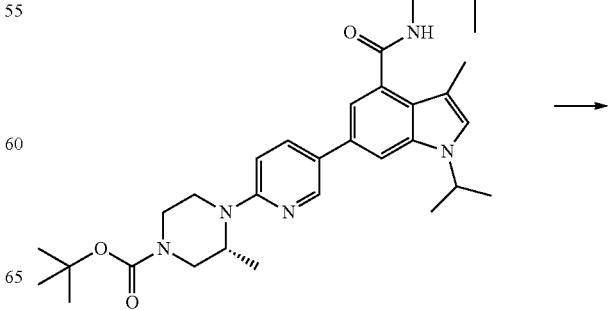

Added 6-(6-chloropyridin-3-yl)-N-((4,6-dimethyl-2-oxo-1,2-dihydropyridin-3-yl)methyl)-1-isopropyl-3-methyl-1H-indole-4-carboxamide (131 mg, 0.283 mmol), (R)-tert-butyl 3-methylpiperazine-1-carboxylate (70.8 mg, 0.354 mmol), sodium tert-butoxide (59.8 mg, 0.623 mmol) and 1,4-Dioxane (2 mL) to a microwave vial and degassed for 10 minutes. Added Pd XPhos (10.45 mg, 0.014 mmol) and heated to 100° C. for 16 hours. Concentrated, added DCM and water. Filtered, separated phases. Extracted aqueous phase twice more with DCM. Combined DCM extracts and washed with water, brine, dried (MgSO$_4$), filtered and rotovapped off DCM. The residue was purified via Biotage (0% to 5% MeOH:DCM; 10 g-HP-silica gel column). Obtained 28 mg of the title compound. $^1$H NMR (400 MHz, CHLOROFORM-d) δ ppm 1.16 (d, J=6.32 Hz, 3H), 1.44-1.57 (m, 15H), 2.06 (s, 3H), 2.28 (s, 3H), 2.39 (s, 3H), 2.87-3.36 (m, 3H), 3.57 (s, 1H), 3.86-4.30 (m, 3H), 4.50 (d, J=9.35 Hz, 1H), 4.58-4.79 (m, 3H), 5.87 (s, 1H), 6.64 (d, J=8.59 Hz, 1H), 7.01 (s, 1H), 7.45 (s, 1H), 7.76 (d, J=8.08 Hz, 1H), 8.46 (d, J=2.27 Hz, 1H), 12.42 (br. s., 1H). LCMS: [M+H]$^+$ 627.5.

b) N-[(4,6-Dimethyl-2-oxo-1,2-dihydro-3-pyridinyl)methyl]-3-methyl-1-(1-methylethyl)-6-{6-[(2R)-2-methyl-1-piperazinyl]-3-pyridinyl}-1H-indole-4-carboxamide -continued

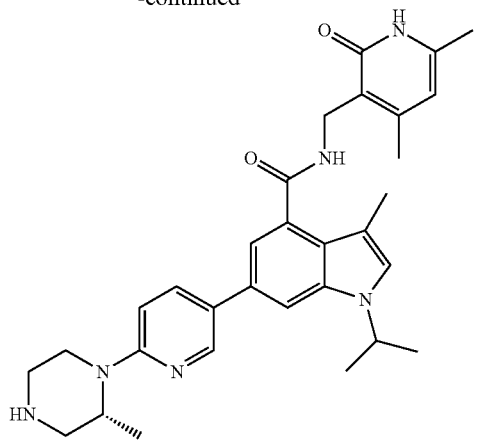

Added trifluoroacetic acid (1 ml, 12.98 mmol) to a solution of (R)-tert-butyl 4-(5-(4-(((4,6-dimethyl-2-oxo-1,2-dihydropyridin-3-yl)methyl)carbamoyl)-1-isopropyl-3-methyl-1H-indol-6-yl)pyridin-2-yl)-3-methylpiperazine-1-carboxylate (57 mg, 0.091 mmol) in DCM (3 mL) and let stir at RT for 1 hour. Concentrated on rotovap. Partitioned between DCM and sat'd Na2CO3, separated and washed DCM phase with water, brine, dried (MgSO4), filtered and rotovapped off DCM. Obtained 25 mg of the title compound as a tan solid. $^1$H NMR (400 MHz, CHLOROFORM-d) δ ppm 1.19 (d, 2H), 1.46-1.59 (m, 6H), 2.21 (s, 3H), 2.27 (s, 3H), 2.44 (s, 3H), 2.83 (dd, J=12.13, 3.54 Hz, 1H), 2.96-3.29 (m, 4H), 3.90 (br. s., 1H), 4.47-4.76 (m, 5H), 6.00 (s, 1H), 6.51 (d, J=8.59 Hz, 1H), 7.05 (s, 1H), 7.45 (s, 1H), 7.68 (dd, J=8.72, 2.40 Hz, 1H), 8.43 (d, J=2.27 Hz, 1H), 10.11-12.70 (m, 1H). LCMS: [M+H]$^+$ 527.5.

Examples 336-346 were prepared by the methods described above for Example 335, or routine variations thereof, using the requisite amine:

| Ex | Structure | Name | $^1$H NMR (400 MHz, DMSO-d$_6$) δ ppm | MS(ES) [M + H]$^+$ |
|---|---|---|---|---|
| 336 | 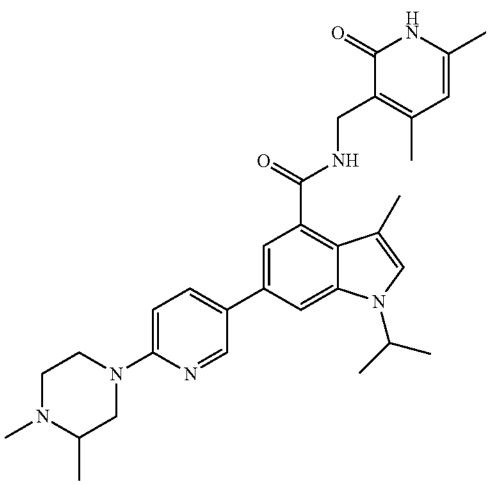 | N-[(4,6-dimethyl-2-oxo-1,2-dihydro-3-pyridinyl)methyl]-6-[6-(3,4-dimethyl-1-piperazinyl)-3-pyridinyl]-3-methyl-1-(1-methylethyl)-1H-indole-4-carboxamide | (CHLOROFORM-d) 1.16 (d, J = 6.06 Hz, 3 H), 1.47 (d, J = 6.57 Hz, 6 H), 2.03 (s, 3 H), 2.14-2.29 (m, 4 H), 2.30-2.42 (m, 7 H), 2.69 (dd, J = 12.25, 10.74 Hz, 1 H), 2.91 (d, J = 11.62 Hz, 1 H), 3.00-3.13 (m, 1 H), 4.06 (d, J = 12.63 Hz, 2 H), 4.38-4.75 (m, 3 H), 5.85 (s, 1 H), 6.64 (d, J = 8.59 Hz, 1 H), 6.99 (s, 1 H), 7.42 (d, J = 1.52 Hz, 1 H), 7.70 (dd, J = 8.84, 2.53 Hz, 1 H), 8.43 (d, J = 2.27 Hz, 1 H), 12.55 (br. s., 1 H) | 541.3 |
| 337 | 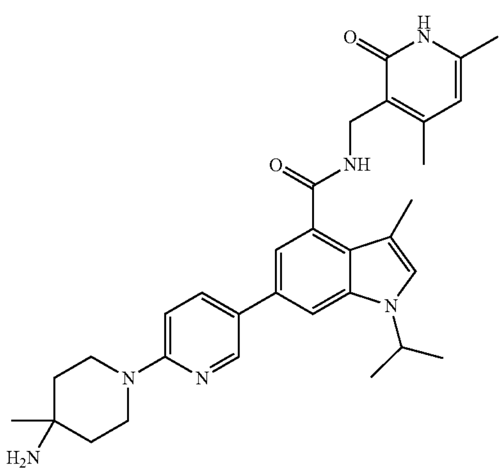 | N-[(4,6-dimethyl-2-oxo-1,2-dihydro-3-pyridinyl)methyl]-6-[6-(hexahydropyrrolo[3,4-b]pyrrol-5(1H)-yl)-3-pyridinyl]-3-methyl-1-(1-methylethyl)-1H-indole-4-carboxamide | (CHLOROFORM-d) 1.24 (s, 3 H), 1.49 (d, J = 6.57 Hz, 6 H), 1.60-1.73 (m, 4 H), 2.10 (s, 3 H), 2.28 (s, 3 H), 2.38 (s, 2 H), 3.39-3.53 (m, 2 H), 3.57-3.70 (m, 2 H), 4.54-4.75 (m, 3 H), 5.88 (s, 1 H), 6.61 (d, J = 8.84 Hz, 1 H), 7.01 (s, 1 H), 7.26 (br. s., 1 H), 7.29 (d, J = 5.81 Hz, 1 H), 7.44 (s, 1 H), 7.66 (dd, J = 8.84, 2.27 Hz, 2 H), 8.41 (d, J = 2.02 Hz, 2 H), 10.07-13.76 (m, 1 H) | 541.5 |

-continued

| Ex | Structure | Name | ¹H NMR (400 MHz, DMSO-d₆) δ ppm | MS(ES) [M + H]⁺ |
|---|---|---|---|---|
| 338 | 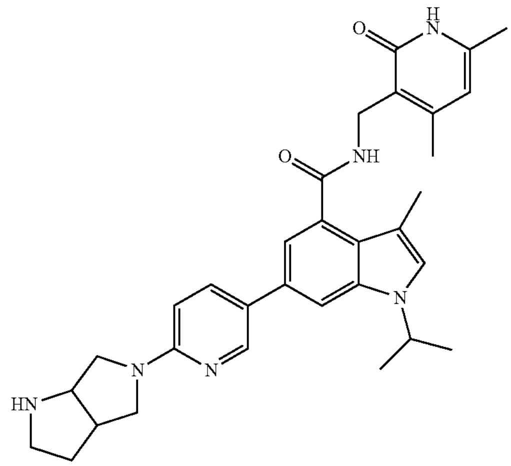 [SMILES: Cc1cc(C)c(CNC(=O)c2cc(-c3ccc(N4CC5CCNC5C4)nc3)cc3c2c(C)cn3C(C)C)c(=O)[nH]1] | N-[(4,6-dimethyl-2-oxo-1,2-dihydro-3-pyridinyl)methyl]-6-[6-(hexahydropyrrolo[3,4-b]pyrrol-5(1H)-yl)-3-pyridinyl]-3-methyl-1-(1-methylethyl)-1H-indole-4-carboxamide | (CHLOROFORM-d) 1.48 (t, J = 6.57 Hz, 6 H), 1.54-1.69 (m, 1 H), 2.10 (s, 3 H), 2.31 (s, 3 H), 2.42 (s, 3 H), 2.77-3.05 (m, 3 H), 3.22 (dd, J = 10.86, 4.55 Hz, 1 H), 3.31-3.46 (m, 2 H), 3.46-3.58 (m, 1 H), 4.03 (d, J = 5.56 Hz, 1 H), 4.39-4.86 (m, 3 H), 5.90 (s, 1 H), 6.16 (d, J = 8.59 Hz, 1 H), 7.03 (s, 1 H), 7.21 (s, 1 H), 7.41 (s, 1 H), 7.53 (d, J = 6.32 Hz, 2 H), 8.32 (d, J = 2.02 Hz, 1 H) | 539.5 |
| 339 | 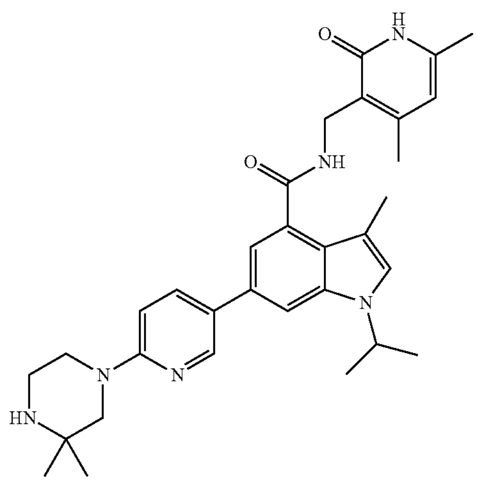 [SMILES: Cc1cc(C)c(CNC(=O)c2cc(-c3ccc(N4CCNC(C)(C)C4)nc3)cc3c2c(C)cn3C(C)C)c(=O)[nH]1] | N-[(4,6-dimethyl-2-oxo-1,2-dihydro-3-pyridinyl)methyl]-6-[6-(3,3-dimethyl-1-piperazinyl)-3-pyridinyl]-3-methyl-1-(1-methylethyl)-1H-indole-4-carboxamide | (CHLOROFORM-d) 1.21 (s, 6 H), 1.49 (d, J = 6.82 Hz, 6 H), 2.09 (s, 3 H), 2.28 (s, 3 H), 2.40 (s, 3 H), 2.99-3.12 (m, 2 H), 3.33 (s, 2 H), 3.45-3.60 (m, 2 H), 4.55-4.77 (m, 3 H), 5.89 (s, 1 H), 6.63 (d, J = 8.84 Hz, 1 H), 7.01 (s, 1 H), 7.22-7.26 (m, 1 H), 7.28 (d, J = 1.26 Hz, 1 H), 7.44 (d, J = 1.01 Hz, 1 H), 7.70 (dd, J = 8.84, 2.53 Hz, 1 H), 8.42 (d, J = 2.27 Hz, 1 H) | 541.6 |
| 340 | 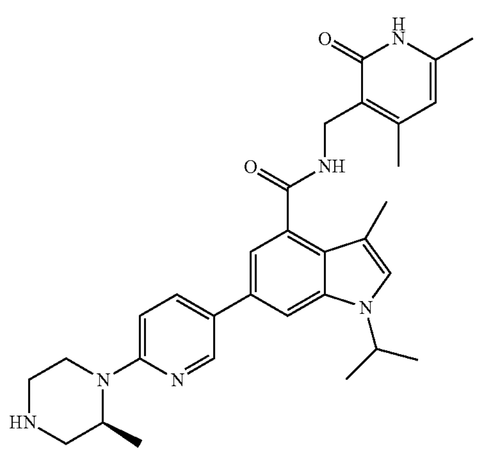 [SMILES: Cc1cc(C)c(CNC(=O)c2cc(-c3ccc(N4CCNC[C@@H]4C)nc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-{6-[(2S)-2-methyl-1-piperazinyl]-3-pyridinyl}-1H-indole-4-carboxamide | (CHLOROFORM-d) 1.21 (d, J = 6.57 Hz, 3 H), 1.49 (d, J = 6.82 Hz, 6 H), 2.07 (s, 3 H), 2.28 (s, 3 H), 2.39 (s, 3 H), 2.76-2.99 (m, 2 H), 3.02-3.21 (m, 3 H), 3.94 (d, J = 12.63 Hz, 1 H), 4.38-4.48 (m, 1 H), 4.56-4.77 (m, 3 H), 5.88 (s, 1 H), 6.59 (d, J = 9.09 Hz, 1 H), 7.01 (s, 1 H), 7.30 (d, 1 H), 7.45 (d, J = 1.01 Hz, 1 H), 7.71 (dd, J = 8.84, 2.53 Hz, 1 H), 8.45 (d, J = 2.27 Hz, 1 H) | 527.5 |

| Ex | Structure | Name | ¹H NMR (400 MHz, DMSO-d₆) δ ppm | MS(ES) [M + H]⁺ |
|---|---|---|---|---|
| 341 | 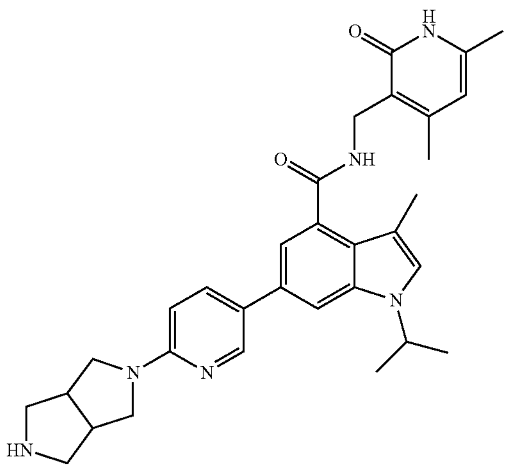 [SMILES: Cc1cc(C)c(CNC(=O)c2cc(-c3ccc(N4CC5CNCC5C4)nc3)cc3c2c(C)cn3C(C)C)c(=O)[nH]1] | N-[(4,6-dimethyl-2-oxo-1,2-dihydro-3-pyridinyl)methyl]-6-[6-(hexahydropyrrolo[3,4-c]pyrrol-2(1H)-yl)-3-pyridinyl]-3-methyl-1-(1-methylethyl)-1H-indole-4-carboxamide | (CHLOROFORM-d) 1.49 (d, 6 H), 2.18 (s, 3 H), 2.33 (s, 3 H), 2.44 (s, 3 H), 2.63 (d, J = 6.32 Hz, 2 H), 2.89 (br. s., 2 H), 3.02 (d, J = 9.60 Hz, 2 H), 3.24 (dd, J = 10.99, 6.19 Hz, 2 H), 3.35 (dd, J = 9.85, 7.07 Hz, 2 H), 4.55-4.72 (m, 3 H), 5.91-6.01 (m, 2 H), 7.09 (s, 1 H), 7.13 (s, 1 H), 7.35-7.49 (m, 2 H), 7.60-7.81 (m, 1 H), 8.26 (d, J = 2.02 Hz, 1 H) | 539.5 |
| 342 | 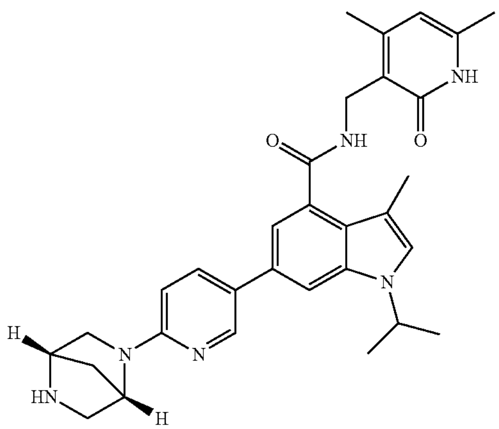 [SMILES: Cc1cc(C)c(CNC(=O)c2cc(-c3ccc(N4C[C@@H]5C[C@H]4CN5)nc3)cc3c2c(C)cn3C(C)C)c(=O)[nH]1] | 6-{6-[(1S,4S)-2,5-diazabicyclo[2.2.1]hept-2-yl]-3-pyridinyl}-N-[(4,6-dimethyl-2-oxo-1,2-dihydro-3-pyridinyl)methyl]-3-methyl-1-(1-methylethyl)-1H-indole-4-carboxamide | 1.43 (d, J = 6.57 Hz, 6 H), 1.68 (d, J = 9.35 Hz, 1 H), 1.80 (d, J = 8.84 Hz, 1 H), 2.11 (s, 3 H), 2.16 (s, 3 H), 2.24 (s, 3 H), 2.82 (d, J = 9.35 Hz, 1 H) ,2.89-2.97 (m, 1 H), 3.16-3.25 (m, 2 H), 3.49 (d, J = 8.34 Hz, 1 H), 3.69 (br. s., 1 H), 4.35 (d, J = 4.80 Hz, 2 H), 4.69 (s, 1 H), 4.83 (quin, J = 6.63 Hz, 1 H), 5.87 (s, 1 H), 6.56 (d, J = 8.84 Hz, 1 H), 7.16 (d, J = 1.26 Hz, 1 H), 7.27 (s, 1 H), 7.68 (d, J = 1.26 Hz, 1 H), 7.86 (dd, J = 8.72, 2.40 Hz, 1 H), 8.14 (t, J = 5.05 Hz, 1 H), 8.44 (d, J = 2.27 Hz, 1 H) | 525.3 |
| 343 | 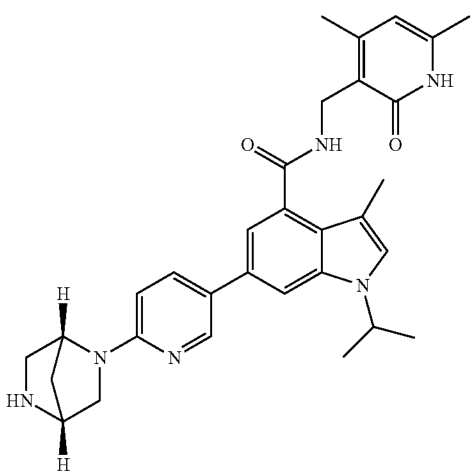 [SMILES: Cc1cc(C)c(CNC(=O)c2cc(-c3ccc(N4C[C@H]5C[C@@H]4CN5)nc3)cc3c2c(C)cn3C(C)C)c(=O)[nH]1] | 6-{6-[(1R,4R)-2,5-diazabicyclo[2.2.1]hept-2-yl]-3-pyridinyl}-N-[(4,6-dimethyl-2-oxo-1,2-dihydro-3-pyridinyl)methyl]-3-methyl-1-(1-methylethyl)-1H-indole-4-carboxamide | 1.43 (d, 6 H), 1.70 (m, 1 H), 1.80 (m, 1 H), 2.11 (s, 3 H), 2.16 (s, 3 H), 2.24 (s, 3 H), 2.80-2.87 (m, 1 H), 2.91-2.98 (m, 1 H,) 3.23 (d, J = 9.35 Hz, 1 H), 3.49 (dd, J = 9.35, 2.02 Hz, 1 H), 3.72 (s, 1 H), 4.35 (d, J = 5.05 Hz, 2 H), 4.70 (s, 1 H), 4.83 (quin, J = 6.63 Hz, 1 H), 5.87 (s, 1 H), 6.56 (d, J = 8.84 Hz, 1 H), 7.16 (d, J = 1.52 Hz, 1 H), 7.27 (s, 1 H), 7.68 (d, J = 1.26 Hz, 1 H), 7.87 (dd, J = 8.84, 2.53 Hz, 1 H), 8.14 (t, J = 4.93 Hz, 1 H), 8.44 (d, J = 2.27 Hz, 1 H) | 525.7 |

| Ex | Structure | Name | ¹H NMR (400 MHz, DMSO-d₆) δ ppm | MS(ES) [M + H]⁺ |
|---|---|---|---|---|
| 344 | 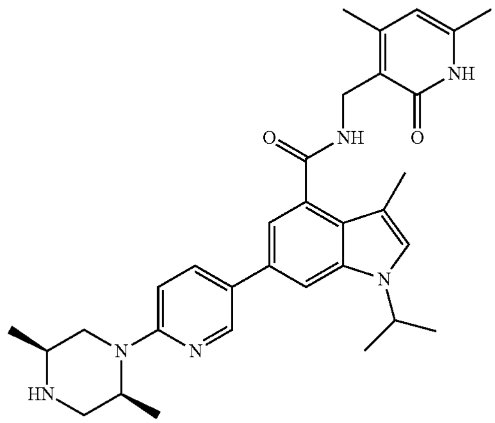 | N-[(4,6-dimethyl-2-oxo-1,2-dihydro-3-pyridinyl)methyl]-6-{6-[(2S,5S)-2,5-dimethyl-1-piperazinyl]-3-pyridinyl}-3-methyl-1-(1-methylethyl)-1H-indole-4-carboxamide | 1.10 (m, 6 H), 1.43 (d, J = 6.82 Hz, 6 H), 2.11 (s, 3 H), 2.14-2.19 (m, 3 H), 2.24 (s, 3 H), 2.61-2.74 (m, 1 H), 2.79-2.96 (m, 2 H), 3.93-4.04 (m, 1 H), 4.35 (d, J = 5.05 Hz, 3 H), 4.76-4.90 (m, 1 H), 5.87 (s, 1 H), 6.82 (d, J = 8.84 Hz, 1 H), 7.17 (d, J = 1.52 Hz, 1 H), 7.28 (s, 1 H), 7.70 (d, J = 1.26 Hz, 1 H), 7.89 (dd, J = 8.84, 2.53 Hz, 1 H), 8.14 (t, J = 5.05 Hz, 1 H), 8.49 (d, J = 2.53 Hz, 1 H) | 541.6 |
| 345 | 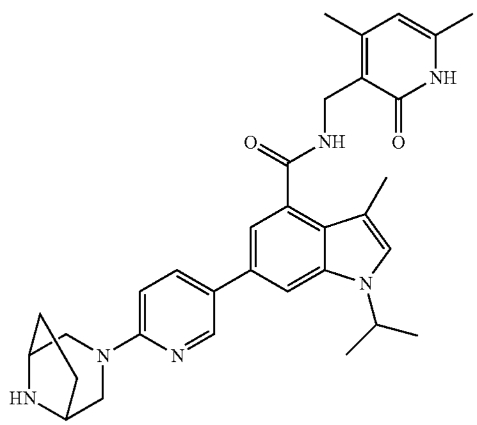 [SMILES: Cc1cc(C)c(CNC(=O)c2cc(-c3ccc(N4CC5CCC(C4)N5)nc3)cc3c2c(C)cn3C(C)C)c(=O)[nH]1] | 6-[6-(3,8-diazabicyclo[3.2.1]oct-3-yl)-3-pyridinyl]-N-[(4,6-dimethyl-2-oxo-1,2-dihydro-3-pyridinyl)methyl]-3-methyl-1-(1-methylethyl)-1H-indole-4-carboxamide | 1.38-1.48 (m, 6 H), 1.60-1.74 (m, 4 H), 2.11 (s, 3 H), 2.16 (s, 3 H), 2.24 (s, 3 H), 2.79-2.95 (m, 2 H), 3.35 (d, J = 1.26 Hz, 5 H), 3.54 (br. s., 2 H), 3.83-3.91 (m, 2 H), 4.35 (d, J = 5.05 Hz, 2 H), 4.83 (quin, J = 6.57 Hz, 1 H), 5.87 (s, 1 H), 6.75 (d, J = 8.84 Hz, 1 H), 7.17 (d, J = 1.52 Hz, 1 H), 7.28 (s, 1 H), 7.70 (d, J = 1.26 Hz, 1 H), 7.89 (dd, J = 8.84, 2.53 Hz, 1 H), 8.15 (t, J = 5.05 Hz, 1 H), 8.45-8.51 (m, 1 H) | 539.6 |
| 346 | 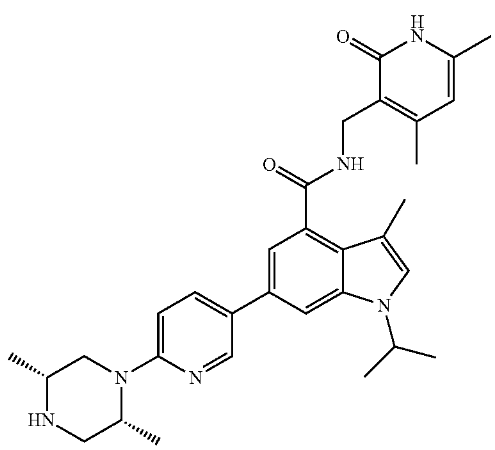 | N-((4,6-dimethyl-2-oxo-1,2-dihydropyridin-3-yl)methyl)-6-(6-((2R,5R)-2,5-dimethylpiperazin-1-yl)pyridin-3-yl)-1-isopropyl-3-methyl-1H-indole-4-carboxamide | (METHANOL-d4) 1.25 (d, 3 H), 1.31 (d, J = 6.32 Hz, 3 H), 1.49 (d, J = 6.57 Hz, 6 H), 2.23 (d, J = 10.11 Hz, 6 H), 2.43 (s, 3 H), 2.81 (dd, J = 13.39, 11.37 Hz, 1 H), 2.92-3.28 (m, 3 H), 4.16 (dd, J = 13.52, 3.16 Hz, 1 H), 4.62 (br. s., 1 H), 4.80 (quin, J = 6.69 Hz, 1 H), 6.12 (s, 1 H), 6.90 (d, J = 8.84 Hz, 1 H), 7.20 (s, 1 H), 7.27 (d, J = 1.52 Hz, 1 H), 7.63 (d, J = 1.26 Hz, 1 H), 7.92 (dd, J = 8.84, 2.53 Hz, 1 H), 8.44 (d, J = 2.27 Hz, 1 H) | 541.3 |

Example 347

N-((4,6-Dimethyl-2-oxo-1,2-dihydropyridin-3-yl)methyl)-1-isopropyl-3-methyl-6-(6-(pyrrolidin-1-ylmethyl)pyridin-3-yl)-1H-indole-4-carboxamide

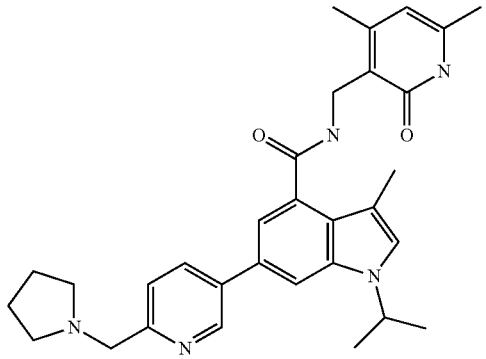 [SMILES: Cc1cc(C)c(CNC(=O)c2cc(-c3ccc(CN4CCCC4)nc3)cc3c2c(C)cn3C(C)C)c(=O)[nH]1]

To a solution of N-((4,6-dimethyl-2-oxo-1,2-dihydropyridin-3-yl)methyl)-6-(6-formylpyridin-3-yl)-1-isopropyl-3-methyl-1H-indole-4-carboxamide (100 mg, 0.219 mmol), in DCM (10 mL) and methanol (2 mL) was added pyrrolidine (0.035 mL, 0.438 mmol), followed by sodium sulfate (31.1 mg, 0.219 mmol). The reaction stirred at rt for 12 h, at which time sodium borohydride (16.57 mg, 0.438 mmol) was added and the reaction stirred rt for 2 h and 45° C. for 2 h. The reaction was quenched with water and extracted with EtOAc. The organic layer was evaporated. Purification by reverse phase Gilson HPLC (10-60% acetonitrile/water+0.1% TFA, YMC ODS-A C18 Column 75×30 mm ID S-5 um, 12 nM Column 7 minutes), followed by isolation and extraction with EtOAc/0.1 N NaOH provided N-((4,6-dimethyl-2-oxo-1,2-dihydropyridin-3-yl)methyl)-1-isopropyl-3-methyl-6-(6-(pyrrolidin-1-ylmethyl)pyridin-3-yl)-1H-indole-4-carboxamide, which was evaporated from the organic layer as a yellow foam solid (68 mg, 0.125 mmol, 57.0% yield). $^1$H NMR (400 MHz, DMSO-$d_6$) δ ppm 11.48 (br. s., 1H) 9.06 (d, J=2.02 Hz, 1H) 8.30 (dd, J=8.08, 2.27 Hz, 1H) 8.20 (t, J=5.18 Hz, 1H) 7.94 (d, J=1.26 Hz, 1H) 7.60 (d, J=8.08 Hz, 1H) 7.40 (s, 1H) 7.32 (s, 1H) 5.88 (s, 1H) 4.92-4.89 (m, 1H) 4.59 (d, J=5.56 Hz, 2H) 4.36 (d, J=5.05 Hz, 2H) 3.34 (br. s., 4H) 2.25 (s, 3H) 2.17 (d, J=1.01 Hz, 3H) 2.11 (s, 3H) 1.99 (br.s., 4H) 1.45 (d, J=6.57 Hz, 6H). LCMS: [M+H]$^+$=512.3.

Examples 348-350 were prepared by the methods described above for Example 347, or routine variations thereof, using the requisite amine:

| Ex | Structure | Name | $^1$H NMR (400 MHz, DMSO-$d_6$) δ ppm | MS(ES) [M + H]$^+$ | EZH2 pIC50 |
|---|---|---|---|---|---|
| 348 | 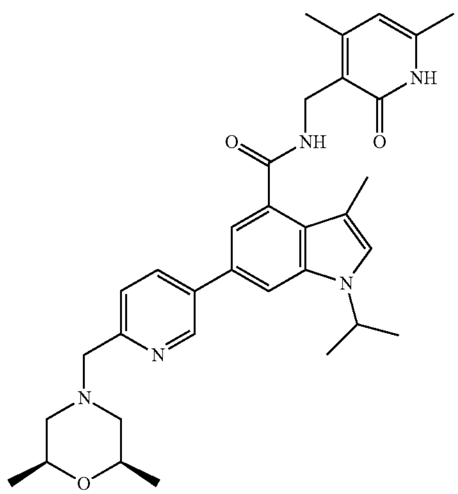 | 6-(6-{[(2R,6S)-2,6-dimethyl-4-morpholinyl]methyl}-3-pyridinyl)-N-[(4,6-dimethyl-2-oxo-1,2-dihydro-3-pyridinyl)methyl]-3-methyl-1-(1-methylethyl)-1H-indole-4-carboxamide | 11.48 (br. s., 1 H) 9.09 (d, J = 2.02 Hz, 1 H) 8.32 (dd, J = 8.08, 2.27 Hz, 1 H) 8.19 (t, J = 5.05 Hz, 1 H) 7.94 (d, J = 1.26 Hz, 1 H) 7.62 (d, J = 8.08 Hz, 1 H) 7.41 (s, 1 H) 7.33 (d, J = 1.52 Hz, 1 H) 5.88 (s, 1 H) 4.87-4.94 (m, 1 H) 4.52 (br. s., 2 H) 4.36 (d, J = 4.80 Hz, 2 H) 3.87-3.96 (m, 2 H) 3.35-3.45 (m, 2 H) 2.75-2.85 (m, 2 H) 2.25 (s, 3 H) 2.17 (s, 3 H) 2.11 (s, 3 H) 1.45 (d, J = 6.57 Hz, 6 H) 1.14 (d, J = 6.06 Hz, 6 H) | 556.4 | 7.44 |
| 349 | 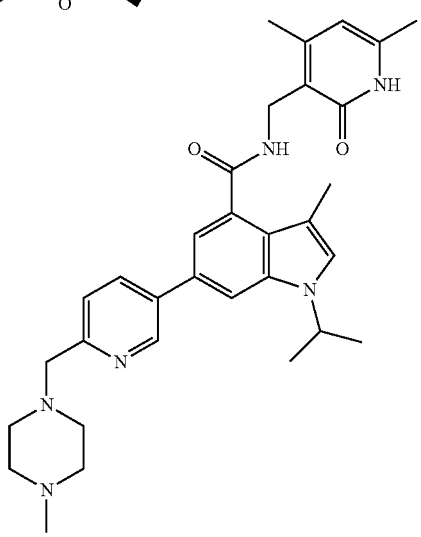 | N-[(4,6-dimethyl-2-oxo-1,2-dihydro-3-pyridinyl)methyl]-3-methyl-1-(1-methylethyl)-6-{6-[(4-methyl-1-piperazinyl)methyl-3-pyridinyl}-1H-indole-4-carboxamide | 11.50 (br. s., 1 H) 9.03 (d, J = 2.02 Hz, 1 H) 8.37 (dd, J = 8.08, 2.02 Hz, 1 H) 8.21 (t, J = 5.05 Hz, 1 H) 7.93 (d, J = 1.26 Hz, 1 H) 7.65 (d, J = 8.08 Hz, 1 H) 7.41 (s, 1 H) 7.32 (d, J = 1.52 Hz, 1 H) 5.88 (s, 1 H) 4.90 (quin, J = 6.63 Hz, 1 H) 4.36 (d, J = 5.05 Hz, 2 H) 4.08 (br. s., 2 H) 3.07-3.56 (m, 8 H) 2.83 (s, 3 H) 2.24-2.28 (m, 3 H) 2.17 (s, 3 H) 2.12 (s, 3 H) 1.45 (d, J = 6.57 Hz, 6 H) | 541.3 | 7.6 |

| Ex | Structure | Name | 1H NMR (400 MHz, DMSO-d6) δ ppm | MS(ES) [M + H]+ | EZH2 pIC50 |
|---|---|---|---|---|---|
| 350 | 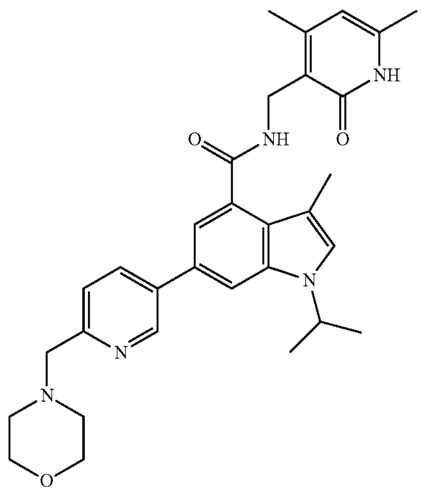 [SMILES: Cc1cc(C)c(CNC(=O)c2cc(-c3ccc(CN4CCOCC4)nc3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-[6-(4-morpholinylmethyl)-3-pyridinyl]-1H-indole-4-carboxamide | 11.49 (br. s., 1 H) 8.88 (d, J = 2.02 Hz, 1 H) 8.21 (t, J = 4.93 Hz, 1 H) 8.12 (dd, J = 8.08, 2.27 Hz, 1 H) 7.86 (d, J = 1.26 Hz, 1 H) 7.51 (d, J = 8.08 Hz, 1 H) 7.36 (s, 1 H) 7.27 (d, J = 1.52 Hz, 1 H) 5.87 (s, 1 H) 4.85-4.93 (m, 1 H) 4.36 (d, J = 4.80 Hz, 2 H) 3.62 (dd, J = 9.47, 4.93 Hz, 6 H) 2.45 (br. s., 4 H) 2.24 (s, 3 H) 2.18 (s, 3 H) 2.11 (s, 3 H) 1.44 (d, J = 6.57 Hz, 6 H) | 528.3 | 7.64 |

Example 351

6-Bromo-N-((6-(hydroxymethyl)-4-methyl-2-oxo-1,2-dihydropyridin-3-yl)methyl)-1-isopropyl-3-methyl-1H-indole-4-carboxamide

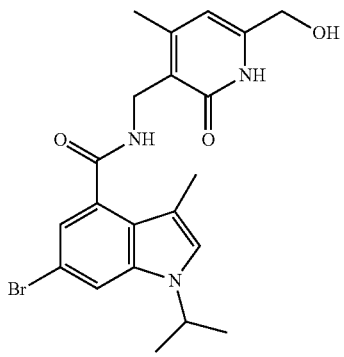 [SMILES: Cc1cc(CO)[nH]c(=O)c1CNC(=O)c1cc(Br)cc2c1c(C)cn2C(C)C]

a) 6-Bromo-N-((6-(hydroxymethyl)-2-methoxy-4-methylpyridin-3-yl)methyl)-1-isopropyl-3-methyl-1H-indole-4-carboxamide

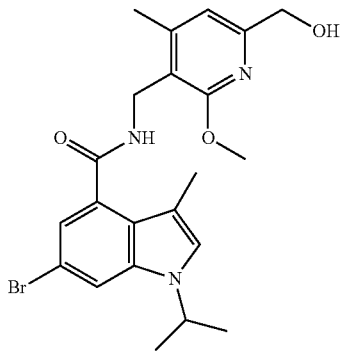 [SMILES: COc1nc(CO)cc(C)c1CNC(=O)c1cc(Br)cc2c1c(C)cn2C(C)C]

To a stirred solution of (5-(aminomethyl)-6-methoxy-4-methylpyridin-2-yl)methanol (0.29 g, 1.591 mmol), 6-bromo-1-isopropyl-3-methyl-1H-indole-4-carboxylic acid (0.48 g, 1.621 mmol), and HOAt (0.22 g, 1.616 mmol) in Dichloromethane (15 mL) and DMF (5 mL) was added EDC free base (0.30 g, 1.932 mmol). The reaction was stirred at RT for 3 h then evaporated to dryness under vacuum. The remaining was purified by silica gel chromatography (Analogix, SF25-60 g, 0 to 20% EtOAc in CH$_2$Cl$_2$) to give the product 6-bromo-N-((6-(hydroxymethyl)-2-methoxy-4-methylpyridin-3-yl)methyl)-1-isopropyl-3-methyl-1H-indole-4-carboxamide (0.73 g, 1.586 mmol, 100% yield) as a white solid. $^1$H NMR (400 MHz, DMSO-d$_6$) δ=8.46 (t, J=4.9 Hz, 1H), 7.77 (d, J=1.8 Hz, 1H), 7.33 (d, J=1.0 Hz, 1H), 6.99 (d, J=1.5 Hz, 1H), 6.90 (s, 1H), 5.31 (t, J=5.9 Hz, 1H), 4.74 (quin, J=6.6 Hz, 1H), 4.45 (d, J=5.1 Hz, 1H), 4.43 (d, J=5.8 Hz, 2H), 3.83 (s, 3H), 2.40 (s, 3H), 2.10 (s, 3H), 1.38 (d, J=6.8 Hz, 6H). MS (ES)+m/e 460.2 [M+H]$^+$.

b) 6-Bromo-N-((6-(hydroxymethyl)-4-methyl-2-oxo-1,2-dihydropyridin-3-yl)methyl)-1-isopropyl-3-methyl-1H-indole-4-carboxamide

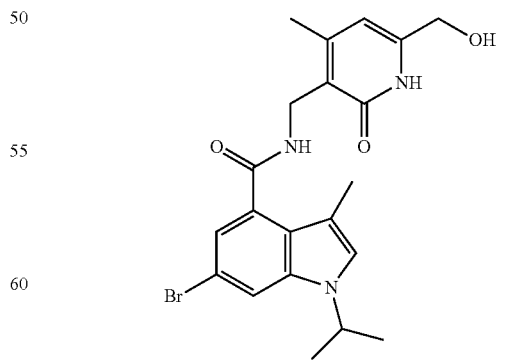

To a stirred solution of 6-bromo-N-((6-(hydroxymethyl)-2-methoxy-4-methylpyridin-3-yl)methyl)-1-isopropyl-3-methyl-1H-indole-4-carboxamide (500 mg, 1.086 mmol) in tetrahydrofuran (5 mL) was added 6 N HCl (15 mL, 15.00 mmol). The reaction was stirred under N₂ with heating at 80° C. for 18 hr. The reaction was cooled to RT and evaporated to dryness under vacuum. The remaining was purified by silica gel chromatography (Analogix, SF25-60 g, 4% MeOH in CH₂Cl₂). The pure fractions were combined and evaporated to dryness under vacuum. Triturated with a small volume of water, filtered, washed with water and dried under vacuum to give the product 6-bromo-N-((6-(hydroxymethyl)-4-methyl-2-oxo-1,2-dihydropyridin-3-yl)methyl)-1-isopropyl-3-methyl-1H-indole-4-carboxamide (189 mg, 0.423 mmol, 39.0% yield) as a white solid. $^1$H NMR (400 MHz, DMSO-d₆) δ=11.30 (s, 1H), 8.27 (t, J=4.9 Hz, 1H), 7.76 (d, J=1.8 Hz, 1H), 7.33 (s, 1H), 7.01 (d, J=1.8 Hz, 1H), 6.05 (s, 1H), 5.38 (t, J=5.9 Hz, 1H), 4.74 (dt, J=6.7, 13.2 Hz, 1H), 4.32 (d, J=5.1 Hz, 2H), 4.25 (d, J=5.8 Hz, 2H), 2.26 (s, 3H), 2.13 (s, 3H), 1.39 (d, J=6.6 Hz, 6H). MS (ES)+m/e 446.1 [M+H]⁺.

Example 352

N-((6-(aminomethyl)-4-methyl-2-oxo-1,2-dihydropyridin-3-yl)methyl)-6-bromo-1-isopropyl-3-methyl-1H-indole-4-carboxamidE

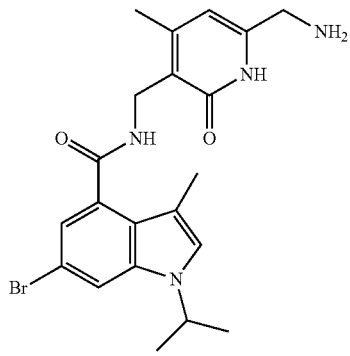 [SMILES: Cc1cc(CN)[nH]c(=O)c1CNC(=O)c1cc(Br)cc2c1c(C)cn2C(C)C]

a) tert-Butyl((5-((6-bromo-1-isopropyl-3-methyl-1H-indole-4-carboxamido)methyl)-6-methoxy-4-methylpyridin-2-yl)methyl)carbamate

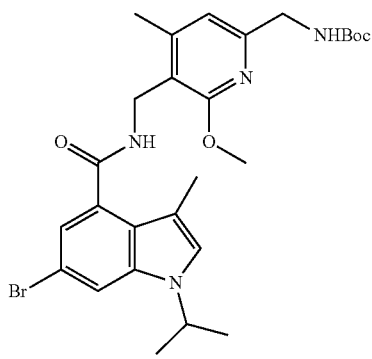 [SMILES: COc1nc(CNC(=O)OC(C)(C)C)cc(C)c1CNC(=O)c1cc(Br)cc2c1c(C)cn2C(C)C]

To a stirred solution of tert-butyl((5-(aminomethyl)-6-methoxy-4-methylpyridin-2-yl)methyl)carbamate (0.55 g, 1.955 mmol), 6-bromo-1-isopropyl-3-methyl-1H-indole-4-carboxylic acid (0.63 g, 2.127 mmol), and HOAt (0.27 g, 1.984 mmol) in Dichloromethane (20 mL) and DMF (5 mL) was added EDC free base (0.34 g, 2.190 mmol). The reaction was stirred at RT for 2 hr then evaporated to dryness under vacuum. The remaining was purified by silica gel chromatography (Analogix, SF25-60 g, 0 to 40% EtOAc in hexanes) to give the product tert-butyl((5-((6-bromo-1-isopropyl-3-methyl-1H-indole-4-carboxamido)methyl)-6-methoxy-4-methylpyridin-2-yl)methyl)carbamate (1.07 g, 1.912 mmol, 98% yield) as a white solid. $^1$H NMR (400 MHz, DMSO-d₆) δ=8.47 (t, J=4.8 Hz, 1H), 7.76 (d, J=1.8 Hz, 1H), 7.35 (t, 1H), 7.33 (d, J=1.0 Hz, 1H), 6.99 (d, J=1.5 Hz, 1H), 6.67 (s, 1H), 4.74 (quin, J=6.6 Hz, 1H), 4.44 (d, J=4.8 Hz, 2H), 4.08 (d, J=6.3 Hz, 2H), 3.85 (s, 3H), 2.37 (s, 3H), 2.10 (s, 3H), 1.41 (s, 9H), 1.38 (d, J=6.6 Hz, 6H). MS (ES)+m/e 559.3 [M+H]⁺.

b) N-((6-(Aminomethyl)-4-methyl-2-oxo-1,2-dihydropyridin-3-yl)methyl)-6-bromo-1-isopropyl-3-methyl-1H-indole-4-carboxamide

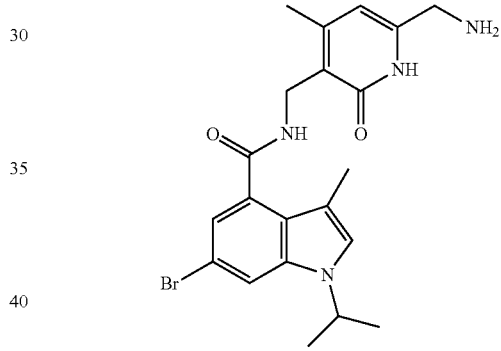

To a stirred solution of tert-butyl((5-((6-bromo-1-isopropyl-3-methyl-1H-indole-4-carboxamido)methyl)-6-methoxy-4-methylpyridin-2-yl)methyl)carbamate (500 mg, 0.894 mmol) in Tetrahydrofuran (THF) (5 mL) was added 6N HCl (15 mL, 15.00 mmol). The reaction was stirred under N2 with heating at 80° C. for 18 hr. The reaction was cooled to RT and evaporated to dryness under vacuum. The remaining was purified by silica gel chromatography (Analogix, SF25-40 g, 0 to 10% (5% NH4OH in MeOH) in CH2Cl2). The pure fractions were combined and evaporated to dryness under vacuum. Dissolved with a small volume of CH2Cl2, scratched out by slowly adding hexanes, filtered, washed with hexanes and dried under vacuum to give the product N-((6-(aminomethyl)-4-methyl-2-oxo-1,2-dihydropyridin-3-yl)methyl)-6-bromo-1-isopropyl-3-methyl-1H-indole-4-carboxamide (328 mg, 0.736 mmol, 82% yield) as an off-white solid. $^1$H NMR (400 MHz, DMSO-d₆) δ=8.26 (t, J=5.1 Hz, 1H), 7.76 (d, J=1.8 Hz, 1H), 7.33 (d, J=1.0 Hz, 1H), 7.01 (d, J=1.5 Hz, 1H), 6.01 (s, 1H), 5.77 (s, 0H), 4.74 (quin, J=6.6

Hz, 1H), 4.32 (d, J=5.1 Hz, 2H), 3.46 (s, 2H), 2.25 (s, 3H), 2.14 (s, 3H), 1.39 (d, J=6.8 Hz, 6H). MS (ES)+m/e 445.2 [M+H]+.

Example 353

3-Methyl-1-(1-methylethyl)-4-({[(6-methyl-2-oxo-4-propyl-1,2-dihydro-3-pyridinyl)methyl]amino}carbonyl)-1H-indole-6-carboxylic acid

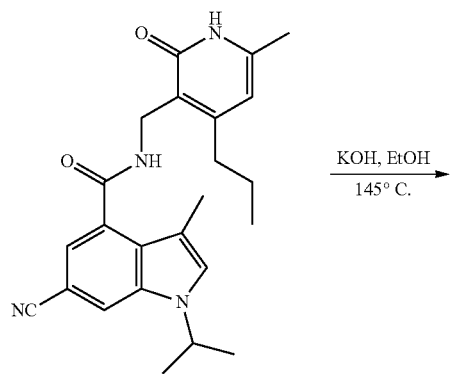

To a 5 ml microwave vial was added, 6-cyano-3-methyl-1-(1-methylethyl)-N-[(6-methyl-2-oxo-4-propyl-1,2-dihydro-3-pyridinyl)methyl]-1H-indole-4-carboxamide (100 mg, 0.247 mmol), KOH (41.6 mg, 0.742 mmol) was ground and added followed by Ethanol (8 mL) the reaction was microwaved at 145° C. for 22 hr. The reaction was poured onto acidic Ice water (20 mL) and was stirred for 20 min. EtOAc was added and the mix was stirred an additional 10 min. The layers were separated and the majority of the product was in the EtOAc which was evaporated. The residue was dissolved in MeOH (1 mL) and material was crashed out with ice and was filtered to give product 3-methyl-1-(1-methylethyl)-4-({[(6-methyl-2-oxo-4-propyl-1,2-dihydro-3-pyridinyl)methyl]amino}carbonyl)-1H-indole-6-carboxylic acid (70 mg, 0.160 mmol, 64.9% yield) $^1$H NMR (400 MHz, DMSO-$d_6$) δ ppm 11.49 (br. s., 1H) 8.18 (s, 1H) 8.10 (s, 1H) 7.53 (d, J=7.58 Hz, 2H) 5.90 (s, 1H) 4.76-4.90 (m, 1H) 4.36 (d, J=4.80 Hz, 2H) 2.55 (br. s., 1H) 2.18 (s, 3H) 2.13 (s, 3H) 1.52-1.61 (m, 2H) 1.44 (d, J=6.57 Hz, 6H) 0.94 (t, J=7.33 Hz, 3H) MS (ES) [M+H]+ 423.8

Example 354

3-[3-Methyl-1-(1-methylethyl)-4-({[(6-methyl-2-oxo-4-propyl-1,2-dihydro-3-pyridinyl)methyl]amino}carbonyl)-1H-indol-6-yl]propanoic acid

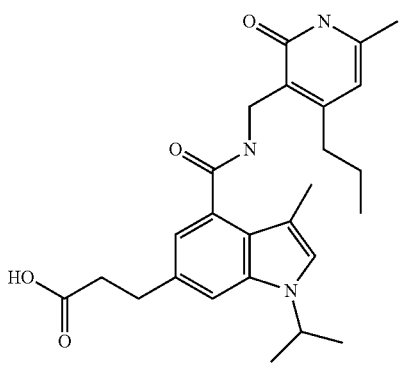 [SMILES: CCCc1cc(C)[nH]c(=O)c1CNC(=O)c1cc(CCC(=O)O)cc2c1c(C)cn2C(C)C]

a) Ethyl (2E)-3-[3-methyl-1-(1-methylethyl)-4-({[(6-methyl-2-oxo-4-propyl-1,2-dihydro-3-pyridinyl)methyl]amino}carbonyl)-1H-indol-6-yl]-2-propenoate

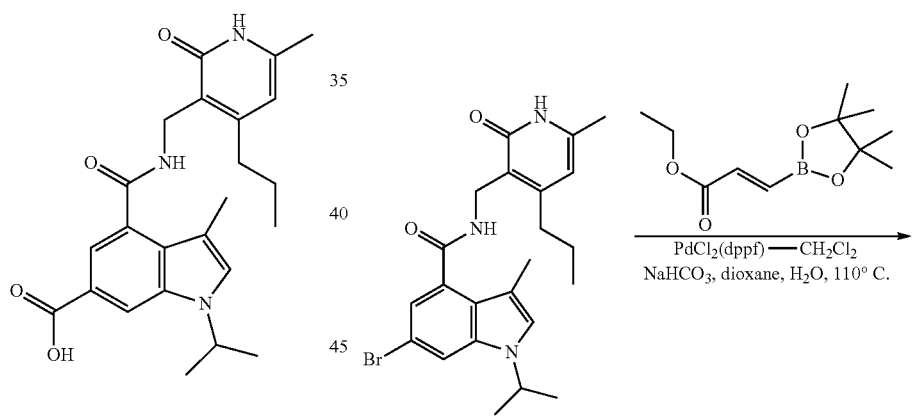

Following the general procedure detailed above for Suzuki cross-couplings (see Example 2), ethyl (2E)-3-[3-methyl-1-(1-methylethyl)-4-({[(6-methyl-2-oxo-4-propyl-1,2-dihydro-3-pyridinyl)methyl]amino}carbonyl)-1H-indol-6-yl]-2-propenoate (120 mg, 0.234 mmol, 53.6% yield) was prepared. $^1$H NMR (400 MHz, DMSO-$d_6$) δ ppm 11.49 (s, 1H) 8.12 (t, J=4.93 Hz, 1H) 7.97 (d, J=1.01 Hz, 1H) 7.74 (d, J=15.92 Hz, 1H) 7.43 (s, 1H) 7.27 (d, J=1.26 Hz, 1H) 6.61 (d, J=15.92 Hz, 1H) 5.90 (s, 1H) 4.78-4.86 (m, 1H) 4.35 (d, J=5.05 Hz, 2H) 4.19 (q, J=7.07 Hz, 2H) 2.53-2.58 (m, 2H) 2.14 (d, J=11.12 Hz, 6H) 1.53-1.62 (m, 2H) 1.43 (d, J=6.82 Hz, 6H) 1.27 (t, J=7.07 Hz, 3H) 0.93-0.97 (m, 3H). MS (ES) [M+H]+ 477.9 b) Ethyl 3-[3-methyl-1-(1-methylethyl)-4-({[(6-methyl-2-oxo-4-propyl-1,2-dihydro-3-pyridinyl)methyl]amino}carbonyl)-1H-indol-6-yl]propanoate

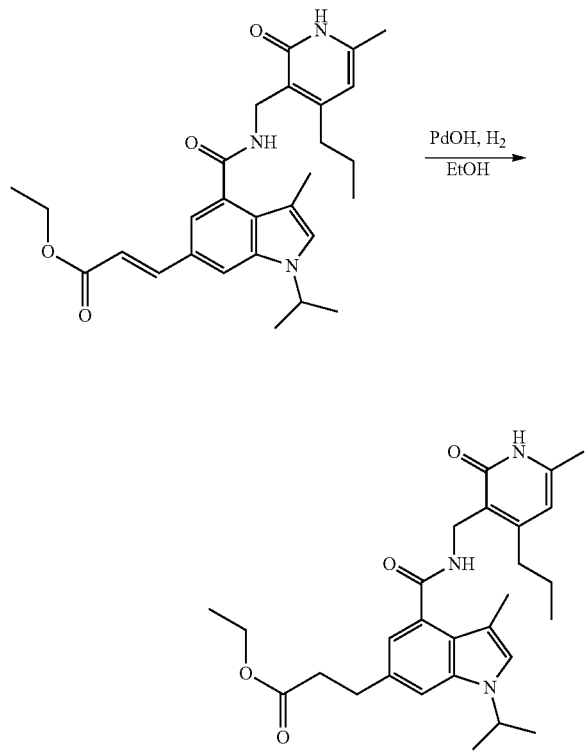

In a 50 ml flask was added ethyl (2E)-3-[3-methyl-1-(1-methylethyl)-4-({[(6-methyl-2-oxo-4-propyl-1,2-dihydro-3-pyridinyl)methyl]amino}carbonyl)-1H-indol-6-yl]-2-propenoate (120 mg, 0.251 mmol), and Ethanol (10 mL). PdOH2 (70.6 mg, 0.503 mmol) was added and the reaction was degassed with N2 for 15 min then H2 was bubbled in (via balloon) and the reaction stirred for 12 hr. The reaction was purged with N2 for 30 min and then filtered through an acro disc and evaporated. The residue was suspended in MeOH/Water (2 mL/4 mL) and filtered and washed with water to give a white solid. ethyl 3-[3-methyl-1-(1-methylethyl)-4-({[(6-methyl-2-oxo-4-propyl-1,2-dihydro-3-pyridinyl)methyl]amino}carbonyl)-1H-indol-6-yl]propanoate (70 mg, 0.146 mmol, 58.1% yield). 1H NMR (400 MHz, DMSO-d6) δ ppm 11.49 (br. s., 1H) 7.90 (br. s., 1H) 7.34 (s, 1H) 7.21 (s, 1H) 6.82 (s, 1H) 5.90 (s, 1H) 4.63-4.73 (m, 1H) 4.34 (d, J=4.55 Hz, 2H) 4.04 (q, J=7.07 Hz, 2H) 2.92 (t, J=7.33 Hz, 2H) 2.64 (t, J=7.45 Hz, 2H) 2.55-2.62 (m, 2H) 2.12 (s, 6H) 1.52-1.62 (m, 2H) 1.40 (d, J=6.32 Hz, 6H) 1.16 (t, J=7.07 Hz, 3H) 0.94 (t, J=7.20 Hz, 3H). MS (ES) [M+H]+ 479.8.

c) 3-[3-Methyl-1-(1-methylethyl)-4-({[(6-methyl-2-oxo-4-propyl-1,2-dihydro-3-pyridinyl)methyl]amino}carbonyl)-1H-indol-6-yl]propanoic acid

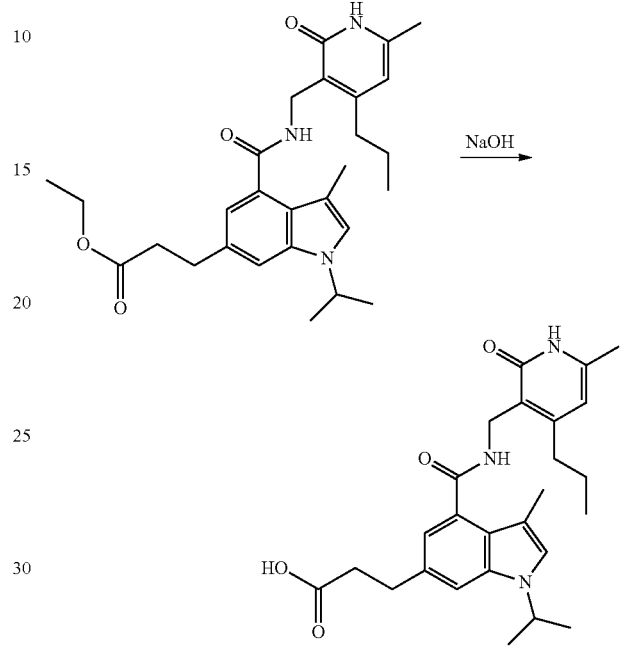

Following the general procedure procedure detailed above for Suzuki cross-couplings (see Example 2), 3-[3-methyl-1-(1-methylethyl)-4-({[(6-methyl-2-oxo-4-propyl-1,2-dihydro-3-pyridinyl)methyl]amino}carbonyl)-1H-indol-6-yl]propanoic acid (45 mg, 0.095 mmol, 64.9% yield) was prepared. 1H NMR (400 MHz, DMSO-d6) δ ppm 12.05 (br.s, 1H) 11.49 (br. s., 1H) 7.88-7.95 (m, 1H) 7.34 (s, 1H) 7.20 (s, 1H) 6.82 (s, 1H) 5.90 (s, 1H) 4.64-4.73 (m, 1H) 4.34 (d, J=4.80 Hz, 2H) 2.89 (t, J=7.71 Hz, 2H) 2.55-2.60 (m, 4H) 2.12 (s, 6H) 1.53-1.61 (m, 2H) 1.40 (d, J=6.57 Hz, 6H) 0.92-0.96 (m, 3H). MS (ES) [M+H]+ 451.9.

Example 355

6-(2-Aminoethyl)-N-[(4,6-dimethyl-2-oxo-1,2-dihydro-3-pyridinyl)methyl]-3-methyl-1-(1-methylethyl)-1H-indole-4-carboxamide

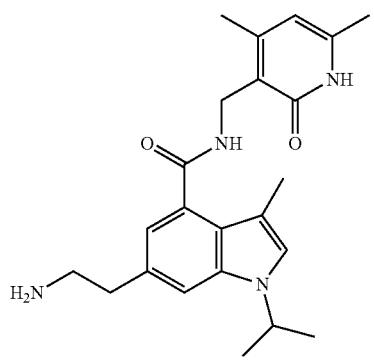 [SMILES: Cc1cc(C)c(CNC(=O)c2cc(CCN)cc3c2c(C)cn3C(C)C)c(=O)[nH]1]

247 a) 6-[2-({[(1,1-Dimethylethyl)oxy]carbonyl}amino) ethyl]-3-methyl-1-(1-methylethyl)-1H-indole-4-carboxylic acid

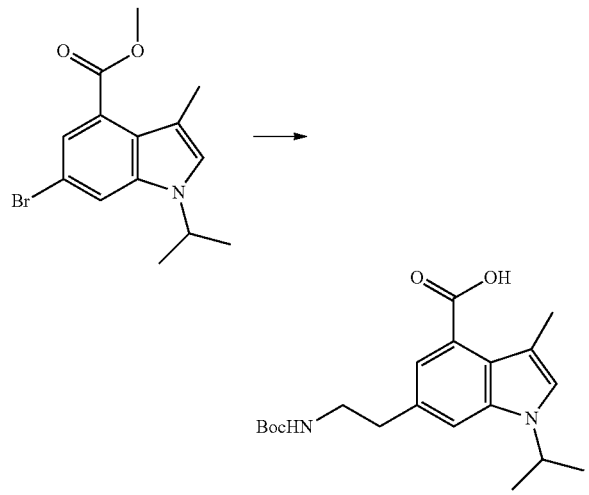

In a glass pressure bottle was added methyl 6-bromo-3-methyl-1-(1-methylethyl)-1H-indole-4-carboxylate (1.00 g, 2.77 mmol), potassium t-butyl-N-[2-(trifluoroboranuidyl) ethyl]carbamate (900 mg, 3.58 mmol), cesium carbonate (3.2 g, 9.82 mmol), toluene (24 mL) and water (8 mL). The mixture was stirred and purged with N2. To the reaction was added palladium(II) acetate (40 mg, 0.178 mmol) and RuPhos (160 mg, 0.342 mmol), the reaction capped and stirred at 95° C. for 18 hr. LCMS showed that the reaction was complete. The reaction was taken up in EtOAc, diluted with water, and filtered to remove insolubles. The organic phase was removed, dried (MgSO4), filtered and concentrated under vacuum. Purification by silica gel chromatography (Analogix, SF25-60 g, 0 to 20% EtOAc in hexanes gave the methyl ester.

To the ester in THF (10 mL) and MeOH (30 mL) was added 1 N NaOH (10 mL, 10 mmol). The solution was stirred at reflux 80° C. for 24 hr (slow saponification). After cooling to RT the reaction was concentrated under vacuum, neutralized with 1 N HCl (10 mL), triturated with water, filtered and dried under vacuum to give the product 6-[2-({[(1,1-dimethylethyl) oxy]carbonyl}amino)ethyl]-3-methyl-1-(1-methylethyl)-1H-indole-4-carboxylic acid (865 mg, 2.31 mmol, 83.0% yield) as a white solid. $^1$H NMR (400 MHz, DMSO-$d_6$) δ 12.69 (br. s., 1H), 7.43 (s, 1H), 7.31 (s, 1H), 7.25 (s, 1H), 6.89 (t, J=5.6 Hz, 1H), 4.71 (dt, J=6.6, 13.3 Hz, 1H), 3.23-3.10 (m, 2H), 2.80 (t, J=7.3 Hz, 2H), 2.30 (s, 3H), 1.42 (d, J=6.6 Hz, 6H), 1.37 (s, 9H). MS (ES)+m/e 361.2 [M+H]$^+$.

b) 6-(2-Aminoethyl)-N-[(4,6-dimethyl-2-oxo-1,2-dihydro-3-pyridinyl)methyl]-3-methyl-1-(1-methylethyl)-1H-indole-4-carboxamide hydrochloride salt

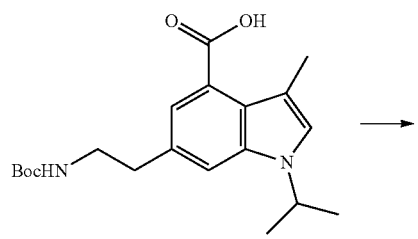

248

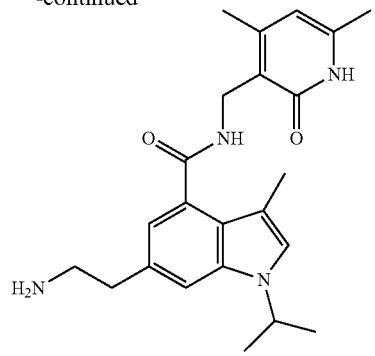

To a stirred suspension of 6-[2-({[(1,1-dimethylethyl)oxy] carbonyl}amino)ethyl]-3-methyl-1-(1-methylethyl)-1H-indole-4-carboxylic acid (500 mg, 1.387 mmol), 3-(aminomethyl)-4,6-dimethyl-2(1H)-pyridinone HCl salt (340 mg, 1.802 mmol), HOAt (245 mg, 1.800 mmol) in DMF (20 mL) was added N-methylmorpholine (200 μL, 1.819 mmol) and EDC free base (280 mg, 1.804 mmol). The reaction was stirred overnight at RT. LCMS showed that the reaction was complete. The reaction was evaporated to dryness and purified by silica gel chromatography (Analogix, SF25-40 g, 0 to 10% CH$_2$Cl$_2$/20% (5% NH$_4$OH in MeOH) in CH$_2$Cl$_2$). The pure fractions were combined and evaporated to dryness. Triturated with 50% MeOH in water, filtered and dried under vacuum to give the Boc protected product as an off-white solid. The Boc protected product was suspended in a small volume of MeOH (2 mL) and treated with 4 N HCl in dioxane (25 mL) and stirred at RT for 1 hr. LCMS showed that the reaction was complete. The reaction was evaporated to dryness, triturated with Et$_2$O, filtered and dried under vacuum to give the product 6-(2-aminoethyl)-N-[(4,6-dimethyl-2-oxo-1,2-dihydro-3-pyridinyl)methyl]-3-methyl-1-(1-methylethyl)-1H-indole-4-carboxamide (460 mg, 1.067 mmol, 77% yield) as an off-white solid. $^1$H NMR (400 MHz, DMSO-$d_6$+ D$_2$O) δ 8.05 (t, J=5.2 Hz, 1H), 8.00 (br. s., 2H), 7.39 (d, J=1.0 Hz, 1H), 7.25 (s, 1H), 6.86 (d, J=1.3 Hz, 1H), 5.93 (s, 1H), 4.69 (dt, J=6.6, 13.3 Hz, 1H), 4.34 (d, J=5.1 Hz, 2H), 3.06 (dd, J=5.8, 7.6 Hz, 2H), 3.01-2.91 (m, 2H), 2.25 (s, 3H), 2.13 (s, 3H), 2.12 (s, 3H), 1.41 (d, J=6.8 Hz, 6H). MS (ES)+m/e 394.9 [M+H]$^+$.

Example 356

6-{3-[(Dimethylamino)methyl]-4-fluorophenyl}-N-[(4,6-dimethyl-2-oxo-1,2-dihydro-3-pyridinyl)methyl]-3-methyl-1-(1-methylethyl)-1H-indole-4-carboxamide

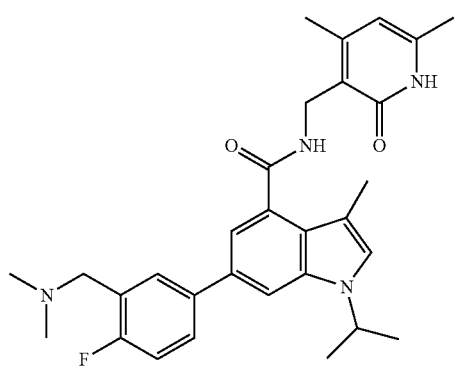

a) Methyl 6-(4-fluoro-3-formylphenyl)-3-methyl-1-(1-methylethyl)-1H-indole-4-carboxylate

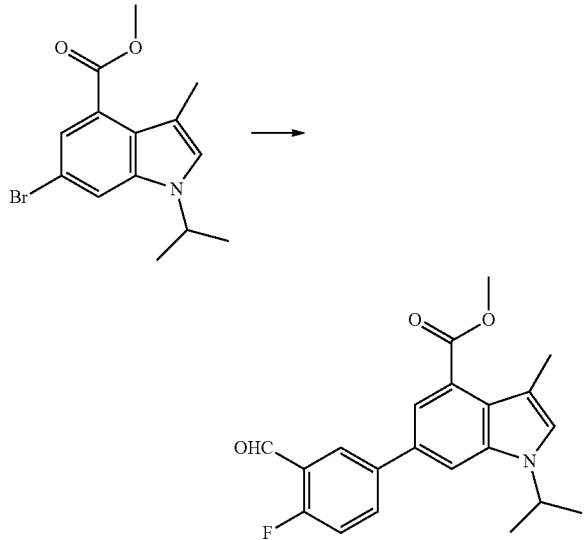

To a glass pressure vessel was added methyl 6-bromo-3-methyl-1-(1-methylethyl)-1H-indole-4-carboxylate (500 mg, 1.612 mmol), 4-fluoro-3-formylbenzeneboronic acid (375 mg, 2.233 mmol), Potassium phosphate (1.1 g, 5.18 mmol), dioxane (12 mL) and water (3 mL). The reaction was purged with $N_2$ and charged with $PdCl_2(dppf)$-$CH_2Cl_2$ adduct (120 mg, 0.147 mmol). The reaction was capped and stirred at 110° C. for 4 hr. LCMS showed that the reaction was complete. The reaction was diluted with water, extracted with EtOAc, washed with brine, dried ($MgSO_4$), filtered, and concentrated under vacuum. Purification by silica gel chromatography (Analogix, SF25-60 g, 0 to 50% EtOAc in hexanes) gave the product methyl 6-(4-fluoro-3-formylphenyl)-3-methyl-1-(1-methylethyl)-1H-indole-4-carboxylate (560 mg, 1.585 mmol, 98% yield) as an off-white solid. $^1$H NMR (400 MHz, DMSO-$d_6$) δ=10.30 (s, 1H), 8.24-8.13 (m, 2H), 8.10 (d, J=1.5 Hz, 1H), 7.75 (d, J=1.8 Hz, 1H), 7.57-7.46 (m, 2H), 4.98 (quip, J=6.6 Hz, 1H), 3.91 (s, 3H), 2.31 (s, 3H), 1.46 (d, J=6.6 Hz, 6H). MS (ES)+m/e 354.2 [M+H]$^+$.

b) 6-{3-[(Dimethylamino)methyl]-4-fluorophenyl}-3-methyl-1-(1-methylethyl)-1H-indole-4-carboxylic acid

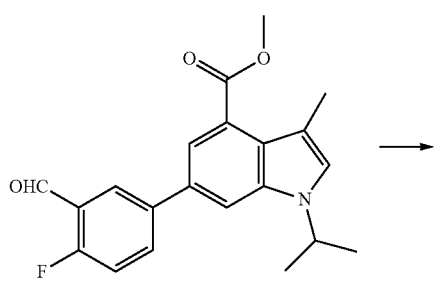

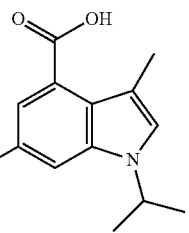

To a stirred solution of methyl 6-(4-fluoro-3-formylphenyl)-3-methyl-1-(1-methylethyl)-1H-indole-4-carboxylate (550 mg, 1.556 mmol) in $CH_2Cl_2$ (25 mL) was added 2N dimethylamine in THF (3.0 mL, 6.00 mmol) and acetic acid (170 µL, 2.97 mmol). After stirring at RT for 1 hr sodium triacetoxyborohydride (1.0 g, 4.72 mmol) was added portionwise over 10 minutes. The reaction was stirred at RT overnight. LCMS showed the product as well as a substantial amount of the alcohol and one unidentifiable side product. The reaction was purified by silica gel chromatography (Analogix, SF25-60 g, 0 to 50% $CH_2Cl_2$/20% (5% $NH_4OH$ in MeOH) in $CH_2Cl_2$). The last fraction contained the desired product and was combined and evaporated to dryness. Trituration with hexanes, filtration and drying under vacuum gave the methyl ester product (0.25 g, 0.65 mMol, 41%) as an off-white solid.

The ester was taken up in THF (15 mL) and MeOH (5 mL) and treated with 1 N NaOH (4 mL). The reaction was refluxed (80° C. oil bath) overnight. LCMS showed that the reaction was complete. The reaction was cooled to RT and concentrated under vacuum. Neutralization with 1 N HCl (4 mL) ppt. out the product, which was triturated with a small amount of cold water, filtered, and dried under vacuum to give the product 6-{3-[(dimethylamino)methyl]-4-fluorophenyl}-3-methyl-1-(1-methylethyl)-1H-indole-4-carboxylic acid (210 mg, 0.570 mmol, 36.6% yield) as a white solid. $^1$H NMR (400 MHz, DMSO-$d_6$) δ=12.84 (br. s., 1H), 10.80 (br. s., 1H), 8.18 (dd, J=2.0, 7.1 Hz, 1H), 8.12 (s, 1H), 8.01-7.85 (m, 1H), 7.76 (d, J=1.3 Hz, 1H), 7.49 (s, 1H), 7.43 (t, J=9.1 Hz, 1H), 4.95 (dt, J=6.6, 13.1 Hz, 1H), 4.43 (br. s., 2H), 2.80 (s, 6H), 2.34 (s, 3H), 1.46 (d, J=6.6 Hz, 6H). MS (ES)+m/e 369.0 [M+H]$^+$.

c) 6-{3-[(Dimethylamino)methyl]-4-fluorophenyl}-N-[(4,6-dimethyl-2-oxo-1,2-dihydro-3-pyridinyl)methyl]-3-methyl-1-(1-methylethyl)-1H-indole-4-carboxamide

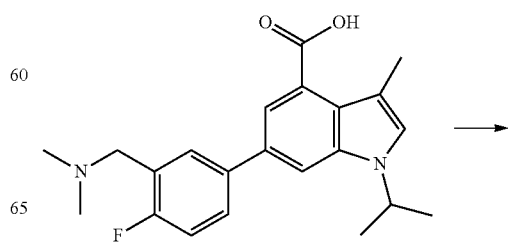

251
-continued

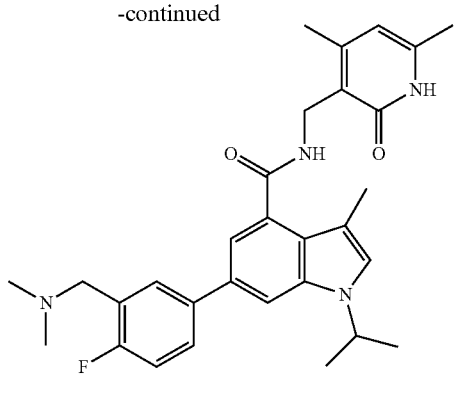

To a stirred suspension of 6-{3-[(dimethylamino)methyl]-4-fluorophenyl}-3-methyl-1-(1-methylethyl)-1H-indole-4-carboxylic acid (210 mg, 0.570 mmol), 3-(aminomethyl)-4,6-dimethyl-2(1H)-pyridinone HCl salt (140 mg, 0.742 mmol) and HOAt (100 mg, 0.735 mmol) in DMF (15 mL) was added N-methylmorpholine (82 μl, 0.746 mmol) and EDC free base (110 mg, 0.709 mmol). The reaction was stirred for 4 h at RT and concentrated to near dryness under vacuum. Water was added till the product ppt. out. The suspension was triturated, filtered, rinsed with cold water water then dried under vacuum to give the product 6-{3-[(dimethylamino)methyl]-4-fluorophenyl}-N-[(4,6-dimethyl-2-oxo-1,2-dihydro-3-pyridinyl)methyl]-3-methyl-1-(1-methylethyl)-1H-indole-4-carboxamide (186 mg, 0.370 mmol, 64.9% yield) as a light tan solid. $^1$H NMR (400 MHz, DMSO-$d_6$) δ=11.47 (br. s., 1H), 8.15 (t, J=4.9 Hz, 1H), 8.04 (d, J=5.3 Hz, 1H), 7.90-7.86 (m, 1H), 7.39 (t, J=9.2 Hz, 1H), 7.35 (s, 1H), 7.27 (d, J=1.3 Hz, 1H), 5.87 (s, 1H), 4.88 (dt, J=6.6, 13.3 Hz, 1H), 4.36 (d, J=5.1 Hz, 2H), 4.26 (br. s., 2H), 2.69 (s, 6H), 2.24 (s, 3H), 2.17 (s, 3H), 2.11 (s, 3H), 1.44 (d, J=6.6 Hz, 6H). MS (ES)+m/e 503.0 [M+H]$^+$.

252

Example 357

6-(4,5-Dihydro-1H-imidazol-2-yl)-N-((4,6-dimethyl-2-oxo-1,2-dihydropyridin-3-yl)methyl)-1-isopropyl-3-methyl-1H-indole-4-carboxamide

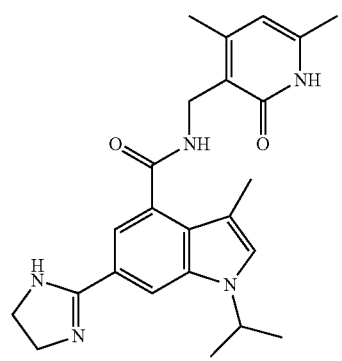 [SMILES: Cc1cc(C)c(CNC(=O)c2cc(C3=NCCN3)cc3c2c(C)cn3C(C)C)c(=O)[nH]1]

To a 10-mL microwave tube were added 6-cyano-N-((4,6-dimethyl-2-oxo-1,2-dihydropyridin-3-yl)methyl)-1-isopropyl-3-methyl-1H-indole-4-carboxamide (33 mg, 0.088 mmol), ethylenediamine (1 mL, 14.81 mmol), and phosphorus pentasulfide (0.585 mg, 2.63 mmol), and the mixture was degassed for 5 min. The tube was sealed and the mixture was heated at 120° C. in a microwave. The mixture was concentrated and the residue was purified using reverse-phase HPLC under acidic conditions to give 32 mg of product as off-white solid. $^1$H NMR (400 MHz, DMSO-$d_6$) ppm 1.46 (m, 6H), 2.11 (s, 3H), 2.17 (s, 3H), 2.24 (s, 3H), 4.35 (d, J=5.05 Hz, 2H), 4.75 (quin, J=6.69 Hz, 1H), 5.87 (s, 1H), 7.49-7.60 (m, 2H), 8.16-8.26 (m, 2H), 8.39 (s, 1H). MS: (M+H)$^+$=419.9.

Examples 358-366 were prepared following the general methods described above and/or well established synthetic procedures:

| Ex | Structure | Name | $^1$H NMR (400 MHz, DMSO-$d_6$) δ ppm | MS(ES) [M + H]$^+$ | EZH2 pIC50 |
|---|---|---|---|---|---|
| 358 | ![structure] | [4-({[(4,6-dimethyl-2-oxo-1,2-dihydro-3-pyridinyl)methyl]amino}carbonyl)-3-methyl-1-(1-methylethyl)-1H-indol-6-yl]boronic acid | 11.48 (br. s., 1H), 8.04 (s, 2H), 7.95 (s, 1H), 7.88 (5, J = 5.05 Hz, 1H), 7.40 (s, 1H), 7.31 (s, 1H), 5.87 (s, 1 H), 4.64-4.76 (m, 1H), 4.34 (d, J = 5.05 Hz, 2H), 2.23 (s, 3H), 2.15 (s, 3H), 2.11 (s, 3H), 1.44 (d, J = 6.57 Hz, 6H) | 396.3 | 6.33 |

| Ex | Structure | Name | ¹H NMR (400 MHz, DMSO-d₆) δ ppm | MS(ES) [M + H]⁺ | EZH2 pIC50 |
|---|---|---|---|---|---|
| 359 | 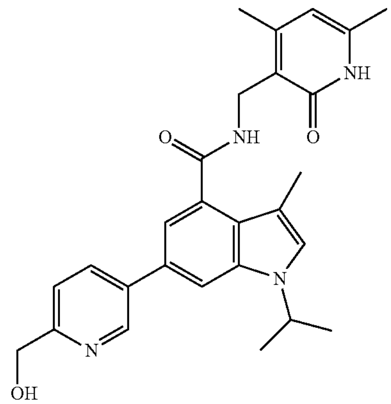 [SMILES: Cc1cc(C)c(CNC(=O)c2cc(-c3ccc(CO)nc3)cc3c2c(C)cn3C(C)C)c(=O)[nH]1] | N-[(4,6-dimethyl-2-oxo-1,2-dihydro-3-pyridinyl)methyl]-6-[6-(hydroxymethyl)-3-pyridinyl]-3-methyl-1-(1-methylethyl)-1H-indole-4-carboxamide | 11.51 (br. s., 1 H) 9.01 (br. s., 1 H) 8.55 (br. s., 1 H) 8.23 (t, J = 5.18 Hz 1 H) 7.99 (s, 1 H) 7.79 (d, J = 8.08 Hz, 1 H) 7.41 (s, 1 H) 7.35 (d, J = 1.26 Hz, 1 H) 5.88 (s, 1 H) 4.86-4.98 (m, 1 H) 4.76 (s, 2 H) 4.36 (d, J = 5.05 Hz, 2 H) 2.25 (s, 3 H) 2.17 (s, 3 H) 2.11 (s, 3 H) 1.45 (d, J = 6.57 Hz, 6 H) | 459.1 | 7.23 |
| 360 | 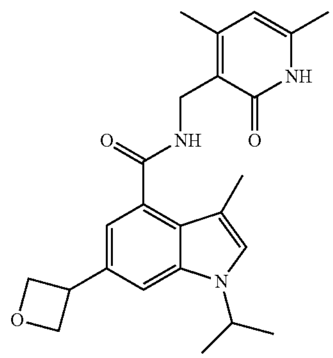 [SMILES: Cc1cc(C)c(CNC(=O)c2cc(C3COC3)cc3c2c(C)cn3C(C)C)c(=O)[nH]1] | N-[(4,6-dimethyl-2-oxo-1,2-dihydro-3-pyridinyl)methyl]-3-methyl-1-(1-methylethyl)-6-(3-oxetanyl)-1H-indole-4-carboxamide | 1.41 (d, J = 6.57 Hz, 6 H), 2.11 (s, 3 H), 2.14 (s, 3 H), 2.23 (s, 3 H), 4.30-4.39 (m, 3 H), 4.67-4.81 (m, 3 H), 4.96 (dd, J = 8.46, 5.68 Hz, 2 H), 5.87 (s, 1 H), 7.03 (d, J = 1.26 Hz, 1 H), 7.25 (d, J = 1.01 Hz, 1 H), 7.48 (d, J = 1.26 Hz, 1 H), 8.05 (t, J = 5.05 Hz, 1 H), 11.47 (br. s., 1 H). | 408 | 6.54 |
| 361 | 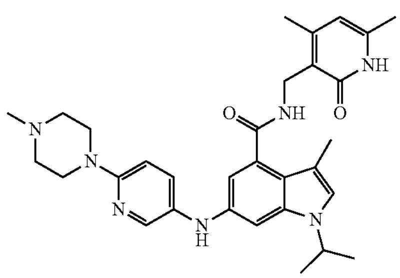 | N-[(4,6-dimethyl-2-oxo-1,2-dihydro-3-pyridinyl)methyl]-3-methyl-1-(1-methylethyl)-6-{[6-(4-methyl-1-piperazinyl)-3-pyridinyl]amino}-1H-indole-4-carboxamide | 1.36 (m, 6 H), 2.08 (s, 3 H), 2.11 (s, 3 H), 2.21 (s, 3 H), 2.24 (s, 3 H), 2.40-2.47 (m, 4 H), 3.33-3.42 (m, 4 H), 4.30 (d, J = 5.05 Hz, 2 H), 4.47 (quin, J = 6.63 Hz, 1 H), 5.86 (s, 1 H), 6.60 (d, J = 2.02 Hz, 1 H), 6.81 (d, J = 8.84 Hz, 1 H), 6.88 (d, J = 1.77 Hz, 1 H), 7.02 (d, J = 1.01 Hz, 1 H), 7.39 (dd, J = 8.84, 2.78 Hz, 1 H), 7.66 (s, 1 H), 7.95-8.04 (m, 2 H) | 542.1 | 7.26 |
| 362 | 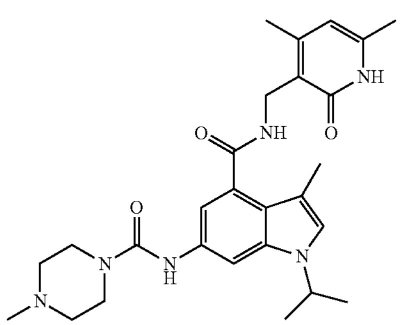 | N-[(4,6-dimethyl-2-oxo-1,2-dihydro-3-pyridinyl)methyl]-3-methyl-1-(1-methylethyl)-6-{[(4-methyl-1-piperazinyl)carbonyl]amino}-1H-indole-4-carboxamide | 1.40 (m, 6 H), 2.11 (s, 6 H), 2.21 (d, J = 9.09 Hz, 6 H), 2.28-2.35 (m, 4 H), 3.40-3.47 (m, 4 H), 4.32 (d, J = 5.31 Hz, 2 H), 4.51 (quin, J = 6.63 Hz, 1 H), 5.87 (s, 1 H), 7.03 (d, J = 1.77 Hz, 1 H), 7.12 (d, J = 1.01 Hz, 1 H), 7.73 (d, J = 1.77 Hz, 1 H), 7.90 (t, J = 5.05 Hz, 1 H), 8.47 (s, 3 H) 11.47 (br. s., 2 H) | 493.3 | 6.89 |

-continued

| Ex | Structure | Name | ¹H NMR (400 MHz, DMSO-d₆) δ ppm | MS(ES) [M + H]⁺ | EZH2 pIC50 |
|---|---|---|---|---|---|
| 363 | 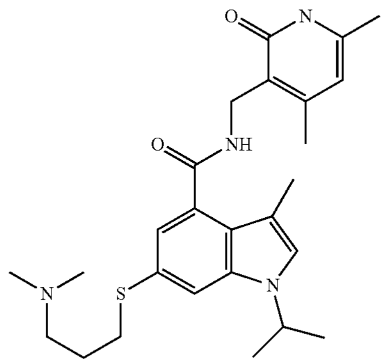 | 6-{[3-(dimethylamino)propyl]thio}-N-[(4,6-dimethyl-2-oxo-1,2-dihydro-3-pyridinyl)methyl]-3-methyl-1-(1-methylethyl)-1H-indole-4-carboxamide | 11.47 (s, 1 H), 8.12 (t, J = 5.1 Hz, 1 H), 7.51 (d, J = 1.5 Hz, 1 H), 7.27 (s, 1 H), 6.91 (d, J = 1.3 Hz, 1 H), 5.86 (s, 1 H), 4.74 (m, 1 H), 4.31 (d, J = 5.1 Hz, 2 H), 2.95 (t, J = 7.2 Hz, 2 H), 2.29 (t, J = 7.1 Hz, 2 H), 2.22 (s, 3 H), 2.10 (m, 12 H), 1.65 (quin, J = 7.1 Hz, 2 H), 1.39 (d, J = 6.6 Hz, 6 H) | 469.1 | |
| 364 | 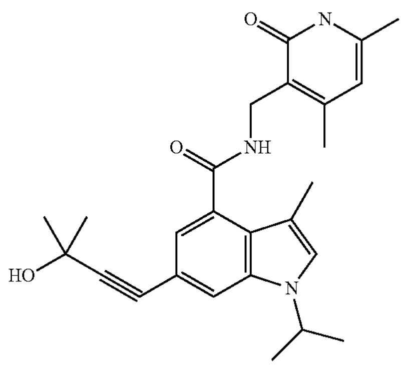 [SMILES: Cc1cc(C)c(CNC(=O)c2cc(C#CC(C)(C)O)cc3c2c(C)cn3C(C)C)c(=O)[nH]1] | N-[(4,6-dimethyl-2-oxo-1,2-dihydro-3-pyridinyl)methyl]-6-(3-hydroxy-3-methyl-1-butyn-1-yl)-3-methyl-1-(1-methylethyl)-1H-indole-4-carboxamide | 11.46 (s, 1 H), 8.16 (t, J = 5.1 Hz, 1 H), 7.54 (d, J = 1.3 Hz, 1 H), 7.37 (s, 1 H), 6.90 (d, J = 1.3 Hz, 1 H), 5.86 (s, 1 H), 5.41 (s, 1 H), 4.75 (m, 1 H), 4.31 (d, J = 5.1 Hz, 2 H), 2.21 (s, 1.47 H), 2.11 (s, 3 H), 2.14 (s, 3 H), 1.47 (s, 6 H), 1.39 (d, J = 6.6 Hz, 6 H) | 434.0 | |
| 365 | 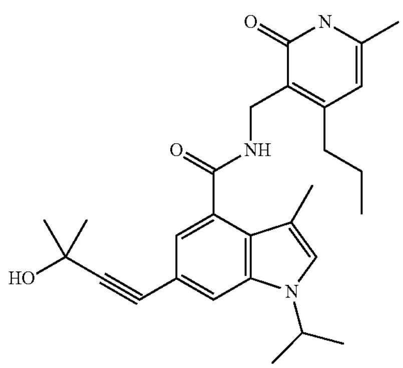 [SMILES: CCCc1cc(C)[nH]c(=O)c1CNC(=O)c1cc(C#CC(C)(C)O)cc2c1c(C)cn2C(C)C] | 6-(3-hydroxy-3-methyl-1-butyn-1-yl)-3-methyl-1-(1-methylethyl)-N-[(6-methyl-2-oxo-4-propyl-1,2-dihydro-3-pyridinyl)methyl]-1H-indole-4-carboxamide | 11.48 (s, 1 H), 8.12 (t, J = 5.1 Hz, 1 H), 7.55 (d, J = 1.3 Hz, 1 H), 7.38 (s, 1 H), 6.90 (d, J = 1.3 Hz, 1 H), 5.89 (s, 1 H), 5.41 (s, 1 H), 4.76 (m, 1 H), 4.32 (d, J = 4.8 Hz, 2 H), 2.54 (s, 1 H), 2.13 (d, J = 9.3 Hz, 6 H), 1.55 (m, 2 H), 1.47 (s, 6 H), 1.40 (m, 6 H), 0.93 (t, J = 7.3 Hz, 3 H) | 462.1 | |
| 366 | 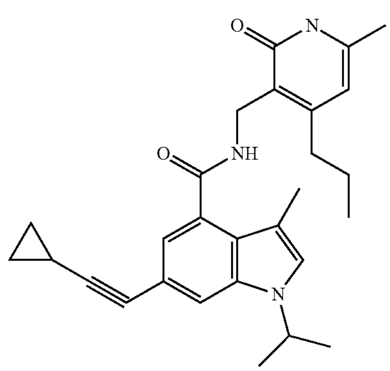 [SMILES: CCCc1cc(C)[nH]c(=O)c1CNC(=O)c1cc(C#CC2CC2)cc2c1c(C)cn2C(C)C] | 6-(cyclopropylethynyl)-3-methyl-1-(1-methylethyl)-N-[(6-methyl-2-oxo-4-propyl-1,2-dihydro-3-pyridinyl)methyl]-1H-indole-4-carboxamide | 11.48 (s, 1 H), 8.09 (t, J = 4.9 Hz, 1 H), 7.54 (d, J = 1.3 Hz, 1 H), 7.35 (s, 1 H), 6.87 (d, J = 1.3 Hz, 1 H), 5.89 (s, 1 H), 4.72 (quin, J = 6.6 Hz, 1 H), 4.31 (d, J = 5.1 Hz, 2 H), 2.13 (d, J = 4.0 Hz, 6 H), 1.54 (m, 3 H), 1.38 (d, J = 6.6 Hz, 6H), 0.93 (t, J = 7.3 Hz, 3 H), 0.87 (m, 2 H), 0.71 (m, 2 H) | 444.1 | |

Scheme 6

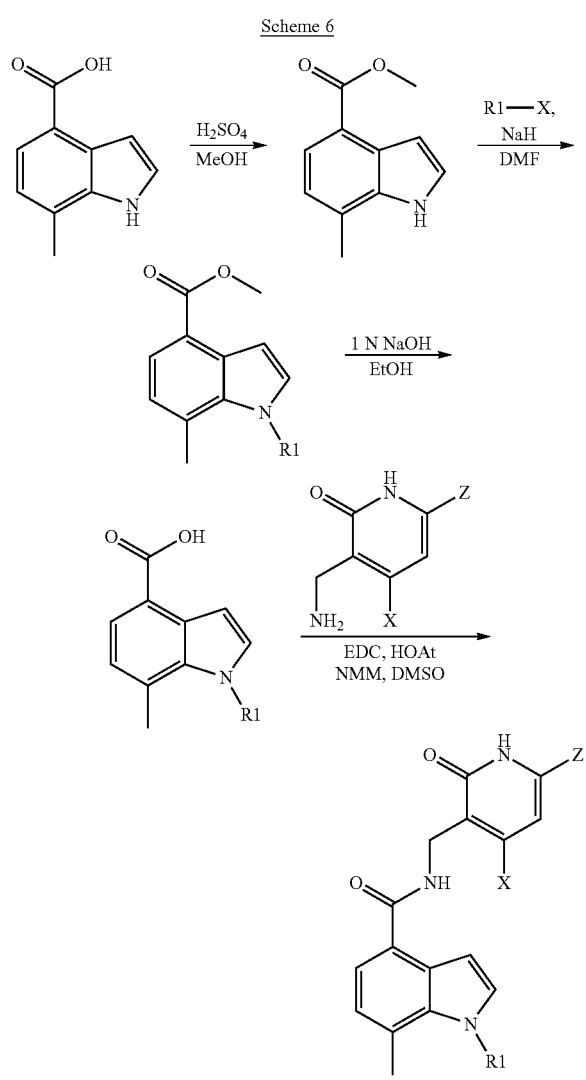

Example 367

N-[(4,6-Dimethyl-2-oxo-1,2-dihydro-3-pyridinyl)methyl]-7-methyl-1-(1-methylethyl)-1H-indole-4-carboxamide a) Methyl 7-methyl-1H-indole-4-carboxylate

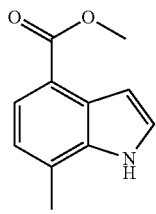

Under N2 atmosphere, 7-methyl-1H-indole-4-carboxylic acid (1 g, 5.71 mmol), sulfuric acid (300 µL, 5.63 mmol) and methanol (50 mL) were heated at reflux for 10 h. The MeOH was removed in vacuo and the residue dissolved in 30 mL DCM. The solution was washed with water and saturated NaHCO₃, dried over MgSO₄, filtered and concentrated. The residue was purified by column chromatography (Biotage; 0% to 100% EtOAc:Hex; 25 g-HP-silica gel column) to give the title compound. ¹H NMR (400 MHz, CHLOROFORM-d) δ ppm 2.59 (s, 3H), 4.00 (s, 3H), 7.08 (d, J=7.58 Hz, 1H), 7.20-7.26 (m, 1H), 7.38 (t, J=2.78 Hz, 1H), 7.88 (d, J=7.58 Hz, 1H), 8.32 (br. s., 1H).

b) Methyl 7-methyl-1-(1-methylethyl)-1H-indole-4-carboxylate

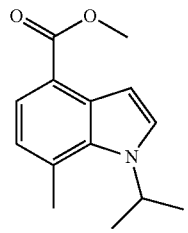 [SMILES: COC(=O)c1ccc(C)c2c1ccn2C(C)C]

A a cooled (ice/water bath) solution of methyl methyl 7-methyl-1H-indole-4-carboxylate (260 mg, 1.374 mmol) in DMF (20 mL) was added sodium hydride (43.4 mg, 1.718 mmol). After 10 minutes 2-iodopropane (0.151 mL, 1.512 mmol) was added and the reaction was stirred for 16 h. LCMS showed reaction only 10% complete. Added sodium hydride (43.4 mg, 1.718 mmol) followed by 2-iodopropane (0.151 mL, 1.512 mmol). After 2 hours LCMS showed reaction was 15% compete. Added more sodium hydride (43.4 mg, 1.718 mmol) and let stir for 5 minutes, then added more 2-bromopropane (0.142 mL, 1.512 mmol). Heated to 70° C. for 16 h. LCMS showed reaction 50% complete. Concentrated reaction mixture. Added DCM and washed with water and brine, dried over MgSO₄, filtered and concentrated. The residue was purified by column chromatography (Biotage; 0% to 100% DCM:Hex; 25 g-HP-silica gel column) to give 137 mg of the title compound. ¹H NMR (400 MHz, CHLOROFORM-d) δ ppm 1.48-1.60 (m, 6H), 2.78 (s, 3H), 3.94-4.02 (m, 3H), 5.17 (dt, J=13.20, 6.66 Hz, 1H), 6.96 (d, J=7.83 Hz, 1H), 7.28 1H, 7.40 (d, J=3.28 Hz, 1H), 7.81 (d, J=7.58 Hz, 1H). MS (ES) [M+H]⁺232.1 c) 7-Methyl-1-(1-methylethyl)-1H-indole-4-carboxylic acid

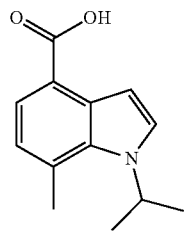 [SMILES: Cc1ccc(C(=O)O)c2ccn(C(C)C)c12]

To a solution of methyl 7-methyl-1-(1-methylethyl)-1H-indole-4-carboxylate (137 mg, 0.592 mmol) in ethanol (30 mL) was added 1 N sodium hydroxide (2.369 mL, 2.369 mmol). The mixture was heated at reflux for 2 h, at which time it was concentrated. The residue was dissolved in water (20 mL) and acidified by addition of 1 N HCl. The mixture was extracted with DCM (4×30 mL) and the combined extracts and washed with water and brine, dried over MgSO₄, filtered and concentrated to give 104 mg of the title compound. ¹H NMR (400 MHz, CHLOROFORM-d) δ ppm 1.55 (d, 6H), 2.82 (s, 3H), 5.11-5.28 (m, 1H), 7.00 (d, J=7.83 Hz, 1H), 7.31

(d, J=3.54 Hz, 1H), 7.44 (d, J=3.28 Hz, 1H), 7.89 (d, J=7.58 Hz, 1H). MS (ES) [M+H]⁺218.3.

d) N-[(4,6-Dimethyl-2-oxo-1,2-dihydro-3-pyridinyl)methyl]-7-methyl-1-(1-methylethyl)-1H-indole-4-carboxamide

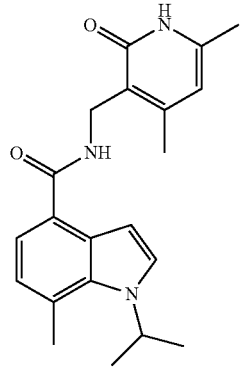 [SMILES: Cc1cc(C)c(CNC(=O)c2ccc(C)c3c2ccn3C(C)C)c(=O)[nH]1]

Added 7-methyl-1-(1-methylethyl)-1H-indole-4-carboxylic acid (52 mg, 0.239 mmol), 3-(aminomethyl)-4,6-dimethyl-2(1H)-pyridinone (56.4 mg, 0.299 mmol), 1-hydroxy-7-azabenzotriazole (65.2 mg, 0.479 mmol), EDC (92 mg, 0.479 mmol) and N-methylmorpholine (0.105 mL, 0.957 mmol) to Dimethyl Sulfoxide (DMSO) (10 mL) and stirred at RT for 16 h. Added 25 ml of water and let stir for 10 minutes. Filtered off solids. Dissolved solids in DCM, washed with water, dried over MgSO₄, filtered and concentrated. The residue was purified by column chromatography (Biotage; 0% to 20% gradient MeOH:DCM; 10 g-HP-silica gel column) to give 55 mg of N-[(4,6-Dimethyl-2-oxo-1,2-dihydro-3-pyridinyl)methyl]-7-methyl-1-(1-methylethyl)-1H-indole-4-carboxamide. ¹H NMR (400 MHz, CHLOROFORM-d) δ ppm 1.49 (d, 6H), 2.24 (s, 3H), 2.44 (s, 3H), 2.75 (s, 3H), 4.63 (d, J=4.55 Hz, 2H), 5.17 (dt, J=13.20, 6.66 Hz, 1H), 5.97 (s, 1H), 6.91 (d, J=7.58 Hz, 1H), 7.01 (d, J=3.54 Hz, 1H), 7.29 (d, J=3.28 Hz, 1H), 7.39 (d, J=7.33 Hz, 1H), 7.69 (br. s., 1H), 12.59 (br. s., 1H). MS (ES) [M+H]⁺352.4.

Example 368

7-Methyl-1-(1-methylethyl)-N-[(6-methyl-2-oxo-4-propyl-1,2-dihydro-3-pyridinyl)methyl]-1H-indole-4-carboxamide

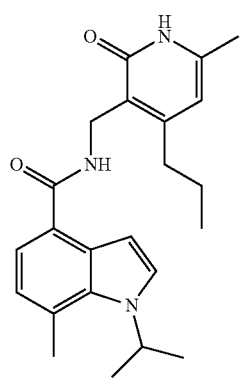 [SMILES: CCCc1cc(C)[nH]c(=O)c1CNC(=O)c1ccc(C)c2c1ccn2C(C)C]

7-Methyl-1-(1-methylethyl)-N-[(6-methyl-2-oxo-4-propyl-1,2-dihydro-3-pyridinyl)methyl]-1H-indole-4-carboxamide was prepared following the procedure of Example 367. ¹H NMR (400 MHz, CHLOROFORM-d) δ ppm 0.95-1.07 (m, 3H), 1.50 (d, J=6.57 Hz, 6H), 1.63 (qt, J=7.56, 7.36 Hz, 2H), 2.27 (s, 3H), 2.68-2.82 (m, 5H), 4.64 (d, J=2.53 Hz, 2H), 5.17 (dq, J=6.82, 6.65 Hz, 1H), 6.04 (s, 1H), 6.91 (d, J=7.58 Hz, 1H), 7.00 (d, J=3.54 Hz, 1H), 7.31 (d, J=3.54 Hz, 1H), 7.39 (d, J=7.33 Hz, 1H), 7.64 (br. s., 1H), 12.13 (br. s., 1H). MS (ES) [M+H]⁺380.2.

Scheme 7

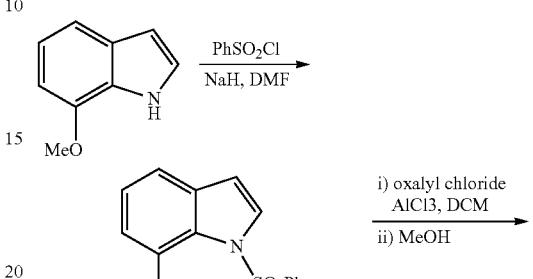

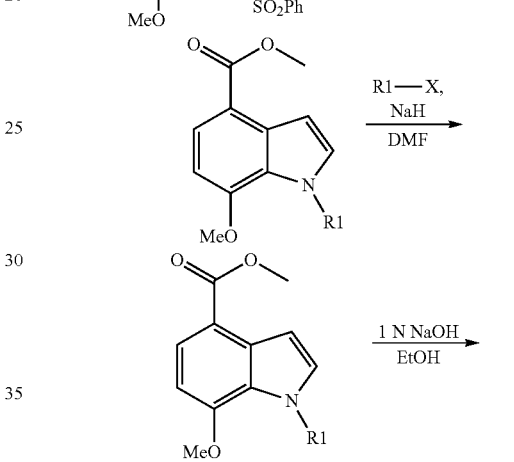

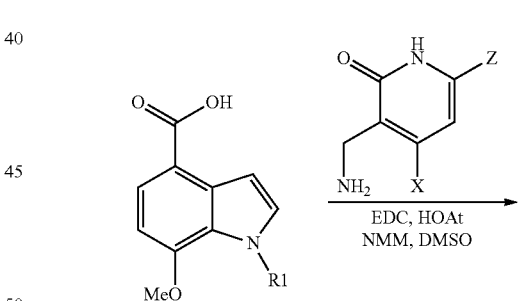

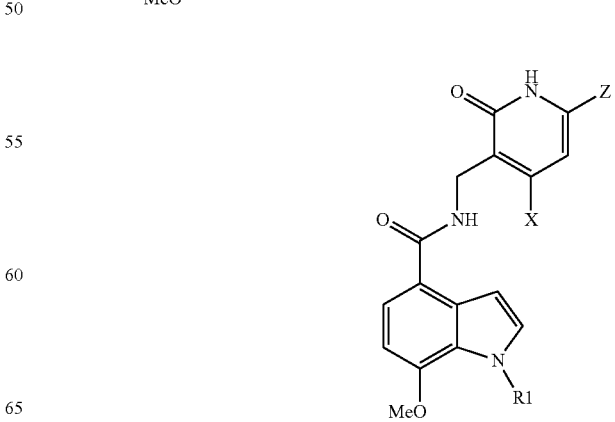

Example 369

1-(1-Methylethyl)-N-[(6-methyl-2-oxo-4-propyl-1,2-dihydro-3-pyridinyl)methyl]-7-(methyloxy)-1H-indole-4-carboxamide

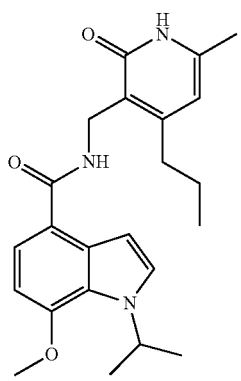 [SMILES: CCCc1cc(C)[nH]c(=O)c1CNC(=O)c1ccc(OC)c2c1ccn2C(C)C]

a) 7-(Methyloxy)-1-(phenylsulfonyl)-1H-indole

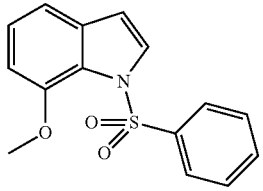 [SMILES: COc1cccc2ccn(S(=O)(=O)c3ccccc3)c12]

To a cooled (ice water bath) solution of 7-(methyloxy)-1H-indole (3 g, 20.38 mmol) in DMF (100 mL) was added sodium hydride (0.618 g, 24.46 mmol) portionwise. After 15 minutes a solution of benzenesulfonyl chloride (3.94 mL, 30.6 mmol) in 20 ml of DMF was added dropwise. The reaction mixture was stirred at RT for 24 h, at which time it was concentrated. The residue was dissolved in DCM (100 ml) and washed with water and brine, dried over MgSO$_4$, filtered and concentrated. The residue was purified by column chromatography (Biotage; 0% to 100% DCM:Hex; 50 g-HP-silica gel column) to give 3.65 g of the title compound. $^1$H NMR (400 MHz, CHLOROFORM-d) δ ppm 3.65 (s, 3H), 6.60-6.75 (m, 2H), 7.08-7.22 (m, 2H), 7.40-7.62 (m, 3H), 7.77-7.92 (m, 3H). MS (ES) [M+H]$^+$ 288.0.

b) Methyl 7-(methyloxy)-1-(phenylsulfonyl)-1H-indole-4-carboxylate

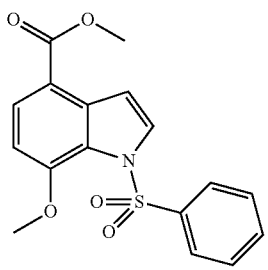 [SMILES: COC(=O)c1ccc(OC)c2c1ccn2S(=O)(=O)c1ccccc1]

To a cooled (0° C.) suspension of aluminium chloride (8.47 g, 63.5 mmol) in DCM (100 mL) was added oxalyl chloride (5.56 mL, 63.5 mmol) dropwise. After stirring for 30 minutes a solution of 7-(methyloxy)-1-(phenylsulfonyl)-1H-indole (3.65 g, 12.70 mmol) in DCM (15 ml) was added dropwise. The reaction was stirred at RT for 1 h, at which time it was poured into brine and extracted with DCM. The DCM extracts were dried over MgSO$_4$, filtered, and evaporated to dryness. Added 100 ml of MeOH to the residue and heated at reflux for 3 h. The mixture was concentrated and the residue purified by column chromatography (Biotage; 0% to 100% DCM:Hex; 50 g-HP-silica gel column) to give 2.3 g of the title compound. $^1$H NMR (400 MHz, CHLOROFORM-d) δ ppm 3.70 (s, 3H), 3.95 (s, 3H), 6.67 (d, J=8.59 Hz, 1H), 7.41 (d, J=3.79 Hz, 1H), 7.46-7.53 (m, 2H), 7.54-7.62 (m, 1H), 7.79-7.86 (m, 2H), 7.94 (d, J=8.59 Hz, 1H), 7.98 (d, J=3.54 Hz, 1H). MS (ES) [M+H]$^+$ 346.0.

c) Methyl 1-(1-methylethyl)-7-(methyloxy)-1H-indole-4-carboxylate

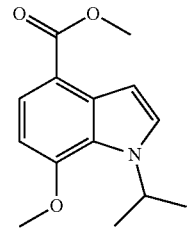 [SMILES: COC(=O)c1ccc(OC)c2c1ccn2C(C)C]

To a cooled (ice/water bath) solution of methyl 7-(methyloxy)-1H-indole-4-carboxylate (350 mg, 1.706 mmol) in DMF (20 mL) was added sodium hydride (56.0 mg, 2.217 mmol). After 10 minutes added 2-iodopropane (0.188 mL, 1.876 mmol). The reaction was stirred at RT for 1 h, followed by heating at 50° C. for 2 h. The reaction was then cooled in an ice water bath and more sodium hydride (56.0 mg, 2.217 mmol) and 2-iodopropane (0.188 mL, 1.876 mmol) were added. The reaction was heated at 50° C. for 3 h, at which time it was concentrated. The residue was dissolved in DCM and washed with water and brine, dried over MgSO$_4$, filtered and concentrated to give 400 mg of the title compound. $^1$H NMR (400 MHz, CHLOROFORM-d) δ ppm 1.49 (d, 6H), 3.95 (s, 3H), 4.01 (s, 3H), 5.46 (dt, J=13.39, 6.69 Hz, 1H), 6.66 (d, J=8.34 Hz, 1H), 7.15 (d, J=3.03 Hz, 1H), 7.34 (d, J=3.28 Hz, 1H), 7.87 (d, J=8.34 Hz, 1H). MS (ES) [M+H]$^+$ 248.2.

d) 1-(1-Methylethyl)-7-(methyloxy)-1H-indole-4-carboxylic acid

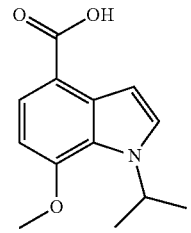 [SMILES: COc1ccc(C(=O)O)c2ccn(C(C)C)c12]

e) 1-(1-Methylethyl)-N-[(6-methyl-2-oxo-4-propyl-1,2-dihydro-3-pyridinyl)methyl]-7-(methyloxy)-1H-indole-4-carboxamide Added 1 N sodium hydroxide (6.47 mL, 6.47 mmol) to a solution of methyl 1-(1-methylethyl)-7-(methyloxy)-1H-indole-4-carboxylate (400 mg, 1.618 mmol) in ethanol (30 mL) and heated at reflux for 3 h. The EtOH was removed in vacuo and the residue dissolved in 20 ml of water. Acidifed solution by addition of 1 N HCl and extracted with DCM. the combined DCM extracts were washed with water and brine, dried over MgSO$_4$, filtered and concentrated to give 350 mg of the title compound. $^1$H NMR (400 MHz, CHLOROFORM-d) δ ppm 1.51 (d, 6H), 4.03 (s, 3H), 5.47 (dt, J=13.39, 6.69 Hz, 2H), 6.70 (d, J=8.34 Hz, 2H), 7.23 (d, J=3.28 Hz, 2H), 7.37 (d, J=3.03 Hz, 2H), 7.99 (d, J=8.34 Hz, 2H). MS (ES) [M+H]$^+$ 234.0.

e) 1-(1-Methylethyl)-N-[(6-methyl-2-oxo-4-propyl-1,2-dihydro-3-pyridinyl)methyl]-7-(methyloxy)-1H-indole-4-carboxamide

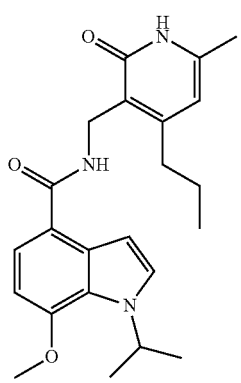 [SMILES: CCCc1cc(C)[nH]c(=O)c1CNC(=O)c1ccc(OC)c2c1ccn2C(C)C]

Added 1-(1-methylethyl)-7-(methyloxy)-1H-indole-4-carboxylic acid (160 mg, 0.686 mmol), 3-(aminomethyl)-6-methyl-4-propyl-2(1H)-pyridinone (186 mg, 0.857 mmol), 1-hydroxy-7-azabenzotriazole (187 mg, 1.372 mmol), EDC (263 mg, 1.372 mmol) and N-methylmorpholine (0.302 mL, 2.74 mmol) to DMSO (10 mL) and stirred mixture at RT for 16 h. Added 25 ml of water and stirred for 10 minutes. Filtered off solids and dried in vacuo. The solids were purified by column chromatography (Biotage; 0% to 15% gradient MeOH:DCM; 10 g-HP-silica gel column) to give 165 mg of 1-(1-methylethyl)-N-[(6-methyl-2-oxo-4-propyl-1,2-dihydro-3-pyridinyl)methyl]-7-(methyloxy)-1H-indole-4-carboxamide.

$^1$H NMR (400 MHz, CHLOROFORM-d) δ ppm 1.01 (t, 3H), 1.45 (d, J=6.57 Hz, 6H), 1.63 (m, J=7.45, 7.45, 7.45, 7.45, 7.33 Hz, 2H), 2.24 (s, 3H), 2.74 (t, J=7.58 Hz, 2H), 3.96 (s, 3H), 4.64 (br. s., 2H), 5.45 (quin, J=6.63 Hz, 1H), 5.97 (s, 1H), 6.62 (d, J=8.08 Hz, 1H), 6.94 (d, J=3.28 Hz, 1H), 7.24 (d, J=3.28 Hz, 1H), 7.53 (d, J=8.08 Hz, 1H), 7.74 (br. s., 1H), 12.46 (br. s., 1H). MS (ES) [M+H]$^+$ 395.7.

Example 370

N-[(4,6-Dimethyl-2-oxo-1,2-dihydro-3-pyridinyl)methyl]-1-(1-methylethyl)-7-(methyloxy)-1H-indole-4-carboxamide

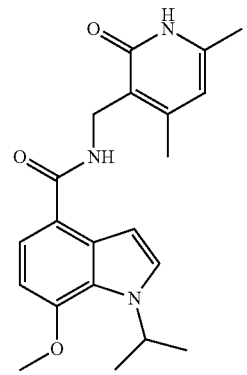 [SMILES: COc1ccc(C(=O)NCc2c(C)cc(C)[nH]c2=O)c2ccn(C(C)C)c12]

N-[(4,6-Dimethyl-2-oxo-1,2-dihydro-3-pyridinyl)methyl]-1-(1-methylethyl)-7-(methyloxy)-1H-indole-4-carboxamide was prepared following the procedure of Example 369. $^1$H NMR (400 MHz, CHLOROFORM-d) δ ppm 1.45 (d, 6H), 2.21 (s, 3H), 2.43 (s, 3H), 3.96 (s, 3H), 4.63 (d, J=5.56 Hz, 2H), 5.35-5.57 (m, 1H), 5.94 (s, 1H), 6.61 (d, J=8.34 Hz, 1H), 6.94 (d, J=3.28 Hz, 1H), 7.23 (d, J=3.03 Hz, 1H), 7.52 (d, J=8.08 Hz, 1H), 7.66 (br. s., 1H), 12.73 (br. s., 1H). MS (ES) [M+H]$^+$ 368.1.

Example 371

6-chloro-1-isopropyl-2,3-dimethyl-N-((6-methyl-2-oxo-4-propyl-1,2-dihydropyridin-3-yl)methyl)-1H-indole-4-carboxamide

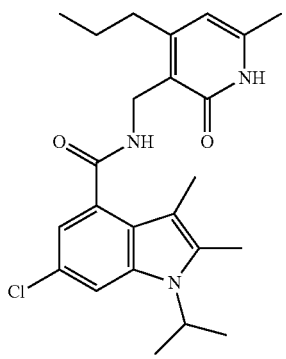 [SMILES: CCCc1cc(C)[nH]c(=O)c1CNC(=O)c1cc(Cl)cc2c1c(C)c(C)n2C(C)C]

265 a) Methyl 6-chloro-1-isopropyl-2,3-dimethyl-1H-indole-4-carboxylate

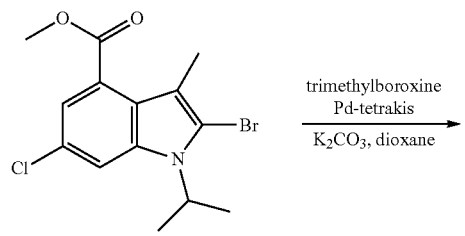

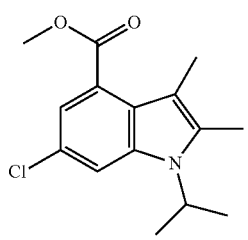

To a stirred solution of methyl 2-bromo-6-chloro-1-isopropyl-3-methyl-1H-indole-4-carboxylate (0.50 g, 1.451 mmol), Trimethylboroxine (0.30 mL, 2.146 mmol) and potassium carbonate (0.31 g, 2.243 mmol) in 1,4-Dioxane (20 mL) under $N_2$ was added palladium tetrakis (0.18 g, 0.156 mmol). The reaction was heated to 110° C. and stirred for 18 hr. After 3 hr an additional 100 uL Trimethylboroxine was added. The reaction was concentrated under vacuum, taken up in EtOAc, washed with water, dried ($MgSO_4$), filtered and concentrated under vacuum. Purification by silica gel chromatography (Analogix, SF25-60 g, 0 to 10% EtOAc in hexanes) gave the product methyl 6-chloro-1-isopropyl-2,3-dimethyl-1H-indole-4-carboxylate (0.33 g, 1.180 mmol, 81% yield) as a clear thick oil. $^1$H NMR (400 MHz, DMSO-$d_6$) δ=7.80 (d, J=2.0 Hz, 1H), 7.28 (d, J=1.8 Hz, 1H), 4.81 (dt, J=6.9, 13.9 Hz, 1H), 3.87 (s, 3H), 2.39 (s, 3H), 2.13 (s, 3H), 1.51 (d, J=7.1 Hz, 6H) MS (ES)+m/e 280.1 [M+H]$^+$.

b) 6-Chloro-1-isopropyl-2,3-dimethyl-N-((6-methyl-2-oxo-4-propyl-1,2-dihydropyridin-3-yl)methyl)-1H-indole-4-carboxamide

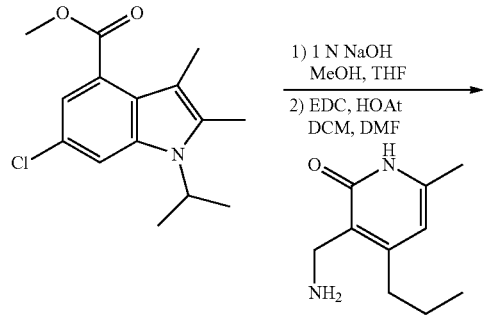

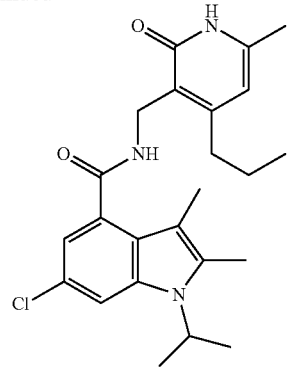

To a stirred solution of methyl 6-chloro-1-isopropyl-2,3-dimethyl-1H-indole-4-carboxylate (320 mg, 1.144 mmol) in Methanol (12 mL) and Tetrahydrofuran (THF) (4 mL) was added 1 N NaOH (4 mL, 4.00 mmol). The reaction was refluxed (70° C. oil bath) for 18 h. The reaction was concentrated under vacuum, diluted with water, acidified with 1 N HCl (4 mL), filtered, washed with water and dried under vacuum to give the carboxylic acid (0.30 g, 1.14 mmol, 100%) as a light yellow solid. MS (ES)+m/e 266.1 [M+H]$^+$.

To the carboxylic acid above was added 3-(aminomethyl)-6-methyl-4-propylpyridin-2(1H)-one (230 mg, 1.276 mmol), HOAt (160 mg, 1.176 mmol), Dichloromethane (12 mL) and N,N-Dimethylformamide (4.00 mL) to dissolve. With stirring was added EDC free base (210 mg, 1.353 mmol) and the reaction stirred at RT for 3 hr. LCMS showed that the reaction was complete. The reaction was evaporated to dryness under vacuum then purified by silica gel chromatography (SF25-40 g, 50 to 100% EtOAc in $CH_2Cl_2$) (streaked off). The pure fractions were combined and evaporated under vacuum. The remaining solid was triturated with 25% $CH_2Cl_2$ in hexanes, filtered, washed with hexanes and dried under vacuum to give the product 6-chloro-1-isopropyl-2,3-dimethyl-N-((6-methyl-2-oxo-4-propyl-1,2-dihydropyridin-3-yl)methyl)-1H-indole-4-carboxamide (431 mg, 1.007 mmol, 88% yield) as an off-white solid. $^1$H NMR (400 MHz, DMSO-$d_6$) δ=11.49 (s, 1H), 8.16 (t, J=5.1 Hz, 1H), 7.58 (d, J=1.8 Hz, 1H), 6.82 (d, J=1.8 Hz, 1H), 5.89 (s, 1H), 4.75 (dt, J=6.9, 13.9 Hz, 1H), 4.31 (d, J=5.1 Hz, 2H), 2.52 (2H under DMSO), 2.33 (s, 3H), 2.12 (s, 3H), 2.04 (s, 3H), 1.61-1.51 (m, 2H), 1.49 (d, J=6.8 Hz, 6H), 0.94 (t, J=7.3 Hz, 3H). MS (ES)+m/e 428.3 [M+H]$^+$.

Example 372

6-Chloro-2-((dimethylamino)methyl)-1-isopropyl-3-methyl-N-((6-methyl-2-oxo-4-propyl-1,2-dihydropyridin-3-yl)methyl)-1H-indole-4-carboxamide

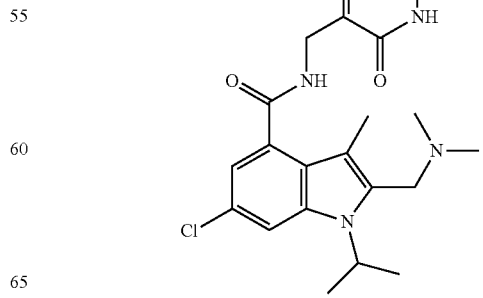

a) Methyl 6-chloro-2-((dimethylamino)methyl)-1-isopropyl-3-methyl-1H-indole-4-carboxylate

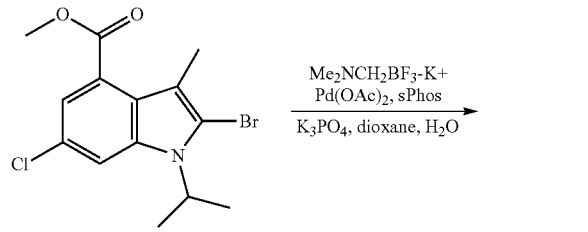

To a stirred mixture of methyl 2-bromo-6-chloro-1-isopropyl-3-methyl-1H-indole-4-carboxylate (1.0 g, 2.90 mmol), potassium ((dimethylamino)methyl)trifluoroborate (0.5 g, 3.03 mmol) and Potassium phosphate (1.9 g, 8.95 mmol) (purged with $N_2$)) in dioxane (3 mL) and water (3 mL) was added palladium(II) acetate (25 mg, 0.111 mmol) and sPhos (90 mg, 0.219 mmol). The reaction was heated to 100° C. and stirred for 18 hr under $N_2$. LCMS showed that the reaction was complete. The reaction was diluted with EtOAc and water, and filtered to remove insolubles. The EtOAc phase was removed, dried ($Na_2SO_4$), filtered, and concentrated under vacuum. The crude was purified by silica gel chromatography (Analogix, SF25-40 g, 0 to 2% (5% $NH_4OH$/MeOH) in $CH_2Cl_2$). The product fractions were combined, evaporated to dryness under vacuum to give the product methyl 6-chloro-2-((dimethylamino)methyl)-1-isopropyl-3-methyl-1H-indole-4-carboxylate (0.45 g, 1.394 mmol, 48.0% yield) as a light yellow oil (Only 84% pure by LCMS). This was used as is in the next reaction. $^1$H NMR (400 MHz, DMSO-$d_6$) δ=7.82 (d, J=1.8 Hz, 1H), 7.28 (d, J=1.8 Hz, 1H), 4.96 (dt, J=7.1, 14.1 Hz, 1H), 3.88 (s, 3H), 3.52 (s, 2H), 2.17 (s, 3H), 2.16 (s, 6H), 1.53 (d, J=7.1 Hz, 6H). MS (ES)+m/e 323.2 [M+H]$^+$, 278.1 [M+H]$^+$ −45 (HNMe$_2$).

b) 6-Chloro-2-((dimethylamino)methyl)-1-isopropyl-3-methyl-1H-indole-4-carboxylic acid hydrochloride salt

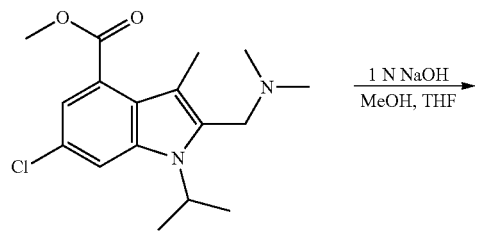

-continued

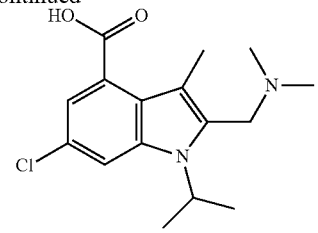

To methyl 6-chloro-2-((dimethylamino)methyl)-1-isopropyl-3-methyl-1H-indole-4-carboxylate (0.44 g, 1.363 mmol) was added 6 N HCl (20 ml, 120 mmol). The reaction was purged with $N_2$, attached a reflux condensor, heated to 80° C., and stirred for 18 hr. LCMS showed that the reaction was complete. The reaction was cooled to RT, diluted with an equal volume of water, washed with EtOAc, and evaporated to dryness under vacuum to give the product 6-chloro-2-((dimethylamino)methyl)-1-isopropyl-3-methyl-1H-indole-4-carboxylic acid hydrochloride salt (0.42 g, 1.216 mmol, 89% yield) as a beige solid. (86% pure by LCMS, contains ~10% of the des-chloro side product from the previous reaction.) Used as is in the next step. $^1$H NMR (400 MHz, DMSO-$d_6$) δ=13.19 (br. s., 1H), 10.45 (br. s., 1H), 7.90 (d, J=1.8 Hz, 1H), 7.33 (d, J=1.8 Hz, 1H), 4.91 (quin, J=6.9 Hz, 1H), 4.58 (d, J=5.6 Hz, 2H), 2.79 (d, J=4.8 Hz, 6H), 2.34 (s, 3H), 1.58 (d, J=6.8 Hz, 6H). MS (ES)+m/e 309.2 [M+H]$^+$, 264.1 [M+H]$^+$ −45 (HNMe$_2$).

c) 6-Chloro-2-((dimethylamino)methyl)-1-isopropyl-3-methyl-N-((6-methyl-2-oxo-4-propyl-1,2-dihydropyridin-3-yl)methyl)-1H-indole-4-carboxamide

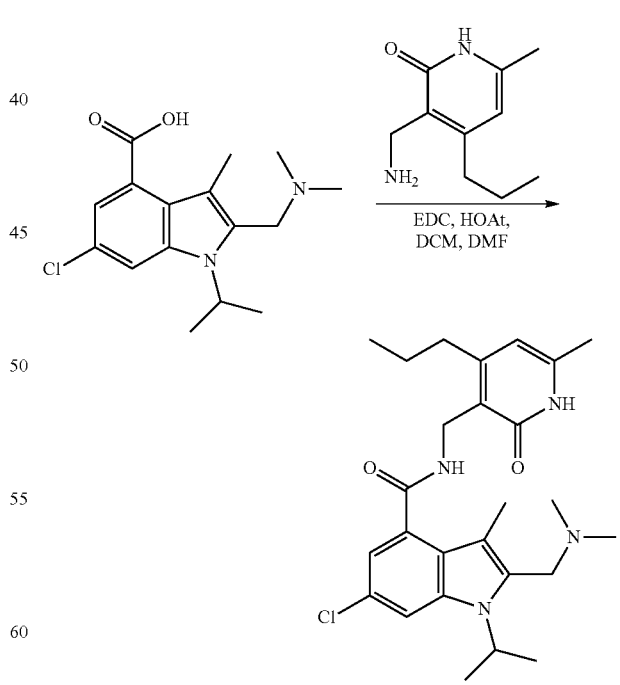

To 6-chloro-2-((dimethylamino)methyl)-1-isopropyl-3-methyl-1H-indole-4-carboxylic acid hydrochloride salt (0.42 g, 1.216 mmol), 3-(aminomethyl)-6-methyl-4-propylpyridin-2(1H)-one (0.22 g, 1.221 mmol), HOAt (0.17 g, 1.249 mmol) was added Dichloromethane (16 mL), N,N-Dimethylformamide (4 mL) and N-methylmorpholine (135 μL, 1.228 mmol). The mixture was stirred and EDC free base (0.20 g, 1.288 mmol) was added. After stirring for 2 hr LCMS showed that the reaction was complete. The reaction was evaporated to dryness under vacuum and purified by silica gel chromatography (Analogix, SF25-60 g, 0 to 8% (5% NH$_4$OH in MeOH) in CH$_2$Cl$_2$). The pure fractions were combined, evaporated to dryness then taken up in 20% EtOAc in hexanes. Scratching crystallized out the product which was filtered and washed with hexanes to give the product 6-chloro-2-((dimethylamino)methyl)-1-isopropyl-3-methyl-N-((6-methyl-2-oxo-4-propyl-1,2-dihydropyridin-3-yl)methyl)-1H-indole-4-carboxamide (362 mg, 0.769 mmol, 63.2% yield) as an off-white solid. $^1$H NMR (400 MHz, DMSO-d$_6$) δ=11.49 (s, 1H), 8.24 (t, J=4.9 Hz, 1H), 7.61 (d, J=1.8 Hz, 1H), 6.83 (d, J=1.8 Hz, 1H), 5.89 (s, 1H), 4.91 (quin, J=7.0 Hz, 1H), 4.31 (d, J=5.1 Hz, 2H), 3.47 (s, 2H), 2.52 (2H under DMSO), 2.14 (s, 6H), 2.12 (s, 3H), 2.10 (s, 3H), 1.62-1.53 (m, 2H), 1.51 (d, J=7.1 Hz, 6H), 0.94 (t, J=7.3 Hz, 3H). MS (ES)+m/e 471.3 [M+H]$^+$.

Example 373

2-(2-Aminoethyl)-6-chloro-1-isopropyl-3-methyl-N-((6-methyl-2-oxo-4-propyl-1,2-dihydropyridin-3-yl)methyl)-1H-indole-4-carboxamide

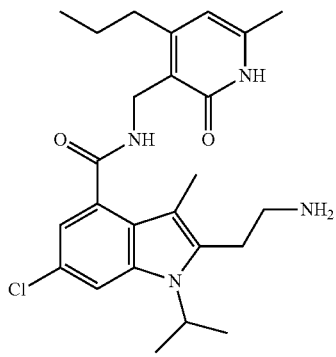 [SMILES: CCCc1cc(C)[nH]c(=O)c1CNC(=O)c1cc(Cl)cc2c1c(C)c(CCN)n2C(C)C]

a) Methyl 2-(2-((tert-butoxycarbonyl)amino)ethyl)-6-chloro-1-isopropyl-3-methyl-1H-indole-4-carboxylate

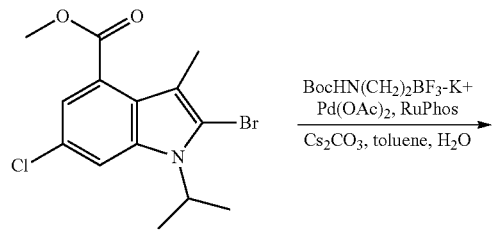

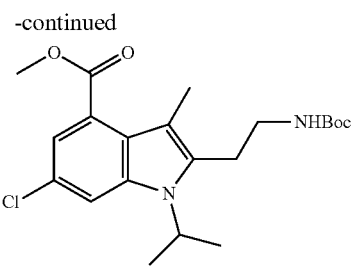

To a stirred mixture of methyl 2-bromo-6-chloro-1-isopropyl-3-methyl-1H-indole-4-carboxylate (0.37 g, 1.074 mmol), potassium (2-((tert-butoxycarbonyl)amino)ethyl)trifluoroborate (0.30 g, 1.195 mmol) and Cs$_2$CO$_3$ (1.0 g, 3.07 mmol) (purged with N$_2$) in toluene (12 mL) and water (4 mL) was added palladium(II) acetate (20 mg, 0.089 mmol) and RuPhos (80 mg, 0.171 mmol). The reaction was heated to 95° C. and stirred for 18 hr under N$_2$. LCMS still showed SM. Another portion of palladium(II) acetate (20 mg, 0.089 mmol) and RuPhos (80 mg, 0.171 mmol) was added and the reaction stirred at 95° C. for another 18 hr. LCMS showed that the reaction was now mostly done. The reaction was diluted with EtOAc and water, and filtered to remove insolubles. The EtOAc phase was removed, dried (MgSO$_4$), filtered, and concentrated under vacuum. The crude was purified by silica gel chromatography (Analogix, SF25-60 g, 0 to 25% EtOAc in hexanes). Three fractions were collected. The first fraction contained a significant amount of the desbromo product, the second fraction was a mixture of unknowns, and the last fraction contained product (Note; opposite order from the TLC). The product fractions were combined, evaporated to dryness, triturated with hexanes, filtered and dried under vacuum to give the product methyl 2-(2-((tert-butoxycarbonyl)amino)ethyl)-6-chloro-1-isopropyl-3-methyl-1H-indole-4-carboxylate (148 mg, 0.362 mmol, 33.7% yield) as a white solid. $^1$H NMR (400 MHz, DMSO-d$_6$) δ=7.81 (d, J=1.5 Hz, 1H), 7.28 (d, J=1.8 Hz, 1H), 7.00 (t, J=5.6 Hz, 1H), 3.87 (s, 3H), 3.07 (q, J=6.7 Hz, 2H), 2.97-2.85 (m, 2H), 2.13 (s, 3H), 1.56 (d, J=7.1 Hz, 6H), 1.36 (s, 9H). MS (ES)+m/e 409.2 [M+H]$^+$.

b) 2-(2-Aminoethyl)-6-chloro-1-isopropyl-3-methyl-N-((6-methyl-2-oxo-4-propyl-1,2-dihydropyridin-3-yl)methyl)-1H-indole-4-carboxamide

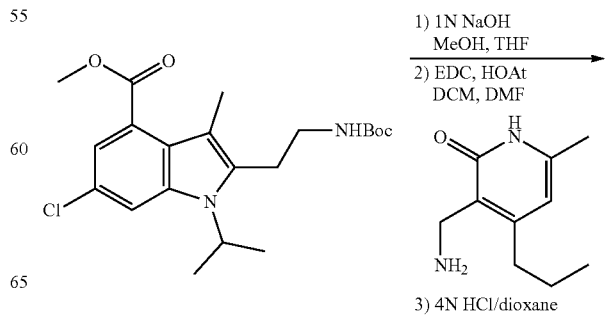

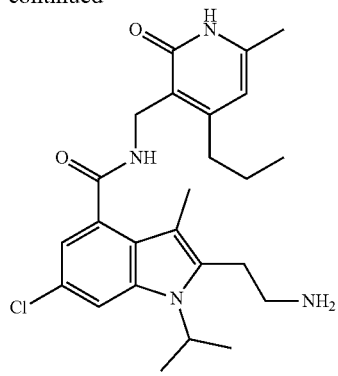

3-Methyl-1H-indole-4-carboxylate (140 mg, 0.342 mmol) in Methanol (9 mL) and Tetrahydrofuran (3 mL) was added 1 N NaOH (2 mL, 2.000 mmol). The reaction was refluxed (70° C. oil bath) for 18 h (reaction proceeded very slowly at 60° C. with only 1 mL 1 N NaOH). The reaction was concentrated under vacuum, diluted with water, acidified with 1 N HCl (2 mL), filtered, washed with water and dried under vacuum to give the carboxylic acid (0.14 g, 0.354 mmol, 100%) as a white solid. MS (ES)+m/e 395.0 [M+H]$^+$.

To the carboxylic acid above was added 3-(aminomethyl)-6-methyl-4-propylpyridin-2(1H)-one (80 mg, 0.444 mmol), HOAt (60 mg, 0.441 mmol), Dichloromethane (12 mL) and N,N-Dimethylformamide (3.00 mL) to dissolve. With stirring was added EDC free base (70 mg, 0.451 mmol) and the reaction stirred at RT overnight. LCMS showed that the reaction was complete. The reaction was evaporated to dryness under vacuum then purified by silica gel chromatography (SF25-40 g, 50 to 100% EtOAc in CH$_2$Cl$_2$) to give the Boc protected final product (0.20 g, 3.59 mmol, 100%) as a white solid. MS (ES)+m/e 557.3 [M+H]$^+$.

The above was dissolved with MeOH (5 mL) then treated, while stirring, with a solution of 4 N HCl in dioxane (10 mL, 40.0 mmol). The reaction was stirred for 30 minutes then evaporated to dryness under vacuum. The solid was triturated with Et$_2$O, filtered, washed with hexanes and dried under vacuum to give the product 2-(2-aminoethyl)-6-chloro-1-isopropyl-3-methyl-N-((6-methyl-2-oxo-4-propyl-1,2-dihydro-pyridin-3-yl)methyl)-1H-indole-4-carboxamide hydrochloride salt (161 mg, 0.326 mmol, 95% yield) as a light yellow solid. MS (ES)+m/e 457.2 [M+H]$^+$.

INTERMEDIATES

Intermediate 1

3-(Aminomethyl)-4,6-dimethyl-2(1H)-pyridinone hydrochloride

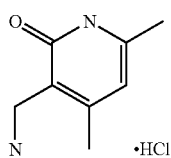

Palladium on carbon (10%) (3.24 g) was charged into a 2 L dry Parr bottle and a small amount of acetic acid was added. Next added 4,6-dimethyl-2-oxo-1,2-dihydro-pyridine-3-carbonitrile (30 g, 202.7 mmol), sodium acetate (30.75 g, 375.0 mmol), platinum oxide (0.218 g), and acetic acid (1 L). The bottle was capped, placed on Parr apparatus, and shaken under an atmosphere of H$_2$ (100 psi) for 2 days. The reaction mixture was filtered. The solvent was removed to give a residue, which was treated with 150 mL of conc. HCl, and the formed solids were filtered. The yellow filtrate was concentrated. To the crude compound was added 30 mL of conc. HCl and 150 mL EtOH, the contents cooled to 0° C., and stirred at 0° C. for 2 h. The formed solids were filtered, washed with cold EtOH, ether, and dried. The product was collected as 36 g. This batch was combined with other batches prepared on smaller scales and triturated with ether to give 51 g of pure compound. $^1$H NMR (400 MHz, DMSO-d$_6$) δ ppm 11.85 (br s, 1H) 8.13 (br s, 3H) 5.93-6.01 (m, 1H) 3.72-3.80 (m, 2H) 2.22 (s, 3H) 2.16 (s, 3H).

Intermediate 2

3-(Aminomethyl)-6-methyl-4-(trifluoromethyl)-2(1H)-pyridinone

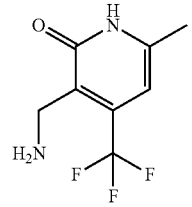

To a dried 500 mL Parr bottle equipped with nitrogen inlet were added sodium acetate (1.502 g, 18.30 mmol), 10% palladium on carbon (1.579 g, 0.742 mmol), platinum(IV) oxide (0.011 g, 0.049 mmol) and a small amount of acetic acid to wet the catalysts, under nitrogen stream. Next was added 2-hydroxy-6-methyl-4-(trifluoromethyl)-3-pyridinecarbonitrile (2.0 g, 9.89 mmol) followed by acetic acid (175 mL) while under nitrogen atmosphere. The contents were sealed, placed on a Parr shaker, and reacted at 40 psi of H$_2$ for ca. 6 hr, keeping the H$_2$ psi between 20 and 40 psi (vessel was refilled twice). The vessel was purged with nitrogen and the reaction mixture filtered through Celite, and the filter pad was further washed with a small amount of acetic acid. The volatiles were removed in vacuo to afford a residue, which was dried under high vacuum for 45 min. The solid was suspended in conc. HCl (12 mL), stirred, and filtered. The clear filtrate was concentrated in vacuo and the residue dried under high vacuum. The collected solid was suspended in conc. HCl (2 mL) and diluted with EtOH (13 mL). The contents were agitated and stored at ca. 0° C. (freezer) for 30 min to give a white solid. The solid was filtered and washed with cold ethanol (5 mL). The solid was filtered and dried in vacuum oven for 1 h to give 3-(aminomethyl)-6-methyl-4-(trifluoromethyl)-2(1H)-pyridinone (0.95 g, 40%). LCMS E-S (M+H)=206.9. $^1$H NMR (400 MHz, DMSO-$d_6$) δ ppm 2.31 (s, 3H), 3.40-3.62 (m, 2H), 3.87 (d, J=5.05 Hz, 2H), 8.12-8.37 (m, 3H).

Intermediate 3

3-(Aminomethyl)-4-cyclohexyl-6-methyl-2(1H)-pyridinone

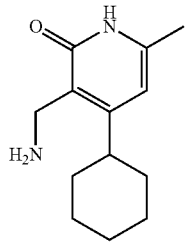 [SMILES: Cc1cc(C2CCCCC2)c(CN)c(=O)[nH]1]

3a) 4-Cyclohexyl-6-methyl-2-oxo-1,2-dihydro-3-pyridinecarbonitrile

To a stirred suspension of CrCl$_2$ (58 g, 472.8 mmol) in THF (1500 mL) was added a THF solution (500 mL) of 1,1-dichloro-2-propanone 10 g, 78.8 mmol) and cyclohexanecarbaldehyde (8.84 g, 78.8 mmol). The reaction mixture was heated at reflux for 2 h, and then quenched by the addition of 1.0 M HCl. The reaction mixture was filtered through a pad of Celite and concentrated in vacuo. The crude residue (10 g) was added to a solution of DMSO (150 mL) containing t-BuOK (7.5 g, 65.7 mmol) and cyanoacetamide (6.1 g, 72.3 mmol) and stirred at room temperature for 30 min. Additional t-BuOK (22.5 g, 197.1 mmol) was added and the reaction mixture was stirred under an atmosphere of oxygen for an additional 1 h. The contents were purged with argon, diluted with 4 volumes of H$_2$O, and then 5 volumes of 4 N HCl, which were added slowly. The reaction mixture was filtered, washed with water and dried to give 4-cyclohexyl-6-methyl-2-oxo-1,2-dihydro-3-pyridinecarbonitrile (4.5 g, 32%). $^1$H NMR (400 MHz, DMSO-$d_6$) δ ppm 6.25 (s, 1H), 2.61-2.65 (m, 1H), 2.22 (s, 3H), 1.66-1.79 (m, 4H), 1.24-1.46 (m, 6H).

3b) 3-(Aminomethyl)-4-cyclohexyl-6-methyl-2(1H)-pyridinone

To an ice-bath cooled THF (100 mL) solution of the product from step 1 (2 g, 9.26 mmol) was added NaBH$_4$ (0.81 g, 21.3 mmol) and I$_2$ (2.3 g, 9.26 mmol), and the mixture stirred for 30 min. The reaction mixture was then heated at reflux for 3 h, and then allowed to cool to room temperature. After cooling to 0° C., the reaction mixture was acidified by slow addition of 3 N HCl (1 mL). The reaction mixture was concentrated in vacuo and the crude product purified by reverse phase HPLC to give 3-(aminomethyl)-4-cyclohexyl-6-methyl-2(1H)-pyridinone as a solid (0.5 g, 25%). LCMS E-S (M+H)=221.1. $^1$H NMR (400 MHz, DMSO-$d_6$) δ ppm 11.8-11.9 (br s, 1H), 7.80-7.93 (br s, 3H), 6.07 (s, 1H), 3.69 (s, 2H), 2.67-2.75 (m, 1H), 2.17 (s, 3H), 1.58-1.72 (m, 5H), 1.19-1.41 (m, 5H).

Intermediate 4

3-(Aminomethyl)-4-cyclopropyl-6-methyl-2(1H)-pyridinone

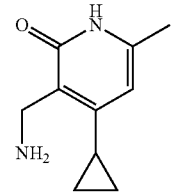

The title compound was prepared in the same manner as described for 3-(aminomethyl)-4-cyclohexyl-6-methyl-2(1H)-pyridinone (Intermediate 3) using 4-cyclopropyl-6-methyl-2-oxo-1,2-dihydro-3-pyridinecarbonitrile (5 g, 28.7 mmol). Obtained: 0.50 g (10%). LCMS E-S (M+H)=179.1. $^1$H NMR (400 MHz, DMSO-$d_6$) δ ppm 11.76-11.78 (br s, 1H), 7.82-7.92 (br s, 3H), 5.61 (s, 1H), 3.94-3.99 (m, 2H), 2.11 (s, 3H), 1.98-2.05 (m, 1H), 0.95-1.01 (m, 2H), 0.74-0.79 (m, 2H).

Intermediate 5

3-(Aminomethyl)-6-methyl-4-propyl-2(1H)-pyridinone

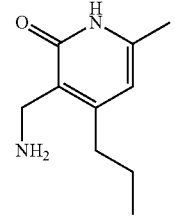

5a) 6-Methyl-2-oxo-4-propyl-1,2-dihydro-3-pyridinecarbonitrile

To a solution of DMSO (300 mL) containing t-BuOK (20 g, 178 mmol) and cyanoacetamide (16.5 g, 196 mmol) was added (3E)-3-hepten-2-one (20 g, 178 mmol), and the contents were stirred at room temperature for 30 min. Additional t-BuOK (60 g, 534 mmol) was added and the reaction mixture was placed under an atmosphere of oxygen for an additional 1 h. The reaction mixture was purged with argon, diluted with 4 volumes of H$_2$O, and then 5 volumes of 4 N HCl, which were added slowly. The reaction mixture was filtered, washed with water, and dried to give 6-methyl-2-oxo-4-propyl-1,2-dihydro-3-pyridinecarbonitrile (10 g, 32%). $^1$H NMR (400 MHz, DMSO-$d_6$) δ ppm 12.25-12.40 (br s, 1H), 6.18 (s, 1H), 2.53 (t, 2H), 2.22 (s, 3H), 1.57-1.64 (m, 2H), 0.84 (t, 3H).

5b) 3-(Aminomethyl)-6-methyl-4-propyl-2(1H)-pyridinone

The title compound was prepared in the same manner as described for 3-(aminomethyl)-4-cyclohexyl-6-methyl-2

(1H)-pyridinone (Intermediate 3) using 6-methyl-2-oxo-4-propyl-1,2-dihydro-3-pyridinecarbonitrile (2 g, 11.2 mmol). Obtained: 1.2 g (60%). LCMS E-S (M+H)=181.1. ¹H NMR (400 MHz, DMSO-d$_6$) δ ppm 7.85-7.95 (br s, 3H), 5.99 (s, 1H), 3.80-3.85 (m, 2H), 2.42 (t, 2H), 2.14 (s, 3H), 1.43-1.49 (m, 2H), 0.86 (t, 3H).

Intermediate 6

3-(Aminomethyl)-6-methyl-4-phenyl-2(1H)-pyridinone

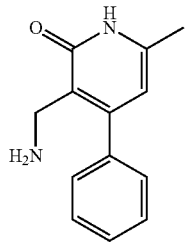 [SMILES: Cc1cc(-c2ccccc2)c(CN)c(=O)[nH]1]

The title compound was prepared in the same manner as described for 3-(aminomethyl)-6-methyl-4-propyl-2(1H)-pyridinone (Intermediate 5) using (3E)-4-phenyl-3-buten-2-one (20 g, 137 mmol). LCMS E-S (M+H)=215.0. ¹H NMR (400 MHz, DMSO-d$_6$) δ ppm 12.2-12.3 (br s, 1H), 7.88-8.00 (br s, 3H), 7.43-7.51 (m, 3H), 7.29-7.38 (m, 2H), 6.08 (s, 1H), 3.67-3.70 (m, 2H), 2.23 (s, 3H).

Intermediate 7

3-(Aminomethyl)-6-methyl-4-(1-methylethyl)-2(1H)-pyridinone

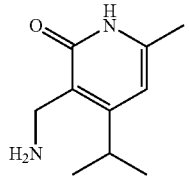

The title compound was prepared in the same manner as described for 3-(aminomethyl)-6-methyl-4-propyl-2(1H)-pyridinone (Intermediate 5) using (3E)-5-methyl-3-hexen-2-one (20 g, 137 mmol). LCMS E-S (M+H)=181.1. ¹H NMR (400 MHz, DMSO-d$_6$) δ ppm 11.8-11.9 (br s, 1H), 7.86-7.96 (br s, 3H), 6.10 (s, 1H), 3.82-3.86 (m, 2H), 3.02-3.09 (m, 1H), 2.17 (s, 3H), 1.08 (d, 6H).

Intermediate 8

3-(Aminomethyl)-4-methyl-6-propyl-2(1H)-pyridinone

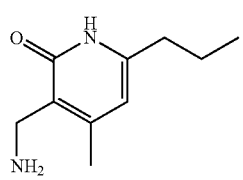

8a) 4-Methyl-2-oxo-6-propyl-1,2-dihydro-3-pyridinecarbonitrile

To a solution of NaNH$_2$ (32.5 g, 862 mmol) in anhydrous ether (500 mL) at 30° C. was added dropwise a mixture of butyric acid ethyl ester (50 g, 431 mmol) and acetone (37.5 g, 646.5 mol). After addition, the reaction mixture was stirred for 4 h. The reaction mixture was poured onto ice water with stirring. Additional ether was added, and the layers were separated. The aqueous layer was acidified to pH 5.0 with 2 N HCl and then to pH 7.5 with Na$_2$CO$_3$. The aqueous layer was then extracted with ether. The combined organic layers were dried over Na$_2$SO$_4$, filtered, and concentrated in vacuo. The crude product, 2,4-heptanedione (20 g, 156 mmol), and 2-cyanoacetamide (13.12 g, 156 mmol) were suspended in EtOH (160 mL) at 75° C., followed by addition of piperidine (13.2 g, 156 mmol). The contents were stirred and heated at reflux for 1 h. The mixture was cooled to room temperature and filtered. The collected solid was suspended in water and stirred for 1 h. The mixture was filtered and dried to give 4-methyl-2-oxo-6-propyl-1,2-dihydro-3-pyridinecarbonitrile (11 g, 40%). LCMS E-S (M+H)=181.1. ¹H NMR (400 MHz, DMSO-d$_6$) δ ppm 12.3-12.4 (br s, 1H), 6.25 (s, 1H), 3.64 (s, 3H), 2.50 (t, 2H), 1.63 (m, 2H), 0.94 (t, 3H).

8b) 3-(Aminomethyl)-4-methyl-6-propyl-2(1H)-pyridinone

Sodium acetate (3.5 g, 42.6 mmol), palladium on carbon (0.81 g) and platinum oxide (0.1 g) were placed in a dried Parr bottle flushed with nitrogen, followed by addition of a small amount of acetic acid (to wet the catalysts). A solution of 4-methyl-2-oxo-6-propyl-1,2-dihydro-pyridine-3-carbonitrile (5 g, 28 mmol) in acetic acid was added to the Parr bottle followed by additional acetic acid (200 mL). The vessel was capped, placed on Parr apparatus and hydrogenated at 45 psi for 12 h. The reaction mixture was filtered and the filtrate concentrated in vacuo. The crude product was purified by preparative HPLC to afford the title compound (TFA salt) as 4.1 g (87%). LCMS E-S (M+H))=181.1. ¹H NMR (400 MHz, DMSO-d$_6$) δ ppm 11.8-11.9 (br s, 1H), 7.83-7.88 (br s, 3H), 5.99 (s, 1H), 3.77-3.81 (m, 2H), 2.37 (t, 2H), 1.53 (m, 2H), 0.83 (t, 3H).

Intermediate 9

3-(Aminomethyl)-6-cyclopropyl-4-methyl-2(1H)-pyridinone hydrochloride

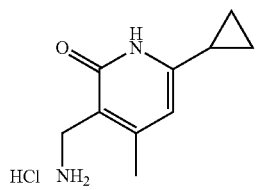

9a) 1-Cyclopropyl-1,3-butanedione

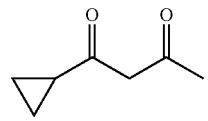

To a stirring solution of THF (100 mL) was added potassium tert-butoxide (5.60 g, 49.5 mmol), followed by a mixture of cyclopropyl methyl ketone (3.27 mL, 33 mmol) and ethyl acetate (9.69 mL, 99 mmol) in 30 mL THF at 35° C., via addition funnel over a 25 min period. The contents were heated and stirred at 60° C. After 3 h, the contents were removed from heating, and allowed to cool to room temperature. The reaction mixture was carefully diluted with 30 mL 2 N HCl and stirred for 10 min. The mixture was extracted with diethyl ether (3×50 mL), and the combined organic layers washed with brine (1×50 mL). The organic layer was dried over MgSO$_4$, filtered, and concentrated in vacuo. Purification by chromatography on silica gel (eluent: 0 to 15% EtOAc in hexanes) with good separation afforded 1-cyclopropyl-1,3-butanedione as a light yellow colored oil, 3.9 g in ~75% purity (residual solvent), for an overall yield of 70%. $^1$H NMR (400 MHz, CDCl$_3$) δ ppm 0.89-0.96 (m, 2H), 1.09-1.15 (m, 2H), 1.59-1.69 (m, 1H), 2.04 (s, 3H), 5.63 (s, 1H), 15.5-16.0 (br s, 1H).

9b) 6-Cyclopropyl-4-methyl-2-oxo-1,2-dihydro-3-pyridinecarbonitrile

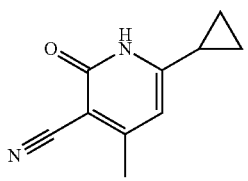

To a stirred solution of ethanol (5 mL) were added 1-cyclopropyl-1,3-butanedione (505 mg, 3.00 mmol) and cyanoacetamide (252 mg, 3.00 mmol), and the heterogenous contents heated until homogenous (ca. 75° C.). Piperidine was added (0.395 mL, 4.00 mmol) and the mixture was heated at reflux for 30 min. The reaction mixture was allowed to cool to room temperature, wherein precipitation ensued. The solid precipitate was filtered and set aside. The filtrate was concentrated in vacuo and the oily residue treated with minimal EtOAc and then 10 mL hexanes to afford a second crop of solid. The solid product crops were combined, suspended in water (7 mL), vigorously stirred, and vacuum filtered to afford 6-cyclopropyl-4-methyl-2-oxo-1,2-dihydro-3-pyridinecarbonitrile as a nearly white solid (380 mg, 73%). LCMS E-S (M+H)=175.1. $^1$H NMR (400 MHz, CDCl$_3$) δ ppm 1.01-1.09 (m, 2H), 1.28 (dd, J=8.59, 2.27 Hz, 2H), 1.95-2.01 (m, 1H), 2.43 (s, 3H), 5.82 (s, 1H).

9c) 1,1-Dimethylethyl[(6-cyclopropyl-4-methyl-2-oxo-1,2-dihydro-3-pyridinyl)methyl]carbamate

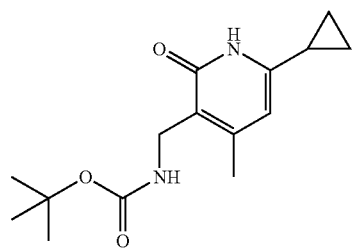 [SMILES: Cc1cc(C2CC2)[nH]c(=O)c1CNC(=O)OC(C)(C)C]

6-Cyclopropyl-4-methyl-2-oxo-1,2-dihydro-3-pyridinecarbonitrile (0.35 g, 2.01 mmol) was added to methanol (20 mL) and the stirred contents cooled to −10° C. Next was added di-tert-butyloxycarbonyl (0.933 mL, 4.02 mmol) and the suspension stirred for 15 min. Next was added in NiCl$_2$·6H$_2$O (0.055 g, 0.201 mmol) as a solid and stirred for 5 min. Then NaBH$_4$ (0.532 g, 14.06 mmol) was added in 6 portions with 5 min. increments between each portion. Then the ice bath was removed and the contents were stirred with warming to room temperature overnight. The reaction mixture was returned to −10° C., followed by addition of 3 more portions of NaBH$_4$ (0.532 g, 14.06 mmol). The ice bath was removed and the mixture stirred at room temperature for 1 h. The contents were quenched by addition of diethylethylene amine (0.218 mL, 2.01 mmol) and stirred for 45 min at room temperature. The volatiles were removed in vacuo and the residue suspended in EtOAc and saturated NaHCO$_3$. The organic layer was washed with additional NaHCO$_3$. The layers were separated, and the organic layer dried over MgSO$_4$, filtered, and concentrated in vacuo. The crude product was purified by silica gel chromatography (eluent: 10% methanol in dichloromethane). The collected product was dried under hi-vacuum for 1 h, and then treated with ether and filtered. After drying in vacuum oven at 45° C. for 2 h, 1,1-dimethylethyl[(6-cyclopropyl-4-methyl-2-oxo-1,2-dihydro-3-pyridinyl)methyl]carbamate was collected (0.28 g, 50%). $^1$H NMR (400 MHz, DMSO-d$_6$) δ ppm 0.73-0.80 (m, 2H), 0.88-0.96 (m, 2H), 1.36 (s, 9H), 1.70-1.82 (m, 1H), 2.11 (s, 3H), 3.95 (d, J=5.31 Hz, 2H), 5.66 (s, 1H), 6.51 (t, J=4.80 Hz, 1H), 11.50 (br. s., 1H).

9d) 3-(Aminomethyl)-6-cyclopropyl-4-methyl-2(1H)-pyridinone hydrochloride 1,1-Dimethylethyl[(6-cyclopropyl-4-methyl-2-oxo-1,2-dihydro-3-pyridinyl)methyl]carbamate (0.28 g, 1.006 mmol) was added to EtOAc (9 mL) and methanol (1.0 mL). The suspension was stirred at room temperature for 5 min, followed by addition of 4 M HCl in dioxane (5.03 mL, 20.12 mmol), and the contents were stirred at room temperature overnight. The volatiles were then removed in vacuo to afford a solid. The solid was triturated with ether, filtered, and dried in a vacuum oven at 45° C. for 4 h. The title compound was collected (0.22 g, 100% yield). $^1$H NMR (400 MHz, DMSO-d$_6$) δ ppm 0.78-0.86 (m, 2H), 0.95-1.03 (m, 2H), 1.83 (tt, J=8.46, 5.05 Hz, 1H), 2.16-2.22 (m, 3H), 3.75 (q, J=5.47 Hz, 2H), 5.79 (s, 1H), 8.02 (br. s., 3H), 11.92 (br. s., 1H).

Intermediate 10

3-(Aminomethyl)-4-ethyl-6-methyl-2(1H)-pyridinone hydrochloride

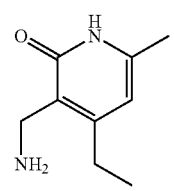

10a) Hex-3-en-2-one

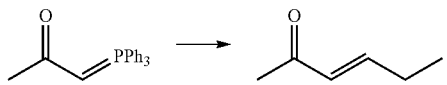

To a stirred solution of 1-(triphenylphosphoranylidene)-2-propanone (100 g, 307 mmol) in DCM (500 mL) was added propionaldehyde (140 mL, 1929 mmol) at room temperature. The reaction mixture was then stirred at room temperature for 18 hours. The reaction was monitored by TLC. The solvent (DCM) was distilled off using ordinary distillation. The residue was then distilled using fractional distillation under vacuum (~450 mbar) and the desired product was isolated. The title compound, hex-3-en-2-one (20 g, 66%), was collected at 110° C. $^1$H NMR (CDCl$_3$, 400 MHz) δ ppm 1.071-1.121 (t, 3H, J=7.4 Hz), 2.250-2.299 (m, 5H), 6.054-6.094 (d, 1H, J=16 Hz), 6.823-6.895 (m, 1H).

10b) 4-Ethyl-1-dihydro-6-methyl-2-oxopyridine-3-carbonitrile

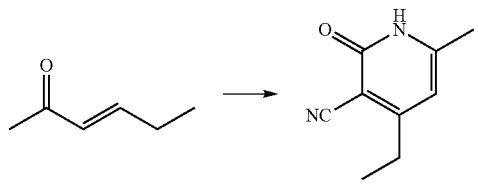

To a stirred solution of t-BuOK (22.85 g, 204.08 mmol) and cyanoacetamide (18.8 g, 224.1 mmol) in DMSO (300 mL) was added hex-3-en-2-one (20 g, 204.08 mmol) under argon atmosphere at room temperature. The reaction mixture was then stirred at room temperature for 30 min and then added additional t-BuOK (68.5 g, 612.05 mmol) was added. Argon gas was displaced by oxygen gas and the mixture stirred for 48 hrs at room temperature in presence of oxygen. Reaction was monitored by TLC. The reaction mixture was cooled to 0° C. and diluted with water (100 mL) followed by 4 N HCl (120 mL). The mixture was stirred for 15 min and the resulting solid was filtered. The solid was washed with water (1 L) and dried to afford the title compound, 4-ethyl-1,2-dihydro-6-methyl-2-oxopyridine-3-carbonitrile (10.5 g, 31%), as an off white solid. $^1$H NMR (CDCl$_3$, 400 MHz): δ ppm 1.148-1.185 (t, 3H, J=7.4 Hz), 2.237 (s, 3H), 2.557-2.614 (m, 2H), 6.211 (s, 1H), 12.330 (broad s, 1H). MS (ES) [M+H]$^+$ 161.06.

10c) 3-(Amino methyl)-4-ethyl-6-methylpyridin-2(1H)-one

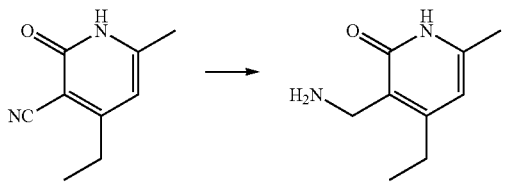

To a suspension of Raney Nickel (6 g) in methanol (200 mL) was added 4-ethyl-1,2-dihydro-6-methyl-2-oxopyridine-3-carbonitrile (10 g, 61.7 mmol) and methanolic ammonia (750 mL). The reaction mixture was stirred at room temperature under hydrogen pressure (80 psi) for 48 hrs. The reaction mixture was filtered through Celite and washed with methanol (250 mL). The filtrate was concentrated under reduced pressure and the residue purified by filter column using silica gel (60-120 mesh), eluted with 10% MeOH in CHCl$_3$, to afford 3-(amino methyl)-4-ethyl-6-methylpyridin-2(1H)-one (5.6 g, 54%) as an off white solid. $^1$H NMR (DMSO-D$_6$, 400 MHz) (free amine): δ ppm 1.063-1.101 (t, 3H, J=7.6 Hz), 2.101 (s, 3H), 2.412-2.449 (m, 2H), 3.448 (s, 2H), 5.835 (s, 1H). MS (ES) [M+H]$^+$ 167.06.

10d) 3-(Aminomethyl)-4-ethyl-6-methylpyridin-2(1H)-one hydrochloride

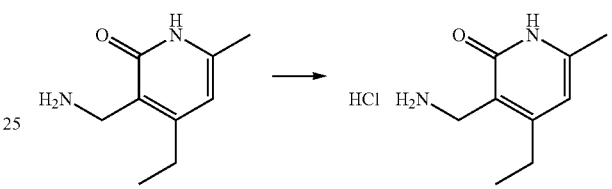

3-(Amino methyl)-4-ethyl-6-methylpyridin-2(1H)-one, (5.6 g, 33 mmol) was suspended in DCM (560 mL) and the insoluble contents/particles were filtered. The filtrate was concentrated and dried. The residue was dissolved in DCM (10 mL) and 4 M HCl in 1,4-dioxane (16 mL, 66 mmol) was added at 0° C. and stirred for 10 min, at which time the reaction mixture was concentrated under high-vacuum and dried. The resulting crude solid was triturated with hexane (150 mL) and filtered. The solid was dried under vacuum. Collected 3-(amino methyl)-4-ethyl-6-methylpyridin-2(1H)-one hydrochloride (5.9 g, 86%).

$^1$H NMR (400 MHz, DMSO-d$_6$) δ ppm 1.082-1.120 (t, 3H, J=7.6 Hz), 2.179 (s, 3H), 2.503-2.544 (m, 2H), 3.785-3.798 (d, 2H, J=5.2 Hz), 6.024 (s, 1H), 7.985 (broad s, 2H), 11.858 (broad s, 1H). MS (ES) [M+H]$^+$ 167.2.

Intermediate 11

3-(aminomethyl)-6-ethyl-4-methyl-2(1H)-pyridinone

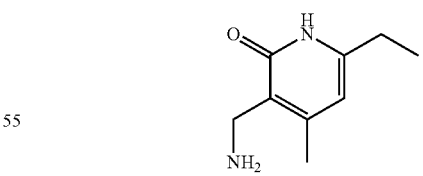

11a) 4-ethyl-6-methyl-2-oxo-1,2-dihydro-3-pyridinecarbonitrile

To a solution of t-BuOK (17.2 g, 153 mmol) and cyanoacetamide (13 g, 153 mmol) in CH$_3$CN (225 mL) was added (3E)-3-hexen-2-one (15 g, 153 mmol) at room temperature under N$_2$ atmosphere. The reaction mixture was stirred for 30 min. To the reaction mixture was added additional t-BuOK (51.4 g), and the N₂ was displaced by oxygen. After stirring for 1 h without external cooling, the mixture was diluted with 4 N HCl, which was added slowly and with good stirring. The mixture was filtered, washed with EtOH, dried to give 6-ethyl-4-methyl-2-oxo-1,2-dihydro-3-pyridinecarbonitrile (5 g, 21%). ¹H NMR (400 MHz, DMSO-d₆) δ 12.33 (br. s., 1H), 6.18 (s, 1H), 2.45 (q, 2H), 2.30 (s, 3H), 1.11 (t, 3H).

11b) 3-(aminomethyl)-6-ethyl-4-methyl-2(1H)-pyridinone

To an ice bath cooled THF solution (200 mL) of 6-ethyl-4-methyl-2-oxo-1,2-dihydro-3-pyridinecarbonitrile (7 g, 43.2 mmol) was added NaBH₄ (4.2 g, 108 mmol), and I₂ (11.2 g, 43.2 mmol), and the contents were stirred for 30 min. The reaction mixture was then heated at reflux overnight. The reaction mixture was cooled, and carefully neutralized by slow addition of 4 N HCl at 0° C. The mixture was dried over MgSO₄, filtered, and concentrated in vacuo. The product was purified by HPLC to give 3-(aminomethyl)-6-ethyl-4-methyl-2(1H)-pyridinone as a TFA salt (1.9 g 26.4%). LCMS MH⁺=167.1 ¹H NMR (400 MHz, DMSO-d₆) δ 11.82 (br. s., 1H), 7.82 (br s, 3H), 5.97 (s, 1H), 3.75-3.77 (m, 2H), 2.39 (q, 2H), 2.17 (s, 3H), 1.09 (t, 3H).

Intermediate 12

3-(aminomethyl)-6-methyl-4,4'-bipyridin-2(1H)-one

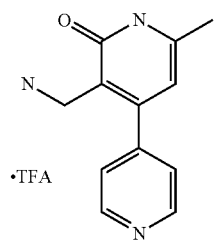 [SMILES: Cc1cc(-c2ccncc2)c(CN)c(=O)[nH]1]

12a) (2Z)-3-Hydroxy-1-(4-pyridinyl)-2-buten-1-one

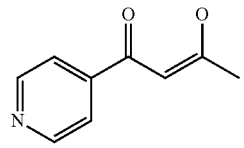

To a solution of ethyl 4-pyridinecarboxylate (30 g, 198 mmol) and acetone (34.58 g, 595 mmol) in THF (150 mL) was slowly added NaOMe (12.87 g, 238 mmol) at 35-40° C. The mixture was stirred at room temperature for 0.5 h, and then heated at reflux for 3 h. The mixture was cooled to room temperature and filtered to give a solid, which was washed with t-BuOMe, and dissolved in H₂O. The solution was acidified with acetic acid and the resulting oily product was extracted with CHCl₃. The solvent was removed in vacuo, and the crude product was obtained (12 g, 37%) and used without further purification. ¹H NMR (400 MHz, DMSO-d₆) δ 8.73 (d, 2H), 7.76 (d, 2H), 6.63 (s, 1H), 2.21 (s, 3H); note: enolic OH does not appear.

12b) 6-Methyl-2-oxo-1,2-dihydro-4,4'-bipyridine-3-carbonitrile and 4-methyl-6-oxo-1,6-dihydro-2,4'-bipyridine-5-carbonitrile

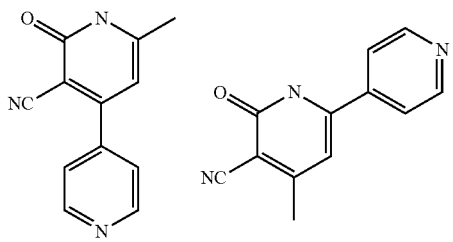 [SMILES: Cc1cc(-c2ccncc2)c(C#N)c(=O)[nH]1 ; Cc1cc(-c2ccncc2)[nH]c(=O)c1C#N]

To a solution of (2Z)-3-hydroxy-1-(4-pyridinyl)-2-buten-1-one (8 g, crude, 49 mmol) and cyanoacetamide (4.12 g, 49 mmol) in anhydrous EtOH (100 mL) was added piperidine (4.17 g, 49 mmol) under N₂ at 75° C. The mixture was heated at reflux for 1 h, and then cooled to room temperature. After filtration, the solid was collected and washed with H₂O to give the crude product (4 g) as two isomers. After separation by HPLC, 1.8 g of 6-methyl-2-oxo-1,2-dihydro-4,4'-bipyridine-3-carbonitrile and 1.2 g of 4-methyl-6-oxo-1,6-dihydro-2,4'-bipyridine-5-carbonitrile were obtained. The identity of 6-methyl-2-oxo-1,2-dihydro-4,4'-bipyridine-3-carbonitrile was established by nOE analysis. ¹H NMR (400 MHz, DMSO-d₆) δ 12.79 (br. s., 1H), 8.75 (d, 2H), 7.58 (d, 2H), 6.37 (s, 1H), 2.31 (s, 3H).

12c) 3-(Aminomethyl)-6-methyl-4,4'-bipyridin-2(1H)-one

To an ice bath cooled THF (100 mL) solution of 6-methyl-2-oxo-1,2-dihydro-4,4'-bipyridine-3-carbonitrile (4 g, 18.9 mmol) was added NaBH₄ (1.43 g, 37.9 mmol), and I₂ (4.81 g, 18.9 mmol), and the mixture was stirred for 0.5 h. The reaction mixture was then heated at reflux for 4 h. After cooling to 0° C., the reaction mixture was adjusted to pH 5 with 4 N HCl. The mixture was concentrated in vacuo to give the crude compound, which was purified by HPLC to give 3-(aminomethyl)-6-methyl-4,4'-bipyridin-2(1H)-one (1.9 g, 31%) as a TFA salt. LCMS MH⁺=216.0 ¹H NMR (400 MHz, DMSO-d₆ in D₂O) δ 8.87 (d, 2H), 7.87 (d, 2H), 6.13 (s, 1H), 3.65 (br s, 2H), 2.17 (s, 3H).

Intermediate 13

3-(Aminomethyl)-6-cyclobutyl-4-methyl-2(1H)-pyridinone

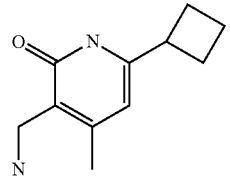

13a) Ethyl cyclobutanecarboxylate

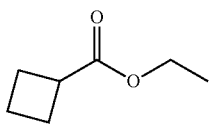

To a solution of cyclobutanecarboxylic acid (50 g, 500 mmol) in EtOH (1.2 L) was slowly added $H_2SO_4$ (20 mL) at room temperature. The solution was stirred at reflux overnight, and then cooled and poured into $H_2O$. The aqueous layer was extracted with ether. The combined organic layers were washed with brine, dried over $Na_2SO_4$, and concentrated in vacuo to give ethyl cyclobutanecarboxylate as a colorless oil (44 g, 69%). $^1H$ NMR (400 MHz, $CDCl_3$-$d_3$) δ 4.04 (q, 2H), 3.04 (m, 1H), 2.12 (m, 4H), 1.88 (m, 2H), 1.18 (t, 3H).

13b) 1-Cyclobutyl-1,3-butanedione

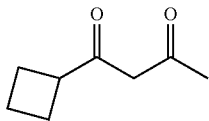

To a solution of $NaNH_2$ (11.7 g, 91 mmol) in anhydrous ether (150 mL) under $N_2$ at 30° C. was added dropwise a mixture of ethyl cyclobutanecarboxylate (19.2 g, 150 mmol) and acetone (21.75 g, 375 mmol). After addition, the reaction mixture was stirred for 4 h, then poured onto ice water with stirring. Ether was added and the unreacted components were extracted into the organic phase. The clear aqueous extract was acidified to pH 5.0 with 2 N HCl, and then to pH 7.5 with $Na_2CO_3$. The solution was extracted with ether. The combined organic layers were dried ($Na_2SO_4$), filtered, and concentrated to give the crude product of 1-cyclobutyl-1,3-butanedione (9.7 g, 76%), which was used in the next step without further purification. $^1H$ NMR (400 MHz, $CDCl_3$-$d_3$) δ 5.42 (s, 1H), 3.66 (s, 1H), 2.11-2.23 (m, 4H), 2.02 (s, 3H), 1.93-1.99 (m, 2H).

13c) 6-Cyclobutyl-4-methyl-2-oxo-1,2-dihydro-3-pyridinecarbonitrile and 4-cyclobutyl-6-methyl-2-oxo-1,2-dihydro-3-pyridinecarbonitrile

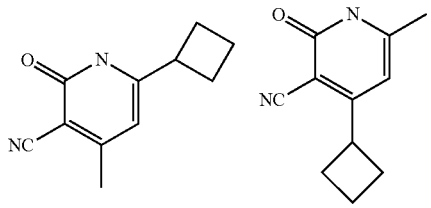

To a solution of 1-cyclobutyl-1,3-butanedione (1.5 g, 10.7 mmol) and cyanoacetamide (1.07 g, 12.8 mmol) in EtOH (25 mL) was added piperidine (1.08 g, 12.8 mmol) at 75° C. After addition, the mixture was stirred with warming to reflux. After 1 h, the mixture was cooled to room temperature during which time precipitation occurred. The contents were filtered, and the filtered solid suspended in water and stirred for 1 h. The heterogenous mixture was filtered and dried to give a mixture of 6-cyclobutyl-4-methyl-2-oxo-1,2-dihydro-3-pyridinecarbonitrile and 4-cyclobutyl-6-methyl-2-oxo-1,2-dihydro-3-pyridinecarbonitrile (1.14 g, 57%). $^1H$ NMR (400 MHz, DMSO-$d_6$ in $D_2O$) δ 12.15-12.30 (br s, 2H), 6.39 (s, 1H), 6.34 (s, 1H), 2.40-2.28 (m, 7H), 2.23-2.25 (m, 3H), 2.18-2.21 (m, 4H), 1.99-2.11 (m, 2H), 1.84-1.90 (m, 2H).

13d) 3-(Aminomethyl)-6-cyclobutyl-4-methyl-2(1H)-pyridinone and 3-(aminomethyl)-4-cyclobutyl-6-methyl-2(1H)-pyridinone

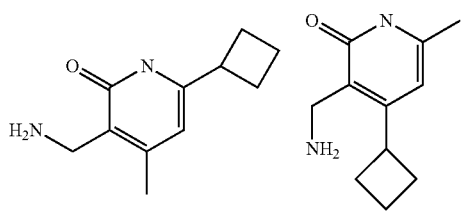

To an ice bath cooled THF (100 mL) solution of 6-cyclobutyl-4-methyl-2-oxo-1,2-dihydro-3-pyridinecarbonitrile and 4-cyclobutyl-6-methyl-2-oxo-1,2-dihydro-3-pyridinecarbonitrile (6 g, 32 mmol) was added $NaBH_4$ (2.73 g, 71.8 mmol), and $I_2$ (8.3 g, 32 mmol), and the mixture was stirred for 30 min. The reaction mixture was then heated at reflux for 3 h. After cooling to 0° C., the reaction mixture was adjusted to pH 5 with 6N HCl. The contents were dried, filtered, and concentrated in vacuo. The crude product was purified by HPLC to give a mixture of 3-(aminomethyl)-6-cyclobutyl-4-methyl-2(1H)-pyridinone and 3-(aminomethyl)-4-cyclobutyl-6-methyl-2(1H)-pyridinone (5.6 g, 91%). $^1H$ NMR (400 MHz, DMSO-$d_6$) δ 11.60-11.70 (br s, 2H), 7.85 (br s, 4H), 6.15 (s, 1H), 6.03 (s, 1H), 3.72-3.79 (m, 2H), 3.29-3.33 (m, 2H), 2.16 (s, 6H), 2.05-2.10 (m, 6H), 1.88-1.93 (m, 4H), 1.69-1.79 (m, 4H).

13e) 1,1-Dimethylethyl[(6-cyclobutyl-4-methyl-2-oxo-1,2-dihydro-3-pyridinyl)methyl]carbamate and 1,1-dimethylethyl[(4-cyclobutyl-6-methyl-2-oxo-1,2-dihydro-3-pyridinyl)methyl]carbamate

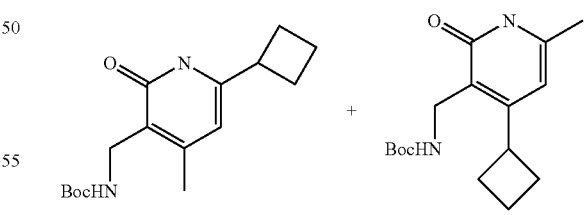

To an ice bath cooled solution of 3-(aminomethyl)-6-cyclobutyl-4-methyl-2(1H)-pyridinone and 3-(aminomethyl)-4-cyclobutyl-6-methyl-2(1H)-pyridinone (3.5 g, 18 mmol) in THF (10 mL) and DMF (10 mL) were added $Boc_2O$ (4.68 g, 21.8 mmol) and triethylamine (5.4 g, 54 mmol). The contents were then stirred for 30 min. at 30° C. The reaction was quenched by addition of ice water, during which time precipitation occurred. The reaction mixture was filtered and dried to give a mixture of the crude products. The crude products were separated by HPLC to give 1,1-dimethylethyl[(6-cyclobutyl-4-methyl-2-oxo-1,2-dihydro-3-pyridinyl)methyl]carbamate (2.1 g, 20%) and 1,1-dimethylethyl[(4-cyclobutyl-6-methyl-2-oxo-1,2-dihydro-3-pyridinyl)methyl]carbamate (1 g, 9.5%). Data for 1,1-dimethylethyl[(6-cyclobutyl-4-methyl-2-oxo-1,2-dihydro-3-pyridinyl)methyl]carbamate:

$^1$H NMR (400 MHz, DMSO-$d_6$) δ 11.28 (br s, 1H), 6.49 (br s, 1H), 5.86 (br s, 1H), 3.85 (br s, 2H), 1.97-2.14 (m, 7H), 1.87-1.94 (m, 1H), 1.72-1.77 (m, 1H), 1.28 (s, 9H).

13f) 3-(Aminomethyl)-6-cyclobutyl-4-methyl-2(1H)-pyridinone hydrochloride

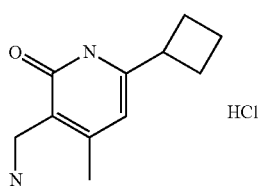

A solution of 1,1-dimethylethyl[(6-cyclobutyl-4-methyl-2-oxo-1,2-dihydro-3pyridinyl)methyl]carbamate (2.1 g, 7.2 mmol) in 4 N HCl (in 15 mL 1,4 dioxane) was heated to 60° C. for 1 h. The mixture was cooled to room temperature. The mixture was filtered and dried to give 3-(aminomethyl)-6-cyclobutyl-4-methyl-2(1H)-pyridinone as an HCl salt (1.95 g, 90%). LCMS MH+=193.1 $^1$H NMR (400 MHz, DMSO-$d_6$) δ 11.70 (br s, 1H), 8.01 (s, 3H), 6.04 (s, 1H), 3.74 (d, 2H), 3.32-3.39 (m, 1H), 2.22 (s, 3H), 2.17-2.20 (m, 2H), 2.06-2.11 (m, 2H), 1.85-1.95 (m, 1H), 1.71-1.79 (m, 1H).

Intermediate 14

3-(Aminomethyl)-6-methyl-4-[(methyloxy)methyl]-2(1H)-pyridinone

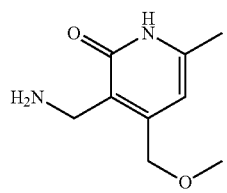

14a) 1-(Methyloxy)-2,4-pentanedione

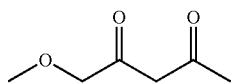

To a solution of sodium (5.83 g, 243.3 mmol) in dry toluene (62.5 mL) was added ethyl (methyloxy)acetate (24 g, 203.4 mmol) at −5° C. After stirring for 3 h, acetone (14 g, 231.4 mmol) was slowly added, upon which the mixture became brown and viscous. Next added 72 mL of tert-butyl methyl ether, and the reaction mixture was stirred at room temperature for 12 h, after which time the sodium salt precipitated. After collection and washing with additional tert-butyl methyl ether, the sodium salt was dissolved in 46 mL of 20% $H_2SO_4$. The contents were extracted with tert-butyl methyl ether and the organic layers concentrated to afford 1-(methyloxy)-2,4-pentanedione (9.76 g, 36.9%). $^1$H NMR (400 MHz, CDCl$_3$-$d_3$) δ 5.76 (s, 1H), 3.96 (s, 2H), 3.38 (s, 3H), 2.07 (s, 3H).

14b) 6-Methyl-4-[(methyloxy)methyl]-2-oxo-1,2-dihydro-3-pyridinecarbonitrile

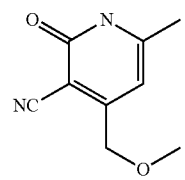

1-(Methyloxy)-2,4-pentanedione (9.51 g, 73.12 mmol) and cyanoacetamide (6.17 g, 73.12 mmol) were dissolved in EtOH (76 mL) and heated until homogenous (ca. 75° C.). Piperidine (6.25 g, 73.12 mmol) was added and the reaction mixture heated at reflux for 20 mins, followed by cooling to room temperature. The contents were filtered to give a solid which was suspended in 140 mL water and stirred vigorously for 20 min. The heterogenous mixture was filtered to afford 6-methyl-4-[(methyloxy)methyl]-2-oxo-1,2-dihydro-3-pyridinecarbonitrile (7.8 g, 65.6%). LCMS MH+=179.0 $^1$H NMR (400 MHz, DMSO-$d_6$) δ 12.47 (br s, 1H), 6.26 (s, 1H), 4.40 (s, 2H), 3.29 (s, 3H), 2.25 (s, 3H).

14c) 3-(Aminomethyl)-6-methyl-4-[(methyloxy)methyl]-2(1H)-pyridinone

6-Methyl-4-[(methyloxy)methyl]-2-oxo-1,2-dihydro-3-pyridine carbonitrile (1.000 g, 5.61 mmol) was suspended in acetic acid (150 ml) and the solution passed through an H-cube instrument equipped with Raney-Ni cartridge at a rate of 1 mL/min at 50 psi and 60° C. After 18 h. the acetic acid was removed under reduced pressure and the remaining residue was dissolved in MeOH. The methanolic solution was passed through a 0.2 μm teflon syringe filter. The methanolic filtrate was purified by reverse phase HPLC (Gemini 50×100 5 μm column. Run 1: 3 min, 90-10%. Run 2, 5 min 0-10%. Run 3, 10 min, 0-20%. The product fractions were concentrated to dryness on a Genevac HT-4 instrument to afford 3-(aminomethyl)-6-methyl-4-[(methyloxy)methyl]-2(1H)-pyridinone as a pale grey waxy solid (900 mg, 70.2% yield) LCMS MH+=183.0 $^1$H NMR (400 MHz, DMSO-$d_6$) δ 8.40 (br. s., 1H), 6.10 (s, 1H), 4.39 (s, 2H), 3.66 (br. s., 2H), 3.32 (s, 3H), 2.19 (s, 3H).

Intermediate 15

3-(Aminomethyl)-6-methyl-4-(phenylmethyl)-2(1H)-pyridinone and 3-(aminomethyl)-4-methyl-6-(phenylmethyl)-2(1H)-pyridinone

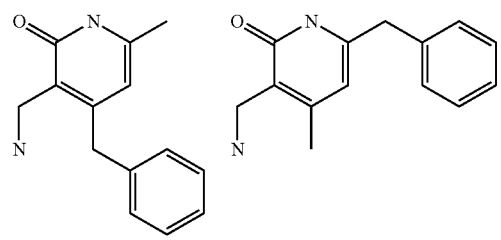

15a) 1-Phenyl-2,4-pentanedione

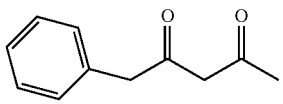

To a solution of NaNH$_2$ (19.02 g, 480 mmol) in anhydrous ether (400 mL) under N$_2$ at −5° C. was added dropwise ethyl phenylacetate (19.2 g, 150 mmol) and then acetone (21.23 g, 370 mmol) with vigorous stirring. After addition, the reaction mixture was stirred at room temperature overnight. The mixture was then acidified to pH 4.0-5.0 with 1N HCl. The organic layer was separated and concentrated in vacuo. The crude product was purified by silica gel chromatography to give 1-phenyl-2,4-pentanedione (18.32 g, 44%). $^1$H NMR (400 MHz, CDCl$_3$-d$_3$) δ 15.49 (br s, 1H), 7.33-7.45 (m, 5H), 5.53 (s, 1H), 3.66 (s, 2H), 2.10 (s, 3H).

15b) 6-Methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile

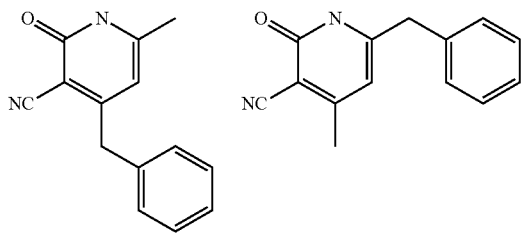 [SMILES: Cc1cc(Cc2ccccc2)c(C#N)c(=O)[nH]1 ; Cc1cc(Cc2ccccc2)[nH]c(=O)c1C#N]

1-Phenyl-2,4-pentanedione (18.32 g, 104 mmol) and cyanoacetamide (8.74 g, 104 mmol) were dissolved in EtOH (104 mL) and heated until homogenous (ca. 75° C.). Piperidine (8.86 g, 104 mmol) was added and the reaction mixture heated at reflux for 15-30 min. followed by cooling to room temperature, during which time precipitation occurred. The heterogenous contents were filtered to give a solid which was suspended in 200 mL water and stirred vigorously for 20 min. The heterogenous mixture was filtered to afford 6-methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile (12.06 g, 52%). LCMS MH+=225.1

$^1$H NMR (400 MHz, DMSO-d$_6$) (mixture of compounds) δ 7.21-7.31 (m, 10H), 6.06 (s, 2H), 3.89 (s, 2H), 3.79 (s, 2H), 2.24 (s, 3H), 2.15 (s, 3H).

15c) 3-(Aminomethyl)-6-methyl-4-(phenylmethyl)-2(1H)-pyridinone and 3-(aminomethyl)-4-methyl-6-(phenylmethyl)-2(1H)-pyridinone

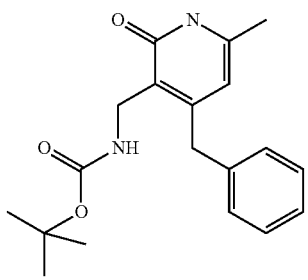

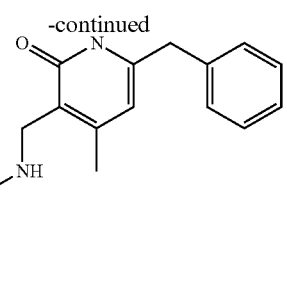

Sodium acetate (6.14 g, 74.8 mmol), Pd/C (0.65 g, 1 mmol), and platinum (II) oxide (45 mg, 1 mmol) were placed in a dried Parr bottle equipped with nitrogen inlet. A small amount of acetic acid was added to wet the catalysts. A solution of 6-methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile (6 g, 26.7 mmol) in acetic acid (300 mL) was added to the vessel. The contents were sealed and hydrogenated on Parr shaker at 45 psi for 12 h. The reaction mixture was filtered and washed with acetic acid. The filtrate was removed under reduced pressure. The residue was washed with methanol and filtered to afford a crude mixture of 3-(aminomethyl)-6-methyl-4-(phenylmethyl)-2(1H)-pyridinone and 3-(aminomethyl)-4-methyl-6-(phenylmethyl)-2(1H)-pyridinone. The reaction was run in duplicate to afford a total crude recovery of 14.5 g. To a solution of the above crude product mixture (4.0 g, 17.5 mmol) in THF (10 mL) and DMF (10 mL) was added di-tert-butoxycarbonyl anhydride (5.0 g, 23.4 mmol.) and triethylamine (5.2 g, 52.5 mmol) at 0° C. The reaction mixture was stirred with warming to room temperature and then stirred for an additional 4 h. The contents were diluted with ice water and then filtered. The collected solid was dried and the products separated by HPLC to furnish 1.2 g of 1,1-dimethylethyl {[4-methyl-2-oxo-6-(phenylmethyl)-1,2-dihydro-3-pyridinyl]methyl}carbamate ($^1$H NMR (400 MHz, DMSO-d$_6$) δ 11.55-1.60 (br s, 1H), 7.20-7.29 (m, 5H), 5.85 (s, 1H), 3.92 (s, 2H), 3.90 (s, 2H), 2.10 (s, 3H), 1.32 (s, 9H) and 1.0 g of 1,1-dimethylethyl {[6-methyl-2-oxo-4-(phenylmethyl)-1,2-dihydro-3-pyridinyl]methyl}carbamate ($^1$H NMR (400 MHz, DMSO-d$_6$) δ 11.50-11.55 (br s, 1H), 7.18-7.25 (m, 5H), 5.75 (s, 1H), 4.02 (s, 2H), 3.85 (s, 2H), 2.05 (s, 3H), 1.32 (s, 9H).

15d) 3-(Aminomethyl)-4-methyl-6-(phenylmethyl)-2(1H)-pyridinone hydrochloride A solution of 1,1-dimethylethyl {[4-methyl-2-oxo-6-(phenylmethyl)-1,2-dihydro-3-pyridinyl]methyl}carbamate (1.2 g, 3.66 mmol) in 4N HCl (in 15 mL 1,4 dioxane) was heated to 60° C. for 1 h. The mixture was cooled to room temperature. The mixture was filtered and dried to give 3-(aminomethyl)-4-methyl-6-(phenylmethyl)-2(1H)-pyridinone as an HCl salt (0.725 g, 87%). LCMS MH+=229.1 $^1$H NMR (400

MHz, DMSO-d$_6$) δ 11.9-12.0 (br s, 1H), 7.99 (br s, 3H), 7.20 (s, 5H), 5.97 (s, 1H), 3.72-3.75 (m, 4H), 2.17 (s, 3H).

15e) 3-(Aminomethyl)-6-methyl-4-(phenylmethyl)-2 (1H)-pyridinone hydrochloride

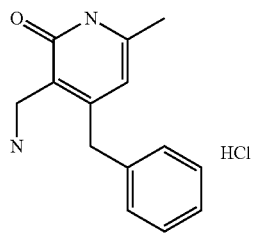 [SMILES: Cc1cc(Cc2ccccc2)c(CN)c(=O)[nH]1 ; Cl]

A solution of 1,1-dimethylethyl {[6-methyl-2-oxo-4-(phenylmethyl)-1,2-dihydro-3-pyridinyl]methyl}carbamate (1.0 g, 3.0 mmol) in 4N HCl (in 15 mL 1,4 dioxane) was heated to 60° C. for 1 h. The mixture was cooled to room temperature. The mixture was filtered and dried to give 3-(aminomethyl)-6-methyl-4-(phenylmethyl)-2(1H)-pyridinone as an HCl salt (0.600 g, 86%). LCMS MH$^+$=229.1 $^1$H NMR (400 MHz, DMSO-d$_6$) δ 11.9-12.0 (br s, 1H), 8.03 (br s, 3H), 7.16-7.30 (m, 5H), 5.84 (s, 1H), 3.91 (s, 2H), 3.81 (s, 2H), 2.10 (s, 3H).

Intermediate 16

3-(Aminomethyl)-6-methyl-4-(4-morpholinylmethyl)-2(1H)-pyridinone

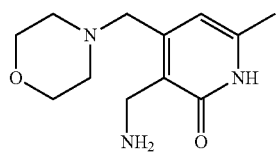 [SMILES: Cc1cc(CN2CCOCC2)c(CN)c(=O)[nH]1]

a) 5-(4-Morpholinyl)-3-pentyn-2-one

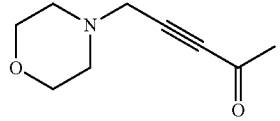

To a cooled (−40° C., CH$_3$CN/CO$_2$) solution of 4-(2-propyn-1-yl)morpholine (2.2 g, 17.58 mmol) in THF (5 mL) was added dropwise via. syringe under N$_2$ a solution of 2 M isopropylmagnesium chloride in THF (10 mL, 20.00 mmol). The reaction was stirred for 1 hr then a solution of N-methoxy-N-methylacetamide (2.2 mL, 20.69 mmol) in THF (5 mL) was added in one portion. The reaction was stirred for 2 hr (allowed to slowly warm to RT), quenched with aq. NH$_4$Cl, extracted with EtOAc, washed with brine, dried (Na$_2$SO$_4$), filtered and evaoprated to dryness under vacuum. The remaining was purified by silica gel chromatography (Analogix, SF25-60 g, 0 to 80% EtOAc in hexanes). The pure fractions were combined and evaporated to dryness to give the product 5-(4-morpholinyl)-3-pentyn-2-one (2.09 g, 12.50 mmol, 71.1% yield) as a yellow oil. $^1$H NMR (400 MHz, DMSO-d$_6$) δ 3.62-3.57 (m, 4H), 3.56 (s, 2H), 2.49-2.43 (m, 4H), 2.34 (s, 3H). MS (ES)+m/e 168.0 [M+H]$^+$.

b) 6-Methyl-4-(4-morpholinylmethyl)-2-oxo-1,2-dihydro-3-pyridinecarbonitrile

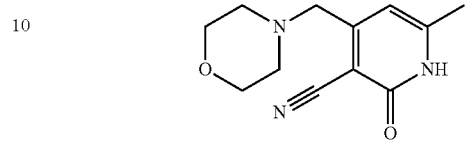

To a stirred solution of 21 wt % sodium ethoxide in EtOH (4.2 g, 12.96 mmol) in EtOH (30 mL) was added 2-cyanoacetamide (1.1 g, 13.08 mmol). The reaction was stirred for 15 min. then a solution of 5-(4-morpholinyl)-3-pentyn-2-one (2.0 g, 11.96 mmol) in EtOH was added to the reaction in one portion. (The reaction quickly turned dark red.) The reaction was stirred overnight at RT, neutralized with 6 N HCl (2.17 mL, 13.02 mmol) and evaporated to dryness under vacuum. Dried under vacuum overnight. The reamaining dark solid was triturated with a solution of (9:1) CH$_2$Cl$_2$, MeOH (50 mL), filtered from insoluble material, washed with (9:1) CH$_2$Cl$_2$, MeOH, and the filtrate evaporated to dryness under vacuum. The dark solid was triturated with a solution of (1:1) EtOAc in hexanes, filtered, washed with (1:1) EtOAc in hexanes, and dried under vacuum to give a brown solid (removed a lot of fast running non-polar impurities). The crude product was purified by silica gel chromatography (Analogix, SF25-60 g, 0 to 15% CH$_2$Cl$_2$/20% (5% NH$_4$OH in MeOH) in CH$_2$Cl$_2$). The pure fractions were combined, evaporated to dryness, triturated with hexanes and dried under vacuum to give the product 6-methyl-4-(4-morpholinylmethyl)-2-oxo-1,2-dihydro-3-pyridinecarbonitrile (0.90 g, 3.86 mmol, 32.3% yield) as a light tan solid.

$^1$H NMR (400 MHz, DMSO-d$_6$) δ 12.44 (br. s., 1H), 6.34 (s, 1H), 3.63-3.56 (m, 4H), 3.48 (s, 2H), 2.45-2.36 (m, 4H), 2.27 (s, 3H) MS (ES)+m/e 234.1 [M+H]$^+$.

c) 3-(Aminomethyl)-6-methyl-4-(4-morpholinylmethyl)-2(1H)-pyridinone

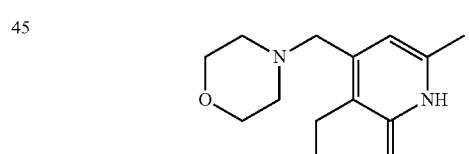

A clear solution of 6-methyl-4-(4-morpholinylmethyl)-2-oxo-1,2-dihydro-3-pyridinecarbonitrile (0.60 g, 2.57 mmol) in HOAc (20 mL) was treated on an H-Cube apparatus (50 psi, 60° C., 1 mL/min., Raney Nickel cartridge) for 18 hr overnight. LCMS showed that the reaction was complete. The reaction was evaporated to dryness, taken up in a small volume of MeOH and treated with 4 N HCl in dioxane (5 mL, 20.00 mmol). The mixture was evaporated to dryness under vacuum (began to ppt. out during evaporation), triturated with Et2O, filtered and dried under vacuum to give the product 3-(aminomethyl)-6-methyl-4-(4-morpholinylmethyl)-2 (1H)-pyridinone (0.76 g, 2.450 mmol, 95% yield) as a light grey solid. $^1$H NMR (400 MHz, DMSO-d$_6$) δ 6.39 (s, 1H), 4.28 (s, 2H), 3.99 (s, 2H), 3.87 (br. s., 4H), 3.27 (br. s., 4H), 2.22 (s, 3H). MS (ES)+m/e 238.0 [M+H]$^+$ (weak), 221.3 [M+H]$^+$ −NH$_3$ (strong).

Intermediate 17 tert-Butyl (5-(aminomethyl)-6-methoxy-4-methylpyridin-2-yl)carbamate

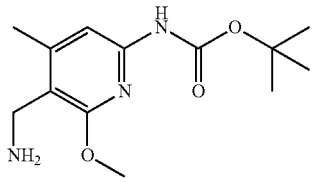 [SMILES: COc1nc(NC(=O)OC(C)(C)C)cc(C)c1CN]

a) Ethyl 4-ethoxy-2-oxopent-3-enoate

To a stirred solution of ethyl 2,4-dioxopentanoate (36.5 g, 231 mmol) and triethyl orthoformate (41 mL, 246 mmol) in ethanol (60 mL) was added ammonium chloride (3.7 g, 69 mmol). The suspension was stirred at RT overnight. LCMS showed that the reaction was mostly complete. (Hydrolyzes on LCMS to some degree?) The reaction was concentrated under vacuum. The remaining oil was taken up in $Et_2O$ (300 mL), filtered to remove insolubles, rinsed with $Et_2O$, and concentrated under vacuum. The product was obtained by short path distillation under vacuum (bp 70 to 77° C. at 0.09 mmHg) to give the product ethyl 4-ethoxy-2-oxopent-3-enoate (36.5 g, 47.3 mmol, 79% yield) as a light yellow oil.

$^1$H NMR (400 MHz, CHLOROFORM-d) δ 6.24 (s, 1H), 4.32 (q, J=7.2 Hz, 2H), 4.02 (q, J=6.9 Hz, 2H), 2.41 (s, 3H), 1.41 (t, J=7.1 Hz, 3H), 1.39 (t, J=7.2 Hz, 3H). MS (ES)+m/e 186.8 [M+H]$^+$, 208.8 M+Na$^+$.

b) Ethyl 5-cyano-4-methyl-6-oxo-1,6-dihydropyridine-2-carboxylate

To a stirred solution of ethyl 4-ethoxy-2-oxopent-3-enoate (22.5 g, 121 mmol) and 2-cyanoacetamide (9.0 g, 107 mmol) in acetone (250 mL) was added potassium carbonate (15.8 g, 114 mmol). The reaction was refluxed (85° C. oil bath) for 10 hr (the reaction formed a thick ppt. in a deep red solution). The slurry was added to cold 1 N HCl (230 mL) in ice. After stirring for 30 min. the suspension was filtered, washed with water and dried under vacuum to give the product ethyl 5-cyano-4-methyl-6-oxo-1,6-dihydropyridine-2-carboxylate (14.51 g, 70.4 mmol, 65.7% yield) as a light pink solid.

$^1$H NMR (400 MHz, DMSO-d$_6$) δ 12.60 (br. s., 1H), 7.05 (br. s., 1H), 4.34 (q, J=7.1 Hz, 2H), 2.45 (s, 3H), 1.32 (t, J=7.1 Hz, 3H). MS (ES)+m/e 206.8 [M+H]$^+$.

c) Ethyl 5-cyano-6-methoxy-4-methylpicolinate

To a stirred suspension of ethyl 5-cyano-4-methyl-6-oxo-1,6-dihydropyridine-2-carboxylate (2.0 g, 9.70 mmol) in $CH_2Cl_2$ (25 mL) was added trimethyloxonium tetrafluoroborate (2.0 g, 13.52 mmol). The reaction was rinsed down with $CH_2Cl_2$ and stirred at RT for 24 hr. (The reaction eventually cleared up.) To the reaction was added 1N NaOH (75 mL). After stirring for 10 minutes the mixture was poured into a separatory funnel. The $CH_2Cl_2$ phase was removed, dried ($Na_2SO_4$), filtered and concentrated under vacuum. Purification by silica gel chromatography (Analogix SF25-40 g, 50 to 100% $CH_2Cl_2$ in hexanes) gave the product ethyl 5-cyano-6-methoxy-4-methylpicolinate (1.13 g, 5.13 mmol, 52.9% yield) as a white solid. $^1$H NMR (400 MHz, DMSO-d$_6$) δ 7.75 (s, 1H), 4.37 (q, J=7.1 Hz, 2H), 4.03 (s, 3H), 2.55 (s, 3H), 1.33 (t, J=7.2 Hz, 3H). MS (ES)+m/e 221.2 [M+H]$^+$.

d) 5-Cyano-6-methoxy-4-methylpicolinic acid

To a stirred solution of ethyl 5-cyano-6-methoxy-4-methylpicolinate (1.0 g, 4.54 mmol) in MeOH (30 mL) and THF (10 mL) was added 6N NaOH (2 mL, 12.00 mmol). The suspension was heated to 60° C. and stirred for 2 hr. (The reaction cleared up right away.) LCMS indicated that the reaction was complete. The reaction was cooled to RT and concentrated to near dryness. The slurry was neutralized with 6N HCl (2 mL) diluted with water, filtered, washed with water and dried under vacuum to give the product 5-cyano-6-methoxy-4-methylpicolinic acid (0.76 g, 3.95 mmol, 87% yield) as a white solid. $^1$H NMR (400 MHz, DMSO-d$_6$) δ 13.65 (br. s., 1H), 7.73 (s, 1H), 4.03 (s, 3H), 2.54 (s, 3H). MS (ES)+m/e 192.9 [M+H]$^+$.

e) tert-Butyl (5-cyano-6-methoxy-4-methylpyridin-2-yl)carbamate

To a stirred solution of 5-cyano-6-methoxy-4-methylpicolinic acid (0.75 g, 3.90 mmol) in tert-butanol (25 mL) was added triethylamine (0.7 mL, 5.02 mmol). After the reaction became clear DPPA (1 mL, 4.64 mmol) was added dropwise over 5 minutes. The reaction was slowly heated to 100° C. and stirred for 4 hr. The reaction was cooled to RT and evaporated to dryness under vacuum. Purified by silica gel chromatography (Analogix, SF25-60 g, 0 to 20% EtOAc in hexanes) to give, after trituration and filtration from hexanes, the product tert-butyl (5-cyano-6-methoxy-4-methylpyridin-2-yl)carbamate (0.61 g, 2.317 mmol, 59.4% yield) as a white solid. $^1$H NMR (400 MHz, DMSO-d$_6$) δ 10.20 (s, 1H), 7.44 (s, 1H), 3.91 (s, 3H), 2.40 (s, 3H), 1.48 (s, 9H). MS (ES)+m/e 264.0 [M+H]$^+$.

f) tert-Butyl (5-(aminomethyl)-6-methoxy-4-methylpyridin-2-yl)carbamate

A clear solution of tert-butyl (5-cyano-6-methoxy-4-methylpyridin-2-yl)carbamate (0.60 g, 2.279 mmol) in HOAc (5 mL) and ethanol (20 mL) was treated on an H-Cube apparatus (50 psi, 40° C., 1 mL/min., Raney Nickel cartridge) for 18 hr. LCMS showed that the reaction was complete (86% pure). The reaction was evaporated to dryness under vacuum. Purified by silica gel chromatography (Analogix, SF25-60 g, 0 to 12% (5% NH$_4$OH/MeOH) in $CH_2Cl_2$). The pure fractions were combined and evaporated to dryness under vacuum to give the product tert-butyl (5-(aminomethyl)-6-methoxy-4-methylpyridin-2-yl)carbamate (0.42 g, 1.571 mmol, 68.9% yield) as a white solid. $^1$H NMR (400 MHz, DMSO-d$_6$) δ 9.33 (s, 1H), 7.16 (s, 1H), 3.80 (s, 3H), 3.57 (s, 2H), 2.28 (s, 3H), 1.46 (s, 9H). MS (ES)+m/e 268.1 [M+H]$^+$.

Intermediate 18

[5-(Aminomethyl)-4-methyl-6-(methyloxy)-2-pyridinyl]methanol

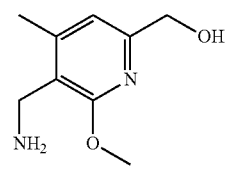

a) 6-(Hydroxymethyl)-2-methoxy-4-methylnicotinonitrile

To a stirred suspension of ethyl 5-cyano-6-methoxy-4-methylpicolinate (5.0 g, 22.70 mmol) and calcium chloride (10 g, 90 mmol) in tetrahydrofuran (50 mL) and ethanol (50.0 mL) at 0° C. in an ice bath was added sodium borohydride (2.5 g, 66.1 mmol). The reaction was slowly allowed to warm to RT and stirred for 18 hr. A large amount of ppt. formed and LCMS showed that the reaction was complete. An equal volume of EtOAc was added and the reaction stirred for 1 hr. The suspension was filtered through a pad of Celite and washed with EtOAc. The filtrate was transferred to a separatory funnel, washed with aq. $NH_4Cl$, brine, dried ($Na_2SO_4$), filtered and concentrated under vacuum. Purification by silica gel chromatography (Analogix, SF40-120 g, 0 to 30% EtOAc in $CH_2Cl_2$) gave the product 6-(hydroxymethyl)-2-methoxy-4-methylnicotinonitrile (3.75 g, 21.05 mmol, 93% yield) as a white solid. $^1$H NMR (400 MHz, DMSO-d$_6$) δ 7.16 (s, 1H), 5.61 (t, J=5.8 Hz, 1H), 4.51 (d, J=5.8 Hz, 2H), 3.94 (s, 3H), 2.47 (s, 3H). MS (ES)+m/e 179.1 [M+H]$^+$.

b) (5-(Aminomethyl)-6-methoxy-4-methylpyridin-2-yl)methanol

A clear solution of 6-(hydroxymethyl)-2-methoxy-4-methylnicotinonitrile (0.50 g, 2.81 mmol) in HOAc (5 mL) and Ethanol (20 mL) was treated on an H-Cube apparatus (50 psi, 40° C., 1 mL/min., Raney Nickel cartridge) for 18 hr overnight. LCMS showed that the reaction was complete (crude contained 57% product and 43% dimeric side product). The reaction was evaporated to dryness under vacuum. Purified by silica gel chromatography (Analogix, SF25-40 g, 0 to 12% (5% $NH_4OH$ in MeOH) in $CH_2Cl_2$) (step gradient to 8% to elute off the dimeric side product then to 12% to elute off the product). The pure fractions were combined and evaporated to dryness under vacuum to give the product (5-(aminomethyl)-6-methoxy-4-methylpyridin-2-yl)methanol (0.30 g, 1.646 mmol, 58.7% yield) as a white solid. MS (ES)+m/e 183.1 [M+H]$^+$, 166.1 [M+H]$^+$ –$NH_3$.

Intermediate 19 tert-Butyl((5-(aminomethyl)-6-methoxy-4-methylpyridin-2-yl)methyl)carbamate

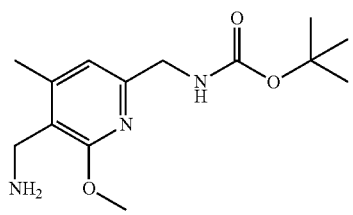 [SMILES: COc1nc(CNC(=O)OC(C)(C)C)cc(C)c1CN]

a) 6-((1,3-Dioxoisoindolin-2-yl)methyl)-2-methoxy-4-methylnicotinonitrile

To a stirred solution of 6-(hydroxymethyl)-2-methoxy-4-methylnicotinonitrile (1.50 g, 8.42 mmol), phthalimide (1.3 g, 8.84 mmol) and triphenylphosphine (2.3 g, 8.77 mmol) in Tetrahydrofuran (THF) (50 mL) at 0° C. in an ice bath was added dropwise DIAD (1.8 mL, 9.26 mmol). Within minutes a white suspension formed. Additional THF (~50 mL) was added to allow stirring. The reaction was allowed to warm to RT and stirred for 3 h. LCMS showed that the reaction was complete. The reaction was evaporated to dryness under vacuum. The remaining solid was triturated with a small volume of EtOAc, filtered, washed with a small volume of EtOAc, then dried under vacuum to give the product 6-((1,3-dioxoisoindolin-2-yl)methyl)-2-methoxy-4-methylnicotinonitrile (2.12 g, 6.90 mmol, 82% yield) as a white solid. $^1$H NMR (400 MHz, DMSO-d$_6$) δ 8.00-7.92 (m, 2H), 7.92-7.87 (m, 2H), 7.15 (s, 1H), 4.86 (s, 2H), 3.74 (s, 3H), 2.43 (s, 3H). MS (ES)+m/e 308.2 [M+H]$^+$.

b) tert-Butyl((5-cyano-6-methoxy-4-methylpyridin-2-yl)methyl)carbamate

To a stirred fine suspension of 6-((1,3-dioxoisoindolin-2-yl)methyl)-2-methoxy-4-methylnicotinonitrile (2.1 g, 6.83 mmol) in Ethanol (100 mL) was added hydrazine monohydrate (1.4 ml, 28.9 mmol). The reaction was stirred at RT for 18 hr. LCMS showed that the reaction was done. The thick white suspension was filtered, pressed dry, washed with EtOH, and the filtrate evaporated to dryness under vacuum. The remaining solid was taken up in Dichloromethane (50 ml), filtered to remove additional insoluble material, and washed with $CH_2Cl_2$. To the clear filtrate with stirring was added $Boc_2O$ (1.809 ml, 7.79 mmol). After stirring at RT for 1 hr LCMS showed that the reaction was complete. The reaction was concentrated under vacuum and purified by silica gel chromatography (Analogix, SF25-60, 0 to 10% EtOAc in hexanes). The pure fractions were combined and evaporated to dryness to give the product tert-butyl((5-cyano-6-methoxy-4-methylpyridin-2-yl)methyl)carbamate (1.42 g, 5.12 mmol, 74.9% yield) as a white solid. $^1$H NMR (400 MHz, DMSO-d$_6$) δ 7.48 (t, J=6.1 Hz, 1H), 6.91 (s, 1H), 4.16 (d, J=6.1 Hz, 2H), 3.96 (s, 3H), 2.45 (s, 3H), 1.41 (s, 9H). MS (ES)+m/e 278.2 [M+H]$^+$.

c) tert-Butyl((5-(aminomethyl)-6-methoxy-4-methylpyridin-2-yl)methyl)carbamate A clear solution of tert-butyl((5-cyano-6-methoxy-4-methylpyridin-2-yl)methyl)carbamate (0.65 g, 2.344 mmol) in HOAc (5 mL) and Ethanol (20 mL) was treated on an H-Cube apparatus (50 psi, 40° C., 1 mL/min., Raney Nickel cartridge) for 18 hr overnight. LCMS showed that the reaction was complete. The reaction was evaporated to dryness under vacuum. Purified by silica gel chromatography (Analogix, SF25-60 g, 0 to 10% (5% $NH_4OH/MeOH$) in $CH_2Cl_2$). The pure fractions were combined and evaporated to dryness under vacuum to give the product tert-butyl((5-(aminomethyl)-6-methoxy-4-methylpyridin-2-yl)methyl)carbamate (0.58 g, 2.061 mmol, 88% yield) as a clear thick oil.

$^1$H NMR (400 MHz, DMSO-d$_6$) δ 7.31 (t, J=6.1 Hz, 1H), 6.63 (s, 1H), 4.06 (d, J=6.3 Hz, 2H), 3.84 (s, 3H), 3.61 (s, 2H), 2.29 (s, 3H), 1.53 (br. s., 2H), 1.41 (s, 9H). MS (ES)+m/e 282.2 [M+H]$^+$.

Intermediate 20

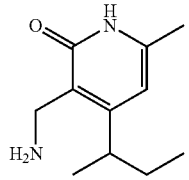

The title compound was prepared in the same manner as described for 3-(aminomethyl)-4-ethyl-6-methyl-2(1H)-pyridinone (Intermediate 10c). LCMS (ES+) m/z=195.22 (M+H). $^1$H NMR (DMSO-d$_6$, 400 MHz): δ 0.809-0.774 (t, 3H, J=6.8 Hz), 1.113-1.097 (d, 3H, J=6.4 Hz), 1.504-1.468 (t, 2H, J=7.2 Hz), 2.184 (s, 3H), 2.839-2.822 (d, 1H, J=6.8 Hz), 3.822 (s, 2H), 6.059 (s, 1H), 8.315 (bs, 2H).

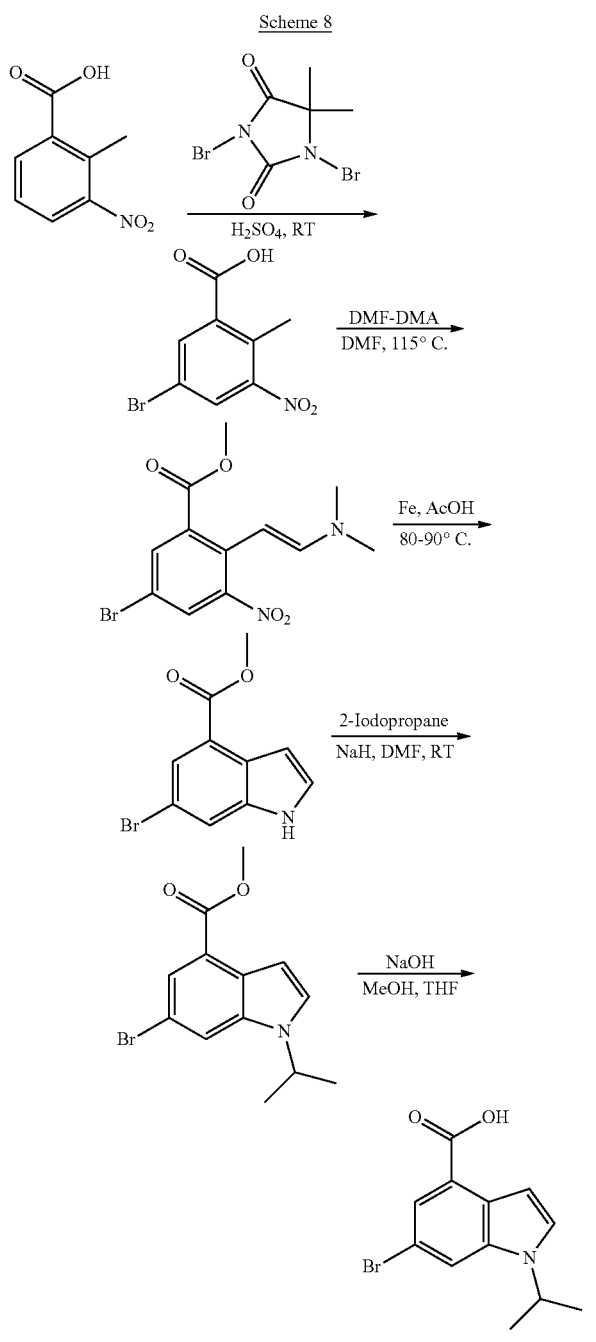

Intermediate 21

Methyl 6-bromo-1-isopropyl-1H-indole-4-carboxylate a) 5-Bromo-2-methyl-3-nitro-benzoic acid

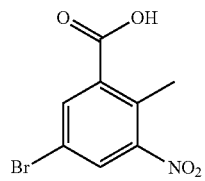

To a stirred solution of 2-methyl-3-nitro benzoic acid (300 g, 1647 mmol) in conc. $H_2SO_4$ (1.5 L) was added 1,3-dibromo-5,5 dimethyl-2,4-imadazolidinedione (258 g, 906 mmol) and the mixture was stirred at room temperature for 5 h. The reaction mixture was slowly added to ice water (4 L), and solid was precipitated out. The solid was filtered off and washed with water (1.2 L), pet ether (1 l) and dried to afford the title compound as a white solid (411 g, 96%), which was used without further purification. $^1$H NMR (DMSO, 400 MHz): δ 2.446 (s, 3H), 8.136 (s, 1H), 8.294 (s, 1H). LCMS (ES−) m/z=257.93 (M−H)⁻ b) Methyl 6-bromo-1H-indole-4-carboxylate

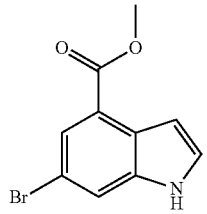

To a stirred solution of 5-bromo-2-methyl-3-nitro-benzoic acid (140 g, 538.4 mmol) in DMF (550 ml) was added DMF-DMA (599 mL, 4846 mmol) at room temperature. The reaction mixture was stirred at 115° C. for 18 h. The reaction mixture was then concentrated in vacuo. The residual contents (176 g, 536.5 mmol) were dissolved in acetic acid (696 mL) and added to a suspension of iron (329.2 g, 5902 mmol) in acetic acid (1.4 L) at 50° C. After completion of addition, the reaction mixture was stirred at 80-90° C. for 4 h. The reaction mixture was then filtered through a Celite pad. The filtrate was poured onto ice water (1 L) and extracted with diethyl ether (3×700 ml). The combined organic layers were washed with sat $NaHCO_3$, brine, and dried over anhydrous $Na_2SO_4$, filtered, and evaporated under vacuum. The crude product was purified by silica gel chromatography (eluent: 10% ethyl acetate in pet ether) and afforded the title compound as a solid (80 g, 59%). $^1$H NMR (DMSO-$d_6$, 400 MHz) δ: 3.980 (s, 3H), 7.168 (d, J=3.2 Hz, 1H), 7.334 (d, J=3.2 Hz, 1H), 7.734 (s, 1H), 8.017 (s, 1H), 8.384 (brs, 1H); LCMS (ES−) m/z=251.9 (M−H).

c) Methyl 6-bromo-1-isopropyl-1H-indole-4-carboxylate

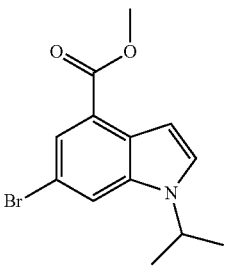 [SMILES: COC(=O)c1cc(Br)cc2c1ccn2C(C)C]

To a stirred solution of methyl 6-bromo-1H-indole-4-carboxylate (100 g, 393.7 mmol) in DMF (800 mL) was added 2-iodopropane (160 g, 944.8 mmol) followed by portionwise addition of sodium hydride (20.4 g, 511.8 mmol) at 0° C. The reaction mixture was stirred at room temperature for 18 h. Diluted the reaction mixture with cold water and extracted with ethylacetate (200 mL×4), finally organic layer was washed with cold water, brine solution dried over anhydrous Na$_2$SO$_4$ and concentrated under reduced pressure to afford crude, which was purified by column chromatography using silica gel (60-120 mesh) with 5% EtOAC: pet ether as an eluent to afford methyl 6-bromo-1-isopropyl-1H-indole-4-carboxylate (65 g, 55.7%) as a solid. $^1$H NMR (CDCl$_3$, 400 MHz) δ 1.53 (d, 6H, J=6.4 Hz), 3.973 (s, 3H), 4.598-4.664 (m, 1H), 7.111 (d, 1H, J=2.4 Hz), 7.338 (d, 1H, J=2.8 Hz), 7.711 (s, 1H), 7.987 (s, 1H).

d) 6-Bromo-1-(1-methylethyl)-1H-indole-4-carboxylic acid

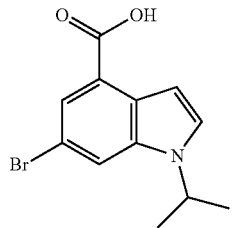

To a solution of methyl 6-bromo-1-(1-methylethyl)-1H-indole-4-carboxylate (0.52 g, 1.756 mmol) in methanol (15 mL) and tetrahydrofuran (3 mL) was added 3 M NaOH (1.756 mL, 5.27 mmol) via syringe drop wise (over 2 min). The solution was maintained at RT for 2 h, at which time LCMS showed only 12% conversion to product. Then 1.5 mL 3 M NaOH was added and the solution was maintained at RT overnight. LCMS showed complete conversion to product. Removed volatiles in vacuo and dissolved the residue in water and slowly acidified with 1 M HCl (solids precipitated). Extracted with EtOAc (2×), combined organics and dried over MgSO$_4$. Filtered and concentrated in vacuo to give 6-bromo-1-(1-methylethyl)-1H-indole-4-carboxylic acid (0.50 g, 1.737 mmol, 99% yield) as a white solid.

Alternatively, the alkylation of the indole nitrogen could be performed as follows: To a cooled (0° C.) suspension of methyl 6-bromo-1H-indole-4-carboxylate (10 g, 39.4 mmol) and (cyanomethyl)(trimethyl)phosphonium chloride (14.91 g, 98 mmol) in THF (400 mL) was added 2-propanol (6.06 mL, 79 mmol), followed by sodium hydride (3.46 g, 87 mmol). The mixture was stirred at ambient temperature for 2 h, at which time LCMS showed no product formation. Heated at 50° C. for 18 h. LC/MS showed reaction complete. Filtered reaction mixture and concentrated in vacuo. The residue was diluted with methylene chloride and passed through a pad of silica (washed with methylene chloride). Purification by flash chromatography (Analogix SF65-200 g; 5-10% EtOAc/hexanes) gave methyl 6-bromo-1-(1-methylethyl)-1H-indole-4-carboxylate (9.7 g, 31.4 mmol, 80% yield). MS (ES) [M+H]$^+$ 296.2, 298.4.

Examples 22-23 were prepared by the methods described above for Intermediate 16 or routine variations thereof, starting from the requisite 2-methyl-3-nitrobenzoic acid:

| Ex | Structure | Name | $^1$H NMR | MS(ES) [M + H]$^+$ |
|----|-----------|------|-----------|--------------------|
| 22 | 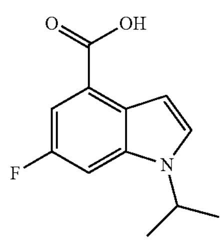 [SMILES: CC(C)n1ccc2c(C(=O)O)cc(F)cc21] | 6-fluoro-1-(1-methylethyl)-1H-indole-4-carboxylic acid | 1.44 (d, 6 H), 4.63-4.96 (m, 1 H), 6.97 (d, J = 3.03 Hz, 1 H), 7.46 (dd, J = 10.36, 2.27 Hz, 1 H), 7.67 (d, J = 3.28 Hz, 1 H), 7.75 (dd, J = 10.11, 2.02 Hz, 1 H), 12.97 (s, 1 H) | 222.1 |
| 23 | 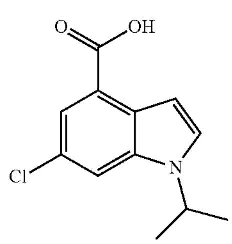 [SMILES: CC(C)n1ccc2c(C(=O)O)cc(Cl)cc21] | 6-chloro-1-(1-methylethyl)-1H-indole-4-carboxylic acid | (CHLOROFORM-d) 1.57 (d, 6 H), 4.67 (spt, J = 6.69 Hz, 1 H), 7.19 (d, J = 3.03 Hz, 1 H), 7.41 (d, J = 3.28 Hz, 1 H), 7.63 (d, J = 1.01 Hz, 1 H), 7.97 (d, J = 1.77 Hz, 1 H) | 237.9 |

Scheme 9

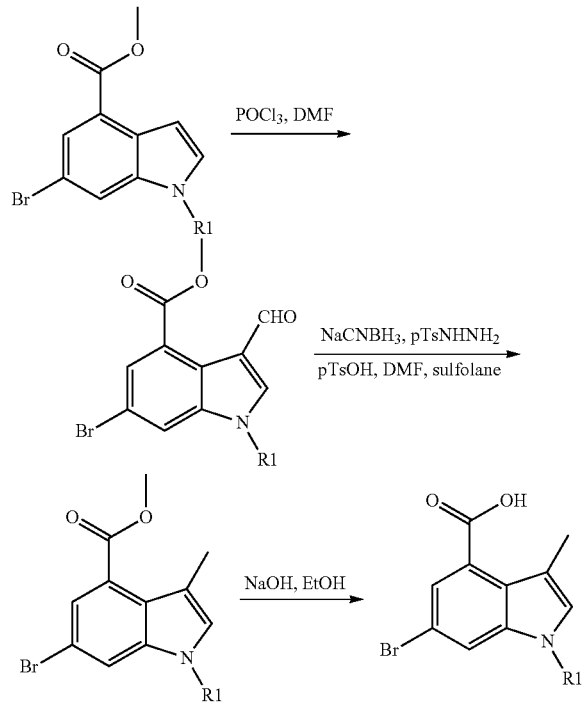

Intermediate 24

Methyl
6-bromo-1-isopropyl-1H-indole-4-carboxylate

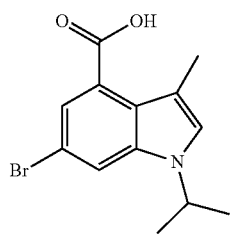

24a) Methyl 6-bromo-3-formyl-1-isopropyl-1H-indole-4-carboxylate

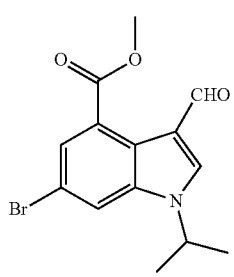

To a stirred solution of DMF (1.04 lit) POCl₃ (40.3 g, 263 mmol) was added at 0° C. and stirred for 20 min. Then methyl 6-bromo-1-isopropyl-1H-indole-4-carboxylate (65 g, 2119.5 mmol) in DMF (260 mL) was added to the reaction mixture at 0° C. The reaction mixture was stirred at room temperature for 3 h. Diluted the reaction mixture with cold water and adjusted PH~8 using with 2N NaOH solution, extracted with ethylacetate (4×1 lit). The organic layer washed with cold water, brine solution, dried over anhydrous Na₂SO₄ and concentrated under reduced pressure to afford desired product methyl 6-bromo-3-formyl-1-isopropyl-1H-indole-4-carboxylate (65 g, 91.3%). ¹H NMR (CDCl₃, 400 MHz): δ 1.588 (d, 6H, J=6.8 Hz), 3.994 (s, 3H), 4.634-4.701 (m, 1H), 7.760 (d, 1H, J=1.6 Hz), 7.958 (d, 1H, J=1.6 Hz), 8.122 (s, 1H), 10.446 (s, 1H). LC-MS (ES+) m/z=324.02 (M+H)

24b) Methyl 6-bromo-1-isopropyl-3-methyl-1H-indole-4-carboxylate

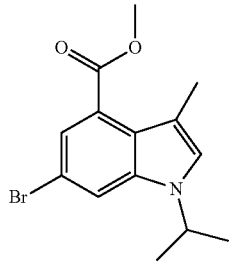 [SMILES: COC(=O)c1cc(Br)cc2c1c(C)cn2C(C)C]

To a stirred solution of methyl 6-bromo-3-formyl-1-isopropyl-1H-indole-4-carboxylate (60 g, 185 mmol) in DMF (220 mL) was added p-toluenesulfonic acid mono hydride (4.57 g, 24 mmol), p-toluenesulfonyl hydrazide (44.8 g, 240 mmol) followed by sulfolane (220 mL). The mixture was stirred at 100° C. for 1 h. The contents were cooled to room temperature and then sodium cyanoborohydride (46.5 g, 740 mmol) was added portion wise over a period of 25 min. Then the mixture was stirred at 100° C. for 2 h. Then the reaction mixture was stirred for 16 h at room temperature. The reaction mixture was diluted with water and extracted with 20% EtOAc: Pet ether, finally organic layer was washed with cold water, brine solution dried over anhydrous Na₂SO₄ and concentrated. Crude compound was purified by column chromatography using silica gel (100-200 mesh) and 20% DCM: Pet ether as an eluent to afford desired product methyl 6-bromo-1-isopropyl-3-methyl-1H-indole-4-carboxylate (24 g, 89.2% purity), (16 g, and 62.2% purity). ¹H NMR (CDCl₃, 400 MHz) δ 1.486 (d, J=6.4 Hz, 6H), 2.361 (s, 3H), 3.947 (s, 3H), 4.535-4.602 (m, 1H), 7.080 (s, 1H), 7.619 (s, 1H), 7.684 (s, 1H). LCMS (ES+) m/z=310.07 (M+H)

24c) 6-Bromo-1-isopropyl-3-methyl-1H-indole-4-carboxylic acid

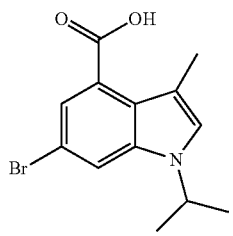 [SMILES: Cc1cn(C(C)C)c2cc(Br)cc(C(=O)O)c12]

To a stirred solution of methyl 6-bromo-1-isopropyl-3-methyl-1H-indole-4-carboxylate (24 g, 77.4 mmol) in ethanol (400 mL) was added sodium hydroxide (4.02 g, 100.6 mmol), water (11 mL) and the mixture was stirred at reflux condition for 6 h. Ethanol was distilled off and residue was diluted with water, extracted with ethylacetate (40 mL) adjusted aqueous layer to PH-3 with 1N HCl and extracted with ethyl acetate (3×250 mL), finally organic layer was washed with brine solution, dried over anhydrous $Na_2SO_4$ and concentrated. The crude was washed with pet ether, filtered the solid and dried to afford desired product 6-bromo-1-isopropyl-3-methyl-1H-indole-4-carboxylic acid (20.6 g, 89.8%).

$^1$H NMR (DMSO-$d_6$, 400 MHz): δ 1.407 (d, J=6.4 Hz, 6H), 2.296 (s, 3H), 4.754-4.819 (m, 1H), 7.455 (s, 1H), 7.472 (s, 1H), 7.938 (s, 1H), 12.950 (brs, 1H). LCMS (ES+) m/z=296.15 (M+H).

Intermediate 25

6-Bromo-1-(sec-butyl)-3-methyl-1H-indole-4-carboxylic acid

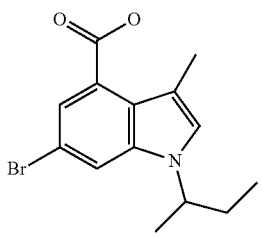 [SMILES: CCC(C)n1cc(C)c2c(C(=O)O)cc(Br)cc21]

a) Methyl 6-bromo-1-sec-butyl-1H-indole-4-carboxylate

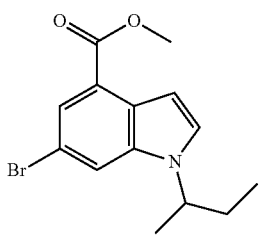 [SMILES: CCC(C)n1ccc2c(C(=O)OC)cc(Br)cc21]

To a stirred suspension of sodium hydride (5.66 g, 141.7 mmol) in DMF (100 mL) was added a solution of methyl 6-bromo-1H-indole-4-carboxylate (4) (30 g, 118.1 mmol) in DMF (50 mL) at 0° C. and stirred for 20 min. Then 2-Bromo butane (29.1 g, 212.5 mmol) was added at 0° C. and the reaction mixture was stirred at room temperature for 16 h. The reaction mixture was diluted with cold water and extracted with ethyl acetate (4×150 mL). The combined organic layer was washed with cold water (150 mL), brine (100 mL) and dried over anhydrous $Na_2SO_4$ and concentrated under reduced pressure to afford crude, which was purified by column chromatography over silica gel (60-120 mesh) using 5% EtOAc: Pet ether as eluent to afford the title compound methyl 6-bromo-1-sec-butyl-1H-indole-4-carboxylate, (14 g, 40.1%) as pale yellow solid. $^1$H NMR (CDCl$_3$, 400 MHz) δ 0.843-0.870 (m, 3H), 1.512 (d, J=6.4 Hz, 3H), 1.844-1.926 (m, 2H), 3.976 (s, 3H), 4.333-4.385 (m, 1H), 7.132 (d, J=3.2 Hz, 1H), 7.302 (d, J=3.6 Hz, 1H), 7.707 (s, 1H), 7.984 (d, J=1.6 Hz, 1H).

b) Methyl 6-bromo-1-sec-butyl-3-formyl-1H-indole-4-carboxylate

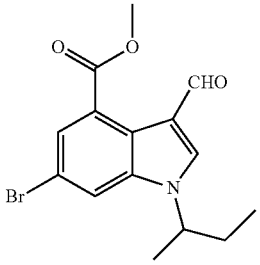 [SMILES: CCC(C)n1cc(C=O)c2c(C(=O)OC)cc(Br)cc21]

POCl$_3$ (8.3 g, 54.3 mmol) was added at 0° C. to anhydrous DMF (230 mL) in a round bottom flask and stirred for 30 min. Then a solution of methyl 6-bromo-1-sec-butyl-1H-indole-4-carboxylate, 5 (14 g, 45.3 mmol) in DMF (60 mL) was added to the reaction mixture at 0° C. and stirred at room temperature for 2.5 h. The reaction mixture was diluted with cold water, adjusted pH~8 using with 2N NaOH solution and extracted with ethyl acetate (4×200 mL). The combined organic layer was washed with cold water (2×100 mL), brine (100 mL), dried over anhydrous $Na_2SO_4$ and concentrated under reduced pressure to afford desired product methyl 6-bromo-1-sec-butyl-3-formyl-1H-indole-4-carboxylate, 6 (15.2 g, 99%) as pale yellow solid. This was used as such in the next step without purification. $^1$H NMR (CDCl$_3$, 400 MHz) δ (0.831-0.859 (m, 3H), 1.515-1.574 (d, J=6.8 Hz, 3H), 1.729-1.972 (m, 2H) 3.997 (s, 3H), 4.394-4.445 (m, 1H), 7.756 (d, J=1.2 Hz, 1H), 7.958 (d, J=2 Hz, 1H), 8.079 (s, 1H), 10.452 (s, 1H).

c) Methyl 6-bromo-1-sec-butyl-3-methyl-1H-indole-4-carboxylate

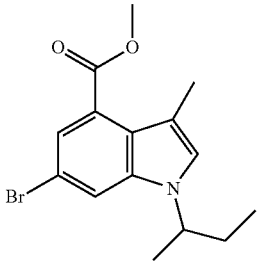 [SMILES: CCC(C)n1cc(C)c2c(C(=O)OC)cc(Br)cc21]

To a stirred solution of methyl 6-bromo-1-sec-butyl-3-formyl-1H-indole-4-carboxylate (15 g, 44.6 mmol) in DMF (115 mL) was added p-toluenesulfonic acid mono hydrate (1.1 g, 5.8 mmol), p-toluenesulfonyl hydrazide (10.8 g, 58 mmol) followed by sulfolane (115 mL) at RT and the reaction mixture was stirred at 100° C. for 1 h. The reaction mixture was cooled to room temperature, treated with sodium cyanoborohydride (11.9 g, 178.5 mmol) portion wise over a period of 5 min and stirred at 100° C. for 2 h. The reaction mixture was cooled to room temperature and stirred at the same temperature for 16 h. The reaction mixture was diluted with water and extracted with 30% EtOAc: Pet ether. The organic layer was washed with cold water (100 mL), brine (100 mL) and dried over anhydrous Na$_2$SO$_4$ and concentrated under reduced pressure to afford crude, which was purified by column chromatography over silica gel (100-200 mesh) using 5% EtOAc: Pet ether as eluent to afford title compound methyl 6-bromo-1-sec-butyl-3-methyl-1H-indole-4-carboxylate (7.88 g, 54.6%) as pale yellow gum. $^1$H NMR (CDCl$_3$, 400 MHz): δ 0.804-0.841 (t, J=7.4 Hz, 3H), 1.454-1.470 (d, J=6.4 Hz, 3H), 1.865-1.884 (m, 2H), 2.363 (s, 3H), 3.950 (s, 3H), 4.265-4.316 (m, 1H), 7.038 (s, 1H), 7.609 (d, J=1.2 Hz, 1H), 7.671 (d, J=2 Hz, 1H). MS (ES+): 324.19 [M+H] ion present.

d) 6-Bromo-1-(sec-butyl)-3-methyl-1H-indole-4-carboxylic acid

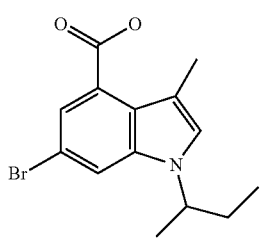

Methyl 6-bromo-1-(sec-butyl)-3-methyl-1H-indole-4-carboxylate (3.24 g, 9.99 mmol) was dissolved in methanol (30 mL) and tetrahydrofuran (THF) (7 mL). The contents were stirred for 5 min., and then aq. 3N NaOH (19.99 mL, 60.0 mmol) was added via addition funnel over 3 min. The contents rapidly became a yellow suspension and were stirred at room temperature for 65 h. The volatiles were removed in vacuo and the residue dissolved in water (60 mL). The contents were washed with ether (1×50 mL). The aq layer was cooled in an ice bath and adjusted to pH 3-4 with 1M HCl, from which an oily residue precipitated. The contents were extracted with EtOAc (2×60 mL). The combined organic layers were dried over magnesium sulfate, filtered through celite, and concentrated in vacuo. The residue obtained was treated with TBME, concentrated in vacuo, and then dried under hi vacuum to afford a yellow foam as 3.08 g (93%). $^1$H NMR (400 MHz, DMSO-d6) δ ppm 0.70 (t, J=7.33 Hz, 3H), 1.39 (d, J=6.82 Hz, 3H), 1.71-1.86 (m, 2H), 2.30 (s, 3H), 4.48-4.62 (m, 1H), 7.40-7.49 (m, 2H), 7.96 (d, J=1.77 Hz, 1H), 12.99 (s, 1H); LCMS=310.0/312.0 (MH+).

Examples 26-27 were prepared by the methods described above for Intermediate 16 or routine variations thereof, starting from the requisite 6-substituted indole:

| Ex | Structure | Name | $^1$H NMR | MS(ES) [M + H]$^+$ |
|---|---|---|---|---|
| 26 | 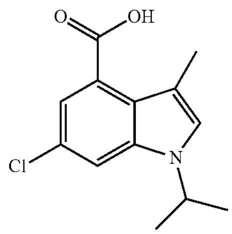 [SMILES: Cc1cn(C(C)C)c2cc(Cl)cc(C(=O)O)c12] | 6-chloro-3-methyl-1-(1-methylethyl)-1H-indole-4-carboxylic acid | 12.99 (br. s., 1 H), 7.82 (d, J = 2.0 Hz, 1 H), 7.47 (d, J = 1.0 Hz, 1 H), 7.36 (d, J = 2.0 Hz, 1 H), 4.78 (quin, J = 6.6 Hz, 1 H), 2.30 (d, J = 1.0 Hz, 3 H), 1.41 (d, J = 6.6 Hz, 6 H) | 252.4 |
| 27 | 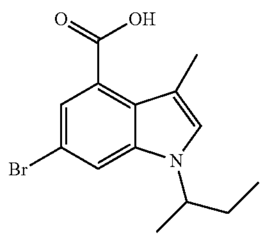 [SMILES: CCC(C)n1cc(C)c2c(C(=O)O)cc(Br)cc21] | 6-bromo-1-(sec-butyl)-3-methyl-1H-indole-4-carboxylic acid | 0.70 (t, J = 7.33 Hz, 3 H) 1.39 (d, J = 6.82 Hz, 3 H) 1.71-1.86 (m, 2 H) 2.30 (s, 3 H) 4.48-4.62 (m, 1 H) 7.40-7.49 (m, 2 H) 7.96 (d, J = 1.77 Hz, 1 H) 12.99 (s, 1 H) | 310.0 |

Intermediate 28

6-Bromo-1-cyclopropyl-1H-indole-4-carboxylic acid

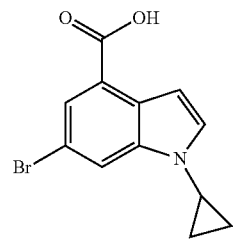 [SMILES: O=C(O)c1cc(Br)cc2c1ccn2C1CC1]

a) Methyl 6-bromo-1-cyclopropyl-1H-indole-4-carboxylate

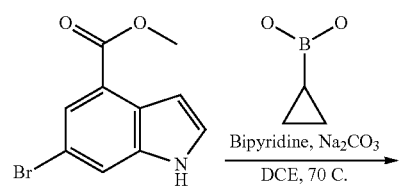

-continued

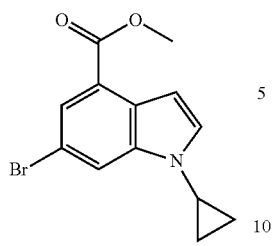

In a oven dried 100 ml RBF equipped, stir bar, septum and Nitrogen inlet was added methyl 6-bromo-1H-indole-4-carboxylate (0.508 g, 2.0 mmol) and 1,2-dichloroethane (7 mL). The solution was stirred for 15 min, then cyclopropylboronic acid (0.344 g, 4.00 mmol) and sodium carbonate (0.424 g, 4.00 mmol) were added. Diluted copper(II) acetate (0.363 g, 2.000 mmol) and 2,2'-bipyridine (0.312 g, 2.000 mmol) in 1,2-dichloroethane (12 mL), heated the mixture, and added the hot suspension to the reaction. The reaction was heated at 70° C. and monitored by LCMS. Stopped heating after 6 h and allowed to sit for 3 days at RT. Added to reaction saturated NH4Cl and water. Extracted with DCM (2×). The combined organics were washed with brine, dried over magnesium sulfate, filtered and concentrated in vacuo. Purification of the residue by column chromatography (24 g Isco silica column; gradient B: 3-25%. A:hexane. B: ethyl acetate) to give methyl 6-bromo-1-cyclopropyl-1H-indole-4-carboxylate (0.43 g, 1.433 mmol, 71.6% yield) as a yellow residue.

$^1$H NMR (400 MHz, DMSO-d$_6$) δ ppm 0.96-1.01 (m, 2H) 1.06-1.12 (m, 2H) 3.52 (dt, J=7.20, 3.47 Hz, 1H) 3.90 (s, 3H) 6.85-6.91 (m, 1H) 7.57 (d, J=3.03 Hz, 1H) 7.82 (d, J=1.77 Hz, 1H) 8.04 (d, J=1.01 Hz, 1H). MS (ES) [M+H]$^+$ 294.1.

b) 6-Bromo-1-cyclopropyl-1H-indole-4-carboxylic acid

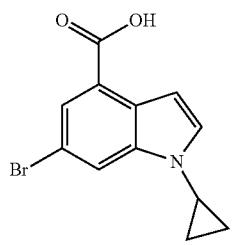 [SMILES: O=C(O)c1cc(Br)cc2c1ccn2C1CC1]

To a solution of methyl 6-bromo-1-cyclopropyl-1H-indole-4-carboxylate (0.43 g, 1.462 mmol) in MeOH (12 mL) and THF (3 mL) was added 3 M NaOH (1.949 mL, 5.85 mmol). The reaction was stirred for 18 h at RT, at which time the volatiles were removed in vacuo. The residue was diluted with water and slowly acidifed with 1 N HCl to pH 4-5, then extracted with EtOAc (2×). The combine organics werewash with brine, dried over magnesium sulfate, filtered, and concentrated to give 6-bromo-1-cyclopropyl-1H-indole-4-carboxylic acid (0.376 g, 1.315 mmol, 90% yield) as a pale yellow solid. $^1$H NMR (400 MHz, DMSO-d6) δ ppm 0.92-1.01 (m, 2H) 1.05-1.12 (m, 2H) 3.51 (tt, J=7.07, 3.66 Hz, 1H) 6.89 (d, J=2.53 Hz, 1H) 7.52 (d, J=3.03 Hz, 1H) 7.80 (d, J=1.77 Hz, 1H) 7.99 (d, J=1.01 Hz, 1H) 13.05 (br. s., 1H). MS (ES) [M+H]$^+$ 280.1.

Intermediate 29

6-Bromo-1-cyclobutyl-1H-indole-4-carboxylic acid

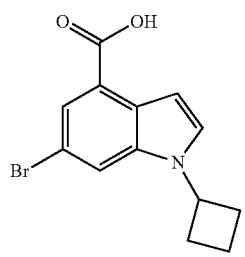 [SMILES: O=C(O)c1cc(Br)cc2c1ccn2C1CCC1]

a) Methyl 6-bromo-1-cyclobutyl-1H-indole-4-carboxylate

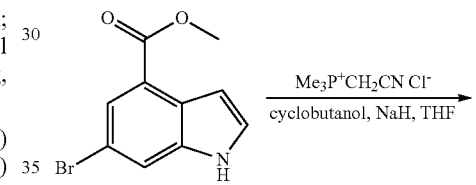

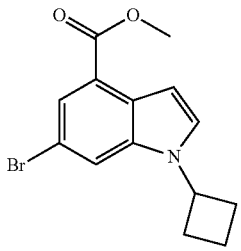

In an oven dried 100 ml RBF, equipped with a stir bar, septum, nitrogen inlet was added methyl 6-bromo-1H-indole-4-carboxylate (1.0 g, 3.94 mmol) and (cyanomethyl)(trimethyl)phosphonium chloride (1.491 g, 9.84 mmol). Added in THF (40 mL) and stirred suspension for 5 min. The reaction was cooled with an ice bath for 10 min, then was added cyclobutanol (0.616 mL, 7.87 mmol), followed by sodium hydride (0.346 g, 8.66 mmol) portionwise. The ice bath was removed and the reaction stirred at ambient temperature for 45 min, then heated at 50° C. for 18 h. LCMS showed mostly SM. Heated at 75° C. for 24 h. The reaction was allowed to cool to RT, then poured into water (200 ml) and extracted with EtOAc (2×). The combined organics were dried over magnesium sulfate, filtered, and concentrated. Purification of the residue by column chromatography (40 g Isco silica column; gradient B: 2-25%; A:hexane, B: EtOAc)

gave methyl 6-bromo-1-cyclobutyl-1H-indole-4-carboxylate (0.3 g, 25% yield, ~45% pure by HPLC). MS (ES) [M+H]+ 308.2.

b) 6-Bromo-1-cyclobutyl-1H-indole-4-carboxylic acid

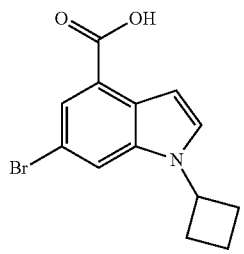 [SMILES: O=C(O)c1cc(Br)cc2c1ccn2C1CCC1]

To a solution of ethyl 6-bromo-1-cyclobutyl-1H-indole-4-carboxylate (0.3 g, 0.973 mmol) (crude residue from above) in MeOH (8 mL) and THF (2 mL) was added 3 M NaOH (1.298 mL, 3.89 mmol). The reaction was stirred at RT for 16 h, at which time the volatiles were removed in vacuo. The residue was diluted with water and slowly acidfed with 1 N HCl to pH 3-4. The solids were filtered and dried on hivac for 16 h to give 6-bromo-1-cyclobutyl-1H-indole-4-carboxylic acid (0.21 g, 0.535 mmol, 55.0% yield). $^1$H NMR (400 MHz, DMSO-d6) δ ppm 1.79-1.89 (m, 2H) 2.34-2.46 (m, 2H) 3.84 (s, 1H) 5.08 (t, J=8.21 Hz, 1H) 6.99 (d, J=3.03 Hz, 1H) 7.75-7.79 (m, 1H) 7.81 (d, J=3.03 Hz, 1H) 8.01-8.05 (m, 1H) 13.03 (br. s., 1H). MS (ES) [M+H]+ 294.1.

Intermediate 30

1-Isopropyl-3-methyl-6-(methylsulfonyl)-1H-indole-4-carboxylic acid

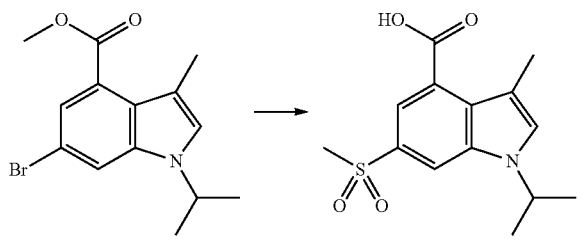 [SMILES: COC(=O)c1cc(Br)cc2c1c(C)cn2C(C)C ; Cc1cn(C(C)C)c2cc(S(C)(=O)=O)cc(C(=O)O)c12]

To a 30-mL microwave tube were added methyl 6-bromo-3-methyl-1-(1-methylethyl)-1H-indole-4-carboxylate (490 mg, 1.580 mmol), methanesulfinic acid (212 mg, 2.054 mmol), DMSO (7 mL), N,N'-dimethyl-1,2-ethanediamine (18.10 mg, 0.205 mmol), and the mixture was degassed for 5 min by bubbling N2. Copper(I) trifluoromethanesulfonate benzene complex (63.6 mg, 0.126 mmol) was added and the tube was sealed. The mixture was heated at 165° C. overnight with stirring. The mixture was allowed to cool, filtered and purified using reverse-phase HPLC (Gemini 5u C18(2) 100A, AXIA; 30×100 mm 5 micron; 30 mL/min, 30% ACN/H2O, 0.1% formic acid to 60% ACN/H2O, 0.1% formic acid) to give the title compound (118 mg, 25%) as a white solid. $^1$H NMR (400 MHz, DMSO-d$_6$) ppm 1.47 (d, J=8.00 Hz, 6H), 2.30-2.41 (m, 3H), 4.94 (quin, J=6.63 Hz, 1H), 7.80 (s, 1H), 7.88 (d, J=1.77 Hz, 1H), 8.24 (d, J=1.52 Hz, 1H), 13.17 (br. s., 1H). MS: (M+H)+296.3.

Intermediate 31

1-Isopropyl-6-(methylsulfonyl)-1H-indole-4-carboxylic acid

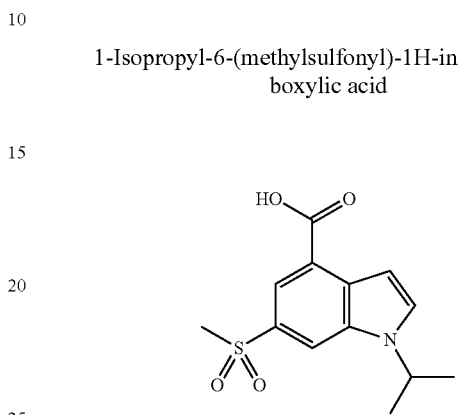

To a 10-mL microwave tube were added methyl 6-bromo-1-(1-methylethyl)-1H-indole-4-carboxylate (160 mg, 0.540 mmol), sodium methanesulfinate (80 mg, 0.702 mmol), DMSO (2 mL), and N,N'-dimethyl-1,2-ethanediamine (6.19 mg, 0.070 mmol), and the mixture was degassed for 5 min by bubbling N$_2$. Copper(I) trifluoromethanesulfonate benzene complex (25.6 mg, 0.043 mmol) was added and the mixture was heated to 165° C. for 2 h with stirring. The mixture was filtered and the DMSO solution was purified using reverse-phase HPLC to give 14 mg of product as white solid. $^1$H NMR (400 MHz, DMSO-d$_6$) ppm 1.51 (d, J=4.00 Hz, 6H), 4.90-5.11 (m, 1H), 7.13 (d, J=3.03 Hz, 1H), 7.98-8.08 (m, 1H), 8.15-8.23 (m, 1H), 8.32-8.46 (m, 1H), 13.19 (br. s., 1H). MS: (M+H)+=281.9.

Intermediate 32

6-(Cyclopropylsulfonyl)-1-(1-methylethyl)-1H-indole-4-carboxylic acid

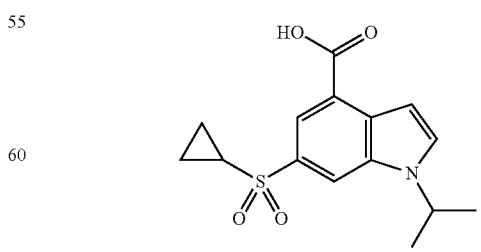

$^1$H NMR (400 MHz, DMSO-d$_6$) δ ppm 1.03 (dd, J=7.71, 2.40 Hz, 2H), 1.17 (dd, J=7.20, 3.41 Hz, 2H), 1.50 (d, 6H), 2.83-2.97 (m, 1H), 5.02 (dt, J=13.14, 6.57 Hz, 1H), 7.17 (d, J=2.27 Hz, 1H), 7.99 (d, J=3.03 Hz, 1H), 8.13 (s, 1H), 8.28 (s, 1H). MS: (M+H)+=308.3.

Intermediate 33

6-Hydroxy-1-isopropyl-1H-indole-4-carboxylic acid methyl ester

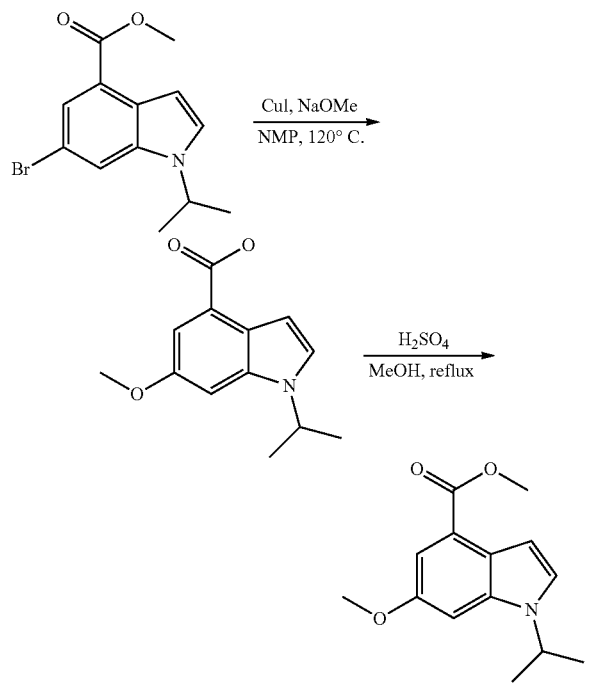

Freshly prepared sodium methoxide (500 mg in 5 mL methanol) was added to a stirred suspension of 6-bromo-1-isopropyl-1H-indole-4-carboxylic acid methyl ester (500 mg, 1.68 mmol) and CuI (480 mg, 2.53 mmol) in NMP (8 mL) and then heated at 120° C. for 2 h. The reaction mixture was cooled to room temperature, diluted with water (5 mL) and acidified with 1N HCl. The reaction mixture was filtered through Celite and washed with EtOAc (5 mL). Separated the EtOAc layer from filtrate, dried over anhydrous Na$_2$SO$_4$ and concentrated under reduced pressure to furnish the crude 1-isopropyl-6-methoxy-1H-indole-4-carboxylic acid (700 mg), which was used in the next stage without further purification. $^1$H NMR (400 MHz, DMSO-d$_6$): δ 1.44 (d, J=6.4 Hz, 6H), 3.84 (s, 3H), 4.80-4.76 (m, 1H), 6.87 (d, 1H), 7.33 (t, J=3.2 Hz, 2H), 7.49 (d, J=3.2 Hz, 1H), 12.65 (bs, 1H). LCMS (ES+): m/z=234.11 [M+H].

To a stirred suspension of 1-isopropyl-6-methoxy-1H-indole-4-carboxylic acid (700 mg, 3.00 mmol) in MeOH was added H$_2$SO$_4$ (440 mg, 4.50 mmol) and then heated at reflux for 3 h. Methanol was distilled off completely under reduced pressure and the residue basified with saturated aqueous NaHCO$_3$ solution and extracted with ethyl acetate (2×5 mL). The combined organic layers were dried over anhyrous Na$_2$SO$_4$, filtered and concentrated. The residue was purified by column chromatography (SiO$_2$, 100-200) by eluting 5% ethyl acetate in petroleum ether to afford 1-isopropyl-6-methoxy-1H-indole-4-carboxylic acid methyl ester (240 mg, 32.4%) as white solid. $^1$H NMR (400 MHz, DMSO-d$_6$): δ 1.45 (d, J=6.8 Hz, 6H), 3.84 (s, 3H), 3.88 (s, 3H), 4.81-4.78 (m, 1H), 6.86 (d, J=3.2 Hz, 1H), 7.34 (d, J=2.4 Hz, 1H), 7.39 (d, J=2 Hz, 1H), 7.54 (d, J=3.6 Hz, 1H). LCMS (ES+): m/z=248.16 [M+H].

Intermediate 34

1-Isopropyl-6-methoxy-1H-indole-4-carboxylic acid

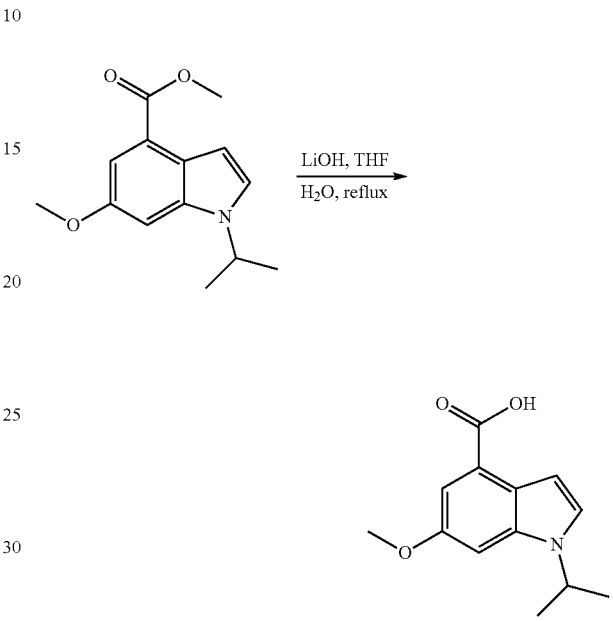

To a stirred solution of 1-isopropyl-6-methoxy-1H-indole-4-carboxylic acid methyl ester (320 mg, 1.29 mmol) in THF (2 mL) was added LiOH.H$_2$O (160 mg, 3.88 mmol) in water (2 mL) at room temperature and heated at reflux for 2 h. The THF was removed under reduced pressure and the resulting aqueous layer was acidified with 1 N HCl (pH ~6) and extracted with ethyl acetate (2×5 mL). The combined organic layer was dried over anhydrous Na$_2$SO$_4$ and concentrated to afford 1-isopropyl-6-methoxy-1H-indole-4-carboxylic acid (210 mg). $^1$H NMR (400 MHz, DMSO-d$_6$): δ 1.42 (d, 6H), 3.88 (s, 3H), 4.85 (m, 1H), 6.81 (d, J=2.8 Hz, 1H), 7.26 (s, 2H), 7.45 (s, 1H), 12.68 (s, 1H).

Intermediate 35

6-Hydroxy-1-isopropyl-1H-indole-4-carboxylic acid methyl ester

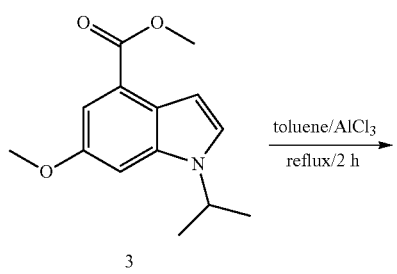

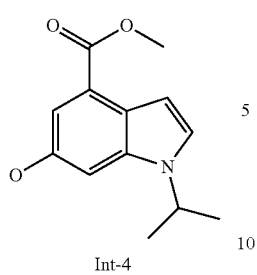

Int-4

To a stirred solution of 1-isopropyl-6-methoxy-1H-indole-4-carboxylic acid methyl ester (1.9 g, 7.69 mmol) in toluene (20 mL) was added anhydrous aluminum chloride (5.11 g, 38.4 mmol) at room temperature and then heated to reflux for 2 h. The reaction mixture was diluted with water and extracted with ethyl acetate (2×20 mL). The combined organic layer was dried over Na$_2$SO$_4$ and concentrated under reduced pressure. The residue was purified by column chromatography by eluting 3-15% Ethyl acetate in petroleum ether to afford the title compound 6-hydroxy-1-isopropyl-1H-indole-4-carboxylic acid methyl ester (1.5 g, 83%) as yellow colored gum. $^1$H NMR (400 MHz, DMSO-d$_6$): δ 1.43 (d, J=6.8 Hz, 6H), 3.86 (s, 3H), 4.65-4.61 (m, 1H), 6.81 (d, J=2.8 Hz, 1H), 7.11 (s, 1H), 7.29 (s, 1H), 7.44 (d, J=2.8 Hz, 1H), 9.32 (bs, 1H). LCMS (ES+): m/z=234.09 [M+H]

Intermediate 36

3-Methyl-1-(1-methylethyl)-6-(methyloxy)-1H-indole-4-carboxylic acid

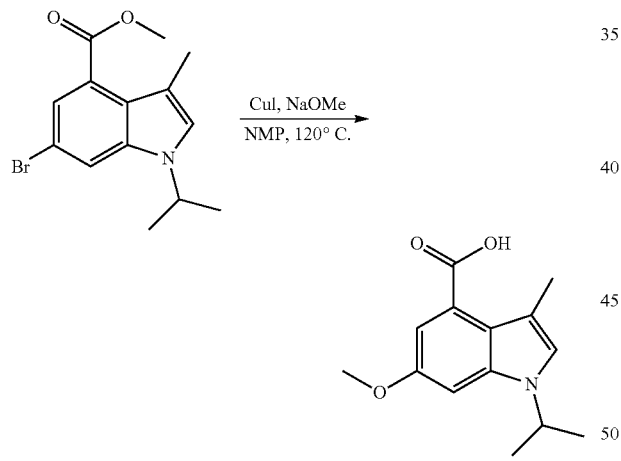

To methyl 6-bromo-3-methyl-1-(1-methylethyl)-1H-indole-4-carboxylate (1.3 g, 4.19 mmol) and copper(I) iodide (1.0 g, 5.25 mmol) was added NMP (8 mL). To the mixture was added dropwise a solution of sodium methoxide 25 wt % in methanol (4.0 mL, 17.49 mmol) with stirring. The reaction was heated to 120° C. and stirred for 1.5 hr. The reaction was allowed to cool and when the temperature reached 80° C., water (200 uL) was added. The reaction was allowed to continue to cool to RT and stirred overnight. The reaction was acidified with 1 N HCl (17 mL) and diluted with water and EtOAc. The mixture was filtered through Celite and washed with EtOAc. The filtrate was poured into a reparatory funnel and the organic phase was separated, washed with brine, dried (MgSO4), filtered, and concentrated under vacuum. Purification by silica gel chromatography (Analogix, SF25-60 g, 20 to 50% EtOAc in hexanes) gave after concentration, trituration with hexanes, filtration and drying under vacuum 3-methyl-1-(1-methylethyl)-6-(methyloxy)-1H-indole-4-carboxylic acid (825 mg, 3.34 mmol, 80% yield) as an light yellow solid. MS (ES)+m/e 248.3 [M+H]$^+$.

Intermediate 37

6-Iodo-1-(1-methylethyl)-1H-indole-4-carboxylic acid

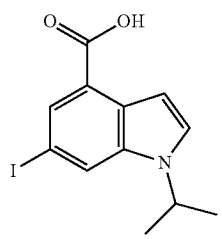 [SMILES: CC(C)n1ccc2c(C(=O)O)cc(I)cc21]

To a stirred solution of methyl 6-bromo-1-(1-methylethyl)-1H-indole-4-carboxylate (1.1 g, 3.71 mmol) in dioxane (50 mL) was added sodium iodide (1.2 g, 8.01 mmol), N,N'-dimethylethylenediamine (200 μL, 1.858 mmol) and copper (I) iodide (150 mg, 0.788 mmol). The reaction was purged with N$_2$ then refluxed (110° C. oil bath) overnight. LCMS indicated that the reaction was 90% complete with 6% remaining SM. Another 0.75 g sodium iodide and 75 mg copper(I) iodide was added and the reaction refluxed for another 24 hr. (LCMS showed less than 4% bromide SM.) The reaction was concentrated under vacuum, taken up in EtOAc, washed with water, brine, dried (MgSO4), filtered and concentrated under vacuum. Purification by silica gel chromatography (Analogix, SF25-60 g, 0 to 10% EtOAc in hexanes) gave the ester product as a light yellow oil. (1.27 g, 100%). MS (ES)+m/e 344.0 [M+H]$^+$.

The above ester was taken up in 40 mL (3:1) MeOH, THF and treated with 1 N NaOH (15 mL). The reaction was refluxed overnight, cooled to RT and concentrated under vacuum. Neutralization with 1 N HCl (15 mL) gave a white suspension that was filtered, washed with cold water and dried under vacuum to give the product 6-iodo-1-(1-methylethyl)-1H-indole-4-carboxylic acid (1.12 g, 3.40 mmol, 92% yield) as a light yellow solid. $^1$H NMR (400 MHz, DMSO-d$_6$) δ=12.94 (br. s., 1H), 8.20 (s, 1H), 7.94 (d, J=1.5 Hz, 1H), 7.66 (d, J=3.3 Hz, 1H), 6.97 (d, 1H), 4.86 (quin, J=6.6 Hz, 1H), 1.44 (d, J=6.6 Hz, 6H). MS (ES)+m/e 330.0 [M+H]$^+$.

Intermediate 38

6-Cyano-1-isopropyl-3-methyl-1H-indole-4-carboxylic acid

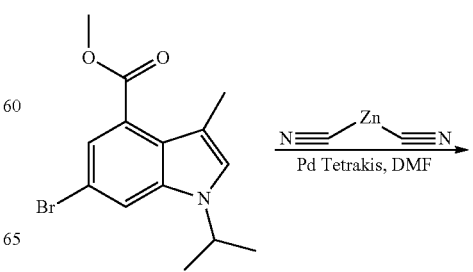

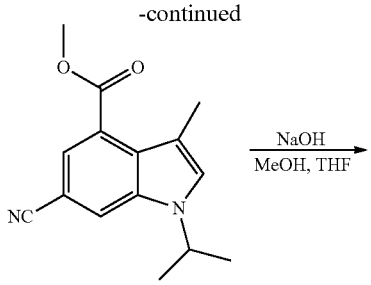

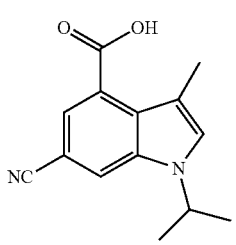

a) Methyl 6-cyano-3-methyl-1-(1-methylethyl)-1H-indole-4-carboxylate

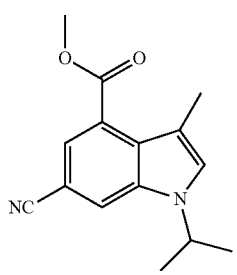 [SMILES: COC(=O)c1cc(C#N)cc2c1c(C)cn2C(C)C]

To a 10 ml microwave vial was added methyl 6-bromo-3-methyl-1-(1-methylethyl)-1H-indole-4-carboxylate (500 mg, 1.612 mmol), dicyanozinc (150 mg, 1.277 mmol) and DMF (5 mL). The mixture was degassed and stirred at rt under N2 for 15 min. To the mixture was added palladium tetrakis (118 mg, 0.102 mmol) and the reaction was stirred at 95° C. for 1 h. The reaction was allowed to cool and poured into saturated aqueous Na₂CO₃ (50 mL) and EtOAc (50 mL) and stirred for 20 min. The mixture was extracted with ether (100 ml) and EtOAc (100 ml) (1:1), followed by filtration and evaporation to yield a residue. The residue was purified by silica gel chromatography (Analogix IF280, 0-8% EtOAc/hexanes, SF25-40 g, 30 minutes) to give methyl 6-cyano-3-methyl-1-(1-methylethyl)-1H-indole-4-carboxylate (130 mg, 0.497 mmol, 38.9% yield) as a white solid. ¹H NMR (400 MHz, DMSO-d₆) δ ppm 8.38 (d, J=1.52 Hz, 1H) 7.82 (s, 1H) 7.71 (d, J=1.52 Hz, 1H) 4.85-4.97 (m, 1H) 3.90 (s, 3H) 2.29 (s, 3H) 1.45 (d, J=6.57 Hz, 6H). MS (ES) [M+H]⁺ 257.4.

b) 6-Cyano-1-isopropyl-3-methyl-1H-indole-4-carboxylic acid

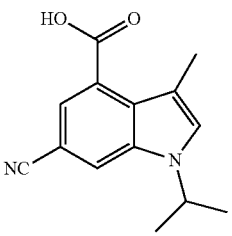 [SMILES: Cc1cn(C(C)C)c2cc(C#N)cc(C(=O)O)c12]

To a 50 ml round bottom was added methyl 6-cyano-3-methyl-1-(1-methylethyl)-1H-indole-4-carboxylate (230 mg, 0.897 mmol), followed by methanol (1 mL) and THF (1 mL). To the solution was added 3 M NaOH (0.449 mL, 2.69 mmol). The reaction stirred at rt for 20 h. The reaction was evaporated and treated with acidic water to pH 5. A brown solid crashed out and was collected by filtration. The solid was an impurity. The pH of the liquid was adjusted to 3 and the liquid was evaporated leaving a residue. Trituration of the residue with water, followed by filtration yielded 6-cyano-3-methyl-1-(1-methylethyl)-1H-indole-4-carboxylic acid (155 mg, 0.576 mmol, 64.2% yield) as a yellow solid. ¹H NMR (400 MHz, DMSO-d₆) δ ppm 13.16 (br. s., 1H) 8.33 (s, 1H) 7.78 (s, 1H) 7.66 (s, 1H) 4.81-4.98 (m, 1H) 2.33 (s, 4H) 1.45 (d, J=6.57 Hz, 6H). MS (ES) [M+H]⁺ 243.3.

Intermediate 39

1-Isopropyl-3-methyl-6-(1H-tetrazol-5-yl)-1H-indole-4-carboxylic acid

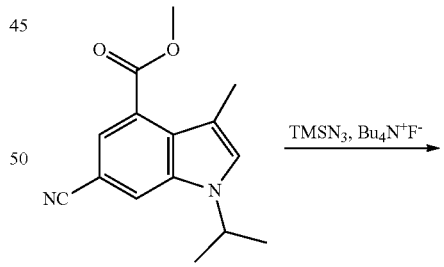

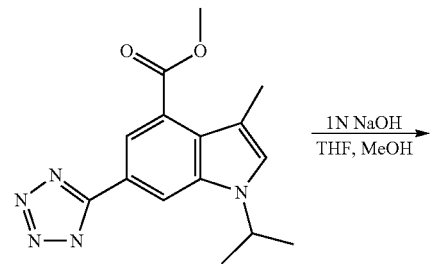

-continued a) Methyl 1-isopropyl-3-methyl-6-(1H-tetrazol-5-yl)-1H-indole-4-carboxylate

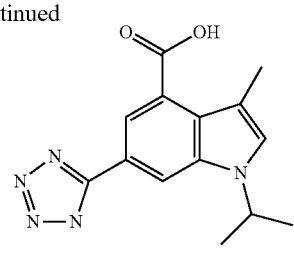

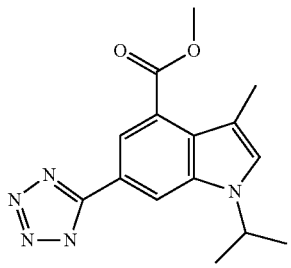 [SMILES: COC(=O)c1cc(-c2nnn[nH]2)cc2c1c(C)cn2C(C)C]

To a stirred suspension of methyl 6-cyano-1-isopropyl-3-methyl-1H-indole-4-carboxylate (0.50 g, 1.951 mmol) in azidotrimethylsilane (1.0 mL, 7.53 mmol) in a small vial was added tetrabutylammonium fluoride trihydrate (300 mg, 0.951 mmol). The reaction was heated to 85° C. and stirred for 18 hr (attached a small reflux condensor). (The reaction became a semi-solid mass.) The reaction was taken up in EtOAc (75 mL), washed with 1 N HCl (75 mL) (stirred till dissolved). The organic phase was removed, dried (Na2SO4), filtered and concentrated under vacuum. Purification by silica gel chromatography (Analogix, SF40-80 g, 0 to 3% MeOH/CH$_2$Cl$_2$ with 0.1% HOAc) gave the product methyl 1-isopropyl-3-methyl-6-(1H-tetrazol-5-yl)-1H-indole-4-carboxylate (0.28 g, 0.935 mmol, 48.0% yield) as a white solid. $^1$H NMR (400 MHz, DMSO-d$_6$) δ 8.40 (d, J=1.3 Hz, 1H), 8.15 (d, J=1.5 Hz, 1H), 7.69 (s, 1H), 4.86 (quin, J=6.6 Hz, 1H), 3.94 (s, 3H), 2.33 (s, 3H), 1.50 (d, J=6.6 Hz, 6H). MS (ES)+m/e 300.3 [M+H]$^+$.

b) 1-isopropyl-3-methyl-6-(1H-tetrazol-5-yl)-1H-indole-4-carboxylic acid

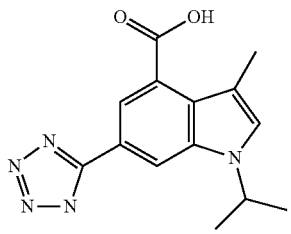 [SMILES: Cc1cn(C(C)C)c2cc(-c3nnn[nH]3)cc(C(=O)O)c12]

To a stirred solution of methyl 1-isopropyl-3-methyl-6-(1H-tetrazol-5-yl)-1H-indole-4-carboxylate (0.27 g, 0.902 mmol) in MeOH (15 mL) and tetrahydrofuran (5 mL) was added 1N NaOH (5 mL, 5.00 mmol). The reaction was heated to 60° C. and stirred for 48 hr. LCMS showed that the reaction was complete. The reaction was concentrated to near dryness under vacuum, acidified with 1 N HCl (5 mL), triturated, filtered and washed with a small volume of water, and dried under vacuum to give the product 1-isopropyl-3-methyl-6-(1H-tetrazol-5-yl)-1H-indole-4-carboxylic acid (0.26 g, 0.911 mmol, 101% yield) as a light yellow solid. $^1$H NMR (400 MHz, DMSO-d$_6$) δ 13.04 (br. s., 1H), 8.36 (d, J=1.5 Hz, 1H), 8.13 (d, J=1.3 Hz, 1H), 7.65 (s, 1H), 4.85 (quin, J=6.6 Hz, 1H), 2.36 (s, 3H), 1.50 (d, J=6.6 Hz, 6H). MS (ES)+m/e 286.1 [M+H]$^+$.

Intermediate 40

6-Bromo-3-chloro-1-isopropyl-1H-indole-4-carboxylic acid

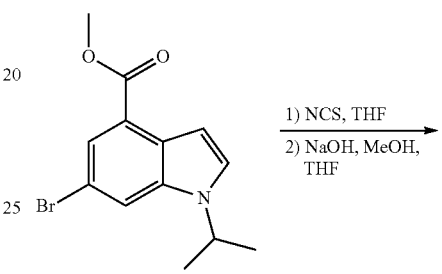

To a 100 ml round bottom flask was added methyl 6-bromo-1-(1-methylethyl)-1H-indole-4-carboxylate (1.100 g, 3.71 mmol) as a solution in THF and a magnetic stir bar. To the same was added 1-chloro-2,5-pyrrolidinedione (0.546 g, 4.09 mmol) and the system stirred at room temperature overnight. The solvent was removed under reduced pressure and the residue dissolved in EtOAc (60 ml) and washed with saturated NaHCO3 (20 ml) and brine (8 ml). The organic layer was dried over Na2SO4, filtered and concentrated. Purification of the residue by column chromatography provided methyl 6-bromo-3-chloro-1-isopropyl-1H-indole-4-carboxylate (as a thick gold oil), which was used in the next step. $^1$H NMR (400 MHz, DMSO-d$_6$) δ 8.15 (d, J=1.52 Hz, 1H), 7.93 (s, 1H), 7.50 (d, J=1.77 Hz, 1H), 4.90 (quin, J=6.63 Hz, 1H), 3.89 (s, 3H), 1.43 (d, J=6.57 Hz, 6H). MS (ES) [M+H]$^+$ 332.2.

To a solution of methyl 6-bromo-3-chloro-1-(1-methylethyl)-1H-indole-4-carboxylate (1.2 g, 3.63 mmol) in THF (2.368 ml) and MeOH (14.21 ml) was added 3 N NaOH (1.573 ml, 4.72 mmol). The resulting mixture was heated at 55° C. for 4 h. The reaction was removed from the heat and the solvent removed in-vacuo. The remaining residue was dissolved with water (12 ml) and made acidic dropwise with 1 N HCl. The product precipitated and the slurry became too thick to stir and was diluted with water (10 ml). After the precipitation haulted no more acid was added. The solid was collected by vacuum filtration, washed with water, and air dried under vacuum overnight to give 6-bromo-3-chloro-1-(1-methylethyl)-1H-indole-4-carboxylic acid (650 mg, 2.033 mmol, 56.0% yield over 2 steps) as a white solid. $^1$H NMR (400 MHz, DMSO-d$_6$) δ 13.22 (s, 1H), 8.09 (d, J=1.77 Hz, 1H), 7.89 (s, 1H), 7.45 (d, J=1.77 Hz, 1H), 4.88 (quin, J=6.63 Hz, 1H), 1.43 (d, J=6.57 Hz, 6H). MS (ES) [M+H]$^+$ 316.0.

Intermediate 41

Methyl 2-bromo-6-chloro-1-isopropyl-3-methyl-1H-indole-4-carboxylate

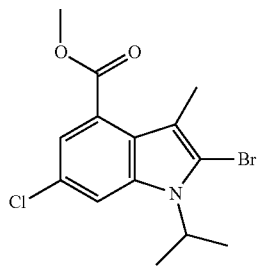 [SMILES: COC(=O)c1cc(Cl)cc2c1c(C)c(Br)n2C(C)C]

To a stirred solution of methyl 6-chloro-1-isopropyl-3-methyl-1H-indole-4-carboxylate (2.5 g, 9.41 mmol) in DMF (25 mL) was added NBS (1.7 g, 9.55 mmol). The reaction was stirred for 18 h then evaporated to dryness under vacuum. The reaction was purified by silica gel chromatography (Analogix, SF40-80 g, 0 to 5% EtOAc in hexanes) then (Analogix, SF25-60 g, 25% $CH_2Cl_2$ in hexanes) to give the product methyl 2-bromo-6-chloro-1-isopropyl-3-methyl-1H-indole-4-carboxylate (1.79 g, 5.19 mmol, 55.2% yield) as a clear oil. $^1$H NMR (400 MHz, DMSO-$d_6$) δ=7.98 (d, J=1.8 Hz, 1H), 7.41 (d, J=1.8 Hz, 1H), 5.05 (dt, J=6.7, 13.4 Hz, 1H), 3.89 (s, 3H), 2.22 (s, 3H), 1.57 (d, J=7.1 Hz, 6H). MS (ES)+ m/e 344.0 [M+H]$^+$.

Intermediate 42

1-Isopropyl-3-methyl-6-(pyridazin-4-yl)-1H-indole-4-carboxylic acid

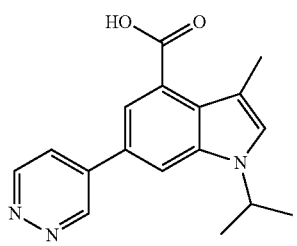 [SMILES: Cc1cn(C(C)C)c2cc(-c3ccnnc3)cc(C(=O)O)c12]

a) Methyl 1-isopropyl-3-methyl-6-(pyridazin-4-yl)-1H-indole-4-carboxylate

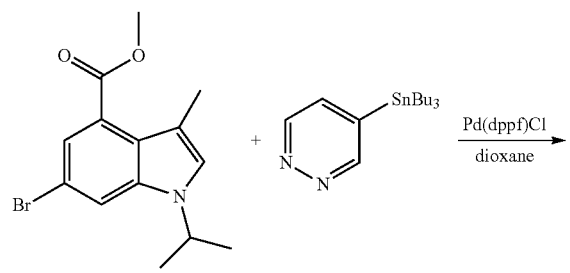

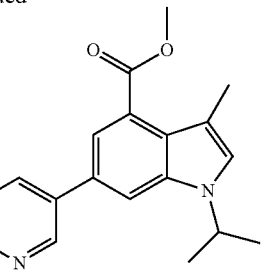

To a 50 ml round bottom flask was added; methyl 6-bromo-1-isopropyl-3-methyl-1H-indole-4-carboxylate (150 mg, 0.484 mmol), PdC12(dppf)-$CH_2Cl_2$ adduct (39.5 mg, 0.048 mmol) and 1,4-Dioxane (4836 µl) followed with 4-(tributylstannyl)pyridazine (179 mg, 0.484 mmol) and a magnetic stir bar. The flask was equipped with a reflux condenser and an exhaust bubbler and heated to 105° C. The reaction solution changed to a dark brown at 30 minutes. LCMS (105 C-3 h) showed the reaction to be complete. The reaction solvent was removed in-vacuo and the remaining residue taken up with DMSO. (1.5 ml). The DMSO solution was purified by reverse phase HPLC using a Phenomenex Gemini 100×30 mm column, neutral acetonitrile and 0.1% formic acid in water, 40-70%, 10 min gradient. The desired fractions were dried in a Genovac EZ-2 evaporator and the solid residues combined. The product, methyl 1-isopropyl-3-methyl-6-(pyridazin-4-yl)-1H-indole-4-carboxylate, was obtained as a white solid. $^1$H NMR (400 MHz, METHANOL-$δ_4$) 9.68 (6, J=1.26 Hz, 1H), 9.19 (d, J=5.56 Hz, 1H), 8.20 (d, J=1.52 Hz, 1H), 8.13 (dd, J=2.53, 5.56 Hz, 1H), 7.98 (d, J=1.52 Hz, 1H), 7.48 (s, 1H), 4.96 (dt, J=6.60, 13.33 Hz, 1H), 4.00 (s, 3H), 2.39 (s, 3H), 1.56 (d, 6H). MS (ES) [M+H]$^+$ 310.2.

b) 1-Isopropyl-3-methyl-6-(pyridazin-4-yl)-1H-indole-4-carboxylic acid

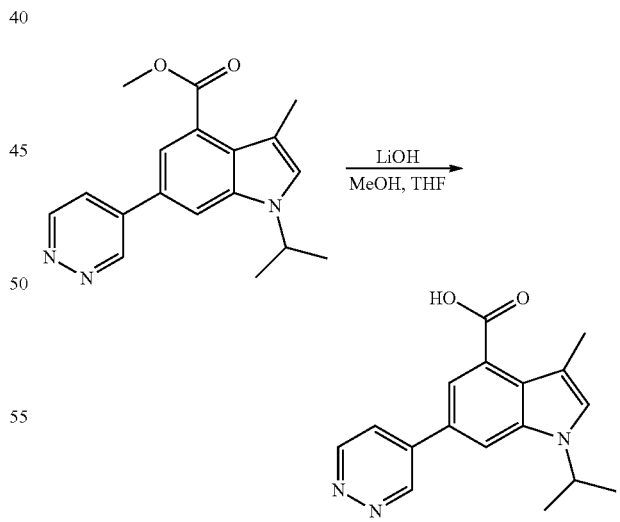

To a 100 ml round bottom flask was added methyl 1-isopropyl-3-methyl-6-(pyridazin-4-yl)-1H-indole-4-carboxylate (74.0 mg, 0.239 mmol), Methanol (1595 µl), Tetrahydrofuran (THF) (3189 µl) and a magnetic stir bar. To the same was added lithium hydroxide, H2O (30.1 mg, 0.718 mmol) and the mixture was stirred at 55° C. Reaction progress was monitored by LCMS. LCMS (weekend) showed 50% conversion. To the reaction mixture was added lithium hydroxide, H2O (20.08 mg, 0.478 mmol) The reaction was continued to stir and heated to 55° C. After complete conversion the reaction solvent was removed and the remaining residue dissolved with water (1.5 ml). The aqueous solution was made acidic drop wise with 1N HCl until precipitation was complete. The solid was collected by vacuum filtration and washed with water (5 ml). The solid was dried under vacuum open to the air overnight. The product, 1-isopropyl-3-methyl-6-(pyridazin-4-yl)-1H-indole-4-carboxylic acid (68 mg, 0.228 mmol, 95% yield), was obtained as a brown solid. $^1$H NMR (400 MHz, DMSO-$d_6$) δ 9.71-9.83 (m, 1H), 9.23 (dd, J=1.26, 5.56 Hz, 1H), 8.32 (s, 1H), 8.11 (dd, J=2.65, 5.43 Hz, 1H), 7.86 (s, 1H), 7.58 (s, 1H), 4.90-5.09 (m, 1H), 2.34 (s, 3H), 1.47 (d, J=6.82 Hz, 6H). MS (ES) [M+H]$^+$ 296.2.

Intermediate 43

6-Bromo-3-fluoro-1-isopropyl-1H-indole-4-carboxylic acid

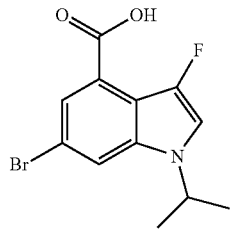

a) Methyl 6-bromo-3-fluoro-1-isopropyl-1H-indole-4-carboxylate

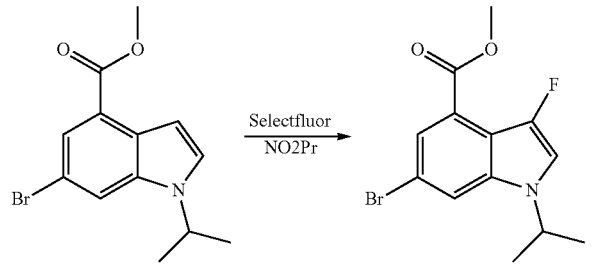 [SMILES: COC(=O)c1cc(Br)cc2c1ccn2C(C)C ; COC(=O)c1cc(Br)cc2c1c(F)cn2C(C)C ; "NO2Pr"]

To a 20 ml vial was added methyl 6-bromo-1-isopropyl-1H-indole-4-carboxylate (50.0 mg, 0.169 mmol), (selectfluor) 1-(chloromethyl)-4-fluoro-1,4-diazoniabicyclo[2.2.2]octane ditetrafluoroborate (78 mg, 0.219 mmol) followed with a magnetic stir bar and nitroethane (2 ml). The vial was capped and the reaction stirred at room temperature. Reaction progress was monitored by LCMS. After reaction completion the reaction solvent was removed in-vacuo. The residue was dissolved with DCM (1.4 ml). The DCM solution was charged onto an analogix Si35 SF10-8 gram column. The compound was eluted with EtOAc/Hexanes, 5-15%, 20 min. The desired product and side MW629 co-eluted. The mixture was dissolved with DMSO (1 ml) and purified by reverse phase HPLC using a Gemini 5μ 30×100 mm column, neutral acetonitrile/0.1% formic acid in water, 50-80%, 7 min gradient. The desired product eluted at 6.8 minutes and the side product MW 629 at 9.5 minutes. The desired fractions were concentrated to a residue. LCMS and NMR support the desired structure and analytical HPLC showed 100% purity.

The product, methyl 6-bromo-3-fluoro-1-isopropyl-1H-indole-4-carboxylate (11 mg, 0.035 mmol, 20.53% yield), was obtained as a white solid. $^1$H NMR (400 MHz, METHANOL-$d_4$) δ 7.95 (t, J=1.77 Hz, 1H), 7.78 (d, J=1.77 Hz, 1H), 7.47 (d, J=2.53 Hz, 1H), 4.76-4.84 (m, J=1.64, 6.65, 6.65, 13.36 Hz, 1H), 3.96 (s, 3H), 1.50 (d, 6H). MS (ES)[M+H]$^+$315.1.

b) 6-Bromo-3-fluoro-1-isopropyl-1H-indole-4-carboxylic acid

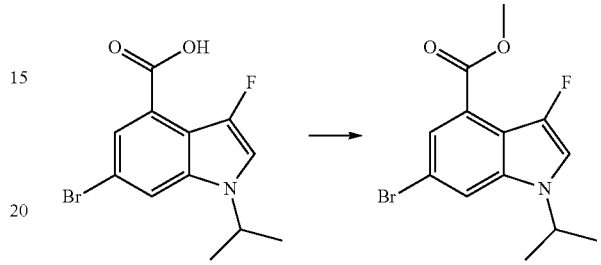

To a 100 ml round bottom flask was added methyl 6-bromo-3-fluoro-1-isopropyl-1H-indole-4-carboxylate (33.0 mg, 0.105 mmol), Methanol (700 μl), Tetrahydrofuran (THF) (1401 μl) and a magnetic stir bar. To the same was added lithium hydroxide, H2O (13.22 mg, 0.315 mmol) and the mixture was stirred at room temperature. Reaction progress was monitored by LCMS. LCMS (18 h) showed 60% conversion. The reaction was heated to 50° C. in an aluminum heating block with stirring. After complete conversion the solvent was removed in-vacuo and the remaining residue was dissolved with water (1 ml) and 1N HCl was added dropwise (9 drops) until precipitation stopped. The fine pale-yellow solid was collected by vacuum filtration. LCMS and HPLC showed 100% purity and NMR supports the desired structure. The product, 6-bromo-3-fluoro-1-isopropyl-1H-indole-4-carboxylic acid (24 mg, 0.080 mmol, 76% yield), was obtained as a yellow solid. $^1$H NMR (400 MHz, DMSO-$d_6$) δ 13.07 (br. s., 1H), 8.12 (t, J=1.89 Hz, 1H), 7.77 (d, J=2.27 Hz, 1H), 7.66 (d, J=1.77 Hz, 1H), 4.88 (qd, J=5.31, 6.65 Hz, 1H), 1.40 (d, 6H). MS (ES) [M+H]$^+$ 300.1.

Intermediate 44

N-[(4,6-dimethyl-2-oxo-1,2-dihydro-3-pyridinyl)methyl]-3-methyl-1-(1-methylethyl)-6-(4,4,5,5-tetramethyl-1,3,2-dioxaborolan-2-yl)-1H-indole-4-carboxamide

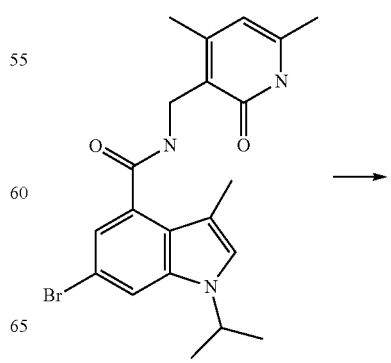

-continued

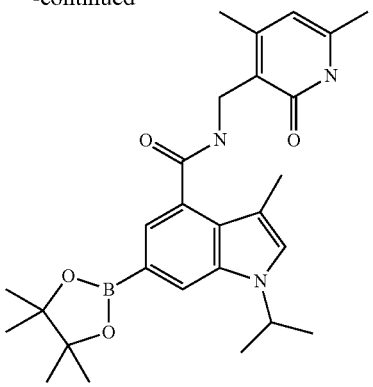

Trial run: A mixture of 6-bromo-N-((4,6-dimethyl-2-oxo-1,2-dihydropyridin-3-yl)methyl)-1-isopropyl-3-methyl-1H-indole-4-carboxamide (1.0 g, 2.32 mmol, 1 equiv), bis(pinacolato)diboron (0.71 g, 2.79 mmol, 1.2 equiv), KOAc (0.47 g, 4.76 mmol, 2 equiv) and PdCl$_2$(dppf)-CH$_2$Cl$_2$ adduct (104 mg, 00.13 mmol, 0.1 equiv) in 10 mL of dioxane in a 20 ml microwave vial was bubbled with nitrogen for 10 min, followed by capping and heating in an oil bath at 80° C. for 3 h. LCMS showed conversion complete. Only 4% debromo byproduct was detected.

Production run: A mixture of 6-bromo-N-((4,6-dimethyl-2-oxo-1,2-dihydropyridin-3-yl)methyl)-1-isopropyl-3-methyl-1H-indole-4-carboxamide (22.0 g, 51.1 mmol, 1 equiv), bis(pinacolato)diboron (15.58 g, 61.3 mmol, 1.2 equiv), KOAc (10.29 g, 105 mmol, 2 equiv) and PdCl$_2$ (dppf)-CH$_2$Cl$_2$ adduct (2.30 g, 2.81 mmol, 0.1 equiv) in 190 mL of dioxane was degassed and backflushed with nitrogen (repeated 4×). The mixture was heated in an oil bath at 90° C. for 2 h. The dark brownish mixture was combined with the crude mixture from the trial run above, and filtered through celite (rinsing with EtOAc). The filtrate was conc in vacuo. The residue was taken up in CHCl$_3$ and split into 9 equal portions. One portion was absorbed onto a celite-packed dryload cartridge. Purification was done on an SF40-80 g silica gel cartridge using gradient elution of 25% EtOAc in hexane to 100% EtOAc (gradient: 0-5 min, 25% EtOAc, 5-20 min, linear gradient 25-100% EtOAc, 25-65 min, 100% EtOAc). The desired product eluted at 100% EtOAc (with a long tail). The DASI portion was clogged during the process, and needed to be removed to continue the chromatography, causing loss of material. Thus the use of FCC was abondoned and switched to gravity column.

The remaining 8 portions were recombined and dissolved in CHCl$_3$, followed by adding to a silica gel column (500 g of coarse grade silica gel packed in 25% EtOAc in hexane), and then elution with 1 L of 25% EtOAc in hexane, 1 L of 50% EtOAc, 1 L of 75% EtOAc in hexane, 2 L of 100% EtOAc, 1 L of EtOAc with 25 mL increments of MeOH. The desired product eluted at 100% EtOAc, 25 mL-100 mL of MeOH in EtOAc fractions.

The EtOAc fractions were combined with the FCC purified material. The mixture was conc in vacuo. The residue was taken up in MTBE (5 mL) and hexane (100 mL) as a suspension, which was filtered. The cake was washed with hexane (30 mL) and dried under vacuum at rt for 4 h to provide N-[(4,6-dimethyl-2-oxo-1,2-dihydro-3-pyridinyl)methyl]-3-methyl-1-(1-methylethyl)-6-(4,4,5,5-tetramethyl-1,3,2-dioxaborolan-2-yl)-1H-indole-4-carboxamide (14.01 g) as light beige solid. $^1$H NMR (400 MHz, DMSO-d$_6$) δ ppm 1.31 (s, 12H), 1.41 (d, J=6.8 Hz, 6H), 2.11 (s, 3H), 2.16 (s, 3H), 2.22 (s, 3H), 4.33 (d, J=8 Hz, 2H), 4.79 (quin, J=6.6 Hz, 1H), 5.87 (s, 1H), 7.23 (s, 1H), 7.40 (d, J=1.0 Hz, 1H), 7.75 (s, 1H), 8.04 (t, J=5.1 Hz, 1H), 11.46 (s, 1H).

Assay Protocol

Compounds contained herein were evaluated for their ability to inhibit the methyltransferase activity of EZH2 within the PRC2 complex. Human PRC2 complex was prepared by co-expressing each of the 5 member proteins (FLAG-EZH2, EED, SUZ12, RbAp48, AEBP2) in Sf9 cells followed by co-purification. Enzyme activity was measured in a scintillation proximity assay (SPA) where a tritiated methyl group is transferred from 3H-SAM to a lysine residue on Histone H3 of a mononucleosome, purified from HeLa cells. Mononucleosomes were captured on SPA beads and the resulting signal is read on a ViewLux plate reader.

Part A. Compound Preparation
1. Prepare 10 mM stock of compounds from solid in 100% DMSO.
2. Set up an 11-point serial dilution (1:3 dilution, top concentration 10 mM) in 100% DMSO for each test compound in a 384 well plate leaving columns 6 and 18 for DMSO controls.
3. Dispense 100 mL of compound from the dilution plate into reaction plates (Grenier Bio-One, 384-well, Cat #784075).

Part B. Reagent Preparation
Prepare the following solutions:
1. 50 mM Tris-HCl, pH 8: Per 1 L of base buffer, combine 1 M Tris-HCl, pH 8 (50 mL) and distilled water (950 mL).
2. 1×Assay Buffer: Per 10 mL of 1×Assay Buffer, combine 50 mM Tris-HCl, pH 8 (9958 uL), 1 M MgCl$_2$ (20 uL), 2 M DTT (20 uL), and 10% Tween-20 (2 uL) to provide a final concentration of 50 mM Tris-HCl, pH 8, 2 mM MgCl$_2$, 4 mM DTT, 0.002% Tween-20.
3. 2× Enzyme Solution: Per 10 mL of 2× Enzyme Solution, combine 1×Assay Buffer and PRC2 complex to provide a final enzyme concentration of 10 nM.
4. SPA Bead Suspension: Per 1 mL of SPA Bead Suspension, combine PS-PEI coated LEADSeeker beads (40 mg) and ddH2O (1 mL) to provide a final concentration of 40 mg/mL.
5. 2× Substrate Solution: Per 10 mL of 2× Substrate Solution, combine 1×Assay Buffer (9728.55 uL), 800 ug/mL mononucleosomes (125 uL), 1 mM cold SAM (4 uL), and 7.02 uM 3H-SAM (142.45 uL; 0.55 mCi/mL) to provide a final concentration of 5 ug/mL nucleosomes, 0.2 uM cold SAM, and 0.05 uM 3H-SAM.
6. 2.67× Quench/Bead Mixture: Per 10 mL of 2.67× Quench/Bead Mixture, combine ddH$_2$O (9358 uL), 10 mM cold SAM (267 uL), 40 mg/mL Bead Suspension (375 uL) to provide a final concentration of 100 uM cold SAM and 0.5 mg/mL SPA beads.

Part C. Assay Reaction in 384-Well Grenier Bio-One Plates
Compound Addition
1. Dispense 100 mL/well of 100× Compound to test wells (as noted above).
2. Dispense 100 mL/well of 100% DMSO to columns 6 & 18 for high and low controls, respectively.

Assay
1. Dispense 5 uL/well of 1× Assay Buffer to column 18 (low control reactions).
2. Dispense 5 uL/well of 2× Enzyme Solution to columns 1-17, 19-24.
3. Spin assay plates for ~1 minute at 500 rpm.

4. Stack the assay plates, covering the top plate.
5. Incubate the compound/DMSO with the enzyme for 30 minutes at room temperature.
6. Dispense 5 uL/well of 2× Substrate Solution to columns 1-24.
7. Spin assay plates for ~1 minute at 500 rpm.
8. Stack the assay plates, covering the top plate.
9. Incubate the assay plates at room temperature for 1 hour.

Quench/Bead Addition
1. Dispense 5 uL/well of the 3× Quench/Bead Mixture to columns 1-24.
2. Seal the top of each assay plate with adhesive TopSeal.
3. Spin assay plates for ~1 minute at 500 rpm.
4. Equilibrate the plates for >20 min.

Read Plates
1. Read the assay plates on the Viewlux Plate Reader utilizing the 613 nm emission filter with a 300 s read time.

Reagent addition can be done manually or with automated liquid handler.
*The final DMSO concentration in this assay is 1%.
*The positive control is in column 6; negative control is in column 18.
*Final starting concentration of compounds is 100 μM.

Part D. Data Analysis

Percent inhibition was calculated relative to the DMSO control for each compound concentration and the resulting values were fit using standard $IC_{50}$ fitting parameters within the ABASE data fitting software package.

Exemplified compounds of the present invention were generally tested according to the above or an analogous assay and were found to be inhibitors of EZH2. The $IC_{50}$ values ranged from about 1 nM to about 10 μM; The $IC_{50}$ values of the more active compounds range from about 1 nM to about 500 nM; The most active compounds are under 50 nM. As tested in the foregoing assay or an analogous assay, compounds of the various Examples gave the $pIC_{50}$ data in the compound table above or the $IC_{50}$ data in the paragraph below. Repeating the assay run(s) may result in a somewhat different.

Ex 78, 1800; Ex 174, 18; Ex 211, 14; Ex 212, 9; Ex 234, 1000; Ex 244, 29; Ex 264, 13; Ex 265, 13; Ex 266, 25; Ex 267, 20; Ex 268, 40; Ex 269, 4; Ex 270, 4; Ex 271, 8; Ex 272, 13; Ex 273, 10; Ex 274, 32; Ex 275, 3; Ex 339, 13.

What is claimed is:

1. A compound which is N-[(4,6-dimethyl-2-oxo-1,2-dihydro-3-pyridinyl)methyl]-3-methyl-1-[(1S)-1-methylpropyl]-6-[6-(1-piperazinyl)-3-pyridinyl]-1H-indole-4-carboxamide, represented by the formula:

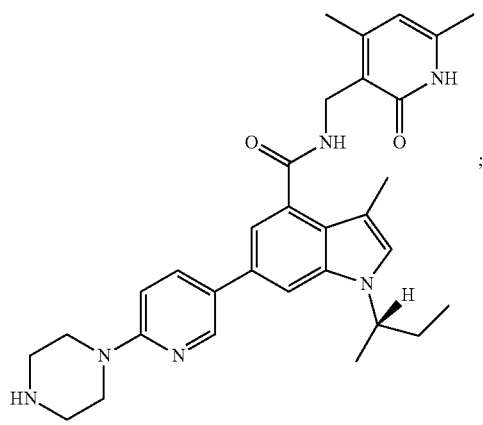 [SMILES: CC[C@H](C)n1cc(C)c2c(C(=O)NCc3c(C)cc(C)[nH]c3=O)cc(-c3ccc(N4CCNCC4)nc3)cc21]

or a pharmaceutically acceptable salt thereof.

2. A compound which is N-[(4,6-dimethyl-2-oxo-1,2-dihydro-3-pyridinyl)methyl]-3-methyl-1-[(1S)-1-methylpropyl]-6-[6-(1-piperazinyl)-3-pyridinyl]-1H-indole-4-carboxamide, represented by the formula:

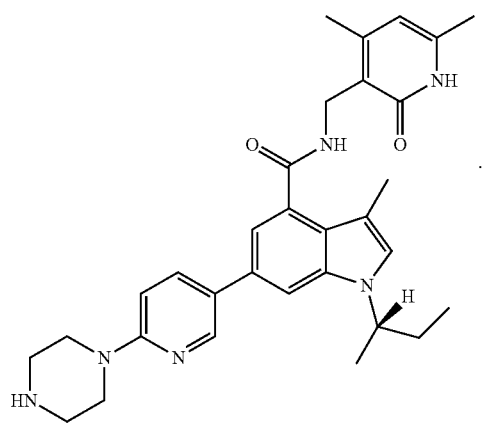 [SMILES: CC[C@H](C)n1cc(C)c2c(C(=O)NCc3c(C)cc(C)[nH]c3=O)cc(-c3ccc(N4CCNCC4)nc3)cc21]

3. A pharmaceutical composition comprising the compound or pharmaceutically acceptable salt thereof according to claim 1 and a pharmaceutically acceptable excipient.

4. A pharmaceutical composition comprising the compound according to claim 2 and a pharmaceutically acceptable excipient.

* * * * *